US010526317B2

(12) United States Patent
Hermanson et al.

(10) Patent No.: US 10,526,317 B2
(45) Date of Patent: Jan. 7, 2020

(54) BENZOCYANINE COMPOUNDS

(71) Applicants: PIERCE BIOTECHNOLOGY, INC., Rockford, IL (US); DYOMICS GMBH, Jena (DE)

(72) Inventors: Greg Hermanson, Loves Park, IL (US); Peter T. Czerney, Weimar (DE); Surbhi Desai, Rockford, IL (US); Matthias S. Wenzel, Jena (DE); Boguslawa R. Dworecki, Rockford, IL (US); Frank G. Lehmann, Jena (DE); Marie Christine Nlend, Rockford, IL (US)

(73) Assignees: Pierce Biotechnology, Inc., Rockford, IL (US); Dyomics GmbH, Jena (DE)

( * ) Notice: Subject to any disclaimer, the term of this patent is extended or adjusted under 35 U.S.C. 154(b) by 0 days.

(21) Appl. No.: 15/641,376

(22) Filed: Jul. 5, 2017

(65) Prior Publication Data

US 2018/0134689 A1   May 17, 2018

Related U.S. Application Data

(62) Division of application No. 13/778,678, filed on Feb. 27, 2013, now Pat. No. 9,751,868.

(60) Provisional application No. 61/607,737, filed on Mar. 7, 2012, provisional application No. 61/604,232, filed on Feb. 28, 2012.

(51) Int. Cl.
| *G01N 33/533* | (2006.01) |
| *A61K 49/00* | (2006.01) |
| *C07D 403/14* | (2006.01) |
| *C07D 209/60* | (2006.01) |
| *C07K 19/00* | (2006.01) |
| *G01N 33/58* | (2006.01) |
| *G01N 33/543* | (2006.01) |

(52) U.S. Cl.
CPC ........ *C07D 403/14* (2013.01); *A61K 49/0032* (2013.01); *A61K 49/0058* (2013.01); *C07D 209/60* (2013.01); *C07K 19/00* (2013.01); *G01N 33/533* (2013.01); *G01N 33/582* (2013.01); *G01N 33/54346* (2013.01)

(58) Field of Classification Search
CPC ....... A61K 49/00; G01N 33/533; C09B 23/08
See application file for complete search history.

(56) References Cited

U.S. PATENT DOCUMENTS

| 1,524,791 A | 2/1925 | Konig |
| 4,839,265 A | 6/1989 | Ohno et al. |
| 4,981,977 A | 1/1991 | Southwick et al. |
| 5,268,486 A | 12/1993 | Waggoner et al. |
| 5,486,616 A | 1/1996 | Waggoner et al. |
| 5,556,959 A | 9/1996 | Brush et al. |
| 5,569,587 A | 10/1996 | Waggoner |
| 5,569,766 A | 10/1996 | Waggoner et al. |
| 5,627,027 A | 5/1997 | Waggoner |
| 5,846,737 A | 12/1998 | Kang |
| 5,972,838 A | 10/1999 | Pearce et al. |
| 5,986,086 A | 11/1999 | Brush et al. |
| 6,048,982 A | 4/2000 | Waggoner |
| 6,083,485 A | 7/2000 | Licha et al. |
| 6,136,612 A | 10/2000 | Della Ciana et al. |
| 6,225,050 B1 | 5/2001 | Waggoner |
| 6,258,340 B1 | 7/2001 | Licha et al. |
| 6,342,326 B1 | 1/2002 | Milton |
| 6,534,041 B1 | 3/2003 | Licha et al. |
| 6,641,093 B2 | 11/2003 | Coudrais |
| 6,761,878 B2 | 7/2004 | Achilefu et al. |
| 6,924,372 B2 | 8/2005 | Czerney et al. |
| 6,939,532 B2 | 9/2005 | Achilefu et al. |
| 6,974,873 B2 | 12/2005 | Leung et al. |
| 6,977,305 B2 | 12/2005 | Leung et al. |
| 7,172,907 B2 | 2/2007 | Chen et al. |
| 7,175,831 B2 | 2/2007 | Achilefu et al. |
| 7,566,790 B2 | 7/2009 | Leung et al. |
| 7,671,214 B2 | 3/2010 | Leung et al. |
| 7,745,640 B2 | 6/2010 | Czerney et al. |
| 7,750,163 B2 | 7/2010 | West et al. |
| 7,790,893 B2 | 9/2010 | Leung et al. |
| 7,820,824 B2 | 10/2010 | Leung et al. |
| 7,855,293 B2 | 12/2010 | Haalck et al. |
| 7,927,830 B2 | 4/2011 | Cheung et al. |
| 7,951,959 B2 | 5/2011 | Brush et al. |
| 8,431,111 B2 | 4/2013 | Nairne et al. |
| 8,889,884 B1 | 11/2014 | Hermanson et al. |
| 9,097,667 B2 | 8/2015 | Mao et al. |
| 9,249,307 B2 | 2/2016 | Hermanson et al. |
| 9,365,598 B2 | 6/2016 | Hermanson et al. |
| 9,676,787 B2 | 6/2017 | Hermanson et al. |
| 9,751,868 B2 | 9/2017 | Hermanson et al. |
| 9,791,450 B2 | 10/2017 | Mao et al. |
| 10,000,467 B2 | 6/2018 | Hermanson et al. |
| 10,053,447 B2 | 8/2018 | Hermanson et al. |
| 10,125,120 B2 | 11/2018 | Hermanson et al. |
| 10,174,045 B2 | 1/2019 | Hermanson et al. |
| 10,351,551 B2 | 7/2019 | Hermanson et al. |

(Continued)

FOREIGN PATENT DOCUMENTS

| AU | 2006200511 | 2/2006 |
| DE | 4445065 | 6/1996 |
| DE | 19717904 | 10/1998 |
| DE | 19926460 | 12/1999 |
| DE | 10046215 | 4/2004 |

(Continued)

OTHER PUBLICATIONS

Search Report issued by the German Patent Office for App #10 2006 029 454.8 dated Oct. 10, 2006 (with English language summary), 5 pages.

(Continued)

*Primary Examiner* — Michael G. Hartley
*Assistant Examiner* — Jagadishwar R Samala
(74) *Attorney, Agent, or Firm* — McNeill Baur PLLC

(57) ABSTRACT

Compounds useful as labels with properties comparable to known fluorescent compounds. The compounds are conjugated to proteins and nucleic acids for biological imaging and analysis. Synthesis of the compounds, formation and use of the conjugated compounds, and specific non-limiting examples of each are provided.

10 Claims, 56 Drawing Sheets

(56) References Cited

U.S. PATENT DOCUMENTS

| | | |
|---|---|---|
| 2001/0055567 A1 | 12/2001 | Licha et al. |
| 2002/0064794 A1 | 5/2002 | Leung et al. |
| 2002/0077487 A1 | 6/2002 | Leung et al. |
| 2004/0166515 A1 | 8/2004 | Terpetschnig et al. |
| 2004/0241095 A1 | 12/2004 | Achilefu et al. |
| 2006/0004188 A1 | 1/2006 | Leung et al. |
| 2006/0099638 A1 | 5/2006 | Leung et al. |
| 2007/0128659 A1 | 6/2007 | Czerney et al. |
| 2007/0178512 A1 | 8/2007 | Leung et al. |
| 2007/0203343 A1 | 8/2007 | West et al. |
| 2008/0233050 A1 | 9/2008 | Achilefu et al. |
| 2009/0035809 A1 | 2/2009 | Leung et al. |
| 2009/0305410 A1* | 12/2009 | Mao ................. C09B 11/08 435/375 |
| 2010/0040547 A1 | 2/2010 | Frangioni |
| 2010/0196282 A1 | 8/2010 | Nairne et al. |
| 2010/0215585 A1 | 8/2010 | Frangioni |
| 2010/0267937 A1 | 10/2010 | West et al. |
| 2010/0303732 A1 | 12/2010 | Bahner |
| 2011/0065876 A1 | 3/2011 | Okamoto et al. |
| 2011/0065896 A1 | 3/2011 | Licha et al. |
| 2011/0171678 A1 | 7/2011 | Leung et al. |
| 2011/0178397 A1 | 7/2011 | Bahner |
| 2012/0114563 A1 | 5/2012 | Carter et al. |
| 2012/0156140 A1 | 6/2012 | Hermanson et al. |
| 2013/0045488 A1 | 2/2013 | Hermanson et al. |
| 2013/0230465 A1 | 9/2013 | Hermanson et al. |
| 2013/0230466 A1 | 9/2013 | Hermanson et al. |
| 2014/0106349 A1 | 4/2014 | Mao et al. |
| 2014/0255312 A1 | 9/2014 | Hermanson et al. |
| 2015/0119281 A1 | 4/2015 | Hermanson et al. |
| 2015/0322078 A1 | 11/2015 | Hermanson et al. |
| 2016/0168383 A1 | 6/2016 | Hermanson et al. |
| 2016/0176852 A1 | 6/2016 | Hermanson et al. |
| 2016/0176853 A1 | 6/2016 | Hermanson et al. |
| 2018/0002340 A1 | 1/2018 | Hermanson et al. |
| 2018/0118723 A1 | 5/2018 | Hermanson et al. |
| 2018/0327387 A1 | 11/2018 | Hermanson et al. |
| 2019/0084964 A1 | 3/2019 | Hermanson et al. |

FOREIGN PATENT DOCUMENTS

| | | |
|---|---|---|
| EP | 1152008 | 11/2001 |
| EP | 1181940 | 2/2002 |
| EP | 1322710 | 1/2007 |
| EP | 1770129 | 4/2007 |
| EP | 1792949 | 6/2007 |
| EP | 1801165 | 6/2007 |
| EP | 2325263 | 5/2011 |
| GB | 434875 | 9/1935 |
| JP | 03217837 | 9/1991 |
| JP | H5-313304 | 11/1993 |
| WO | 96/17628 | 6/1996 |
| WO | 98/48838 | 11/1998 |
| WO | 00/075237 | 12/2000 |
| WO | 02/26891 | 4/2002 |
| WO | 02/32466 | 4/2002 |
| WO | 2004/065491 | 8/2004 |
| WO | 2005/044923 | 5/2005 |
| WO | 2005/103162 | 11/2005 |
| WO | 2006/020947 | 2/2006 |
| WO | 2009/016180 | 2/2009 |
| WO | 2009/016181 | 2/2009 |
| WO | 2009/078970 | 6/2009 |
| WO | 2010/091126 | 8/2010 |
| WO | 2010/106169 | 9/2010 |
| WO | 2012/088007 | 6/2012 |
| WO | 2012/129128 | 9/2012 |

OTHER PUBLICATIONS

Search Report issued by the German Patent Office for App #10 2006 057 345.5 dated May 21, 2007 (with English language summary), 5 pages.

International Search Report and Written Opinion for PCT/US2011/065975, dated Mar. 15, 2012 (8 pages).

United Kingdom Search and Examination Report GB1214580.1, dated Nov. 22, 2012, 4 pages.

Alvarez-Maubecin et al. Functional Coupling Between Neurons and Glia. The Journal of Neuroscience. Jun. 1, 2000, 20(11):4091-4098.

Bharaj et al. Rapid sequencing of the p53 gene with a new automated DNA sequencer. Clinical Chemistry. 44:7 1397-1403 (1998).

Biotium. Product brochure titled CF™ Dyes The next-generation dyes for protein labeling. Apr. 6, 2009.

Burns et al. An Integrated Nanoliter DNA Analysis Device. Science. vol. 282, pp. 484-487, Oct. 16, 1998.

DeRisi et al. Exploring the Metabolic and Genetic Control of Gene Expression on a Genomic Scale. Science. vol. 278, ppl. 680-686, Oct. 24, 1997.

Fradelizi et al. Quantitative Measurement of Proteins by Western Blotting with Cy5™-Coupled Secondary Antibodies. BioTechniques. 26:484-494 Mar. 1999.

Gragg. Synthesis of Near-Infrared Heptamethine Cyanine Dyes. Chemistry Theses. Paper 28 (Apr. 26, 2010.). http://digitalarchive.gsu.edu/chemistry_theses/28.

MacBeath and Schreiber. Printing Proteins as Microarrays for High-Throughput Function Determination. Science. vol. 289, pp. 1760-1763, Sep. 8, 2000.

Manders et al. Direct Imaging of DNA in Living Cells Reveals the Dynamics of Chromosome Formation. The Journal of Cell Biology. vol. 144, No. 5, Mar. 8, 1999 813-821.

Mank et al., Visible Diode Laser-Induced Fluorescence Detection in Liquid Chromatography after Precolumn Derivatization of Amines. Anal. Chem. vol. 67, pp. 1742-1748, 1995.

Mujumdar et al. Cyanine Dye Labeling Reagents: Sulfoindocyanine Succinimidyl Esters. Bioconjug Chem. vol. 4, No. 2, pp. 105-111, Mar./Apr. 1993.

Patonay et al. Noncovalent Labeling of Biomolecules with Red and Near-Infrared Dyes. Molecules. 9, 40-49, 2004.

Pharmacia Biotech. Table of Contents p. 294 and p. 295 of the Pharmacia Biotech Catalogue. 1994.

Roman et al. Non-Radioisotopic AFLP Method Using PCR Primers Fluorescently Labeled with Cy™5. BioTechniques. vol. 26, No. 2, pp. 236-238, Feb. 1999.

Schena et al. Parallel human genome analysis: Microarray-based expression monitoring of 1000 genes. Proc. Natl. Acad. Sci. USA. vol. 93, pp. 10614-10619, Oct. 1996.

Shao et al. Monofunctional Carbocyanine Dyes for Bio- and Bioorthogonal Conjugation. Bioconjugate Chemistry. 19(12): 2487-2491, Dec. 2008.

Voss et al. Automated Cycle Sequencing with Taquenase™: Protocols for Internal Labeling, Dye Primer and "Doublex" Simultaneous Sequencing. BioTechniques. vol. 23, No. 2, pp. 312-318, Aug. 1997.

Wilchek and Miron. Activation of Sepharose with N, N'-disuccinimidyl carbonate. Applied Biochemistry and Biotechnology, vol. 11, pp. 191-193 (1985).

Knop et al. Poly(ethylene glycol) in Drug Delivery: Pros and Cons as Well as Potential Alternatives. Angew Chem. Int. Ed. 2010, 49, 6288-6308.

International Search Report and Written Opinion, PCT/US2013/028252, issued by the European Patent Office, dated Apr. 25, 2013 (12 pages).

Examination Report, Great Britain Application No. 1214580.1, dated May 31, 2013 (4 pages).

Hermanson, Bioconjugate Techniques, 2nd Ed., London, Elsevier Inc. 2008, pp. 464-474; 690-697.

Strekowski (ed.), Heterocyclic Polymethine Dyes: Synthesis, Properties and Applications, (2008) Springer-Verlag, Berlin Heidelberg, pp. 1-241.

International Preliminary Report on Patentability, PCT/US2011/065975, dated Jul. 4, 2013 (8 pages).

Licha et al., Synthesis and Characterization of Cyanine Dye-Poly(ethylene Glycol) Conjugates as Contrast Agents for In Vivo Fluorescence Imaging. SPIE 3196 (1998), 98-102.

(56) References Cited

OTHER PUBLICATIONS

Riefke et al., Tumor Detection wit Cyanine Dye-Poly(ethylene Glycol) Conjugates as Contrast Agents for Near-Infrared Imaging. SPIE 3196 (1998), 103-110.
Extended European Search Report issued in European Patent Application No. 15198169.3 (dated Mar. 29, 2016, 8 pages).
Second Office Action with English translation issued in Chinese Patent Application No. 201380005497.X (dated Apr. 28, 2016, 21 pages).
Extended European Search Report and Written Opinion, issued in European Patent Application No. 16169172.0 (dated Jul. 14, 2016, 7 pages).
Rejection Decision with English translation issued in Chinese Patent Application No. 201380005497.X (dated Nov. 2, 2016, 11 pages).

\* cited by examiner

FIG. 16

| Signal/Background @ 125ng/well | |
|---|---|
| V08-15173-2.5X | 2.2 |
| V08-15173-5X | 2.1 |
| V08-15173-10X | 2.4 |
| V08-15173-15X | 2.0 |
| COMPANY A-680-2.5X | 2.8 |
| COMPANY A-5X | 2.8 |
| COMPANY A-7.5X | 2.3 |
| COMPANY A-15X | 2.4 |
| 679 Compound 1/1-2.5X | 1.2 |
| 679 Compound 1/1-5X | 1.9 |
| 679 Compound 1/1-10X | 1.8 |
| 679 Compound 1/1-15X | 3.9 |

FIG. 18

| Signal/Background | @ 125ng/well |
|---|---|
| V08-15173-5X | 2.1 |
| V08-15173-15X | 1.8 |
| V08-15173-25X | 2.2 |
| COMPANY A-5X | 1.9 |
| COMPANY A-15X | 1.8 |
| COMPANY A-25X | 1.9 |
| V10-04152-5X | 1.4 |
| V10-04152-15X | 1.3 |
| V10-04152-25X | 1.3 |
| 679 Compound 1/1-5X | 1.6 |
| 679 Compound 1/1-15X | 1.8 |
| 679 Compound 1/1-25X | 1.7 |

FIG. 28
A 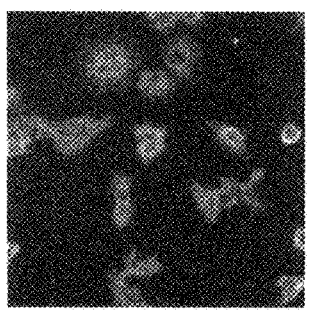
B 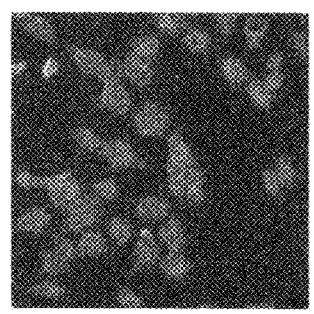
C 

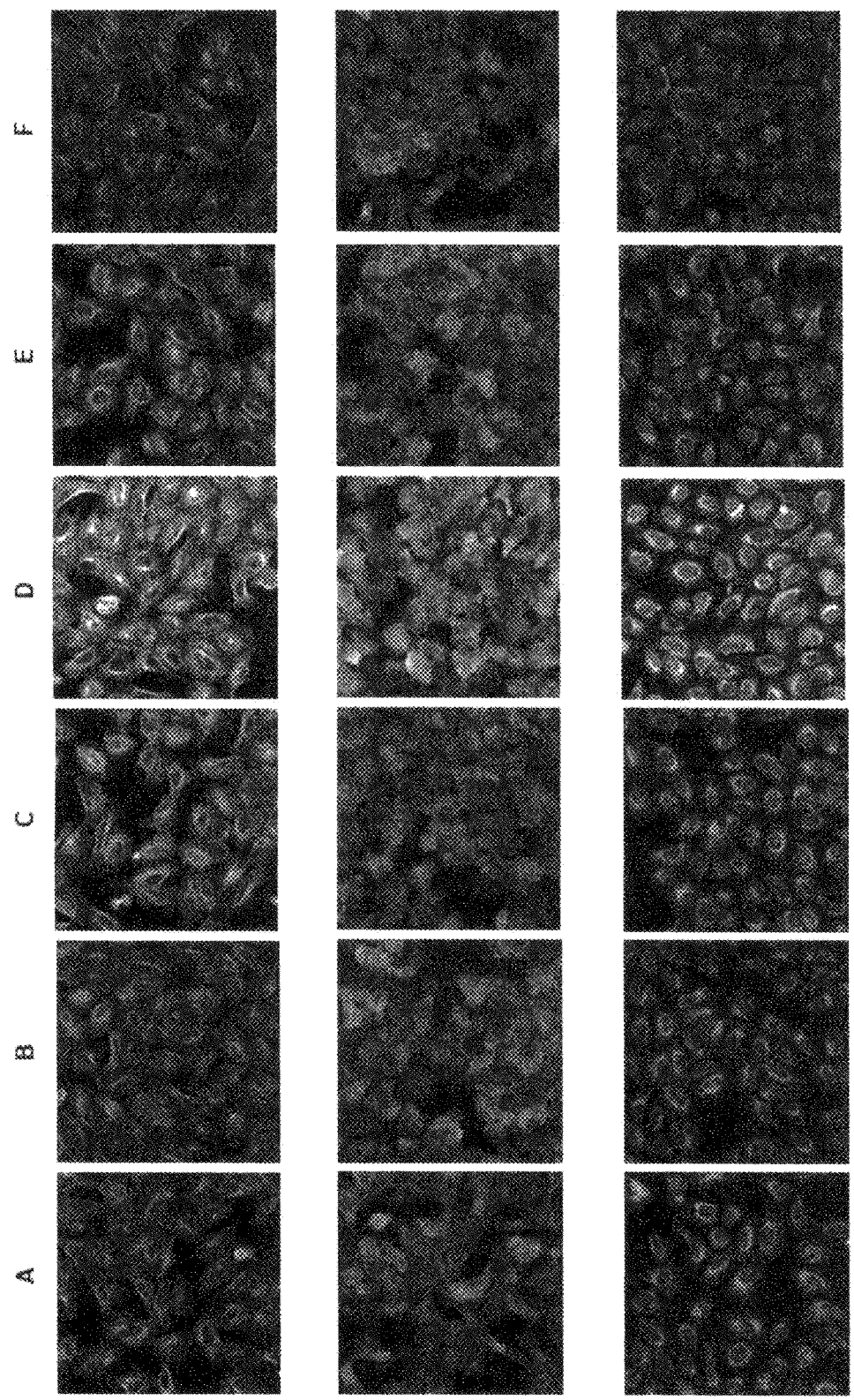

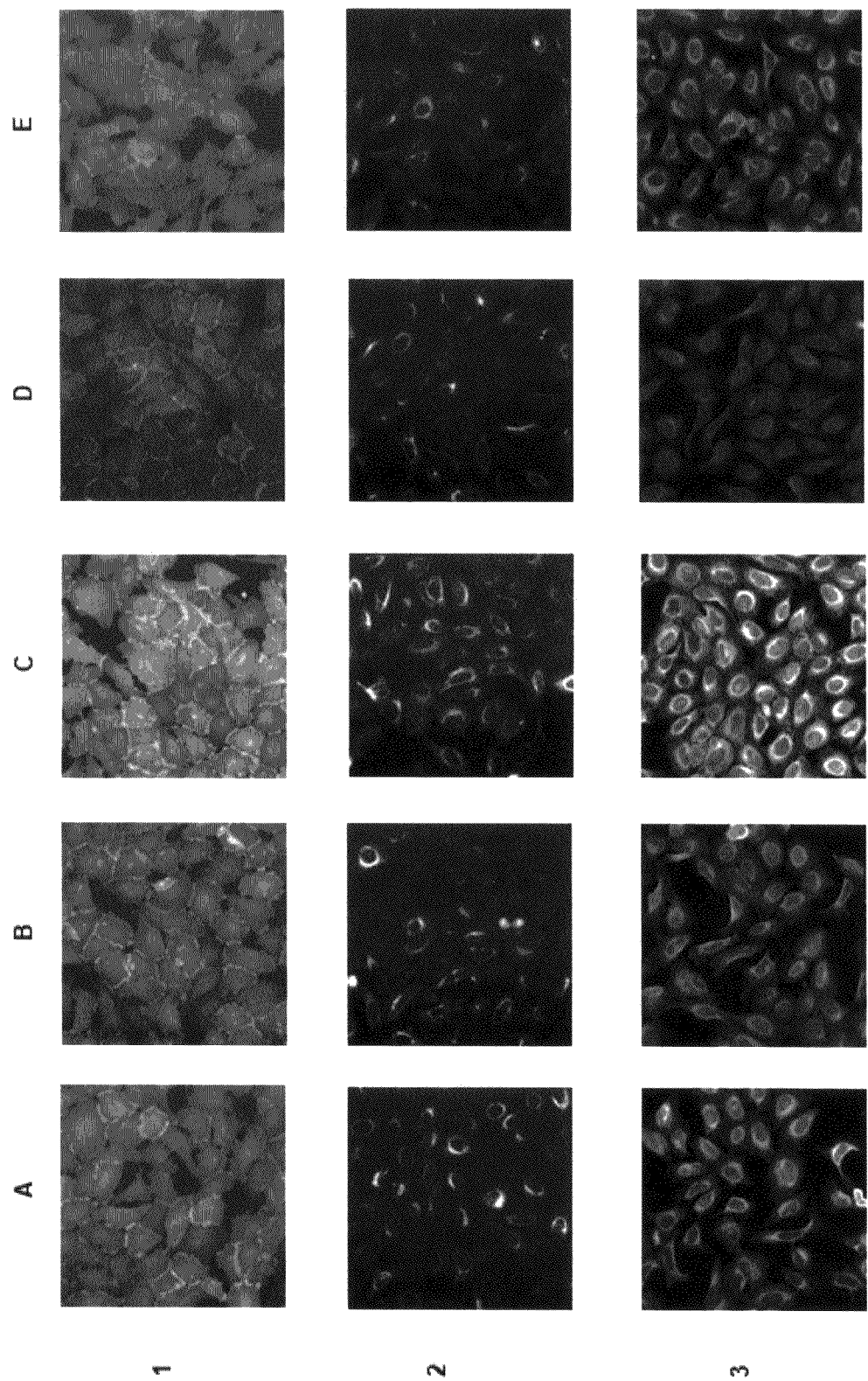

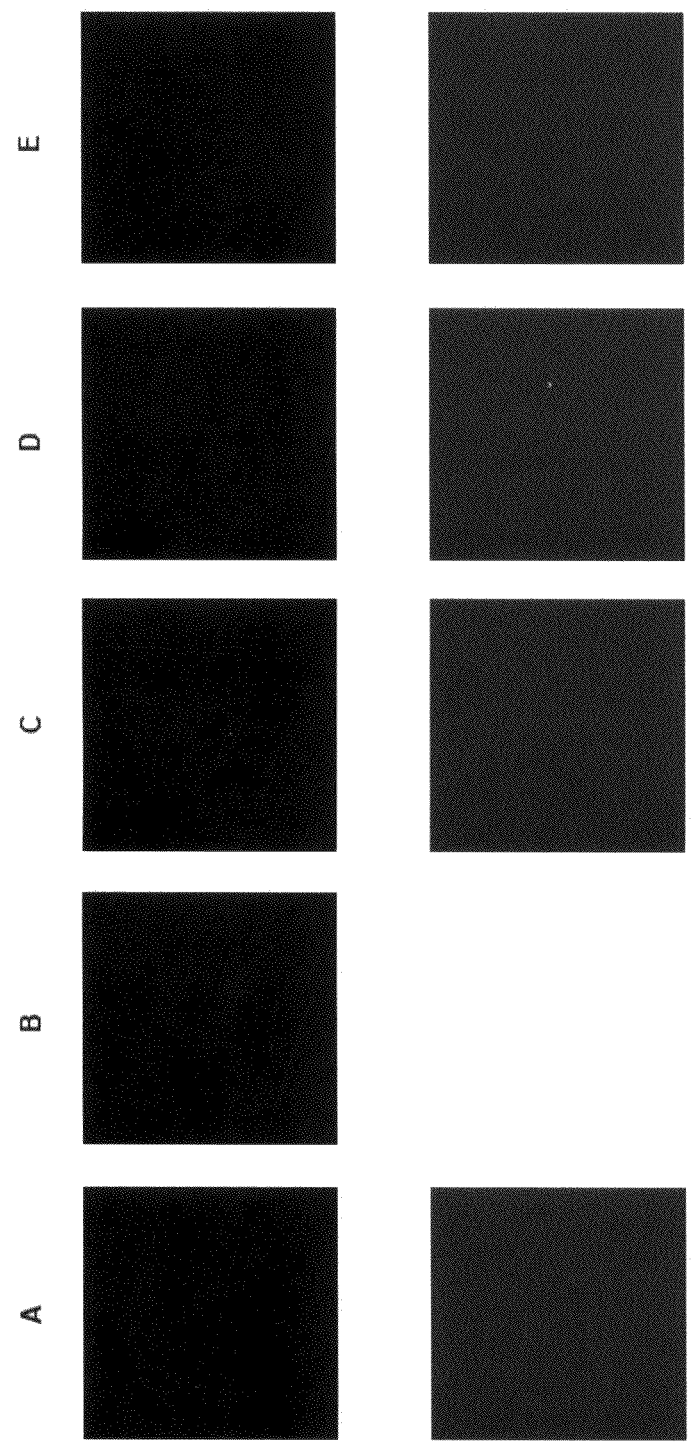

FIG. 45
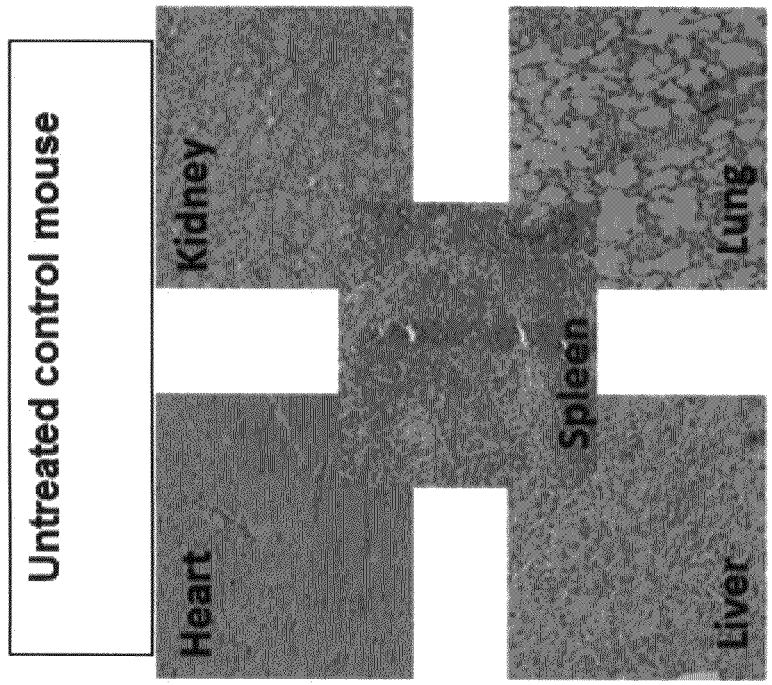
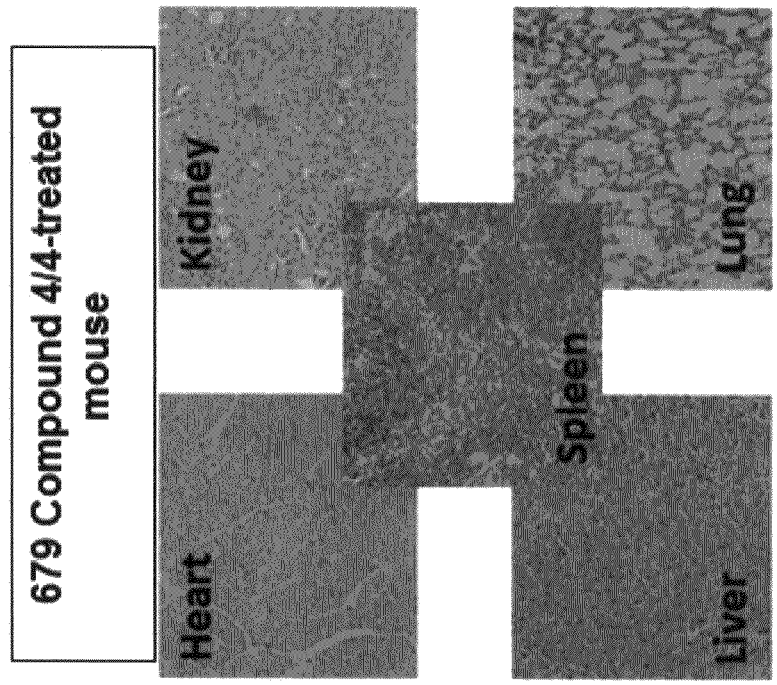

BENZOCYANINE COMPOUNDS

This application is a division of co-pending U.S. patent application Ser. No. 13/778,678 filed on Feb. 27, 2013, which claims the benefit of provisional U.S. Patent Application Ser. Nos. 61/607,737 filed Mar. 7, 2012, and 61/604,232 filed Feb. 28, 2012, each of which is expressly incorporated by reference herein in its entirety.

Compounds useful as labels with properties comparable to known fluorescent compounds are disclosed. The compounds can be conjugated to proteins and nucleic acids for biological imaging and analysis. Synthesis of the compounds, formation and use of the conjugated compounds, and specific non-limiting examples of each are disclosed.

Compounds that react with biomolecules (e.g., antigens, antibodies, DNA-segments with the corresponding complimentary species for measuring enzyme kinetics, receptor-ligand interactions, nucleic acid hybridization kinetics in vitro as well as in vivo, etc.), termed labels or dyes, are useful for, e.g., pharmacological characterization of receptors and drugs, binding data, etc. Compounds such as xanthylium salts (U.S. Pat. No. 5,846,737) and/or cyanines (U.S. Pat. No. 5,627,027) are used for such applications, but aggregate and form dimers, especially in aqueous solution, due to planarity of their π-system. Compounds that have insufficient hydrophilicity undergo non-specific interactions with various surfaces, resulting in problems when attempting to purify the corresponding conjugate, and an unsatisfactory signal to noise ratio.

Efforts are directed to reducing undesirable properties by introducing substituents that increase the hydrophilicity of the compounds. For example, sulfonic acid function substituents have been introduced into the cyanine chromophore. U.S. Pat. No. 6,083,485 (Licha) and U.S. Pat. Nos. 6,977,305 and 6,974,873 (Molecular Probes) disclose cyanine compounds having one of the common methyl groups in the 3-position of the terminal indole heterocycle substituted by an ω-carboxyalkyl function, and in which the previously present (e.g. in Cy3 or Cy5) N-alkyl or N-ω-carboxyalkyl functions are replaced by N-ω-alkyl sulfonic acid functions. WO 05/044923 discloses cyanine compounds having the common methyl substituent in the 3-position of the terminal indole heterocycle substituted by a N-ω-alkyl sulfonic acid function. In these publications, cyanine compounds having more than two sulfonic acid function substituents exhibited higher solubility and correspondingly a lower tendency to dimer formation, in comparison to cyanine compounds (Cy3, Cy5) described in U.S. Pat. No. 5,627,027.

The disclosed benzocyanine compounds are useful as labels in optical, e.g., fluorescence optical, determination and detection methods. The compounds have high hydrophilicity, high molar absorbance, high photo-stability, and high storage stability. These compounds were excited by monochromatic (e.g., lasers, laser diodes) or polychromatic (e.g., white light sources) light in the ultraviolet (UV), visible, and near infrared (NIR) spectral region to generate emission of fluorescence light.

Typical application methods are based on the reaction of the compounds with biomolecules, e.g., proteins (e.g., antigens, antibodies, etc.), DNA and/or RNA segments, etc. with the corresponding complimentary species. Thus, among other embodiments, the compounds are used to measure enzyme kinetics, receptor-ligand interactions, and nucleic acid hybridization kinetics in vitro and/or in vivo. The compounds are used for the pharmacological characterization of receptors and/or drugs. Applications include, but are not limited to, uses in medicine, pharmacy, biological sciences, materials sciences, environmental control, detection of organic and inorganic micro samples occurring in nature, etc.

The following nomenclature is used to describe embodiments of the compounds.

For compounds having at least one ethylene glycol, diethylene glycol, or (poly)ethylene glycol, collectively PEGs, on N, the following nomenclature is used, noting that the first compound is explained in detail, and all other compounds follow this same nomenclature format: 579 Compound 1 ((ethylene glycol) is a 579 compound, 1 is the length of the ethylene glycol)); 579 Compound 2 (diethylene glycol); 579 Compound 3 ((poly)ethylene glycol (3)); 579 Compound 4 ((poly)ethylene glycol (4)); 579 Compound 5 ((poly)ethylene glycol (5)); 579 Compound 6 ((poly)ethylene glycol (6)); 679 Compound 1 (ethylene glycol); 679 Compound 2 (diethylene glycol); 679 Compound 3 ((poly)ethylene glycol (3)); 679 Compound 4 ((poly)ethylene glycol (4)); 679 Compound 5 ((poly)ethylene glycol (5)); 679 Compound 6 ((poly)ethylene glycol (6)); 779 Compound 1 (ethylene glycol); 779 Compound 2 (diethylene glycol); 779 Compound 3 ((poly)ethylene glycol (3)); 779 Compound 4 ((poly)ethylene glycol (4)); 779 Compound 5 ((poly)ethylene glycol (5)); 779 Compound 6 ((poly)ethylene glycol (6)).

For compounds having either (a) no ethylene glycol, diethylene glycol, or (poly)ethylene glycol, collectively PEGs, on N, or (b) multiple PEGs at any substituent position on the compound, the following nomenclature is used: 550 Compound 0/X, 550 Compound 1/X, 550 Compound 2/X, 550 Compound 3/X, 550 Compound 4/X, 550 Compound 5/X, 550 Compound 6/X, 650 Compound 0/X, 650 Compound 1/X, 650 Compound 2/X, 650 Compound 3/X, 650 Compound 4/X, 650 Compound 5/X, 650 Compound 6/X, 755 Compound 0/X, 755 Compound 1/X, 755 Compound 2/X, 755 Compound 3/X, 755 Compound 4/X, 755 Compound 5/X, 755 Compound 6/X, where 550, 650, and 755 Compounds comprise a polymethine chain of 3 carbon, 5 carbon, and 7 carbon atoms, respectively; the first number is the length of a ethylene glycol, diethylene glycol, or (poly)ethylene glycol (collectively referred to herein as PEG) on an indole N, e.g. 0 is no PEG on an indole N, 1 is ethylene glycol ($PEG_1$) on an indole N, 2 is diethylene glycol ($PEG_2$) on an indole N, 3 is (poly)ethylene glycol (poly=3, $PEG_3$) on an indole N, 4 is (poly)ethylene glycol (poly=4, $PEG_4$) on an indole N, 5 is (poly)ethylene glycol (poly=5, $PEG_5$) on an indole N, and 6 is (poly)ethylene glycol (poly=6, $PEG_6$) on an indole N; and X is the total number of PEG groups on the compound. For example, 650 Compound 4/4 contains $PEG_4$ on an indole N and a total of four PEG groups on the compound.

In one embodiment, the benzocyanine compounds have, in an N-position of one heterocycle, an ethylene glycol group or an ethylene glycol polymer (i.e., poly(ethylene) glycol, collectively abbreviated PEG), and the other heterocycle has, in an N-position, a function for conjugating the compound to a biomolecule. In one embodiment, the benzocyanine compound has, in any position of the compound, at least one sulfo ($SO_3^-$) and/or sulfoalkyl group. In one embodiment, the benzocyanine compound has, in any position of the compound, a sulfonamide and/or carboxamide group comprising an ethylene glycol group or an ethylene glycol polymer (i.e., poly(ethylene) glycol, collectively abbreviated PEG), either directly or indirectly attached to the compound. Indirect attachment indicates use of a linker, direct attachment indicates lack of such a linker. A linker can be any moiety.

In one embodiment, the benzocyanine compounds have, in an N-position of one heterocycle, an ethylene glycol group or an ethylene glycol polymer (i.e., poly(ethylene) glycol, collectively abbreviated PEG), and the other heterocycle has, at N, an ethylene glycol group or an ethylene glycol polymer (i.e., poly(ethylene) glycol, collectively abbreviated PEG) and a function for conjugating the compound to a biomolecule. In one embodiment, the benzocyanine compounds have an ethylene glycol group or an ethylene glycol polymer (i.e., poly(ethylene) glycol, collectively abbreviated PEG) in another position of the benzocyanine compound. In one embodiment, the benzocyanine compound has, in any position of the compound, at least one sulfo and/or sulfoalkyl group. In one embodiment, the benzocyanine compound has, in any position of the compound, a sulfonamide and/or carboxamide group comprising an ethylene glycol group or an ethylene glycol polymer (i.e., poly(ethylene) glycol, collectively abbreviated PEG), either directly or indirectly attached to the compound.

In one embodiment, the benzocyanine compounds have, at N of one heterocycle, an alkyl group, and the other heterocycle has, at N, a function for conjugating the compound to a biomolecule, and an ethylene glycol group or an ethylene glycol polymer (i.e., poly(ethylene) glycol, abbreviated PEG) in another position of the benzocyanine compound. In one embodiment, the benzocyanine compound has, in any position of the compound, at least one sulfo and/or sulfoalkyl group. In one embodiment, the benzocyanine compound has, in any position of the compound, a sulfonamide and/or carboxamide group comprising an ethylene glycol group or an ethylene glycol polymer (i.e., poly(ethylene) glycol, abbreviated PEG), either directly or indirectly attached to the compound. Indirect attachment indicates use of a linker, direct attachment indicates lack of such a linker. A linker can be any moiety.

BRIEF DESCRIPTION OF THE DRAWINGS

FIG. 16 tabulates functional fluorescence plate assay results with some commercial dyes and inventive compounds in one embodiment.

FIG. 18 tabulates functional fluorescence plate assay results with some commercial dyes and inventive compounds in one embodiment.

FIG. 28 shows immunofluorescence data with commercial dyes and inventive compounds in one embodiment.

FIG. 30A shows immunofluorescence data with commercial dyes and inventive compounds in one embodiment.

FIG. 31A shows immunofluorescence data with commercial dyes and inventive compounds in one embodiment. FIG. 31B shows immunofluorescence data with commercial dyes and inventive compounds in one embodiment.

FIG. 45 shows toxicity during in vivo imaging with commercial dyes and inventive compounds in one embodiment.

Figure 1:
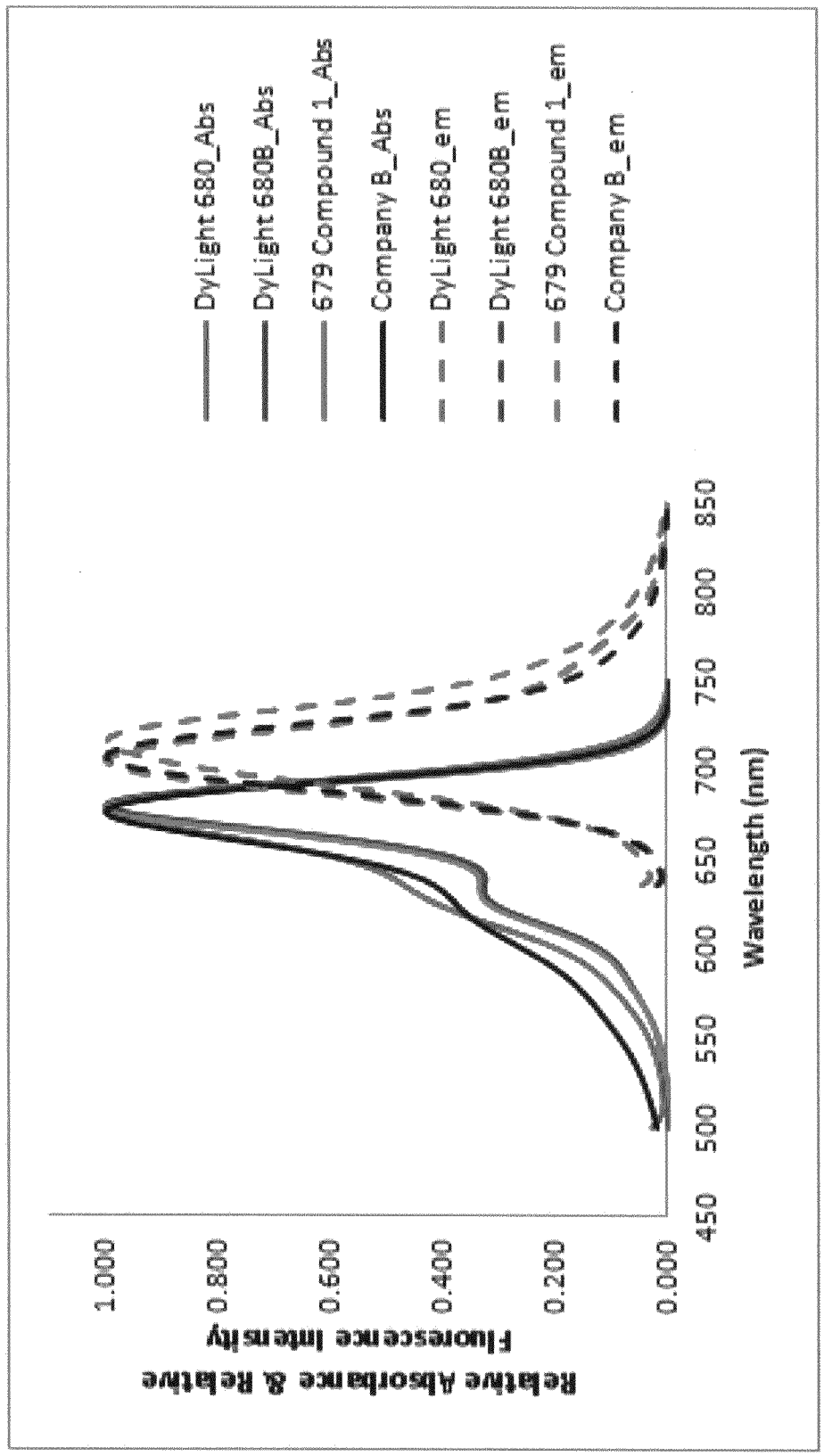
FIG. 1 shows absorption/emission profiles of some inventive compounds and commercial dyes.

Unless otherwise noted, reference to general formulas (e.g., I, II, III, IV, V, and VI, each subsequently described), encompasses their respective a, b, c, etc. structures.

In one embodiment, the compound is general formula Ia with "a" indicating the right N chain terminates in COX:

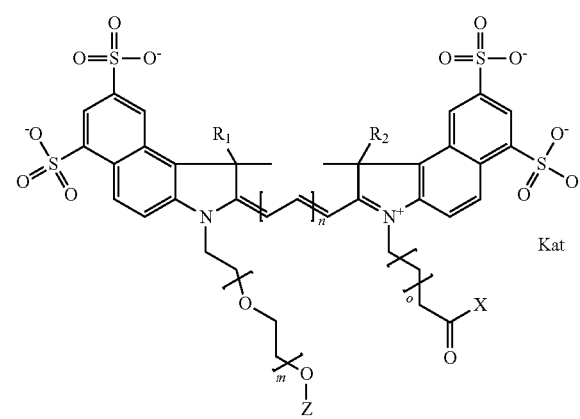

or general formula Ib with "b" indicating the right N chain terminates in OH:

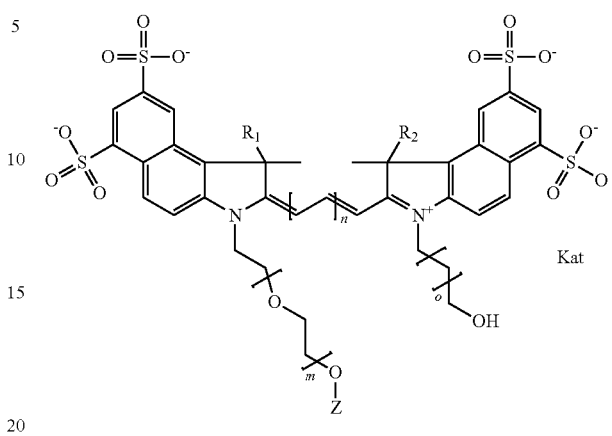

or general formula Ic with "c" indicating ethylene, diethylene, or (poly)ethylene glycol is not required on the left N:

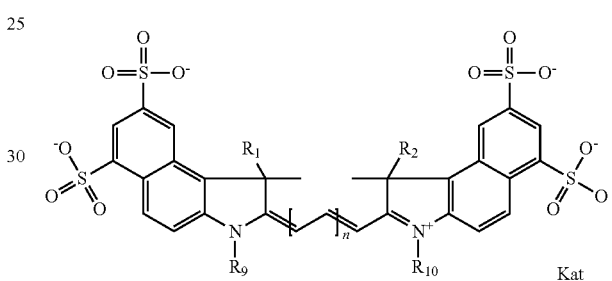

where each of $R^1$ and $R^2$ is the same or different and is independently selected from the group consisting of an aliphatic, heteroaliphatic, sulfoalkyl group, heteroaliphatic with terminal $SO_3$, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-$SO_2$NH—P—Z, and a carboxamide group -L-CONH—P—Z, and Z is selected from H, a $CH_3$, a $CH_3$ group, an alkyl group, a heteroalkyl group, or —CO—NHS; each of $R^9$ and $R^{10}$ is the same or different and is independently selected from the group consisting of an alkyl, a sulfoalkyl, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a PEG group P-L-X, L-Z, L-X; X is selected from the group consisting of —OH, —SH, —$NH_2$, —NH—$NH_2$, —F, —Cl, —Br, I, —NHS hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—$CH_2$—, imidazole, azide, —NR-L-O—$NH_2$, and —NR-L-O—CO—NHS, where R is —H or an aliphatic or heteroaliphatic group, and L is selected from the group consisting of a divalent linear (—$(CH_2)_t$—, t=0 to 15), crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive. In one embodiment, at least one of $R^1$ and $R^2$ contains a PEG group.

In one embodiment, one of R9 and R10 is a C1-C6 alkyl, or a C1-C6 alkyl substituted once by hydroxyl, sulfo, carboxy, or amino, and the other of R9 and R10 is an alkyl terminating in reactive group. In one embodiment, the reactive group is selected from X or Z, as defined above.

In one embodiment, the PEG group P is selected from the group consisting of —C—C—O—C(ethylene glycol with terminal methyl), —C—C—O—C—C—O—C(diethylene glycol with terminal methyl), —C—C—O—C—C—O—C—C—O—C((poly)ethylene glycol (3) with terminal methyl), —C—C—O—C—C—O—C—C—O—C—C—O—C((poly)ethylene glycol (4) with terminal methyl), —C—C—O—C—C—O—C—C—O—C—C—O—C—C—O—C((poly)ethylene glycol (5) with terminal methyl), and C—C—O—C—C—O—C—C—O—C—C—O—C—C—O—C—C—O—C((poly)ethylene glycol (6) with terminal methyl). In one embodiment, the PEG group P may be either uncapped, e.g., lack a terminal methyl, or may be capped with an atom or group other than a methyl. In one embodiment, the PEG group P terminates with a Z group, where Z is selected from H, $CH_3$, a $CH_3$ group, an alkyl group, or a heteroalkyl group.

In one embodiment, the compound is general formula Ia or general formula Ib, collectively referred to as general formula I, where R1 is methyl and R2 is sulfoalkyl; X is —OH, —NHS, —O-TFP, or —NR-L-maleimide; m is 0; o is 3; and n is 1. In one embodiment, the compound is general formula I, where R1 is methyl and R2 is sulfoalkyl; X is —OH, —NHS, —O-TFP, or —NR-L-maleimide; m is 1; o is 3; and n is 1. In one embodiment, the compound is general formula I, where R1 is methyl and R2 is sulfoalkyl; X is —OH, —NHS, —O-TFP, or —NR-L-maleimide; m is 2; o is 3; and n is 1. In one embodiment, the compound is general formula I, where R1 is methyl and R2 is sulfoalkyl; X is —OH, —NHS, —O-TFP, or —NR-L-maleimide; m is 3; o is 3; and n is 1. In one embodiment, the compound is general formula I, where R1 is methyl and R2 is sulfoalkyl; X is —OH, —NHS, —O-TFP, or —NR-L-maleimide; m is 4; o is 3; and n is 1. In one embodiment, the compound is general formula I, where R1 is methyl and R2 is sulfoalkyl; X is —OH, —NHS, —O-TFP, or —NR-L-maleimide; m is 5; o is 3; and n is 1.

In one embodiment, the compound is general formula I, where R1 is methyl and R2 is sulfoalkyl; X is —OH, —NHS, —O-TFP, or —NR-L-maleimide; m is 0; o is 3; and n is 2. In one embodiment, the compound is general formula I, where R1 is methyl and R2 is sulfoalkyl; X is —OH, —NHS, —O-TFP, or —NR-L-maleimide; m is 1; o is 3; and n is 2. In one embodiment, the compound is general formula I, where R1 is methyl and R2 is sulfoalkyl; X is —OH, —NHS, —O-TFP, or —NR-L-maleimide; m is 2; o is 3; and n is 2. In one embodiment, the compound is general formula I, where R1 is methyl and R2 is sulfoalkyl; X is —OH, —NHS, —O-TFP, or —NR-L-maleimide; m is 3; o is 3; and n is 2. In one embodiment, the compound is general formula I, where R1 is methyl and R2 is sulfoalkyl; X is —OH, —NHS, —O-TFP, or —NR-L-maleimide; m is 4; o is 3; and n is 2. In one embodiment, the compound is general formula I, where R1 is methyl and R2 is sulfoalkyl; X is —OH, —NHS, —O-TFP, or —NR-L-maleimide; m is 5; o is 3; and n is 2.

In one embodiment, the compound is general formula I, where R1 is methyl and R2 is sulfoalkyl; X is —OH, —NHS, —O-TFP, or —NR-L-maleimide; m is 0; o is 3; and n is 3. In one embodiment, the compound is general formula I, where R1 is methyl and R2 is sulfoalkyl; X is —OH, —NHS, —O-TFP, or —NR-L-maleimide; m is 1; o is 3; and n is 3. In one embodiment, the compound is general formula I, where R1 is methyl and R2 is sulfoalkyl; X is —OH, —NHS, —O-TFP, or —NR-L-maleimide; m is 2; o is 3; and n is 3. In one embodiment, the compound is general formula I, where R1 is methyl and R2 is sulfoalkyl; X is —OH, —NHS, —O-TFP, or —NR-L-maleimide; m is 3; o is 3; and n is 3. In one embodiment, the compound is general formula I, where R1 is methyl and R2 is sulfoalkyl; X is —OH, —NHS, —O-TFP, or —NR-L-maleimide; m is 4; o is 3; and n is 3. In one embodiment, the compound is general formula I, where R1 is methyl and R2 is sulfoalkyl; X is —OH, —NHS, —O-TFP, or —NR-L-maleimide; m is 5; o is 3; and n is 3.

In one embodiment, the compound is general formula I, where R1 is sulfoalkyl and R2 is a PEG group; X is —OH, —NHS, —O-TFP, or —NR-L-maleimide; m is 0; o is 3; and n is 1. In one embodiment, the compound is general formula I, where R1 is sulfoalkyl and R2 is a PEG group; X is —OH, —NHS, —O-TFP, or —NR-L-maleimide; m is 1; o is 3; and n is 1. In one embodiment, the compound is general formula I, where R1 is sulfoalkyl and R2 is a PEG group; X is —OH, —NHS, —O-TFP, or —NR-L-maleimide; m is 2; o is 3; and n is 1. In one embodiment, the compound is general formula I, where R1 is sulfoalkyl and R2 is a PEG group; X is —OH, —NHS, —O-TFP, or —NR-L-maleimide; m is 3; o is 3; and n is 1. In one embodiment, the compound is general formula I, where R1 is sulfoalkyl and R2 is a PEG group; X is —OH, —NHS, —O-TFP, or —NR-L-maleimide; m is 4; o is 3; and n is 1. In one embodiment, the compound is general formula I, where R1 is sulfoalkyl and R2 is a PEG group; X is —OH, —NHS, —O-TFP, or —NR-L-maleimide; m is 5; o is 3; and n is 1.

In one embodiment, the compound is general formula I, where R1 is sulfoalkyl and R2 is a PEG group; X is —OH, —NHS, —O-TFP, or —NR-L-maleimide; m is 0; o is 3; and n is 2. In one embodiment, the compound is general formula I, where R1 is sulfoalkyl and R2 is a PEG group; X is —OH, —NHS, —O-TFP, or —NR-L-maleimide; m is 1; o is 3; and n is 2. In one embodiment, the compound is general formula I, where R1 is sulfoalkyl and R2 is a PEG group; X is —OH, —NHS, —O-TFP, or —NR-L-maleimide; m is 2; o is 3; and n is 2. In one embodiment, the compound is general formula I, where R1 is sulfoalkyl and R2 is a PEG group; X is —OH, —NHS, —O-TFP, or —NR-L-maleimide; m is 3; o is 3; and n is 2. In one embodiment, the compound is general formula I, where R1 is sulfoalkyl and R2 is a PEG group; X is —OH, —NHS, —O-TFP, or —NR-L-maleimide; m is 4; o is 3; and n is 2. In one embodiment, the compound is general formula I, where R1 is sulfoalkyl and R2 is a PEG group; X is —OH, —NHS, —O-TFP, or —NR-L-maleimide; m is 5; o is 3; and n is 2.

In one embodiment, the compound is general formula I, where R1 is sulfoalkyl and R2 is a PEG group; X is —OH, —NHS, —O-TFP, or —NR-L-maleimide; m is 0; o is 3; and n is 3. In one embodiment, the compound is general formula I, where R1 is sulfoalkyl and R2 is a PEG group; X is —OH, —NHS, —O-TFP, or —NR-L-maleimide; m is 1; o is 3; and n is 3. In one embodiment, the compound is general formula I, where R1 is sulfoalkyl and R2 is a PEG group; X is —OH, —NHS, —O-TFP, or —NR-L-maleimide; m is 2; o is 3; and n is 3. In one embodiment, the compound is general formula I, where R1 is sulfoalkyl and R2 is a PEG group; X is —OH, —NHS, —O-TFP, or —NR-L-maleimide; m is 3; o is 3; and n is 3. In one embodiment, the compound is general formula I, where R1 is sulfoalkyl and R2 is a PEG group; X is —OH, —NHS, —O-TFP, or —NR-L-maleimide; m is 4; o is 3; and n is 3. In one embodiment, the compound is general formula I, where R1 is sulfoalkyl and R2 is a PEG group; X is —OH, —NHS, —O-TFP, or —NR-L-maleimide; m is 5; o is 3; and n is 3.

In one embodiment, the compound is general formula I, where R1 is methyl and R2 is a PEG group; X is —OH, —NHS, —O-TFP, or —NR-L-maleimide; m is 0; o is 3; and n is 1. In one embodiment, the compound is general formula I, where R1 is methyl and R2 is a PEG group; X is —OH, —NHS, —O-TFP, or —NR-L-maleimide; m is 1; o is 3; and n is 1. In one embodiment, the compound is general formula I, where R1 is methyl and R2 is a PEG group; X is —OH, —NHS, —O-TFP, or —NR-L-maleimide; m is 2; o is 3; and n is 1. In one embodiment, the compound is general formula I, where R1 is methyl and R2 is a PEG group; X is —OH, —NHS, —O-TFP, or —NR-L-maleimide; m is 3; o is 3; and n is 1. In one embodiment, the compound is general formula I, where R1 is methyl and R2 is a PEG group; X is —OH, —NHS, —O-TFP, or —NR-L-maleimide; m is 4; o is 3; and n is 1. In one embodiment, the compound is general formula I, where R1 is methyl and R2 is a PEG group; X is —OH, —NHS, —O-TFP, or —NR-L-maleimide; m is 5; o is 3; and n is 1.

In one embodiment, the compound is general formula I, where R1 is methyl and R2 is a PEG group; X is —OH, —NHS, —O-TFP, or —NR-L-maleimide; m is 0; o is 3; and n is 2. In one embodiment, the compound is general formula I, where R1 is methyl and R2 is a PEG group; X is —OH, —NHS, —O-TFP, or —NR-L-maleimide; m is 1; o is 3; and n is 2. In one embodiment, the compound is general formula I, where R1 is methyl and R2 is a PEG group; X is —OH, —NHS, —O-TFP, or —NR-L-maleimide; m is 2; o is 3; and n is 2. In one embodiment, the compound is general formula I, where R1 is methyl and R2 is a PEG group; X is —OH, —NHS, —O-TFP, or —NR-L-maleimide; m is 3; o is 3; and n is 2. In one embodiment, the compound is general formula I, where R1 is methyl and R2 is a PEG group; X is —OH, —NHS, —O-TFP, or —NR-L-maleimide; m is 4; o is 3; and n is 2. In one embodiment, the compound is general formula I, where R1 is methyl and R2 is a PEG group; X is —OH, —NHS, —O-TFP, or —NR-L-maleimide; m is 5; o is 3; and n is 2.

In one embodiment, the compound is general formula I, where R1 is methyl and R2 is a PEG group; X is —OH, —NHS, —O-TFP, or —NR-L-maleimide; m is 0; o is 3; and n is 3. In one embodiment, the compound is general formula I, where R1 is methyl and R2 is a PEG group; X is —OH, —NHS, —O-TFP, or —NR-L-maleimide; m is 1; o is 3; and n is 3. In one embodiment, the compound is general formula I, where R1 is methyl and R2 is a PEG group; X is —OH, —NHS, —O-TFP, or —NR-L-maleimide; m is 2; o is 3; and n is 3. In one embodiment, the compound is general formula I, where R1 is methyl and R2 is a PEG group; X is —OH, —NHS, —O-TFP, or —NR-L-maleimide; m is 3; o is 3; and n is 3. In one embodiment, the compound is general formula I, where R1 is methyl and R2 is a PEG group; X is —OH, —NHS, —O-TFP, or —NR-L-maleimide; m is 4; o is 3; and n is 3. In one embodiment, the compound is general formula I, where R1 is methyl and R2 is a PEG group; X is —OH, —NHS, —O-TFP, or —NR-L-maleimide; m is 5; o is 3; and n is 3.

In one embodiment, the compound is general formula I, where each of R1 and R2 is a PEG group; X is —OH, —NHS, —O-TFP, or —NR-L-maleimide; m is 0; o is 3; and n is 1. In one embodiment, the compound is general formula I, where each of R1 and R2 is a PEG group; X is —OH, —NHS, —O-TFP, or —NR-L-maleimide; m is 1; o is 3; and n is 1. In one embodiment, the compound is general formula I, where each of R1 and R2 is a PEG group; X is —OH, —NHS, —O-TFP, or —NR-L-maleimide; m is 2; o is 3; and n is 1. In one embodiment, the compound is general formula I, where each of R1 and R2 is a PEG group; X is —OH, —NHS, —O-TFP, or —NR-L-maleimide; m is 3; o is 3; and n is 1. In one embodiment, the compound is general formula I, where each of R1 and R2 is a PEG group; X is —OH, —NHS, —O-TFP, or —NR-L-maleimide; m is 4; o is 3; and n is 1. In one embodiment, the compound is general formula I, where each of R1 and R2 is a PEG group; X is —OH, —NHS, —O-TFP, or —NR-L-maleimide; m is 5; o is 3; and n is 1.

In one embodiment, the compound is general formula I, where each of R1 and R2 is a PEG group; X is —OH, —NHS, —O-TFP, or —NR-L-maleimide; m is 0; o is 3; and n is 2. In one embodiment, the compound is general formula I, where each of R1 and R2 is a PEG group; X is —OH, —NHS, —O-TFP, or —NR-L-maleimide; m is 1; o is 3; and n is 2. In one embodiment, the compound is general formula I, where each of R1 and R2 is a PEG group; X is —OH, —NHS, —O-TFP, or —NR-L-maleimide; m is 2; o is 3; and n is 2. In one embodiment, the compound is general formula I, where each of R1 and R2 is a PEG group; X is —OH, —NHS, —O-TFP, or —NR-L-maleimide; m is 3; o is 3; and n is 2. In one embodiment, the compound is general formula I, where each of R1 and R2 is a PEG group; X is —OH, —NHS, —O-TFP, or —NR-L-maleimide; m is 4; o is 3; and n is 2. In one embodiment, the compound is general formula I, where each of R1 and R2 is a PEG group; X is —OH, —NHS, —O-TFP, or —NR-L-maleimide; m is 5; o is 3; and n is 2.

In one embodiment, the compound is general formula I, where each of R1 and R2 is a PEG group; X is —OH, —NHS, —O-TFP, or —NR-L-maleimide; m is 0; o is 3; and n is 3. In one embodiment, the compound is general formula I, where each of R1 and R2 is a PEG group; X is —OH, —NHS, —O-TFP, or —NR-L-maleimide; m is 1; o is 3; and n is 3. In one embodiment, the compound is general formula I, where each of R1 and R2 is a PEG group; X is —OH, —NHS, —O-TFP, or —NR-L-maleimide; m is 2; o is 3; and n is 3. In one embodiment, the compound is general formula I, where each of R1 and R2 is a PEG group; X is —OH, —NHS, —O-TFP, or —NR-L-maleimide; m is 3; o is 3; and n is 3. In one embodiment, the compound is general formula I, where each of R1 and R2 is a PEG group; X is —OH, —NHS, —O-TFP, or —NR-L-maleimide; m is 4; o is 3; and n is 3. In one embodiment, the compound is general formula I, where each of R1 and R2 is a PEG group; X is —OH, —NHS, —O-TFP, or —NR-L-maleimide; m is 5; o is 3; and n is 3.

In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 0; o is 3; and n is 1. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 1; o is 3; and n is 1. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 2; o is 3; and n is 1. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 3; o is 3; and n is 1. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 4; o is 3; and n is 1. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 5; o is 3; and n is 1.

In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 0; o is 3; and n is 2. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 1; o is 3; and n is 2. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 2; o is 3; and n is 2. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 3; o is 3; and n is 2. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 4; o is 3; and n is 2. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 5; o is 3; and n is 2.

In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 0; o is 3; and n is 3. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 1; o is 3; and n is 3. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 2; o is 3; and n is 3. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 3; o is 3; and n is 3. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 4; o is 3; and n is 3. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 5; o is 3; and n is 3.

In one embodiment, the compound is general formula Ic, where R1 is sulfoalkyl and R2 is a PEG group P—Z where P is an ethylene glycol group, and Z is CH$_3$; R9 is an alkyl; R10 is an alkyl terminating in —OH, —COOH, —NHS, —O-TFP, or —NR-L-maleimide; and n is 1. In one embodiment, the compound is general formula Ic, where R1 is sulfoalkyl and R2 is a PEG group P—Z where P is a diethylene glycol group, and Z is CH$_3$; R9 is an alkyl; R10 is an alkyl terminating in —OH, —COOH, —NHS, —O-TFP, or —NR-L-maleimide; and n is 1. In one embodiment, the compound is general formula Ic, where R1 is sulfoalkyl and R2 is a PEG group P—Z where P is a (poly)ethylene glycol group, where the (poly)ethylene glycol group is (CH$_2$CH$_2$O)$_s$, where s is 3, and Z is CH$_3$; R9 is an alkyl; R10 is an alkyl terminating in —OH, —COOH, —NHS, —O-TFP, or —NR-L-maleimide; and n is 1. In one embodiment, the compound is general formula Ic, where R1 is sulfoalkyl and R2 is a PEG group P—Z where P is a (poly)ethylene glycol group, where the (poly)ethylene glycol group is (CH$_2$CH$_2$O)$_s$, where s is 4, and Z is CH$_3$; R9 is an alkyl; R10 is an alkyl terminating in —OH, —COOH, —NHS, —O-TFP, or —NR-L-maleimide; and n is 1. In one embodiment, the compound is general formula Ic, where R1 is sulfoalkyl and R2 is a PEG group P—Z where P is a (poly)ethylene glycol group, where the (poly)ethylene glycol group is (CH$_2$CH$_2$O)$_s$, where s is 5, and Z is CH$_3$; R9 is an alkyl; R10 is an alkyl terminating in —OH, —COOH, —NHS, —O-TFP, or —NR-L-maleimide; and n is 1. In one embodiment, the compound is general formula Ic, where R1 is sulfoalkyl and R2 is a PEG group P—Z where P is a (poly)ethylene glycol group, where the (poly)ethylene glycol group is (CH$_2$CH$_2$O)$_s$, where s is 6, and Z is CH$_3$; R9 is an alkyl; R10 is an alkyl terminating in —OH, —COOH, —NHS, —O-TFP, or —NR-L-maleimide; and n is 1. In one embodiment, the alkyl of R9 is ethyl, the alkyl of R10 is pentyl, and R1 is sulfopentyl or sulfopropyl.

In one embodiment, the compound is general formula Ic, where R1 is sulfoalkyl and R2 is a PEG group P—Z where P is an ethylene glycol group, and Z is CH$_3$; R9 is an alkyl; R10 is an alkyl terminating in —OH, —COOH, —NHS, —O-TFP, or —NR-L-maleimide; and n is 2. In one embodiment, the compound is general formula Ic, where R1 is sulfoalkyl and R2 is a PEG group P—Z where P is a diethylene glycol group, and Z is CH$_3$; R9 is an alkyl; R10 is an alkyl terminating in —OH, —COOH, —NHS, —O-TFP, or —NR-L-maleimide; and n is 2. In one embodiment, the compound is general formula Ic, where R1 is sulfoalkyl and R2 is a PEG group P—Z where P is a (poly)ethylene glycol group, where the (poly)ethylene glycol group is (CH$_2$CH$_2$O)$_s$, where s is 3, and Z is CH$_3$; R9 is an alkyl; R10 is an alkyl terminating in —OH, —COOH, —NHS, —O-TFP, or —NR-L-maleimide; and n is 2. In one embodiment, the compound is general formula Ic, where R1 is sulfoalkyl and R2 is a PEG group P—Z where P is a (poly)ethylene glycol group, where the (poly)ethylene glycol group is (CH$_2$CH$_2$O)$_s$, where s is 4, and Z is CH$_3$; R9 is an alkyl; R10 is an alkyl terminating in —OH, —COOH, —NHS, —O-TFP, or —NR-L-maleimide; and n is 2. In one embodiment, the compound is general formula Ic, where R1 is sulfoalkyl and R2 is a PEG group P—Z where P is a (poly)ethylene glycol group, where the (poly)ethylene glycol group is (CH$_2$CH$_2$O)$_s$, where s is 5, and Z is CH$_3$; R9 is an alkyl; R10 is an alkyl terminating in —OH, —COOH, —NHS, —O-TFP, or —NR-L-maleimide; and n is 2. In one embodiment, the compound is general formula Ic, where R1 is sulfoalkyl and R2 is a PEG group P—Z where P is a (poly)ethylene glycol group, where the (poly)ethylene glycol group is (CH$_2$CH$_2$O)$_s$, where s is 6, and Z is CH$_3$; R9 is an alkyl; R10 is an alkyl terminating in —OH, —COOH, —NHS, —O-TFP, or —NR-L-maleimide; and n is 2. In one embodiment, the alkyl of R9 is ethyl, the alkyl of R10 is pentyl, and R1 is sulfopentyl or sulfopropyl.

In one embodiment, the compound is general formula Ic, where R1 is sulfoalkyl and R2 is a PEG group P—Z where P is an ethylene glycol group, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R1 is sulfoalkyl and R2 is a PEG group P—Z where P is a diethylene glycol group, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R1 is sulfoalkyl and R2 is a PEG group P—Z where P is a (poly)ethylene glycol group, where the (poly)ethylene glycol group is $(CH_2CH_2O)_s$, where s is 3, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R1 is sulfoalkyl and R2 is a PEG group P—Z where P is a (poly)ethylene glycol group, where the (poly)ethylene glycol group is $(CH_2CH_2O)_s$, where s is 4, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R1 is sulfoalkyl and R2 is a PEG group P—Z where P is a (poly)ethylene glycol group, where the (poly)ethylene glycol group is $(CH_2CH_2O)_s$, where s is 5, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R1 is sulfoalkyl and R2 is a PEG group P—Z where P is a (poly)ethylene glycol group, where the (poly)ethylene glycol group is $(CH_2CH_2O)_s$, where s is 6, and Z is $CH_3$; R9 is an alkyl; R10 is an alkyl terminating in —OH, —COOH, —NHS, —O-TFP, or —NR-L-maleimide; and n is 3. In one embodiment, the alkyl of R9 is ethyl, the alkyl of R10 is pentyl, and R1 is sulfopentyl or sulfopropyl.

In one embodiment, the compound is general formula Ic, where R2 is sulfoalkyl and R1 is a PEG group P—Z where P is an ethylene glycol group, and Z is $CH_3$; R9 is an alkyl; R10 is an alkyl terminating in —OH, —COOH, —NHS, —O-TFP, or —NR-L-maleimide; and n is 1. In one embodiment, the compound is general formula Ic, where R2 is sulfoalkyl and R1 is a PEG group P—Z where P is a diethylene glycol group, and Z is $CH_3$; R9 is an alkyl; R10 is an alkyl terminating in —OH, —COOH, —NHS, —O-TFP, or —NR-L-maleimide; and n is 1. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 3, and Z is $CH_3$; R9 is an alkyl; R10 is an alkyl terminating in —OH, —COOH, —NHS, —O-TFP, or —NR-L-maleimide; and n is 1. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 4, and Z is $CH_3$; R9 is an alkyl; R10 is an alkyl terminating in —OH, —COOH, —NHS, —O-TFP, or —NR-L-maleimide; and n is 1. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 5, and Z is $CH_3$; R9 is an alkyl; R10 is an alkyl terminating in —OH, —COOH, —NHS, —O-TFP, or —NR-L-maleimide; and n is 1. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 6, and Z is $CH_3$; R9 is an alkyl; R10 is an alkyl terminating in —OH, —COOH, —NHS, —O-TFP, or —NR-L-maleimide; and n is 1. In one embodiment, the alkyl of R9 is ethyl, the alkyl of R10 is pentyl, and R2 is sulfopentyl or sulfopropyl.

In one embodiment, the compound is general formula Ic, where R2 is sulfoalkyl and R1 is a PEG group P—Z where P is an ethylene glycol group, and Z is $CH_3$; R9 is an alkyl; R10 is an alkyl terminating in —OH, —COOH, —NHS, —O-TFP, or —NR-L-maleimide; and n is 2. In one embodiment, the compound is general formula Ic, where R2 is sulfoalkyl and R1 is a PEG group P—Z where P is a diethylene glycol group, and Z is $CH_3$; R9 is an alkyl; R10 is an alkyl terminating in —OH, —COOH, —NHS, —O-TFP, or —NR-L-maleimide; and n is 2. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 3, and Z is $CH_3$; R9 is an alkyl; R10 is an alkyl terminating in —OH, —COOH, —NHS, —O-TFP, or —NR-L-maleimide; and n is 2. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 4, and Z is $CH_3$; R9 is an alkyl; R10 is an alkyl terminating in —OH, —COOH, —NHS, —O-TFP, or —NR-L-maleimide; and n is 2. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 5, and Z is $CH_3$; R9 is an alkyl; R10 is an alkyl terminating in —OH, —COOH, —NHS, —O-TFP, or —NR-L-maleimide; and n is 2. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 6, and Z is $CH_3$; R9 is an alkyl; R10 is an alkyl terminating in —OH, —COOH, —NHS, —O-TFP, or —NR-L-maleimide; and n is 2. In one embodiment, the alkyl of R9 is ethyl, the alkyl of R10 is pentyl, and R2 is sulfopentyl or sulfopropyl.

In one embodiment, the compound is general formula Ic, where R2 is sulfoalkyl and R1 is a PEG group P—Z where P is an ethylene glycol group, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R2 is sulfoalkyl and R1 is a PEG group P—Z where P is a diethylene glycol group, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 3, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 4, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 5, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R2 is sulfoalkyl and R1 is a PEG group P—Z where P is a (poly)ethylene glycol group, where the (poly)ethylene glycol group is $(CH_2CH_2O)_s$, where s is 6, and Z is $CH_3$; R9 is an alkyl; R10 is an alkyl terminating in —OH, —COOH, —NHS, —O-TFP, or —NR-L-maleimide; and n is 3. In one embodiment, the alkyl of R9 is ethyl, the alkyl of R10 is pentyl, and R2 is sulfopentyl or sulfopropyl.

In one embodiment, the compound is general formula Ic, where R1 and R2 are a PEG group P—Z where P is an ethylene glycol group, and Z is $CH_3$; R9 is an alkyl; R10 is an alkyl terminating in —OH, —COOH, —NHS, —O-TFP, or —NR-L-maleimide; and n is 1. In one embodiment, the compound is general formula Ic, where R1 and R2 are a PEG group P—Z where P is a diethylene glycol group, and Z is $CH_3$; R9 is an alkyl; R10 is an alkyl terminating in —OH, —COOH, —NHS, —O-TFP, or —NR-L-maleimide; and n is 1. In one embodiment, the compound is general formula Ic, where R1 and R2 are a PEG group P—Z where P is a (poly)ethylene glycol group, where the (poly)ethylene glycol group is $(CH_2CH_2O)_s$, where s is 3, and Z is $CH_3$; R9 is an alkyl; R10 is an alkyl terminating in —OH, —COOH, —NHS, —O-TFP, or —NR-L-maleimide; and n is 1. In one embodiment, the compound is general formula Ic, where R1 and R2 are a PEG group P—Z where P is a (poly)ethylene glycol group, where the (poly)ethylene glycol group is $(CH_2CH_2O)_s$, where s is 4, and Z is $CH_3$; R9 is an alkyl; R10 is an alkyl terminating in —OH, —COOH, —NHS, —O-TFP, or —NR-L-maleimide; and n is 1. In one embodiment, the compound is general formula Ic, where R1 and R2 are a PEG group P—Z where P is a (poly)ethylene glycol group, where the (poly)ethylene glycol group is $(CH_2CH_2O)_s$, where s is 5, and Z is $CH_3$; R9 is an alkyl; R10 is an alkyl terminating in —OH, —COOH, —NHS, —O-TFP, or —NR-L-maleimide; and n is 1. In one embodiment, the compound is general formula Ic, where R1 and R2 are a PEG group P—Z where P is a (poly)ethylene glycol group, where the (poly)ethylene glycol group is $(CH_2CH_2O)_s$, where s is 6, and Z is $CH_3$; R9 is an alkyl; R10 is an alkyl terminating in —OH, —COOH, —NHS, —O-TFP, or —NR-L-maleimide; and n is 1. In one embodiment, the alkyl of R9 is ethyl, and the alkyl of R10 is pentyl.

In one embodiment, the compound is general formula Ic, where R1 and R2 are a PEG group P—Z where P is an ethylene glycol group, and Z is $CH_3$; R9 is an alkyl; R10 is an alkyl terminating in —OH, —COOH, —NHS, —O-TFP, or —NR-L-maleimide; and n is 2. In one embodiment, the compound is general formula Ic, where R1 and R2 are a PEG group P—Z where P is a diethylene glycol group, and Z is $CH_3$; R9 is an alkyl; R10 is an alkyl terminating in —OH, —COOH, —NHS, —O-TFP, or —NR-L-maleimide; and n is 2. In one embodiment, the compound is general formula Ic, where R1 and R2 are a PEG group P—Z where P is a (poly)ethylene glycol group, where the (poly)ethylene glycol group is $(CH_2CH_2O)_s$, where s is 3, and Z is $CH_3$; R9 is an alkyl; R10 is an alkyl terminating in —OH, —COOH, —NHS, —O-TFP, or —NR-L-maleimide; and n is 2. In one embodiment, the compound is general formula Ic, where R1 and R2 are a PEG group P—Z where P is a (poly)ethylene glycol group, where the (poly)ethylene glycol group is $(CH_2CH_2O)_s$, where s is 4, and Z is $CH_3$; R9 is an alkyl; R10 is an alkyl terminating in —OH, —COOH, —NHS, —O-TFP, or —NR-L-maleimide; and n is 2. In one embodiment, the compound is general formula Ic, where R1 and R2 are a PEG group P—Z where P is a (poly)ethylene glycol group, where the (poly)ethylene glycol group is $(CH_2CH_2O)_s$, where s is 5, and Z is $CH_3$; R9 is an alkyl; R10 is an alkyl terminating in —OH, —COOH, —NHS, —O-TFP, or —NR-L-maleimide; and n is 2. In one embodiment, the compound is general formula Ic, where R1 and R2 are a PEG group P—Z where P is a (poly)ethylene glycol group, where the (poly)ethylene glycol group is $(CH_2CH_2O)_s$, where s is 6, and Z is $CH_3$; R9 is an alkyl; R10 is an alkyl terminating in —OH, —COOH, —NHS, —O-TFP, or —NR-L-maleimide; and n is 2. In one embodiment, the alkyl of R9 is ethyl, and the alkyl of R10 is pentyl.

In one embodiment, the compound is general formula Ic, where R1 and R2 are a PEG group P—Z where P is an ethylene glycol group, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R1 and R2 are a PEG group P—Z where P is a diethylene glycol group, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R1 and R2 are a PEG group P—Z where P is a (poly)ethylene glycol group, where the (poly)ethylene glycol group is $(CH_2CH_2O)_s$, where s is 3, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R1 and R2 are a PEG group P—Z where P is a (poly)ethylene glycol group, where the (poly)ethylene glycol group is $(CH_2CH_2O)_s$, where s is 4, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R1 and R2 are a PEG group P—Z where P is a (poly)ethylene glycol group, where the (poly)ethylene glycol group is $(CH_2CH_2O)_s$, where s is 5, and Z is $CH_3$; R9 is an alkyl; R10 is an alkyl terminating in —OH, —COOH, —NHS, —O-TFP, or —NR-L-maleimide; and n is 3. In one embodiment, the compound is general formula Ic, where R1 and R2 are a PEG group P—Z where P is a (poly)ethylene glycol group, where the (poly)ethylene glycol group is $(CH_2CH_2O)_s$, where s is 6, and Z is $CH_3$; R9 is an alkyl; R10 is an alkyl terminating in —OH, —COOH, —NHS, —O-TFP, or —NR-L-maleimide; and n is 3. In one embodiment, the alkyl of R9 is ethyl, and the alkyl of R10 is pentyl.

In one embodiment, an isolated enantiomeric mixture selected from diastereomer Ia of general formula Ia

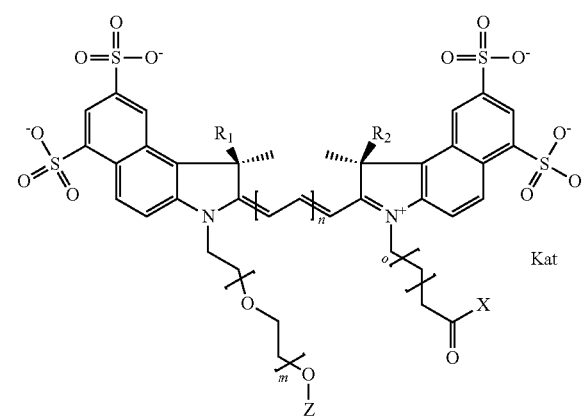

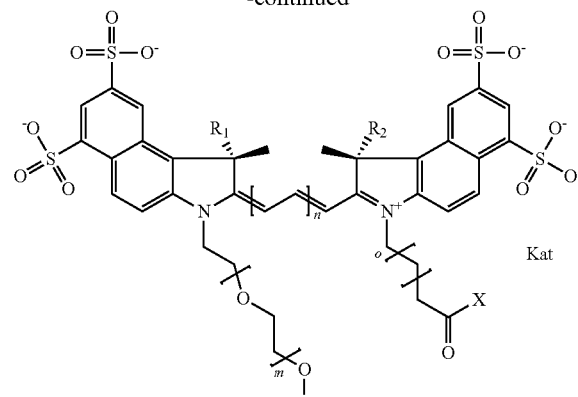
diastereomer Ib of general formula Ia
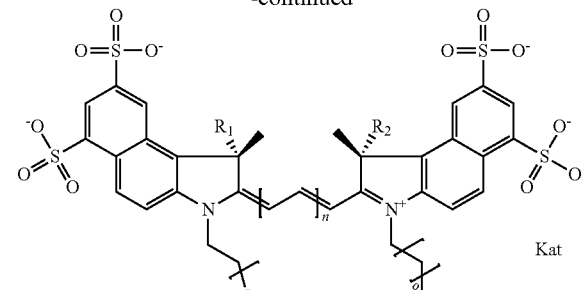
diastereomer Id of general formula Ib
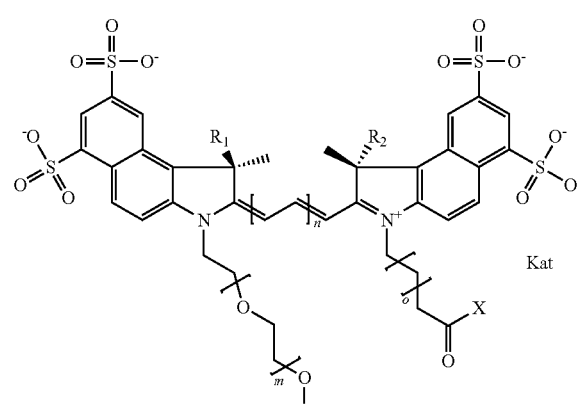
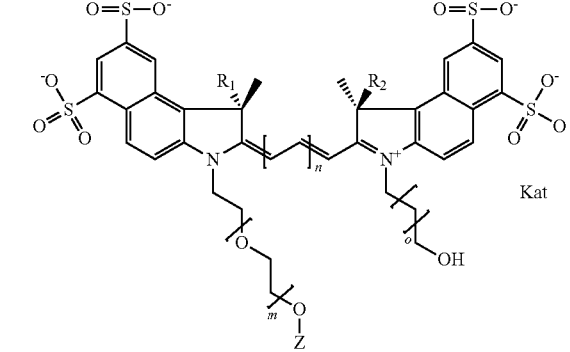
diastereomer Ie of general formula Ic
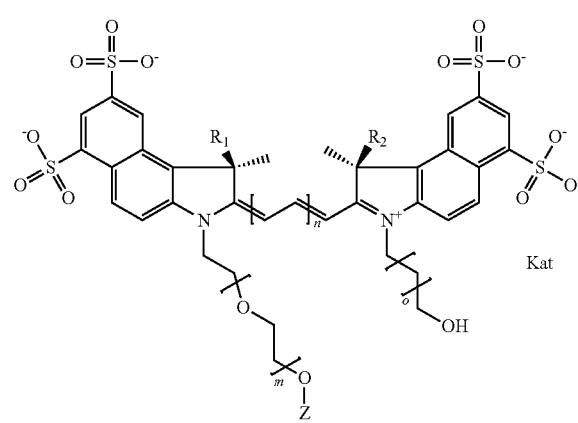
diastereomer Ic of general formula Ib
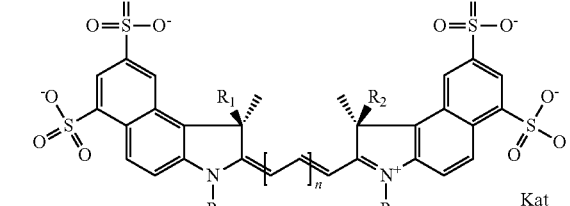
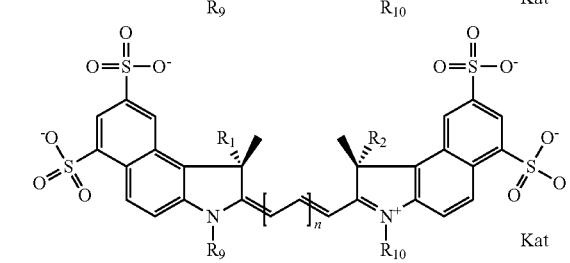

or diastereomer If of general formula Ic

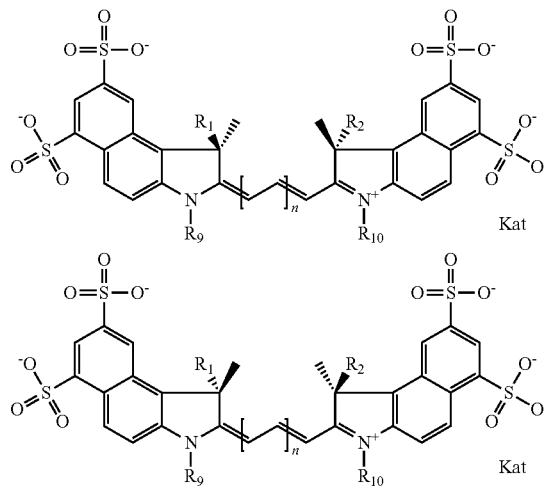

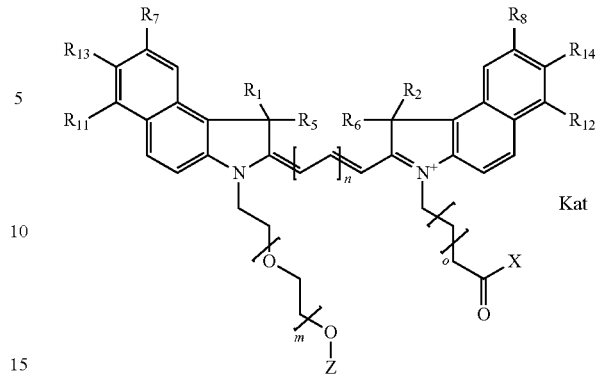

general formula IIb with "b" indicating the right N chain terminates in OH:

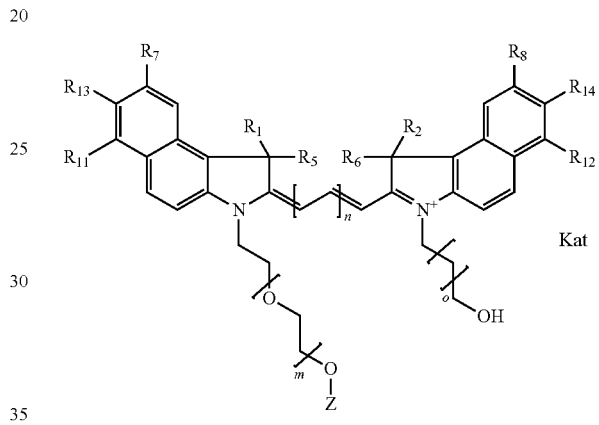

or general formula IIc with "c" indicating ethylene, diethylene, or (poly)ethylene glycol is not required on the left N:

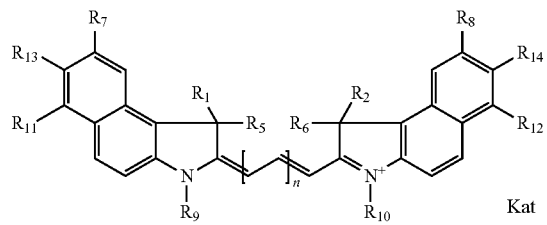

where each of $R^1$ and $R^2$ is the same or different and is independently selected from the group consisting of an aliphatic, heteroaliphatic, sulfoalkyl group, heteroaliphatic with terminal $SO_3$, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-SO$_2$NH—P—Z, and a carboxamide group -L-CONH—P—Z, and Z is selected from H, a CH$_3$, a CH$_3$ group, an alkyl group, a heteroalkyl group, or —CO—NHS; each of $R^9$ and $R^{10}$ is the same or different and is independently selected from the group consisting of an alkyl, a sulfoalkyl, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a PEG group P-L-X, L-Z, L-X; X is selected from the group consisting of —OH, —SH, —NH$_2$, —NH—NH$_2$, —F, —Cl, —Br, I, —NHS hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole), —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—CH$_2$—, imidazole, azide, —NR-L-O—NH$_2$, and —NR-L-O—CO—NHS, where R is —H or an aliphatic or heteroaliphatic group, and L is selected from the group consisting of a divalent linear (—(CH$_2$)$_t$—, t=0 to 15), crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive. In one embodiment, at least one of $R^1$ and $R^2$ contains a PEG group.

In one embodiment, one of R9 and R10 is a C1-C6 alkyl, or a C1-C6 alkyl substituted once by hydroxyl, sulfo, carboxy, or amino, and the other of R9 and R10 is an alkyl terminating in a reactive group. In one embodiment, the reactive group is selected from X or Z, as defined above. In one embodiment, the compound is general formula IIa with "a" indicating the right N chain terminates in COX:

where each of $R^1$, $R^2$, $R^5$, and $R^6$ is the same or different and is independently selected from the group consisting of an aliphatic, heteroaliphatic, sulfoalkyl group, heteroaliphatic with terminal $SO_3$, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-SO$_2$NH—P—Z, and a carboxamide group -L-CONH—P—Z, and Z is selected from H, a CH$_3$ group, an alkyl group, a heteroalkyl group, or —CO—NHS; each of $R^7$, $R^8$, $R^{11}$, $R^{12}$, $R^{13}$, and $R^{14}$ is the same or different and is independently selected from the group consisting of H, SO$_3$, a PEG group P—Z where P is selected from an ethylene glycol group, a diethylene glycol group, and a (poly)ethylene glycol group, where the (poly) ethylene glycol group is $(CH_2CH_2O)_s$, where s is an integer from 3-6 inclusive, a sulfonamide group -L-SO$_2$NH—P—Z, and a carboxamide group -L-CONH—P—Z, and Z is selected from H, a $CH_3$ group, an alkyl group, or a heteroalkyl group; each of $R^9$ and $R^{10}$ is the same or different and is independently selected from the group consisting of an alkyl, a sulfoalkyl, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a PEG group P-L-X, L-Z, L-X; X is selected from the group consisting of —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—$CH_2$—I, imidazole, azide, —NR-L-O—$NH_2$, and —NR-L-O—CO—NHS, where R is —H or an aliphatic or heteroaliphatic group, and L is selected from the group consisting of a divalent linear (—$(CH_2)_t$—, t=0 to 15), crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive.

In one embodiment, one of R9 and R10 is a C1-C6 alkyl, or a C1-C6 alkyl substituted once by hydroxyl, sulfo, carboxy, or amino, and the other of R9 and R10 is an alkyl terminating in a reactive group. In one embodiment, the reactive group is selected from X or Z, as defined above.

In one embodiment, the compound is general formulas IIa or IIb, collectively general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 0; o is 3; and n is 1. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 1; o is 3; and n is 1. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 2; o is 3; and n is 1. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 3; o is 3; and n is 1. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 4; o is 3; and n is 1. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 5; o is 3; and n is 1.

In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 0; o is 3; and n is 2. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 1; o is 3; and n is 2. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 2; o is 3; and n is 2. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 3; o is 3; and n is 2. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 4; o is 3; and n is 2. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 5; o is 3; and n is 2.

In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 0; o is 3; and n is 3. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 1; o is 3; and n is 3. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 2; o is 3; and n is 3. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 3; o is 3; and n is 3. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 4; o is 3; and n is 3. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 5; o is 3; and n is 3.

In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; o is 3; and n is 1. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; o is 3; and n is 1. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; o is 3; and n is 1. In one embodiment, the compound is general formula II, where each of R5 and R6 is methyl; each of R1 and R2 is a PEG group; each of R7, R8, R11, and R12 is H;

each of R13 and R14 is sulfo; X is —OH, —NHS, —O-TFP, or —NR-L-maleimide; m is 3; o is 3; and n is 1. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 4; o is 3; and n is 1. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 5; o is 3; and n is 1.

In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; o is 3; and n is 2. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; o is 3; and n is 2. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; o is 3; and n is 2. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 3; o is 3; and n is 2. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 4; o is 3; and n is 2. In one embodiment, the compound is general formula II, where each of R5 and R6 is methyl; each of R1 and R2 is a PEG group; each of R7, R8, R11, and R12 is H; each of R13 and R14 is sulfo; X4 is —OH, —NHS, —O-TFP, or —NR-L-maleimide; m is 5; o is 3; and n is 2.

In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; o is 3; and n is 3. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; o is 3; and n is 3. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; o is 3; and n is 3. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 3; o is 3; and n is 3. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 4; o is 3; and n is 3. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 5; o is 3; and n is 3.

In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 0; o is 3; and n is 1. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; o is 3; and n is 1. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; o is 3; and n is 1. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; o is 3; and n is 1. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; o is 3; and n is 1. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; o is 3; and n is 1.

In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 0; o is 3; and n is 2. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; o is 3; and n is 2. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; o is 3; and n is 2. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; o is 3; and n is 2. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; o is 3; and n is 2. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; o is 3; and n is 2.

In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 0; o is 3; and n is 3. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; o is 3; and n is 3. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; o is 3; and n is 3. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; o is 3; and n is 3. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; o is 3; and n is 3. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; o is 3; and n is 3.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; o is 3; and n is 1. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; o is 3; and n is 1. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; o is 3; and n is 1. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; o is 3; and n is 1. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; o is 3; and n is 1. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; o is 3; and n is 1.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; o is 3; and n is 2. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; o is 3; and n is 2. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; o is 3; and n is 2. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; o is 3; and n is 2. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; o is 3; and n is 2. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; o is 3; and n is 2.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; o is 3; and n is 3. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; o is 3; and n is 3. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; o is 3; and n is 3. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; o is 3; and n is 3. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; o is 3; and n is 3. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; o is 3; and n is 3.

In one embodiment, the compound is general formula II, where each of R5 and R6 is methyl; each of R1 and R2 is a PEG group; each of R7 and R8 is sulfo; each of R11

R12 is a carboxamide group —CONH—P where P is a PEG group; each of R13 and R14 is H; X is —OH, —NHS, —O-TFP, or —NR-L-maleimide; m is 0; o is 3; and n is 1. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 1; o is 3; and n is 1. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 2; o is 3; and n is 1. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 3; o is 3; and n is 1. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 4; o is 3; and n is 1. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 5; o is 3; and n is 1.

In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 0; o is 3; and n is 2. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 1; o is 3; and n is 2. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 2; o is 3; and n is 2. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 3; o is 3; and n is 2. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 4; o is 3; and n is 2. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 5; o is 3; and n is 2.

In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 0; o is 3; and n is 3. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 1; o is 3; and n is 3. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 2; o is 3; and n is 3. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 3; o is 3; and n is 3. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 4; o is 3; and n is 3. In one embodiment, the compound is general formula II, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 5; o is 3; and n is 3.

In one embodiment, the compound is general formula IIc where R1, R5, and R6 are methyl and R2 is a PEG group P—Z, where P is an ethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1, R5, and R6 are methyl and R2 is a PEG group P—Z, where P is a diethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the alkyl of R9 is ethyl, and the alkyl of R10 is pentyl.

In one embodiment, the compound is general formula IIc where R1, R5, and R6 are methyl and R2 is a PEG group P—Z, where P is an ethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1, R5, and R6 are methyl and R2 is a PEG group P—Z, where P is a diethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the alkyl of R9 is ethyl, and the alkyl of R10 is pentyl.

In one embodiment, the compound is general formula IIc where R1, R5, and R6 are methyl and R2 is a PEG group P—Z, where P is an ethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1, R5, and R6 are methyl and R2 is a PEG group P—Z, where P is a diethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the alkyl of R9 is ethyl, and the alkyl of R10 is pentyl.

In one embodiment, the compound is general formula IIc where R1, R5, and R6 are methyl and R2 is a PEG group P—Z, where P is an ethylene glycol group and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 1. In one embodiment, the compound is general formula IIc where R1, R5, and R6 are methyl and R2 is a PEG group P—Z, where P is a diethylene glycol group and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 1. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 1. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 1. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 1. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 1. In one embodiment, the alkyl of R9 is ethyl, and the alkyl of R10 is pentyl.

In one embodiment, the compound is general formula IIc where R1, R5, and R6 are methyl and R2 is a PEG group P—Z, where P is an ethylene glycol group and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 2. In one embodiment, the compound is general formula IIc where R1, R5, and R6 are methyl and R2 is a PEG group P—Z, where P is a diethylene glycol group and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 2. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 2. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 2. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 2. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 2. In one embodiment, the alkyl of R9 is ethyl, and the alkyl of R10 is pentyl.

In one embodiment, the compound is general formula IIc where R1, R5, and R6 are methyl and R2 is a PEG group P—Z, where P is an ethylene glycol group and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 3. In one embodiment, the compound is general formula IIc where R1, R5, and R6 are methyl and R2 is a PEG group P—Z, where P is a diethylene glycol group and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 3. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 3. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 3. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 3. In one embodiment, the compound is general formula IIc where R1, R5, and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is sulfo; each of R13 and R14 is H; R9 is an alkyl; R10 is an alkyl terminating in —OH, —COOH, —NHS, —O-TFP, or —NR-L-maleimide; and n is 3. In one embodiment, the alkyl of R9 is ethyl, and the alkyl of R10 is pentyl.

In one embodiment, the compound is general formula IIc where R1 is sulfoalkyl, R5 and R6 are methyl and R2 is a PEG group P—Z, where P is an ethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a diethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the alkyl of R9 is ethyl, the alkyl of R10 is pentyl, and R1 is sulfopentyl or sulfopropyl.

In one embodiment, the compound is general formula IIc where R1 is sulfoalkyl, R5 and R6 are methyl and R2 is a PEG group P—Z, where P is an ethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a diethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the alkyl of R9 is ethyl, the alkyl of R10 is pentyl, and R1 is sulfopentyl or sulfopropyl.

In one embodiment, the compound is general formula IIc where R1 is sulfoalkyl, R5 and R6 are methyl and R2 is a PEG group P—Z, where P is an ethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a diethylene glycol group and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the alkyl of R9 is ethyl, the alkyl of R10 is pentyl, and R1 is sulfopentyl or sulfopropyl.

In one embodiment, the compound is general formula IIc where R1 is sulfoalkyl, R5 and R6 are methyl and R2 is a PEG group P—Z, where P is an ethylene glycol group and Z is $CH_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a diethylene glycol group and Z is $CH_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 5, and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is (CH$_2$CH$_2$O)$_s$, where s is 6, and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, R9 is sulfopentyl or sulfopropyl, the alkyl of R10 is pentyl, and R1 is sulfopentyl or sulfopropyl.

In one embodiment, the compound is general formula IIc where R1 is sulfoalkyl, R5 and R6 are methyl and R2 is a PEG group P—Z, where P is an ethylene glycol group and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a diethylene glycol group and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is (CH$_2$CH$_2$O)$_s$, where s is 3, and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is (CH$_2$CH$_2$O)$_s$, where s is 4, and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is (CH$_2$CH$_2$O)$_s$, where s is 5, and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is (CH$_2$CH$_2$O)$_s$, where s is 6, and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, R9 is sulfopentyl or sulfopropyl, the alkyl of R10 is pentyl, and R1 is sulfopentyl or sulfopropyl.

In one embodiment, the compound is general formula IIc where R1 is sulfoalkyl, R5 and R6 are methyl and R2 is a PEG group P—Z, where P is an ethylene glycol group and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a diethylene glycol group and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is (CH$_2$CH$_2$O)$_s$, where s is 3, and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is (CH$_2$CH$_2$O)$_s$, where s is 4, and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is (CH$_2$CH$_2$O)$_s$, where s is 5, and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is (CH$_2$CH$_2$O)$_s$, where s is 6, and Z is CH$_3$; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, R9 is sulfopentyl or sulfopropyl, the alkyl of R10 is pentyl, and R1 is sulfopentyl or sulfopropyl.

In one embodiment, the compound is general formula IIc where R1 is sulfoalkyl, R5 and R6 are methyl and R2 is a PEG group P—Z, where P is an ethylene glycol group and Z is CH$_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a diethylene glycol group and Z is CH$_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is (CH$_2$CH$_2$O)$_s$, where s is 3, and Z is CH$_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is (CH$_2$CH$_2$O)$_s$, where s is 4, and Z is CH$_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide;

and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 1. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 1. In one embodiment, R9 is sulfopentyl or sulfopropyl, the alkyl of R10 is pentyl, and R1 is sulfopentyl or sulfopropyl.

In one embodiment, the compound is general formula IIc where R1 is sulfoalkyl, R5 and R6 are methyl and R2 is a PEG group P—Z, where P is an ethylene glycol group and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a diethylene glycol group and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, R9 is sulfopentyl or sulfopropyl, the alkyl of R10 is pentyl, and R1 is sulfopentyl or sulfopropyl.

In one embodiment, the compound is general formula IIc where R1 is sulfoalkyl, R5 and R6 are methyl and R2 is a PEG group P—Z, where P is an ethylene glycol group and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a diethylene glycol group and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 3, and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 4, and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 5, and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, the compound is general formula IIc where R1 is sulfoalkyl, R5 and R6 are methyl and R2 is a PEG group P—Z, where P is a (poly)ethylene glycol group, where the (poly)ethylene glycol group is $(CH_2CH_2O)_s$, where s is 6, and Z is $CH_3$; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, R9 is sulfopentyl or sulfopropyl, the alkyl of R10 is pentyl, and R1 is sulfopentyl or sulfopropyl.

In one embodiment, the compound is general formula IIc where R1 and R2 are a PEG group P—Z, where P is an ethylene glycol group and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a diethylene glycol group and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 1. In one embodiment, R9 is sulfopentyl or sulfopropyl, and the alkyl of R10 is pentyl.

In one embodiment, the compound is general formula IIc where R1 and R2 are a PEG group P—Z, where P is an ethylene glycol group and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a diethylene glycol group and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 2. In one embodiment, R9 is sulfopentyl or sulfopropyl, and the alkyl of R10 is pentyl.

In one embodiment, the compound is general formula IIc where R1 and R2 are a PEG group P—Z, where P is an ethylene glycol group and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a diethylene glycol group and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an sulfoalkyl; R10 is an alkyl terminating in —OH, —COOH, —NHS, —O-TFP, or —NR-L-maleimide; and n is 3. In one embodiment, R9 is sulfopentyl or sulfopropyl, and the alkyl of R10 is pentyl.

In one embodiment, the compound is general formula IIc where R1 and R2 are a PEG group P—Z, where P is an ethylene glycol group and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a diethylene glycol group and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 1. In one embodiment, R9 is sulfopentyl or sulfopropyl, and the alkyl of R10 is pentyl.

In one embodiment, the compound is general formula IIc where R1 and R2 are a PEG group P—Z, where P is an ethylene glycol group and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a diethylene glycol group and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 2. In one embodiment, R9 is sulfopentyl or sulfopropyl, and the alkyl of R10 is pentyl.

In one embodiment, the compound is general formula IIc where R1 and R2 are a PEG group P—Z, where P is an ethylene glycol group and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a diethylene glycol group and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is sulfo; each of R13 and R14 is H; R9 is an sulfoalkyl; R10 is an alkyl terminating in —OH, —COOH, —NHS, —O-TFP, or —NR-L-maleimide; and n is 3. In one embodiment, R9 is sulfopentyl or sulfopropyl, and the alkyl of R10 is pentyl.

In one embodiment, the compound is general formula IIc where R1 and R2 are a PEG group P—Z, where P is an ethylene glycol group and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a diethylene glycol group and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, the compound is general formula IIc where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 1. In one embodiment, R9 is ethyl, and the alkyl of R10 is pentyl.

In one embodiment, the compound is general formula IIc where R1 and R2 are a PEG group P—Z, where P is an ethylene glycol group and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a diethylene glycol group and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, the compound is general formula IIc where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 2. In one embodiment, R9 is ethyl, and the alkyl of R10 is pentyl.

In one embodiment, the compound is general formula IIc where R1 and R2 are a PEG group P—Z, where P is an ethylene glycol group and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a diethylene glycol group and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, the compound is general formula IIc where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an alkyl; R10 is an alkyl terminating in —OH, —COOH, —NHS, —O-TFP, or —NR-L-maleimide; and n is 3. In one embodiment, R9 is ethyl, and the alkyl of R10 is pentyl.

In one embodiment, the compound is general formula IIIa with "a" indicating an ethylene or (poly)ethylene glycol at both left N and right N and the right N chain that terminates in COX:

general formula IIIb with "b" indicating an ethylene or (poly)ethylene glycol at both left N and right N and the right N chain that terminates in COH:

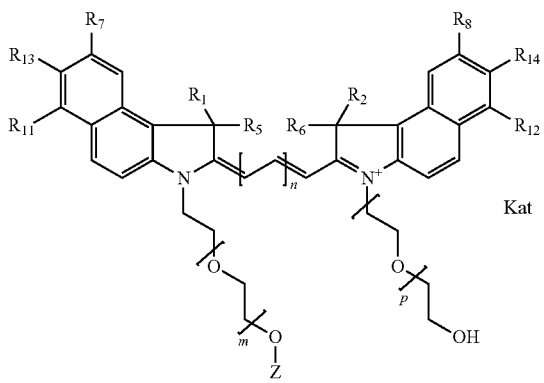

general formula IIIc with "c" indicating an ethylene or (poly)ethylene glycol at only the right N and the right N chain that terminates in COX:

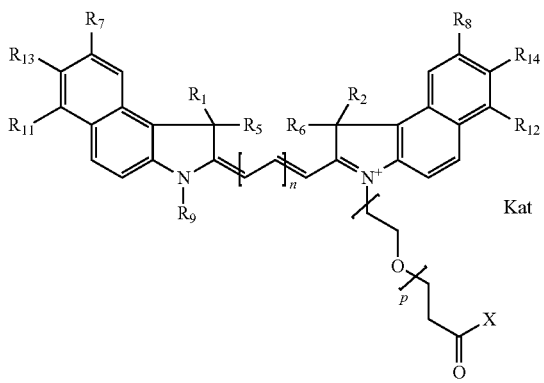

or general formula IIId with "d" indicating an ethylene or (poly)ethylene glycol at only the right N and the right N chain that terminates in COH:

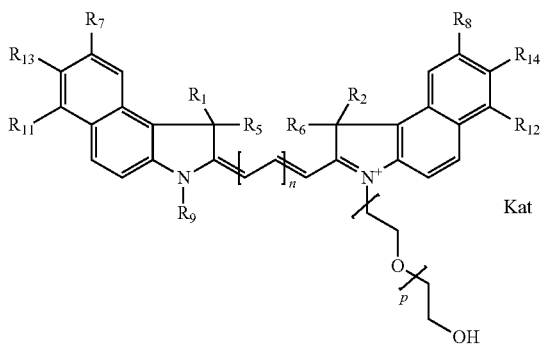

where each of $R^1$, $R^2$, $R^5$, and $R^6$ is the same or different and is independently selected from the group consisting of an aliphatic, heteroaliphatic, sulfoalkyl group, heteroaliphatic with terminal $SO_3$, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-$SO_2$NH—P—Z, and a carboxamide group -L-CONH—P—Z, and Z is selected from H, a $CH_3$ group, an alkyl group, or a heteroalkyl group; each of $R^7$, $R^8$, $R^{11}$, $R^{12}$, $R^{13}$, and $R^{14}$ is the same or different and is independently selected from the group consisting of H, $SO_3$, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group —$SO_2$NH—P—Z, and a carboxamide group —CONH—P—Z, and Z is selected from H, a $CH_3$ group, an alkyl group, a heteroalkyl group, or —CO—NHS; $R^9$ is selected from the group consisting of an alkyl, a sulfoalkyl, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a PEG group P-L-X, L-Z, L-X; X is selected from the group consisting of —OH, —SH, —$NH_2$, —NH—$NH_2$, —F, —Cl, —Br, I, —NHS hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—CH2-I, imidazole, azide, —NR-L-O—$NH_2$, and —NR-L-O—CO—NHS, where R is —H or an aliphatic or heteroaliphatic group, and L is selected from the group consisting of a divalent linear (—$(CH_2)_t$—, t=0 to 15), crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; p is an integer from 1 to 6 inclusive; and n is an integer from 1 to 3 inclusive.

In one embodiment, the compound is general formulas IIIa or IIIb, collectively termed general formula III where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 0; p is 1; and n is 1. In one embodiment, the compound is general formula III where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 1; p is 2; and n is 1. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 2; p is 3; and n is 1. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 3; p is 4; and n is 1. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 4; p is 5; and n is 1. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 5; p is 6; and n is 1.

In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 0; p is 1; and n is 2. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 1; p is 2; and n is 2. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 2; p is 3; and n is 2. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 3; p is 4; and n is 2. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 4; p is 5; and n is 2. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 5; p is 6; and n is 2.

In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 0; p is 1; and n is 3. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 1; p is 2; and n is 3. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 2; p is 3; and n is 3. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 3; p is 4; and n is 3. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 4; p is 5; and n is 3. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 5; p is 6; and n is 3.

In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 0; p is 1; and n is 1. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 1; p is 2; and n is 1. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 2; p is 3; and n is 1. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 3; p is 4; and n is 1. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 4; p is 5; and n is 1. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 5; p is 6; and n is 1.

In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 0; p is 1; and n is 2. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 1; p is 2; and n is 2. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 2; p is 3; and n is 2. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 3; p is 4; and n is 2. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 4; p is 5; and n is 2. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 5; p is 6; and n is 2.

In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 0; p is 1; and n is 3. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 1; p is 2; and n is 3. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 2; p is 3; and n is 3. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 3; p is 4; and n is 3. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 4; p is 5; and n is 3. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 5; p is 6; and n is 3.

In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 0; p is 1; and n is 1. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; p is 2; and n is 1. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; p is 3; and n is 1. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; p is 4; and n is 1. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; p is 5; and n is 1. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; p is 6; and n is 1.

In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 0; p is 1; and n is 2. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; p is 2; and n is 2. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; p is 3; and n is 2. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; p is 4; and n is 2. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; p is 5; and n is 2. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; p is 6; and n is 2.

In one embodiment, the compound is general formula III, where each of R5 and R6 is methyl; each of R1 and R2 is a PEG group; each of R7, R8, R11, and R12 is sulfo; each of R13 and R14 is H; X is —OH, NHS, —O-TFP, or —NR-L-maleimide; m is 0; p is 1; and n is 3. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; p is 2; and n is 3. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; p is 3; and n is 3. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; p is 4; and n is 3. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; p is 5; and n is 3. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; p is 6; and n is 3.

In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; p is 1; and n is 1. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; p is 2; and n is 1. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; p is 3; and n is 1. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 3; p is 4; and n is 1. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 4; p is 5; and n is 1. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 5; p is 6; and n is 1.

In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; p is 1; and n is 2. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; p is 2; and n is 2. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; p is 3; and n is 2. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 3; p is 4; and n is 2. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L- maleimide; m is 4; p is 5; and n is 2. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 5; p is 6; and n is 2.

In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; p is 1; and n is 3. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; p is 2; and n is 3. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; p is 3; and n is 3. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 3; p is 4; and n is 3. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 4; p is 5; and n is 3. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 5; p is 6; and n is 3.

In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; p is 1; and n is 1. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; p is 2; and n is 1. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; p is 3; and n is 1. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; p is 4; and n is 1. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; p is 5; and n is 1. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; p is 6; and n is 1.

In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; p is 1; and n is 2. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; p is 2; and n is 2. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; p is 3; and n is 2. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; p is 4; and n is 2. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; p is 5; and n is 2. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; p is 6; and n is 2.

In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; p is 1; and n is 3. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; p is 2; and n is 3. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; p is 3; and n is 3. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; p is 4; and n is 3. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; p is 5; and n is 3. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; p is 6; and n is 3.

In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 0; p is 1; and n is 1. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 1; p is 2; and n is 1. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 2; p is 3; and n is 1. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 3; p is 4; and n is 1. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 4; p is 5; and n is 1. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 5; p is 6; and n is 1.

In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 0; p is 1; and n is 2. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 1; p is 2; and n is 2. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 2; p is 3; and n is 2. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 3; p is 4; and n is 2. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 4; p is 5; and n is 2. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 5; p is 6; and n is 2.

In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 0; p is 1; and n is 3. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 1; p is 2; and n is 3. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 2; p is 3; and n is 3. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 3; p is 4; and n is 3. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 4; p is 5; and n is 3. In one embodiment, the compound is general formula III, where each of R5 and R6 is methyl; each of R1 and R2 is a PEG group; each of R7 and R8 is sulfo; each of R11 and R12 is a carboxamide group —CONH—P where P is a PEG group; each of R13 and R14 is H; X is —OH, —NHS, —O-TFP, or —NR-L-maleimide; m is 5; p is 6; and n is 3.

In one embodiment, the compound is general formula IIIc or IIId where R1 and R2 are a PEG group P—Z, where P is an ethylene glycol group and Z is CH$_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 1; and n is 1. In one embodiment, the compound is general formula IIIc or IIId where R1 and R2 are a PEG group P—Z, where P is a diethylene glycol group and Z is CH$_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 2; and n is 1. In one embodiment, the compound is general formula IIIc or IIId where R1 and R2 are a PEG group P—Z, where P is a (poly)ethylene glycol group, where the (poly)ethylene glycol group is (CH$_2$CH$_2$O)$_s$, where s is 3, and Z is CH$_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 3; and n is 1. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 4; and n is 1. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 5; and n is 1. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 6; and n is 1. In one embodiment, R9 is ethyl, sulfopentyl or sulfopropyl.

In one embodiment, the compound is general formula IIIc or IIId where R1 and R2 are a PEG group P—Z, where P is an ethylene glycol group and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 1; and n is 2. In one embodiment, the compound is general formula IIIc or IIId where R1 and R2 are a PEG group P—Z, where P is a diethylene glycol group and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 2; and n is 2. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 3; and n is 2. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 4; and n is 2. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 5; and n is 2. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 6; and n is 2. In one embodiment, R9 is ethyl, sulfopentyl or sulfopropyl.

In one embodiment, the compound is general formula IIIc or IIId where R1 and R2 are a PEG group P—Z, where P is an ethylene glycol group and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 1; and n is 3. In one embodiment, the compound is general formula IIIc or IIId where R1 and R2 are a PEG group P—Z, where P is a diethylene glycol group and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 2; and n is 3. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 3; and n is 3. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 4; and n is 3. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 5; and n is 3. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 6; and n is 3. In one embodiment, R9 is ethyl, sulfopentyl or sulfopropyl.

In one embodiment, the compound is general formula IIIc or IIId where R1 and R2 are a PEG group P—Z, where P is an ethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 1; and n is 1. In one embodiment, the compound is general formula IIIc or IIId where R1 and R2 are a PEG group P—Z, where P is a diethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 2; and n is 1. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 3; and n is 1. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 4; and n is 1. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 5; and n is 1. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 6; and n is 1. In one embodiment, R9 is ethyl, sulfopentyl or sulfopropyl.

In one embodiment, the compound is general formula IIIc or IIId where R1 and R2 are a PEG group P—Z, where P is an ethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 1; and n is 2. In one embodiment, the compound is general formula IIIc or IIId where R1 and R2 are a PEG group P—Z, where P is a diethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 2; and n is 2. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 3; and n is 2. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 4; and n is 2. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 5; and n is 2. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 6; and n is 2. In one embodiment, R9 is ethyl, sulfopentyl or sulfopropyl.

In one embodiment, the compound is general formula IIIc or IIId where R1 and R2 are a PEG group P—Z, where P is an ethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 1; and n is 3. In one embodiment, the compound is general formula IIIc or IIId where R1 and R2 are a PEG group P—Z, where P is a diethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 2; and n is 3. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 3; and n is 3. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 4; and n is 3. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 5; and n is 3. In one embodiment, the compound is general formula IIIc or IIId where R1 and R2 are a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 6; and n is 3. In one embodiment, R9 is ethyl, sulfopentyl or sulfopropyl.

In one embodiment, the compound is general formula IIIc or IIId where R1 is alkyl or sulfoalkyl; R2 is a PEG group P—Z, where P is an ethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 1; and n is 1. In one embodiment, the compound is general formula IIIc or IIId where R1 is alkyl or sulfoalkyl; R2 is a PEG group P—Z, where P is a diethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 2; and n is 1. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 3; and n is 1. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 4; and n is 1. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 5; and n is 1. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 6; and n is 1. In one embodiment, each of R1 and R9 are independently selected from methyl, ethyl, sulfopentyl or sulfopropyl.

In one embodiment, the compound is general formula IIIc or IIId where R1 is alkyl or sulfoalkyl; R2 is a PEG group P—Z, where P is an ethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 1; and n is 2. In one embodiment, the compound is general formula IIIc or IIId where R1 is alkyl or sulfoalkyl; R2 is a PEG group P—Z, where P is a diethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 2; and n is 2. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 3; and n is 2. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 4; and n is 2. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 5; and n is 2. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 6; and n is 2. In one embodiment, each of R1 and R9 are independently selected from methyl, ethyl, sulfopentyl or sulfopropyl.

In one embodiment, the compound is general formula IIIc or IIId where R1 is alkyl or sulfoalkyl; R2 is a PEG group P—Z, where P is an ethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 1; and n is 3. In one embodiment, the compound is general formula IIIc or IIId where R1 is alkyl or sulfoalkyl; R2 is a PEG group P—Z, where P is a diethylene glycol group and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 2; and n is 3. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 3; and n is 3. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 4; and n is 3. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 5; and n is 3. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is sulfo; each of R13 and R14 is H; R9 is an alkyl or sulfoalkyl; X is a —OH, —COOH, —NHS, —O-TFP, or —NR-L-maleimide; p is 6; and n is 3. In one embodiment, each of R1 and R9 are independently selected from methyl, ethyl, sulfopentyl or sulfopropyl.

In one embodiment, the compound is general formula IIIc or IIId where R1 is alkyl or sulfoalkyl; R2 is a PEG group P—Z, where P is an ethylene glycol group and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 1; and n is 1. In one embodiment, the compound is general formula IIIc or IIId where R1 is alkyl or sulfoalkyl; R2 is a PEG group P—Z, where P is a diethylene glycol group and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 2; and n is 1. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 3; and n is 1. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 4; and n is 1. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 5; and n is 1. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 6; and n is 1. In one embodiment, each of R1 and R9 are independently selected from methyl, ethyl, sulfopentyl or sulfopropyl.

In one embodiment, the compound is general formula IIIc or IIId where R1 is alkyl or sulfoalkyl; R2 is a PEG group P—Z, where P is an ethylene glycol group and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 1; and n is 2. In one embodiment, the compound is general formula IIIc or IIId where R1 is alkyl or sulfoalkyl; R2 is a PEG group P—Z, where P is a diethylene glycol group and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 2; and n is 2. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 3; and n is 2. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 4; and n is 2. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 5; and n is 2. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 6; and n is 2. In one embodiment, each of R1 and R9 are independently selected from methyl, ethyl, sulfopentyl or sulfopropyl.

In one embodiment, the compound is general formula IIIc or IIId where R1 is alkyl or sulfoalkyl; R2 is a PEG group P—Z, where P is an ethylene glycol group and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 1; and n is 3. In one embodiment, the compound is general formula IIIc or IIId where R1 is alkyl or sulfoalkyl; R2 is a PEG group P—Z, where P is a diethylene glycol group and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 2; and n is 3. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 3, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 3; and n is 3. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 4, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 4; and n is 3. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 5, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 5; and n is 3. In one embodiment, the compound is general formula IIIc or IIId where R1 is alkyl or sulfoalkyl; R2 is a PEG group P—Z, where P is a (poly)ethylene glycol group, where the (poly)ethylene glycol group is $(CH_2CH_2O)_s$, where s is 6, and Z is $CH_3$; R5 and R6 are methyl; each of R7, R8, R11, and R12 is H; each of R13 and R14 is sulfo; R9 is an alkyl or sulfoalkyl; X is a —OH, —COOH, —NHS, —O-TFP, or —NR-L-maleimide; p is 6; and n is 3. In one embodiment, each of R1 and R9 are independently selected from methyl, ethyl, sulfopentyl or sulfopropyl.

In one embodiment, the compound is 579 Compound 1

579 Compound 1 (6-((E)-2-((E)-3-(3-(2-methoxyethyl)-1-methyl-6,8-disulfonato-1-(3-sulfonatopropyl)-1H-benzo[e]indol-3-ium-2-yl)allylidene)-1,1-dimethyl-6,8-disulfonato-1H-benzo[e]indol-3(2H)-yl)hexanoate) contains an ethylene glycol on the indole N of the left heterocycle, i.e., a methylated ethylene glycol. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 579 Compound 1, but one skilled in the art appreciates that activation is not limited to these examples. One non-limiting example of an activated compound is the NHS-ester of 579 Compound 1, shown below:

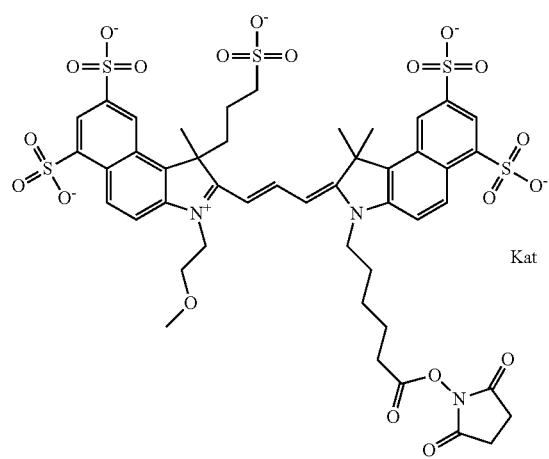 [SMILES: COCC[N+]1=C(/C=C/C=C2/N(CCCCCC(=O)ON3C(=O)CCC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example of a NHS-ester of 579 Compound 1, according to general formula III, where m=1 and p=1, is shown below:

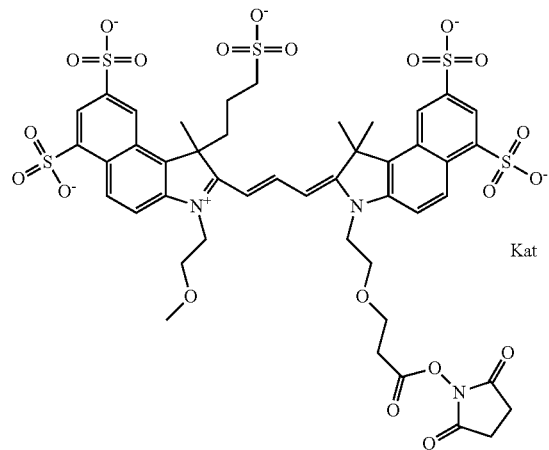

One non-limiting example of a NHS-ester of 579 Compound 1, according to general formula III, where m=1 and p=2, is shown below:

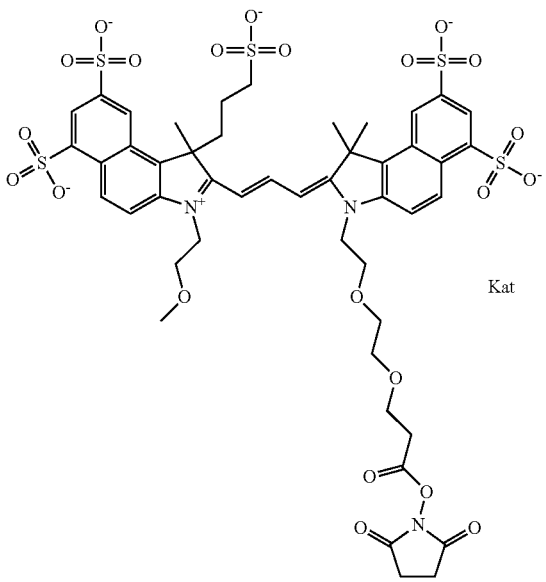

One non-limiting example of a NHS-ester of 579 Compound 1, according to general formula III, where m=1 and p=3, is shown below:

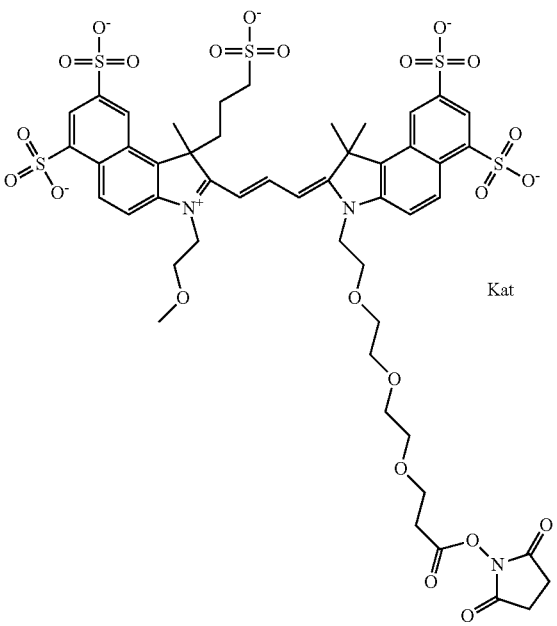

One non-limiting example of a NHS-ester of 579 Compound 1, according to general formula III, where m=1 and p=4, is shown below:

One non-limiting example of a NHS-ester of 579 Compound 1, according to general formula III, where m=1 and p=5, is shown below:

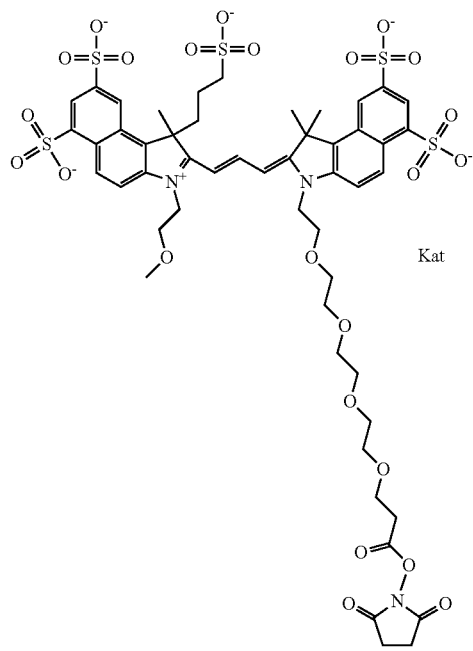

One non-limiting example of a NHS-ester of 579 Compound 1, according to general formula III, where m=1 and p=6, is shown below:

One non-limiting example of an activated 579 Compound 1 is a tetrafluorophenyl (TFP)-ester form of 579 Compound 1, shown below:

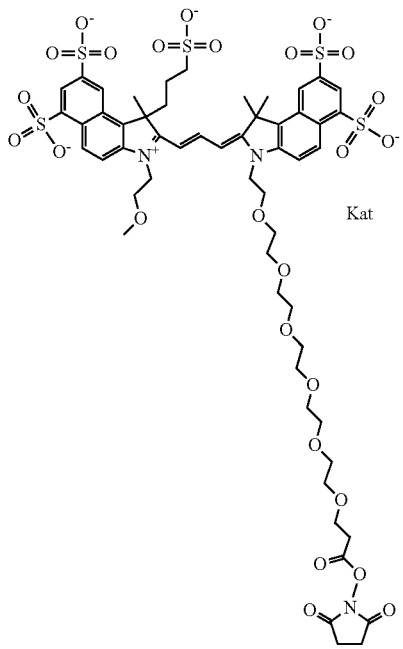 [SMILES: COCC[N+]1=C(/C=C/C=C2/N(CCOCCOCCOCCOCCOCCOCCC(=O)ON3C(=O)CCC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example of an activated 579 Compound 1 is a sulfotetrafluorophenyl (STP)-ester form of 579 Compound 1, shown below:

One non-limiting example of an activated 579 Compound 1 is a hydrazide form of 579 Compound 1, shown below:

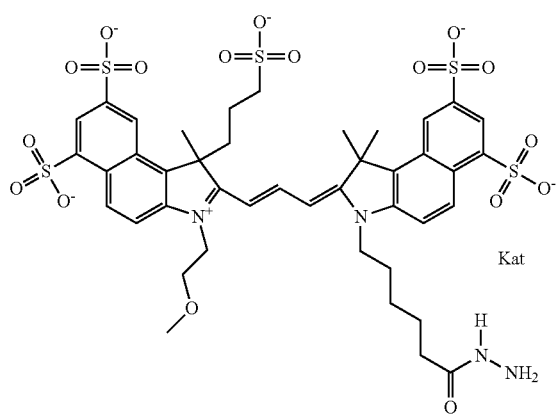 [SMILES: COCC[N+]1=C(/C=C/C=C2/N(CCCCCC(=O)NN)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example of an activated 579 Compound 1 is a maleimide form of 579 Compound 1, shown below:

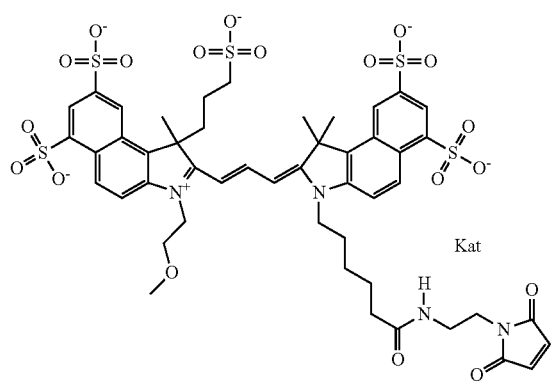 [SMILES: COCC[N+]1=C(/C=C/C=C2/N(CCCCCC(=O)NCCN3C(=O)C=CC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

In one embodiment, the compound is 579 Compound 2

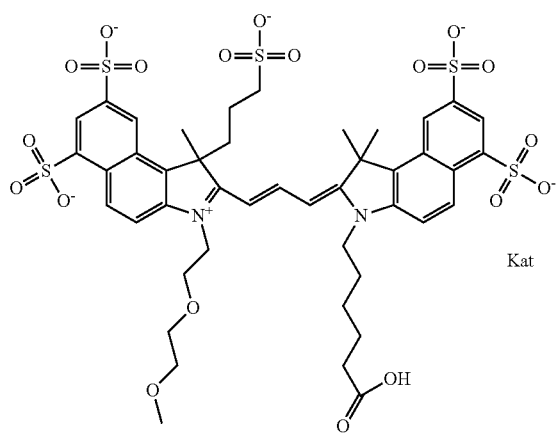 [SMILES: COCCOCC[N+]1=C(/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

579 Compound 2 (6-((E)-2-((E)-3-(3-(2-(2-methoxyethoxy)ethyl)-1-methyl-6,8-disulfonato-1-(3-sulfonatopropyl)-1H-benzo[e]indol-3-ium-2-yl)allylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 2 is activated as described above.

In one embodiment, the compound is 579 Compound 3

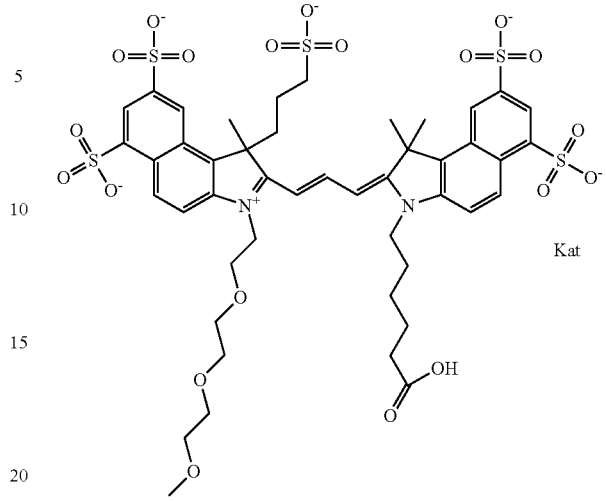

579 Compound 3 (6-((E)-2-((E)-3-(3-(2-(2-(2-methoxyethoxy)ethoxy)ethyl)-1-methyl-6,8-disulfonato-1-(3-sulfonatopropyl)-1H-benzo[e]indol-3-ium-2-yl)allylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 3 is activated as described above.

In one embodiment, the compound is 579 Compound 4

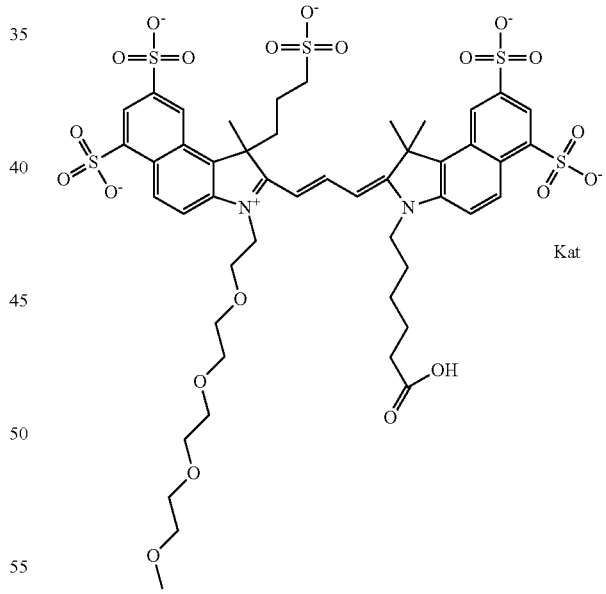

579 Compound 4 (6-((E)-1,1-dimethyl-2-((E)-3-(1-methyl-6,8-disulfonato-1-(3-sulfonatopropyl)-3-(2,5,8,11-tetraoxatridecan-13-yl)-1H-benzo[e]indol-3-ium-2-yl)allylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 4 is activated as described above.

In one embodiment, the compound is 579 Compound 5

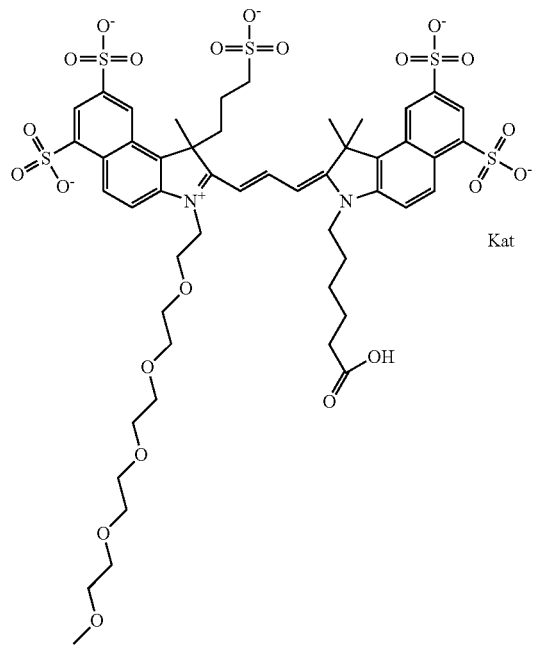 [SMILES: COCCOCCOCCOCCOCC[N+]1=C(/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

579 Compound 5 (6-((E)-2-((E)-3-(3-(2,5,8,11,14-pentaoxahexadecan-16-yl)-1-methyl-6,8-disulfonato-1-(3-sulfonatopropyl)-1H-benzo[e]indol-3-ium-2-yl)allylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 5 is activated as described above.

In one embodiment, the compound is 579 Compound 6

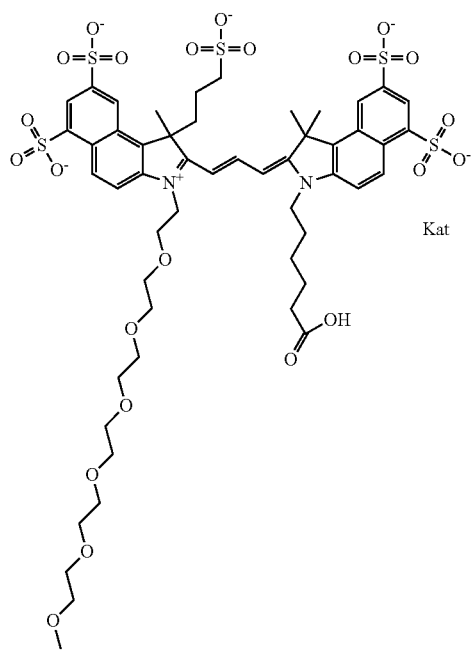 [SMILES: COCCOCCOCCOCCOCCOCC[N+]1=C(/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

579 Compound 6 (6-((E)-1,1-dimethyl-2-((E)-3-(1-methyl-3-(2,5,8,11,14,17-hexaoxanonadecan-19-yl)-6,8-disulfonato-1-(3-sulfonatopropyl)-1H-benzo[e]indol-3-ium-2-yl)allylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 6 is activated as described above.

In one embodiment, the compound is 579 Compound 0/1

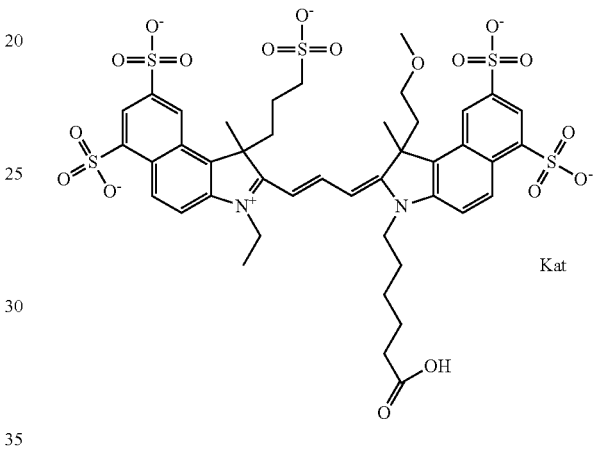

579 Compound 0/1 (2-((1E,3E)-3-(3-(5-carboxypentyl)-1-(2-methoxyethyl)-1-methyl-6,8-disulfonato-1H-benzo[e]indol-2(3H)-ylidene)prop-1-enyl)-3-ethyl-1-methyl-1-(3-sulfonatopropyl)-1H-benzo[e]indolium-6,8-disulfonate) contains ethylene glycol at R2, sulfoalkyl at R1, ethyl at R9, and carboxyalkyl at R10.

One non-limiting example of an activated compound is the NHS-ester of 579 Compound 0/1, shown below:

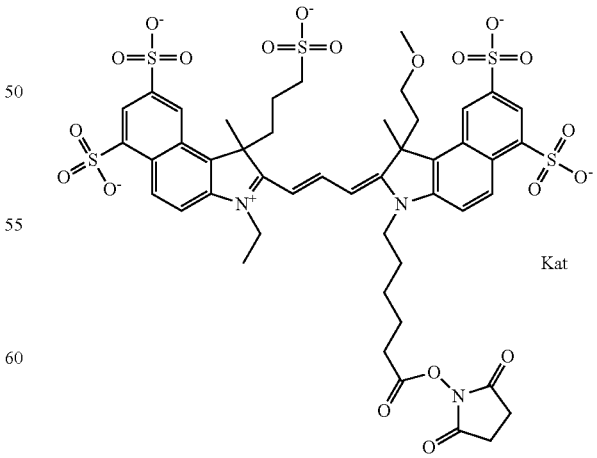

One non-limiting example of an activated 579 Compound 0/1 is a tetrafluorophenyl (TFP)-ester form, shown below:

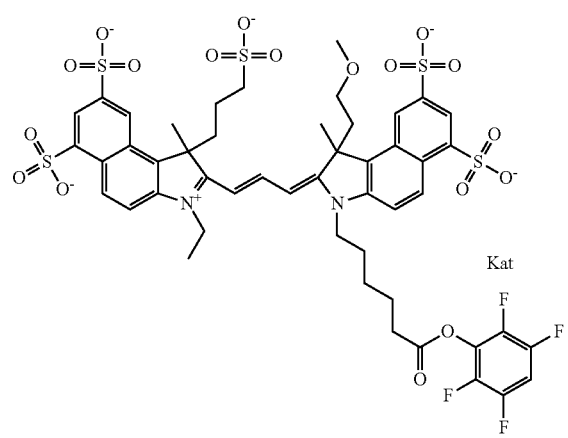 [SMILES: CC[N+]1=C(/C=C/C=C2/N(CCCCCC(=O)Oc3c(F)c(F)cc(F)c3F)c3ccc4c(S(=O)(=O)[O-])cc(S(=O)(=O)[O-])cc4c3C2(C)CCOC)C(C)(CCCS(=O)(=O)[O-])c2c1ccc1c(S(=O)(=O)[O-])cc(S(=O)(=O)[O-])cc21]
One non-limiting example of an activated 579 Compound 0/1 is a sulfotetrafluorophenyl (STP)-ester form, shown below:
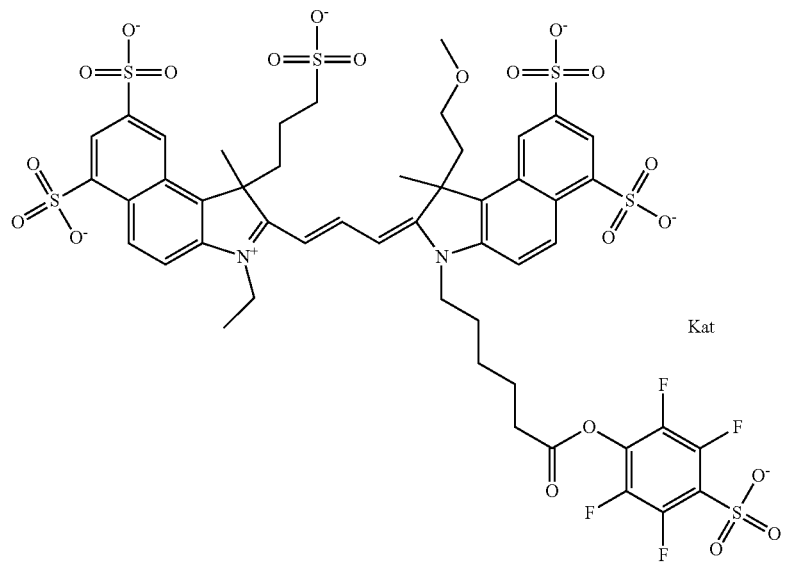 [SMILES: CC[N+]1=C(/C=C/C=C2/N(CCCCCC(=O)Oc3c(F)c(F)c(S(=O)(=O)[O-])c(F)c3F)c3ccc4c(S(=O)(=O)[O-])cc(S(=O)(=O)[O-])cc4c3C2(C)CCOC)C(C)(CCCS(=O)(=O)[O-])c2c1ccc1c(S(=O)(=O)[O-])cc(S(=O)(=O)[O-])cc21]
One non-limiting example of an activated 579 Compound 0/1 is a hydrazide form, shown below:
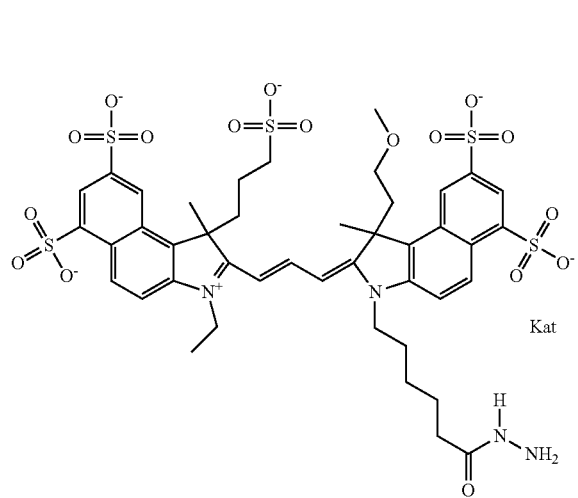 [SMILES: CC[N+]1=C(/C=C/C=C2/N(CCCCCC(=O)NN)c3ccc4c(S(=O)(=O)[O-])cc(S(=O)(=O)[O-])cc4c3C2(C)CCOC)C(C)(CCCS(=O)(=O)[O-])c2c1ccc1c(S(=O)(=O)[O-])cc(S(=O)(=O)[O-])cc21]
One non-limiting example of an activated 579 Compound 0/1 is a maleimide form, shown below:
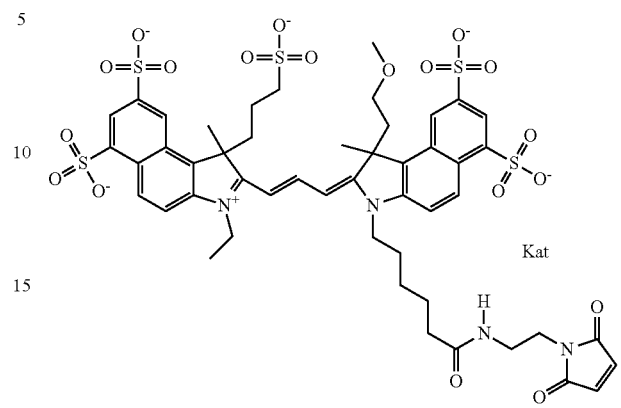
In one embodiment, the compound is 579 Compound 0/1

579 Compound 0/1 (2-((1E,3E)-3-(3-(5-carboxypentyl)-1-(2-(2-methoxyethoxy)ethyl)-1-methyl-6,8-disulfonato-1H-benzo[e]indol-2(3H)-ylidene)prop-1-enyl)-3-ethyl-1-methyl-1-(3-sulfonatopropyl)-1H-benzo[e]indolium-6,8-disulfonate) contains diethylene glycol at R2, sulfoalkyl at R1, ethyl at R9, and carboxyalkyl at R10.

In one embodiment, the compound is 579 Compound 0/1

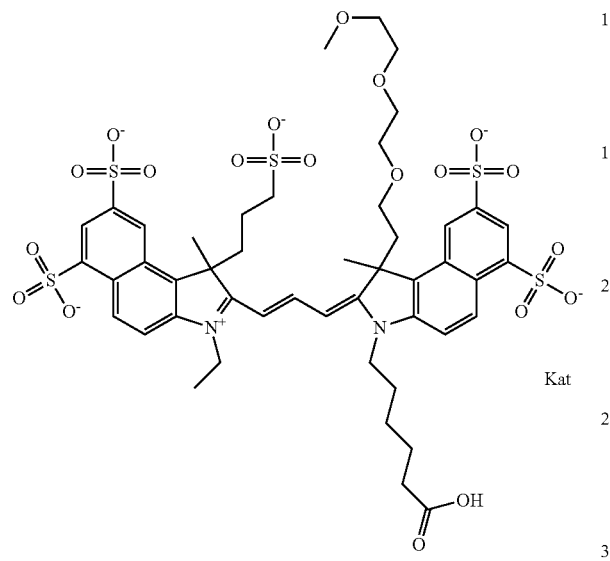

579 Compound 0/1 (2-((1E,3E)-3-(3-(5-carboxypentyl)-1-(2-(2-(2-methoxyethoxy)ethoxy)ethyl)-1-methyl-6,8-disulfonato-1H-benzo[e]indol-2(3H)-ylidene)prop-1-enyl)-3-ethyl-1-methyl-1-(3-sulfonatopropyl)-1H-benzo[e]indolium-6,8-disulfonate) contains (poly)ethylene glycol (PEG$_3$) at R2, sulfoalkyl at R1, ethyl at R9, and carboxyalkyl at R10.

In one embodiment, the compound is 579 Compound 0/1

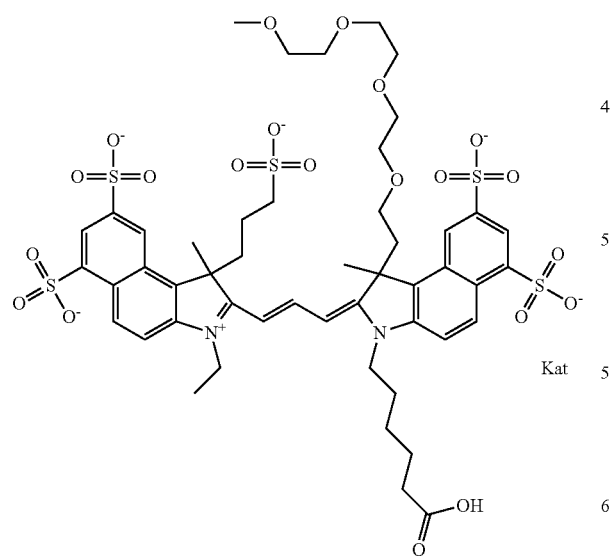

579 Compound 0/1 (2-((1E,3E)-3-(3-(5-carboxypentyl)-1-methyl-6,8-disulfonato-1-(2,5,8,11-tetraoxatridecan-13-yl)-1H-benzo[e]indol-2(3H)-ylidene)prop-1-enyl)-3-ethyl-1-methyl-1-(3-sulfonatopropyl)-1H-benzo[e]indolium-6,8-disulfonate) contains (poly)ethylene glycol (PEG$_4$) at R2, lfoalkyl at R1, ethyl at R9, and carboxyalkyl at R10.

In one embodiment, the compound is 579 Compound 0/1

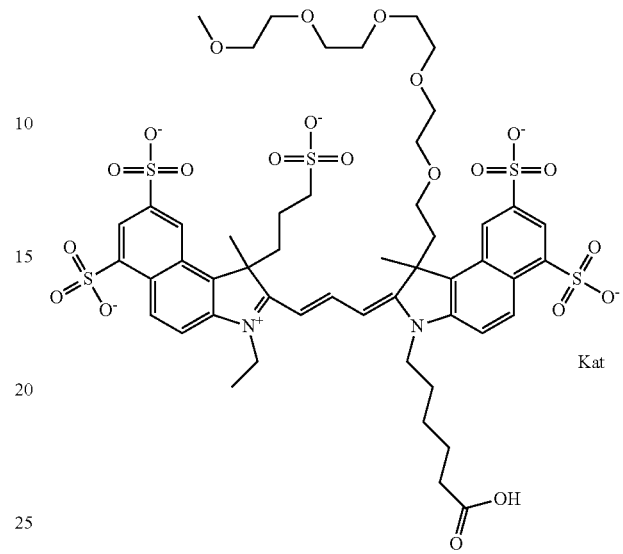

579 Compound 0/1 (2-((1E,3E)-3-(3-(5-carboxypentyl)-1-(2,5,8,11,14-pentaoxahexadecan-16-yl)-1-methyl-6,8-disulfonato-1H-benzo[e]indol-2(3H)-ylidene)prop-1-enyl)-3-ethyl-1-methyl-1-(3-sulfonatopropyl)-1H-benzo[e]indolium-6,8-disulfonate) contains a (poly)ethylene glycol (PEG$_5$) at R2, a sulfoalkyl at R1, an ethyl at R9, and carboxyalkyl at R10.

In one embodiment, the compound is 579 Compound 0/1

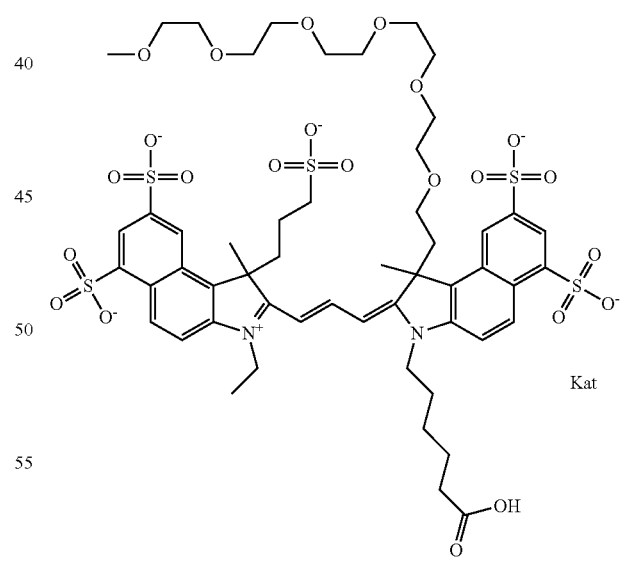

579 Compound 0/1 (2-((1E,3E)-3-(3-(5-carboxypentyl)-1-methyl-1-(2,5,8,11,14,17-hexaoxanonadecan-19-yl)-6,8-disulfonato-1H-benzo[e]indol-2(3H)-ylidene)prop-1-enyl)-3-ethyl-1-methyl-1-(3-sulfonatopropyl)-1H-benzo[e]indolium-6,8-disulfonate) contains (poly)ethylene glycol (PEG$_6$) at R2, sulfoalkyl at R1, ethyl at R9, and carboxyalkyl at R10.

In one embodiment, the compound is 579 Compound 0/1

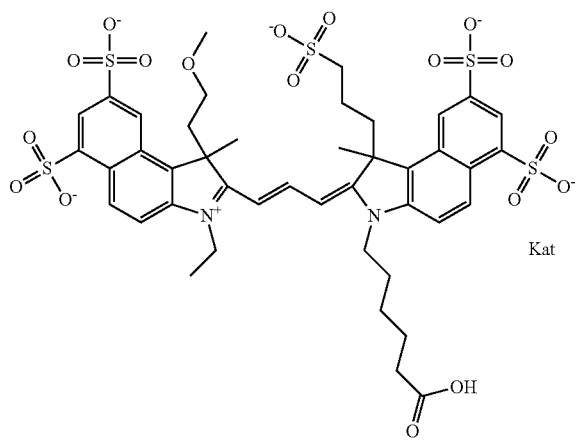

579 Compound 0/1 (2-((1E,3E)-3-(3-(5-carboxypentyl)-1-methyl-6,8-disulfonato-1-(3-sulfonatopropyl)-1H-benzo[e]indol-2(3H)-ylidene)prop-1-enyl)-3-ethyl-1-(2-methoxyethyl)-1-methyl-1H-benzo[e]indolium-6,8-disulfonate) contains ethylene glycol at R1, sulfoalkyl at R2, ethyl at R9, and carboxyalkyl at R10.

One non-limiting example of an activated compound is the NHS-ester of 579 Compound 0/1, shown below:

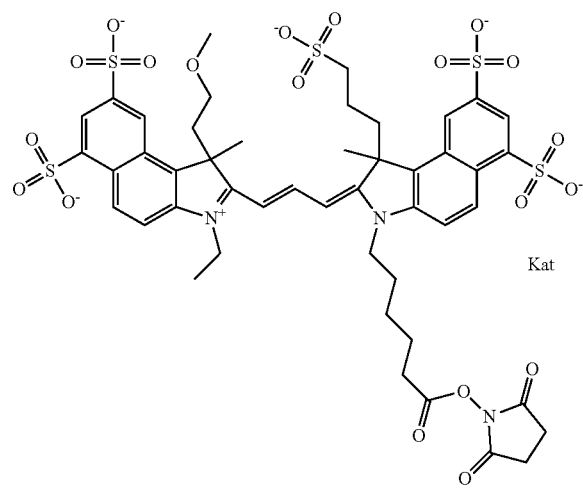

In one embodiment, the compound is 579 Compound 0/1

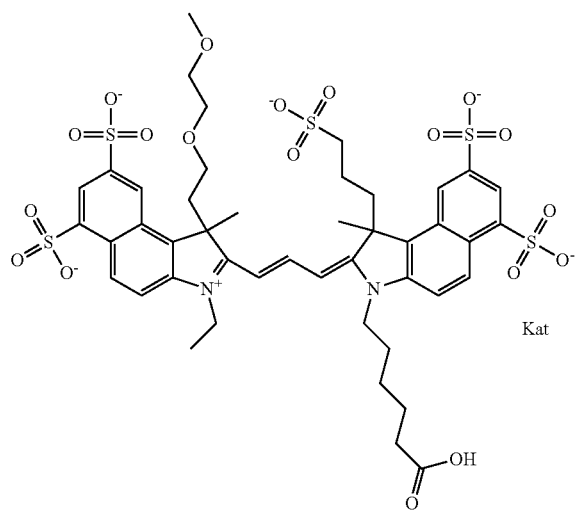

579 Compound 0/1 (2-((1E,3E)-3-(3-(5-carboxypentyl)-1-methyl-6,8-disulfonato-1-(3-sulfonatopropyl)-1H-benzo[e]indol-2(3H)-ylidene)prop-1-enyl)-3-ethyl-1-(2-(2-methoxyethoxy)ethyl)-1-methyl-1H-benzo[e]indolium-6,8-disulfonate) contains diethylene glycol at R1, sulfoalkyl at R2, ethyl at R9, and carboxyalkyl at R10.

In one embodiment, the compound is 579 Compound 0/1

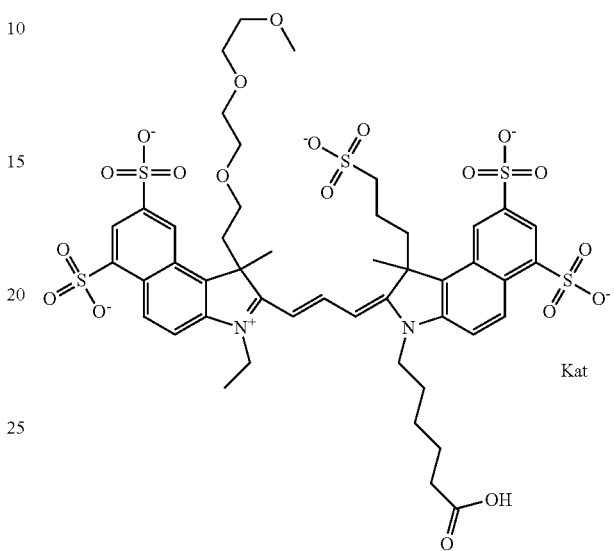

579 Compound 0/1 (2-((1E,3E)-3-(3-(5-carboxypentyl)-1-methyl-6,8-disulfonato-1-(3-sulfonatopropyl)-1H-benzo[e]indol-2(3H)-ylidene)prop-1-enyl)-3-ethyl-1-(2-(2-(2-methoxyethoxy)ethoxy)ethyl)-1-methyl-1H-benzo[e]indolium-6,8-disulfonate) contains (poly)ethylene glycol (PEG₃) at R1, sulfoalkyl at R2, ethyl at R9, and carboxyalkyl at R10.

In one embodiment, the compound is 579 Compound 0/1

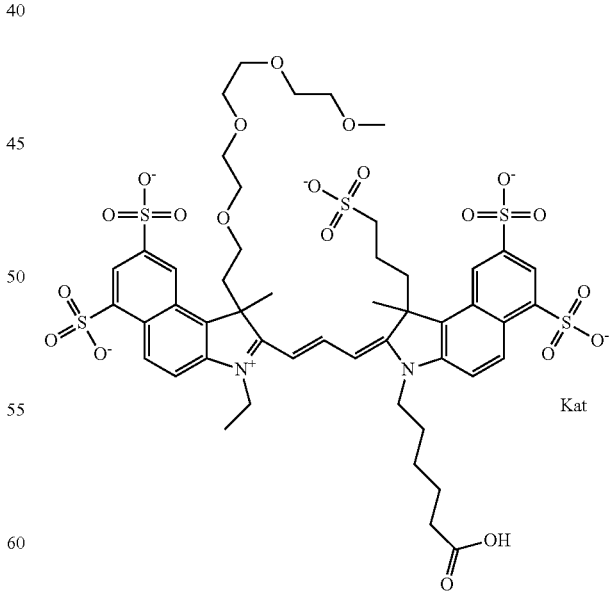

579 Compound 0/1 (2-((1E,3E)-3-(3-(5-carboxypentyl)-1-methyl-6,8-disulfonato-1-(3-sulfonatopropyl)-1H-benzo[e]indol-2(3H)-ylidene)prop-1-enyl)-3-ethyl-1-methyl-1-(2,5,8,11-tetraoxatridecan-13-yl)-1H-benzo[e]indolium-6,8- disulfonate) contains (poly)ethylene glycol (PEG$_4$) at R1, sulfoalkyl at R2, ethyl at R9, and carboxyalkyl at R10.

In one embodiment, the compound is 579 Compound 0/1

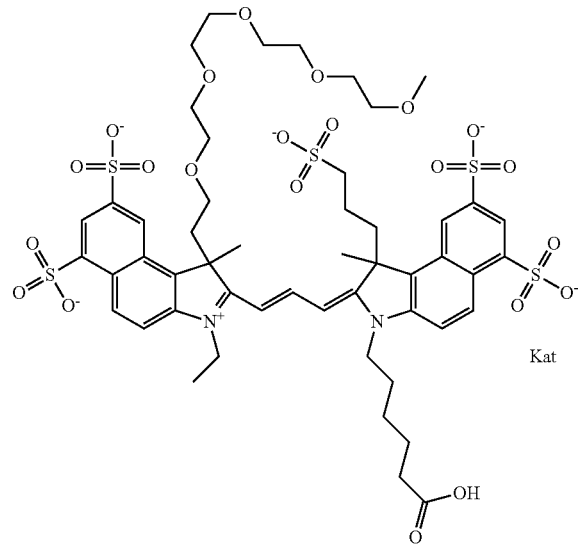

579 Compound 0/1 (2-((1E,3E)-3-(3-(5-carboxypentyl)-1-methyl-6,8-disulfonato-1-(3-sulfonatopropyl)-1H-benzo[e]indol-2(3H)-ylidene)prop-1-enyl)-3-ethyl-1-(2,5,8,11,14-pentaoxahexadecan-16-yl)-1-methyl-1H-benzo[e]indolium-6,8-disulfonate) contains (poly)ethylene glycol (PEG$_5$) at R1, sulfoalkyl at R2, ethyl at R9, and carboxyalkyl at R10.

In one embodiment, the compound is 579 Compound 0/1

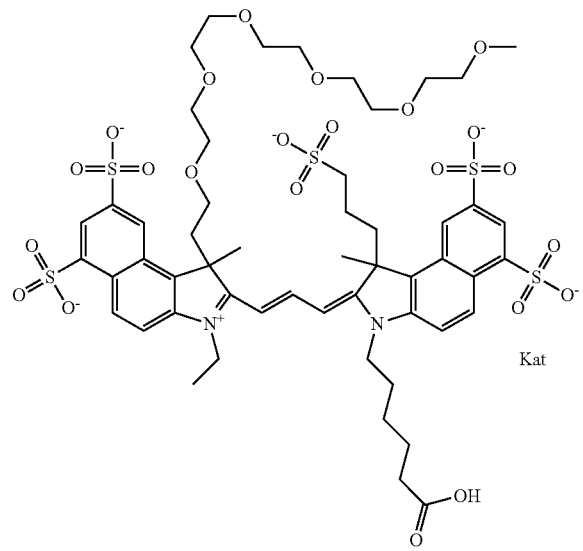

579 Compound 0/1 (2-((1E,3E)-3-(3-(5-carboxypentyl)-1-methyl-6,8-disulfonato-1-(3-sulfonatopropyl)-1H-benzo[e]indol-2(3H)-ylidene)prop-1-enyl)-3-ethyl-1-methyl-1-(2,5,8,11,14,17-hexaoxanonadecan-19-yl)-1H-benzo[e]indolium-6,8-disulfonate) contains a (poly)ethylene glycol (PEG$_6$) at R1, a sulfoalkyl at R2, an ethyl at R9, and carboxyalkyl at R10.

In one embodiment, the compound is 579 Compound 0/2

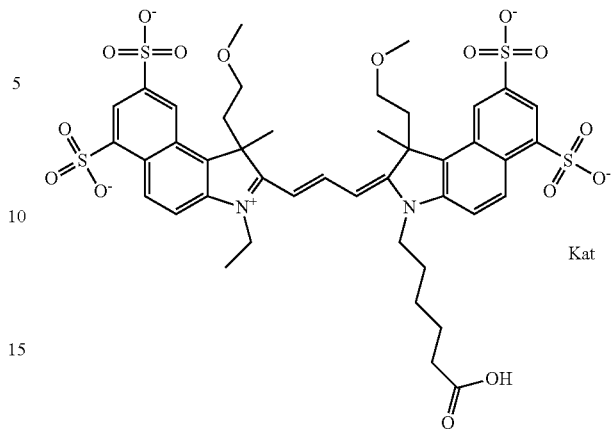

579 Compound 0/2 (2-((1E,3E)-3-(3-(5-carboxypentyl)-1-(2-methoxyethyl)-1-methyl-6,8-disulfonato-1H-benzo[e]indol-2(3H)-ylidene)prop-1-enyl)-3-ethyl-1-(2-methoxyethyl)-1-methyl-1H-benzo[e]indolium-6,8-disulfonate) contains an ethylene glycol at R1 and R2, ethyl at R9, and carboxyalkyl at R10.

One non-limiting example of an activated compound is the NHS-ester of 579 Compound 0/2, shown below:

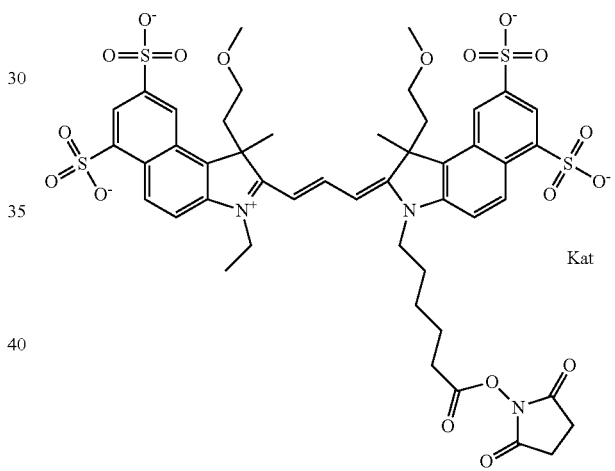

In one embodiment, the compound is 579 Compound 0/2

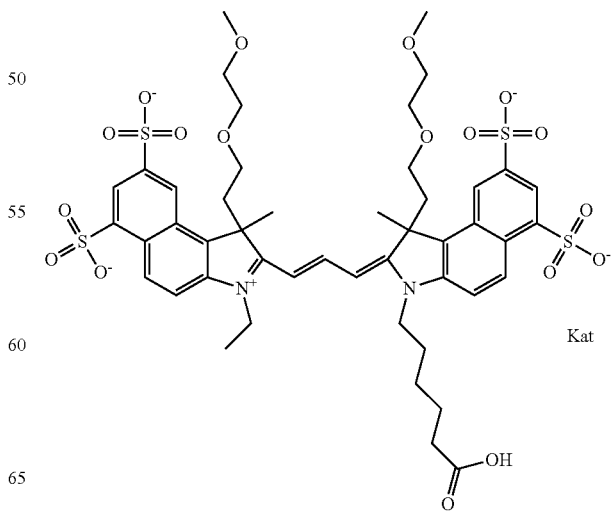

579 Compound 0/2 (2-((1E,3E)-3-(3-(5-carboxypentyl)-1-(2-(2-methoxyethoxy)ethyl)-1-methyl-6,8-disulfonato-1H-benzo[e]indol-2(3H)-ylidene)prop-1-enyl)-3-ethyl-1-(2-(2-methoxyethoxy)ethyl)-1-methyl-1H-benzo[e]indolium-6,8-disulfonate) contains a diethylene glycol at R1 and R2, ethyl at R9, and carboxyalkyl at R10.

In one embodiment, the compound is 579 Compound 0/2

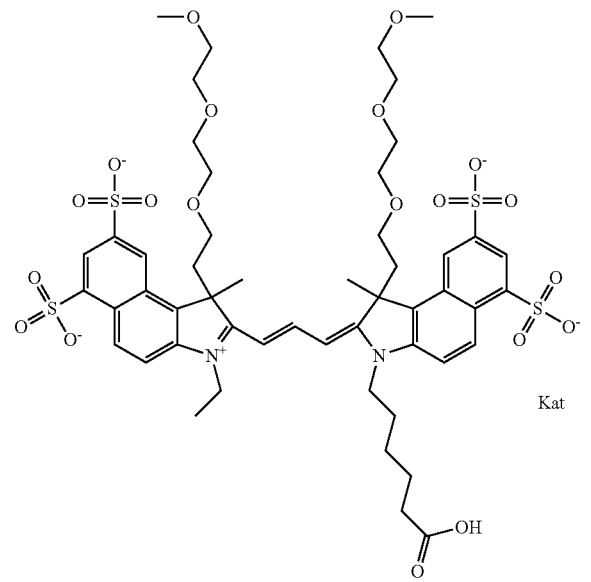 [SMILES: CC[N+]1=C(/C=C/C=C2/N(CCCCCC(=O)O)c3ccc4c(S(=O)(=O)[O-])cc(S(=O)(=O)[O-])cc4c3C2(C)CCOCCOCCOC)C(C)(CCOCCOCCOC)c2c1ccc1c(S(=O)(=O)[O-])cc(S(=O)(=O)[O-])cc21]

579 Compound 0/2 (2-((1E,3E)-3-(3-(5-carboxypentyl)-1-(2-(2-(2-methoxyethoxy)ethoxy)ethyl)-1-methyl-6,8-disulfonato-1H-benzo[e]indol-2(3H)-ylidene)prop-1-enyl)-3-ethyl-1-(2-(2-(2-methoxyethoxy)ethoxy)ethyl)-1-methyl-1H-benzo[e]indolium-6,8-disulfonate) contains a (poly)ethylene glycol (PEG$_3$) at R1 and R2, ethyl at R9, and carboxyalkyl at R10.

In one embodiment, the compound is 579 Compound 0/2

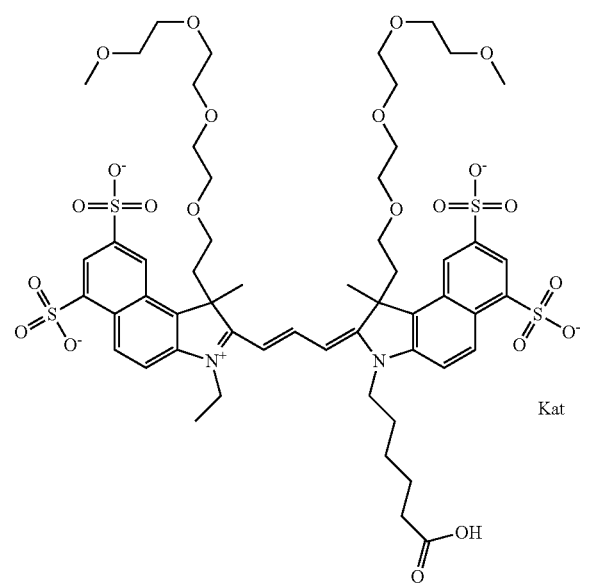 [SMILES: CC[N+]1=C(/C=C/C=C2/N(CCCCCC(=O)O)c3ccc4c(S(=O)(=O)[O-])cc(S(=O)(=O)[O-])cc4c3C2(C)CCOCCOCCOCCOC)C(C)(CCOCCOCCOCCOC)c2c1ccc1c(S(=O)(=O)[O-])cc(S(=O)(=O)[O-])cc21]

579 Compound 0/2 (2-((1E,3E)-3-(3-(5-carboxypentyl)-1-methyl-6,8-disulfonato-1-(2,5,8,11-tetraoxatridecan-13-yl)-1H-benzo[e]indol-2(3H)-ylidene)prop-1-enyl)-3-ethyl-1-methyl-1-(2,5,8,11-tetraoxatridecan-13-yl)-1H-benzo[e]indolium-6,8-disulfonate) contains a (poly)ethylene glycol (PEG$_4$) at R1 and R2, ethyl at R9, and carboxyalkyl at R10.

In one embodiment, the compound is 579 Compound 0/2

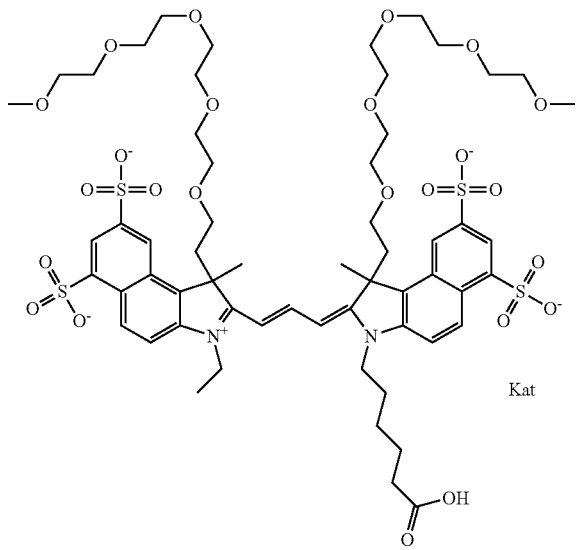

579 Compound 0/2 (2-((1E,3E)-3-(3-(5-carboxypentyl)-1-(2,5,8,11,14-pentaoxahexadecan-16-yl)-1-methyl-6,8-disulfonato-1H-benzo[e]indol-2(3H)-ylidene)prop-1-enyl)-3-ethyl-1-(2,5,8,11,14-pentaoxahexadecan-16-yl)-1-methyl-1H-benzo[e]indolium-6,8-disulfonate) contains a (poly)ethylene glycol (PEG$_5$) at R1 and R2, ethyl at R9, and carboxyalkyl at R10.

In one embodiment, the compound is 579 Compound 0/2

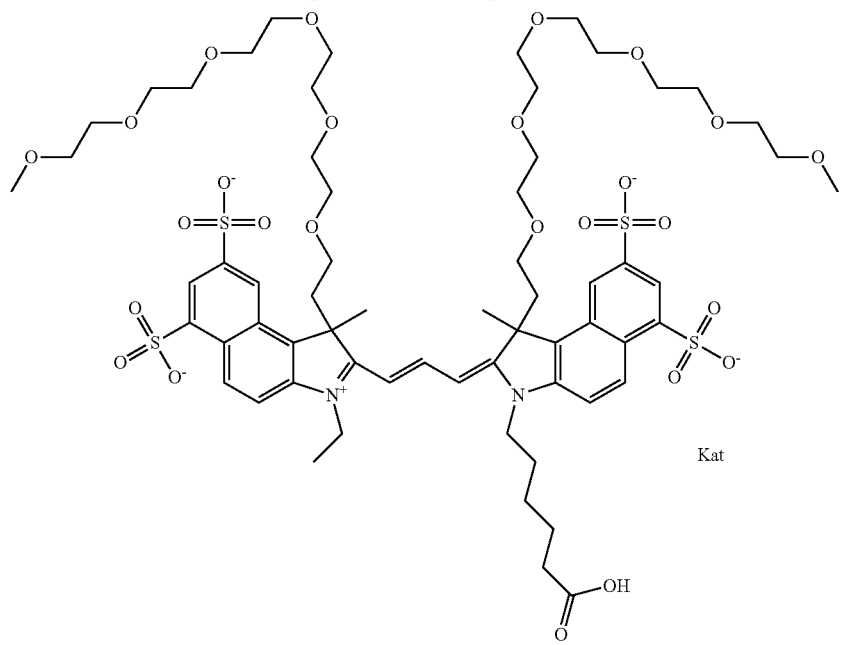

579 Compound 0/2 (2-((1E,3E)-3-(3-(5-carboxypentyl)-1-methyl-1-(2,5,8,11,14,17-hexaoxanonadecan-19-yl)-6,8-disulfonato-1H-benzo[e]indol-2(3H)-ylidene)prop-1-enyl)-3-ethyl-1-methyl-1-(2,5,8,11,14,17-hexaoxanonadecan-19-yl)-1H-benzo[e]indolium-6,8-disulfonate) contains a (poly) ethylene glycol (PEG$_6$) at R1 and R2, ethyl at R9, and carboxyalkyl at R10.

In one embodiment, the compound is 579 Compound 0/1

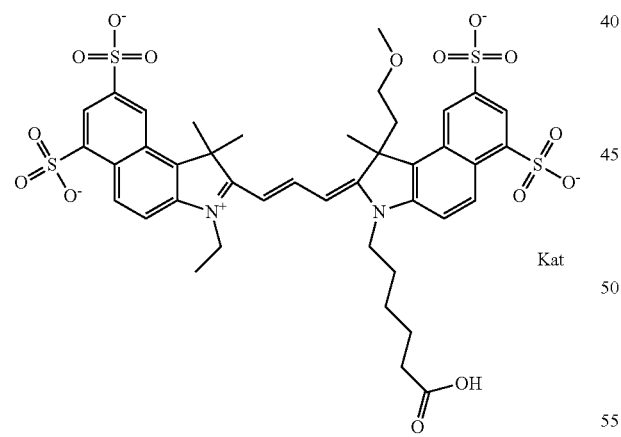

579 Compound 0/1 (2-((1E,3E)-3-(3-(5-carboxypentyl)-1-(2-methoxyethyl)-1-methyl-6,8-disulfonato-1H-benzo[e]indol-2(3H)-ylidene)prop-1-enyl)-3-ethyl-1,1-dimethyl-1H-benzo[e]indolium-6,8-disulfonate) contains an ethylene glycol at R2, a methyl at R1, ethyl at R9, and carboxyalkyl at R10.

One non-limiting example of an activated compound is the NHS-ester of 579 Compound 0/1, shown below:

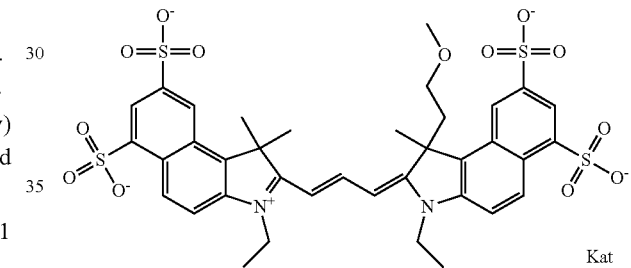

In one embodiment, the compound is 579 Compound 0/1

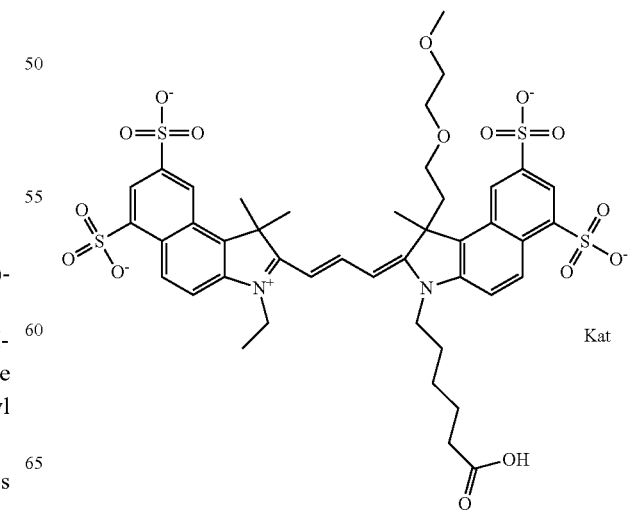

579 Compound 0/1 (2-((1E,3E)-3-(3-(5-carboxypentyl)-1-(2-(2-methoxyethoxy)ethyl)-1-methyl-6,8-disulfonato-1H-benzo[e]indol-2(3H)-ylidene)prop-1-enyl)-3-ethyl-1,1-dimethyl-1H-benzo[e]indolium-6,8-disulfonate) contains a diethylene glycol at R2, a methyl at R1, ethyl at R9, and carboxyalkyl at R10.

In one embodiment, the compound is 579 Compound 0/1

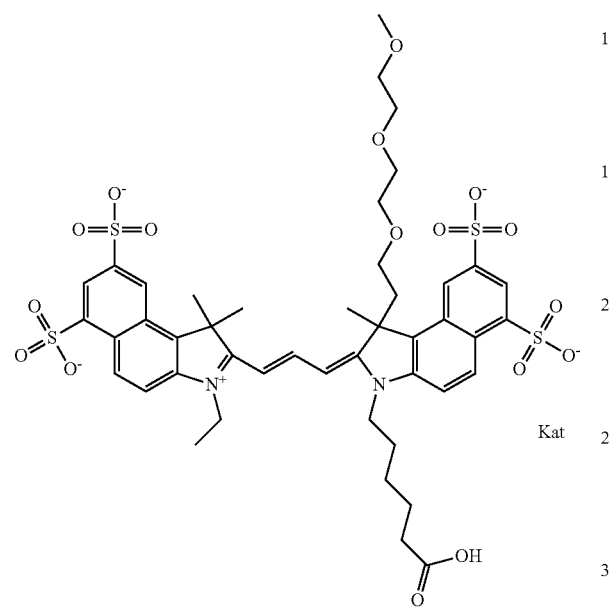

579 Compound 0/1 (2-((1E,3E)-3-(3-(5-carboxypentyl)-1-(2-(2-(2-methoxyethoxy)ethoxy)ethyl)-1-methyl-6,8-disulfonato-1H-benzo[e]indol-2(3H)-ylidene)prop-1-enyl)-3-ethyl-1,1-dimethyl-1H-benzo[e]indolium-6,8-disulfonate) contains a (poly)ethylene glycol ($PEG_3$) at R2, a methyl at R1, ethyl at R9, and carboxyalkyl at R10.

In one embodiment, the compound is 579 Compound 0/1

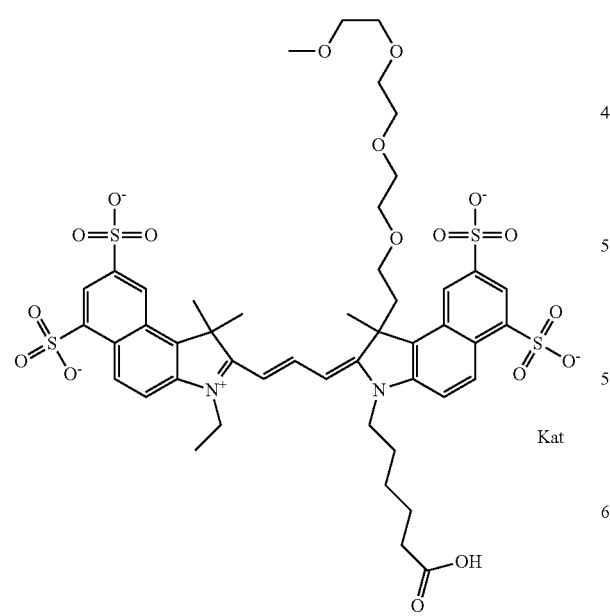

579 Compound 0/1 (2-((1E,3E)-3-(3-(5-carboxypentyl)-1-methyl-6,8-disulfonato-1-(2,5,8,11-tetraoxatridecan-13-yl)-1H-benzo[e]indol-2(3H)-ylidene)prop-1-enyl)-3-ethyl-1,1-dimethyl-1H-benzo[e]indolium-6,8-disulfonate) contains a (poly)ethylene glycol ($PEG_4$) at R2, a methyl at R1, ethyl at R9, and carboxyalkyl at R10.

In one embodiment, the compound is 579 Compound 0/1

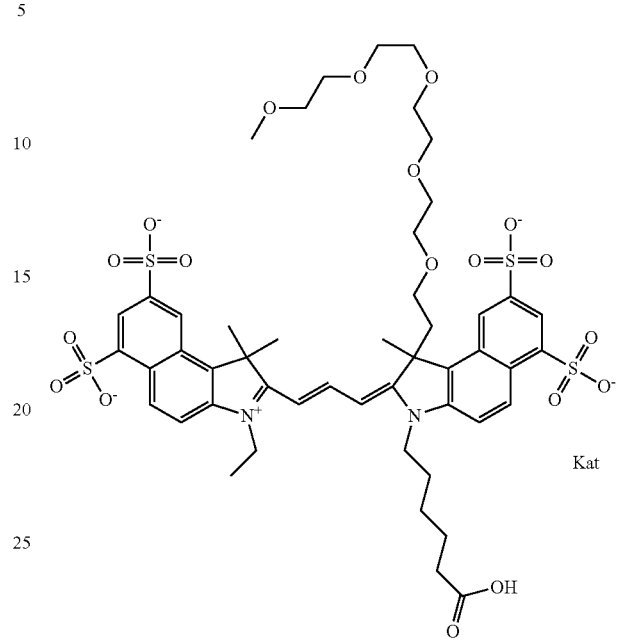

579 Compound 0/1 (2-((1E,3E)-3-(3-(5-carboxypentyl)-1-(2,5,8,11,14-pentaoxahexadecan-16-yl)-1-methyl-6,8-disulfonato-1H-benzo[e]indol-2(3H)-ylidene)prop-1-enyl)-3-ethyl-1,1-dimethyl-1H-benzo[e]indolium-6,8-disulfonate) contains a (poly)ethylene glycol ($PEG_5$) at R2, a methyl at R1, ethyl at R9, and carboxyalkyl at R10.

In one embodiment, the compound is 579 Compound 0/1

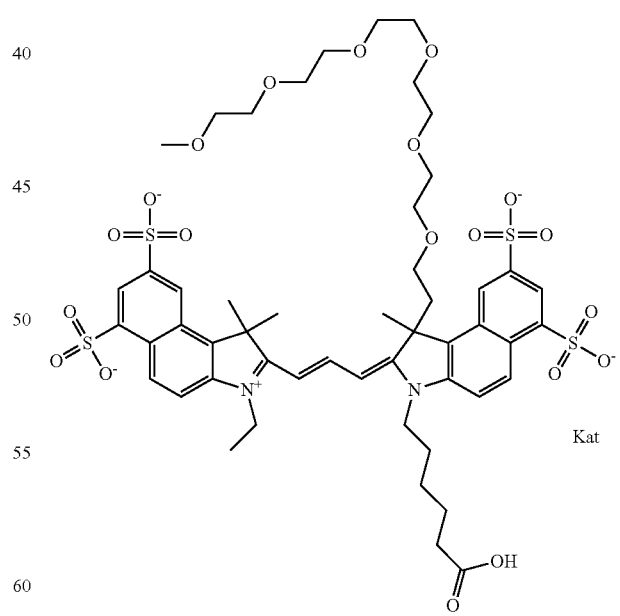

579 Compound 0/1 (2-((1E,3E)-3-(3-(5-carboxypentyl)-1-methyl-1-(2,5,8,11,14,17-hexaoxanonadecan-19-yl)-6,8-disulfonato-1H-benzo[e]indol-2(3H)-ylidene)prop-1-enyl)-3-ethyl-1,1-dimethyl-1H-benzo[e]indolium-6,8-disulfonate) contains a (poly)ethylene glycol ($PEG_6$) at R2, a methyl at R1, ethyl at R9, and carboxyalkyl at R10.

In one embodiment, the compound is 579 Compound 0/1

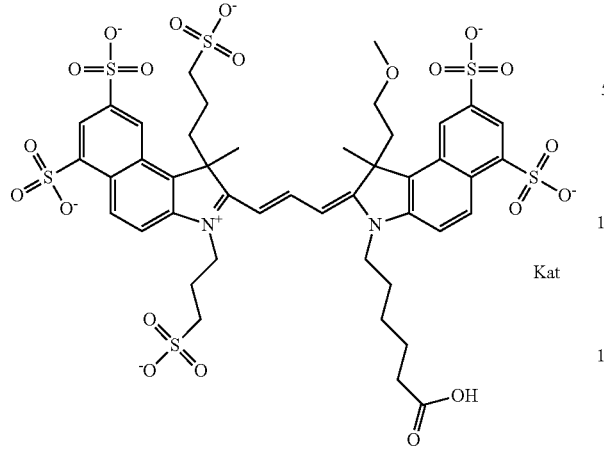

579 Compound 0/1 (2-((1E,3E)-3-(3-(5-carboxypentyl)-1-(2-methoxyethyl)-1-methyl-6,8-disulfonato-1H-benzo[e]indol-2(3H)-ylidene)prop-1-enyl)-1-methyl-1,3-bis(3-sulfonatopropyl)-1H-benzo[e]indolium-6,8-disulfonate) contains an ethylene glycol at R2, a sulfoalkyl at R1, a sulfoalkyl at R9, and carboxyalkyl at R10.

One non-limiting example of an activated compound is the NHS-ester of 579 Compound 0/1, shown below:

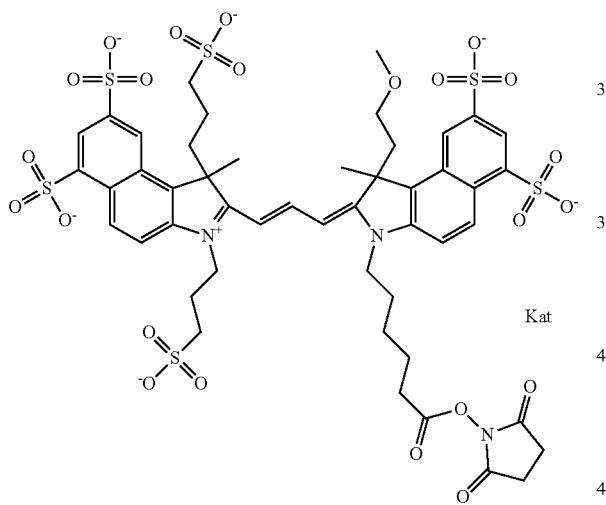

In one embodiment, the compound is 579 Compound 0/1

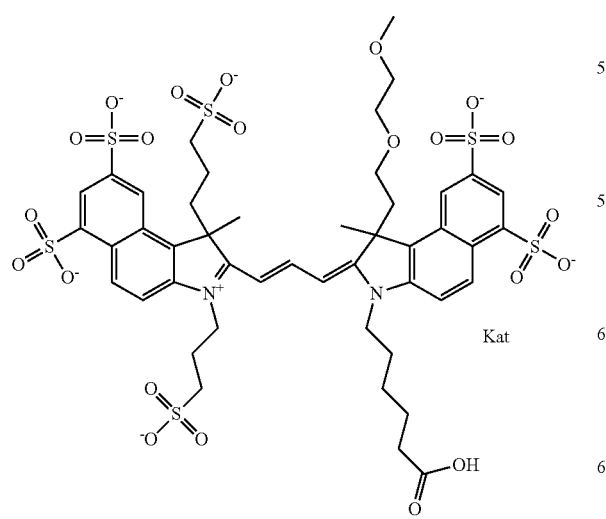

579 Compound 0/1 (2-((1E,3E)-3-(3-(5-carboxypentyl)-1-(2-(2-methoxyethoxy)ethyl)-1-methyl-6,8-disulfonato-1H-benzo[e]indol-2(3H)-ylidene)prop-1-enyl)-1-methyl-1,3-bis(3-sulfonatopropyl)-1H-benzo[e]indolium-6,8-disulfonate) contains a diethylene glycol at R2, a sulfoalkyl at R1, a sulfoalkyl at R9, and carboxyalkyl at R10.

In one embodiment, the compound is 579 Compound 0/1

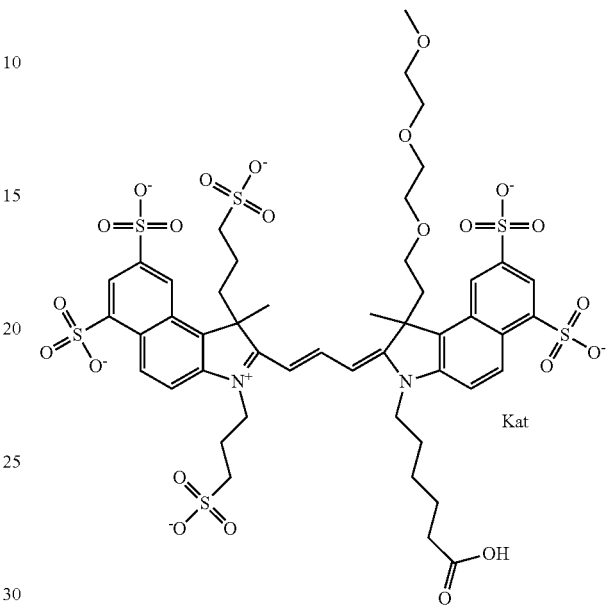

579 Compound 0/1 (2-((1E,3E)-3-(3-(5-carboxypentyl)-1-(2-(2-(2-methoxyethoxy)ethoxy)ethyl)-1-methyl-6,8-disulfonato-1H-benzo[e]indol-2(3H)-ylidene)prop-1-enyl)-1-methyl-1,3-bis(3-sulfonatopropyl)-1H-benzo[e]indolium-6,8-disulfonate) contains a (poly)ethylene glycol (PEG$_3$) at R2, a sulfoalkyl at R1, a sulfoalkyl at R9, and carboxyalkyl at R10.

In one embodiment, the compound is 579 Compound 0/1

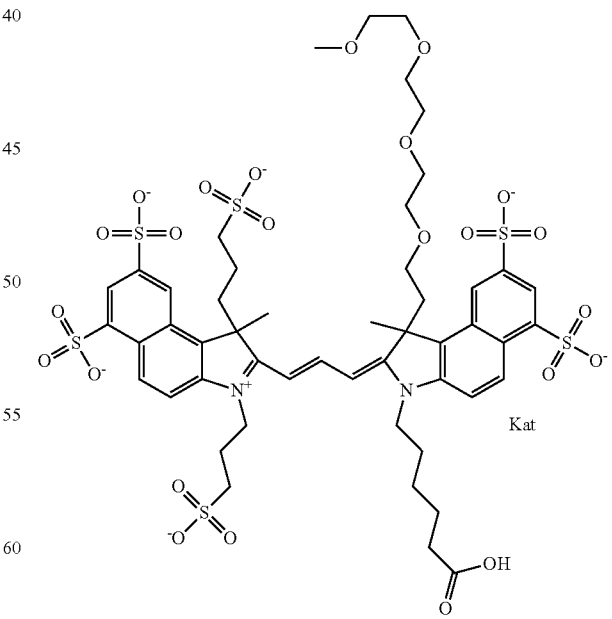

579 Compound 0/1 (2-((1E,3E)-3-(3-(5-carboxypentyl)-1-methyl-6,8-disulfonato-1-(2,5,8,11-tetraoxatridecan-13-yl)-1H-benzo[e]indol-2(3H)-ylidene)prop-1-enyl)-1-methyl-1,3-bis(3-sulfonatopropyl)-1H-benzo[e]indolium-6, 8-disulfonate) contains a (poly)ethylene glycol (PEG$_4$) at R2, a sulfoalkyl at R1, a sulfoalkyl at R9, and carboxyalkyl at R10.

In one embodiment, the compound is 579 Compound 0/1

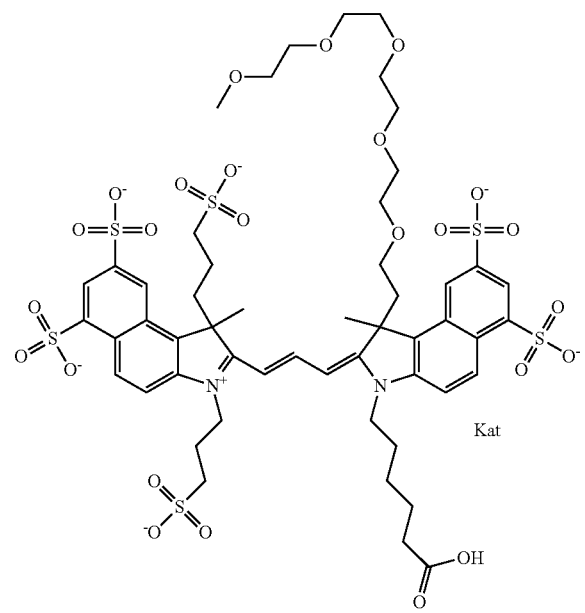

579 Compound 0/1 (2-((1E,3E)-3-(3-(5-carboxypentyl)-1-(2,5,8,11,14-pentaoxahexadecan-16-yl)-1-methyl-6,8-disulfonato-1H-benzo[e]indol-2(3H)-ylidene)prop-1-enyl)-1-methyl-1,3-bis(3-sulfonatopropyl)-1H-benzo[e]indolium-6,8-disulfonate) contains a (poly)ethylene glycol (PEG$_5$) at R2, a sulfoalkyl at R1, ethyl at R9, and carboxyalkyl at R10.

In one embodiment, the compound is 579 Compound 0/1

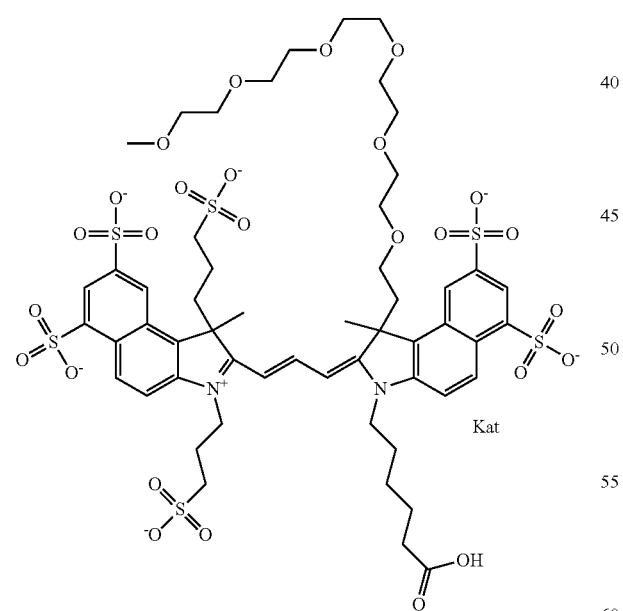

579 Compound 0/1 (2-((1E,3E)-3-(3-(5-carboxypentyl)-1-methyl-1-(2,5,8,11,14,17-hexaoxanonadecan-19-yl)-6,8-disulfonato-1H-benzo[e]indol-2(3H)-ylidene)prop-1-enyl)-1-methyl-1,3-bis(3-sulfonatopropyl)-1H-benzo[e]indolium-6,8-disulfonate) contains a (poly)ethylene glycol (PEG$_6$) at R2, a sulfoalkyl at R1, ethyl at R9, and carboxyalkyl at R10.

In one embodiment, the compound is 579 Compound 0/2

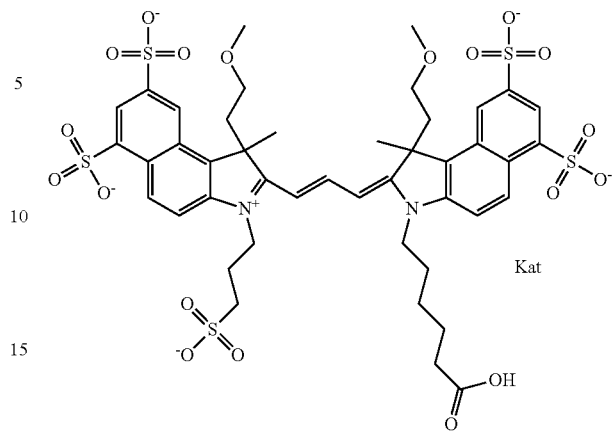

579 Compound 0/2 (2-((1E,3E)-3-(3-(5-carboxypentyl)-1-(2-methoxyethyl)-1-methyl-6,8-disulfonato-1H-benzo[e]indol-2(3H)-ylidene)prop-1-enyl)-1-(2-methoxyethyl)-1-methyl-3-(3-sulfonatopropyl)-1H-benzo[e]indolium-6,8-disulfonate) contains ethylene glycol at R1 and R2, a sulfoalkyl at R9, and carboxyalkyl at R10.

One non-limiting example of an activated compound is the NHS-ester of 579 Compound 0/2, shown below:

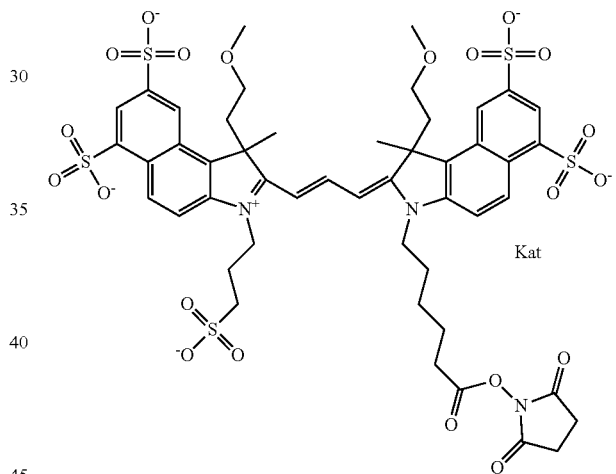

In one embodiment, the compound is 579 Compound 0/2

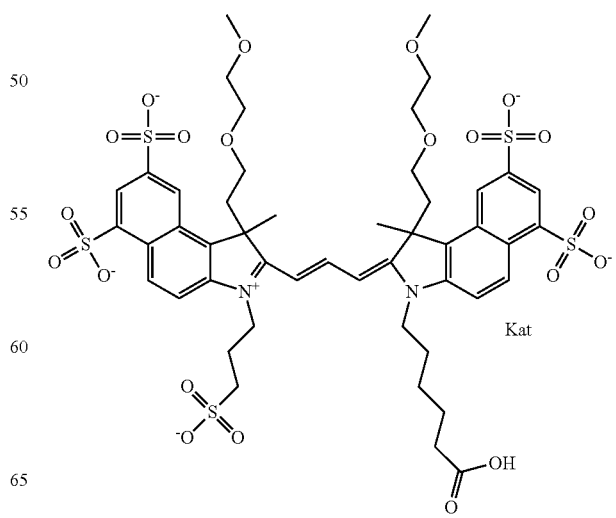

579 Compound 0/2 (2-((1E,3E)-3-(3-(5-carboxypentyl)-1-(2-(2-methoxyethoxy)ethyl)-1-methyl-6,8-disulfonato-1H-benzo[e]indol-2(3H)-ylidene)prop-1-enyl)-1-(2-(2-methoxyethoxy)ethyl)-1-methyl-3-(3-sulfonatopropyl)-1H-benzo[e]indolium-6,8-disulfonate) contains a diethylene glycol at R1 and R2, a sulfoalkyl at R9, and carboxyalkyl at R10.

In one embodiment, the compound is 579 Compound 0/2

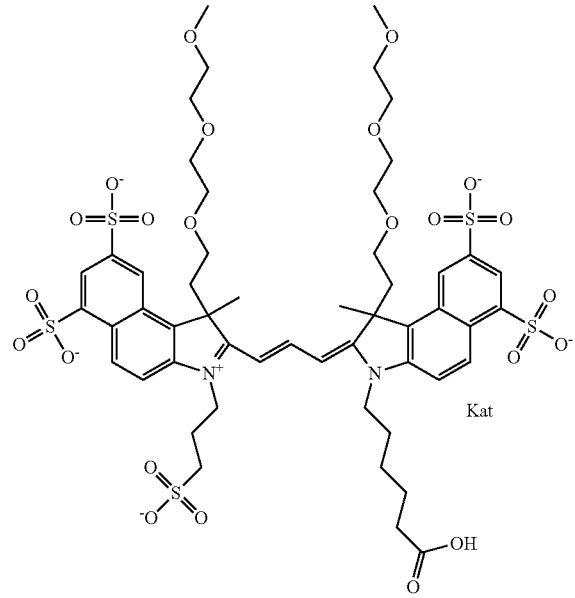

579 Compound 0/2 (2-((1E,3E)-3-(3-(5-carboxypentyl)-1-(2-(2-(2-methoxyethoxy)ethoxy)ethyl)-1-methyl-6,8-disulfonato-1H-benzo[e]indol-2(3H)-ylidene)prop-1-enyl)-1-(2-(2-(2-methoxyethoxy)ethoxy)ethyl)-1-methyl-3-(3-sulfonatopropyl)-1H-benzo[e]indolium-6,8-disulfonate) contains a (poly)ethylene glycol (PEG$_3$) at R1 and R2, a sulfoalkyl at R9, and carboxyalkyl at R10.

In one embodiment, the compound is 579 Compound 0/2

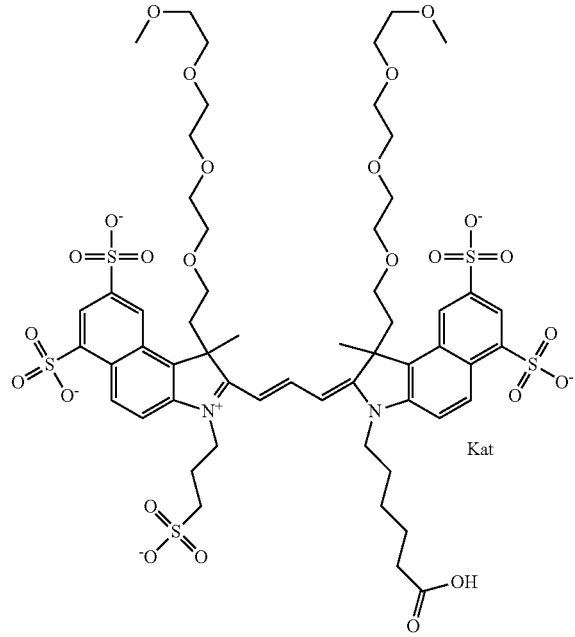

579 Compound 0/2 (2-((1E,3E)-3-(3-(5-carboxypentyl)-1-methyl-6,8-disulfonato-1-(2,5,8,11-tetraoxatridecan-13-yl)-1H-benzo[e]indol-2(3H)-ylidene)prop-1-enyl)-1-methyl-3-(3-sulfonatopropyl)-1-(2,5,8,11-tetraoxatridecan-13-yl)-1H-benzo[e]indolium-6,8-disulfonate) contains a (poly)ethylene glycol (PEG$_4$) at R1 and R2, a sulfoalkyl at R9, and carboxyalkyl at R10.

In one embodiment, the compound is 579 Compound 0/2

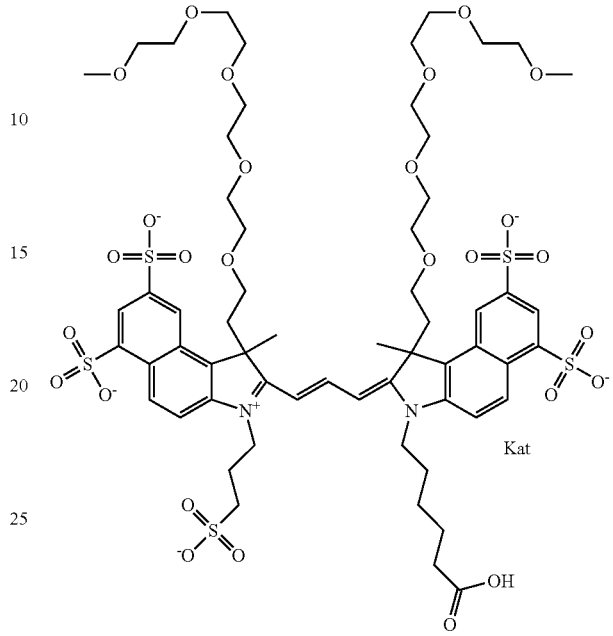

579 Compound 0/2 (2-((1E,3E)-3-(3-(5-carboxypentyl)-1-(2,5,8,11,14-pentaoxahexadecan-16-yl)-1-methyl-6,8-disulfonato-1H-benzo[e]indol-2(3H)-ylidene)prop-1-enyl)-1-(2,5,8,11,14-pentaoxahexadecan-16-yl)-1-methyl-3-(3-sulfonatopropyl)-1H-benzo[e]indolium-6,8-disulfonate) contains a (poly)ethylene glycol (PEG$_5$) at R1 and R2, ethyl at R9, and carboxyalkyl at R10.

In one embodiment, the compound is 579 Compound 0/2

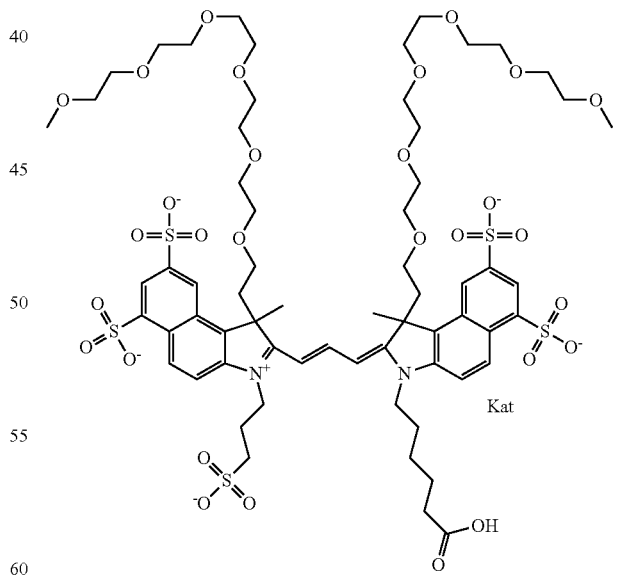

579 Compound 0/2 (2-((1E,3E)-3-(3-(5-carboxypentyl)-1-methyl-1-(2,5,8,11,14,17-hexaoxanonadecan-19-yl)-6,8-disulfonato-1H-benzo[e]indol-2(3H)-ylidene)prop-1-enyl)-1-methyl-1-(2,5,8,11,14,17-hexaoxanonadecan-19-yl)-3-(3-sulfonatopropyl)-1H-benzo[e]indolium-6,8-disulfonate) contains a (poly)ethylene glycol (PEG$_6$) at R1 and R2, ethyl at R9, and carboxyalkyl at R10.

In embodiments, the degree and/or location of sulfonation is varied to, e.g., vary the compound's degree of hydrophilicity or hydrophobicity. One non-limiting example is a monosulfonate form of 579 Compound 1, shown below:

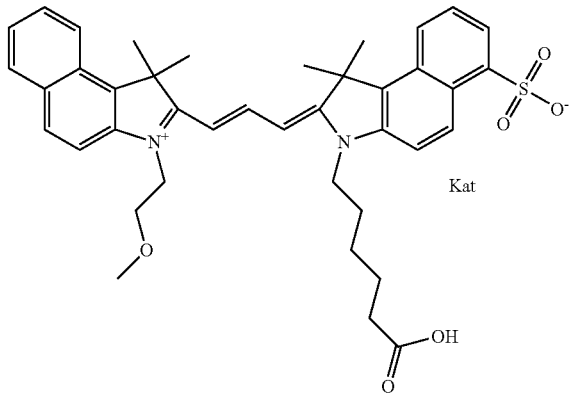 [SMILES: COCC[N+]1=C(/C=C/C=C2/N(CCCCCC(=O)O)c3ccc4c(S(=O)(=O)[O-])cccc4c3C2(C)C)C(C)(C)c2c1ccc1ccccc21]

One non-limiting example is a disulfonate form of 579 Compound 1, shown below:

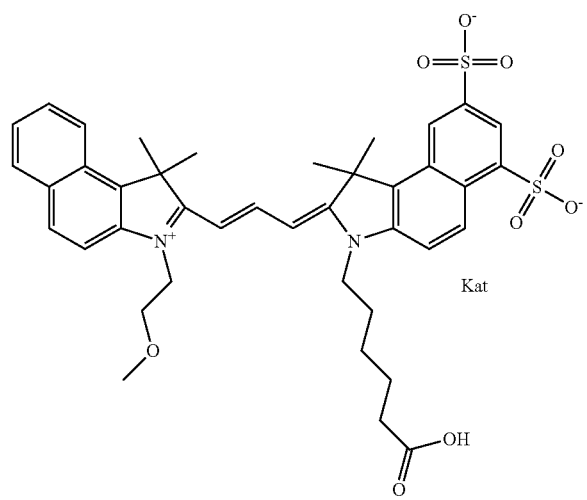 [SMILES: COCC[N+]1=C(/C=C/C=C2/N(CCCCCC(=O)O)c3ccc4c(S(=O)(=O)[O-])cc(S(=O)(=O)[O-])cc4c3C2(C)C)C(C)(C)c2c1ccc1ccccc21]

One non-limiting example is a trisulfonate form of 579 Compound 1, shown below:

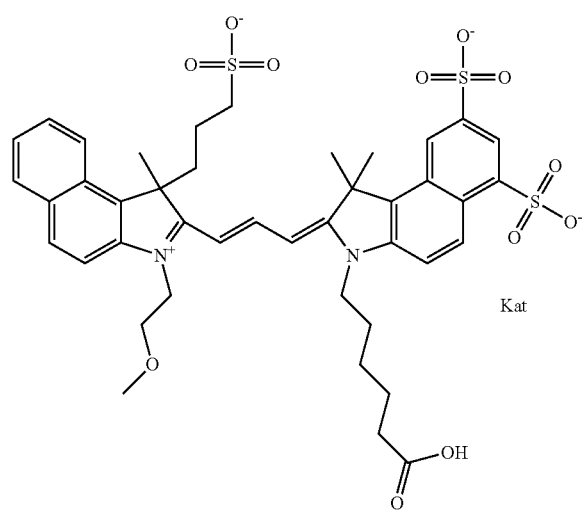 [SMILES: COCC[N+]1=C(/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1ccccc21]

One non-limiting example is a tetrasulfonate form of 579 Compound 1, shown below:

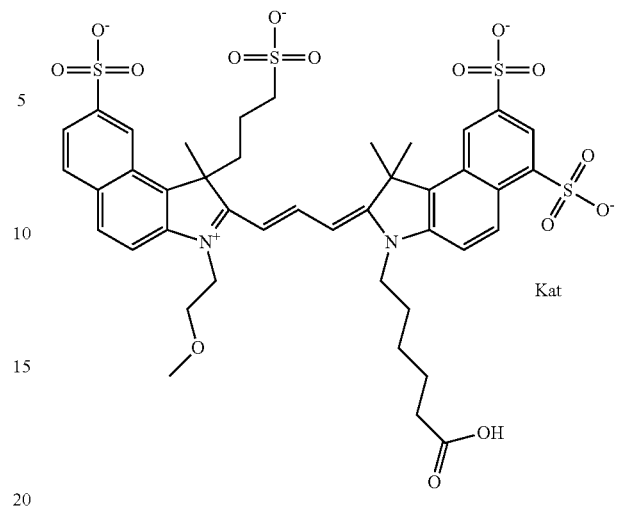

One non-limiting example is a pentasulfonate form of 579 Compound 1, shown below:

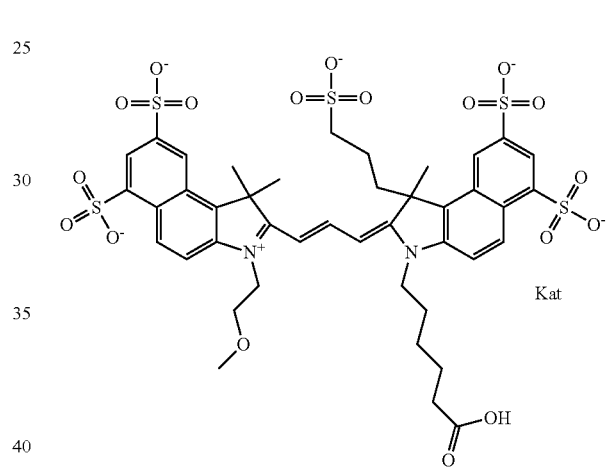

One non-limiting example is a monosulfonate form of 579 Compound 0/1, shown below:

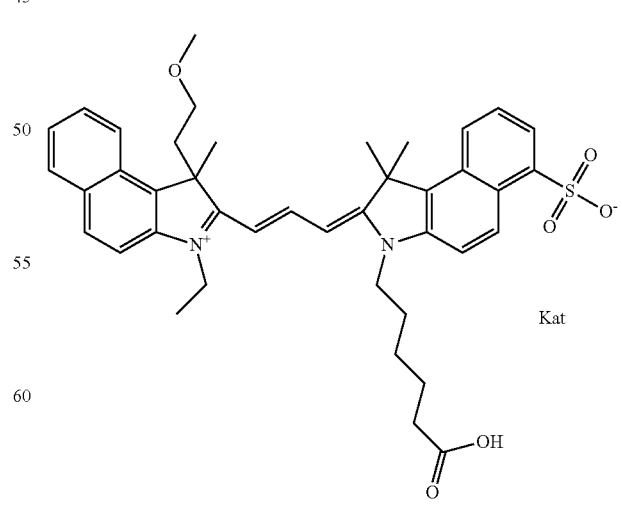

One non-limiting example is a disulfonate form of 579 Compound 0/1, shown below:

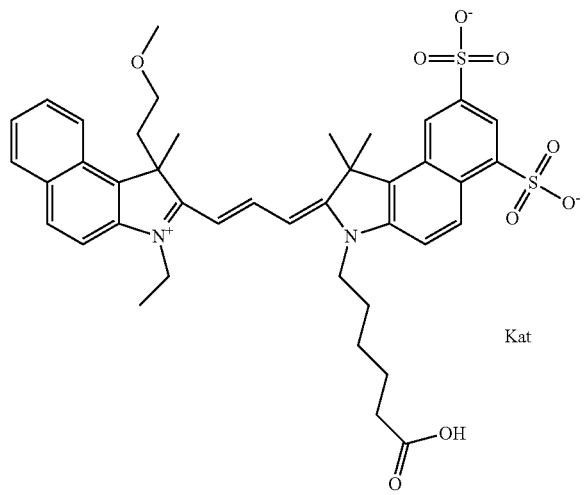 [SMILES: CC[N+]1=C(/C=C/C=C2/N(CCCCCC(=O)O)c3ccc4c(S(=O)(=O)[O-])cc(S(=O)(=O)[O-])cc4c3C2(C)C)C(C)(CCOC)c2c1ccc1ccccc21]

One non-limiting example is a trisulfonate form of 579 Compound 0/1, shown below:

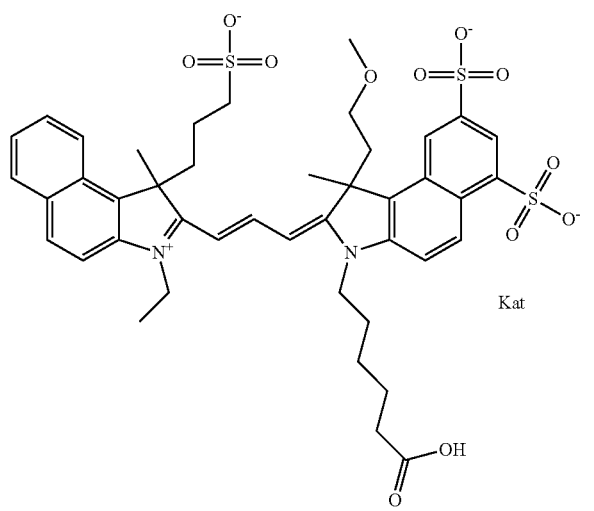 [SMILES: CC[N+]1=C(/C=C/C=C2/N(CCCCCC(=O)O)c3ccc4c(S(=O)(=O)[O-])cc(S(=O)(=O)[O-])cc4c3C2(C)CCOC)C(C)(CCCS(=O)(=O)[O-])c2c1ccc1ccccc21]

One non-limiting example is a tetrasulfonate form of 579 Compound 0/1, shown below:

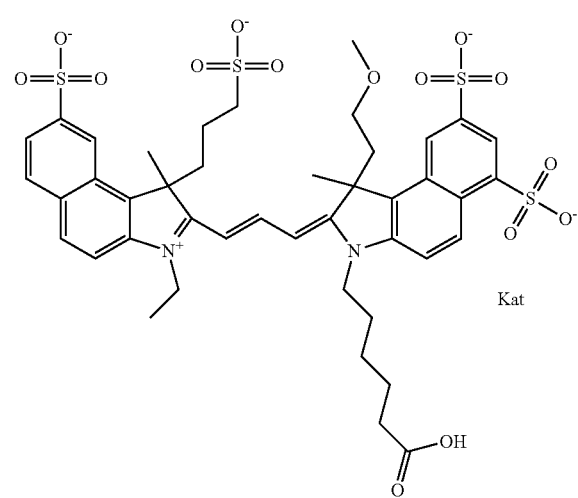 [SMILES: CC[N+]1=C(/C=C/C=C2/N(CCCCCC(=O)O)c3ccc4c(S(=O)(=O)[O-])cc(S(=O)(=O)[O-])cc4c3C2(C)CCOC)C(C)(CCCS(=O)(=O)[O-])c2c1ccc1ccc(S(=O)(=O)[O-])cc21]

One non-limiting example is a pentasulfonate form of 579 Compound 0/1, shown below:

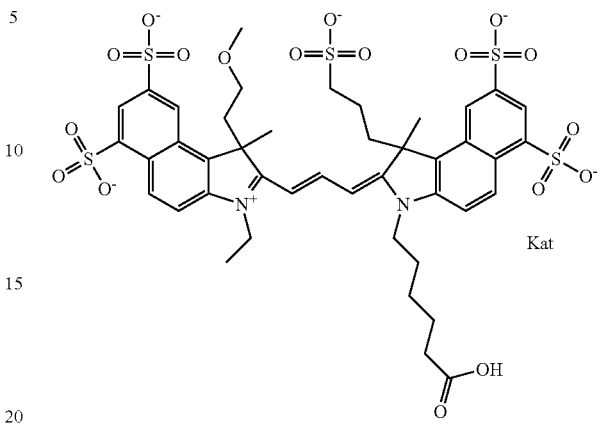

In one embodiment, the compound is 579 Compound 1/2 (PEG$_4$)

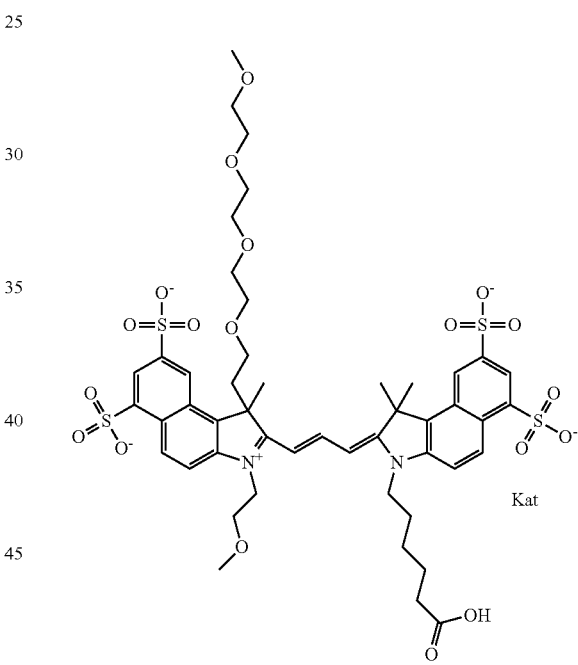

One non-limiting example of 579 Compound 1/2 (PEG$_4$) (2-((1E,3E)-3-(3-(5-carboxypentyl)-1,1-dimethyl-6,8-disulfonato-1H-benzo[e]indol-2(3H)-ylidene)prop-1-enyl)-3-(2-methoxyethyl)-1-methyl-1-(2,5,8,11-tetraoxatridecan-13-yl)-1H-benzo[e]indolium-6,8-disulfonate) contains an ethylene glycol on the indole N of the left heterocycle, i.e., a methylated ethylene glycol, and a methylated PEG$_4$ group. The methyl group on the ethylene glycol/PEG prevents the terminal —OH from oxidation. Oxidation is known to occur, over time, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 579 Compound 1/2 (PEG$_4$), but one skilled in the art appreciates that activation is not limited to these examples. One non-limiting example of an activated compound is the NHS-ester of 579 Compound 1/2 (PEG$_4$), shown below:

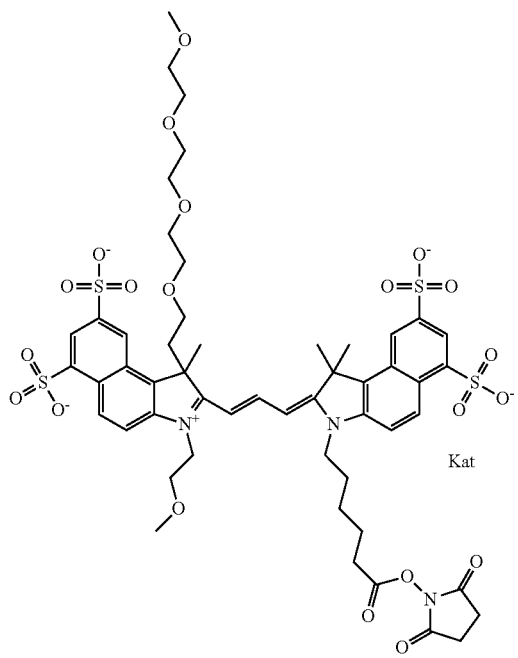 [SMILES: COCCOCCOCCOCCC1(C)C(/C=C/C=C2/N(CCCCCC(=O)ON3C(=O)CCC3=O)c3ccc4c(S(=O)(=O)[O-])cc(S(=O)(=O)[O-])cc4c3C2(C)C)=[N+](CCOC)c2ccc3c(S(=O)(=O)[O-])cc(S(=O)(=O)[O-])cc3c21]

One non-limiting example of a NHS-ester of 579 Compound 1/3 (PEG$_4$), according to general formula III, where m=1 and p=1, is shown below:

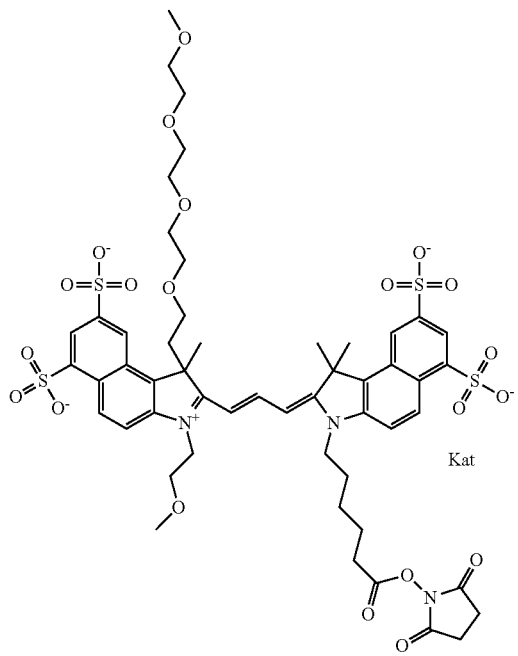

One non-limiting example of a NHS-ester of 579 Compound 1/3 (PEG$_4$), according to general formula III, where m=1 and p=2, is shown below:

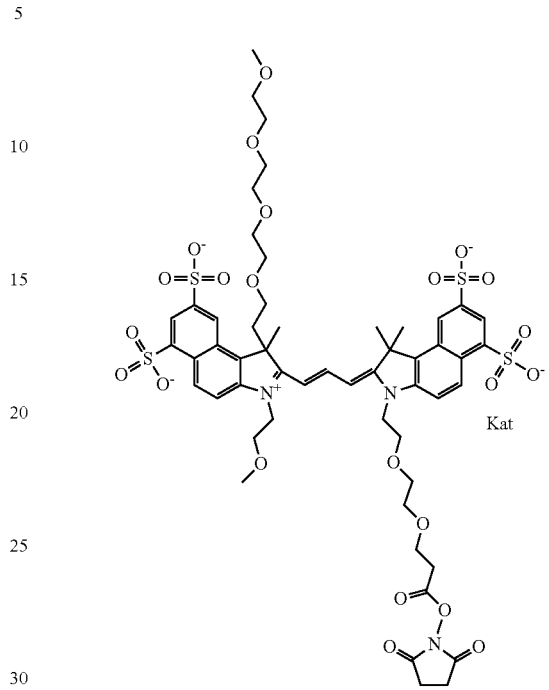

One non-limiting example of a NHS-ester of 579 Compound 1/3 (PEG$_4$), according to general formula III, where m=1 and p=3, is shown below:

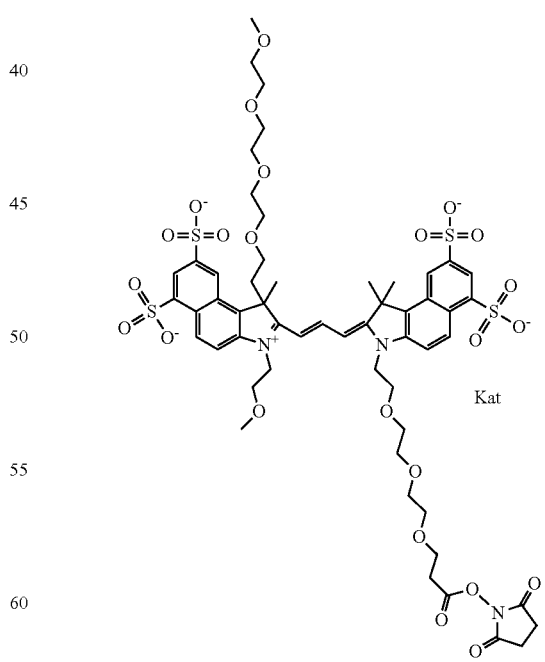

One non-limiting example of a NHS-ester of 579 Compound 1/3 (PEG$_4$), according to general formula III, where m=1 and p=4, is shown below:

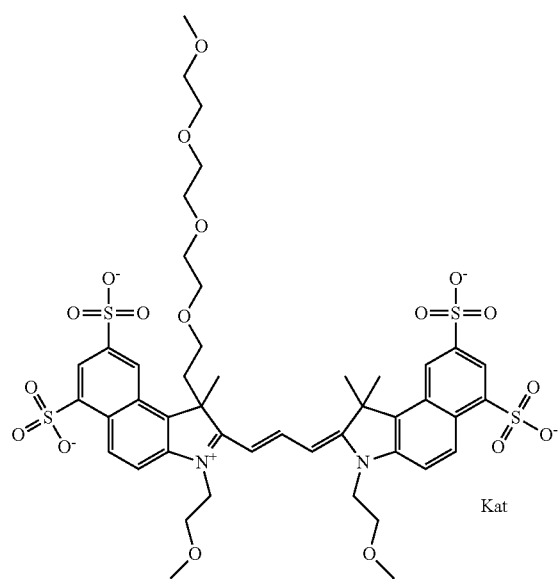
One non-limiting example of a NHS-ester of 579 Compound 1/3 (PEG$_4$), according to general formula III, where m=1 and p=5, is shown below:
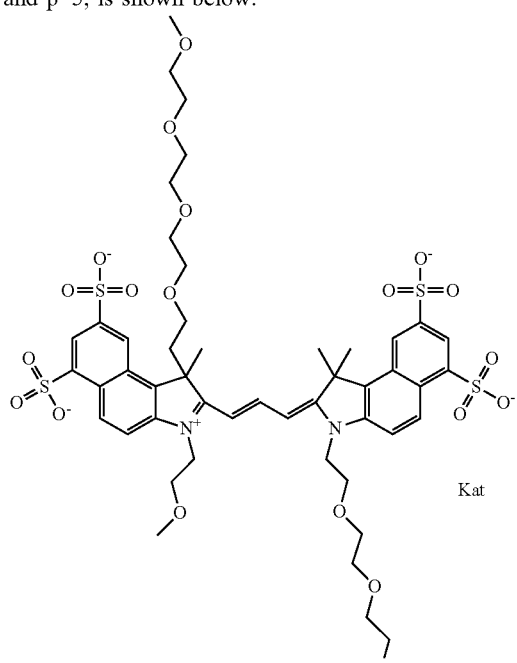
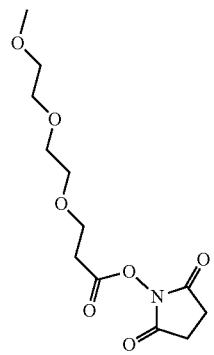
One non-limiting example of a NHS-ester of 579 Compound 1/3 (PEG$_4$), according to general formula III, where m=1 and p=6, is shown below:
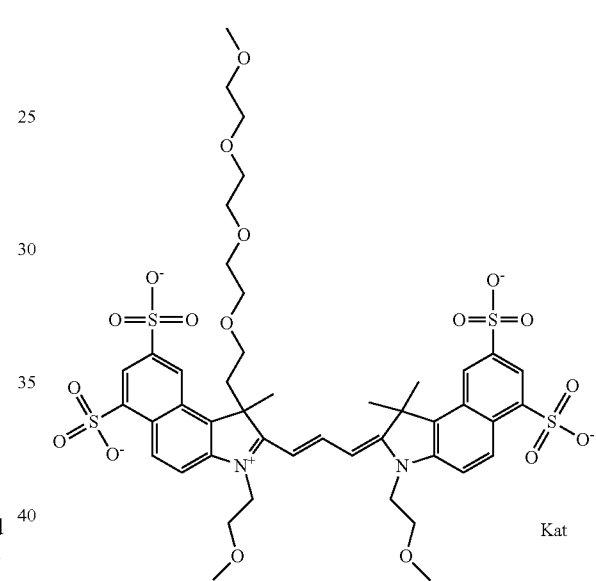

One non-limiting example of an activated 579 Compound 1/2 (PEG$_4$) is a tetrafluorophenyl (TFP)-ester form of 579 Compound 1, shown below:

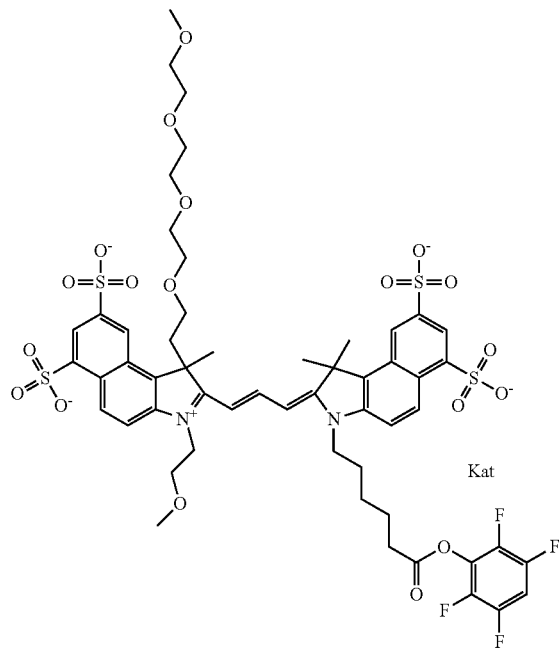 [SMILES: COCCOCCOCCOCCC1(C)C(/C=C/C=C2/N(CCCCCC(=O)Oc3c(F)c(F)cc(F)c3F)c3ccc4c(S(=O)(=O)[O-])cc(S(=O)(=O)[O-])cc4c3C2(C)C)=[N+](CCOC)c2ccc3c(S(=O)(=O)[O-])cc(S(=O)(=O)[O-])cc3c21]

One non-limiting example of an activated 579 Compound 1/2 (PEG$_4$) is a sulfotetrafluorophenyl (STP)-ester form of 579 Compound 1, shown below:

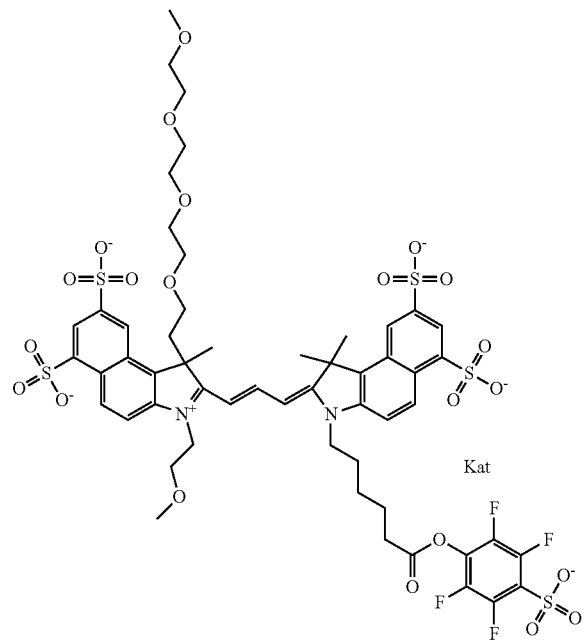 [SMILES: COCCOCCOCCOCCC1(C)C(/C=C/C=C2/N(CCCCCC(=O)Oc3c(F)c(F)c(S(=O)(=O)[O-])c(F)c3F)c3ccc4c(S(=O)(=O)[O-])cc(S(=O)(=O)[O-])cc4c3C2(C)C)=[N+](CCOC)c2ccc3c(S(=O)(=O)[O-])cc(S(=O)(=O)[O-])cc3c21]

One non-limiting example of an activated 579 Compound 1/2 is a hydrazide form of 579 Compound 1 (PEG$_4$), shown below:

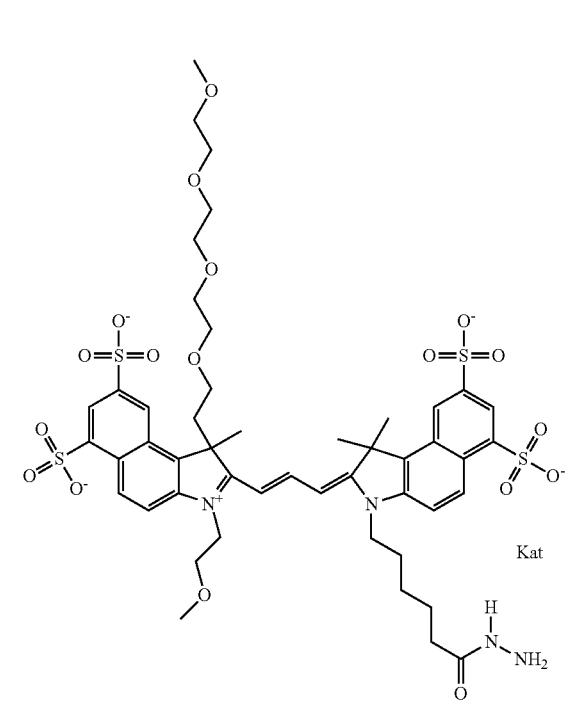 [SMILES: COCCOCCOCCOCCC1(C)C(/C=C/C=C2/N(CCCCCC(=O)NN)c3ccc4c(S(=O)(=O)[O-])cc(S(=O)(=O)[O-])cc4c3C2(C)C)=[N+](CCOC)c2ccc3c(S(=O)(=O)[O-])cc(S(=O)(=O)[O-])cc3c21]

One non-limiting example of an activated 579 Compound 1/2 (PEG$_4$) is a maleimide form of 579 Compound 1, shown below:

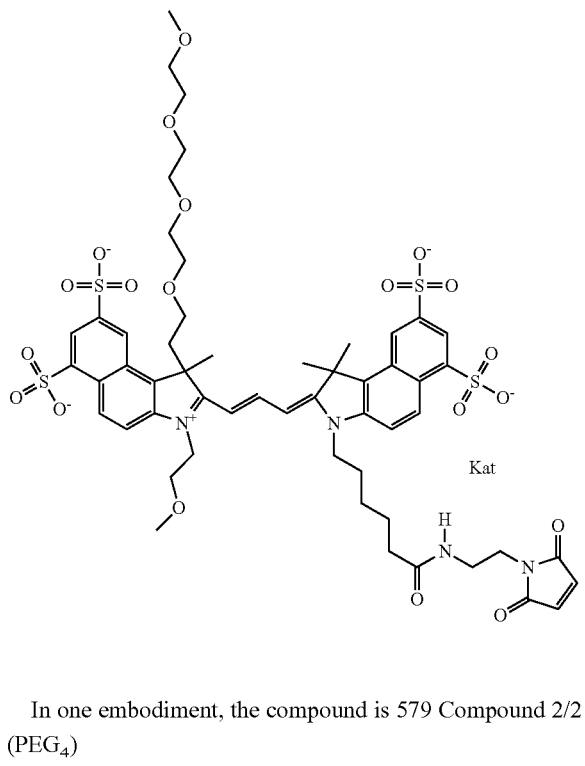

In one embodiment, the compound is 579 Compound 2/2 (PEG$_4$)

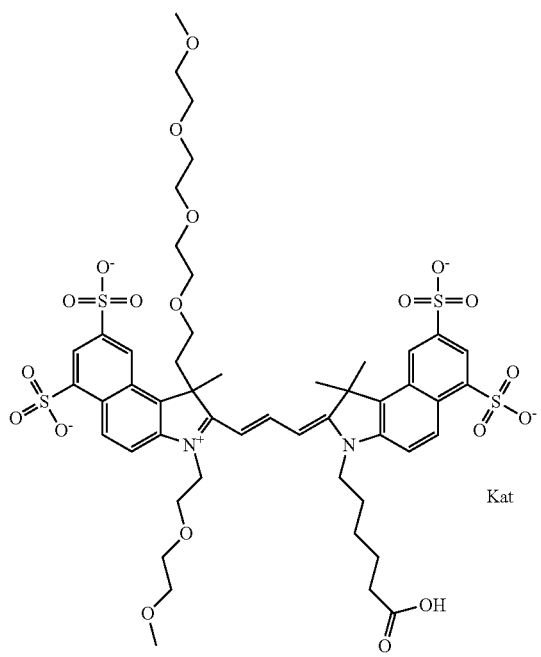 [SMILES: COCCOCCOCCOCCC1(C)C(/C=C/C=C2/N(CCCCCC(=O)O)c3ccc4c(S(=O)(=O)[O-])cc(S(=O)(=O)[O-])cc4c3C2(C)C)=[N+](CCOCCOC)c2ccc3c(S(=O)(=O)[O-])cc(S(=O)(=O)[O-])cc3c21]

One non-limiting example of 579 Compound 2/2 (PEG$_4$) (2-((1E,3E)-3-(3-(5-carboxypentyl)-1,1-dimethyl-6,8-disulfonato-1H-benzo[e]indol-2(3H)-ylidene)prop-1-enyl)-3-(2-(2-methoxyethoxy)ethyl)-1-methyl-1-(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the (poly)ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 2/2 (PEG$_4$) is activated as described above.

In one embodiment, the compound is 579 Compound 3/2 (PEG$_4$)

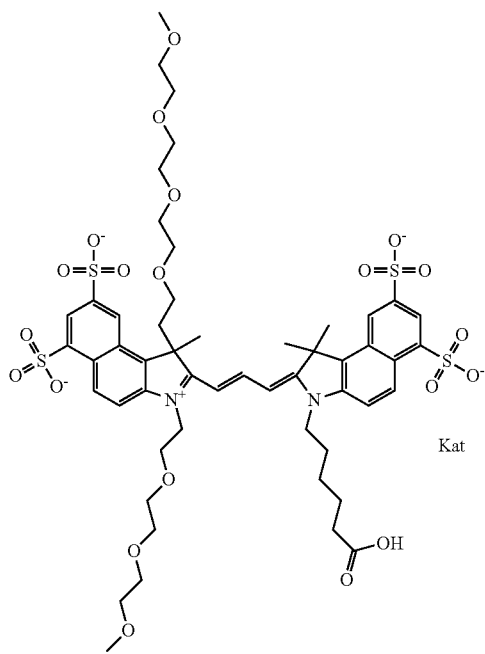 [SMILES: COCCOCCOCCOCCC1(C)C(/C=C/C=C2/N(CCCCCC(=O)O)c3ccc4c(S(=O)(=O)[O-])cc(S(=O)(=O)[O-])cc4c3C2(C)C)=[N+](CCOCCOCCOC)c2ccc3c(S(=O)(=O)[O-])cc(S(=O)(=O)[O-])cc3c21]

One non-limiting example of 579 Compound 3/2 (PEG$_4$) (2-((1E,3E)-3-(3-(5-carboxypentyl)-1,1-dimethyl-6,8-disulfonato-1H-benzo[e]indol-2(3H)-ylidene)prop-1-enyl)-3-(2-(2-methoxyethoxy)ethyl)-1-methyl-1-(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 3/2 (PEG$_4$) is activated as described above.

In one embodiment, the compound is 579 Compound 4/2 (PEG$_4$)

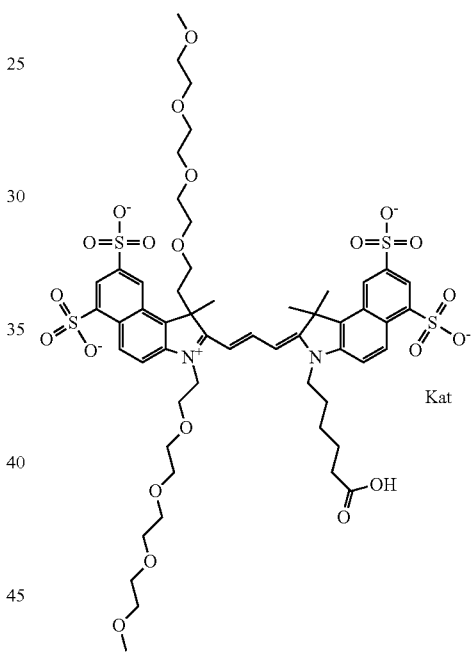

One non-limiting example of 579 Compound 4/2 (PEG$_4$) (2-((1E,3E)-3-(3-(5-carboxypentyl)-1,1-dimethyl-6,8-disulfonato-1H-benzo[e]indol-2(3H)-ylidene)prop-1-enyl)-1-methyl-1,3-di(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 4/2 (PEG$_4$) is activated as described above.

In one embodiment, the compound is 579 Compound 5/2 (PEG$_4$)

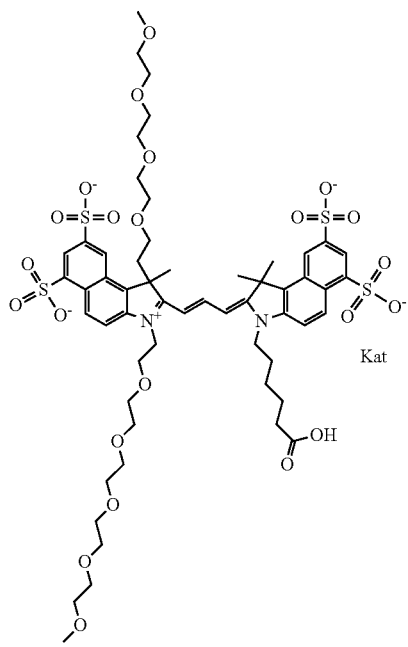 [SMILES: COCCOCCOCCOCCOCC[N+]1=C(/C=C/C=C2/N(CCCCCC(=O)O)c3ccc4c(S(=O)(=O)[O-])cc(S(=O)(=O)[O-])cc4c3C2(C)C)C(C)(CCOCCOCCOCCOC)c2c1ccc1c(S(=O)(=O)[O-])cc(S(=O)(=O)[O-])cc21]

One non-limiting example of 579 Compound 5/2 (PEG$_4$) (2-(((1E,3E)-3-(3-(5-carboxypentyl)-1,1-dimethyl-6,8-disulfonato-1H-benzo[e]indol-2(3H)-ylidene)prop-1-enyl)-3-(2,5,8,11,14-pentaoxahexadecan-16-yl)-1-methyl-1-(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 5/2 (PEG$_4$) is activated as described above.

In one embodiment, the compound is 579 Compound 6/2 (PEG$_4$)

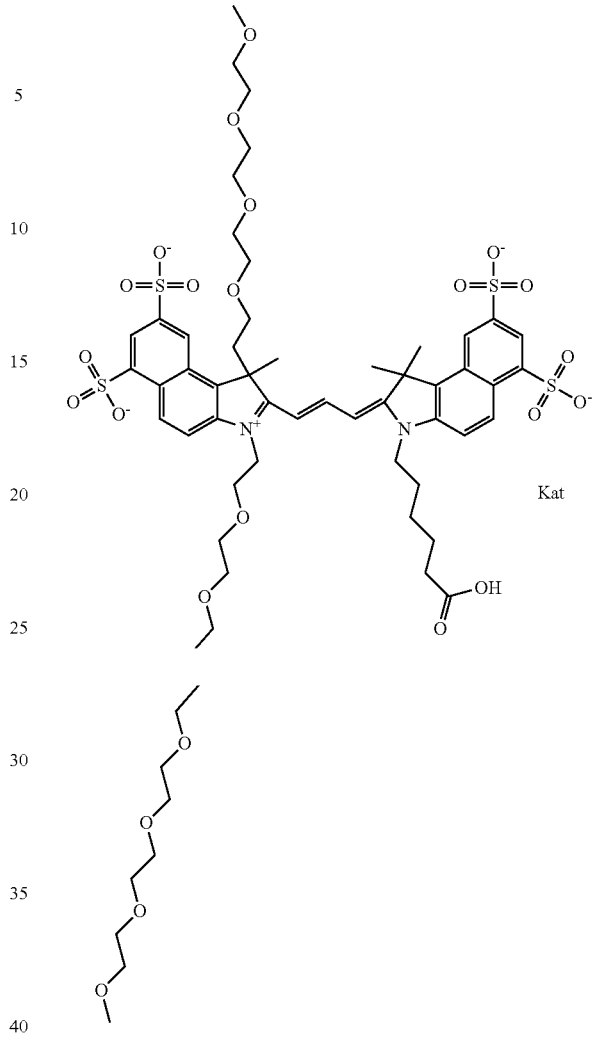

One non-limiting example of 579 Compound 6/2 (PEG$_4$) (2-(((1E,3E)-3-(3-(5-carboxypentyl)-1,1-dimethyl-6,8-disulfonato-1H-benzo[e]indol-2(3H)-ylidene)prop-1-enyl)-1-methyl-3-(2,5,8,11,14,17-hexaoxanonadecan-19-yl)-1-(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 6/2 (PEG$_4$) is activated as described above.

In embodiments, the degree and/or location of sulfonation is varied to, e.g., vary the compound's degree of hydrophilicity or hydrophobicity. One non-limiting example is a monosulfonate form of 579 Compound 1/2 (PEG$_4$), shown below:

105
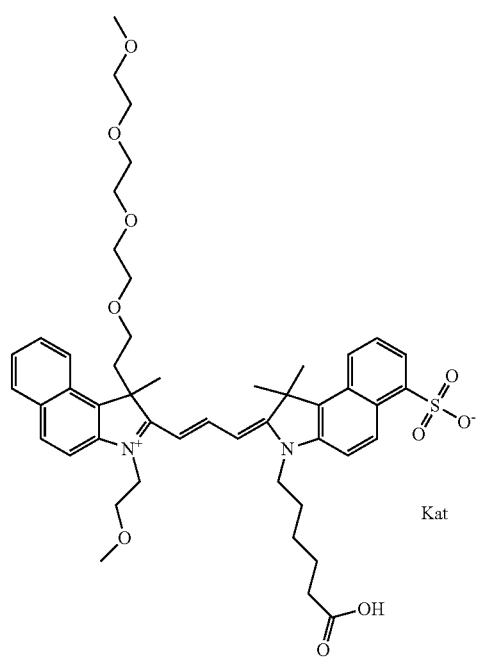 [SMILES: COCCOCCOCCOCCC1(C)C(/C=C/C=C2/N(CCCCCC(=O)O)c3ccc4c(S(=O)(=O)[O-])cccc4c3C2(C)C)=[N+](CCOC)c2ccc3ccccc3c21]
One non-limiting example is a disulfonate form of 579 Compound 1/2 (PEG$_4$), shown below:
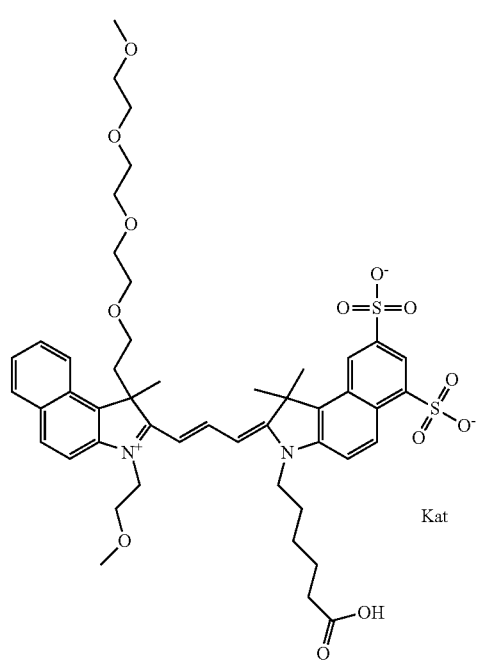 [SMILES: COCCOCCOCCOCCC1(C)C(/C=C/C=C2/N(CCCCCC(=O)O)c3ccc4c(S(=O)(=O)[O-])cc(S(=O)(=O)[O-])cc4c3C2(C)C)=[N+](CCOC)c2ccc3ccccc3c21]
One non-limiting example is a trisulfonate form of 579 Compound 1/2 (PEG$_4$), shown below:
106
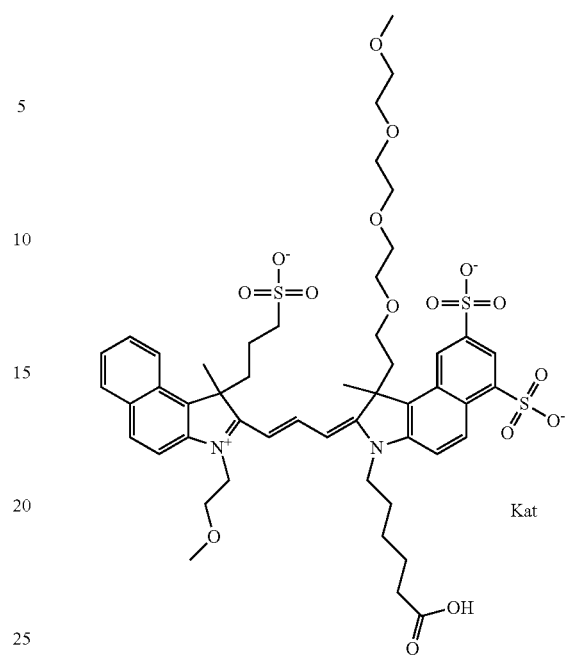
One non-limiting example is a tetrasulfonate form of 579 Compound 1/2 (PEG$_4$), shown below:
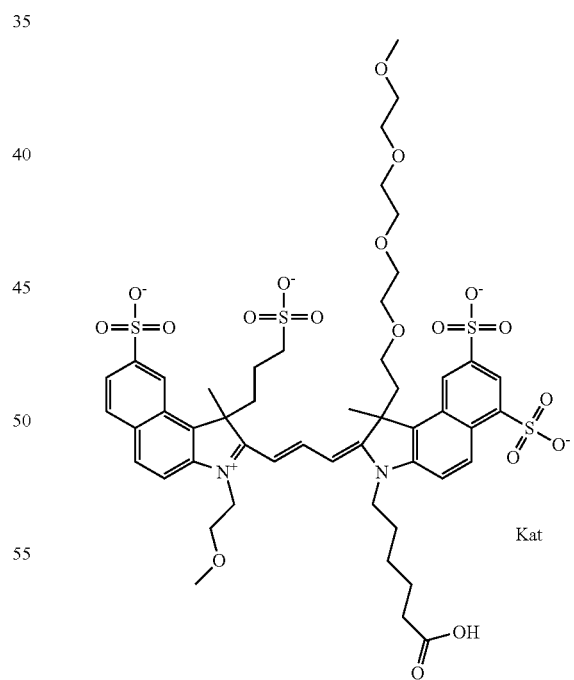
One non-limiting example is a pentasulfonate form of 579 Compound 1/2 (PEG$_4$), shown below:

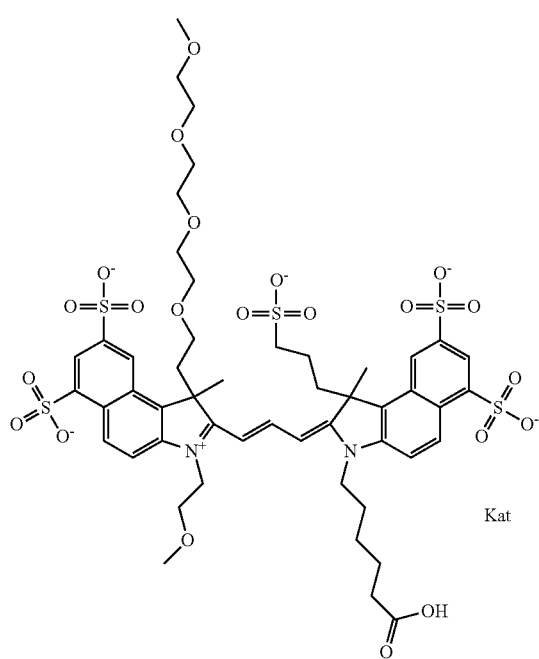 [SMILES: COCCOCCOCCOCCC1(C)C(/C=C/C=C2/N(CCCCCC(=O)O)c3ccc4c(S(=O)(=O)[O-])cc(S(=O)(=O)[O-])cc4c3C2(C)CCCS(=O)(=O)[O-])=[N+](CCOC)c2ccc3c(S(=O)(=O)[O-])cc(S(=O)(=O)[O-])cc3c21]

In embodiments, the compound contains one or more substitutions of the polymethine linker. In one embodiment, the compound has general formula IVa

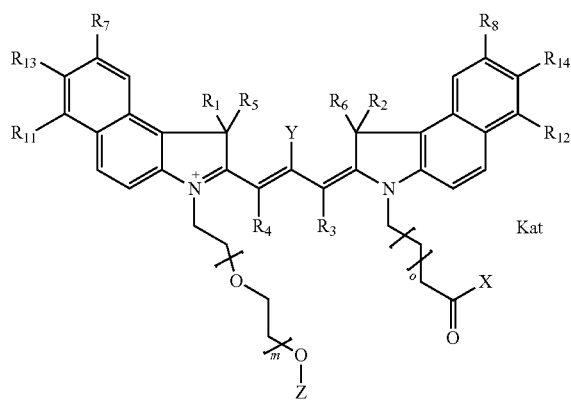

general formula IVb

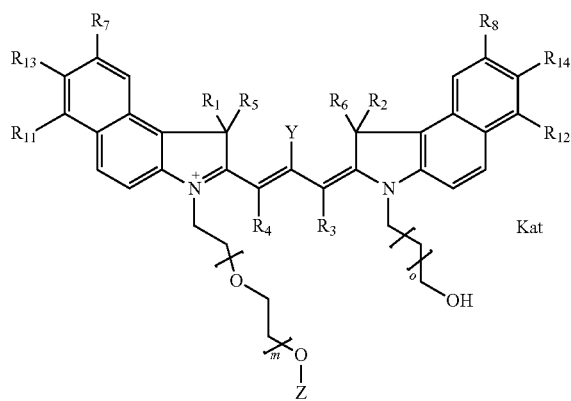

general formula IVc

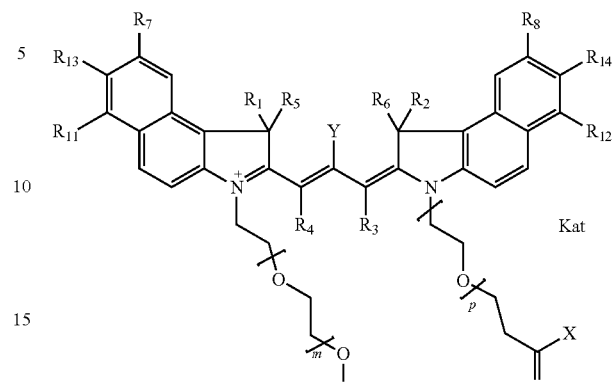

general formula IVd

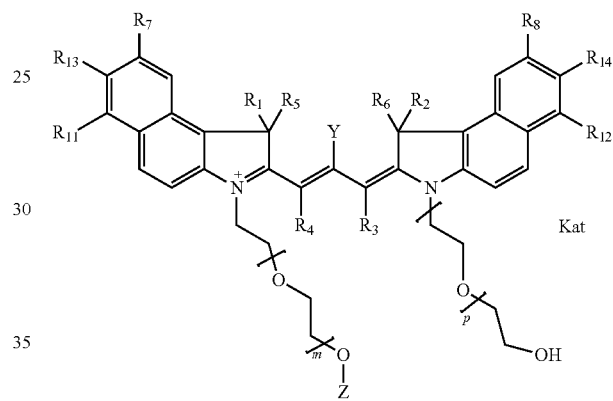

or general formula IVe

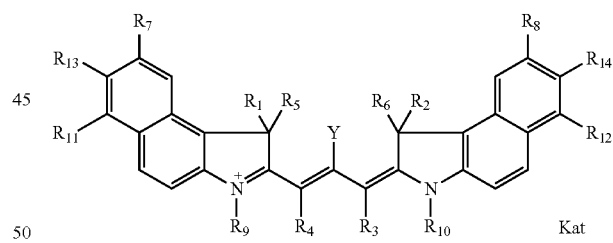

where each of $R^1$, $R^2$, $R^5$, and $R^6$ is the same or different and is independently selected from the group consisting of an aliphatic, heteroaliphatic, sulfoalkyl group, heteroaliphatic with terminal $SO_3$, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-$SO_2$NH—P—Z, and a carboxamide group -L-CONH—P—Z, and Z is selected from H, $CH_3$, a $CH_3$ group, an alkyl group, a heteroalkyl group, or —CO—NHS; each of $R^7$, $R^8$, $R^{11}$, $R^{12}$, $R^{13}$, and $R^{14}$ is the same or different and is independently selected from either H, $SO_3$, a PEG group P—Z where P is selected from an ethylene glycol group, a diethylene glycol group, and a (poly)ethylene glycol group, where the (poly)ethylene glycol group is (CH₂CH₂O)ₛ, where s is an integer from 3-6 inclusive, a sulfonamide group -L-SO₂NH—P—Z, or a carboxamide group -L-CONH—P—Z, and Z is selected from H, a CH₃ group, an alkyl group, or a heteroalkyl group; each of $R^9$ and $R^{10}$ is the same or different and is independently selected from the group consisting of an alkyl, a sulfoalkyl, a PEG group P-L-Z where P is selected from an ethylene glycol group, a diethylene glycol group, and a (poly)ethylene glycol group, where the (poly)ethylene glycol group is (CH₂CH₂O)ₛ, where s is an integer from 3-6 inclusive, a PEG group P-L-X, L-Z, L-X; X is selected from the group consisting of —OH, —SH, —NH₂, —NH—NH₂, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH₂, —NR-L-NH—NH₂, —NR-L-CO₂H, —NR-L-CO—NHS, —NR-L-CO-STP, —NR-L-CO-TFP, —NR-L-CO-benzotriazole, —NR-L-CHO, —NR-L-maleimide, —NR-L-NH—CO—CH₂—I, imidazole, azide, —NR-L-O—NH₂, and —NR-L-O—CO—NHS, where R is —H or an aliphatic or heteroaliphatic group, and L is selected from the group consisting of a divalent linear (—(CH₂)ₜ—, t=0 to 15), crossed, or cyclic alkyl group optionally substituted by at least one oxygen atom and/or sulfur atom; Kat is a number of Na⁺, K⁺, Ca²⁺, ammonia, or other cation(s) needed to compensate the negative charge brought by the cyanine; m is an integer from 0 to 5 inclusive; o is an integer from 0 to 12 inclusive; p is an integer from 1 to 6 inclusive; each of R3 and R4 is the same or different and is independently hydrogen, an aliphatic group, a heteroaliphatic group, or a PEG group P—Z where P is selected from an ethylene glycol group, a diethylene glycol group, and a (poly)ethylene glycol group, where the (poly)ethylene glycol group is (CH₂CH₂O)ₛ, where s is an integer from 3-6 inclusive, and Z is selected from H, a CH₃ group, an alkyl group, or a heteroalkyl group; or R3 and R4 together form a cyclic structure where R3 and R4 are joined using a divalent structural element selected from the group consisting of —(CH₂)_q—, —(CH₂)_qO(CH₂)_q'—, —(CH₂)_qS(CH₂)_q'—, —(CH₂)_qCH═CH—, and —OCH═CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy-, phenylmercapto function, and a PEG group P—Z where P is selected from an ethylene glycol group, a diethylene glycol group, and a (poly)ethylene glycol group, where the (poly)ethylene glycol group is (CH₂CH₂O)ₛ, where s is an integer from 3-6 inclusive, and Z is selected from H, CH₃, a CH₃ group, an alkyl group, or a heteroalkyl group.

In one embodiment, the compound of general formula IV wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —(CH₂)_q— and CH═CH, where q is an integer from 1 to 2 inclusive, to result in a 3-, 4-, or 5-membered ring.

One non-limiting example is a substituted polymethine form of 579 Compound 0/1, shown below.

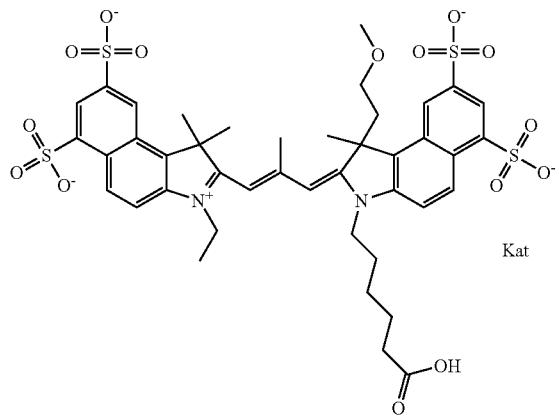 [SMILES: CC[N+]1=C(/C=C(C)/C=C2/N(CCCCCC(=O)O)c3ccc4c(S(=O)(=O)[O-])cc(S(=O)(=O)[O-])cc4c3C2(C)CCOC)C(C)(C)c2c1ccc1c(S(=O)(=O)[O-])cc(S(=O)(=O)[O-])cc21]

One non-limiting example is a substituted polymethine form of 579 Compound 0/1, shown below.

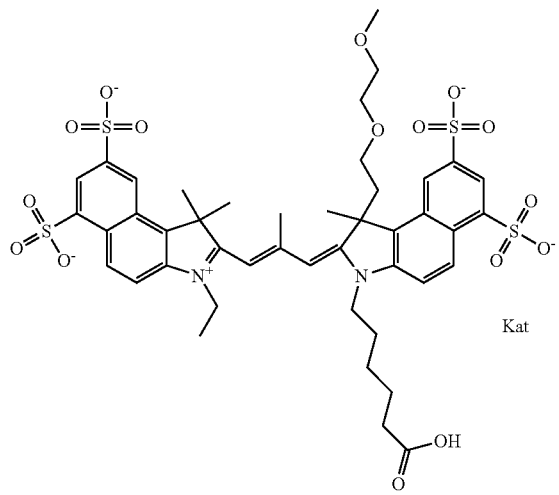 [SMILES: CC[N+]1=C(/C=C(C)/C=C2/N(CCCCCC(=O)O)c3ccc4c(S(=O)(=O)[O-])cc(S(=O)(=O)[O-])cc4c3C2(C)CCOCCOC)C(C)(C)c2c1ccc1c(S(=O)(=O)[O-])cc(S(=O)(=O)[O-])cc21]

One non-limiting example is a substituted polymethine form of 579 Compound 0/1, shown below.

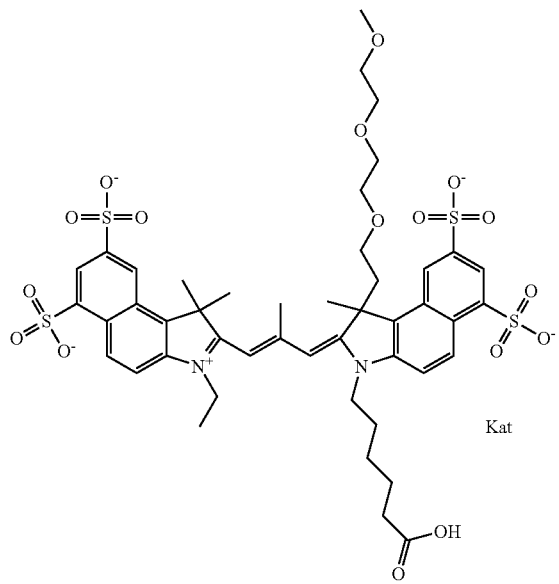 [SMILES: CC[N+]1=C(/C=C(C)/C=C2/N(CCCCCC(=O)O)c3ccc4c(S(=O)(=O)[O-])cc(S(=O)(=O)[O-])cc4c3C2(C)CCOCCOCCOC)C(C)(C)c2c1ccc1c(S(=O)(=O)[O-])cc(S(=O)(=O)[O-])cc21]

One non-limiting example is a substituted polymethine form of 579 Compound 0/1, shown below.

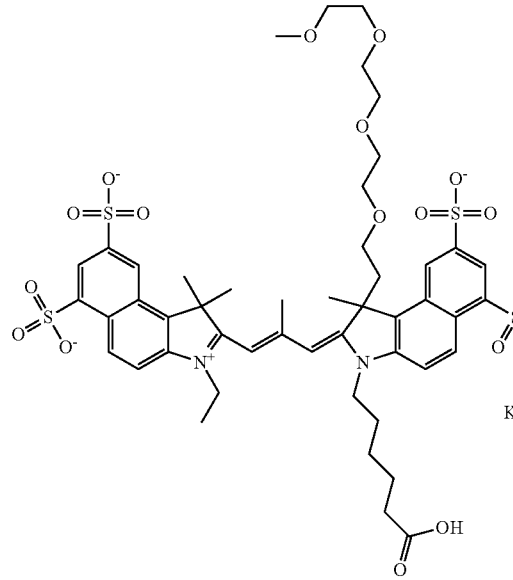

One non-limiting example is a substituted polymethine form of 579 Compound 0/1, shown below.

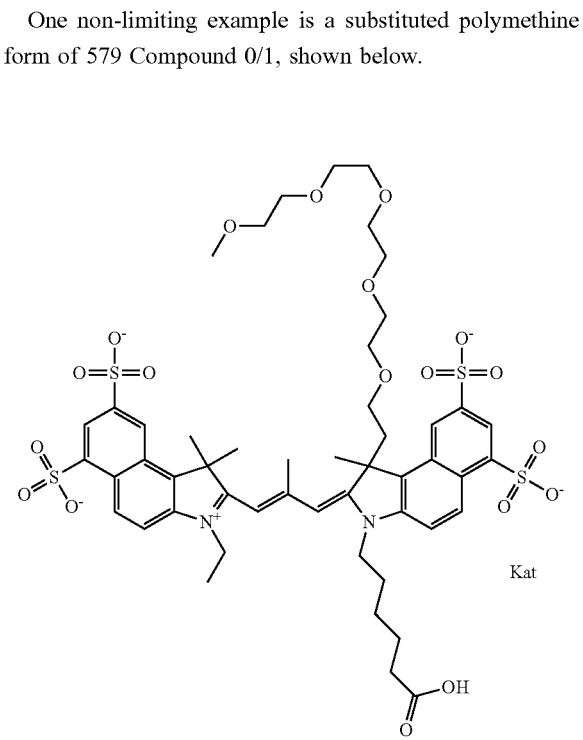

One non-limiting example is a substituted polymethine form of 579 Compound 0/1, shown below.

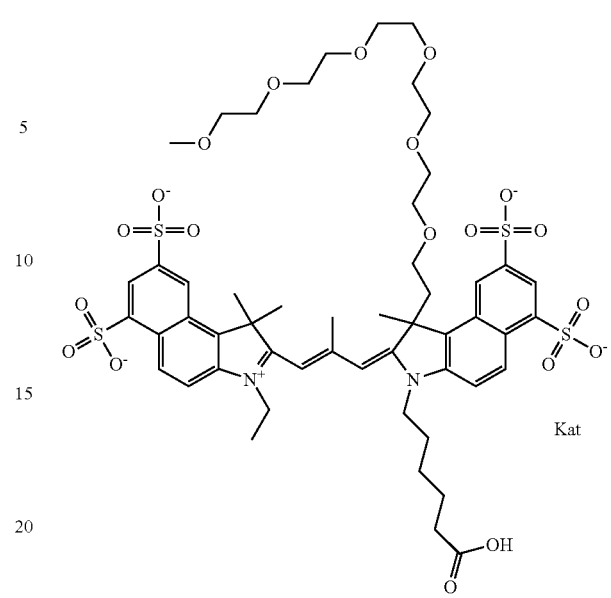

In various embodiments, an ethylene glycol group, diethylene glycol group, and/or a (poly)ethylene glycol group, which will collectively be referred to as a PEG group, unless specifically defined, may be present at position(s) in addition to such groups being present on the N atom(s) of the indole structure.

One non-limiting example of an additionally PEG-substituted compound is a 579 Compound 1/2 according to general formula II where R1 is an ethylene glycol group (PEG$_1$) terminating with a methyl group, shown below:

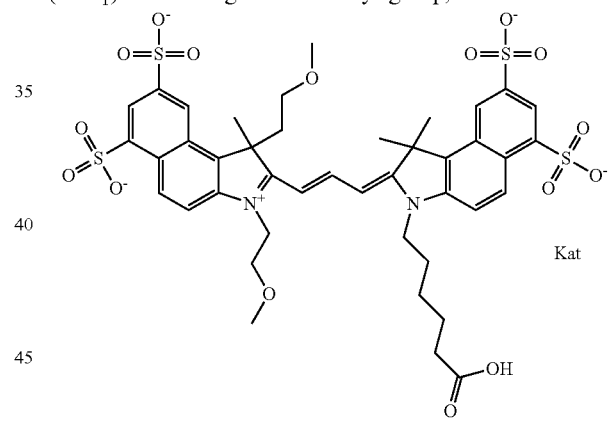

One non-limiting example of an additionally PEG-substituted compound is a 579 Compound 1/2 according to general formula II where R2 is an ethylene glycol group (PEG$_1$) terminating with a methyl group, shown below:

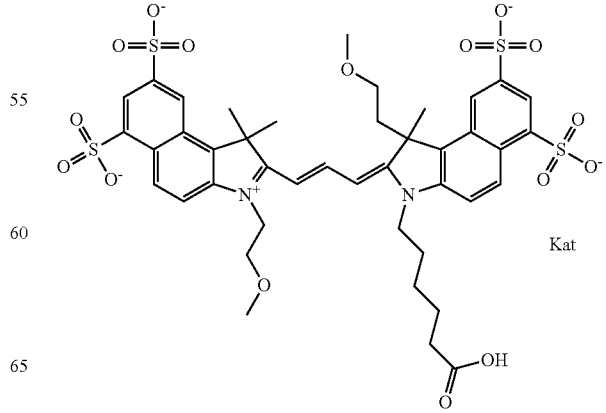

One non-limiting example of an additionally PEG-substituted compound is a 579 Compound 1/2 according to general formula II where R8 is an ethylene glycol group (PEG$_1$) terminating with a methyl group, shown below:

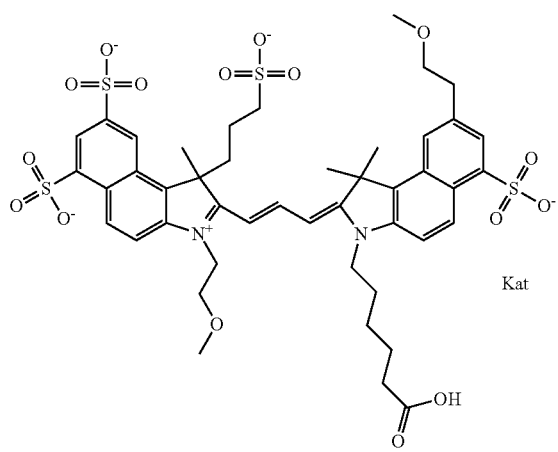

One non-limiting example of an additionally PEG-substituted compound is a 579 Compound 1/2 according to general formula II where R8 is a sulfonamide group with an ethylene glycol group (PEG$_1$) terminating with a methyl group, shown below:

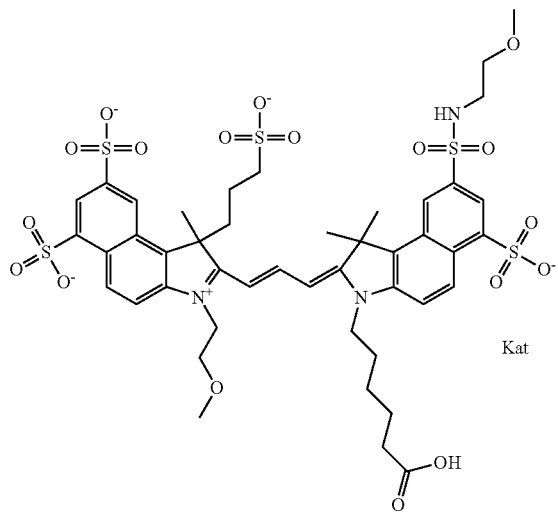

One non-limiting example of an additionally PEG-substituted compound is a 579 Compound 1/2 according to general formula II where R8 is a carboxamide group with an ethylene glycol group (PEG$_1$) terminating with a methyl group, shown below:

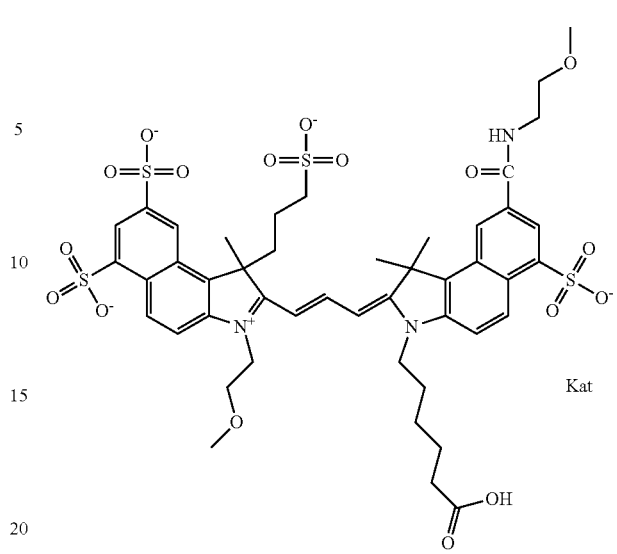

One non-limiting example of an additionally PEG-substituted compound is a 579 Compound 1/2 according to general formula II where R7 is an ethylene glycol group (PEG$_1$) terminating with a methyl group, shown below:

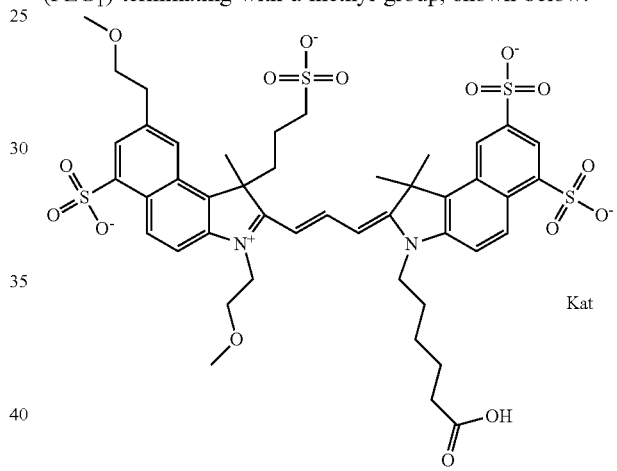

One non-limiting example of an additionally PEG-substituted compound is a 579 Compound 1/2 according to general formula II where R7 is a sulfonamide group with an ethylene glycol group (PEG$_1$) terminating with a methyl group, shown below:

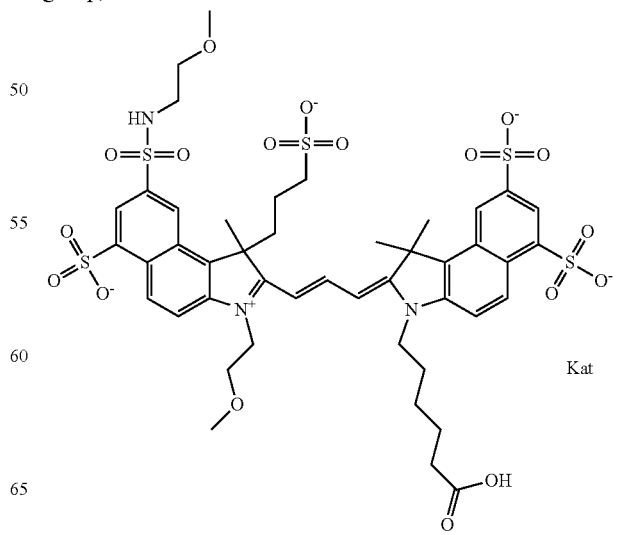

One non-limiting example of an additionally PEG-substituted compound is a 579 Compound 1/2 according to general formula II where R7 is a carboxamide group with an ethylene glycol group (PEG₁) terminating with a methyl group, shown below:

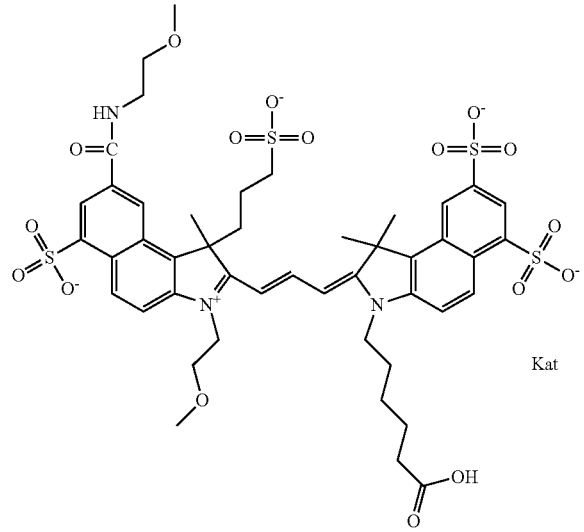

One non-limiting example of an additionally PEG-substituted compound is a 579 Compound 1/2 according to general formula II where R12 is an ethylene glycol group terminating with a methyl group, shown below:

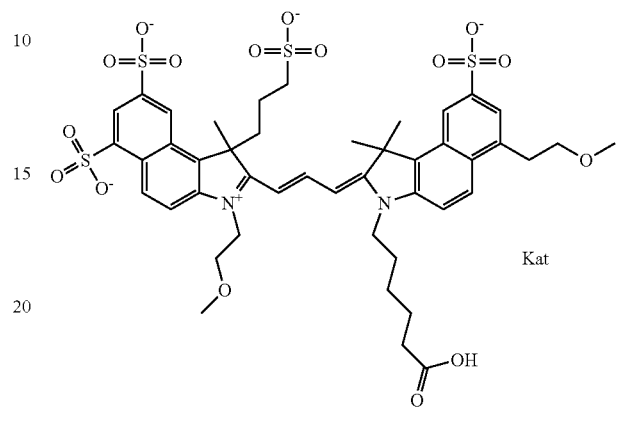

One non-limiting example of an additionally PEG-substituted compound is a 579 Compound 1/2 according to general formula II where R12 is a sulfonamide group with an ethylene glycol group (PEG₁) terminating with a methyl group, shown below:

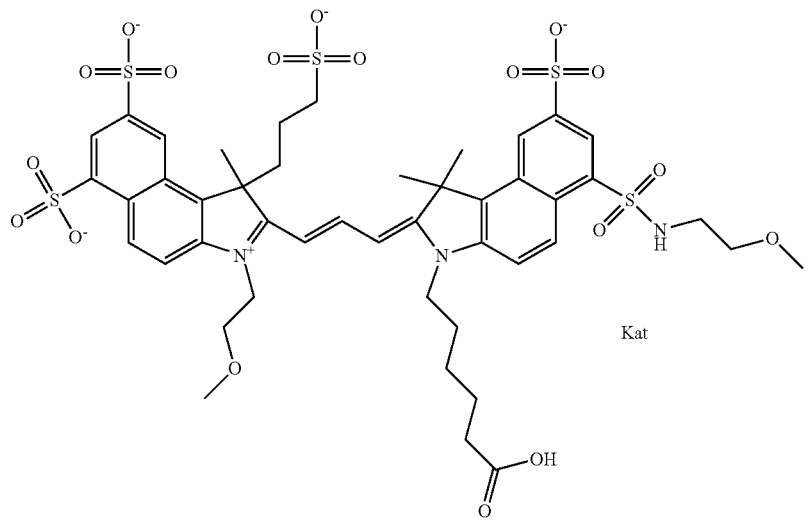

One non-limiting example of an additionally PEG-substituted compound is a 579 Compound 1/2 according to general formula II where R12 is a carboxamide group with an ethylene glycol group (PEG₁) terminating with a methyl group, shown below:

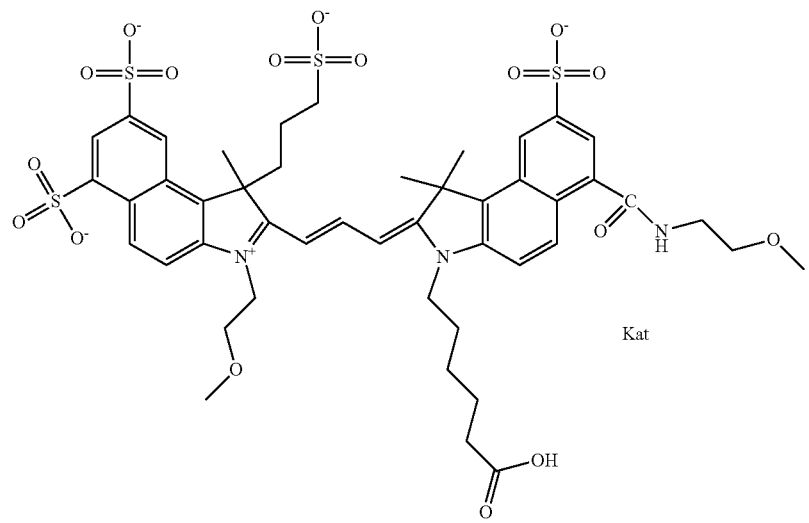

One non-limiting example of an additionally PEG-substituted compound is a 579 Compound 1/2 according to general formula II where R11 is an ethylene glycol group terminating with a methyl group, One non-limiting example of an additionally PEG-substituted compound is a 579 Compound 1/2 according to general formula II where R11 is a sulfonamide group with an ethylene glycol group (PEG$_1$) terminating with a methyl group, shown below:

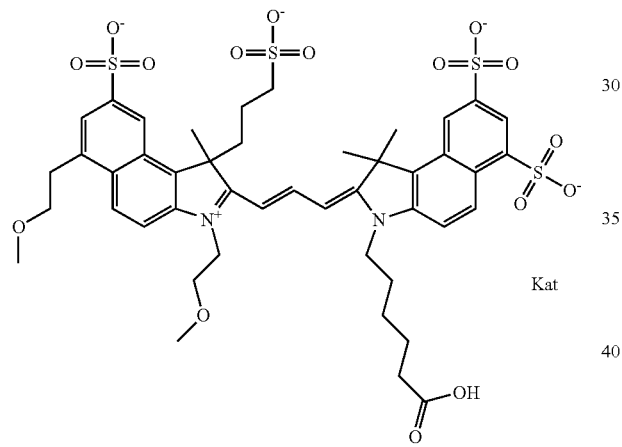

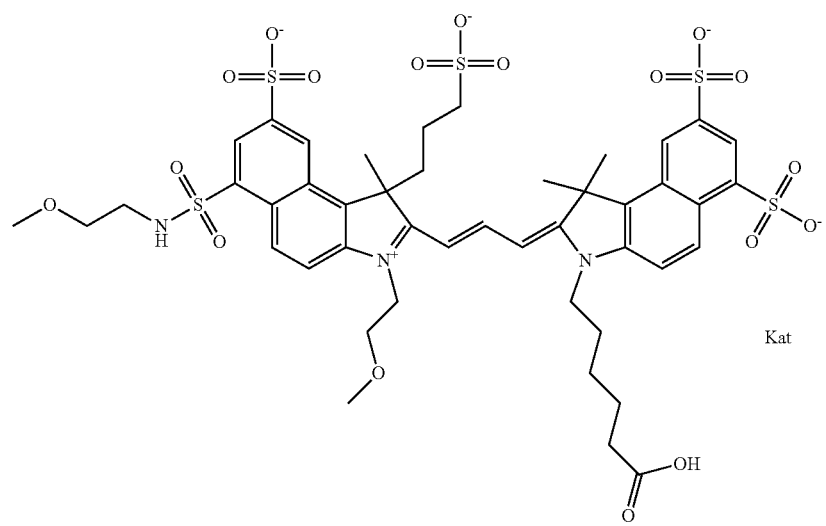

One non-limiting example of an additionally PEG-substituted compound is a 579 Compound 1/2 according to general formula II where R11 is a carboxamide group with an ethylene glycol group (PEG$_1$) terminating with a methyl group, shown below:

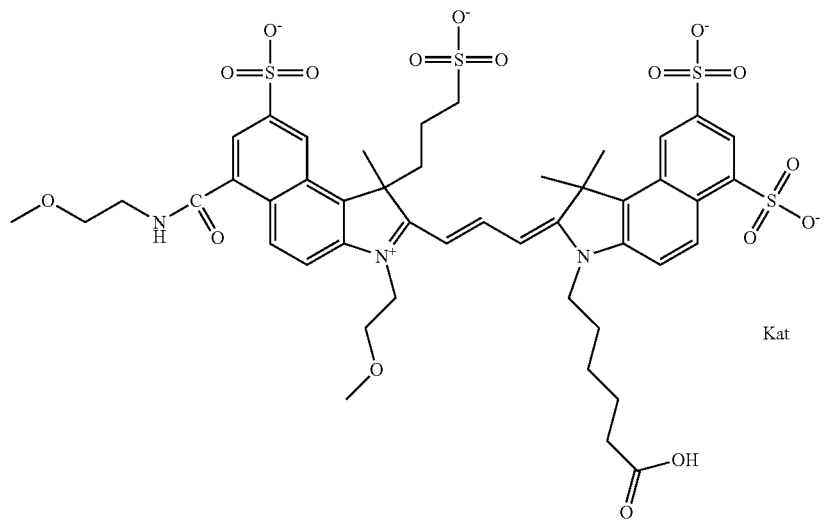

One non-limiting example of an additionally PEG-substituted compound is a 579 Compound 1/2 according to general formula II where R14 is an ethylene glycol group terminating with a methyl group, shown below:

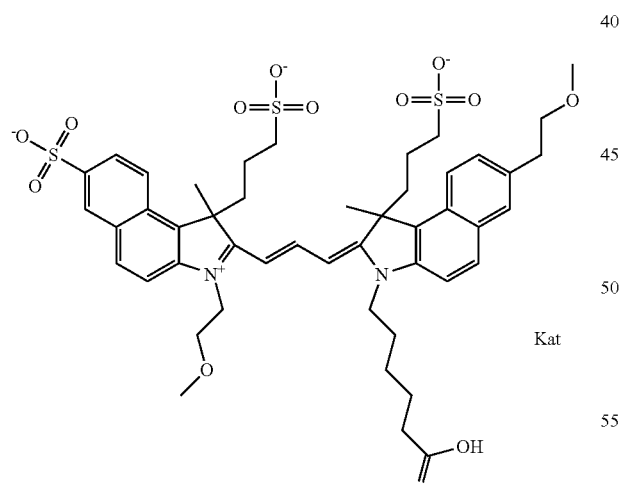

One non-limiting example of an additionally PEG-substituted compound is a 579 Compound 1/2 according to general formula II where R14 is a sulfonamide group with an ethylene glycol group (PEG$_1$) terminating with a methyl group, shown below:

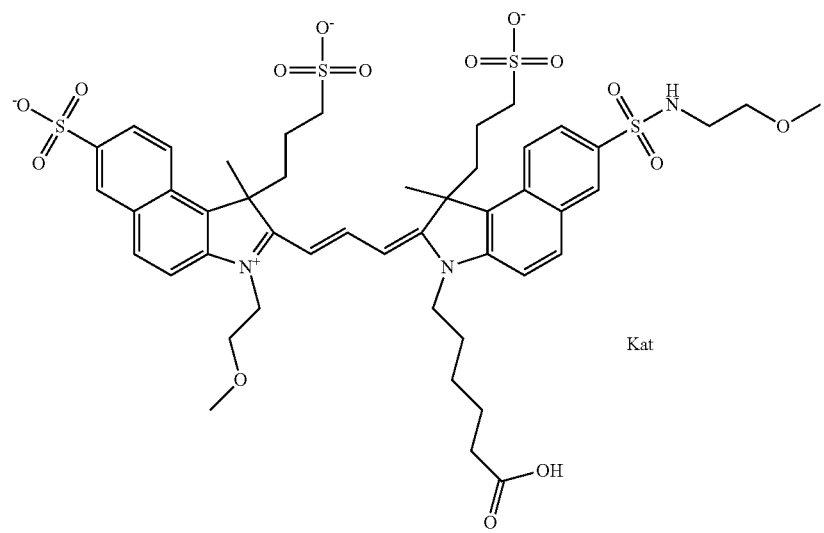

One non-limiting example of an additionally PEG-substituted compound is a 579 Compound 1/2 according to general formula II where R14 is a carboxamide group with an ethylene glycol group (PEG$_1$) terminating with a methyl group, shown below:

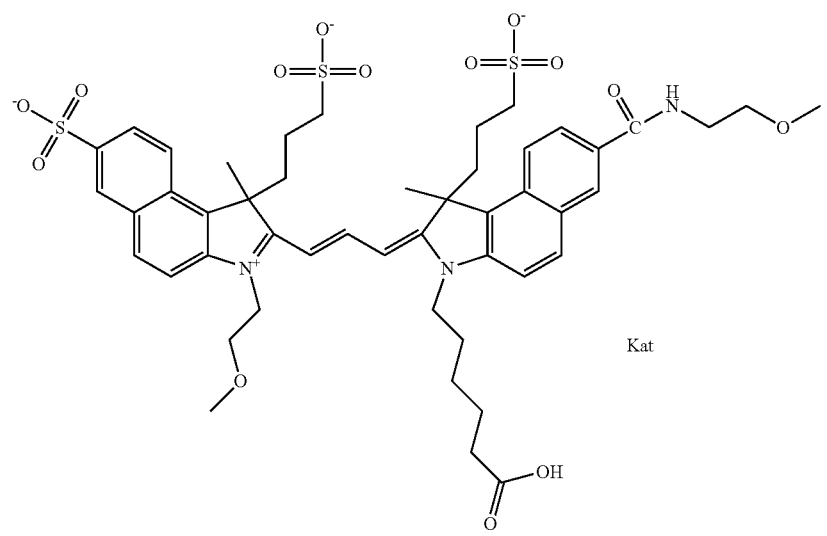

One non-limiting example of an additionally PEG-substituted compound is a 579 Compound 1/2 according to general formula II where R13 is an ethylene glycol group terminating with a methyl group,

123

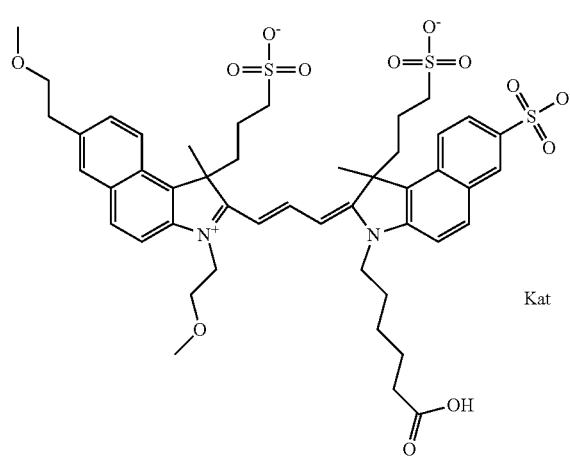 [SMILES: COCCc1ccc2c3c(ccc2c1)[N+](CCOC)=C(/C=C/C=C1/N(CCCCCC(=O)O)c2ccc4cc(S(=O)(=O)[O-])ccc4c2C1(C)CCCS(=O)(=O)[O-])C3(C)CCCS(=O)(=O)[O-]]

One non-limiting example of an additionally PEG-substituted compound is a 579 Compound 1/2 according to general formula II where R13 is a sulfonamide group with an ethylene glycol group (PEG₁) terminating with a methyl group, shown below:

124

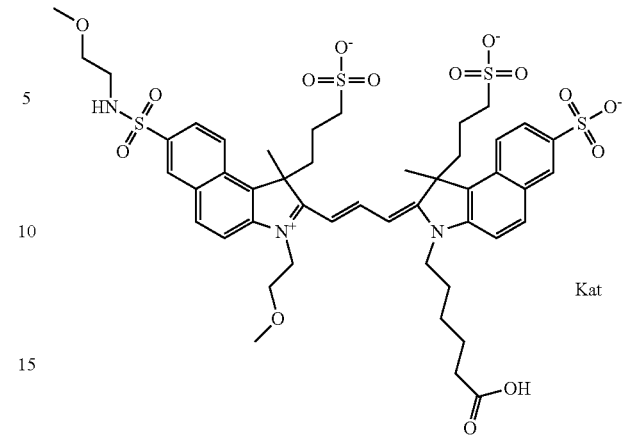

One non-limiting example of an additionally PEG-substituted compound is a 579 Compound 1/2 according to general formula II where R13 is a carboxamide group with an ethylene glycol group (PEG₁) terminating with a methyl group, shown below:

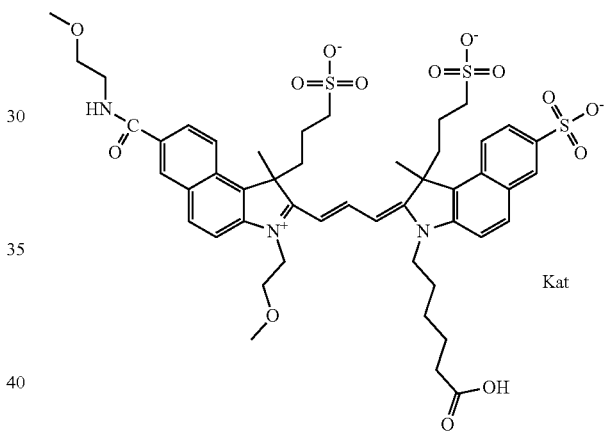

In one embodiment, the compound is 679 Compound 1

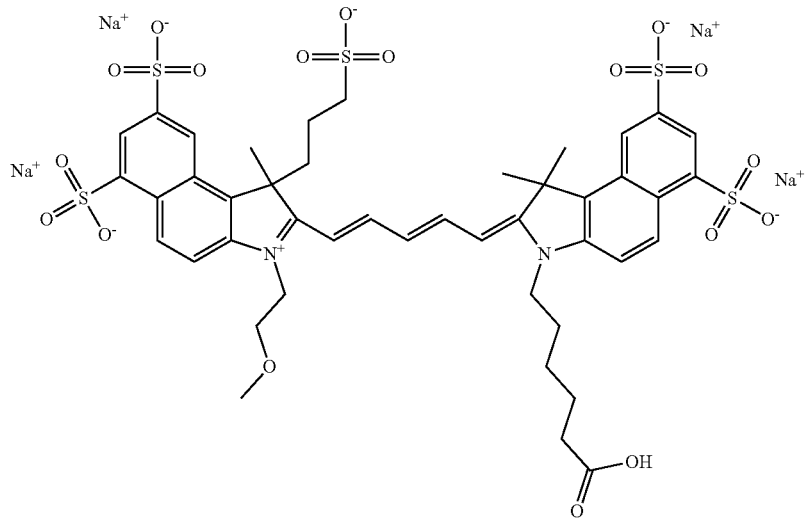 [SMILES: [Na+] ; COCC[N+]1=C(/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21 ; [Na+] ; [Na+] ; [Na+]]

679 Compound 1 (6-((E)-2-((2E,4E)-5-(3-(2-methoxyethyl)-1-methyl-6,8-disulfonato-1-(3-sulfonatopropyl)-1H-benzo[e]indol-3-ium-2-yl)penta-2,4-dien-1-ylidene)-1,1-dimethyl-6,8-disulfonato-1H-benzo[e]indol-3(2H)-yl)hexanoate) contains an ethylene glycol on the indole N of the left heterocycle, i.e., a methylated ethylene glycol. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 679 Compound 1, but one skilled in the art appreciates that activation is not limited to these examples. One non-limiting example of an activated compound is the NHS-ester of 679 Compound 1,

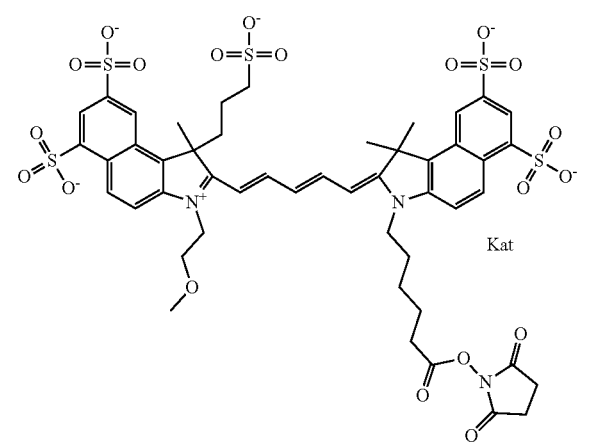 [SMILES: COCC[N+]1=C(/C=C/C=C/C=C2/N(CCCCCC(=O)ON3C(=O)CCC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example of a NHS-ester of 679 Compound 1, according to general formula III, where m=1 and p=1, is shown below:

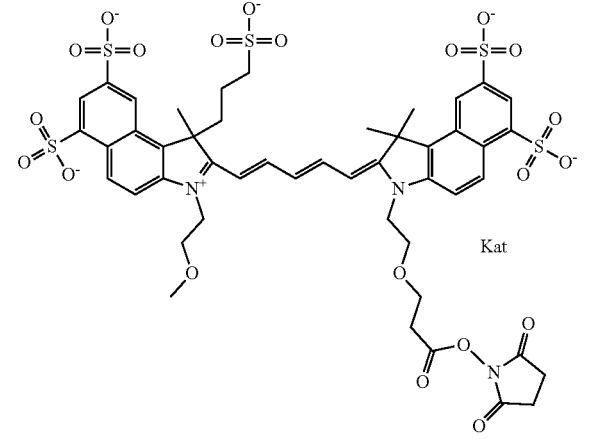

One non-limiting example of a NHS-ester of 679 Compound 1, according to general formula III, where m=1 and p=2, is shown below:

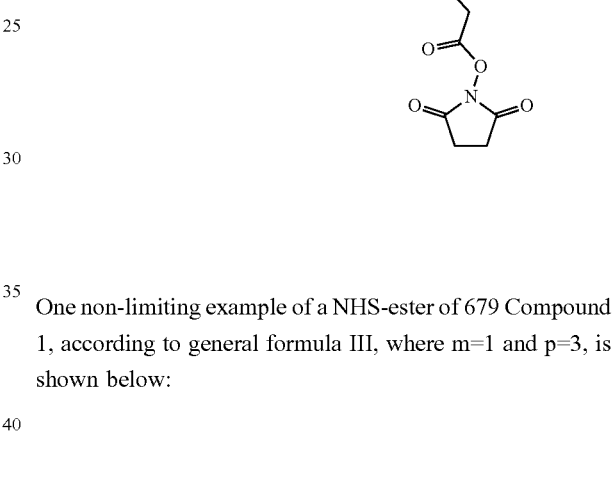

One non-limiting example of a NHS-ester of 679 Compound 1, according to general formula III, where m=1 and p=3, is shown below:

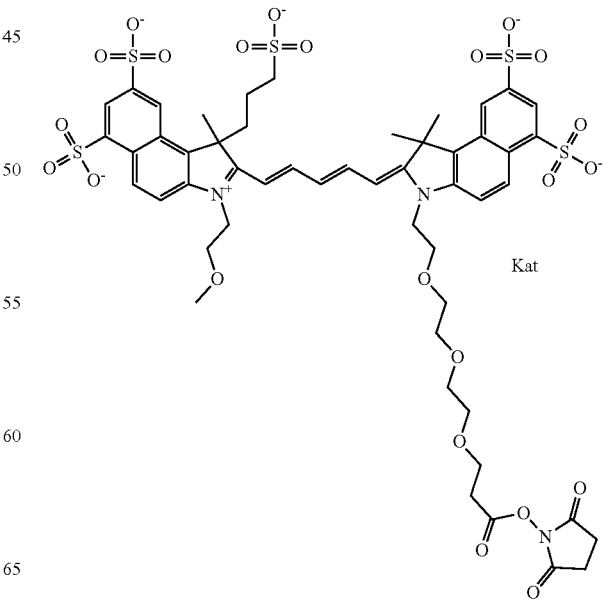

One non-limiting example of a NHS-ester of 679 Compound 1, according to general formula III, where m=1 and p=4, is shown below:

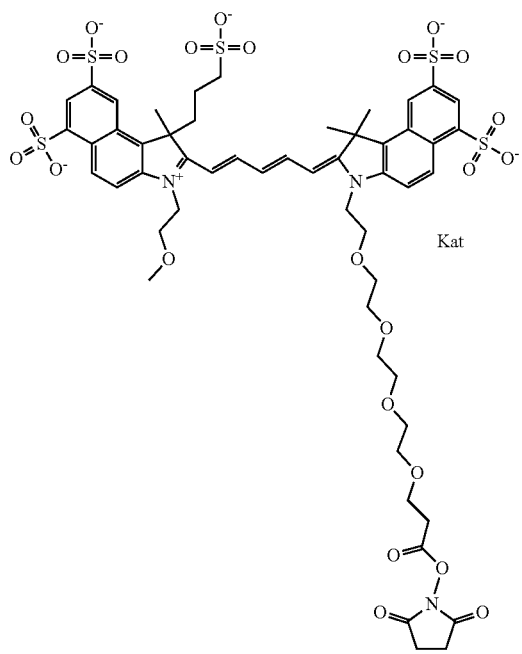

One non-limiting example of a NHS-ester of 679 Compound 1, according to general formula III, where m=1 and p=5, is shown below:

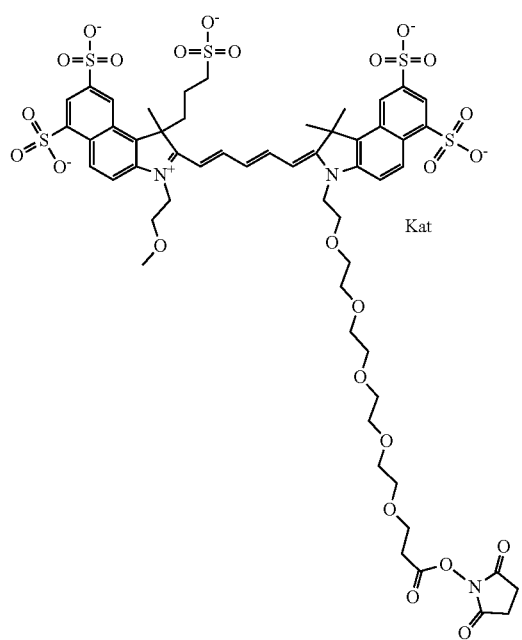

One non-limiting example of a NHS-ester of 679 Compound 1, according to general formula III, where m=1 and p=6, is shown below:

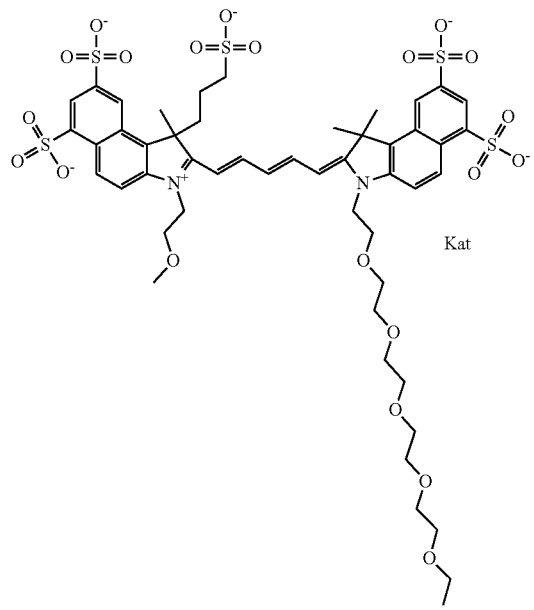

One non-limiting example of an activated 679 Compound 1 is a tetrafluorophenyl (TFP)-ester form of 679 Compound 1, shown below:

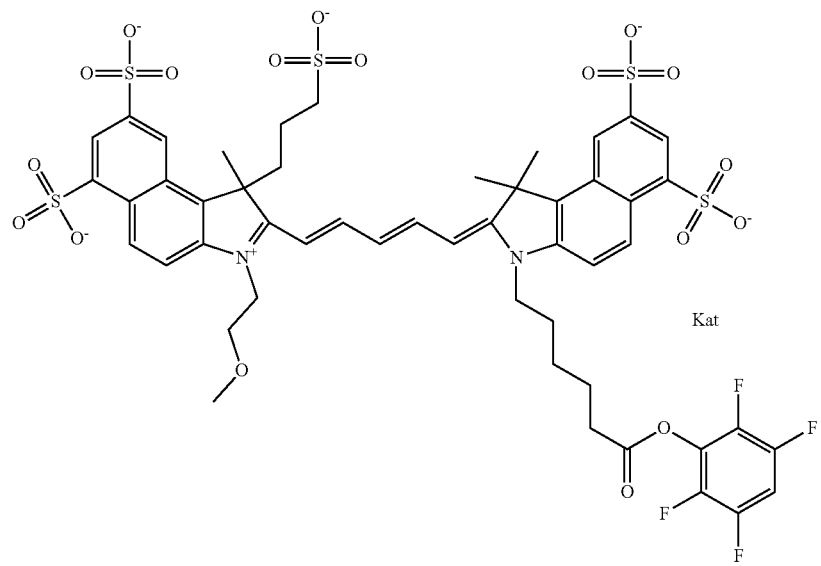 [SMILES: COCC[N+]1=C(/C=C/C=C/C=C2/N(CCCCCC(=O)Oc3c(F)c(F)cc(F)c3F)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]
One non-limiting example of an activated 679 Compound 1 is a sulfotetrafluorophenyl (STP)-ester form of 679 Compound 1, shown below:
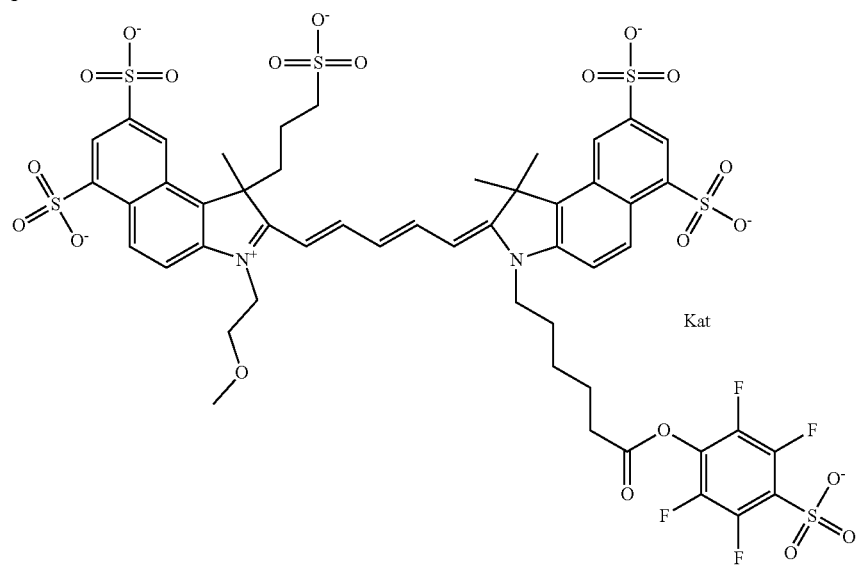
One non-limiting example of an activated 679 Compound 1 is a hydrazide form of 679 Compound 1,
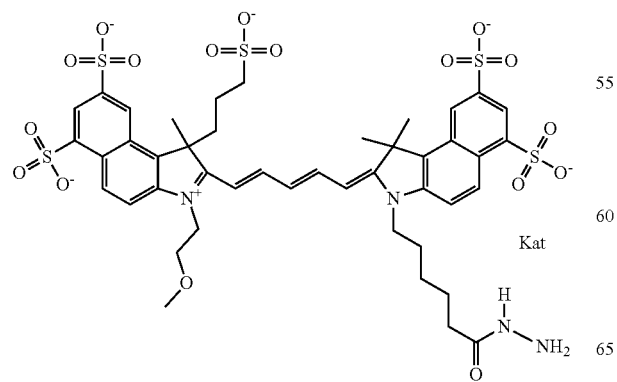

One non-limiting example of an activated 679 Compound 1 is a maleimide form of 679 Compound 1, shown below:

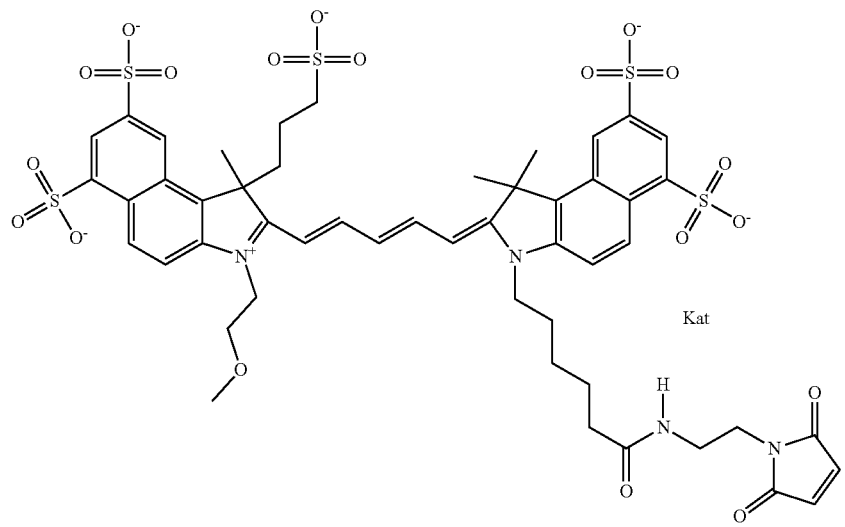 [SMILES: COCC[N+]1=C(/C=C/C=C/C=C2/N(CCCCCC(=O)NCCN3C(=O)C=CC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

In one embodiment, the compound is 679 Compound 2

In one embodiment, the compound is 679 Compound 3

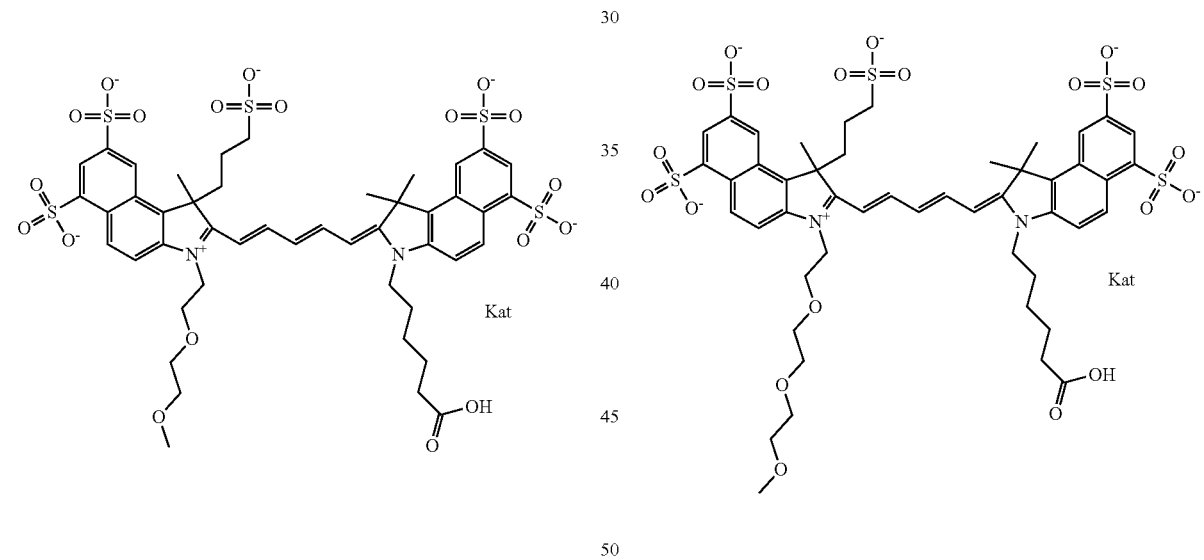

679 Compound 2 (6-((E)-2-((2E,4E)-5-(3-(2-(2-methoxyethoxy)ethyl)-1-methyl-6,8-disulfonato-1-(3-sulfonatopropyl)-1H-benzo[e]indol-3-ium-2-yl)penta-2,4-dien-1-ylidene)-1,1-dimethyl-6,8-disulfonato-1H-benzo[e]indol-3(2H)-yl)hexanoate) contains a diethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 2 is activated as described above.

679 Compound 3 (6-((E)-2-((2E,4E)-5-(3-(2-(2-(2-methoxyethoxy)ethoxy)ethyl)-1-methyl-6,8-disulfonato-1-(3-sulfonatopropyl)-1H-benzo[e]indol-3-ium-2-yl)penta-2,4-dien-1-ylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 3 is activated as described above.

In one embodiment, the compound is 679 Compound 4

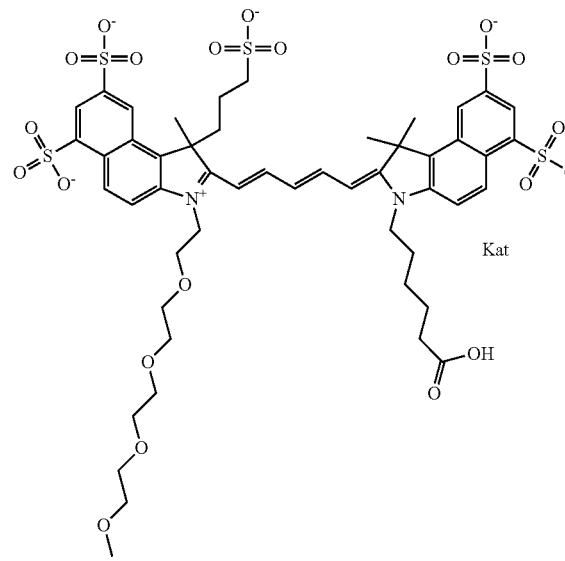

679 Compound 4 (6-((E)-1,1-dimethyl-2-((2E,4E)-5-(1-methyl-6,8-disulfonato-1-(3-sulfonatopropyl)-3-(2,5,8,11-tetraoxatridecan-13-yl)-1H-benzo[e]indol-3-ium-2-yl)penta-2,4-dien-1-ylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 679 Compound 4 is activated as described above.

In one embodiment, the compound is 679 Compound 5

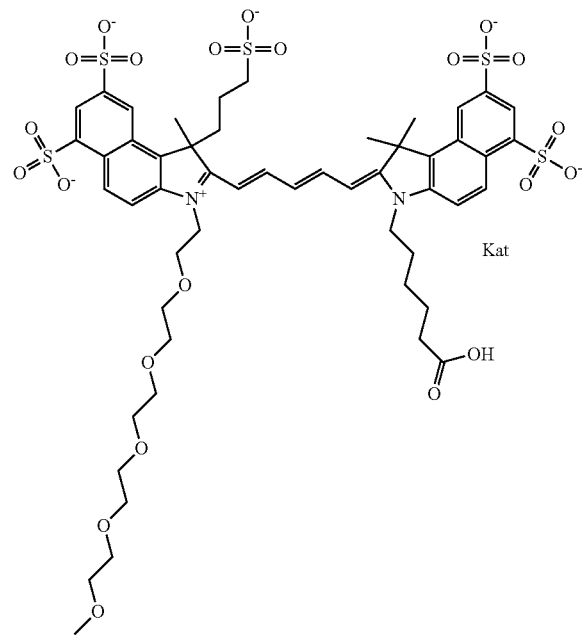 [SMILES: COCCOCCOCCOCCOCC[N+]1=C(/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

679 Compound 5 (6-((E)-2-((2E,4E)-5-(3-(2,5,8,11,14-pentaoxahexadecan-16-yl)-1-methyl-6,8-disulfonato-1-(3-sulfonatopropyl)-1H-benzo[e]indol-3-ium-2-yl)penta-2,4-dien-1-ylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 5 is activated as described above.

In one embodiment, the compound is 679 Compound 6

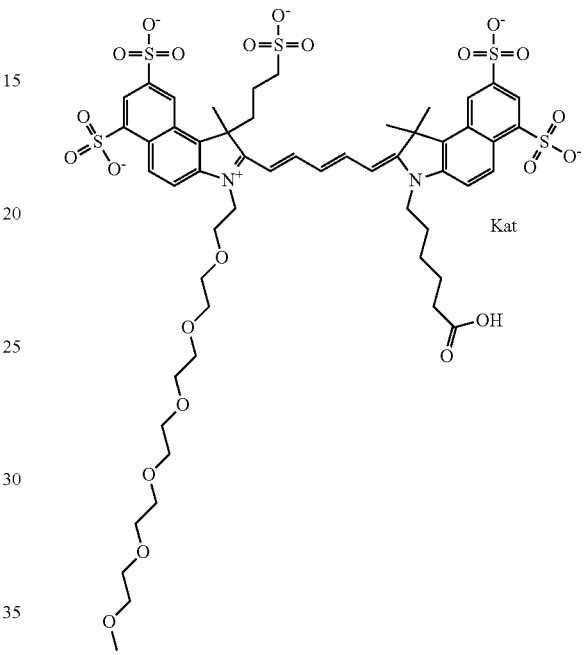

679 Compound 6 (6-((E)-1,1-dimethyl-2-((2E,4E)-5-(1-methyl-3-(2,5,8,11,14,17-hexaoxanonadecan-19-yl)-6,8-disulfonato-1-(3-sulfonatopropyl)-1H-benzo[e]indol-3-ium-2-yl)penta-2,4-dien-1-ylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 649 Compound 6 is activated as described above.

In one embodiment, the compound is 679 Compound 0/1

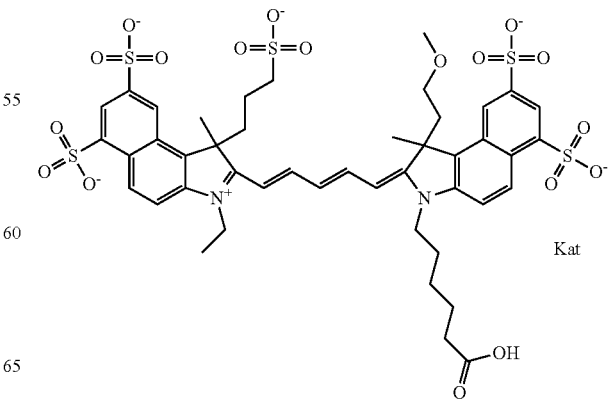

679 Compound 0/1 (2-((1E,3E,5E)-5-(3-(5-carboxypentyl)-1-(2-methoxyethyl)-1-methyl-6,8-disulfonato-1H-benzo[e]indol-2(3H)-ylidene)penta-1,3-dienyl)-3-ethyl-1-methyl-1-(3-sulfonatopropyl)-1H-benzo[e]indolium-6,8-disulfonate) contains ethylene glycol at R2, sulfoalkyl at R1, an ethyl at R9, and carboxyalkyl at R10.

One non-limiting example of an activated compound is the NHS-ester of 679 Compound 0/1, shown below:

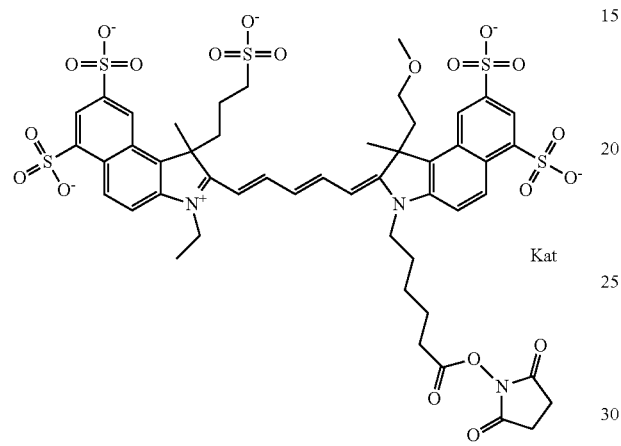

One non-limiting example of an activated 679 Compound 0/1 is tetrafluorophenyl (TFP)-ester form, shown below:

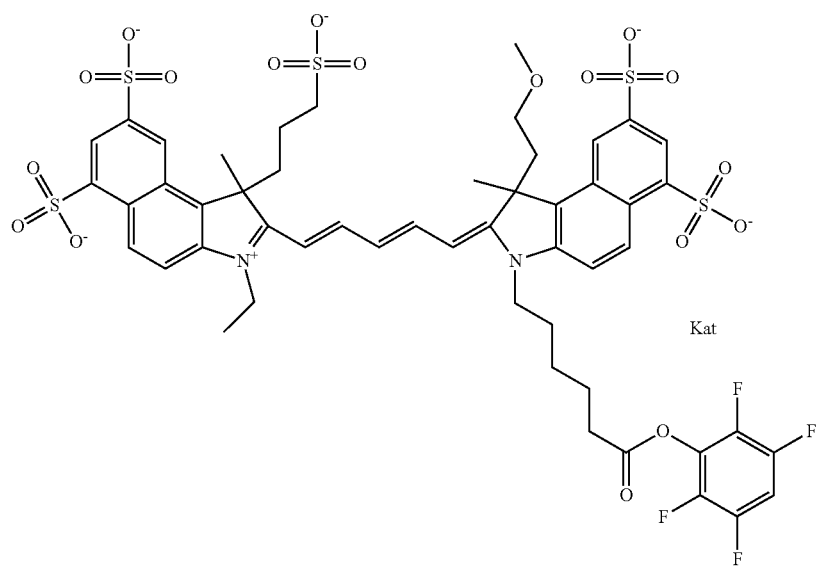 [SMILES: CC[N+]1=C(/C=C/C=C/C=C2/N(CCCCCC(=O)Oc3c(F)c(F)cc(F)c3F)c3ccc4c(S(=O)(=O)[O-])cc(S(=O)(=O)[O-])cc4c3C2(C)CCOC)C(C)(CCCS(=O)(=O)[O-])c2c1ccc1c(S(=O)(=O)[O-])cc(S(=O)(=O)[O-])cc21]

One non-limiting example of an activated 679 Compound 0/1 is sulfotetrafluorophenyl (STP)-ester form, shown below:

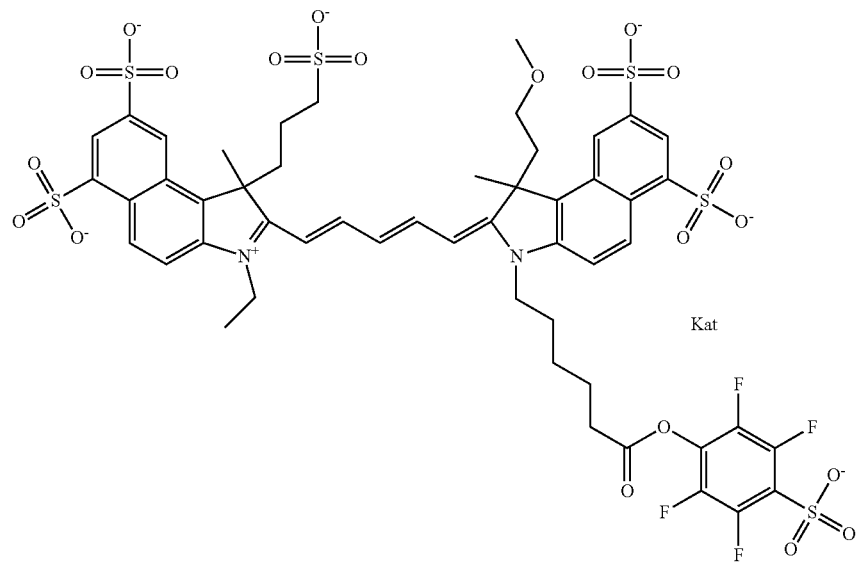 [SMILES: CC[N+]1=C(/C=C/C=C/C=C2/N(CCCCCC(=O)Oc3c(F)c(F)c(S(=O)(=O)[O-])c(F)c3F)c3ccc4c(S(=O)(=O)[O-])cc(S(=O)(=O)[O-])cc4c3C2(C)CCOC)C(C)(CCCS(=O)(=O)[O-])c2c1ccc1c(S(=O)(=O)[O-])cc(S(=O)(=O)[O-])cc21]
One non-limiting example of an activated 679 Compound 0/1 is a hydrazide form, shown below:
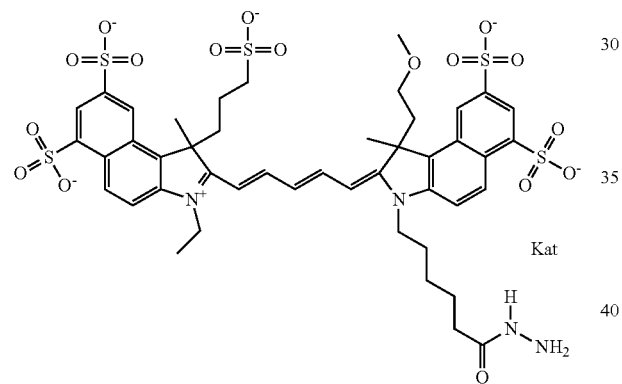
One non-limiting example of an activated 679 Compound 0/1 is a maleimide form, shown below:
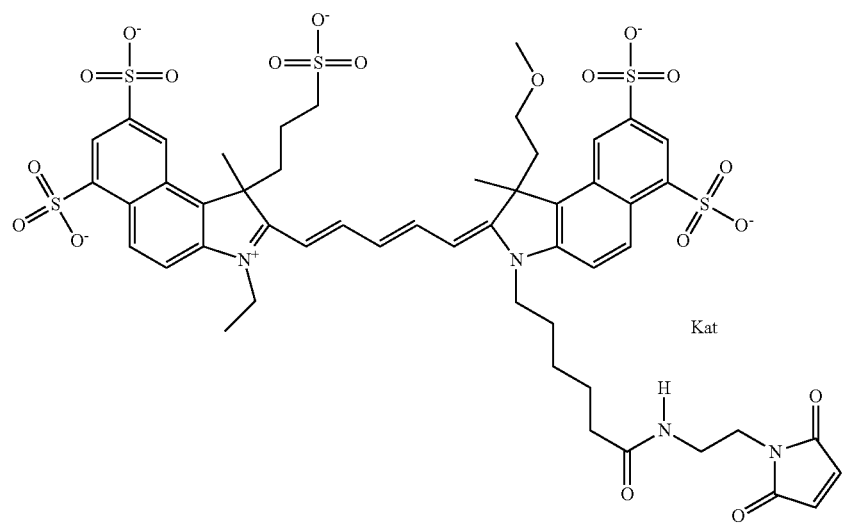 [SMILES: CC[N+]1=C(/C=C/C=C/C=C2/N(CCCCCC(=O)NCCN3C(=O)C=CC3=O)c3ccc4c(S(=O)(=O)[O-])cc(S(=O)(=O)[O-])cc4c3C2(C)CCOC)C(C)(CCCS(=O)(=O)[O-])c2c1ccc1c(S(=O)(=O)[O-])cc(S(=O)(=O)[O-])cc21]

In one embodiment, the compound is 679 Compound 0/1

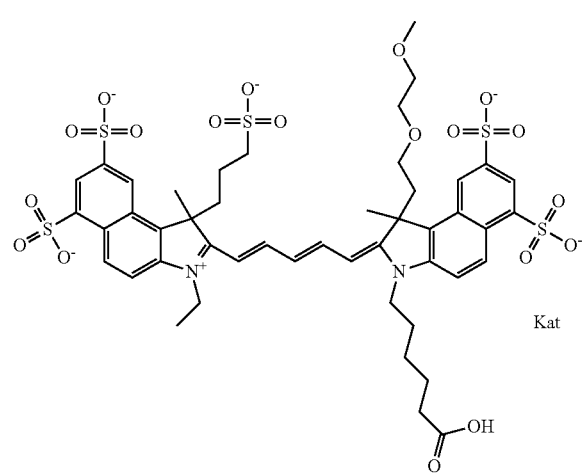 [SMILES: CC[N+]1=C(/C=C/C=C/C=C2/N(CCCCCC(=O)O)c3ccc4c(S(=O)(=O)[O-])cc(S(=O)(=O)[O-])cc4c3C2(C)CCOCCOC)C(C)(CCCS(=O)(=O)[O-])c2c1ccc1c(S(=O)(=O)[O-])cc(S(=O)(=O)[O-])cc21]

679 Compound 0/1 (2-((1E,3E,5E)-5-(3-(5-carboxypentyl)-1-(2-(2-methoxyethoxy)ethyl)-1-methyl-6,8-disulfonato-1H-benzo[e]indol-2(3H)-ylidene)penta-1,3-dienyl)-3-ethyl-1-methyl-1-(3-sulfonatopropyl)-1H-benzo[e]indolium-6,8-disulfonate) contains diethylene glycol at R2, sulfoalkyl at R1, ethyl at R9, and carboxyalkyl at R10.

In one embodiment, the compound is 679 Compound 0/1

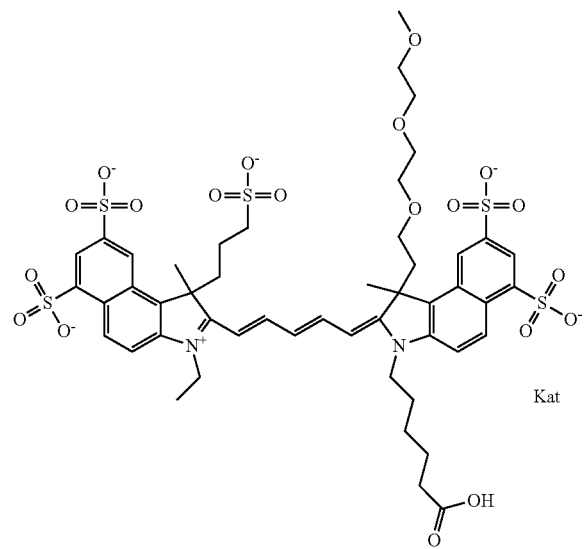 [SMILES: CC[N+]1=C(/C=C/C=C/C=C2/N(CCCCCC(=O)O)c3ccc4c(S(=O)(=O)[O-])cc(S(=O)(=O)[O-])cc4c3C2(C)CCOCCOCCOC)C(C)(CCCS(=O)(=O)[O-])c2c1ccc1c(S(=O)(=O)[O-])cc(S(=O)(=O)[O-])cc21]

679 Compound 0/1 (2-((1E,3E,5E)-5-(3-(5-carboxypentyl)-1-(2-(2-(2-methoxyethoxy)ethoxy)ethyl)-1-methyl-6,8-disulfonato-1H-benzo[e]indol-2(3H)-ylidene)penta-1,3-dienyl)-3-ethyl-1-methyl-1-(3-sulfonatopropyl)-1H-benzo[e]indolium-6,8-disulfonate) contains (poly)ethylene glycol (PEG$_3$) at R2, sulfoalkyl at R1, an ethyl at R9, and carboxyalkyl at R10.

In one embodiment, the compound is 679 Compound 0/1

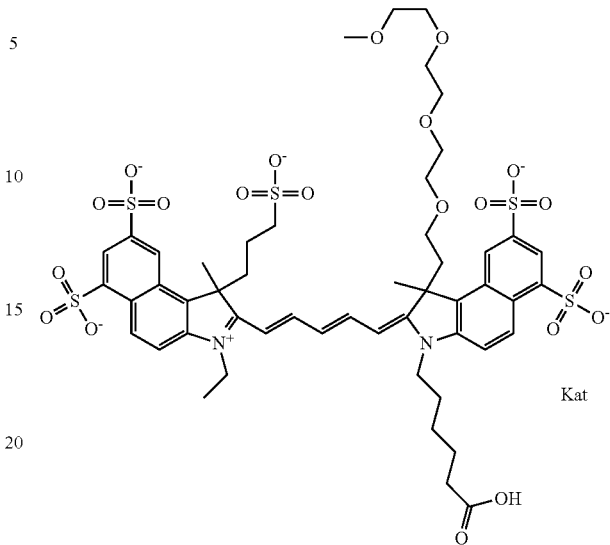

679 Compound 0/1 (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-3-ethyl-1-methyl-1-(3-sulfonatopropyl)-1H-benzo[e]indolium-6,8-disulfonate) contains (poly)ethylene glycol (PEG$_4$) at R2, sulfoalkyl at R1, ethyl at R9, and carboxyalkyl at R10.

In one embodiment, the compound is 679 Compound 0/1

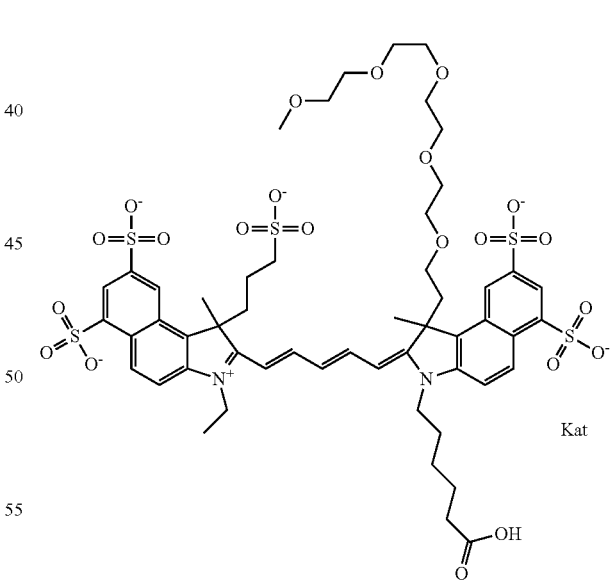

679 Compound 0/1 (2-((1E,3E,5E)-5-(3-(5-carboxypentyl)-1-(2,5,8,11,14-pentaoxahexadecan-16-yl)-1-methyl-6,8-disulfonato-1H-benzo[e]indol-2(3H)-ylidene)penta-1,3-dienyl)-3-ethyl-1-methyl-1-(3-sulfonatopropyl)-1H-benzo[e]indolium-6,8-disulfonate) contains (poly)ethylene glycol (PEG$_5$) at R2, sulfoalkyl at R1, ethyl at R9, and carboxyalkyl at R10.

In one embodiment, the compound is 679 Compound 0/1

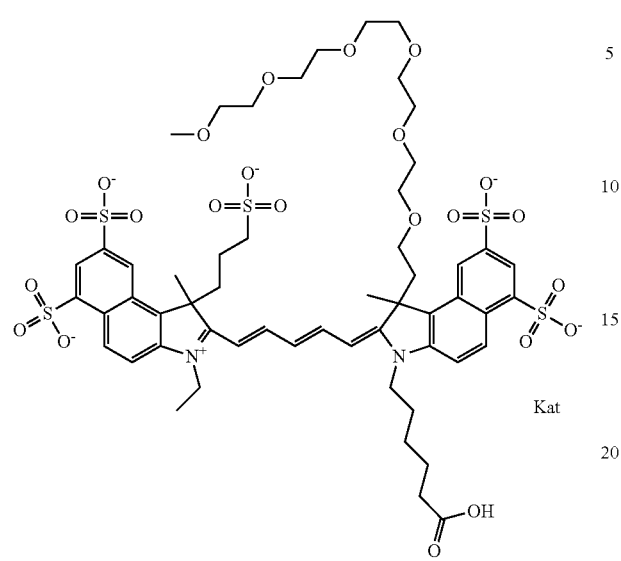

679 Compound 0/1 (2-((1E,3E,5E)-5-(3-(5-carboxypentyl)-1-methyl-1-(2,5,8,11,14,17-hexaoxanonadecan-19-yl)-6,8-disulfonato-1H-benzo[e]indol-2(3H)-ylidene)penta-1,3-dienyl)-3-ethyl-1-methyl-1-(3-sulfonatopropyl)-1H-benzo[e]indolium-6,8-disulfonate) contains (poly)ethylene glycol (PEG$_6$) at R2, sulfoalkyl at R1, ethyl at R9, and carboxyalkyl at R10.

In one embodiment, the compound is 679 Compound 0/1

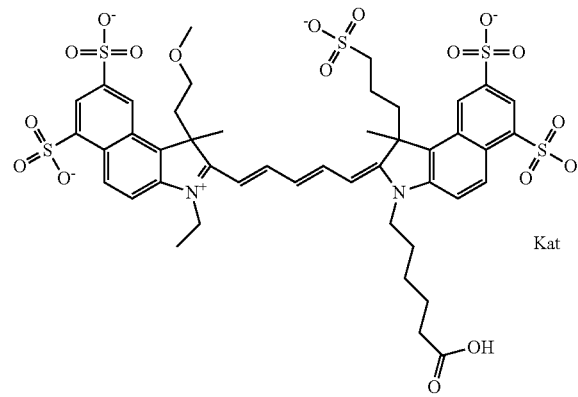

679 Compound 0/1 (2-((1E,3E,5E)-5-(3-(5-carboxypentyl)-1-methyl-6,8-disulfonato-1-(3-sulfonatopropyl)-1H-benzo[e]indol-2(3H)-ylidene)penta-1,3-dienyl)-3-ethyl-1-(2-methoxyethyl)-1-methyl-1H-benzo[e]indolium-6,8-disulfonate) contains ethylene glycol at R1, sulfoalkyl at R2, ethyl at R9, and carboxyalkyl at R10.

One non-limiting example of an activated compound is the NHS-ester of 679 Compound 0/1, shown below:

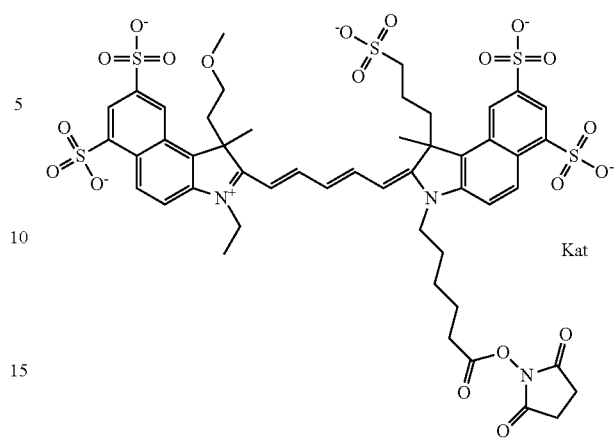

In one embodiment, the compound is 679 Compound 0/1

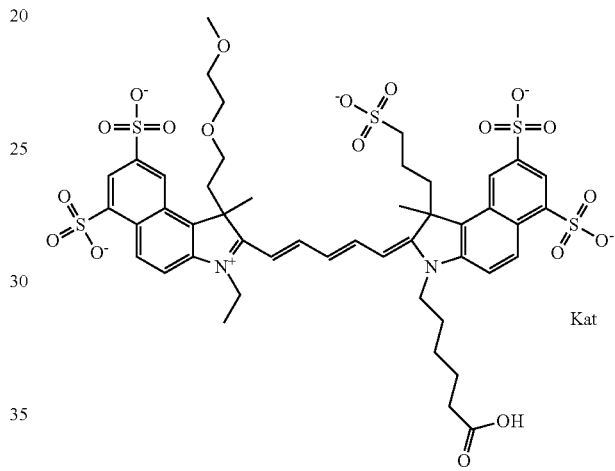

679 Compound 0/1 (2-((1E,3E,5E)-5-(3-(5-carboxypentyl)-1-methyl-6,8-disulfonato-1-(3-sulfonatopropyl)-1H-benzo[e]indol-2(3H)-ylidene)penta-1,3-dienyl)-3-ethyl-1-(2-(2-methoxyethoxy)ethyl)-1-methyl-1H-benzo[e]indolium-6,8-disulfonate) contains diethylene glycol at R1, sulfoalkyl at R2, ethyl at R9, and carboxyalkyl at R10.

In one embodiment, the compound is 679 Compound 0/1

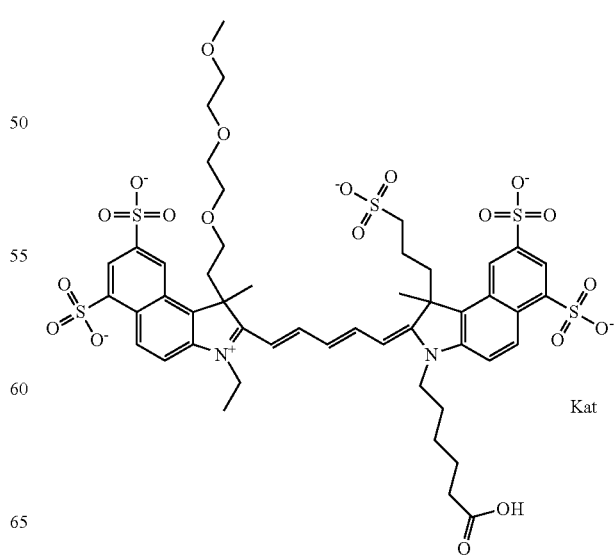

679 Compound 0/1 (2-((1E,3E,5E)-5-(3-(5-carboxypentyl)-1-methyl-6,8-disulfonato-1-(3-sulfonatopropyl)-1H-benzo[e]indol-2(3H)-ylidene)penta-1,3-dienyl)-3-ethyl-1-(2-(2-(2-methoxyethoxy)ethoxy)ethyl)-1-methyl-1H-benzo[e]indolium-6,8-disulfonate) contains (poly)ethylene glycol (PEG$_3$) at R1, sulfoalkyl at R2, ethyl at R9, and carboxyalkyl at R10.

In one embodiment, the compound is 679 Compound 0/1

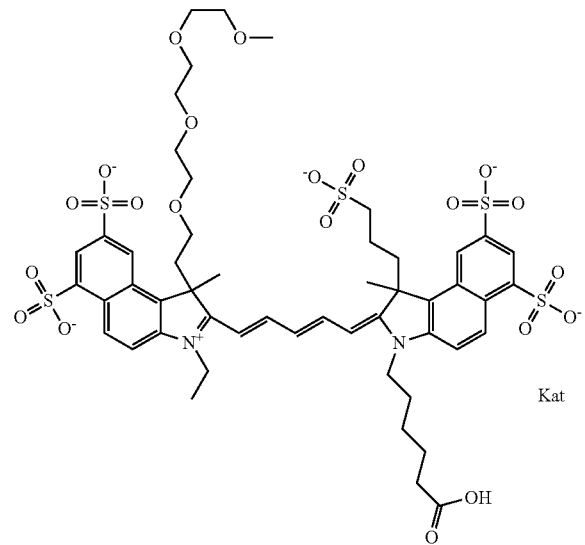

679 Compound 0/1 (2-((1E,3E,5E)-5-(3-(5-carboxypentyl)-1-methyl-6,8-disulfonato-1-(3-sulfonatopropyl)-1H-benzo[e]indol-2(3H)-ylidene)penta-1,3-dienyl)-3-ethyl-1-methyl-1-(2,5,8,11-tetraoxatridecan-13-yl)-1H-benzo[e]indolium-6,8-disulfonate) contains (poly)ethylene glycol (PEG$_4$) at R1, sulfoalkyl at R2, ethyl at R9, and carbon/alkyl at R10.

In one embodiment, the compound is 679 Compound 0/1

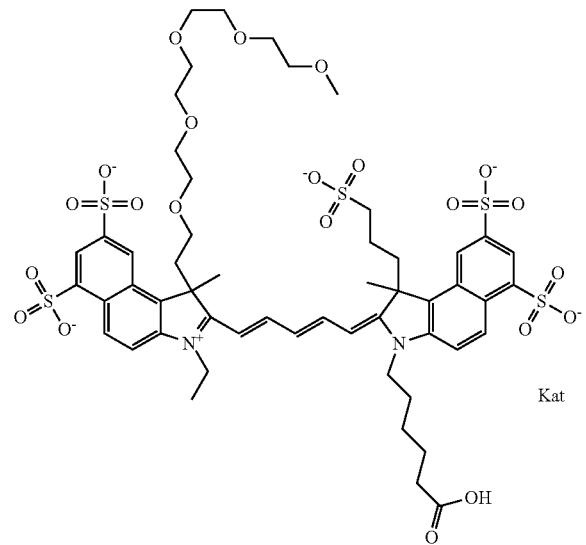

679 Compound 0/1 (2-((1E,3E,5E)-5-(3-(5-carboxypentyl)-1-methyl-6,8-disulfonato-1-(3-sulfonatopropyl)-1H-benzo[e]indol-2(3H)-ylidene)penta-1,3-dienyl)-3-ethyl-1-(2,5,8,11,14-pentaoxahexadecan-16-yl)-1-methyl-1H-benzo[e]indolium-6,8-disulfonate) contains (poly)ethylene glycol (PEG$_5$) at R1, sulfoalkyl at R2, ethyl at R9, and carboxyalkyl at R10.

In one embodiment, the compound is 679 Compound 0/1

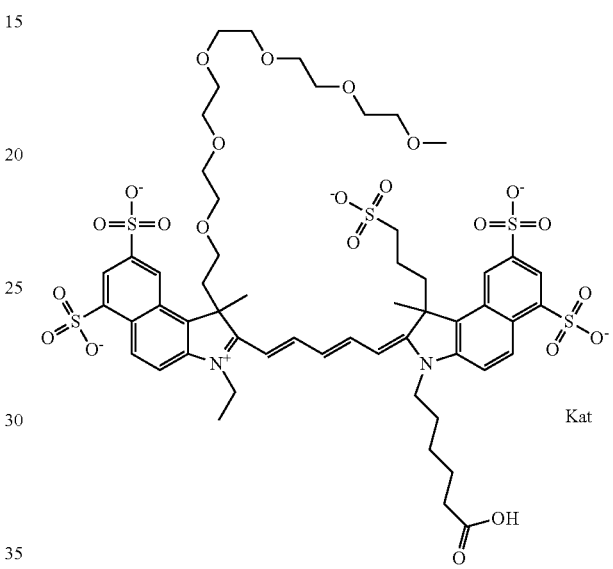

679 Compound 0/1 (2-((1E,3E,5E)-5-(3-(5-carboxypentyl)-1-methyl-6,8-disulfonato-1-(3-sulfonatopropyl)-1H-benzo[e]indol-2(3H)-ylidene)penta-1,3-dienyl)-3-ethyl-1-methyl-1-(2,5,8,11,14,17-hexaoxanonadecan-19-yl)-1H-benzo[e]indolium-6,8-disulfonate) contains (poly)ethylene glycol (PEG$_6$) at R1, sulfoalkyl at R2, ethyl at R9, and carboxyalkyl at R10.

In one embodiment, the compound is 679 Compound 0/2

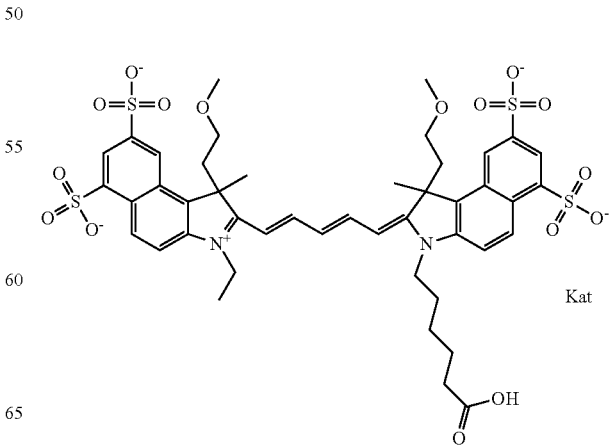

679 Compound 0/2 (2-((1E,3E,5E)-5-(3-(5-carboxypentyl)-1-(2-methoxyethyl)-1-methyl-6,8-disulfonato-1H-benzo[e]indol-2(3H)-ylidene)penta-1,3-dienyl)-3-ethyl-1-(2-methoxyethyl)-1-methyl-1H-benzo[e]indolium-6,8-disulfonate) contains ethylene glycol at R1 and R2, ethyl at R9, and carboxyalkyl at R10.

One non-limiting example of an activated compound is the NHS-ester of 679 Compound 0/2, shown below:

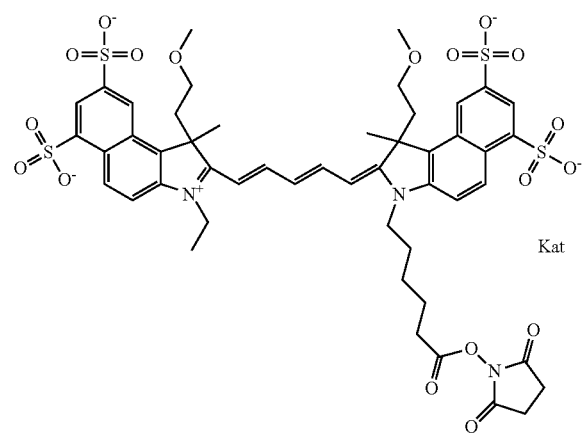 [SMILES: CC[N+]1=C(/C=C/C=C/C=C2/N(CCCCCC(=O)ON3C(=O)CCC3=O)c3ccc4c(S(=O)(=O)[O-])cc(S(=O)(=O)[O-])cc4c3C2(C)CCOC)C(C)(CCOC)c2c1ccc1c(S(=O)(=O)[O-])cc(S(=O)(=O)[O-])cc21]

In one embodiment, the compound is 679 Compound 0/2

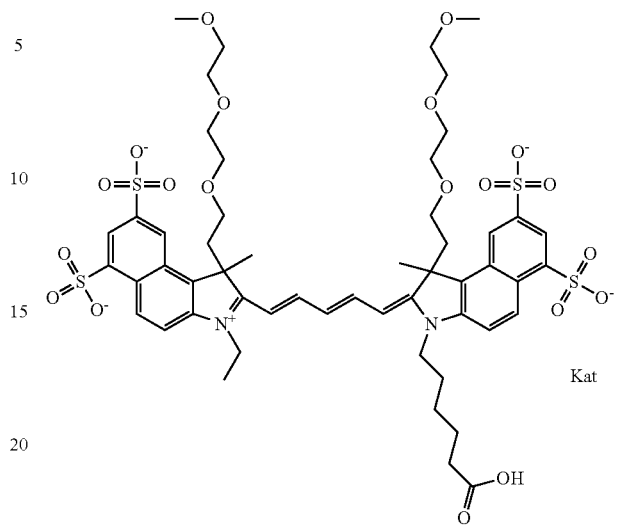

679 Compound 0/2 (2-((1E,3E,5E)-5-(3-(5-carboxypentyl)-1-(2-(2-(2-methoxyethoxy)ethoxy)ethyl)-1-methyl-6,8-disulfonato-1H-benzo[e]indol-2(3H)-ylidene)penta-1,3-dienyl)-3-ethyl-1-(2-(2-(2-methoxyethoxy)ethoxy)ethyl)-1-methyl-1H-benzo[e]indolium-6,8-disulfonate) contains (poly)ethylene glycol (PEG$_3$) at R1 and R2, ethyl at R9, and carboxyalkyl at R10.

In one embodiment, the compound is 679 Compound 0/2

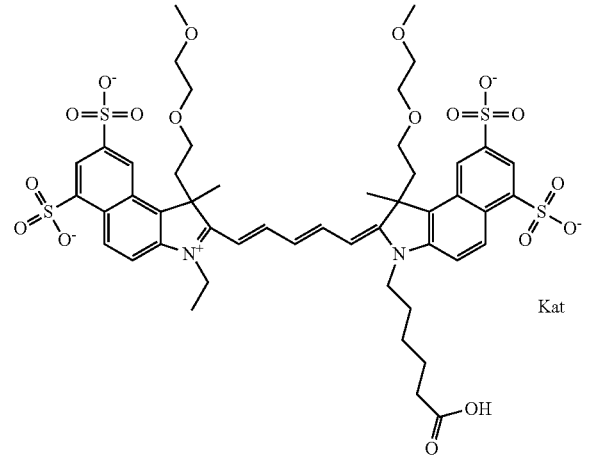 [SMILES: CC[N+]1=C(/C=C/C=C/C=C2/N(CCCCCC(=O)O)c3ccc4c(S(=O)(=O)[O-])cc(S(=O)(=O)[O-])cc4c3C2(C)CCOCCOC)C(C)(CCOCCOC)c2c1ccc1c(S(=O)(=O)[O-])cc(S(=O)(=O)[O-])cc21]

679 Compound 0/2 (2-((1E,3E,5E)-5-(3-(5-carboxypentyl)-1-(2-(2-methoxyethoxy)ethyl)-1-methyl-6,8-disulfonato-1H-benzo[e]indol-2(3H)-ylidene)penta-1,3-dienyl)-3-ethyl-1-(2-(2-methoxyethoxy)ethyl)-1-methyl-1H-benzo[e]indolium-6,8-disulfonate) contains diethylene glycol at R1 and R2, ethyl at R9, and carboxyalkyl at R10.

679 Compound 0/2 (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-3-ethyl-1-methyl-1-(2,5,8,11-tetraoxatridecan-13-yl)-1H-benzo[e]indolium-6,8-disulfonate) contains (poly)ethylene glycol (PEG$_4$) at R1 and R2, ethyl at R9, and carboxyalkyl at R10.

In one embodiment, the compound is 679 Compound 0/2
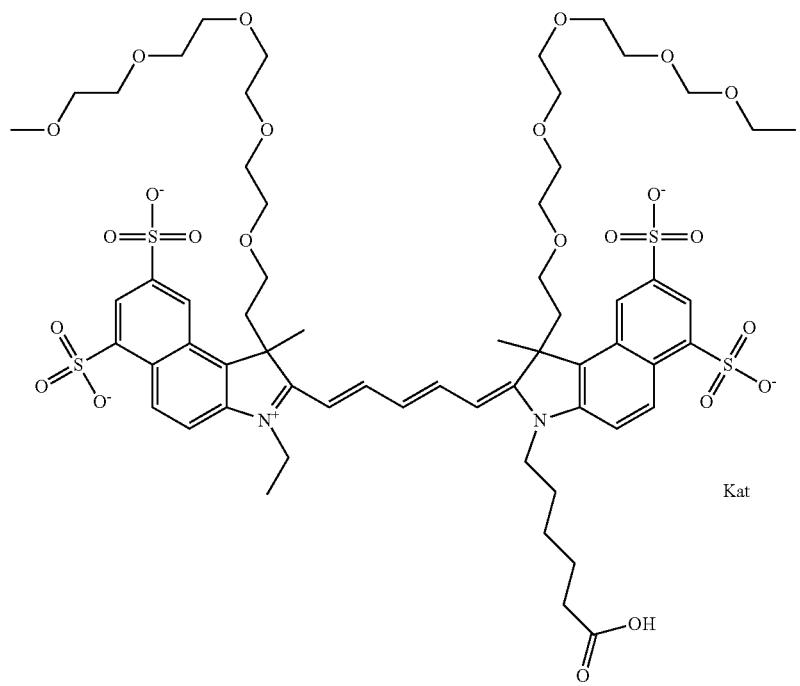 [SMILES: CCOCOCCOCCOCCOCCC1(C)\C(=C/C=C/C=C/C2=[N+](CC)c3ccc4c(S(=O)(=O)[O-])cc(S(=O)(=O)[O-])cc4c3C2(C)CCOCCOCCOCCOCCOC)N(CCCCCC(=O)O)c2ccc3c(S(=O)(=O)[O-])cc(S(=O)(=O)[O-])cc3c21]
679 Compound 0/2 (2-((1E,3E,5E)-5-(3-(5-carboxypentyl)-1-(2,5,8,11,14-pentaoxahexadecan-16-yl)-1-methyl-6,8-disulfonato-1H-benzo[e]indol-2(3H)-ylidene)penta-1,3-dienyl)-3-ethyl-1-(2,5,8,11,14-pentaoxahexadecan-16-yl)-1-methyl-1H-benzo[e]indolium-6,8-disulfonate) contains (poly)ethylene glycol ($PEG_5$) at R1 and R2, ethyl at R9, and carboxyalkyl at R10.
In one embodiment, the compound is 679 Compound 0/2
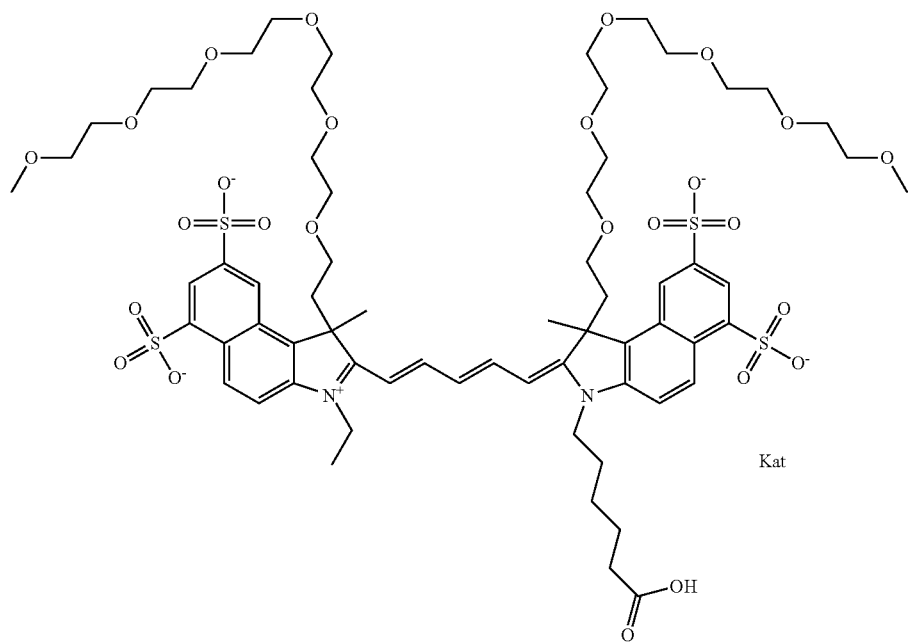

679 Compound 0/2 (2-((1E,3E,5E)-5-(3-(5-carboxypentyl)-1-methyl-1-(2,5,8,11,14,17-hexaoxanonadecan-19-yl)-6,8-disulfonato-1H-benzo[e]indol-2(3H)-ylidene)penta-1,3-dienyl)-3-ethyl-1-methyl-1-(2,5,8,11,14,17-hexaoxanonadecan-19-yl)-1H-benzo[e]indolium-6,8-disulfonate) contains (poly)ethylene glycol (PEG$_6$) at R1 and R2, ethyl at R9, and carboxyalkyl at R10.

In one embodiment, the compound is 679 Compound 0/1

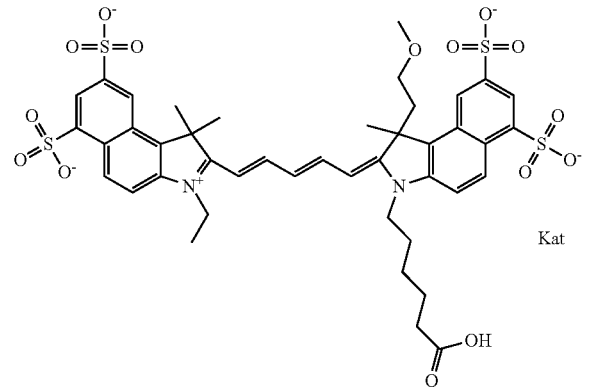 [SMILES: CC[N+]1=C(/C=C/C=C/C=C2/N(CCCCCC(=O)O)c3ccc4c(S(=O)(=O)[O-])cc(S(=O)(=O)[O-])cc4c3C2(C)CCOC)C(C)(C)c2c1ccc1c(S(=O)(=O)[O-])cc(S(=O)(=O)[O-])cc21]

679 Compound 0/1 (2-((1E,3E,5E)-5-(3-(5-carboxypentyl)-1-(2-methoxyethyl)-1-methyl-6,8-disulfonato-1H-benzo[e]indol-2(3H)-ylidene)penta-1,3-dienyl)-3-ethyl-1,1-dimethyl-1H-benzo[e]indolium-6,8-disulfonate) contains ethylene glycol at R2, methyl at R1, ethyl at R9, and carboxyalkyl at R10.

One non-limiting example of an activated compound is the NHS-ester of 679 Compound 0/1, shown below:

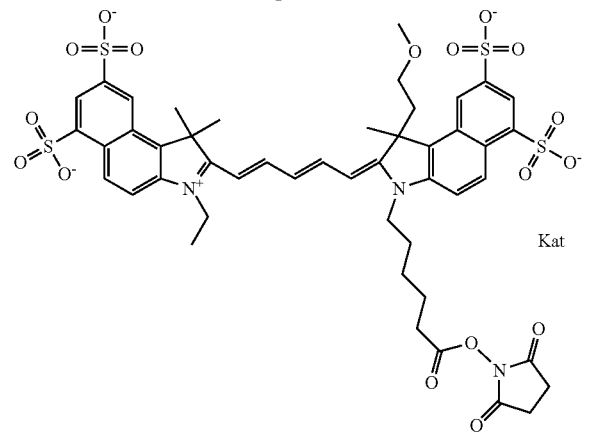 [SMILES: CC[N+]1=C(/C=C/C=C/C=C2/N(CCCCCC(=O)ON3C(=O)CCC3=O)c3ccc4c(S(=O)(=O)[O-])cc(S(=O)(=O)[O-])cc4c3C2(C)CCOC)C(C)(C)c2c1ccc1c(S(=O)(=O)[O-])cc(S(=O)(=O)[O-])cc21]

In one embodiment, the compound is 679 Compound 0/1

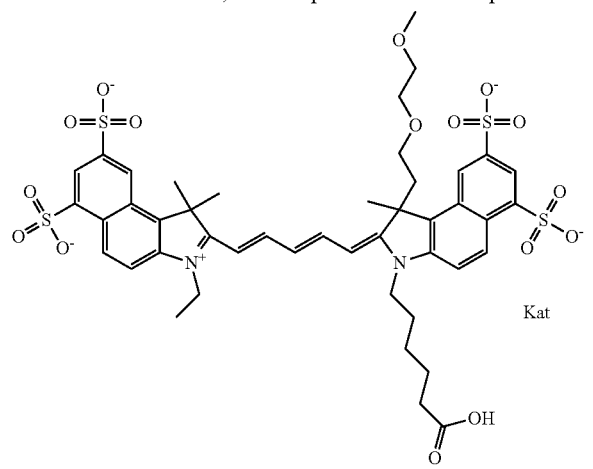

679 Compound 0/1 (2-((1E,3E,5E)-5-(3-(5-carboxypentyl)-1-(2-(2-methoxyethoxy)ethyl)-1-methyl-6,8-disulfonato-1H-benzo[e]indol-2(3H)-ylidene)penta-1,3-dienyl)-3-ethyl-1,1-dimethyl-1H-benzo[e]indolium-6,8-disulfonate) contains a diethylene glycol at R2, a methyl at R1, ethyl at R9, and carboxyalkyl at R10.

In one embodiment, the compound is 679 Compound 0/1

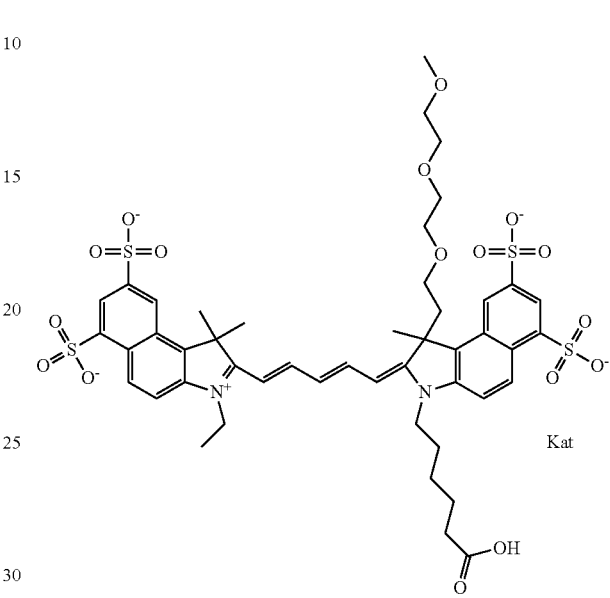

679 Compound 0/1 (2-((1E,3E,5E)-5-(3-(5-carboxypentyl)-1-(2-(2-(2-methoxyethoxy)ethoxy)ethyl)-1-methyl-6,8-disulfonato-1H-benzo[e]indol-2(3H)-ylidene)penta-1,3-dienyl)-3-ethyl-1,1-dimethyl-1H-benzo[e]indolium-6,8-disulfonate) contains a (poly)ethylene glycol (PEG$_3$) at R2, a methyl at R1, ethyl at R9, and carboxyalkyl at R10.

In one embodiment, the compound is 679 Compound 0/1

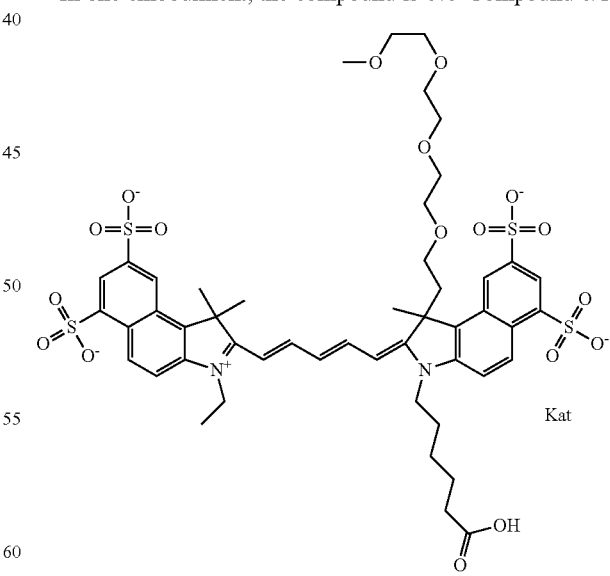

679 Compound 0/1 (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-3-ethyl-1,1-dimethyl-1H-benzo[e]indolium-6,8-disulfonate) contains a (poly)ethylene glycol (PEG$_4$) at R2, a methyl at R1, ethyl at R9, and carboxyalkyl at R10.

In one embodiment, the compound is 679 Compound 0/1

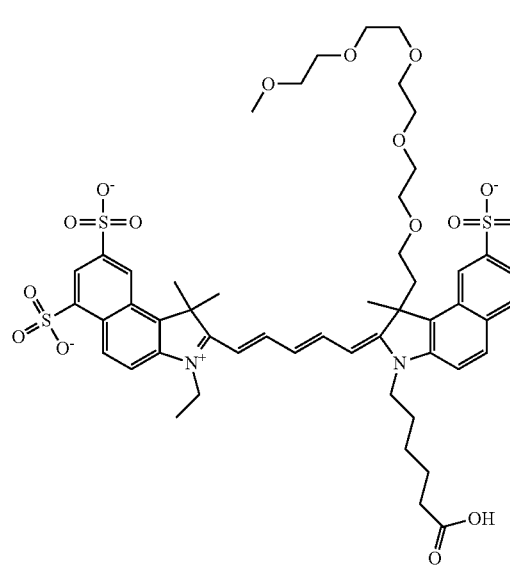

679 Compound 0/1 (2-((1E,3E,5E)-5-(3-(5-carboxypentyl)-1-(2,5,8,11,14-pentaoxahexadecan-16-yl)-1-methyl-6,8-disulfonato-1H-benzo[e]indol-2(3H)-ylidene)penta-1,3-dienyl)-3-ethyl-1,1-dimethyl-1H-benzo[e]indolium-6,8-disulfonate) contains a (poly)ethylene glycol (PEG$_5$) at R2, a methyl at R1, ethyl at R9, and carboxyalkyl at R10.

In one embodiment, the compound is 679 Compound 0/1

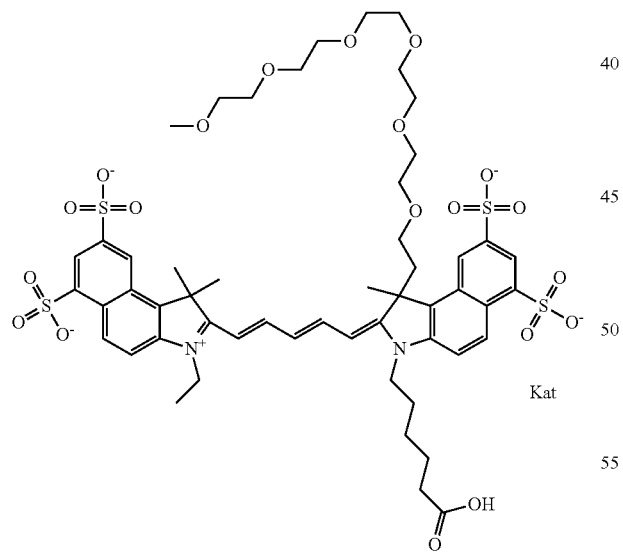

679 Compound 0/1 (2-((1E,3E,5E)-5-(3-(5-carboxypentyl)-1-methyl-1-(2,5,8,11,14,17-hexaoxanonadecan-19-yl)-6,8-disulfonato-1H-benzo[e]indol-2(3H)-ylidene)penta-1,3-dienyl)-3-ethyl-1,1-dimethyl-1H-benzo[e]indolium-6,8-disulfonate) contains a (poly)ethylene glycol (PEG$_6$) at R2, a methyl at R1, ethyl at R9, and carboxyalkyl at R10.

In one embodiment, the compound is 679 Compound 0/1

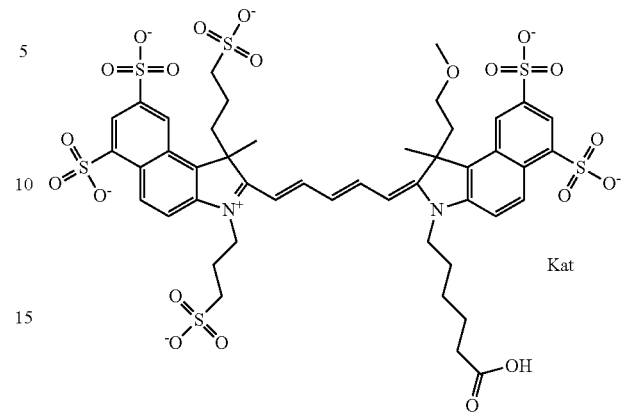

679 Compound 0/1 (2-((1E,3E,5E)-5-(3-(5-carboxypentyl)-1-(2-methoxyethyl)-1-methyl-6,8-disulfonato-1H-benzo[e]indol-2(3H)-ylidene)penta-1,3-dienyl)-1-methyl-1,3-bis(3-sulfonatopropyl)-1H-benzo[e]indolium-6,8-disulfonate) contains ethylene glycol at R2, a sulfoalkyl at R1, a sulfoalkyl at R9, and carboxyalkyl at R10.

One non-limiting example of an activated compound is the NHS-ester of 679 Compound 0/1, shown below:

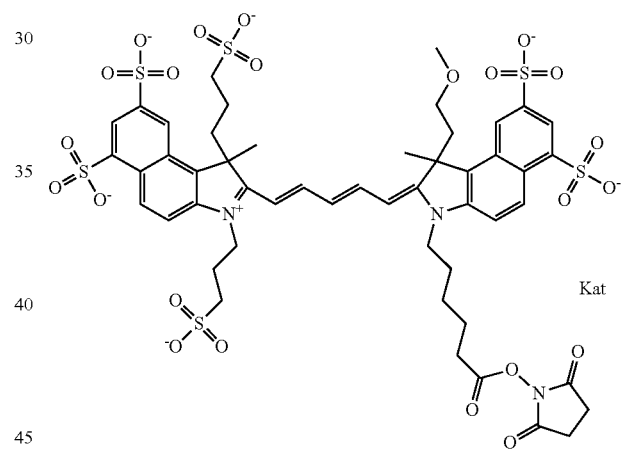

In one embodiment, the compound is 679 Compound 0/1

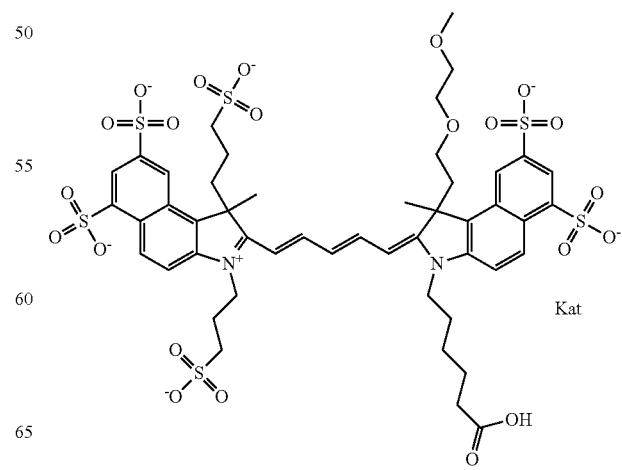

679 Compound 0/1 (2-((1E,3E,5E)-5-(3-(5-carboxypentyl)-1-(2-(2-methoxyethoxy)ethyl)-1-methyl-6,8-disulfonato-1H-benzo[e]indol-2(3H)-ylidene)penta-1,3-dienyl)-1-methyl-1,3-bis(3-sulfonatopropyl)-1H-benzo[e]indolium-6,8-disulfonate) contains a diethylene glycol at R2, a sulfoalkyl at R1, a sulfoalkyl at R9, and carboxyalkyl at R10.

In one embodiment, the compound is 679 Compound 0/1

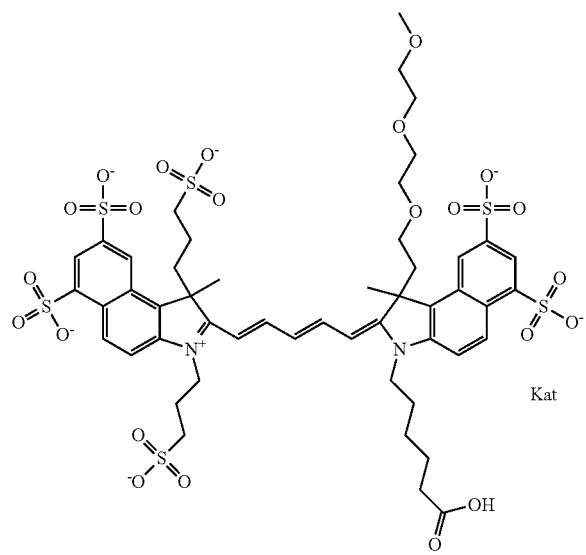

679 Compound 0/1 (2-((1E,3E,5E)-5-(3-(5-carboxypentyl)-1-(2-(2-(2-methoxyethoxy)ethoxy)ethyl)-1-methyl-6,8-disulfonato-1H-benzo[e]indol-2(3H)-ylidene)penta-1,3-dienyl)-1-methyl-1,3-bis(3-sulfonatopropyl)-1H-benzo[e]indolium-6,8-disulfonate) contains a (poly)ethylene glycol ($PEG_3$) at R2, a sulfoalkyl at R1, a sulfoalkyl at R9, and carboxyalkyl at R10.

In one embodiment, the compound is 679 Compound 0/1

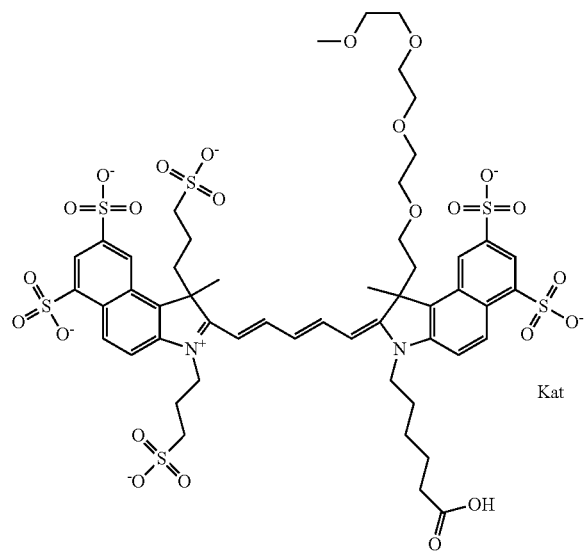

679 Compound 0/1 (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-1-methyl-1,3-bis(3-sulfonatopropyl)-1H-benzo[e]indolium-6,8-disulfonate) contains a (poly)ethylene glycol ($PEG_4$) at R2, a sulfoalkyl at R1, a sulfoalkyl at R9, and carboxyalkyl at R10.

In one embodiment, the compound is 679 Compound 0/1

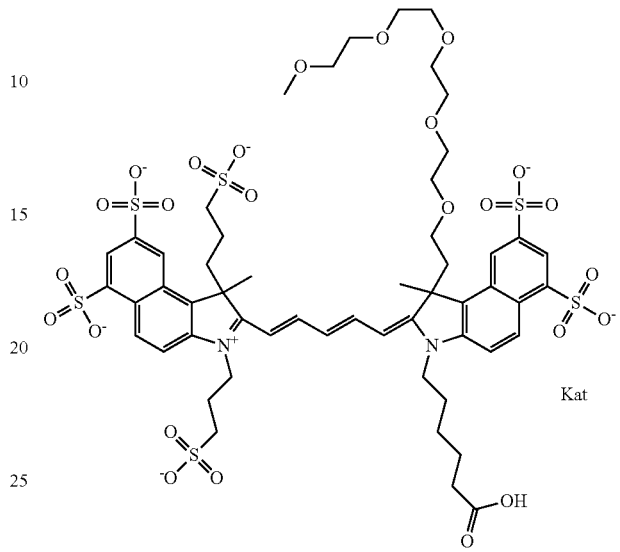

679 Compound 0/1 (2-((1E,3E,5E)-5-(3-(5-carboxypentyl)-1-(2,5,8,11,14-pentaoxahexadecan-16-yl)-1-methyl-6,8-disulfonato-1H-benzo[e]indol-2(3H)-ylidene)penta-1,3-dienyl)-1-methyl-1,3-bis(3-sulfonatopropyl)-1H-benzo[e]indolium-6,8-disulfonate) contains a (poly)ethylene glycol ($PEG_5$) at R2, a sulfoalkyl at R1, ethyl at R9, and carboxyalkyl at R10.

In one embodiment, the compound is 679 Compound 0/1

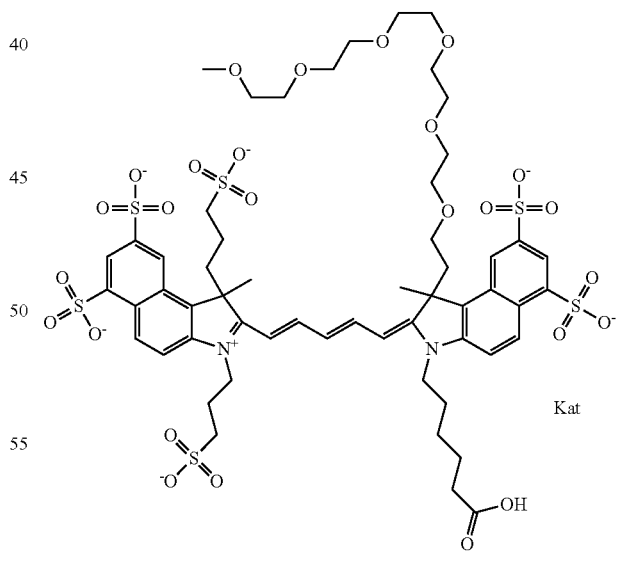

679 Compound 0/1 (2-((1E,3E,5E)-5-(3-(5-carboxypentyl)-1-methyl-1-(2,5,8,11,14,17-hexaoxanonadecan-19-yl)-6,8-disulfonato-1H-benzo[e]indol-2(3H)-ylidene)penta-1,3-dienyl)-1-methyl-1,3-bis(3-sulfonatopropyl)-1H-benzo[e]indolium-6,8-disulfonate) contains a (poly)ethylene glycol ($PEG_6$) at R2, a sulfoalkyl at R1, ethyl at R9, and carboxyalkyl at R10.

In one embodiment, the compound is 679 Compound 0/2

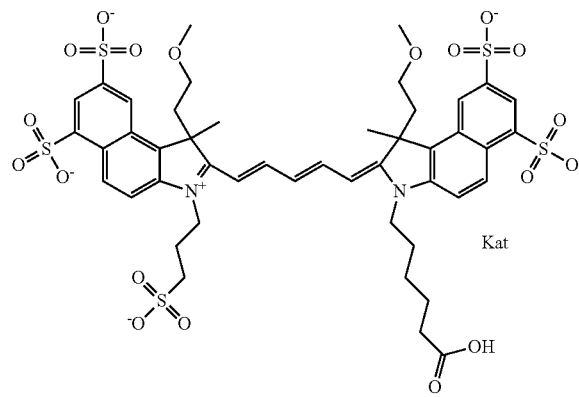

679 Compound 0/2 (2-((1E,3E,5E)-5-(3-(5-carboxypentyl)-1-(2-methoxyethyl)-1-methyl-6,8-disulfonato-1H-benzo[e]indol-2(3H)-ylidene)penta-1,3-dienyl)-1-(2-methoxyethyl)-1-methyl-3-(3-sulfonatopropyl)-1H-benzo[e]indolium-6,8-disulfonate) contains ethylene glycol at R1 and R2, a sulfoalkyl at R9, and carboxyalkyl at R10.

One non-limiting example of an activated compound is the NHS-ester of 679 Compound 0/2, shown below:

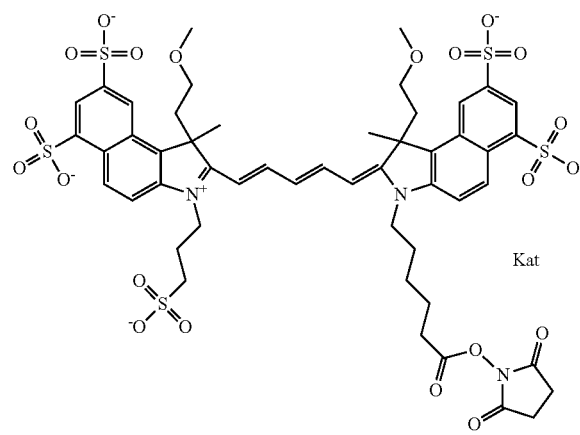

In one embodiment, the compound is 679 Compound 0/2

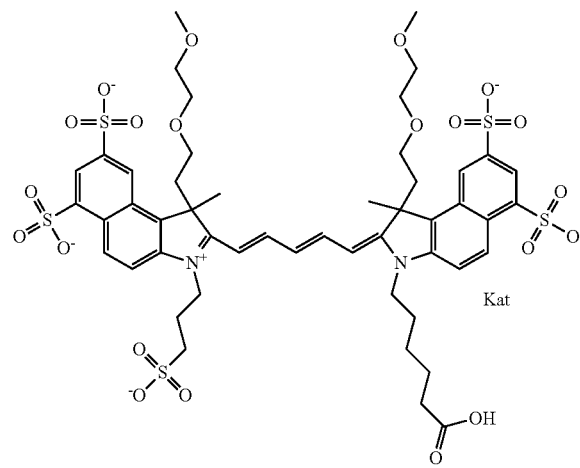

679 Compound 0/2 (2-((1E,3E,5E)-5-(3-(5-carboxypentyl)-1-(2-(2-methoxyethoxy)ethyl)-1-methyl-6,8-disulfonato-1H-benzo[e]indol-2(3H)-ylidene)penta-1,3-dienyl)-1-(2-(2-methoxyethoxy)ethyl)-1-methyl-3-(3-sulfonatopropyl)-1H-benzo[e]indolium-6,8-disulfonate) contains a diethylene glycol at R1 and R2, a sulfoalkyl at R9, and carboxyalkyl at R10.

In one embodiment, the compound is 679 Compound 0/2

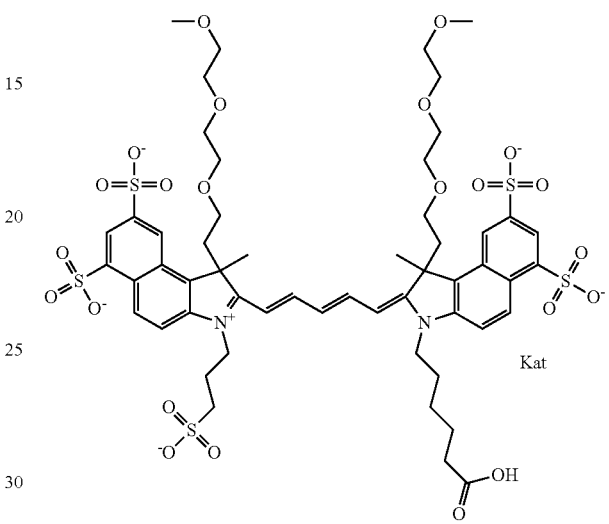

679 Compound 0/2 (2-((1E,3E,5E)-5-(3-(5-carboxypentyl)-1-(2-(2-(2-methoxyethoxy)ethoxy)ethyl)-1-methyl-6,8-disulfonato-1H-benzo[e]indol-2(3H)-ylidene)penta-1,3-dienyl)-1-(2-(2-(2-methoxyethoxy)ethoxy)ethyl)-1-methyl-3-(3-sulfonatopropyl)-1H-benzo[e]indolium-6,8-disulfonate) contains a (poly)ethylene glycol (PEG$_3$) at R1 and R2, a sulfoalkyl at R9, and carboxyalkyl at R10.

In one embodiment, the compound is 679 Compound 0/2

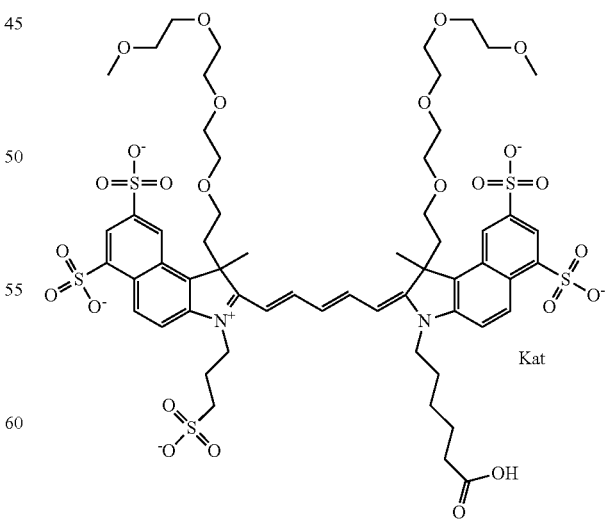

679 Compound 0/2 (2-((1E,3E,5E)-5-(3-(5-carboxypentyl)-1-methyl-6,8-disulfonato-1-(2,5,8,11-tetraoxatridecan- 13-yl)-1H-benzo[e]indol-2(3H)-ylidene)penta-1,3-dienyl)-1-methyl-3-(3-sulfonatopropyl)-1-(2,5,8,11-tetraoxatridecan-13-yl)-1H-benzo[e]indolium-6,8-disulfonate) contains a (poly)ethylene glycol (PEG$_4$) at R1 and R2, a sulfoalkyl at R9, and carboxyalkyl at R10.

In one embodiment, the compound is 679 Compound 0/2

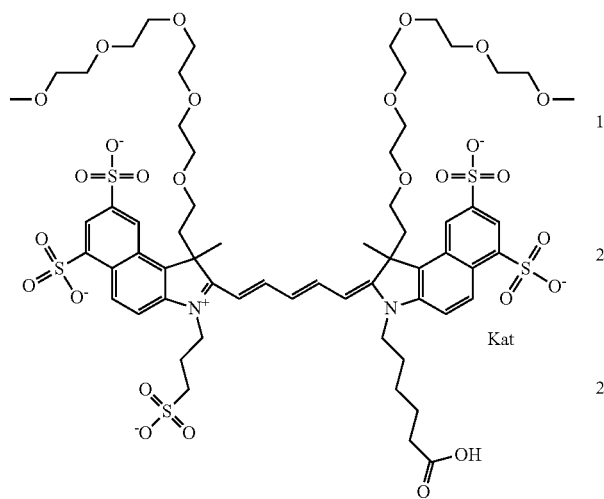

679 Compound 0/2 (2-((1E,3E,5E)-5-(3-(5-carboxypentyl)-1-(2,5,8,11,14-pentaoxahexadecan-16-yl)-1-methyl-6,8-disulfonato-1H-benzo[e]indol-2(3H)-ylidene)penta-1,3-dienyl)-1-(2,5,8,11,14-pentaoxahexadecan-16-yl)-1-methyl-3-(3-sulfonatopropyl)-1H-benzo[e]indolium-6,8-disulfonate) contains a (poly)ethylene glycol (PEG$_5$) at R1 and R2, ethyl at R9, and carboxyalkyl at R10.

In one embodiment, the compound is 679 Compound 0/2

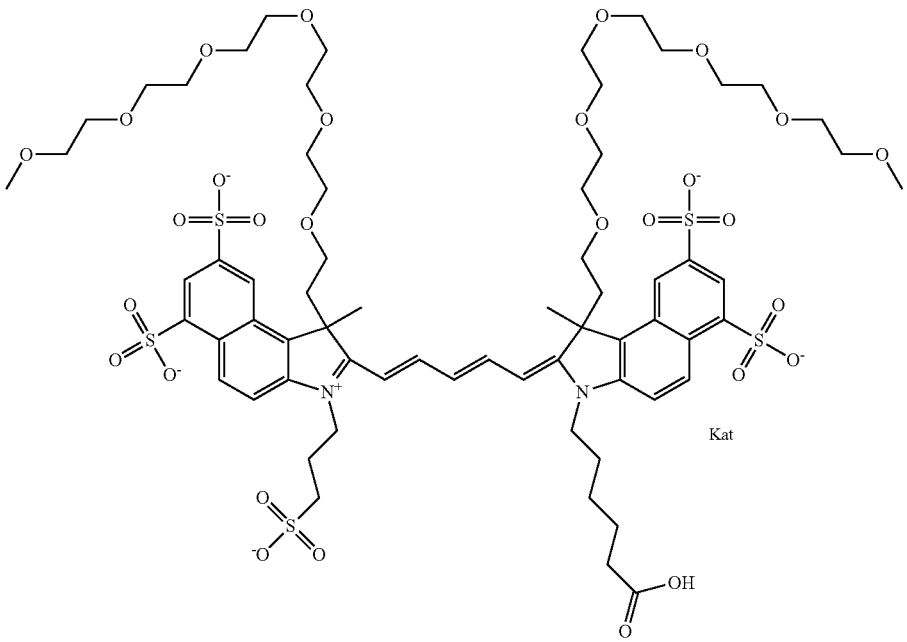

679 Compound 0/2 (2-((1E,3E,5E)-5-(3-(5-carboxypentyl)-1-methyl-1-(2,5,8,11,14,17-hexaoxanonadecan-19-yl)-6,8-disulfonato-1H-benzo[e]indol-2(3H)-ylidene)penta-1,3-dienyl)-1-methyl-1-(2,5,8,11,14,17-hexaoxanonadecan-19-yl)-3-(3-sulfonatopropyl)-1H-benzo[e]indolium-6,8-disulfonate) contains a (poly)ethylene glycol (PEG$_6$) at R1 and R2, ethyl at R9, and carboxyalkyl at R10.

In embodiments, the degree and/or location of sulfonation is varied to, e.g., vary the compound's degree of hydrophilicity or hydrophobicity. One non-limiting example is a monosulfonate form of 679 Compound 1, shown below:

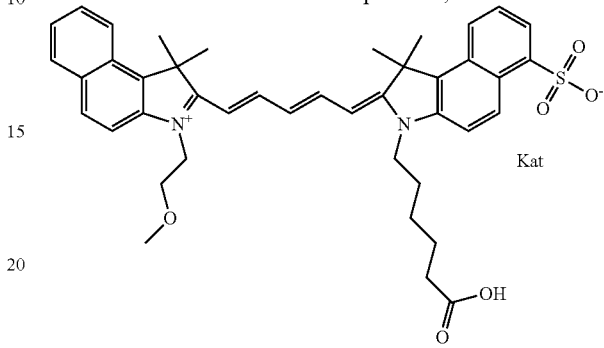

One non-limiting example is a disulfonate form of 679 Compound 1, shown below:

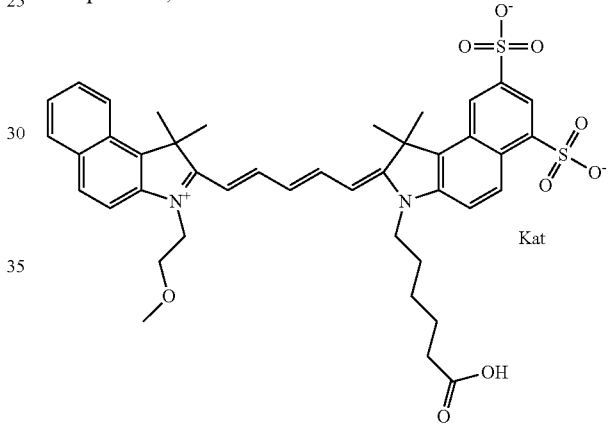

One non-limiting example is a trisulfonate form of 679 Compound 1, shown below:

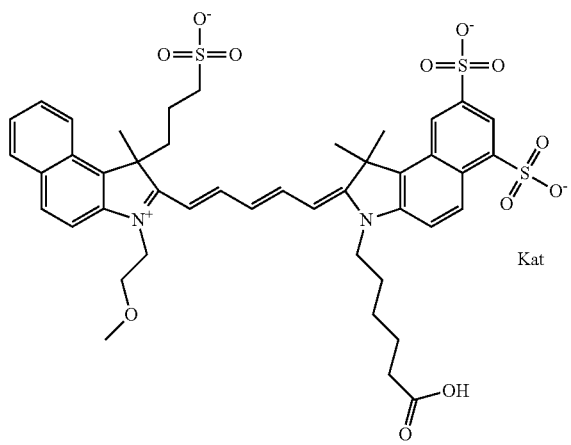 [SMILES: COCC[N+]1=C(/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1ccccc21]

One non-limiting example is a monosulfonate form of 679 Compound 0/1, shown below:

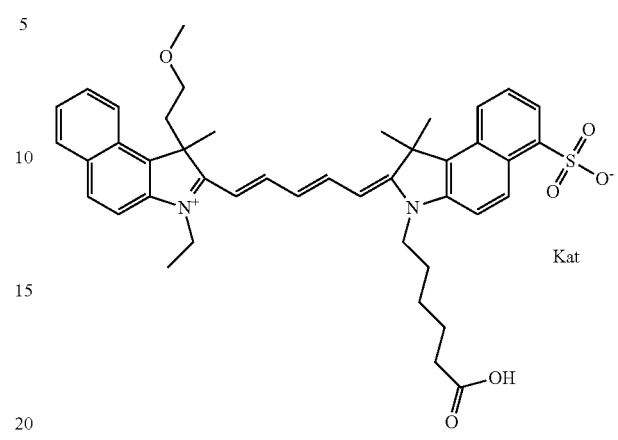

One non-limiting example is a tetrasulfonate form of 679 Compound 1, shown below:

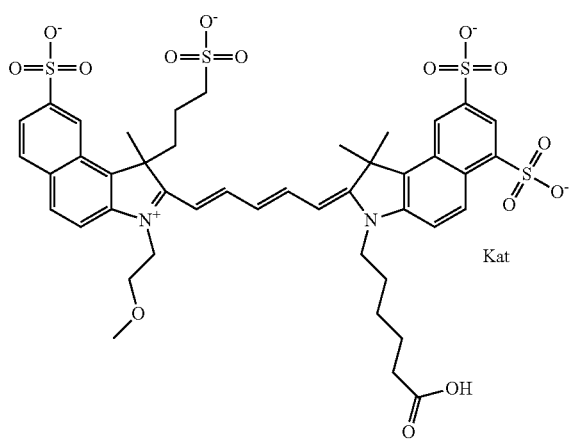 [SMILES: COCC[N+]1=C(/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1ccc(S(=O)(=O)[O-])cc21]

One non-limiting example is a disulfonate form of 679 Compound 0/1, shown below:

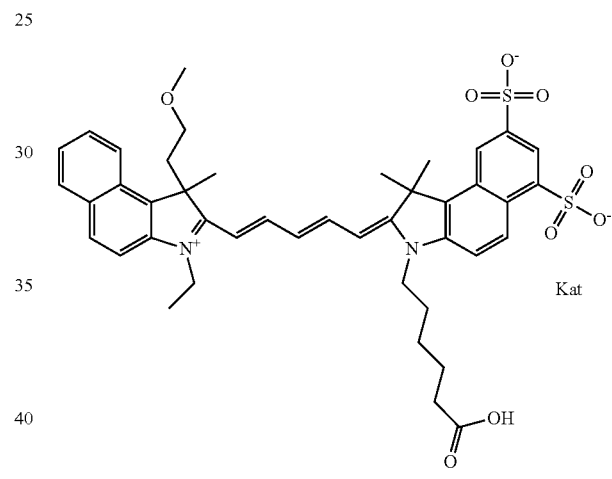

One non-limiting example is a pentasulfonate form of 679 Compound 1, shown below:

One non-limiting example is a trisulfonate form of 679 Compound 0/1, shown below:

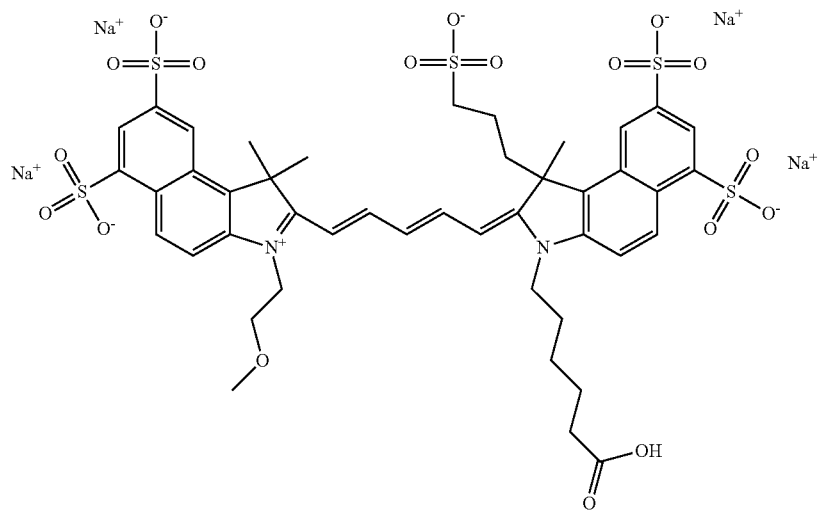 [SMILES: [Na+] ; [Na+] ; COCC[N+]1=C(/C=C/C=C/C=C2/N(CCCCCC(=O)O)c3ccc4c(S(=O)(=O)[O-])cc(S(=O)(=O)[O-])cc4c3C2(C)CCCS(=O)(=O)[O-])C(C)(C)c2c1ccc1c(S(=O)(=O)[O-])cc(S(=O)(=O)[O-])cc21 ; [Na+] ; [Na+]]

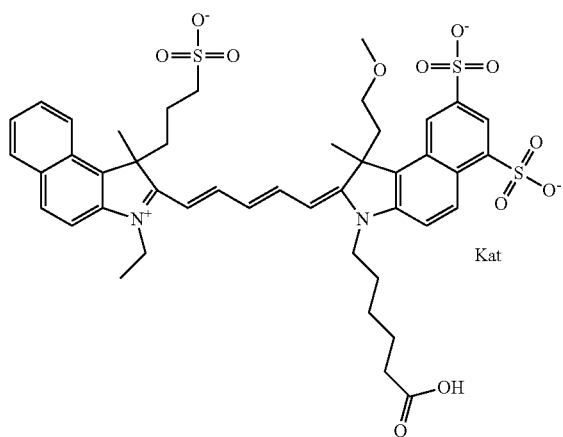 [SMILES: CC[N+]1=C(/C=C/C=C/C=C2/N(CCCCCC(=O)O)c3ccc4c(S(=O)(=O)[O-])cc(S(=O)(=O)[O-])cc4c3C2(C)CCOC)C(C)(CCCS(=O)(=O)[O-])c2c1ccc1ccccc21]

One non-limiting example is a tetrasulfonate form of 679 Compound 0/1, shown below:

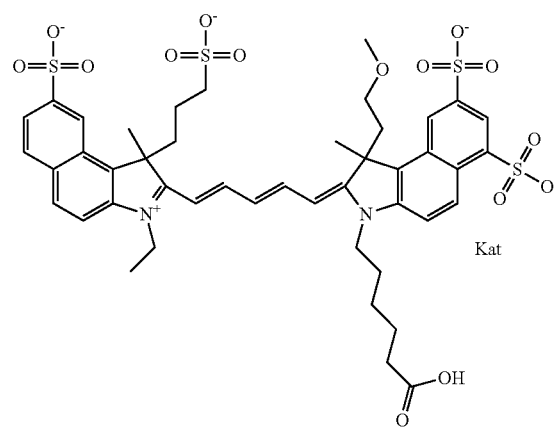

One non-limiting example is a pentasulfonate form of 679 Compound 0/1, shown below:

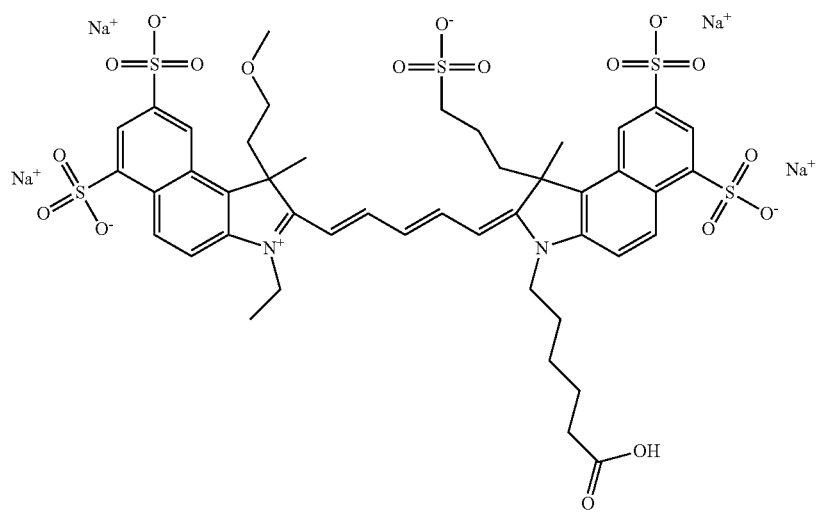 [SMILES: [Na+] ; CC[N+]1=C(/C=C/C=C/C=C2/N(CCCCCC(=O)O)c3ccc4c(S(=O)(=O)[O-])cc(S(=O)(=O)[O-])cc4c3C2(C)CCCS(=O)(=O)[O-])C(C)(CCOC)c2c1ccc1c(S(=O)(=O)[O-])cc(S(=O)(=O)[O-])cc21 ; [Na+] ; [Na+] ; [Na+]]

In one embodiment, the compound is 679 Compound 1/2 (PEG$_4$)

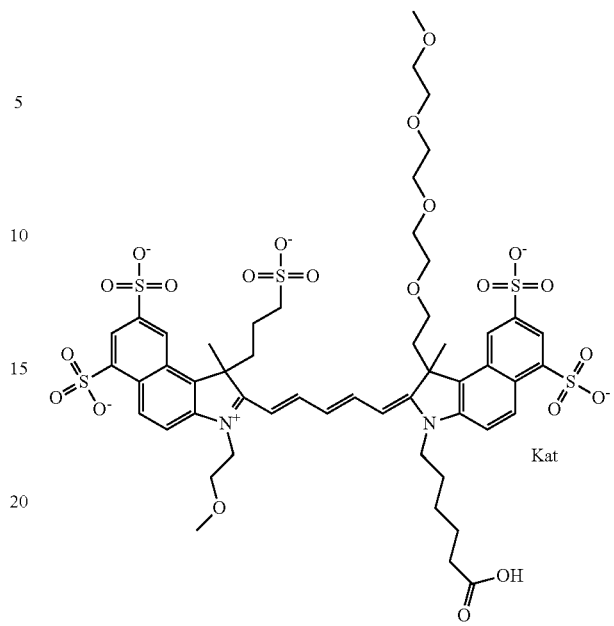

One non-limiting example of 679 Compound 1/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-3-(2-methoxyethyl)-1-methyl-1-(3-sulfonatopropyl)-1H-benzo[e]indolium-6,8-disulfonate) contains ethylene glycol on the indole N of the left heterocycle, i.e., a methylated ethylene glycol, and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 679 Compound 1/2 (PEG$_4$), but one skilled in the art appreciates that activation is not limited to these examples. One non-limiting example of an activated compound is the NHS-ester of 679 Compound 1/2 (PEG$_4$), shown below:

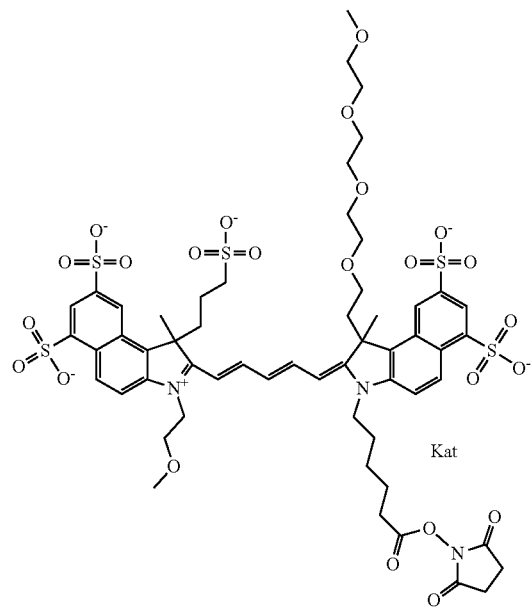 [SMILES: COCCOCCOCCOCCC1(C)\C(=C/C=C/C=C/C2=[N+](CCOC)c3ccc4c(S(=O)(=O)[O-])cc(S(=O)(=O)[O-])cc4c3C2(C)CCCS(=O)(=O)[O-])N(CCCCCC(=O)ON2C(=O)CCC2=O)c2ccc3c(S(=O)(=O)[O-])cc(S(=O)(=O)[O-])cc3c21]

One non-limiting example of a NHS-ester of 679 Compound 1/3 (PEG$_4$), according to general formula III, where m=1 and p=1, is shown below:

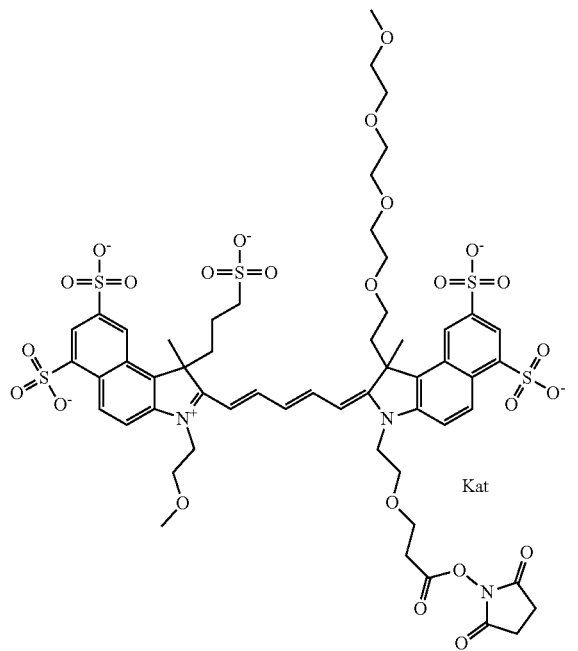

One non-limiting example of a NHS-ester of 679 Compound 1/3 (PEG$_4$), according to general formula III, where m=1 and p=2, is shown below:

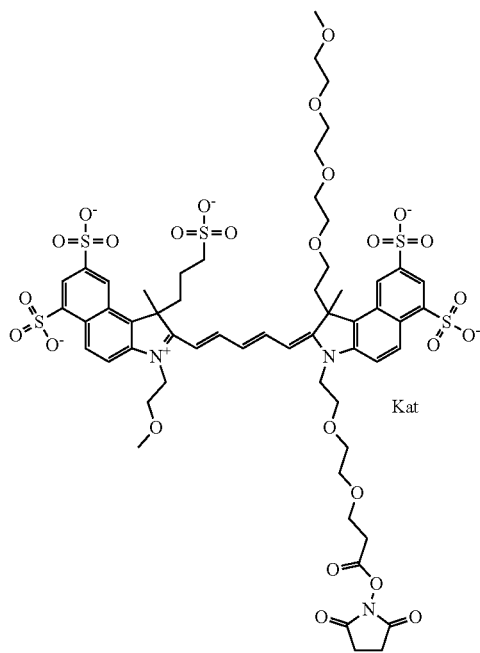

One non-limiting example of a NHS-ester of 679 Compound 1/3 (PEG$_4$), according to general formula III, where m=1 and p=3, is shown below:

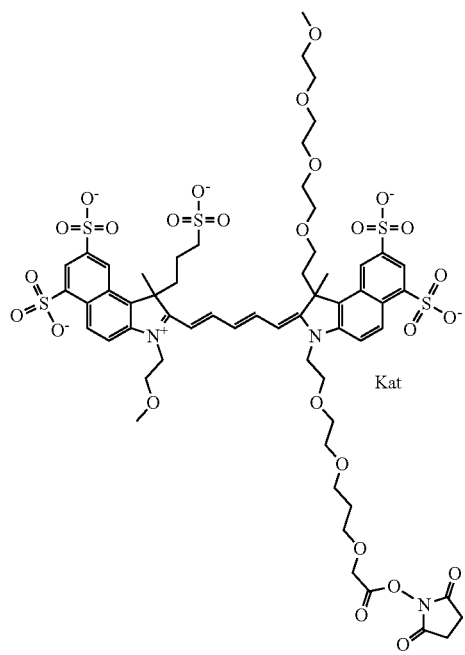

One non-limiting example of a NHS-ester of 679 Compound 1/3 (PEG$_4$), according to general formula III, where m=1 and p=4, is shown below:

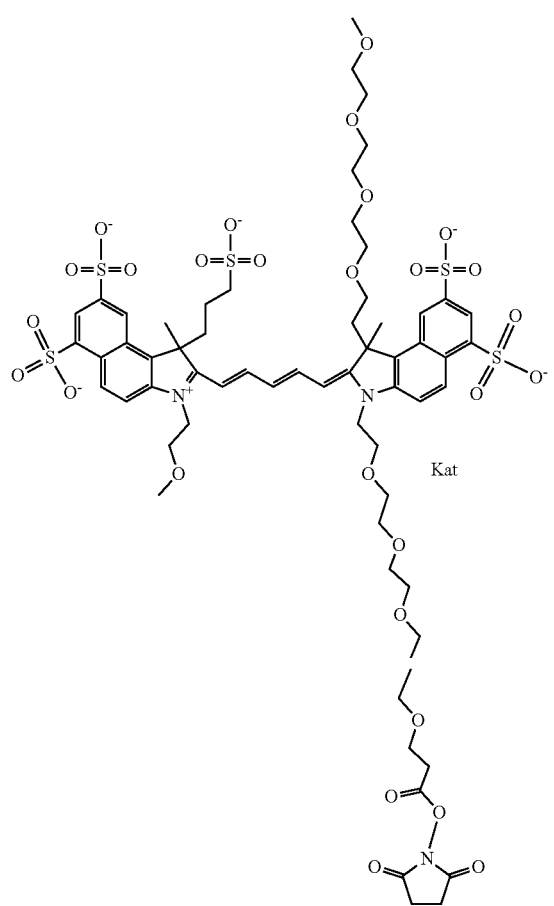

One non-limiting example of a NHS-ester of 679 Compound 1/3 (PEG$_4$), according to general formula III, where m=1 and p=5, is shown below:

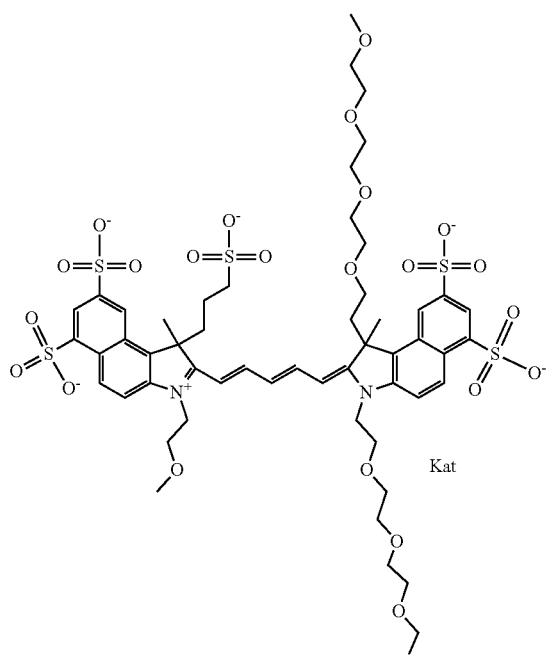

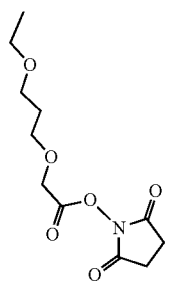

One non-limiting example of a NHS-ester of 679 Compound 1/3 (PEG$_4$), according to general formula III, where m=1 and p=6, is shown below:

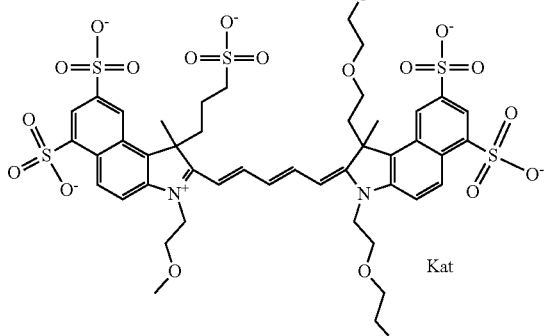

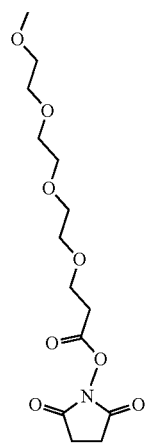

One non-limiting example of an activated 679 Compound 1/2 (PEG$_4$) is a tetrafluorophenyl (TFP)-ester form of 679 Compound 1, shown below:

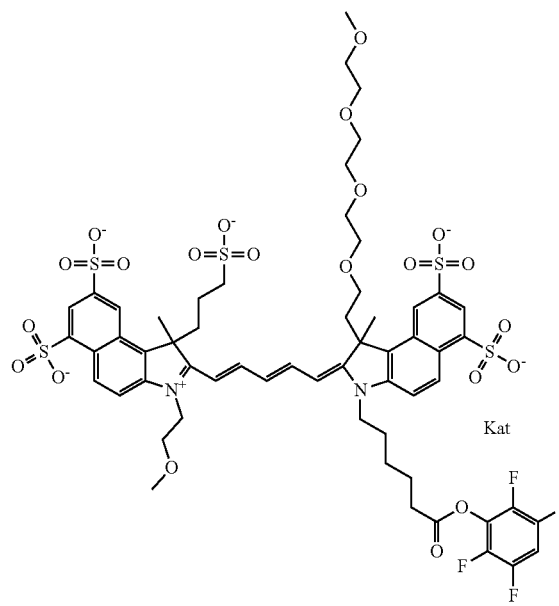

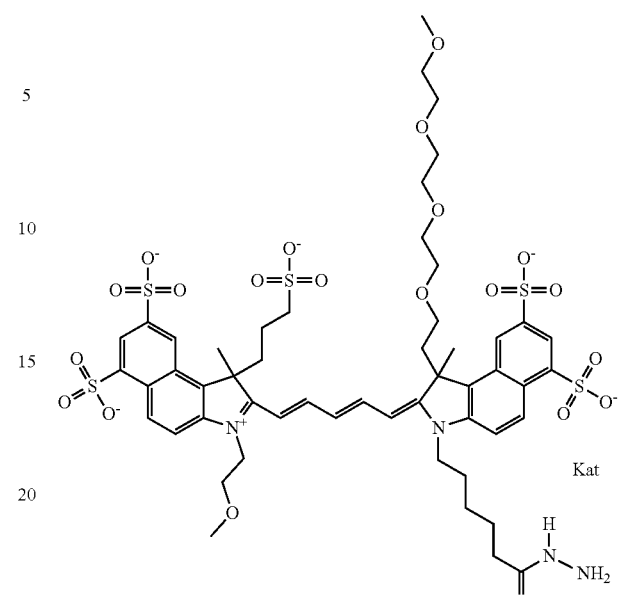

One non-limiting example of an activated 679 Compound 1/2 (PEG$_4$) is a sulfotetrafluorophenyl (STP)-ester form of 679 Compound 1, shown below:

One non-limiting example of an activated 679 Compound 1/2 (PEG$_4$) is a maleimide form of 679 Compound 1, shown below:

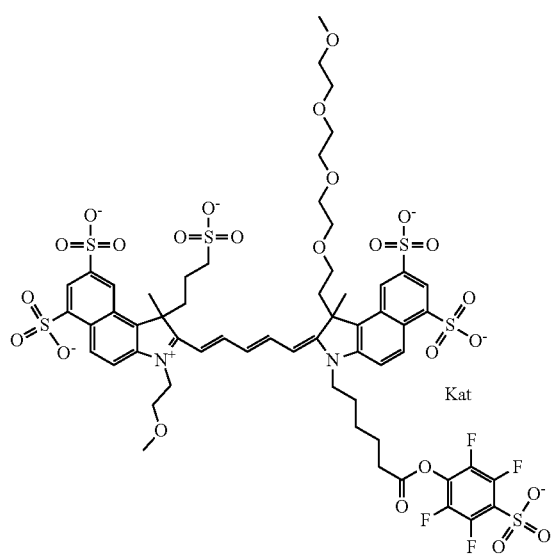 [SMILES: COCCOCCOCCOCCC1(C)\C(=C/C=C/C=C/C2=[N+](CCOC)c3ccc4c(S(=O)(=O)[O-])cc(S(=O)(=O)[O-])cc4c3C2(C)CCCS(=O)(=O)[O-])N(CCCCCC(=O)Oc2c(F)c(F)c(S(=O)(=O)[O-])c(F)c2F)c2ccc3c(S(=O)(=O)[O-])cc(S(=O)(=O)[O-])cc3c21]

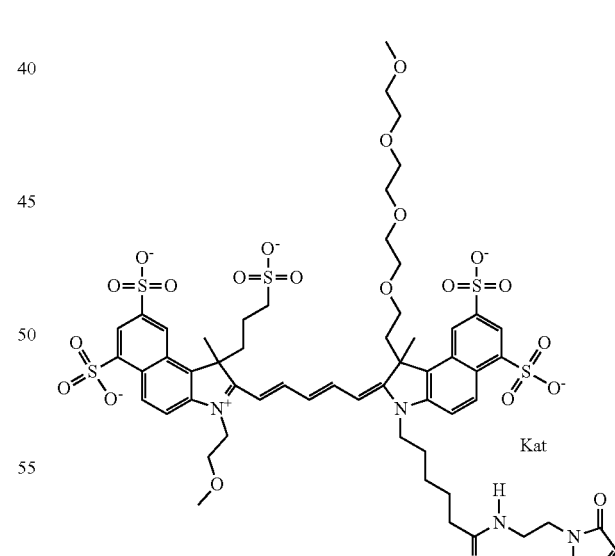

One non-limiting example of an activated 679 Compound 1/2 (PEG$_4$) is a hydrazide form of 679 Compound 1, shown below:

In one embodiment, the compound is 679 Compound 2/2 (PEG$_4$)

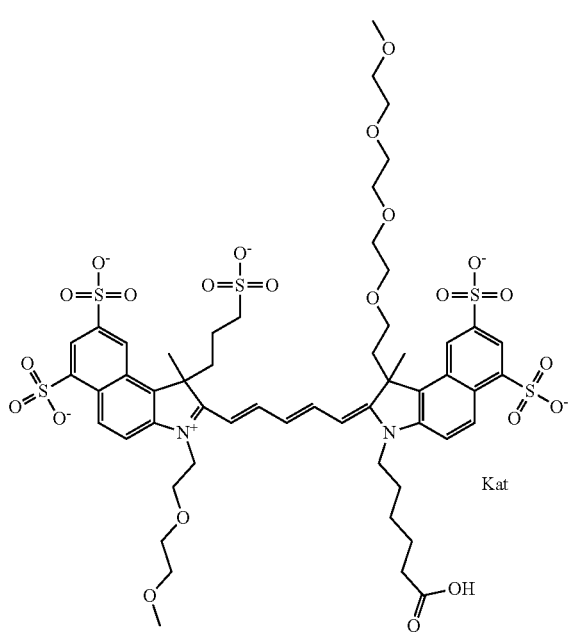 [SMILES: COCCOCCOCCOCCC1(C)\C(=C/C=C/C=C/C2=[N+](CCOCCOC)c3ccc4c(S(=O)(=O)[O-])cc(S(=O)(=O)[O-])cc4c3C2(C)CCCS(=O)(=O)[O-])N(CCCCCC(=O)O)c2ccc3c(S(=O)(=O)[O-])cc(S(=O)(=O)[O-])cc3c21]

One non-limiting example of 679 Compound 2/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-3-(2-(2-methoxyethoxy)ethyl)-1-methyl-1-(3-sulfonatopropyl)-1H-benzo[e]indolium-6,8-disulfonate) contains a diethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 2/2 (PEG$_4$) is activated as described above.

In one embodiment, the compound is 679 Compound 3/2 (PEG$_4$)

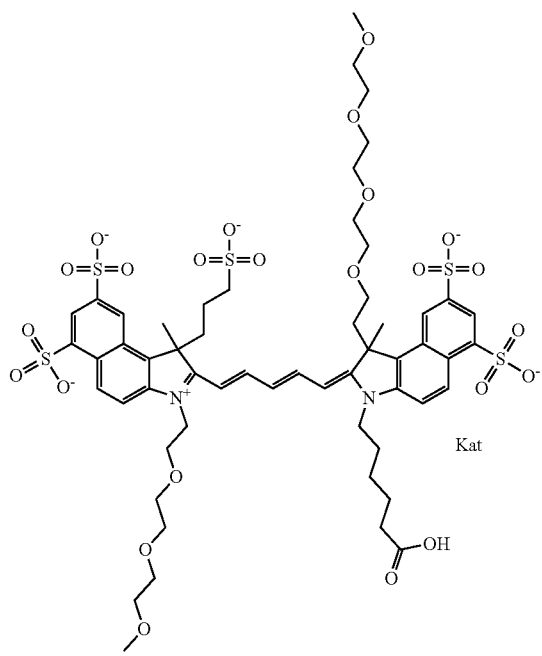 [SMILES: COCCOCCOCCOCCC1(C)\C(=C/C=C/C=C/C2=[N+](CCOCCOCCOC)c3ccc4c(S(=O)(=O)[O-])cc(S(=O)(=O)[O-])cc4c3C2(C)CCCS(=O)(=O)[O-])N(CCCCCC(=O)O)c2ccc3c(S(=O)(=O)[O-])cc(S(=O)(=O)[O-])cc3c21]

One non-limiting example of 679 Compound 3/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-3-(2-(2-(2-methoxyethoxy)ethoxy)ethyl)-1-methyl-1-(3-sulfonatopropyl)-1H-benzo[e]indolium-6,8-disulfonate) contains a (poly) ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 3/2 (PEG$_4$) is activated as described above.

In one embodiment, the compound is 679 Compound 4/2 (PEG$_4$)

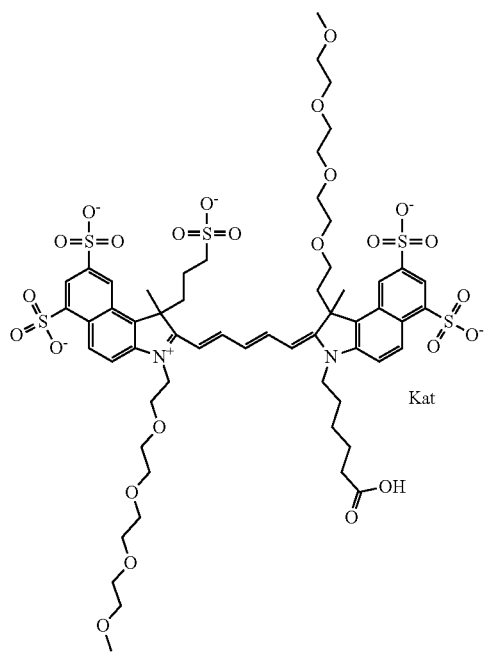 [SMILES: COCCOCCOCCOCC[N+]1=C(/C=C/C=C/C=C2/N(CCCCCC(=O)O)c3ccc4c(S(=O)(=O)[O-])cc(S(=O)(=O)[O-])cc4c3C2(C)CCOCCOCCOCCOC)C(C)(CCCS(=O)(=O)[O-])c2c1ccc1c(S(=O)(=O)[O-])cc(S(=O)(=O)[O-])cc21]

One non-limiting example of 679 Compound 4/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-1-methyl-1-(3-sulfonatopropyl)-3-(2,5,8,11-tetraoxatridecan-13-yl)-1H-benzo[e]indolium-6,8-disulfonate) contains a (poly) ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 4/2 (PEG$_4$) is activated as described above.

In one embodiment, the compound is 679 Compound 5/2 (PEG$_4$)

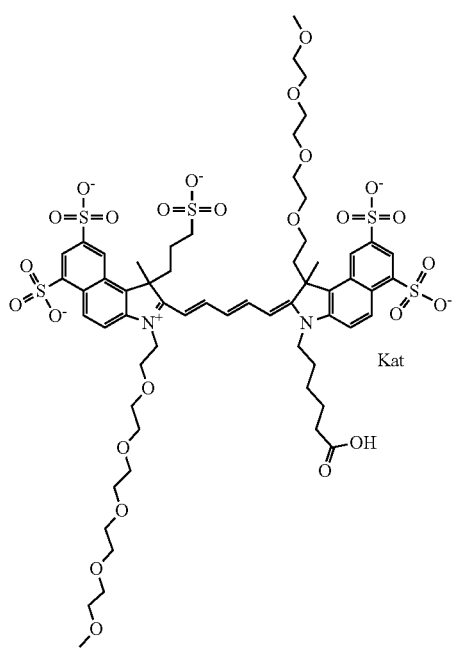 [SMILES: COCCOCCOCCOCCOCC[N+]1=C(/C=C/C=C/C=C2/N(CCCCCC(=O)O)c3ccc4c(S(=O)(=O)[O-])cc(S(=O)(=O)[O-])cc4c3C2(C)CCOCCOCCOCCOC)C(C)(CCCS(=O)(=O)[O-])c2c1ccc1c(S(=O)(=O)[O-])cc(S(=O)(=O)[O-])cc21]

One non-limiting example of 679 Compound 5/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-3-(2,5,8,11,14-pentaoxahexadecan-16-yl)-1-methyl-1-(3-sulfonatopropyl)-1H-benzo[e]indolium-6,8-disulfonate) contains a (poly) ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 5/2 (PEG$_4$) is activated as described above.

In one embodiment, the compound is 679 Compound 6/2 (PEG$_4$)

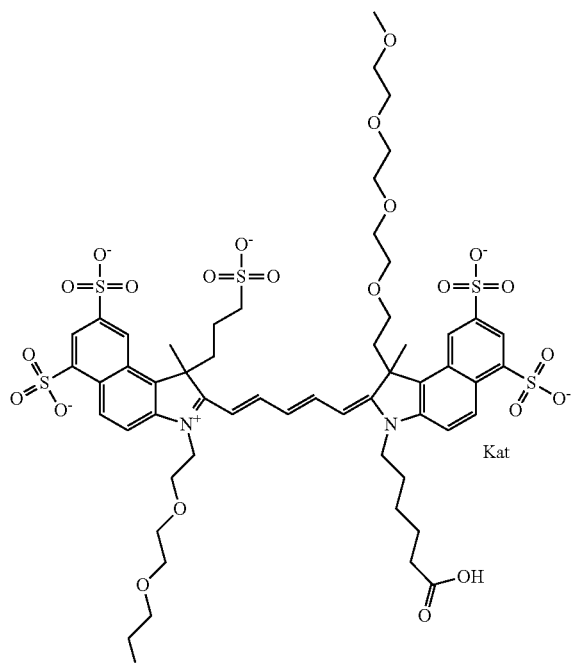

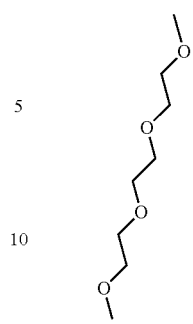

One non-limiting example of 679 Compound 6/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-1-methyl-3-(2,5,8,11,14,17-hexaoxanonadecan-19-yl)-1-(3-sulfonatopropyl)-1H-benzo[e]indolium-6,8-disulfonate) contains a (poly) ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 649 Compound 6/2 (PEG$_4$) is activated as described above.

In embodiments, the degree and/or location of sulfonation is varied to, e.g., vary the compound's degree of hydrophilicity or hydrophobicity. One non-limiting example is a monosulfonate form of 679 Compound 1/2 (PEG$_4$), shown below:

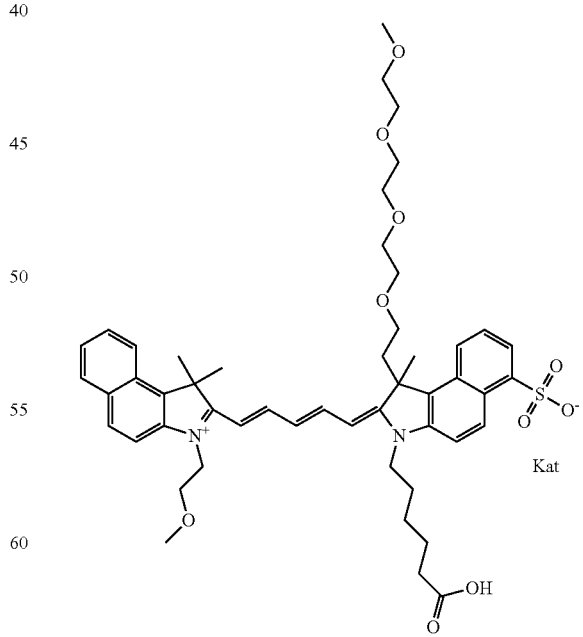

One non-limiting example is a disulfonate form of 679 Compound 1/2 (PEG$_4$), shown below:

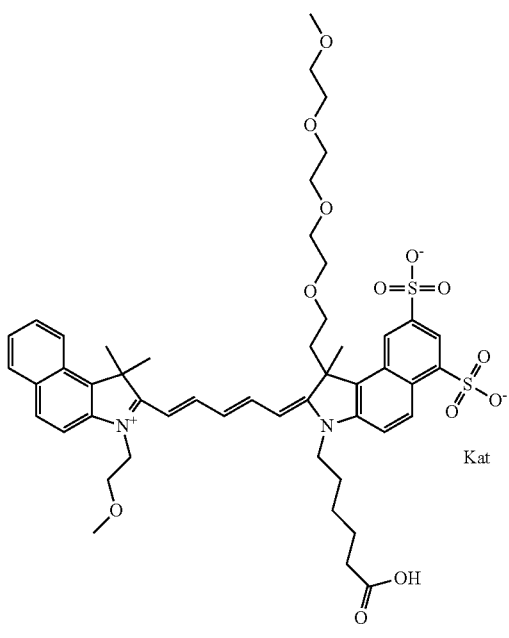 [SMILES: COCCOCCOCCOCCC1(C)\C(=C/C=C/C=C/C2=[N+](CCOC)c3ccc4ccccc4c3C2(C)C)N(CCCCCC(=O)O)c2ccc3c(S(=O)(=O)[O-])cc(S(=O)(=O)[O-])cc3c21]

One non-limiting example is a trisulfonate form of 679 Compound 1/2 (PEG$_4$), shown below:

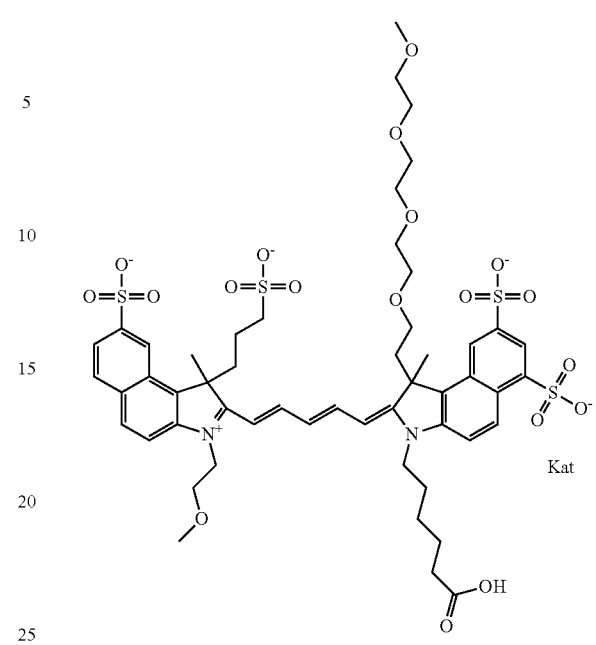

One non-limiting example is a pentasulfonate form of 679 Compound 1/2 (PEG$_4$), shown below:

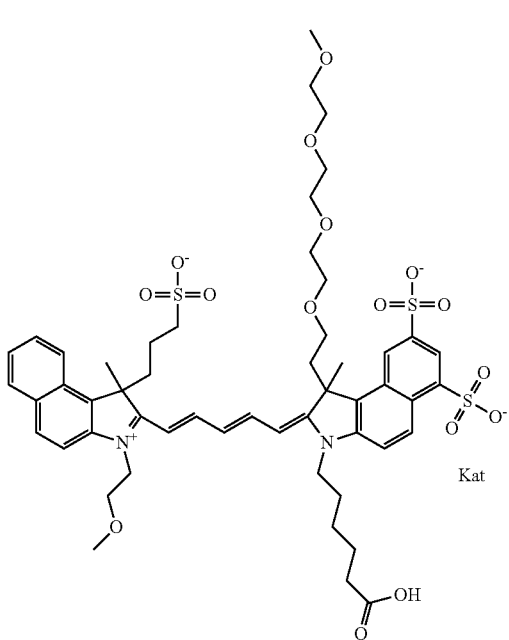 [SMILES: COCCOCCOCCOCCC1(C)\C(=C/C=C/C=C/C2=[N+](CCOC)c3ccc4ccccc4c3C2(C)CCCS(=O)(=O)[O-])N(CCCCCC(=O)O)c2ccc3c(S(=O)(=O)[O-])cc(S(=O)(=O)[O-])cc3c21]

One non-limiting example is a tetrasulfonate form of 679 Compound 1/2 (PEG$_4$), shown below:

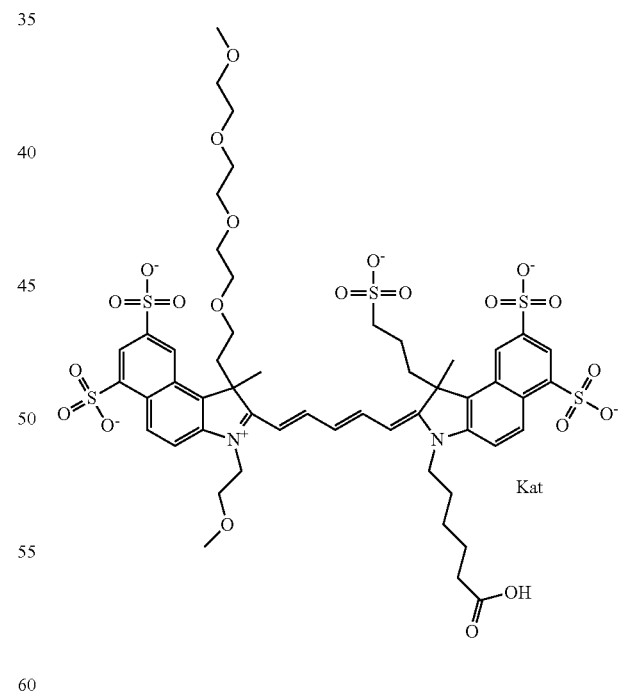

In embodiments, the compound contains one or more substitutions of the polymethine linker. In one embodiment, the compound has general formula Va

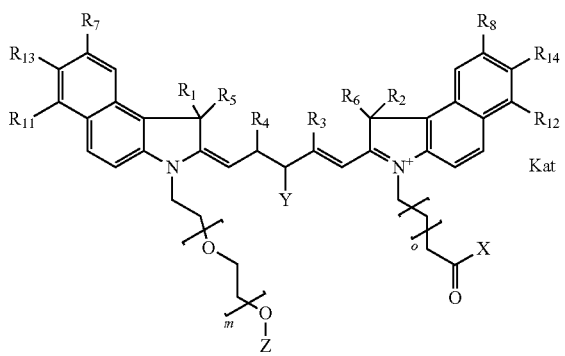

general formula Vb

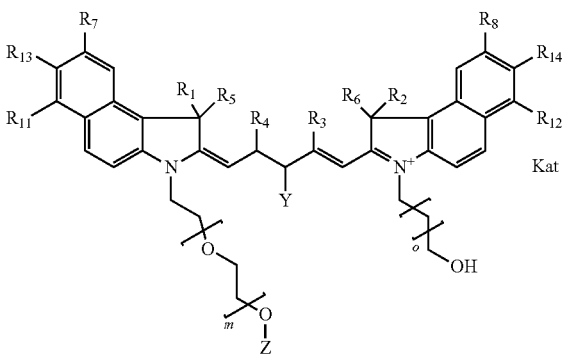

general formula Vc

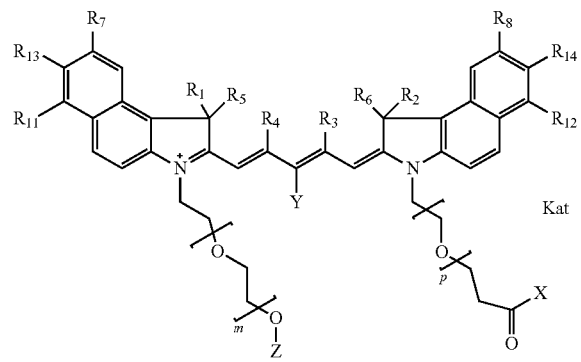

general formula Vd

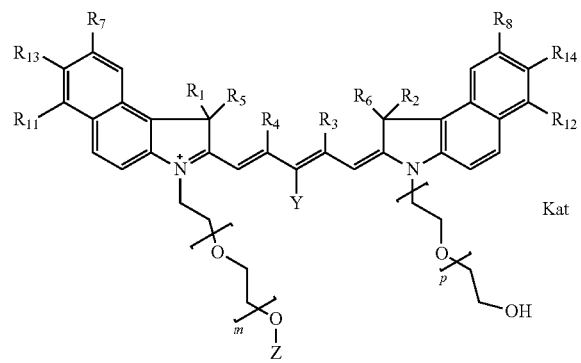

or general formula Ve

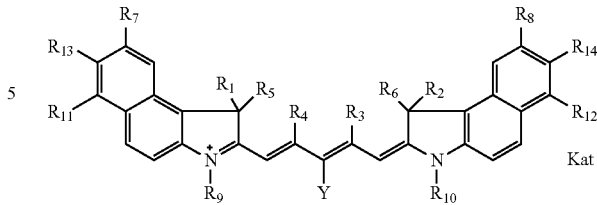

where each of $R^1$, $R^2$, $R^5$, and $R^6$ is the same or different and is independently selected from the group consisting of an aliphatic, heteroaliphatic, sulfoalkyl group, heteroaliphatic with terminal $SO_3$, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-$SO_2$NH—P—Z, and a carboxamide group -L-CONH—P—Z, and Z is selected from H, a $CH_3$ group, an alkyl group, a heteroalkyl group, or —CO—NHS; each of $R^7$, $R^8$, $R^{11}$, $R^{12}$, $R^{13}$, and $R^{14}$ is the same or different and is independently selected from either H, $SO_3$, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group —$SO_2$NH—P—Z, or a carboxamide group —CONH—P—Z, and Z is selected from H, a $CH_3$ group, an alkyl group, a heteroalkyl group, or —CO—NHS; each of $R^9$ and $R^{10}$ is the same or different and is independently selected from the group consisting of an alkyl, a sulfoalkyl, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a PEG group P-L-X, L-Z, L-X; X is selected from the group consisting of —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—$CH_2$—I, imidazole, azide, —NR-L-O—$NH_2$, and —NR-L-O—CO—NHS, where R is —H or an aliphatic or heteroaliphatic group, and L is selected from the group consisting of a divalent linear (—$(CH_2)_t$—, t=0 to 15), crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; p is an integer from 1 to 6 inclusive; each of R3 and R4 is the same or different and is independently hydrogen, an aliphatic group, a heteroaliphatic group, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, and Z is selected from H, $CH_3$, a $CH_3$ group, an alkyl group, or a heteroalkyl group; or R3 and R4 together form a cyclic structure where R3 and R4 are joined using a divalent structural element selected from the group consisting of —$(CH_2)_q$—, —$(CH_2)_qO(CH_2)_{q'}$—, —$(CH_2)_qS(CH_2)_{q'}$—, —$(CH_2)_q$CH=CH—, and —OCH=CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy-, phenylmercapto function, and a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, and Z is selected from H, $CH_3$, a $CH_3$ group, an alkyl group, a heteroalkyl group, or —CO—NHS.

In one embodiment, the compound of general formula V wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of $—(CH_2)_q—$ and CH═CH, where q is an integer from 1 to 2 inclusive, to result in a 3-, 4-, or 5-membered ring.

One non-limiting example is a substituted polymethine form of 679 Compound 1, shown below:

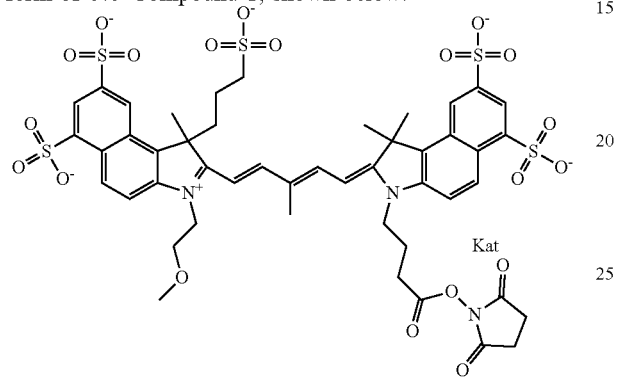

One non-limiting example is a substituted polymethine form of 679 Compound 2, shown below:

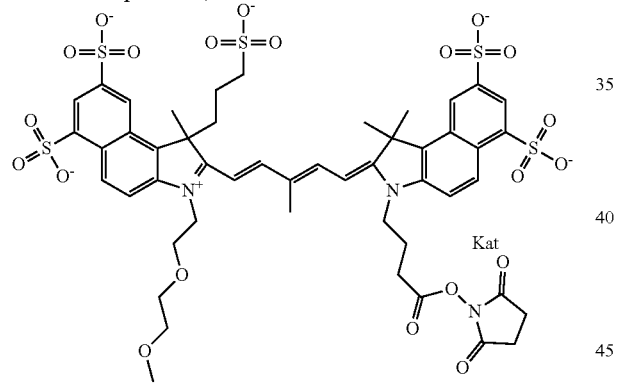

One non-limiting example is a substituted polymethine form of 679 Compound 3, shown below:

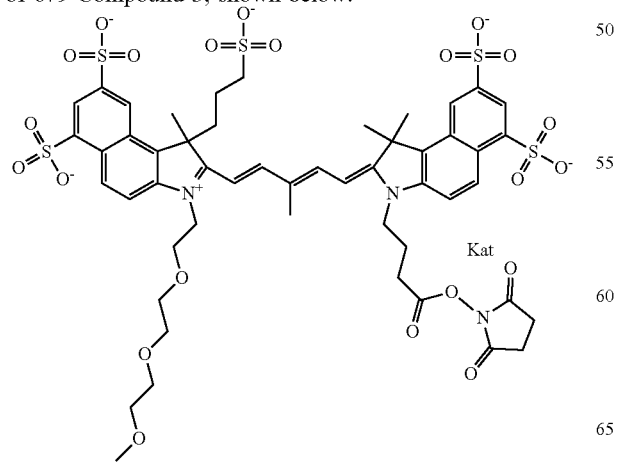

One non-limiting example is a substituted polymethine form of 679 Compound 4, shown below:

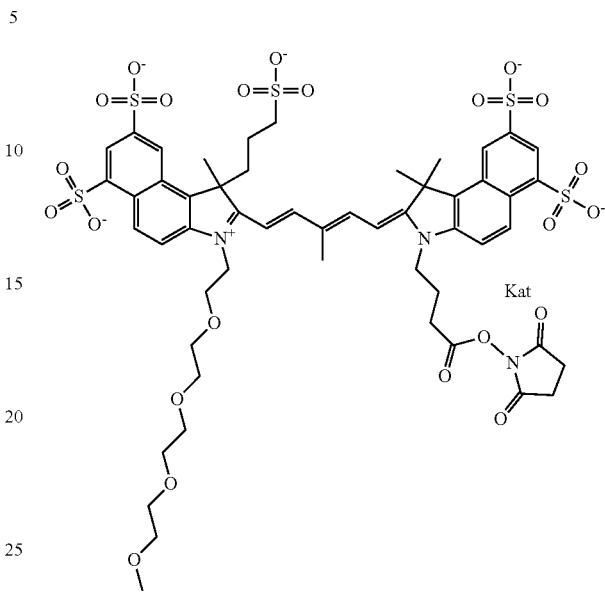

One non-limiting example is a substituted polymethine form of 679 Compound 5, shown below:

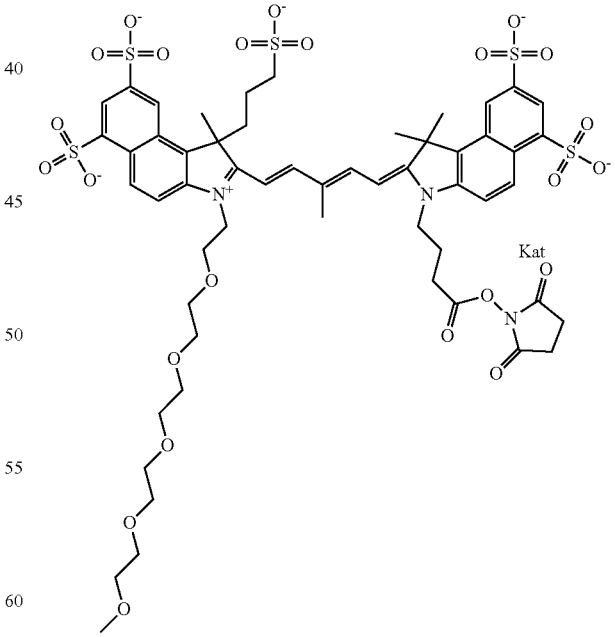

One non-limiting example is a substituted polymethine form of 679 Compound 6, shown below:

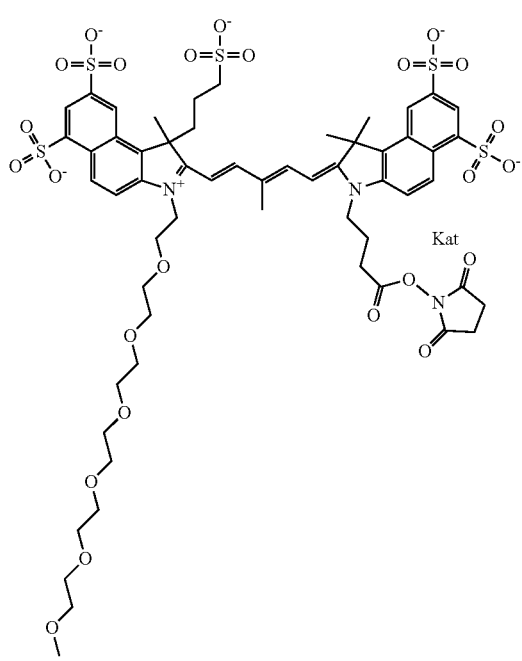 [SMILES: COCCOCCOCCOCCOCCOCC[N+]1=C(/C=C/C(C)=C/C=C2/N(CCCC(=O)ON3C(=O)CCC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 0/1, shown below:

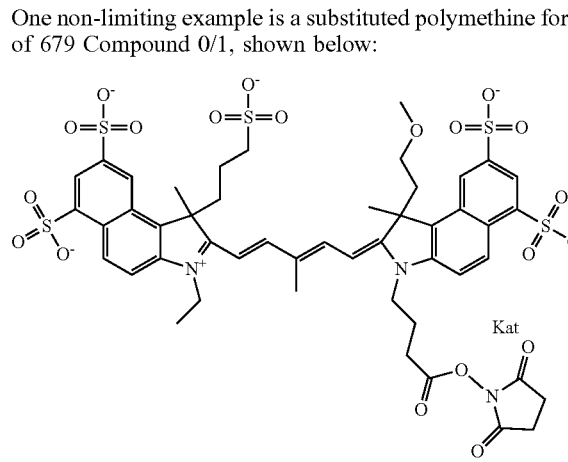

One non-limiting example is a substituted polymethine form of 679 Compound 0/1, shown below:

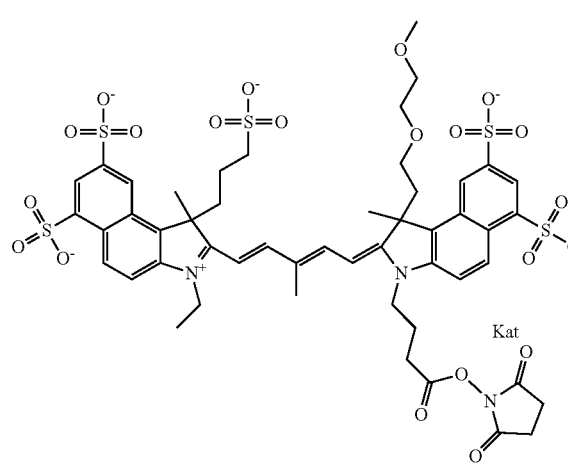

One non-limiting example is a substituted polymethine form of 679 Compound 0/1, shown below:

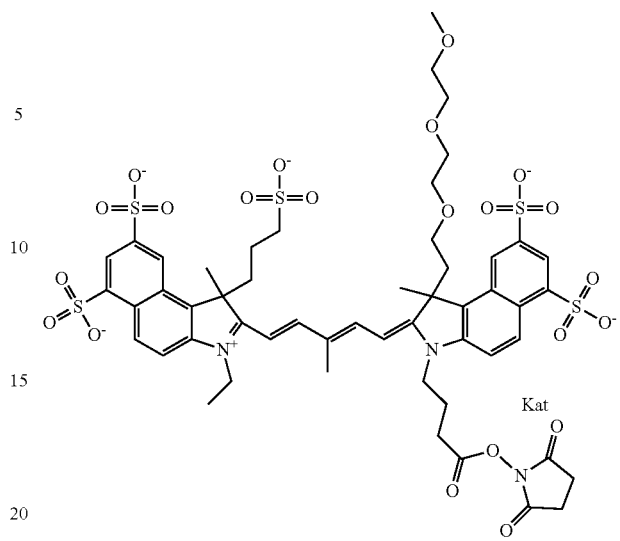

One non-limiting example is a substituted polymethine form of 679 Compound 0/1, shown below:

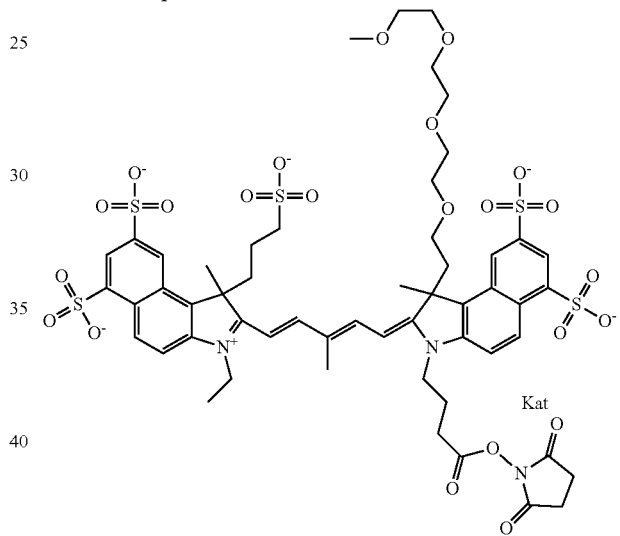

One non-limiting example is a substituted polymethine form of 679 Compound 0/1, shown below:

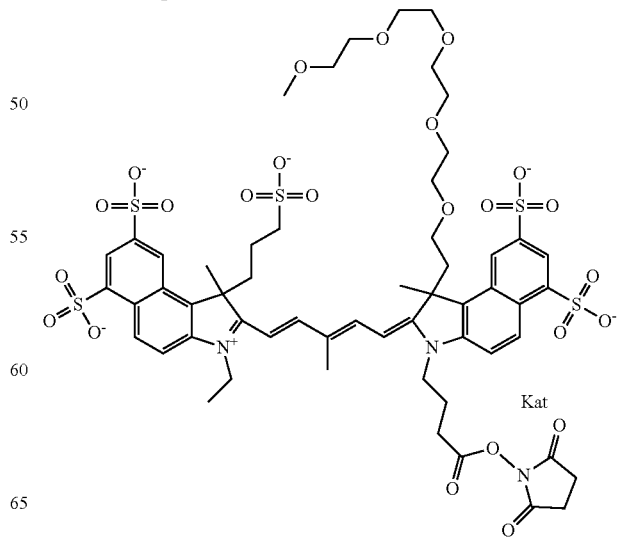

One non-limiting example is a substituted polymethine form of 679 Compound 0/1, shown below:

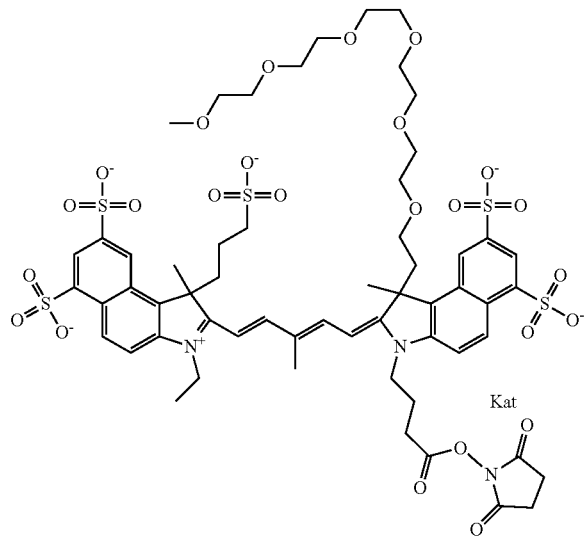 [SMILES: CC[N+]1=C(/C=C/C(C)=C/C=C2/N(CCCC(=O)ON3C(=O)CCC3=O)c3ccc4c(S(=O)(=O)[O-])cc(S(=O)(=O)[O-])cc4c3C2(C)CCOCCOCCOCCOCCOCCOC)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 1, shown below:

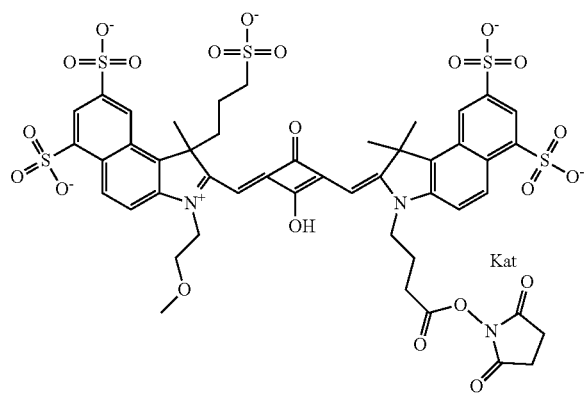 [SMILES: COCC[N+]1=C(/C=C2\C(=O)C(/C=C3/N(CCCC(=O)ON4C(=O)CCC4=O)c4ccc5c(S(=O)(=O)[O-])cc(S(=O)(=O)[O-])cc5c4C3(C)C)=C2O)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 2, shown below:

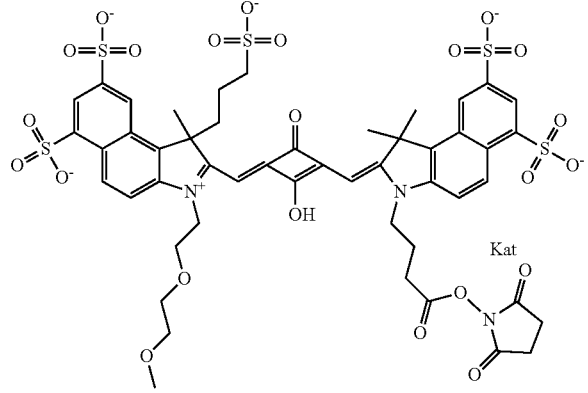 [SMILES: COCCOCC[N+]1=C(/C=C2\C(=O)C(/C=C3/N(CCCC(=O)ON4C(=O)CCC4=O)c4ccc5c(S(=O)(=O)[O-])cc(S(=O)(=O)[O-])cc5c4C3(C)C)=C2O)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 3, shown below:

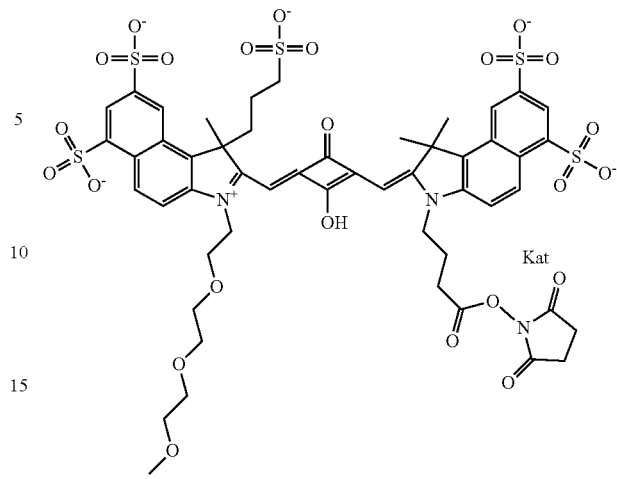

One non-limiting example is a substituted polymethine form of 679 Compound 4, shown below:

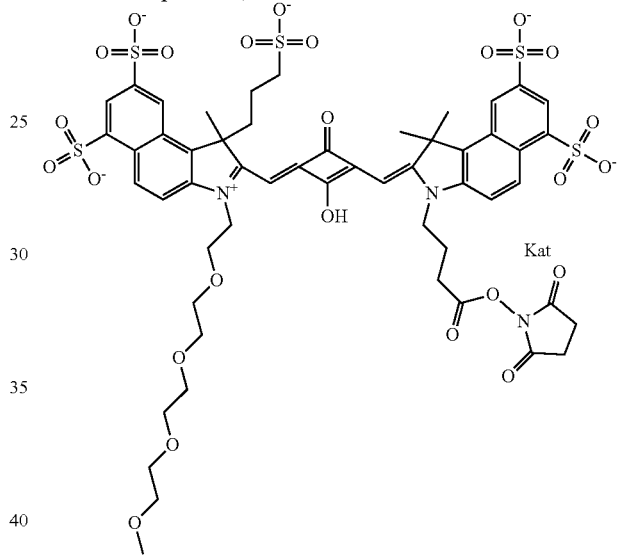

One non-limiting example is a substituted polymethine form of 679 Compound 5, shown below:

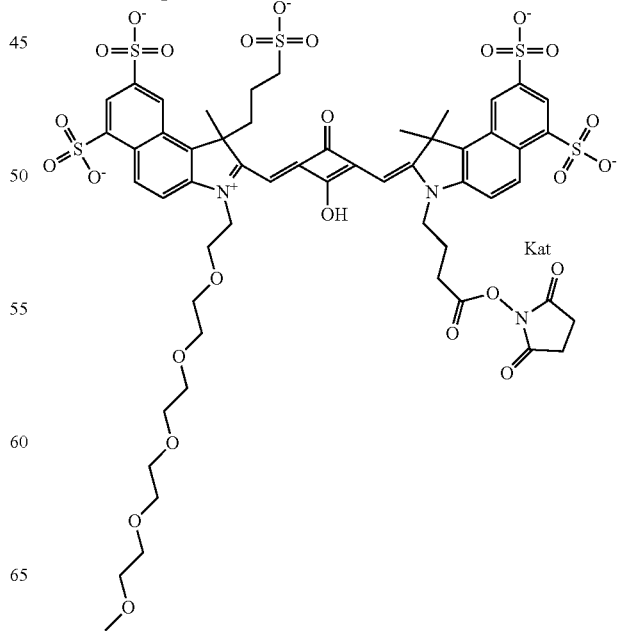

One non-limiting example is a substituted polymethine form of 679 Compound 6, shown below:

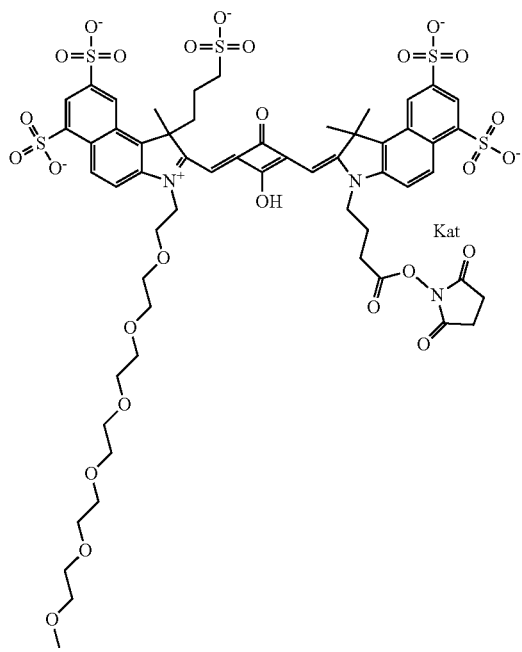 [SMILES: COCCOCCOCCOCCOCCOCC[N+]1=C(/C=C2\C(=O)C(/C=C3/N(CCCC(=O)ON4C(=O)CCC4=O)c4ccc5c(S(=O)(=O)[O-])cc(S(=O)(=O)[O-])cc5c4C3(C)C)=C2O)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 0/1, shown below:

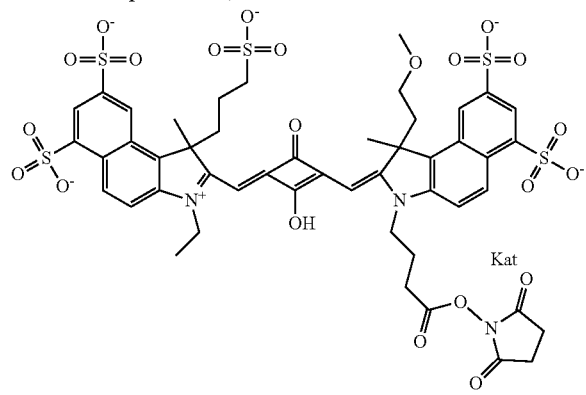

One non-limiting example is a substituted polymethine form of 679 Compound 0/1, shown below:

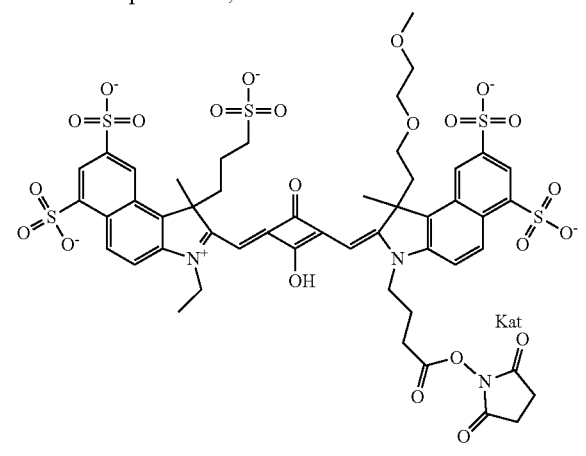

One non-limiting example is a substituted polymethine form of 679 Compound 0/1, shown below:

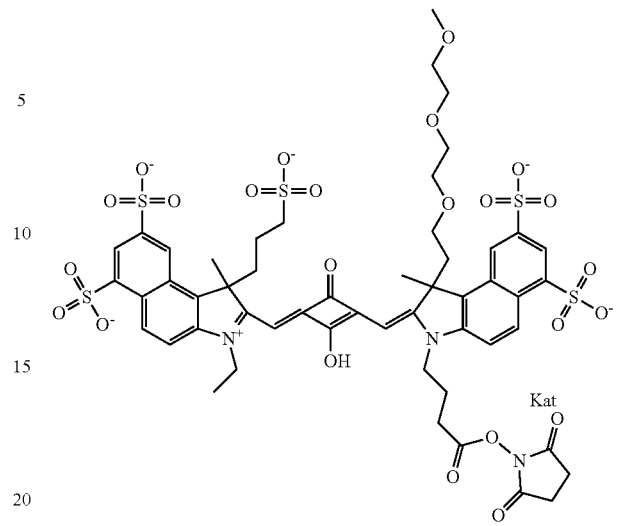

One non-limiting example is a substituted polymethine form of 679 Compound 0/1, shown below:

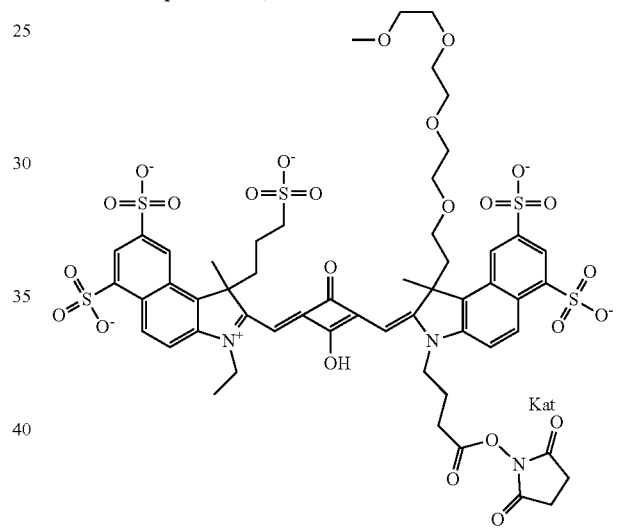

One non-limiting example is a substituted polymethine form of 679 Compound 0/1, shown below:

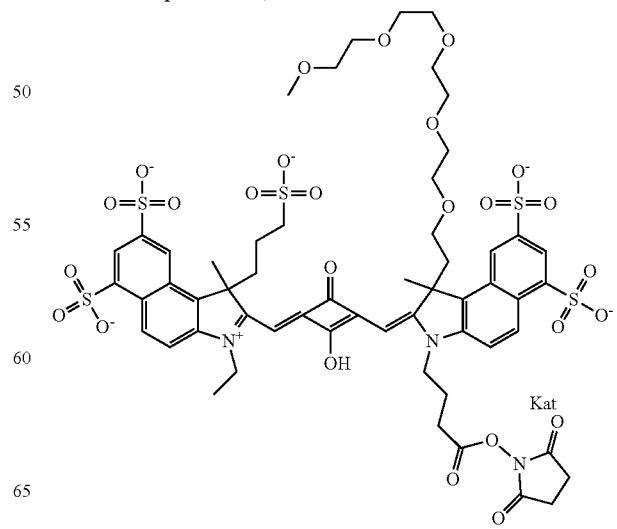

One non-limiting example is a substituted polymethine form of 679 Compound 0/1, shown below:

One non-limiting example is a substituted polymethine form of 679 Compound 3/2 (PEG$_4$), shown below:

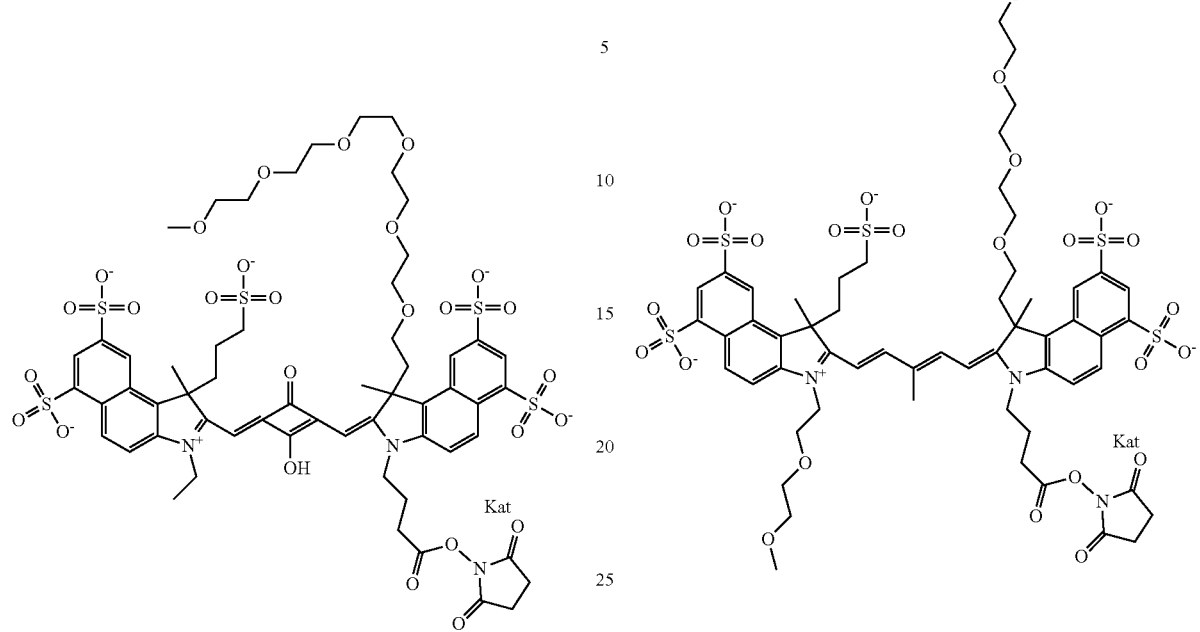

One non-limiting example is a substituted polymethine form of 679 Compound 1/2 (PEG$_4$), shown below:

One non-limiting example is a substituted polymethine form of 679 Compound 4/2 (PEG$_4$), shown below:

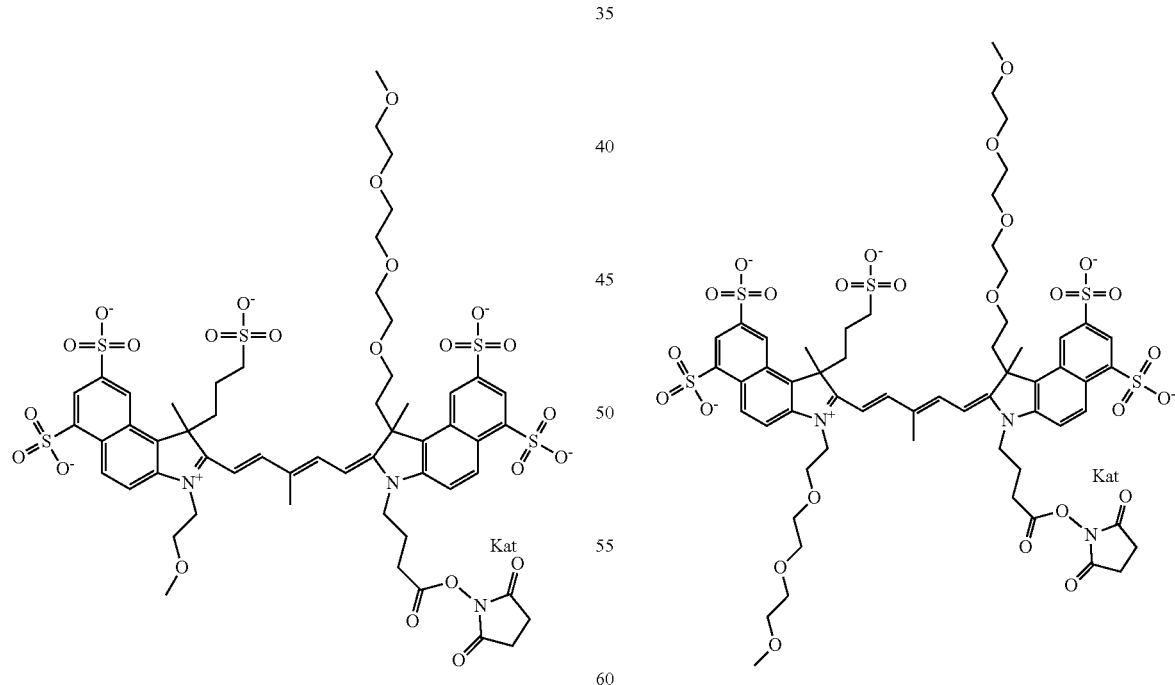

One non-limiting example is a substituted polymethine form of 679 Compound 2/2 (PEG$_4$), shown below:

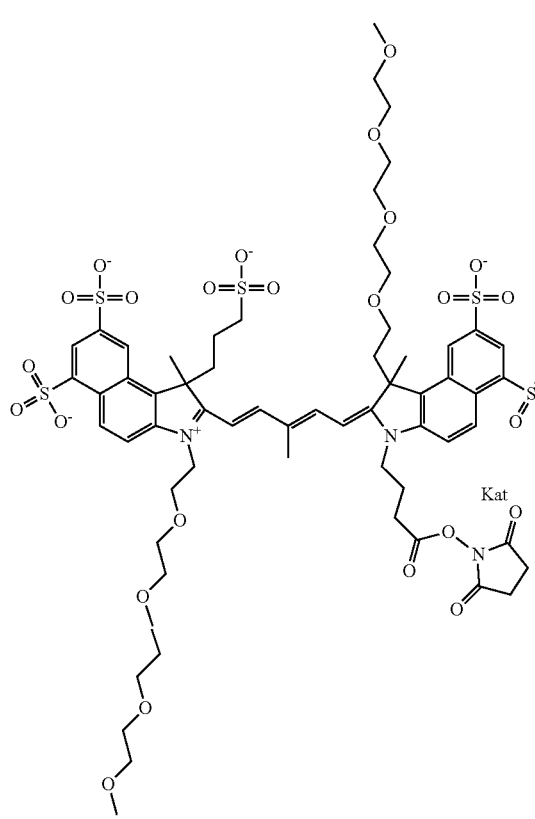
One non-limiting example is a substituted polymethine form of 679 Compound 5/2 (PEG$_4$), shown below:
One non-limiting example is a substituted polymethine form of 679 Compound 6/2 (PEG$_4$), shown below:
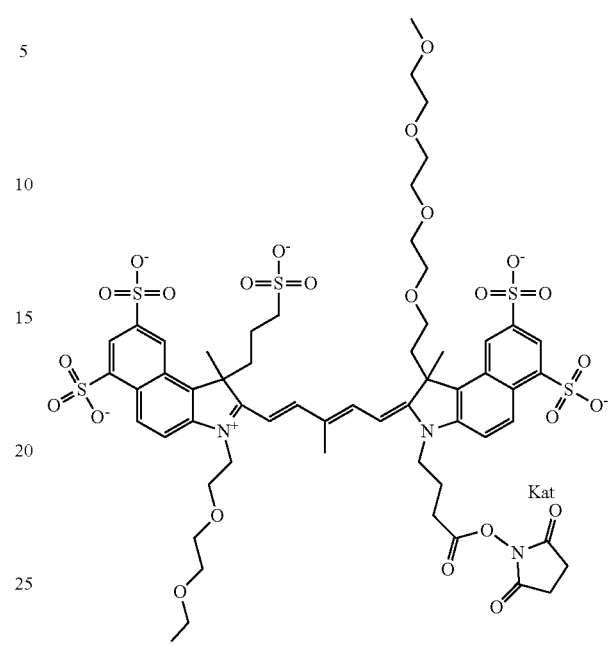
One non-limiting example is a substituted polymethine form of 679 Compound 1/2 (PEG$_4$), shown below:
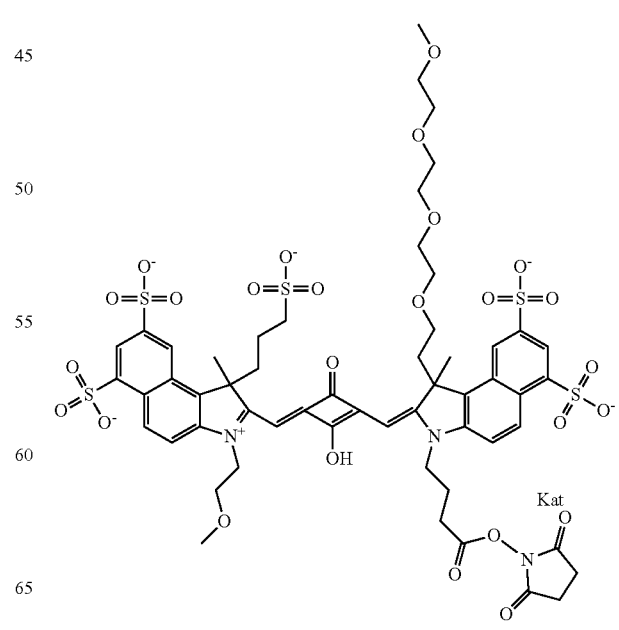

One non-limiting example is a substituted polymethine form of 679 Compound 2/2 (PEG₄), shown below:

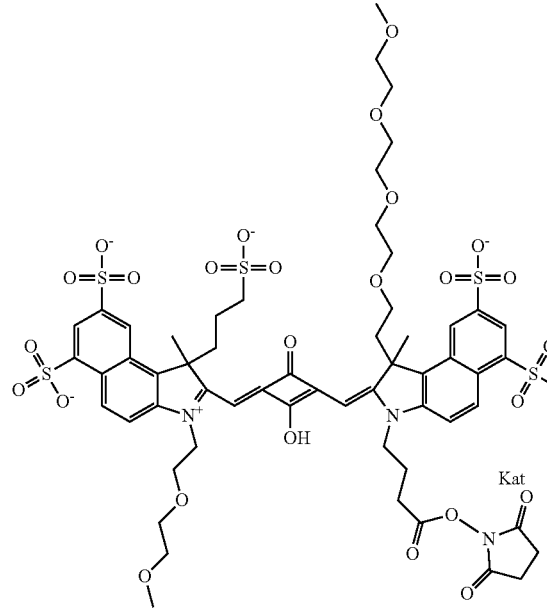

One non-limiting example is a substituted polymethine form of 679 Compound 3/2 (PEG₄), shown below:

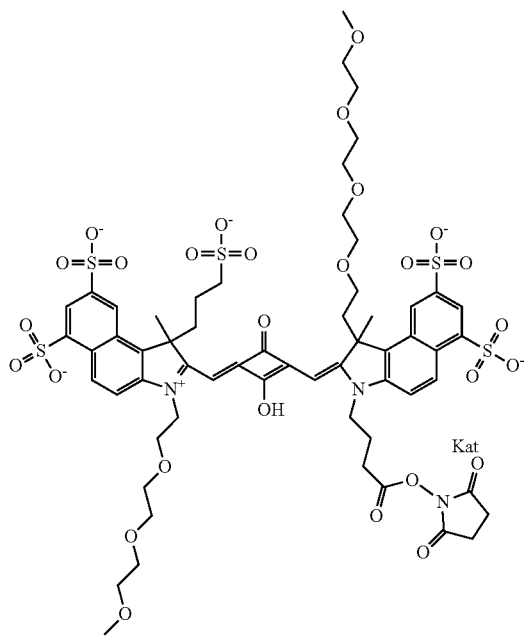 [SMILES: COCCOCCOCCOCCC1(C)/C(=C\C2=C(O)C(=C/C3=[N+](CCOCCOCCOC)c4ccc5c(S(=O)(=O)[O-])cc(S(=O)(=O)[O-])cc5c4C3(C)CCCS(=O)(=O)[O-])/C2=O)N(CCCC(=O)ON2C(=O)CCC2=O)c2ccc3c(S(=O)(=O)[O-])cc(S(=O)(=O)[O-])cc3c21]

One non-limiting example is a substituted polymethine form of 679 Compound 4/2 (PEG₄), shown below:

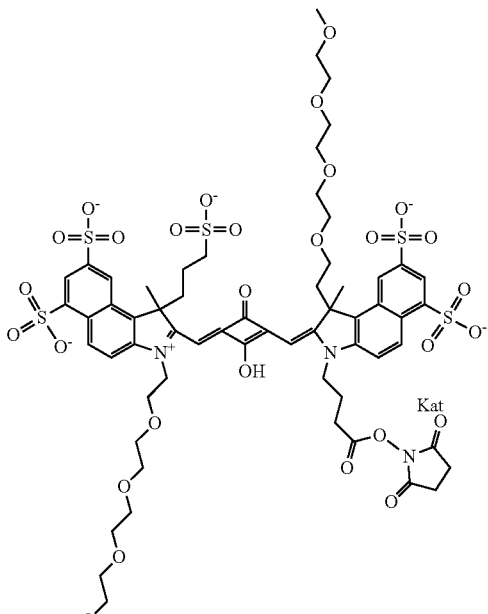

One non-limiting example is a substituted polymethine form of 679 Compound 5/2 (PEG₄), shown below:

One non-limiting example is a substituted polymethine form of 679 Compound 6/2 (PEG₄), shown below:

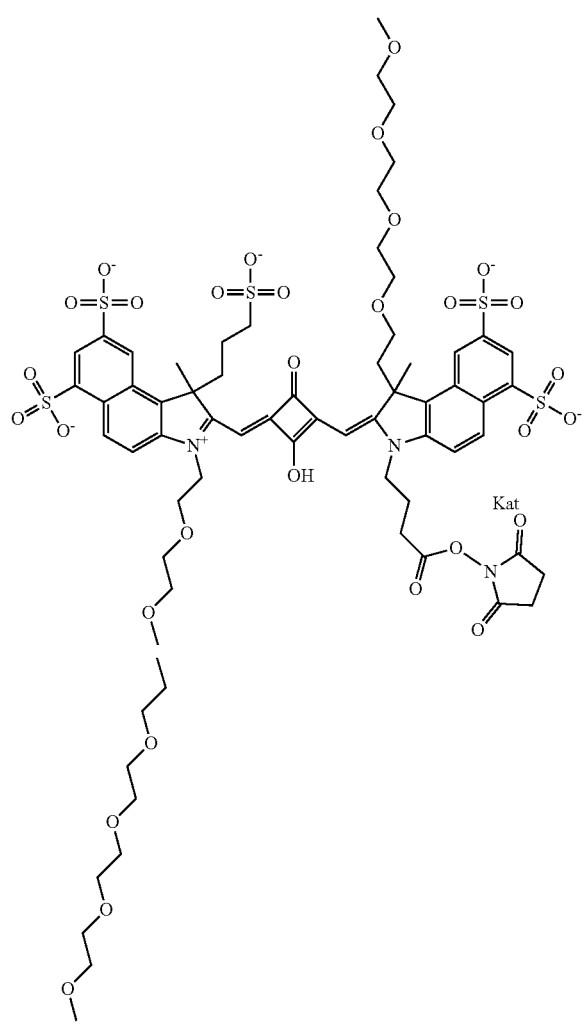

In various embodiments, an ethylene glycol group, diethylene glycol group, and/or a (poly)ethylene glycol group, which will collectively be referred to as a PEG group, unless specifically defined, may be present at position(s) in addition to such groups being present on the N atom(s) of the indole structure.

One non-limiting example of an additionally PEG-substituted compound is a 679 Compound 1/2 according to general formula II where R1 is an ethylene glycol group terminating with a methyl group,

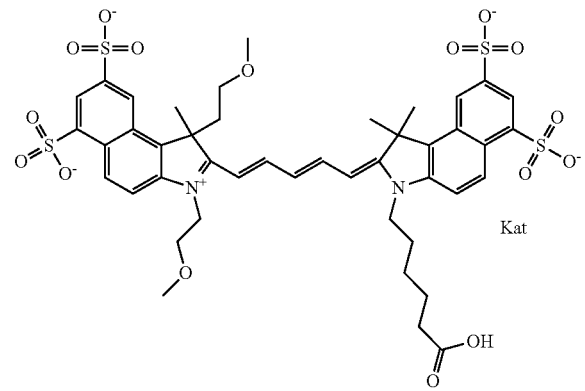

One non-limiting example of an additionally PEG-substituted compound is a 679 Compound 1/2 according to general formula II where R2 is an ethylene glycol group terminating with a methyl group, shown below:

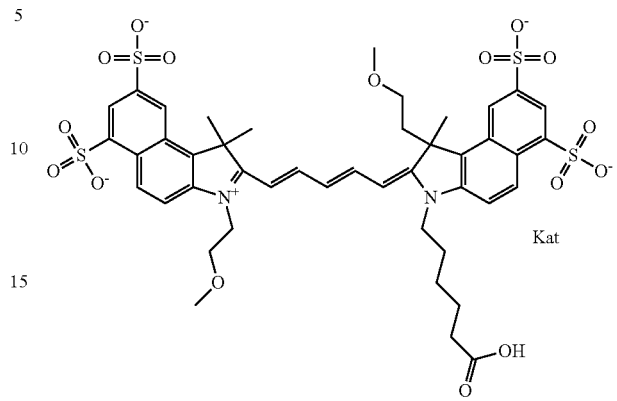

One non-limiting example of an additionally PEG-substituted compound is a 679 Compound 1/2 according to general formula II where R8 is an ethylene glycol group terminating with a methyl group,

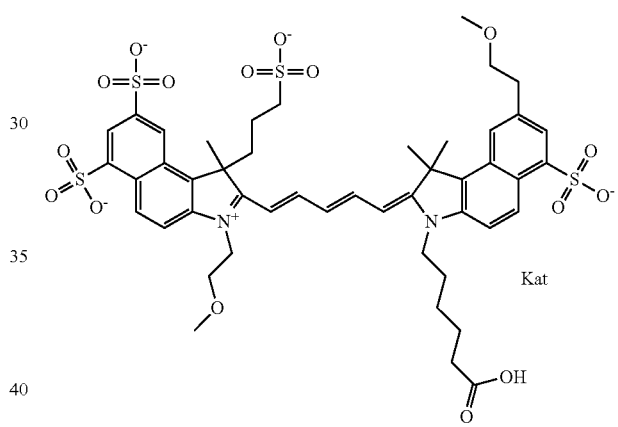

One non-limiting example of an additionally PEG-substituted compound is a 679 Compound 1/2 according to general formula II where R8 is a sulfonamide group with an ethylene glycol group (PEG$_1$) terminating with a methyl group, shown below:

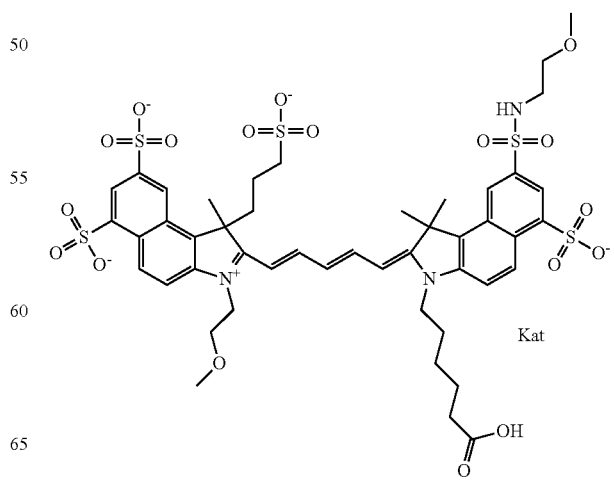

One non-limiting example of an additionally PEG-substituted compound is a 679 Compound 1/2 according to general formula II where R8 is a carboxamide group with an ethylene glycol group (PEG$_1$) terminating with a methyl group, shown below:

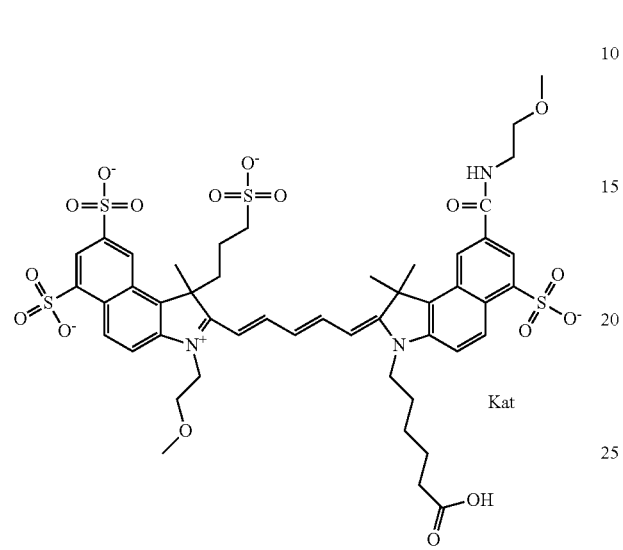

One non-limiting example of an additionally PEG-substituted compound is a 679 Compound 1/2 according to general formula II where R7 is an ethylene glycol group terminating with a methyl group, shown below:

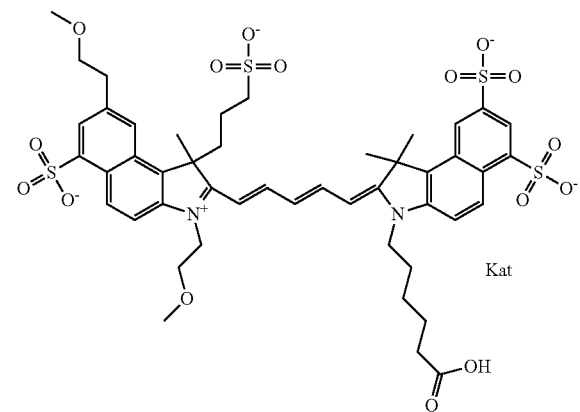

One non-limiting example of an additionally PEG-substituted compound is a 679 Compound 1/2 according to general formula II where R7 is a sulfonamide group with an ethylene glycol group (PEG$_1$) terminating with a methyl group, shown below:

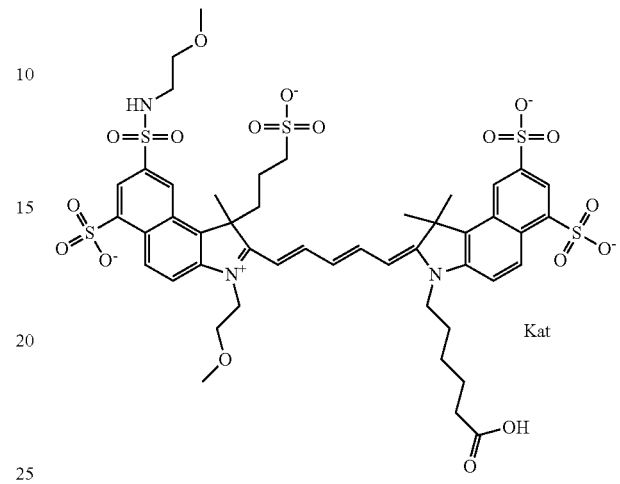

One non-limiting example of an additionally PEG-substituted compound is a 679 Compound 1/2 according to general formula II where R7 is a carboxamide group with an ethylene glycol group (PEG$_1$) terminating with a methyl group, shown below:

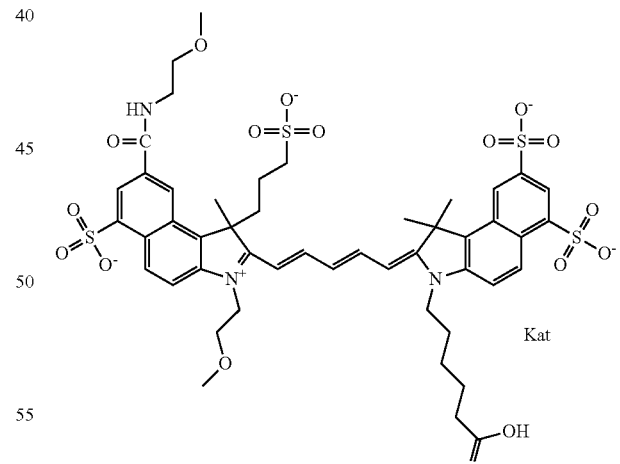

One non-limiting example of an additionally PEG-substituted compound is a 679 Compound 1/2 according to general formula II where R12 is an ethylene glycol group terminating with a methyl group,

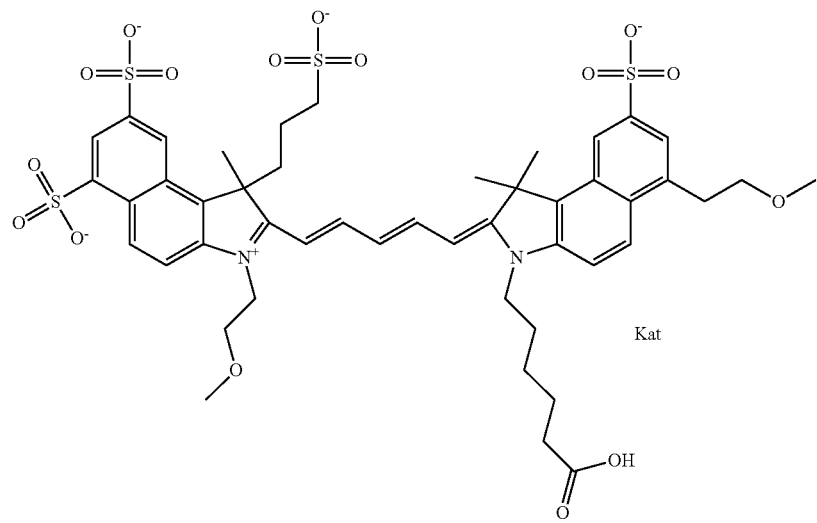

One non-limiting example of an additionally PEG-substituted compound is a 679 Compound 1/2 according to general formula II where R12 is a sulfonamide group with an ethylene glycol group (PEG$_1$) terminating with a methyl group, shown below:

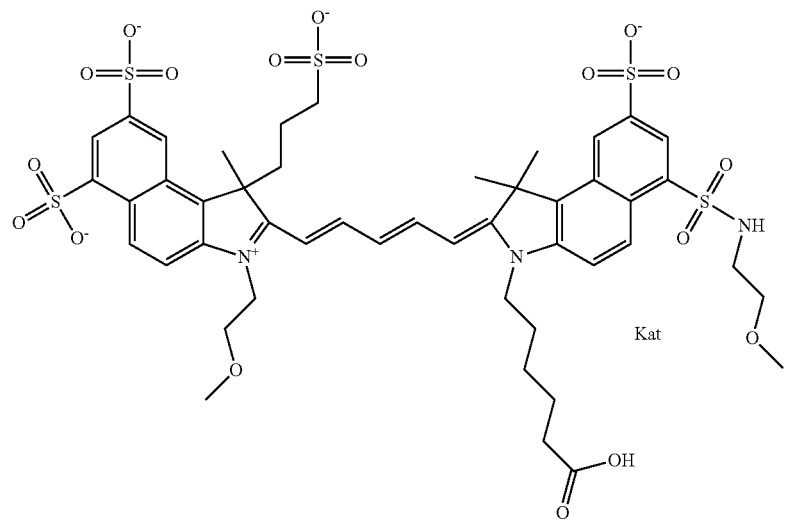

One non-limiting example of an additionally PEG-substituted compound is a 679 Compound 1/2 according to general formula II where R12 is a carboxamide group with an ethylene glycol group (PEG$_1$) terminating with a methyl group, shown below:

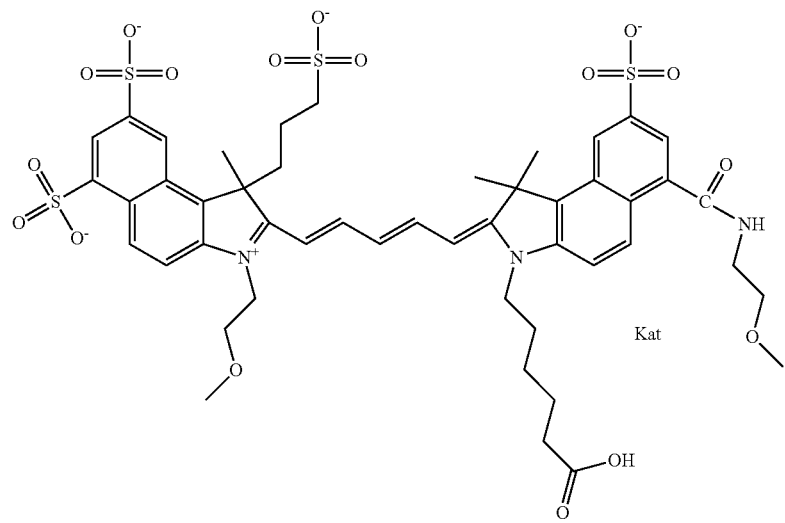

One non-limiting example of an additionally PEG-substituted compound is a 679 Compound 1/2 according to general formula II where R11 is an ethylene glycol group terminating with a methyl group, shown below:

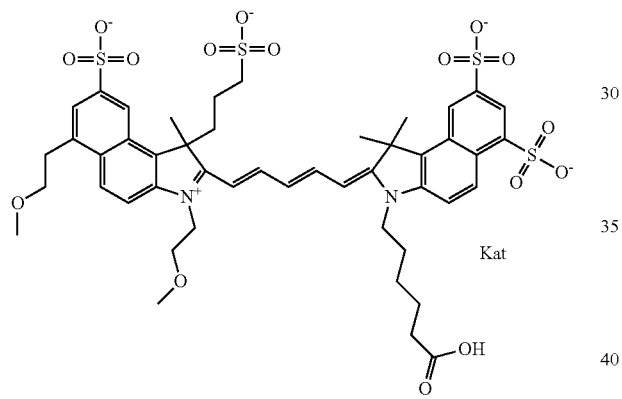

One non-limiting example of an additionally PEG-substituted compound is a 679 Compound 1/2 according to general formula II where R11 is a sulfonamide group with an ethylene glycol group ($PEG_1$) terminating with a methyl group, shown below:

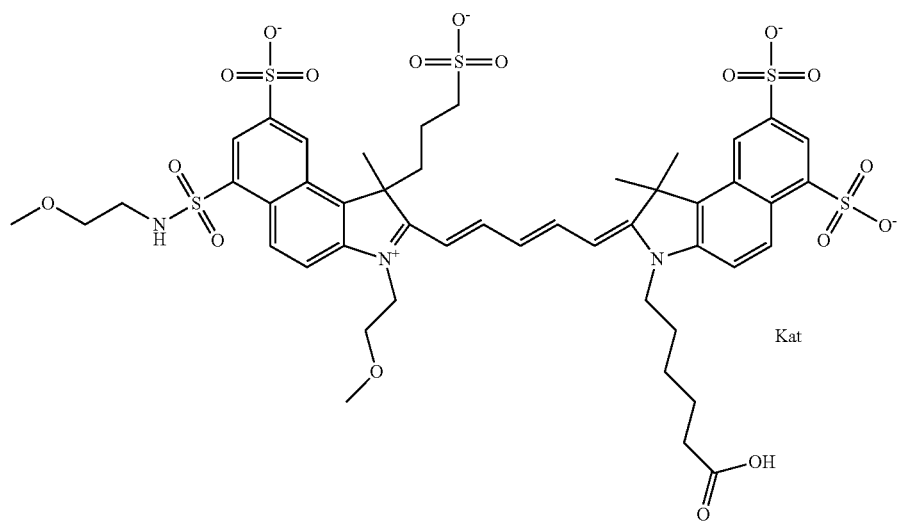

One non-limiting example of an additionally PEG-substituted compound is a 679 Compound 1/2 according to general formula II where R11 is a carboxamide group with an ethylene glycol group (PEG$_1$) terminating with a methyl group, shown below:

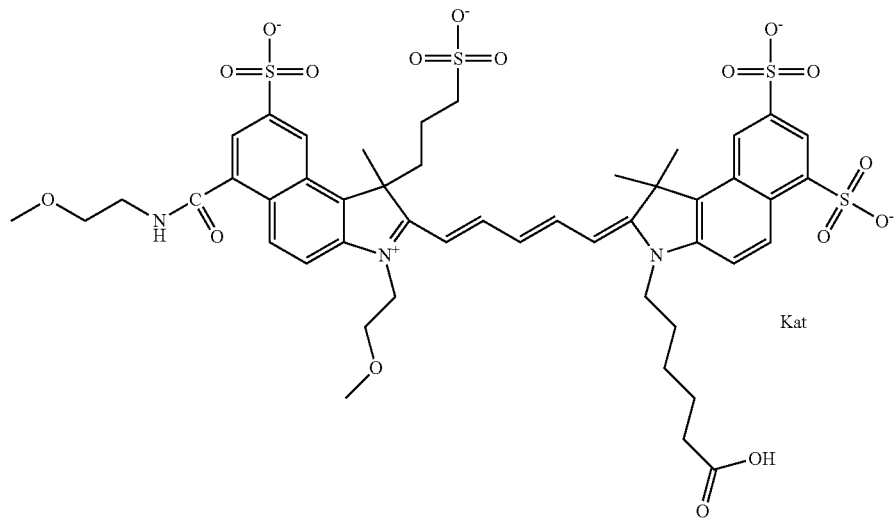

One non-limiting example of an additionally PEG-substituted compound is a 679 Compound 1/2 according to general formula II where R13 is an ethylene glycol group terminating with a methyl group, shown below:

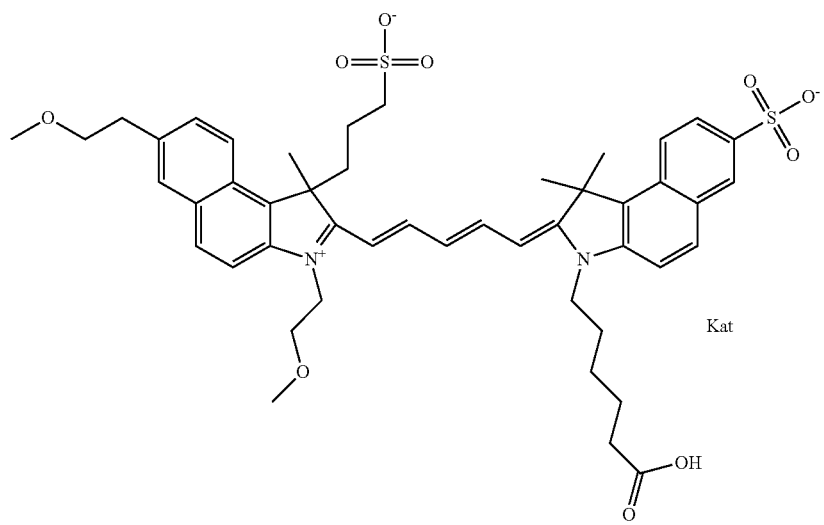

One non-limiting example of an additionally PEG-substituted compound is a 679 Compound 1/2 according to general formula II where R13 is a sulfonamide group with an ethylene glycol group (PEG$_1$) terminating with a methyl group, shown below:

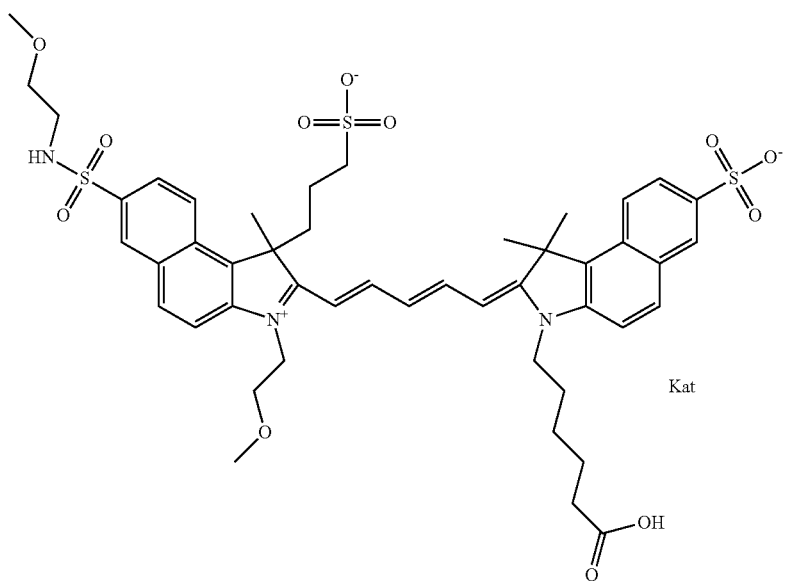

One non-limiting example of an additionally PEG-substituted compound is a 679 Compound 1/2 according to general formula II where R13 is a carboxamide group with an ethylene glycol group (PEG$_1$) terminating with a methyl group, shown below:

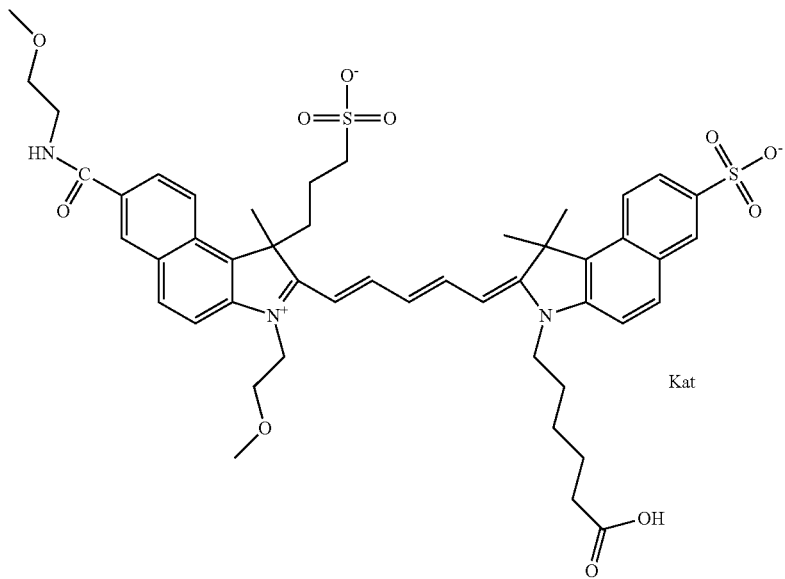

One non-limiting example of an additionally PEG-substituted compound is a 679 Compound 1/2 according to general formula II where R14 is an ethylene glycol group terminating with a methyl group, shown below:

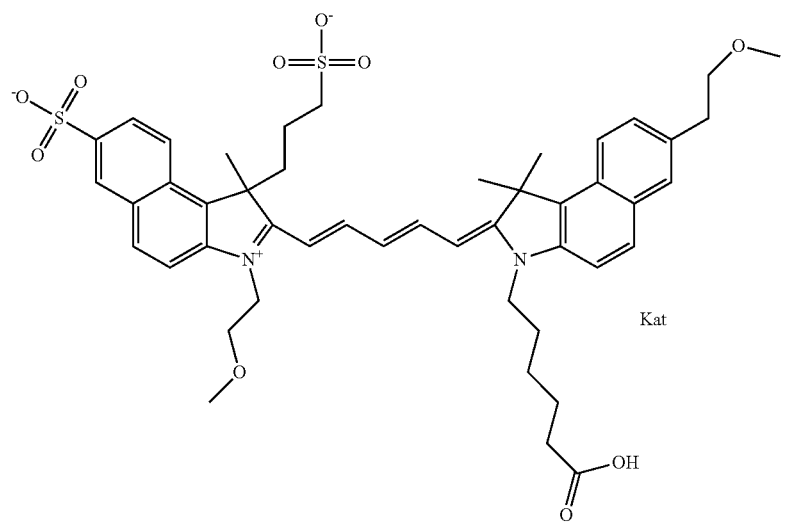

One non-limiting example of an additionally PEG-substituted compound is a 679 Compound 1/2 according to general formula II where R13 is a sulfonamide group with an ethylene glycol group (PEG$_1$) terminating with a methyl group, shown below:

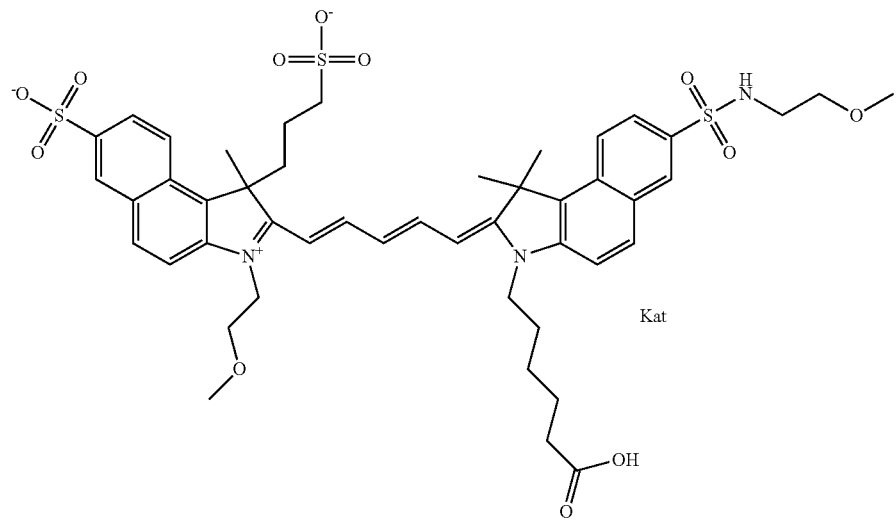

One non-limiting example of an additionally PEG-substituted compound is a 679 Compound 1/2 according to general formula II where R13 is a carboxamide group with an ethylene glycol group (PEG$_1$) terminating with a methyl group, shown below:

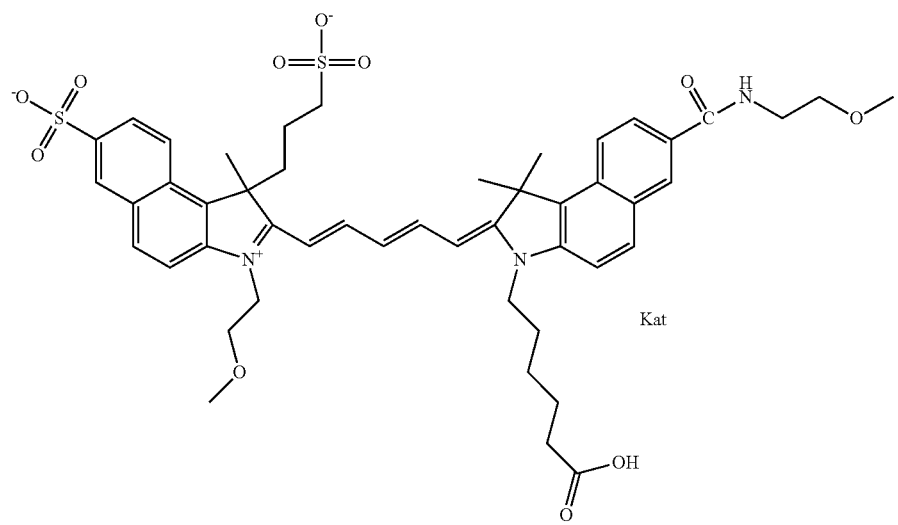

One non-limiting example of an additionally PEG-substituted compound is a 679 Compound 4/4 (V08-15173) according to general formula III where each of R1 and R2 is a (poly)ethylene glycol (4) group terminating with a methyl group, p=4, X=NHS, and each of R7, R8, R11, and R12 are SO$_3$, shown below:

One non-limiting example of an additionally PEG-substituted compound is a 679 Compound 4/4 (V10-04152) according to general formula III where each of R1 and R2 is a (poly)ethylene glycol (4) group terminating with a methyl group, p=4, X=OH, and each of R13 and R14 are SO$_3$, shown below:

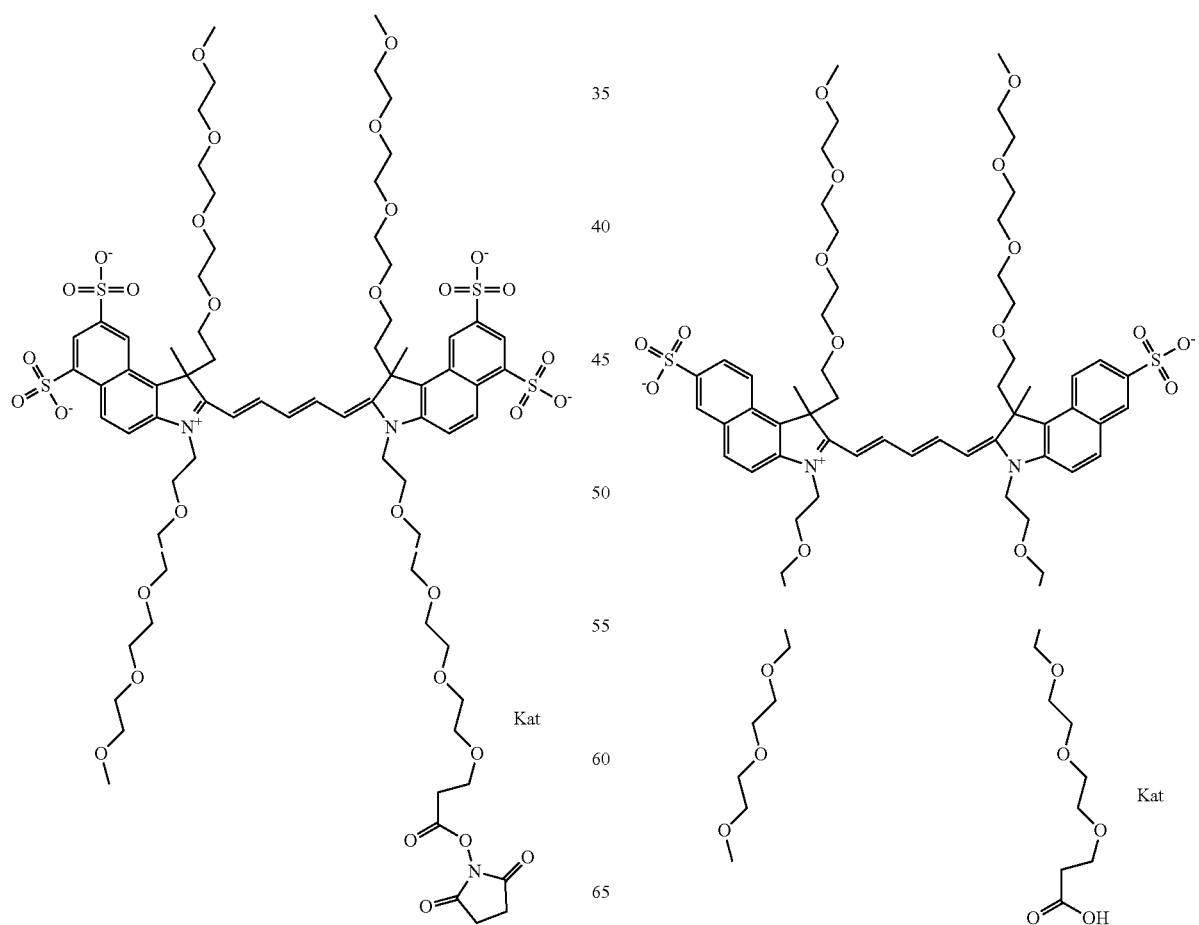

In one embodiment, the compound is 779 Compound 1

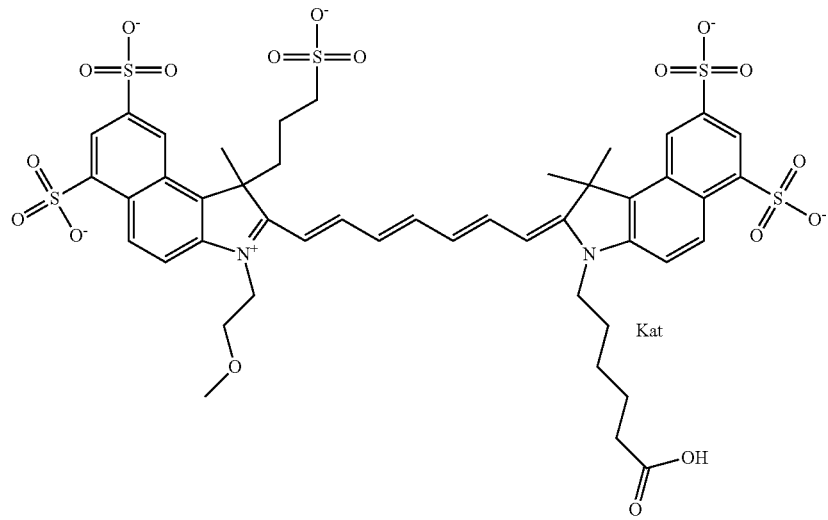 [SMILES: COCC[N+]1=C(/C=C/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

779 Compound 1 (6-((E)-2-((2E,4E,6E)-7-(3-(2-methoxyethyl)-1-methyl-6,8-disulfonato-1-(3-sulfonatopropyl)-1H-benzo[e]indol-3-ium-2-yl)hepta-2,4,6-trien-1-ylidene)-1,1-dimethyl-6,8-disulfonato-1H-benzo[e]indol-3(2H)-yl)hexanoate) contains an ethylene glycol on the indole N of the left heterocycle, i.e., a methylated ethylene glycol. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 779 Compound 1, but one skilled in the art appreciates that activation is not limited to these examples. One non-limiting example of an activated compound is the NHS-ester of 779 Compound 1, shown below:

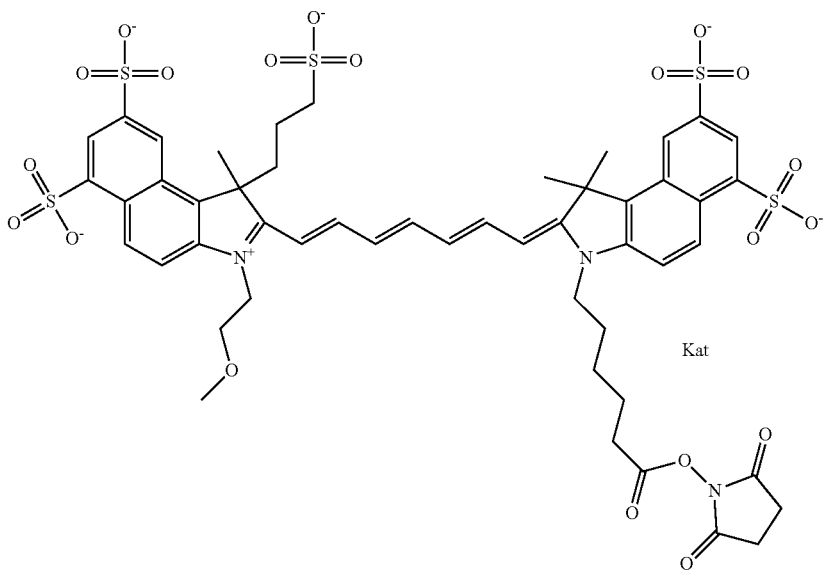 [SMILES: COCC[N+]1=C(/C=C/C=C/C=C/C=C2/N(CCCCCC(=O)ON3C(=O)CCC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example of a NHS-ester of 779 Compound 1, according to general formula III, where m=1 and p=1, is shown below:

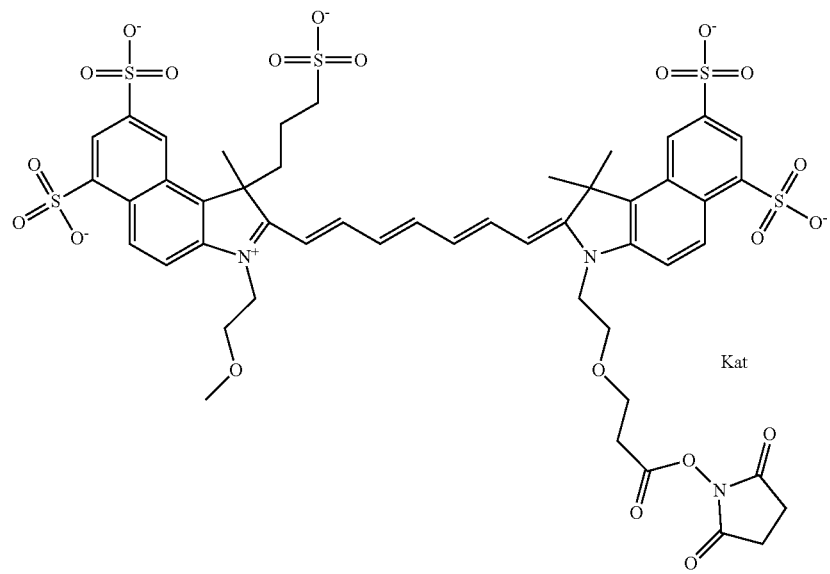
One non-limiting example of a NHS-ester of 779 Compound 1, according to general formula III, where m=1 and p=2, is shown below:
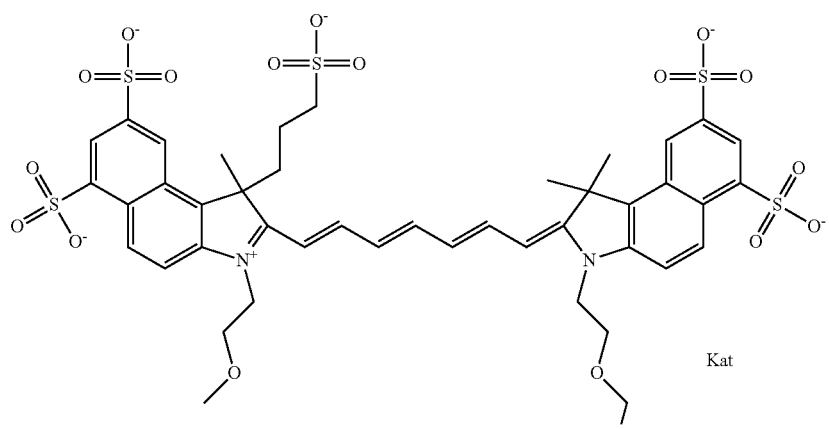
One non-limiting example of a NHS-ester of 779 Compound 1, according to general formula III, where m=1 and p=3, is shown below:

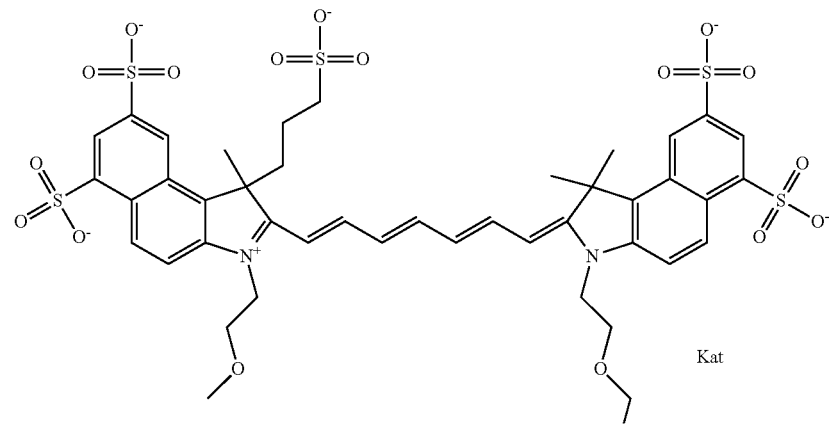
Kat
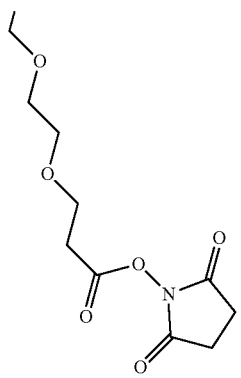
One non-limiting example of a NHS-ester of 779 Compound 1, according to general formula III, where m=1 and p=4, is shown below:
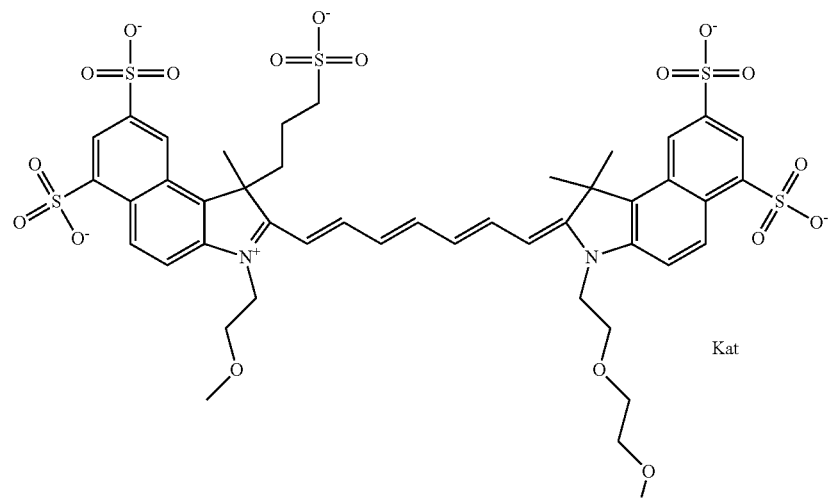
Kat

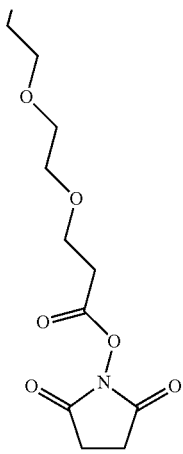
One non-limiting example of a NHS-ester of 779 Compound 1, according to general formula III, where m=1 and p=5, is shown below:
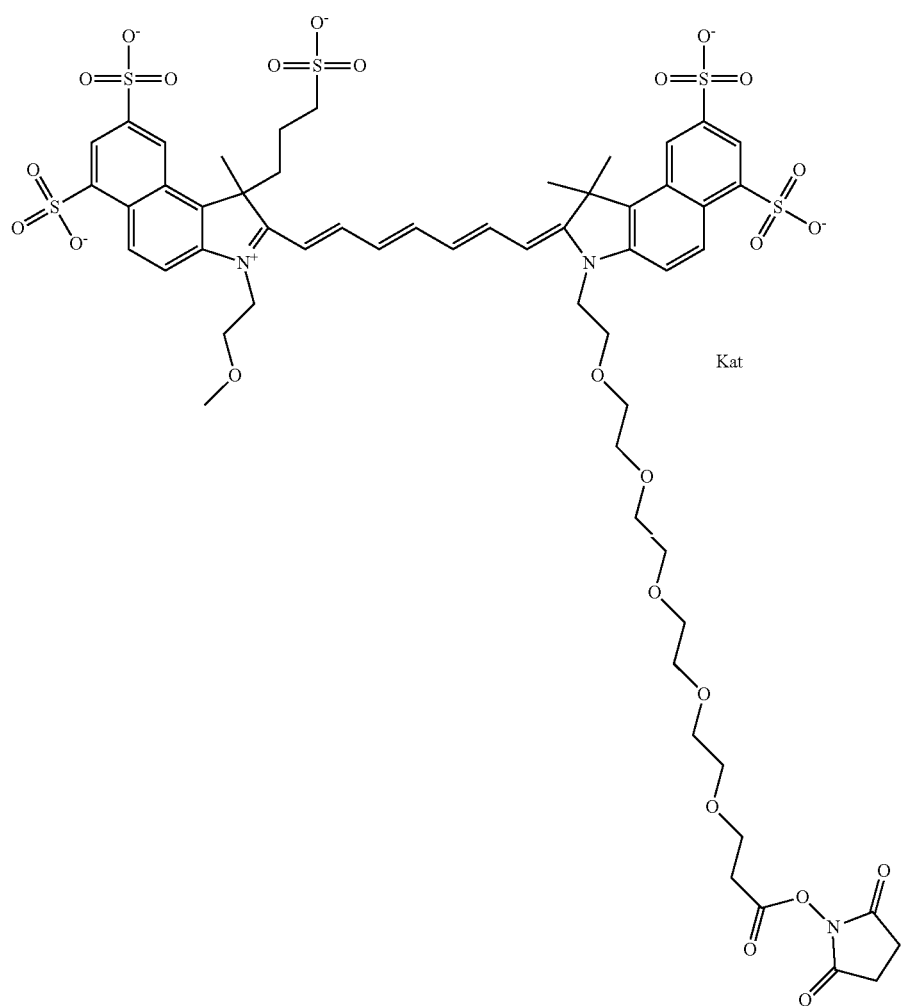
One non-limiting example of a NHS-ester of 779 Compound 1, according to general formula III, where m=1 and p=6, is shown below:

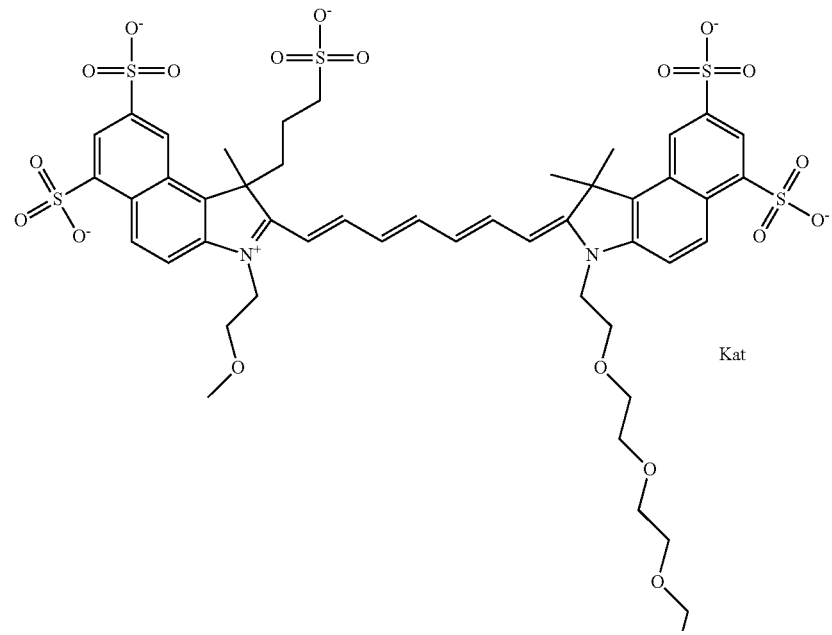
One non-limiting example of an activated 779 Compound 1 is a tetrafluorophenyl (TFP)-ester form of 779 Compound 1, shown below:
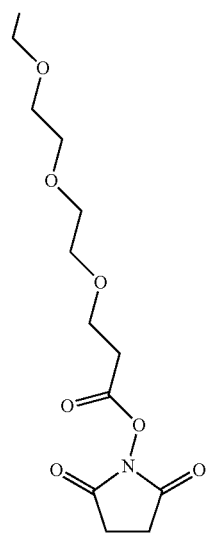

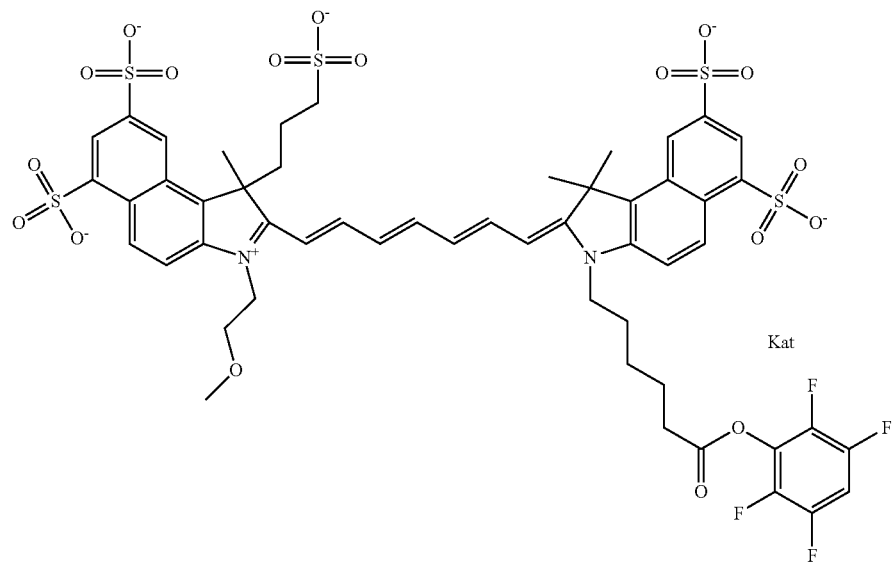 [SMILES: COCC[N+]1=C(/C=C/C=C/C=C/C=C2/N(CCCCCC(=O)Oc3c(F)c(F)cc(F)c3F)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]
One non-limiting example of an activated 779 Compound 1 is a sulfotetrafluorophenyl (STP)-ester form of 779 Compound 1, shown below:
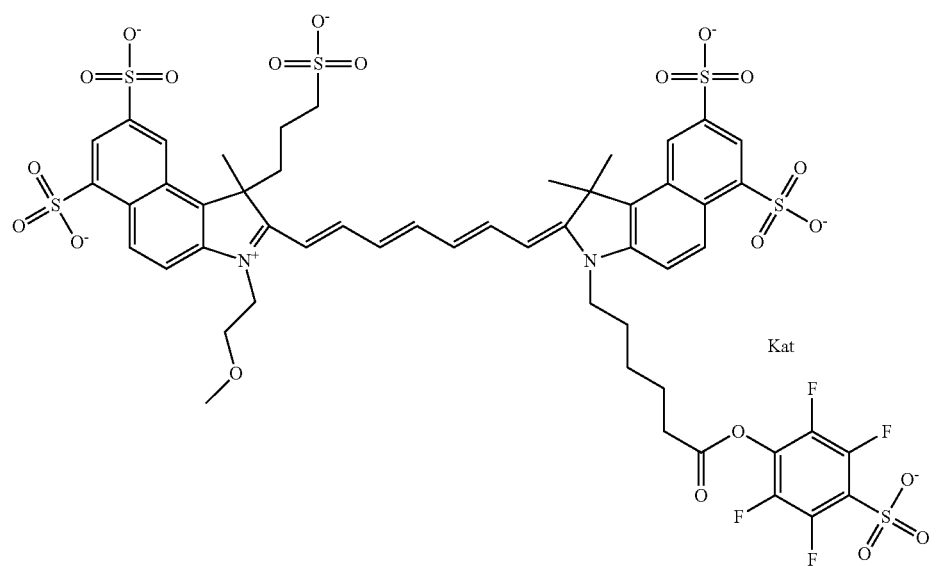 [SMILES: COCC[N+]1=C(/C=C/C=C/C=C/C=C2/N(CCCCCC(=O)Oc3c(F)c(F)c(S(=O)(=O)[O-])c(F)c3F)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]
One non-limiting example of an activated 779 Compound 1 is a hydrazide form of 779 Compound 1, shown below:

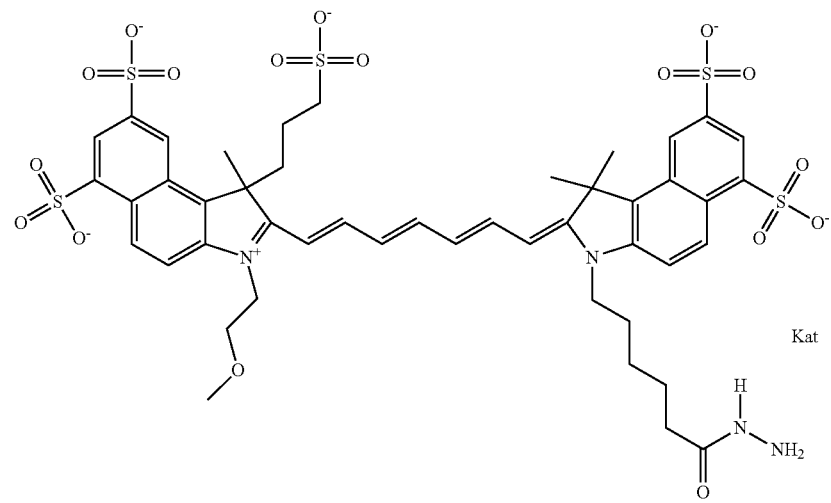 [SMILES: COCC[N+]1=C(/C=C/C=C/C=C/C=C2/N(CCCCCC(=O)NN)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]
One non-limiting example of an activated 779 Compound 1 is a maleimide form of 779 Compound 1, shown below:
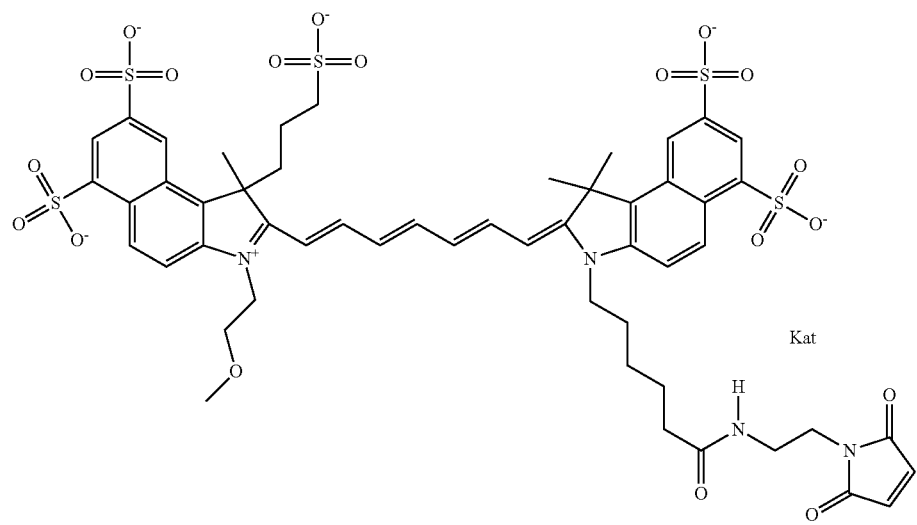 [SMILES: COCC[N+]1=C(/C=C/C=C/C=C/C=C2/N(CCCCCC(=O)NCCN3C(=O)C=CC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]
In one embodiment, the compound is 779 Compound 2
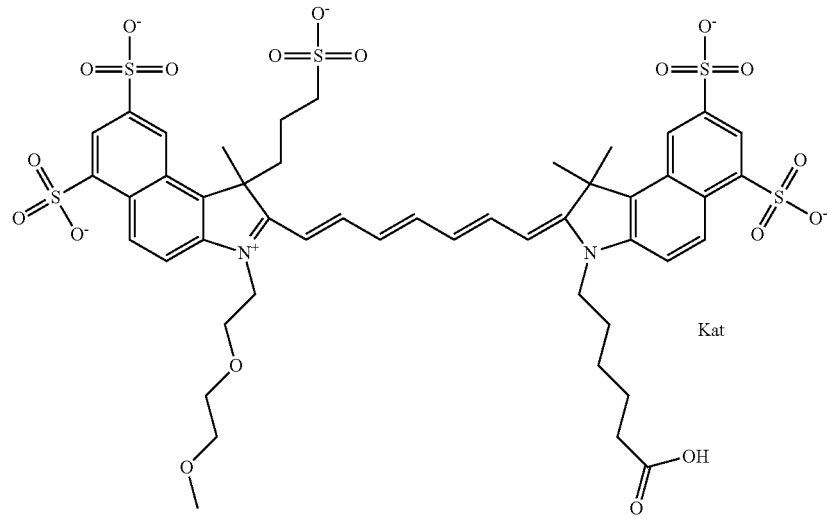 [SMILES: COCCOCC[N+]1=C(/C=C/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

779 Compound 2 (6-((E)-2-((2E,4E,6E)-7-(3-(2-(2-methoxyethoxy)ethyl)-1-methyl-6,8-disulfonato-1-(3-sulfonatopropyl)-1H-benzo[e]indol-3-ium-2-yl)hepta-2,4,6-trien-1-ylidene)-1,1-dimethyl-6,8-disulfonato-1H-benzo[e]indol-3(2H)-yl)hexanoate) contains a diethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 779 Compound 2 is activated as described above.

In one embodiment, the compound is 779 Compound 3

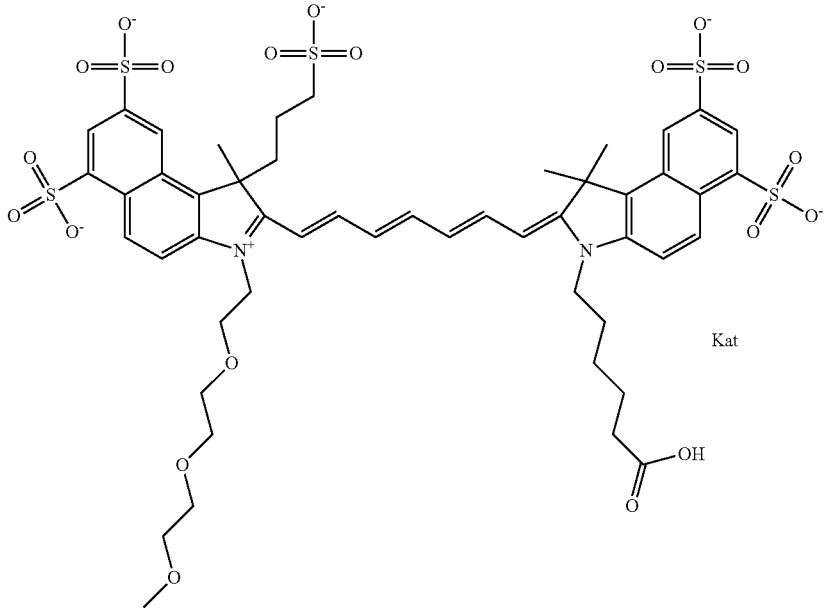 [SMILES: COCCOCCOCC[N+]1=C(/C=C/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

779 Compound 3 (6-((E)-2-((2E,4E,6E)-7-(3-(2-(2-(2-methoxyethoxy)ethoxy)ethyl)-1-methyl-6,8-disulfonato-1-(3-sulfonatopropyl)-1H-benzo[e]indol-3-ium-2-yl)hepta-2,4,6-trien-1-ylidene)-1,1-dimethyl-6,8-disulfonato-1H-benzo[e]indol-3(2H)-yl)hexanoate) contains a (poly) ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 779 Compound 3 is activated as described above.

In one embodiment, the compound is 779 Compound 4

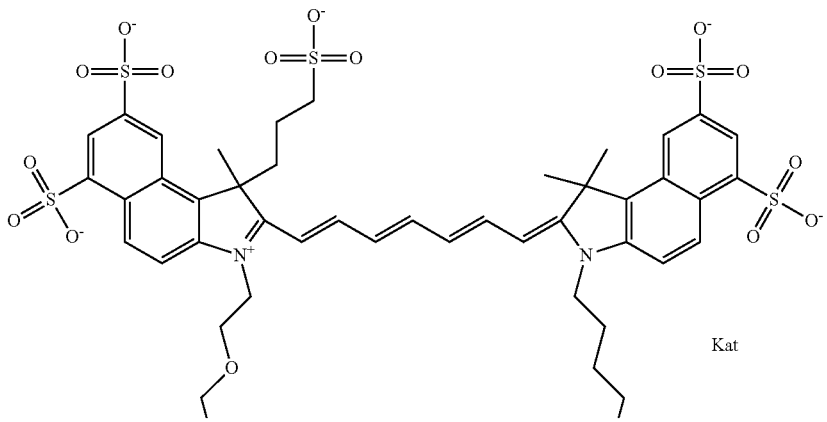

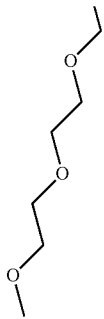
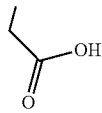

779 Compound 4 (6-((E)-1,1-dimethyl-2-((2E,4E,6E)-7-(1-methyl-6,8-disulfonato-1-(3-sulfonatopropyl)-3-(2,5,8,11-tetraoxatridecan-13-yl)-1H-benzo[e]indol-3-ium-2-yl)hepta-2,4,6-trien-1-ylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 779 Compound 4 is activated as described above.

In one embodiment, the compound is 779 Compound 5

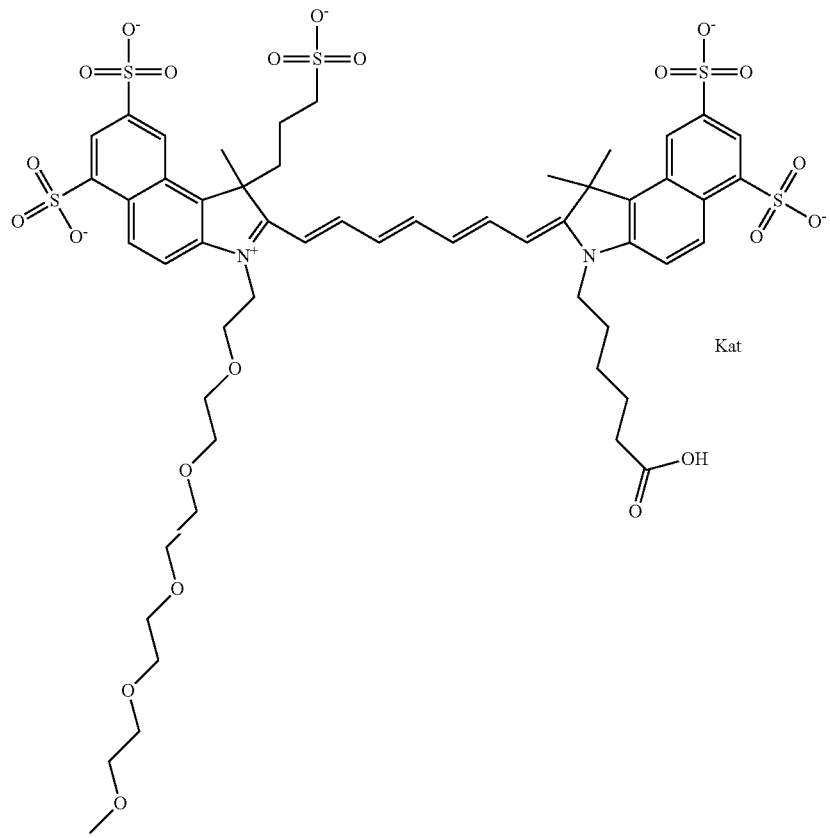 [SMILES: COCCOCCOCCOCCOCC[N+]1=C(/C=C/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

779 Compound 5 (6-((E)-2-((2E,4E,6E)-7-(3-(2,5,8,11,14-pentaoxahexadecan-16-yl)-1-methyl-6,8-disulfonato-1-(3-sulfonatopropyl)-1H-benzo[e]indol-3-ium-2-yl)hepta-2,4,6-trien-1-ylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 779 Compound 5 is activated as described above.

In one embodiment, the compound is 779 Compound 6

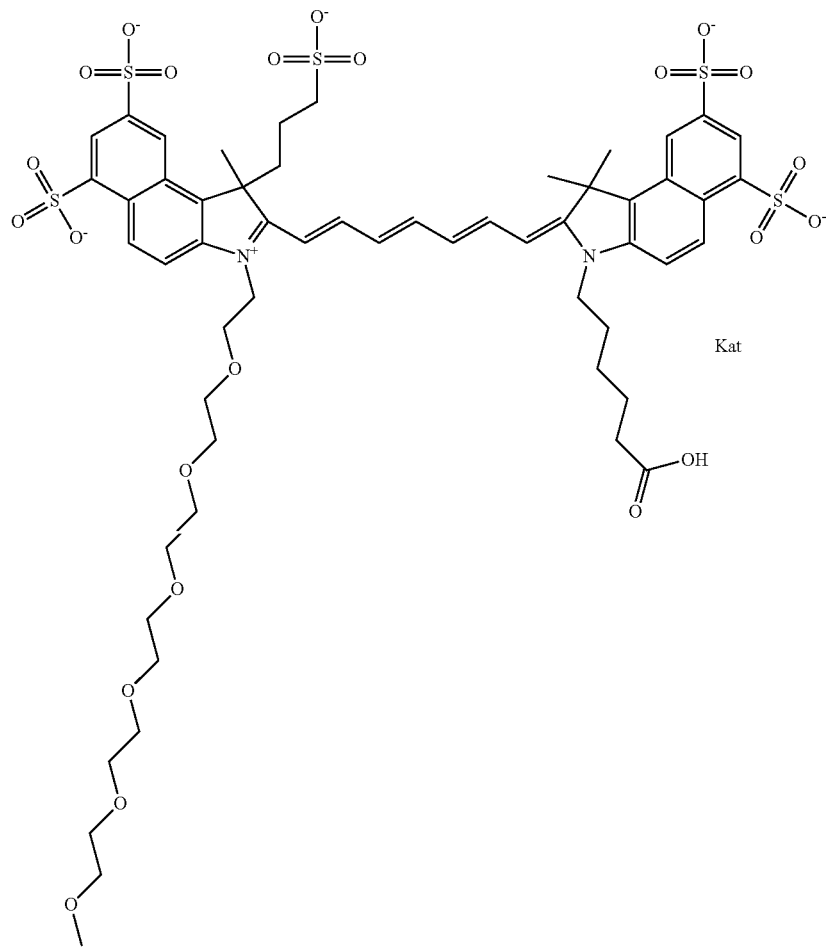 [SMILES: COCCOCCOCCOCCOCCOCC[N+]1=C(/C=C/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

779 Compound 6 (6-((E)-1,1-dimethyl-2-((2E,4E,6E)-7-(1-methyl-3-(2,5,8,11,14,17-hexaoxanonadecan-19-yl)-6,8-disulfonato-1-(3-sulfonatopropyl)-1H-benzo[e]indol-3-ium-2-yl)hepta-2,4,6-trien-1-ylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 779 Compound 6 is activated as described above.

In one embodiment, the compound is 779 Compound 0/1

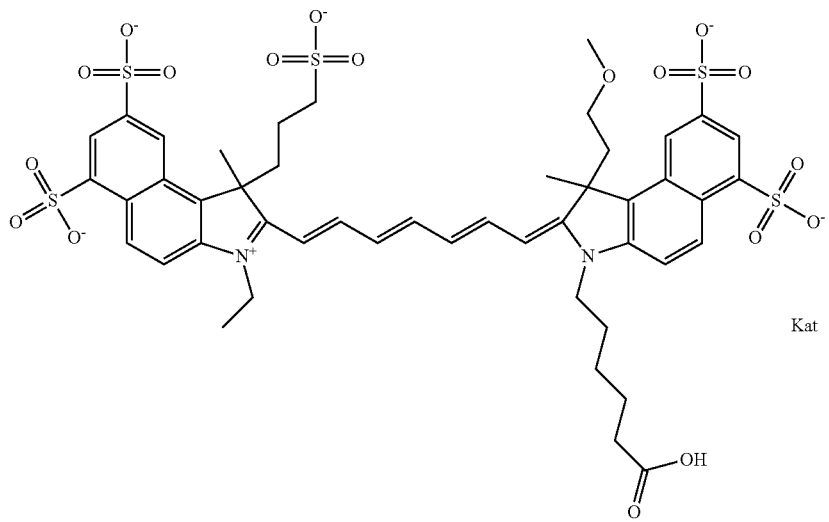 [SMILES: CC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOC)C(C)(CCCS(=O)(=O)[O-])c2c1ccc1c(S(=O)(=O)[O-])cc(S(=O)(=O)[O-])cc21]

779 Compound 0/1 (2-((1E,3E,5E,7E)-7-(3-(5-carboxypentyl)-1-(2-methoxyethyl)-1-methyl-6,8-disulfonato-1H-benzo[e]indol-2(3H)-ylidene)hepta-1,3,5-trienyl)-3-ethyl-1-methyl-1-(3-sulfonatopropyl)-1H-benzo[e]indolium-6,8-disulfonate) contains an ethylene glycol at R2, a sulfoalkyl at R1, an ethyl at R9, and carboxyalkyl at R10.

One non-limiting example of an activated compound is the NHS-ester of 779 Compound 0/1, shown below:

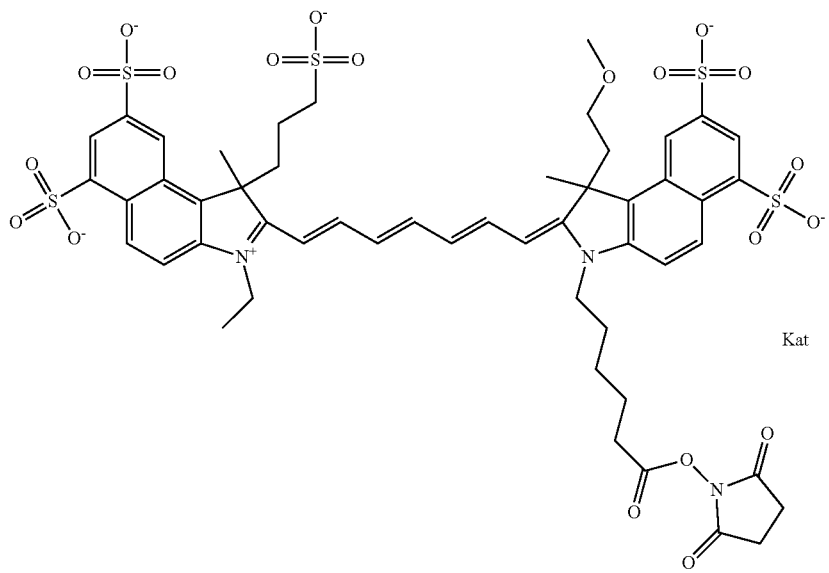 [SMILES: CC[N+]1=C(/C=C/C=C/C=C/C=C2/N(CCCCCC(=O)ON3C(=O)CCC3=O)c3ccc4c(S(=O)(=O)[O-])cc(S(=O)(=O)[O-])cc4c3C2(C)CCOC)C(C)(CCCS(=O)(=O)[O-])c2c1ccc1c(S(=O)(=O)[O-])cc(S(=O)(=O)[O-])cc21]

One non-limiting example of an activated 779 Compound 0/1 is a tetrafluorophenyl (TFP)-ester form, shown below:

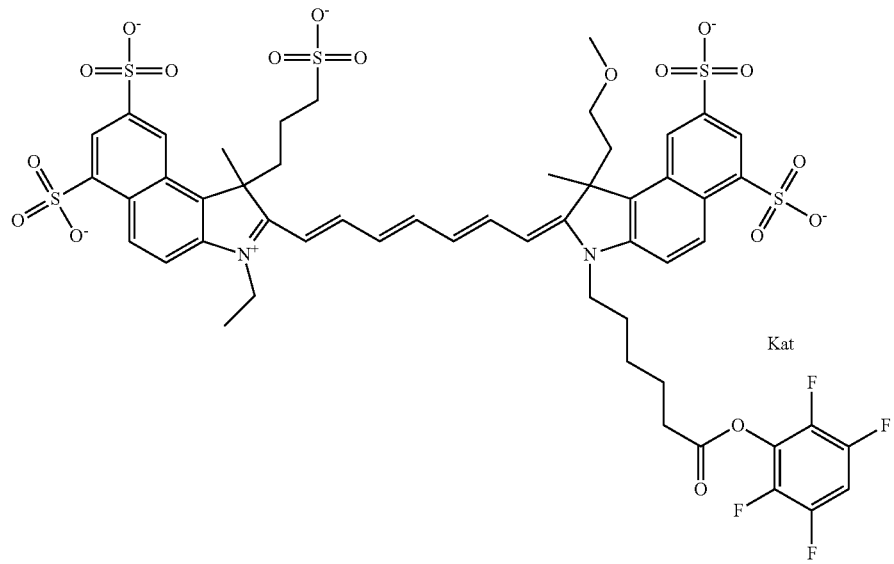 [SMILES: CC[N+]1=C(/C=C/C=C/C=C/C=C2/N(CCCCCC(=O)Oc3c(F)c(F)cc(F)c3F)c3ccc4c(S(=O)(=O)[O-])cc(S(=O)(=O)[O-])cc4c3C2(C)CCOC)C(C)(CCCS(=O)(=O)[O-])c2c1ccc1c(S(=O)(=O)[O-])cc(S(=O)(=O)[O-])cc21]

One non-limiting example of an activated 779 Compound 0/1 is a sulfotetrafluorophenyl (STP)-ester form, shown below:

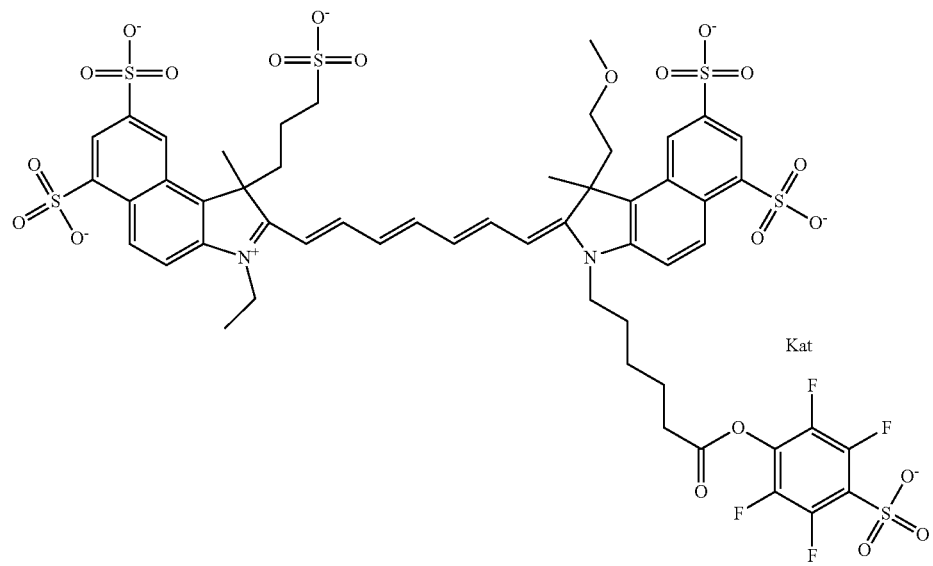 [SMILES: CC[N+]1=C(/C=C/C=C/C=C/C=C2/N(CCCCCC(=O)Oc3c(F)c(F)c(S(=O)(=O)[O-])c(F)c3F)c3ccc4c(S(=O)(=O)[O-])cc(S(=O)(=O)[O-])cc4c3C2(C)CCOC)C(C)(CCCS(=O)(=O)[O-])c2c1ccc1c(S(=O)(=O)[O-])cc(S(=O)(=O)[O-])cc21]
One non-limiting example of an activated 779 Compound 0/1 is a hydrazide form, shown below:
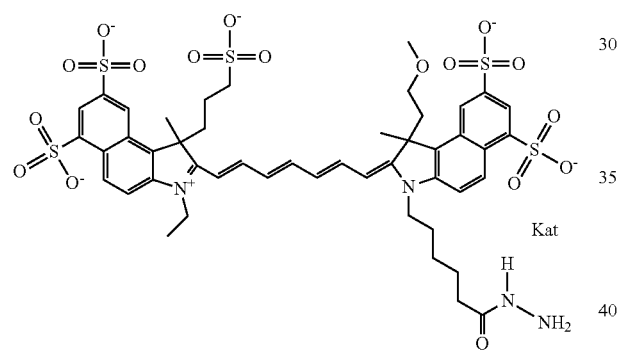
One non-limiting example of an activated 779 Compound 0/1 is a maleimide form, shown below:
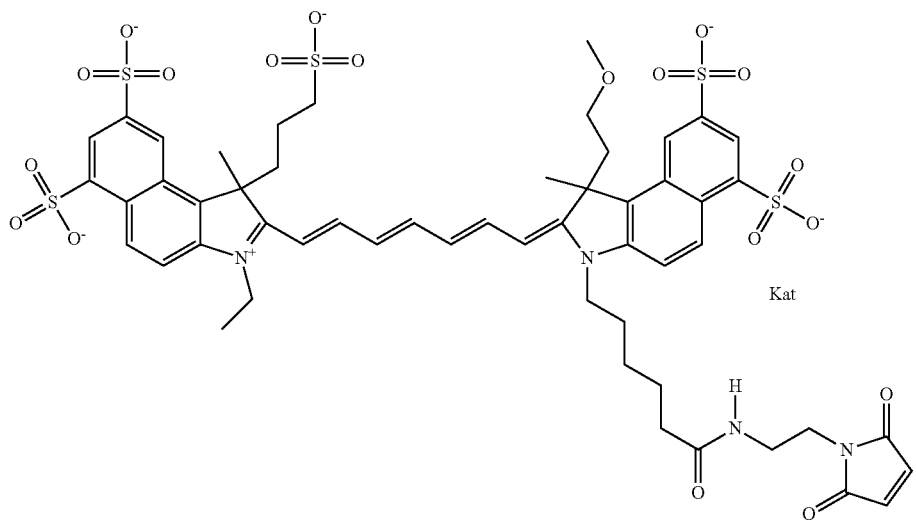 [SMILES: CC[N+]1=C(/C=C/C=C/C=C/C=C2/N(CCCCCC(=O)NCCN3C(=O)C=CC3=O)c3ccc4c(S(=O)(=O)[O-])cc(S(=O)(=O)[O-])cc4c3C2(C)CCOC)C(C)(CCCS(=O)(=O)[O-])c2c1ccc1c(S(=O)(=O)[O-])cc(S(=O)(=O)[O-])cc21]

In one embodiment, the compound is 779 Compound 0/1

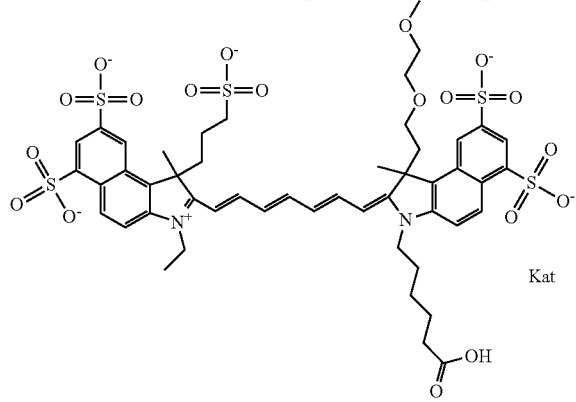 [SMILES: CC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOCCOC)C(C)(CCCS(=O)(=O)[O-])c2c1ccc1c(S(=O)(=O)[O-])cc(S(=O)(=O)[O-])cc21]

779 Compound 0/1 (2-((1E,3E,5E,7E)-7-(3-(5-carboxy-pentyl)-1-(2-(2-methoxyethoxy)ethyl)-1-methyl-6,8-disulfonato-1H-benzo[e]indol-2(3H)-ylidene)hepta-1,3,5-trienyl)-3-ethyl-1-methyl-1-(3-sulfonatopropyl)-1H-benzo[e]indolium-6,8-disulfonate) contains a diethylene glycol at R2, a sulfoalkyl at R1, an ethyl at R9, and carboxyalkyl at R10.

In one embodiment, the compound is 779 Compound 0/1

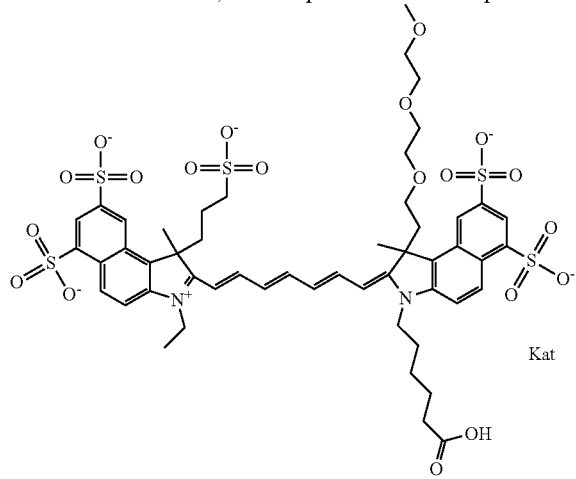 [SMILES: CC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOCCOCCOC)C(C)(CCCS(=O)(=O)[O-])c2c1ccc1c(S(=O)(=O)[O-])cc(S(=O)(=O)[O-])cc21]

779 Compound 0/1 (2-((1E,3E,5E,7E)-7-(3-(5-carboxy-pentyl)-1-(2-(2-(2-methoxyethoxy)ethoxy)ethyl)-1-methyl-6,8-disulfonato-1H-benzo[e]indol-2(3H)-ylidene)hepta-1,3,5-trienyl)-3-ethyl-1-methyl-1-(3-sulfonatopropyl)-1H-benzo[e]indolium-6,8-disulfonate) contains a (poly)ethylene glycol (PEG$_3$) at R2, a sulfoalkyl at R1, an ethyl at R9, and carbon/alkyl at R10.

In one embodiment, the compound is 779 Compound 0/1

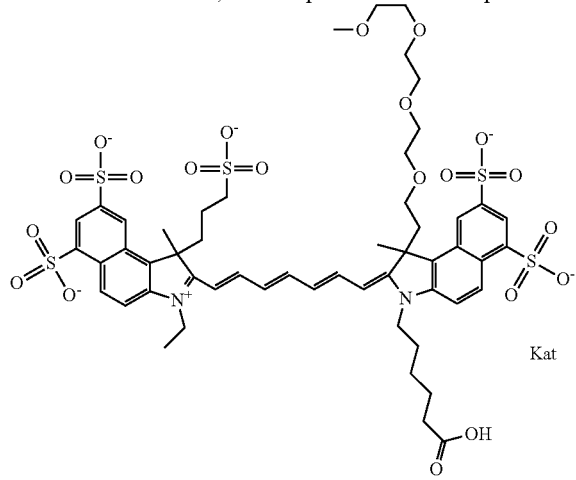 [SMILES: CC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOCCOCCOCCOC)C(C)(CCCS(=O)(=O)[O-])c2c1ccc1c(S(=O)(=O)[O-])cc(S(=O)(=O)[O-])cc21]

779 Compound 0/1 (2-((1E,3E,5E,7E)-7-(3-(5-carboxy-pentyl)-1-methyl-6,8-disulfonato-1-(2,5,8,11-tetraoxatride-can-13-yl)-1H-benzo[e]indol-2(3H)-ylidene)hepta-1,3,5-trienyl)-3-ethyl-1-methyl-1-(3-sulfonatopropyl)-1H-benzo[e]indolium-6,8-disulfonate) contains a (poly)ethylene glycol (PEG$_4$) at R2, a sulfoalkyl at R1, an ethyl at R9, and carboxyalkyl at R10.

In one embodiment, the compound is 779 Compound 0/1

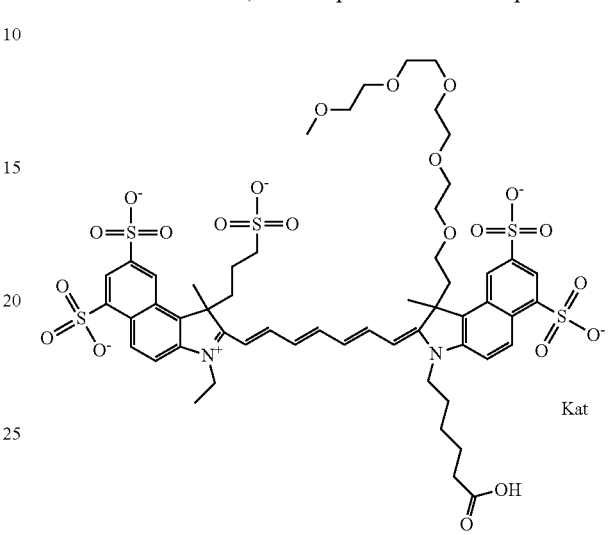

779 Compound 0/1 (2-((1E,3E,5E,7E)-7-(3-(5-carboxy-pentyl)-1-(2,5,8,11,14-pentaoxahexadecan-16-yl)-1-methyl-6,8-disulfonato-1H-benzo[e]indol-2(3H)-ylidene)hepta-1,3,5-trienyl)-3-ethyl-1-methyl-1-(3-sulfonatopropyl)-1H-benzo[e]indolium-6,8-disulfonate) contains a (poly)ethylene glycol (PEG$_5$) at R2, a sulfoalkyl at R1, an ethyl at R9, and carboxyalkyl at R10.

In one embodiment, the compound is 779 Compound 0/1

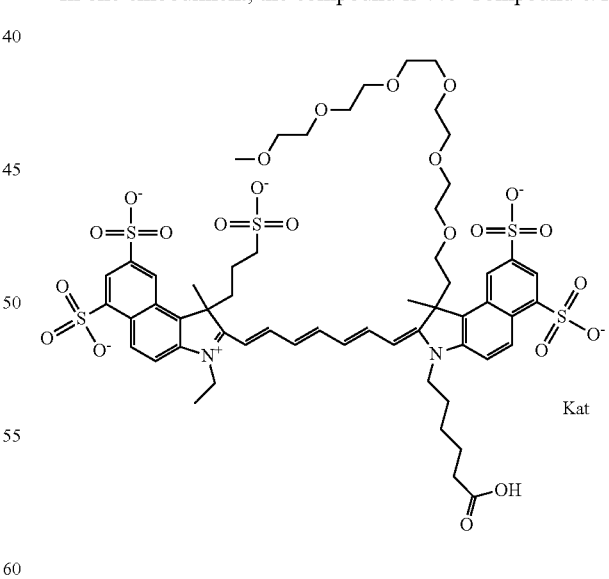

779 Compound 0/1 (2-((1E,3E,5E,7E)-7-(3-(5-carboxy-pentyl)-1-methyl-1-(2,5,8,11,14,17-hexaoxanonadecan-19-yl)-6,8-disulfonato-1H-benzo[e]indol-2(3H)-ylidene)hepta-1,3,5-trienyl)-3-ethyl-1-methyl-1-(3-sulfonatopropyl)-1H-benzo[e]indolium-6,8-disulfonate) contains a (poly)ethylene glycol (PEG$_6$) at R2, a sulfoalkyl at R1, an ethyl at R9, and carboxyalkyl at R10.

In one embodiment, the compound is 679 Compound 0/1

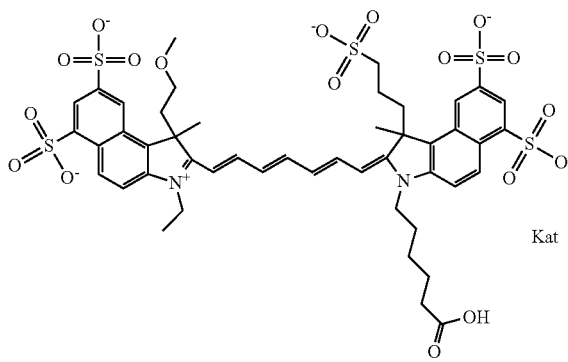

779 Compound 0/1 (2-((1E,3E,5E,7E)-7-(3-(5-carboxypentyl)-1-methyl-6,8-disulfonato-1-(3-sulfonatopropyl)-1H-benzo[e]indol-2(3H)-ylidene)hepta-1,3,5-trienyl)-3-ethyl-1-(2-methoxyethyl)-1-methyl-1H-benzo[e]indolium-6,8-disulfonate) contains an ethylene glycol at R1, a sulfoalkyl at R2, an ethyl at R9, and carboxyalkyl at R10.

One non-limiting example of an activated compound is the NHS-ester of 779 Compound 0/1, shown below:

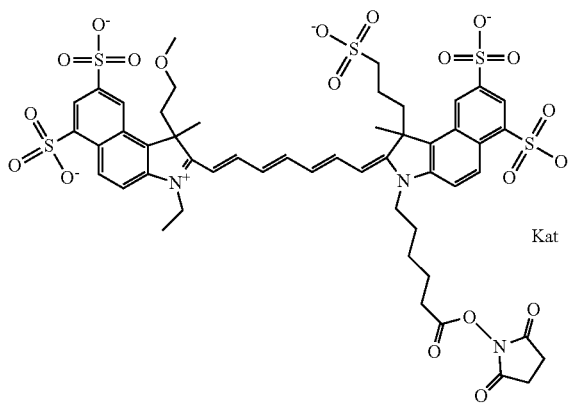

In one embodiment, the compound is 779 Compound 0/1

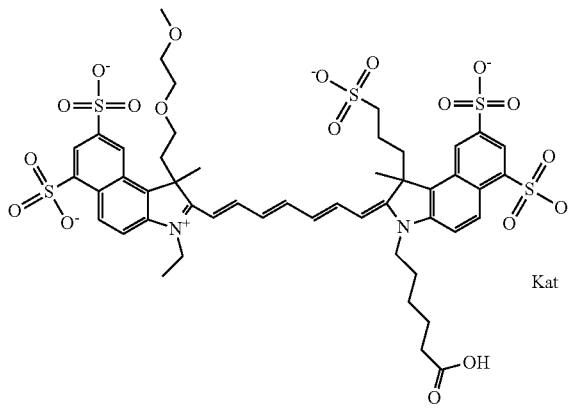

779 Compound 0/1 (2-((1E,3E,5E,7E)-7-(3-(5-carboxypentyl)-1-methyl-6,8-disulfonato-1-(3-sulfonatopropyl)-1H-benzo[e]indol-2(3H)-ylidene)hepta-1,3,5-trienyl)-3-ethyl-1-(2-(2-methoxyethoxy)ethyl)-1-methyl-1H-benzo[e]indolium-6,8-disulfonate) contains a diethylene glycol at R1, a sulfoalkyl at R2, an ethyl at R9, and carboxyalkyl at R10.

In one embodiment, the compound is 779 Compound 0/1

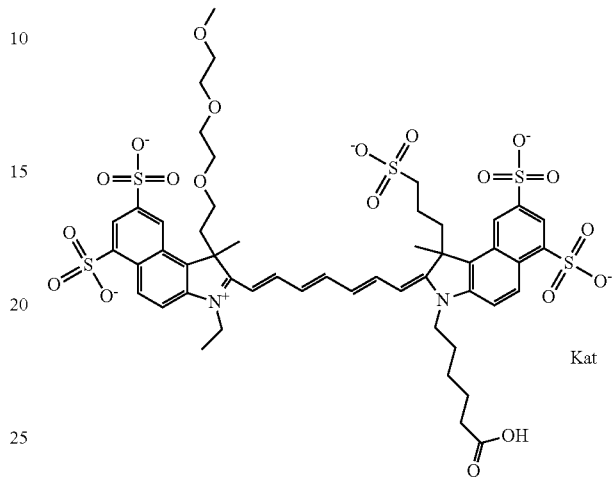

779 Compound 0/1 (2-((1E,3E,5E,7E)-7-(3-(5-carboxypentyl)-1-methyl-6,8-disulfonato-1-(3-sulfonatopropyl)-1H-benzo[e]indol-2(3H)-ylidene)hepta-1,3,5-trienyl)-3-ethyl-1-(2-(2-(2-methoxyethoxy)ethoxy)ethyl)-1-methyl-1H-benzo[e]indolium-6,8-disulfonate) contains a (poly)ethylene glycol (PEG$_3$) at R1, a sulfoalkyl at R2, an ethyl at R9, and carboxyalkyl at R10.

In one embodiment, the compound is 779 Compound 0/1

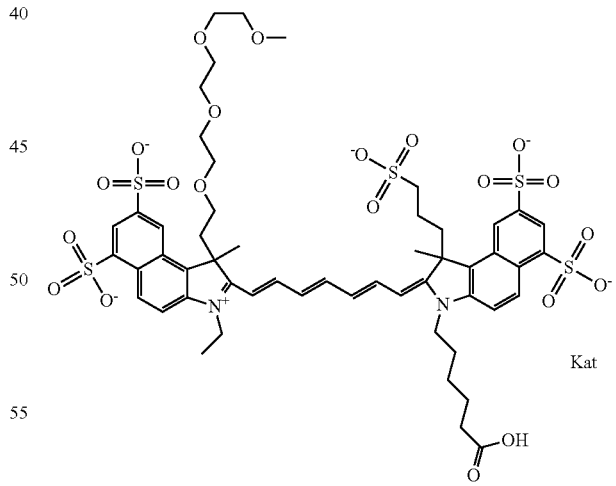

779 Compound 0/1 (2-((1E,3E,5E,7E)-7-(3-(5-carboxypentyl)-1-methyl-6,8-disulfonato-1-(3-sulfonatopropyl)-1H-benzo[e]indol-2(3H)-ylidene)hepta-1,3,5-trienyl)-3-ethyl-1-methyl-1-(2,5,8,11-tetraoxatridecan-13-yl)-1H-benzo[e]indolium-6,8-disulfonate) contains a (poly)ethylene glycol (PEG$_4$) at R1, a sulfoalkyl at R2, an ethyl at R9, and carbon/alkyl at R10.

In one embodiment, the compound is 779 Compound 0/1

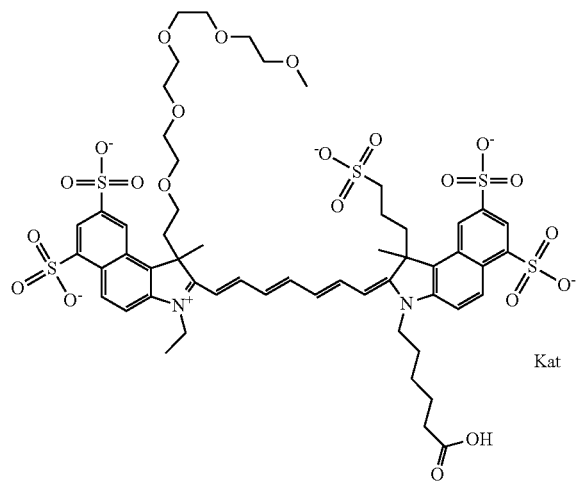

779 Compound 0/1 (2-((1E,3E,5E,7E)-7-(3-(5-carboxypentyl)-1-methyl-6,8-disulfonato-1-(3-sulfonatopropyl)-1H-benzo[e]indol-2(3H)-ylidene)hepta-1,3,5-trienyl)-3-ethyl-1-(2,5,8,11,14-pentaoxahexadecan-16-yl)-1-methyl-1H-benzo[e]indolium-6,8-disulfonate) contains a (poly) ethylene glycol (PEG$_5$) at R1, a sulfoalkyl at R2, an ethyl at R9, and carboxyalkyl at R10.

In one embodiment, the compound is 779 Compound 0/1

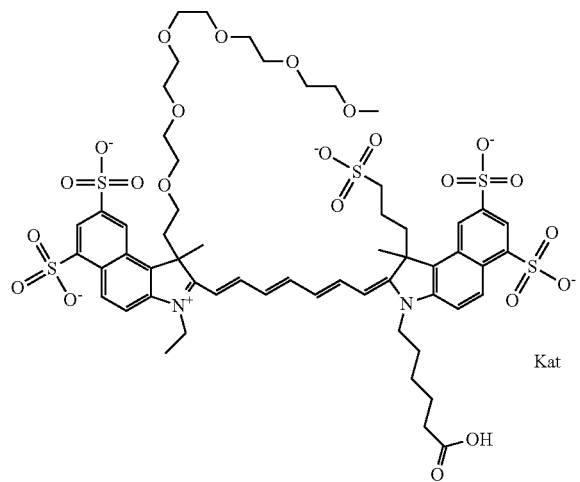

779 Compound 0/1 (2-((1E,3E,5E,7E)-7-(3-(5-carboxypentyl)-1-methyl-6,8-disulfonato-1-(3-sulfonatopropyl)-1H-benzo[e]indol-2(3H)-ylidene)hepta-1,3,5-trienyl)-3-ethyl-1-methyl-1-(2,5,8,11,14,17-hexaoxanonadecan-19-yl)-1H-benzo[e]indolium-6,8-disulfonate) contains a (poly) ethylene glycol (PEG$_6$) at R1, a sulfoalkyl at R2, an ethyl at R9, and carboxyalkyl at R10.

In one embodiment, the compound is 779 Compound 0/2

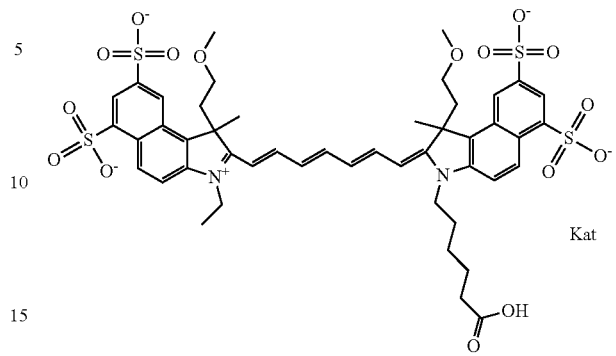

779 Compound 0/2 (2-((1E,3E,5E,7E)-7-(3-(5-carboxypentyl)-1-(2-methoxyethyl)-1-methyl-6,8-disulfonato-1H-benzo[e]indol-2(3H)-ylidene)hepta-1,3,5-trienyl)-3-ethyl-1-(2-methoxyethyl)-1-methyl-1H-benzo[e]indolium-6,8-disulfonate) contains an ethylene glycol at R1 and R2, an ethyl at R9, and carboxyalkyl at R10.

One non-limiting example of an activated compound is the NHS-ester of 779 Compound 0/2, shown below:

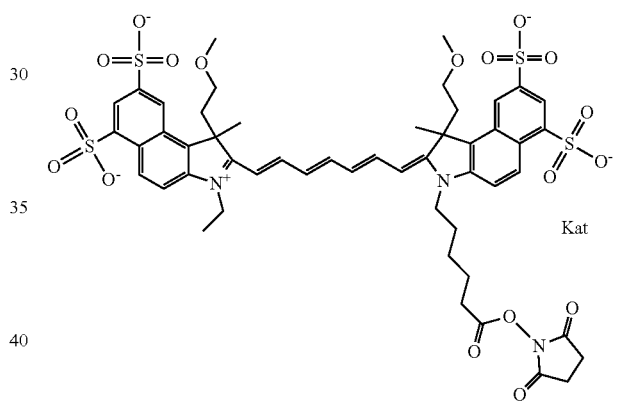

In one embodiment, the compound is 779 Compound 0/2

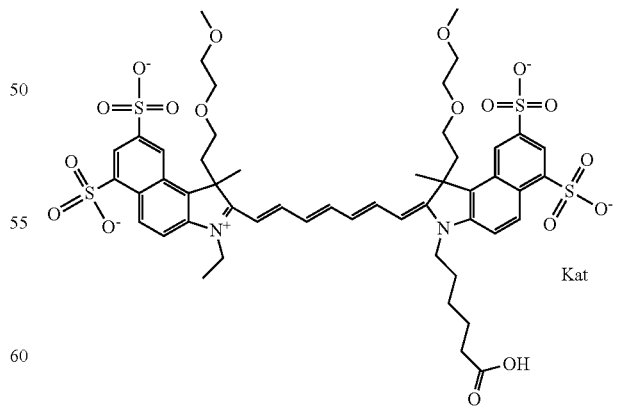

779 Compound 0/2 (2-((1E,3E,5E,7E)-7-(3-(5-carboxypentyl)-1-(2-(2-methoxyethoxy)ethyl)-1-methyl-6,8-disulfonato-1H-benzo[e]indol-2(3H)-ylidene)hepta-1,3,5-trienyl)-3-ethyl-1-(2-(2-methoxyethoxy)ethyl)-1-methyl-1H- benzo[e]indolium-6,8-disulfonate) contains a diethylene glycol at R1 and R2, an ethyl at R9, and carboxyalkyl at R10.

In one embodiment, the compound is 779 Compound 0/2

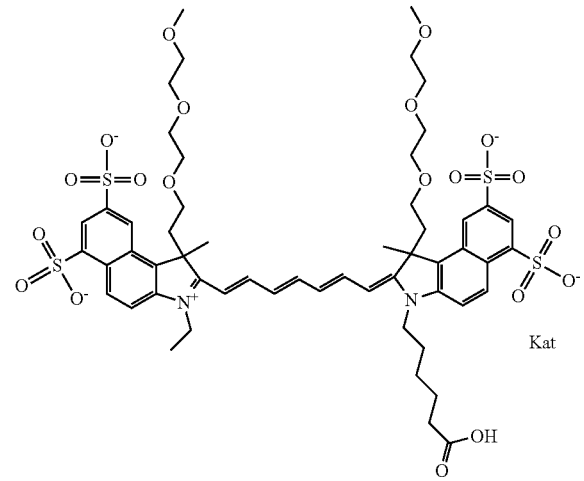 [SMILES: CC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOCCOCCOC)C(C)(CCOCCOCCOC)c2c1ccc1c(S(=O)(=O)[O-])cc(S(=O)(=O)[O-])cc21]

779 Compound 0/2 (2-((1E,3E,5E,7E)-7-(3-(5-carboxy-pentyl)-1-(2-(2-(2-methoxyethoxy)ethoxy)ethyl)-1-methyl-6,8-disulfonato-1H-benzo[e]indol-2(3H)-ylidene)hepta-1,3,5-trienyl)-3-ethyl-1-(2-(2-(2-methoxyethoxy)ethoxy)ethyl)-1-methyl-1H-benzo[e]indolium-6,8-disulfonate) contains a (poly)ethylene glycol (PEG$_3$) at R1 and R2, an ethyl at R9, and carboxyalkyl at R10.

In one embodiment, the compound is 779 Compound 0/2

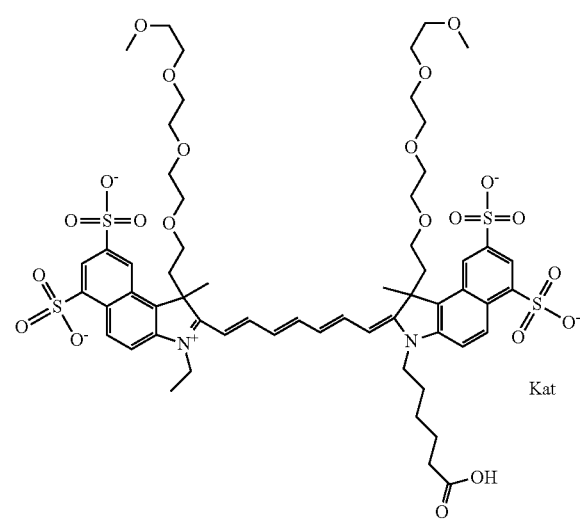 [SMILES: CC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOCCOCCOCCOC)C(C)(CCOCCOCCOCCOC)c2c1ccc1c(S(=O)(=O)[O-])cc(S(=O)(=O)[O-])cc21]

779 Compound 0/2 (2-((1E,3E,5E,7E)-7-(3-(5-carboxy-pentyl)-1-methyl-6,8-disulfonato-1-(2,5,8,11-tetraoxatridecan-13-yl)-1H-benzo[e]indol-2(3H)-ylidene)hepta-1,3,5-trienyl)-3-ethyl-1-methyl-1-(2,5,8,11-tetraoxatridecan-13-yl)-1H-benzo[e]indolium-6,8-disulfonate) contains a (poly)ethylene glycol (PEG$_4$) at R1 and R2, an ethyl at R9, and carboxyalkyl at R10.

In one embodiment, the compound is 779 Compound 0/2

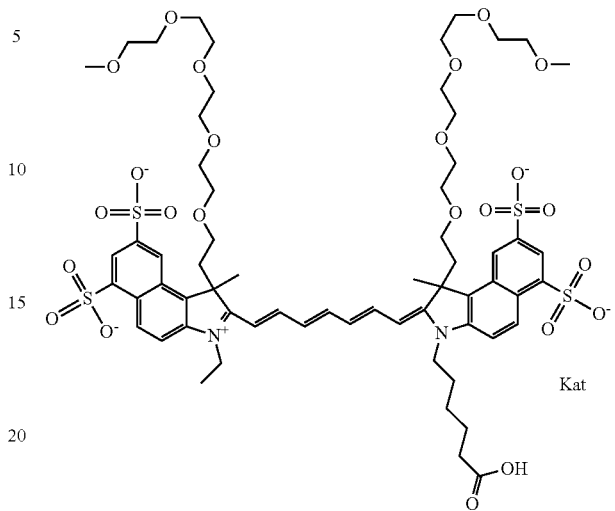

779 Compound 0/2 (2-((1E,3E,5E,7E)-7-(3-(5-carboxy-pentyl)-1-(2,5,8,11,14-pentaoxahexadecan-16-yl)-1-methyl-6,8-disulfonato-1H-benzo[e]indol-2(3H)-ylidene)hepta-1,3,5-trienyl)-3-ethyl-1-(2,5,8,11,14-pentaoxahexadecan-16-yl)-1-methyl-1H-benzo[e]indolium-6,8-disulfonate) contains a (poly)ethylene glycol (PEG$_5$) at R1 and R2, an ethyl at R9, and carboxyalkyl at R10.

In one embodiment, the compound is 779 Compound 0/2

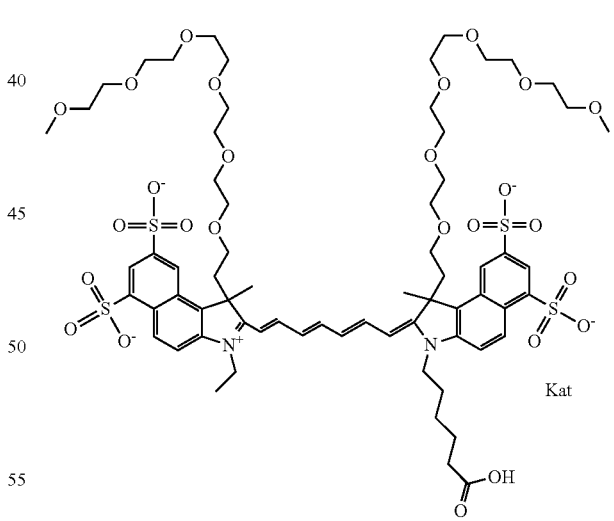

779 Compound 0/2 (2-((1E,3E,5E,7E)-7-(3-(5-carboxy-pentyl)-1-methyl-1-(2,5,8,11,14,17-hexaoxanonadecan-19-yl)-6,8-disulfonato-1H-benzo[e]indol-2(3H)-ylidene)hepta-1,3,5-trienyl)-3-ethyl-1-methyl-1-(2,5,8,11,14,17-hexaoxanonadecan-19-yl)-1H-benzo[e]indolium-6,8-disulfonate) contains a (poly)ethylene glycol (PEG$_6$) at R1 and R2, an ethyl at R9, and carboxyalkyl at R10.

In one embodiment, the compound is 779 Compound 0/1

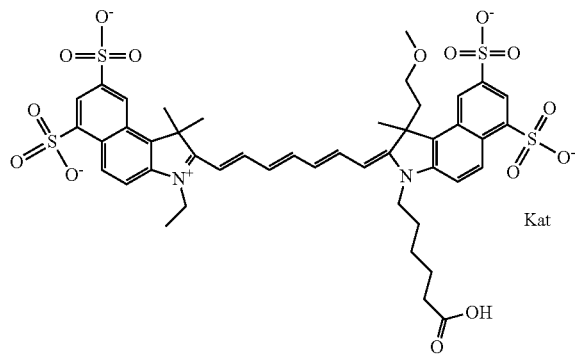 [SMILES: CC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOC)C(C)(C)c2c1ccc1c(S(=O)(=O)[O-])cc(S(=O)(=O)[O-])cc21]

779 Compound 0/1 (2-((1E,3E,5E,7E)-7-(3-(5-carboxypentyl)-1-(2-methoxyethyl)-1-methyl-6,8-disulfonato-1H-benzo[e]indol-2(3H)-ylidene)hepta-1,3,5-trienyl)-3-ethyl-1,1-dimethyl-1H-benzo[e]indolium-6,8-disulfonate) contains an ethylene glycol at R2, methyl at R1, an ethyl at R9, and carboxyalkyl at R10.

One non-limiting example of an activated compound is the NHS-ester of 779 Compound 0/1,

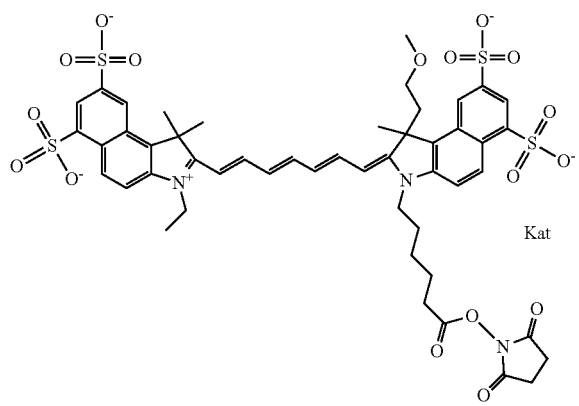 [SMILES: CC[N+]1=C(/C=C/C=C/C=C/C=C2/N(CCCCCC(=O)ON3C(=O)CCC3=O)c3ccc4c(S(=O)(=O)[O-])cc(S(=O)(=O)[O-])cc4c3C2(C)CCOC)C(C)(C)c2c1ccc1c(S(=O)(=O)[O-])cc(S(=O)(=O)[O-])cc21]

In one embodiment, the compound is 779 Compound 0/1

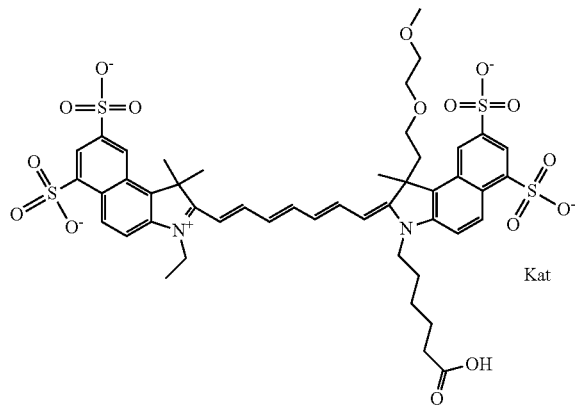 [SMILES: CC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOCCOC)C(C)(C)c2c1ccc1c(S(=O)(=O)[O-])cc(S(=O)(=O)[O-])cc21]

779 Compound 0/1 (2-((1E,3E,5E,7E)-7-(3-(5-carboxypentyl)-1-(2-(2-methoxyethoxy)ethyl)-1-methyl-6,8-disulfonato-1H-benzo[e]indol-2(3H)-ylidene)hepta-1,3,5-trienyl)-3-ethyl-1,1-dimethyl-1H-benzo[e]indolium-6,8-disulfonate) contains a diethylene glycol at R2, methyl at R1, an ethyl at R9, and carboxyalkyl at R10.

In one embodiment, the compound is 779 Compound 0/1

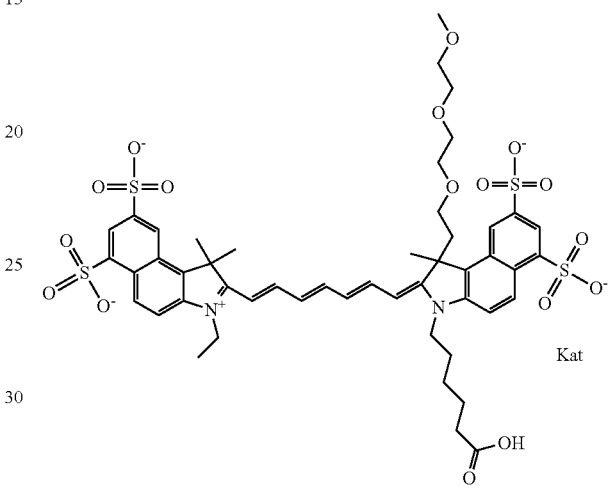

779 Compound 0/1 (2-((1E,3E,5E,7E)-7-(3-(5-carboxypentyl)-1-(2-(2-(2-methoxyethoxy)ethoxy)ethyl)-1-methyl-6,8-disulfonato-1H-benzo[e]indol-2(3H)-ylidene)hepta-1,3,5-trienyl)-3-ethyl-1,1-dimethyl-1H-benzo[e]indolium-6,8-disulfonate) contains a (poly)ethylene glycol (PEG$_3$) at R2, methyl at R1, an ethyl at R9, and carbon/alkyl at R10.

In one embodiment, the compound is 779 Compound 0/1

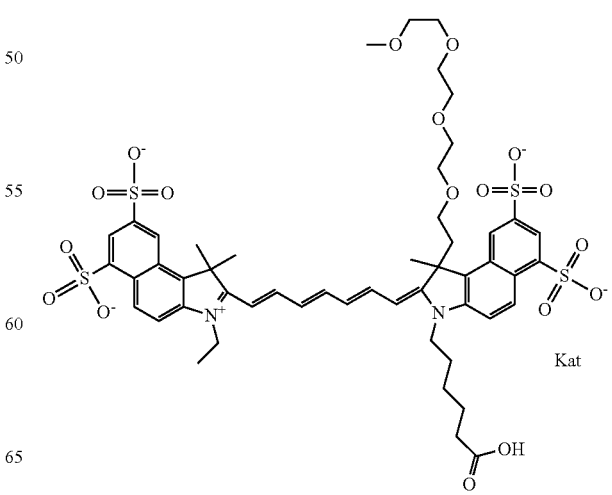

779 Compound 0/1 (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene)hepta-1,3,5-trienyl)-3-ethyl-1,1-dimethyl-1H-benzo[e]indolium-6,8-disulfonate) contains a (poly)ethylene glycol (PEG$_4$) at R2, methyl at R1, an ethyl at R9, and carboxyalkyl at R10.

In one embodiment, the compound is 779 Compound 0/1

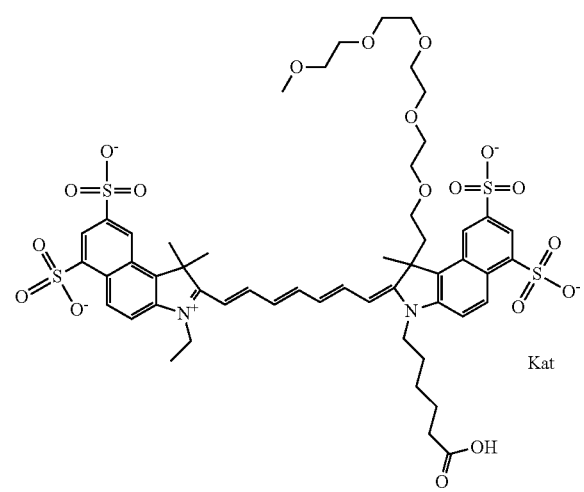 [SMILES: CC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOCCOCCOCCOCCOC)C(C)(C)c2c1ccc1c(S(=O)(=O)[O-])cc(S(=O)(=O)[O-])cc21]

779 Compound 0/1 (2-((1E,3E,5E,7E)-7-(3-(5-carboxypentyl)-1-(2,5,8,11,14-pentaoxahexadecan-16-yl)-1-methyl-6,8-disulfonato-1H-benzo[e]indol-2(3H)-ylidene)hepta-1,3,5-trienyl)-3-ethyl-1,1-dimethyl-1H-benzo[e]indolium-6,8-disulfonate) contains a (poly)ethylene glycol (PEG$_5$) at R2, methyl at R1, an ethyl at R9, and carboxyalkyl at R10.

In one embodiment, the compound is 779 Compound 0/1

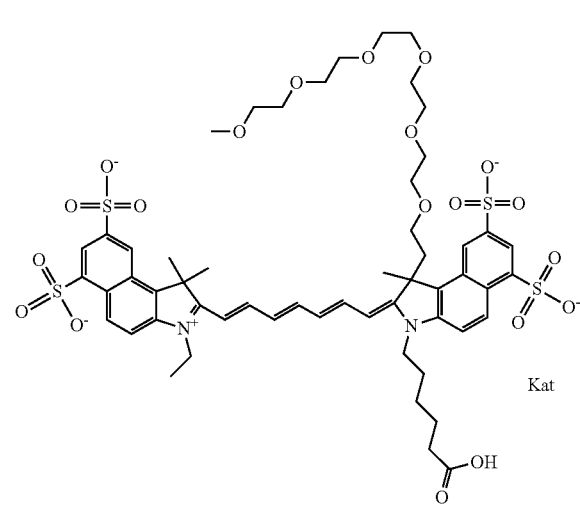 [SMILES: CC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOCCOCCOCCOCCOCCOC)C(C)(C)c2c1ccc1c(S(=O)(=O)[O-])cc(S(=O)(=O)[O-])cc21]

779 Compound 0/1 (2-((1E,3E,5E,7E)-7-(3-(5-carboxypentyl)-1-methyl-1-(2,5,8,11,14,17-hexaoxanonadecan-19-yl)-6,8-disulfonato-1H-benzo[e]indol-2(3H)-ylidene)hepta-1,3,5-trienyl)-3-ethyl-1,1-dimethyl-1H-benzo[e]indolium-6,8-disulfonate) contains a (poly)ethylene glycol (PEG$_6$) at R2, methyl at R1, an ethyl at R9, and carboxyalkyl at R10.

In one embodiment, the compound is 779 Compound 0/1

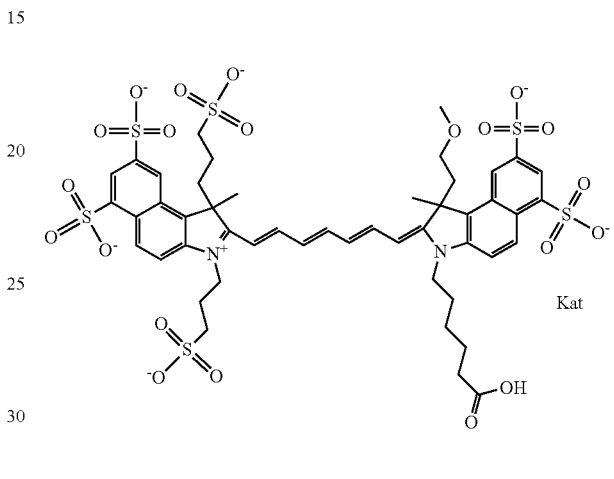

779 Compound 0/1 (2-((1E,3E,5E,7E)-7-(3-(5-carboxypentyl)-1-(2-methoxyethyl)-1-methyl-6,8-disulfonato-1H-benzo[e]indol-2(3H)-ylidene)hepta-1,3,5-trienyl)-1-methyl-1,3-bis(3-sulfonatopropyl)-1H-benzo[e]indolium-6,8-disulfonate) contains an ethylene glycol at R2, a sulfoalkyl at R1, a sulfoalkyl at R9, and carboxyalkyl at R10.

One non-limiting example of an activated compound is the NHS-ester of 779 Compound 0/1, shown below:

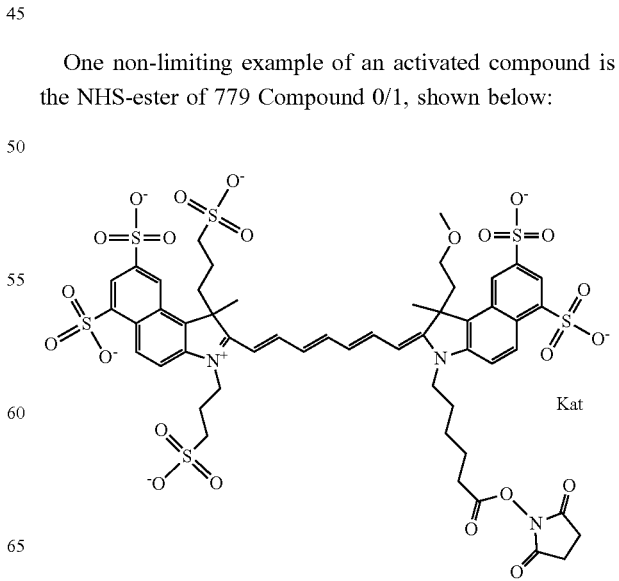

In one embodiment, the compound is 779 Compound 0/1

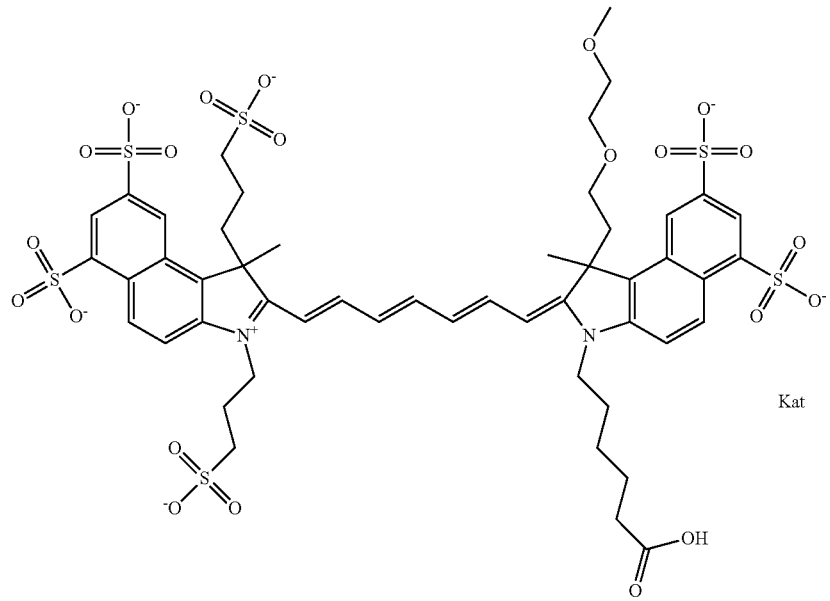

779 Compound 0/1 (2-((1E,3E,5E,7E)-7-(3-(5-carboxy-pentyl)-1-(2-(2-methoxyethoxy)ethyl)-1-methyl-6,8-disulfonato-1H-benzo[e]indol-2(3H)-ylidene)hepta-1,3,5-trienyl)-1-methyl-1,3-bis(3-sulfonatopropyl)-1H-benzo[e]indolium-6,8-disulfonate) contains a diethylene glycol at R2, a sulfoalkyl at R1, a sulfoalkyl at R9, and carboxyalkyl at R10.

In one embodiment, the compound is 779 Compound 0/1

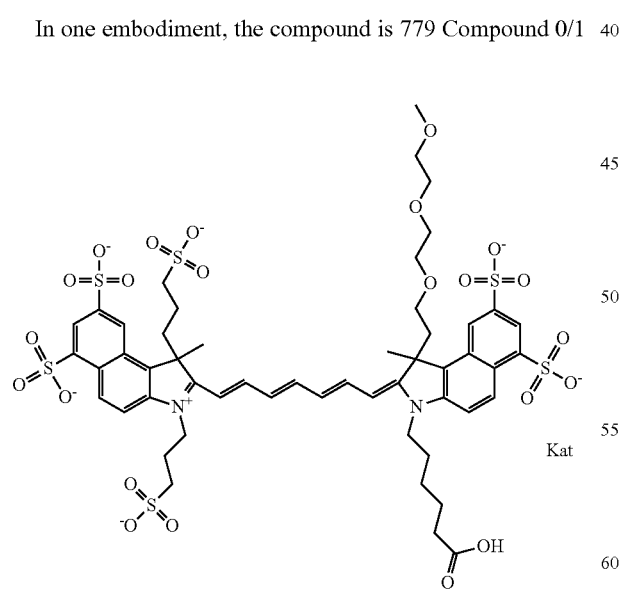

779 Compound 0/1 (2-((1E,3E,5E,7E)-7-(3-(5-carboxy-pentyl)-1-(2-(2-(2-methoxyethoxy)ethoxy)ethyl)-1-methyl-6,8-disulfonato-1H-benzo[e]indol-2(3H)-ylidene)hepta-1,3,5-trienyl)-1-methyl-1,3-bis(3-sulfonatopropyl)-1H-benzo[e]indolium-6,8-disulfonate) contains a (poly)ethylene glycol (PEG$_3$) at R2, a sulfoalkyl at R1, a sulfoalkyl at R9, and carboxyalkyl at R10.

In one embodiment, the compound is 779 Compound 0/1

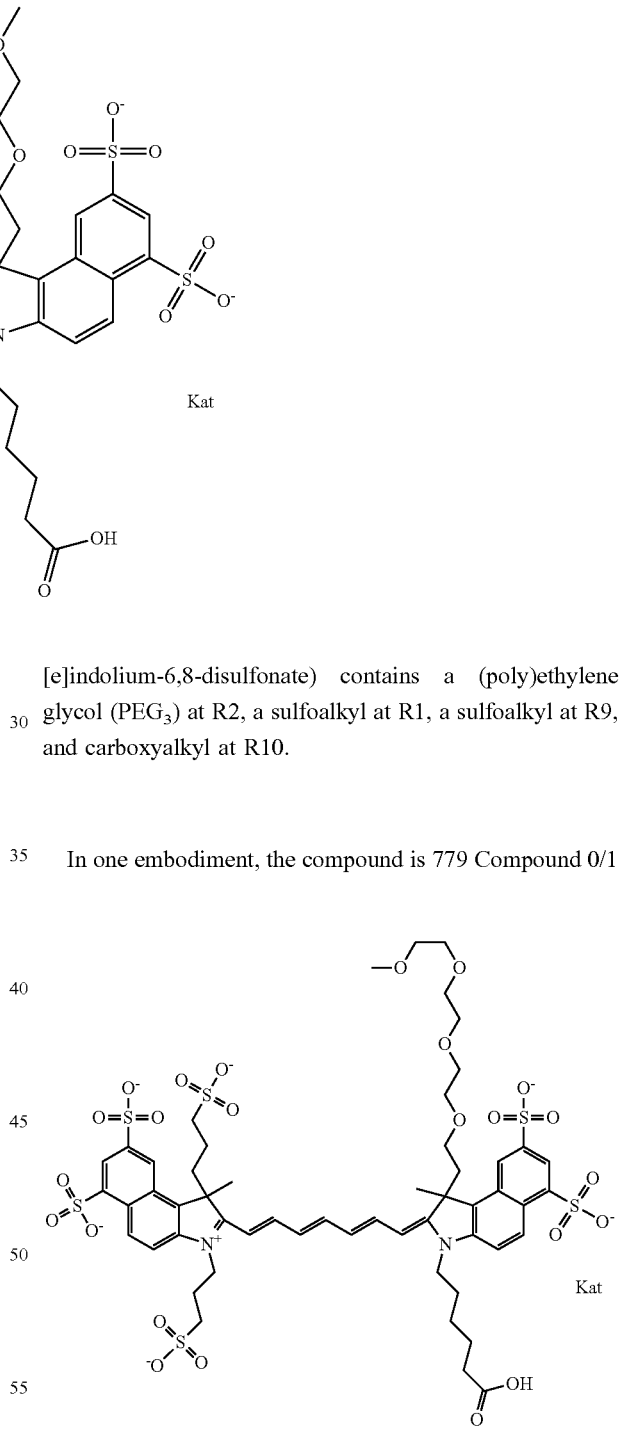

779 Compound 0/1 (2-((1E,3E,5E,7E)-7-(3-(5-carboxy-pentyl)-1-methyl-6,8-disulfonato-1-(2,5,8,11-tetraoxatridecan-13-yl)-1H-benzo[e]indol-2(3H)-ylidene)hepta-1,3,5-trienyl)-1-methyl-1,3-bis(3-sulfonatopropyl)-1H-benzo[e]indolium-6,8-disulfonate) contains a (poly)ethylene glycol (PEG$_4$) at R2, a sulfoalkyl at R1, a sulfoalkyl at R9, and carboxyalkyl at R10.

In one embodiment, the compound is 779 Compound 0/1

In one embodiment, the compound is 779 Compound 0/1

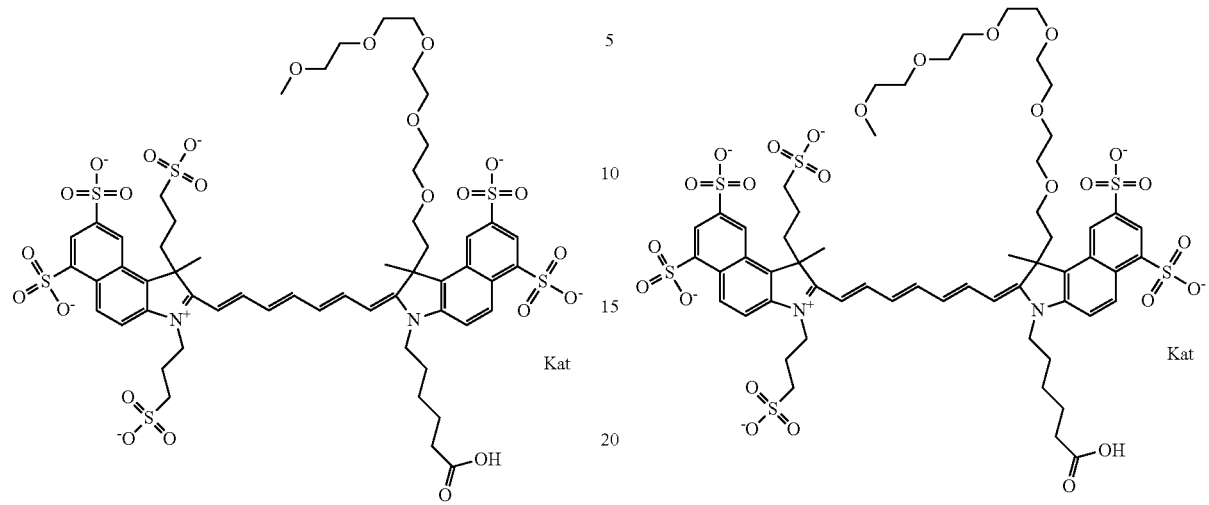

779 Compound 0/1 (2-((1E,3E,5E,7E)-7-(3-(5-carboxypentyl)-1-(2,5,8,11,14-pentaoxahexadecan-16-yl)-1-methyl-6,8-disulfonato-1H-benzo[e]indol-2(3H)-ylidene)hepta-1,3,5-trienyl)-1-methyl-1,3-bis(3-sulfonatopropyl)-1H-benzo[e]indolium-6,8-disulfonate) contains a (poly) ethylene glycol (PEG$_5$) at R2, a sulfoalkyl at R1, an ethyl at R9, and carboxyalkyl at R10.

779 Compound 0/1 (2-((1E,3E,5E,7E)-7-(3-(5-carboxypentyl)-1-methyl-1-(2,5,8,11,14,17-hexaoxanonadecan-19-yl)-6,8-disulfonato-1H-benzo[e]indol-2(3H)-ylidene)hepta-1,3,5-trienyl)-1-methyl-1,3-bis(3-sulfonatopropyl)-1H-benzo[e]indolium-6,8-disulfonate) contains a (poly) ethylene glycol (PEG$_6$) at R2, a sulfoalkyl at R1, an ethyl at R9, and carboxyalkyl at R10.

In one embodiment, the compound is 779 Compound 0/2

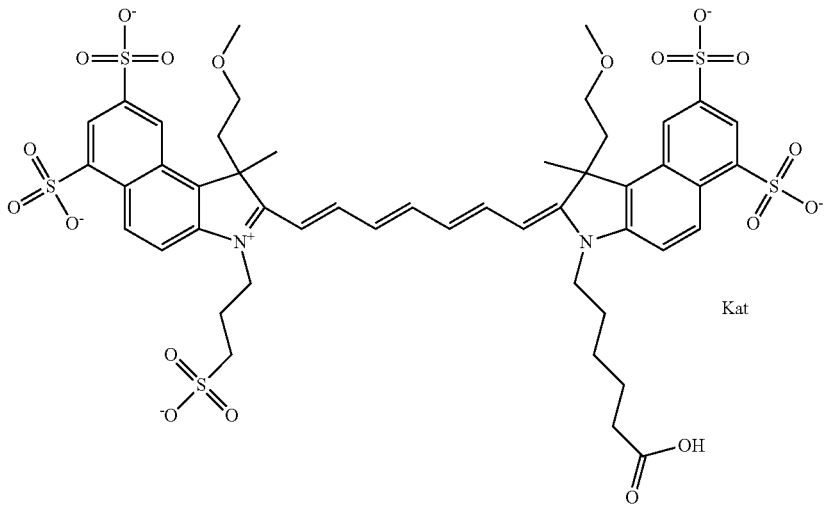

779 Compound 0/2 (2-((1E,3E,5E,7E)-7-(3-(5-carboxypentyl)-1-(2-methoxyethyl)-1-methyl-6,8-disulfonato-1H-benzo[e]indol-2(3H)-ylidene)hepta-1,3,5-trienyl)-1-(2-methoxyethyl)-1-methyl-3-(3-sulfonatopropyl)-1H-benzo[e]indolium-6,8-disulfonate) contains an ethylene glycol at R1 and R2, a sulfoalkyl at R9, and carboxyalkyl at R10.

One non-limiting example of an activated compound is the NHS-ester of 779 Compound 0/2, shown below:

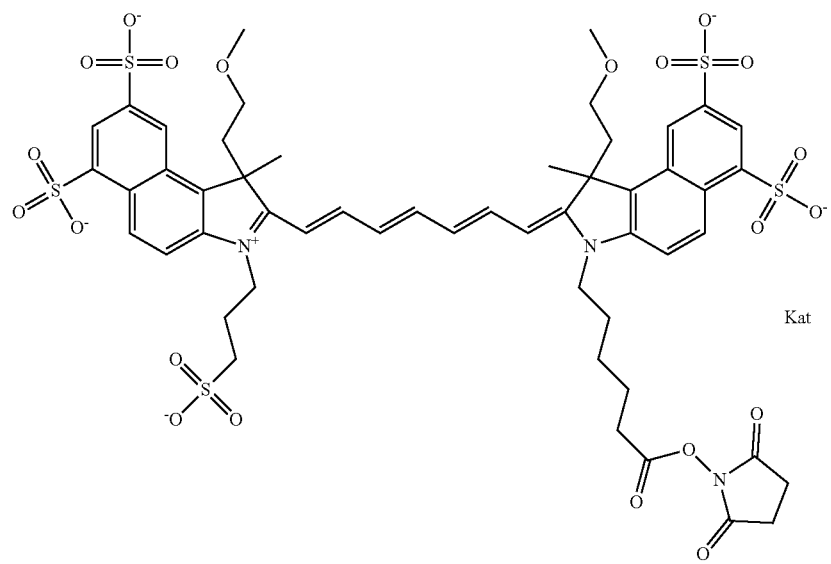
In one embodiment, the compound is 779 Compound 0/2
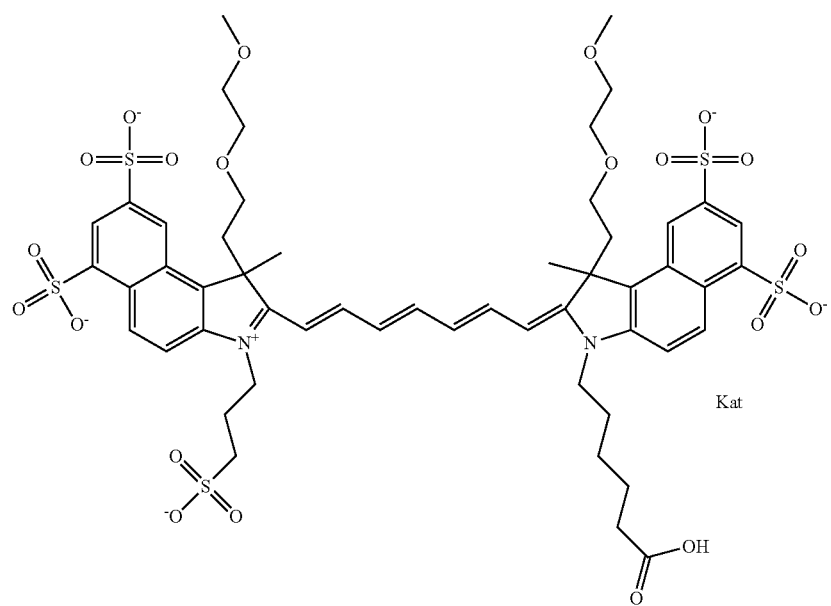
779 Compound 0/2 (2-((1E,3E,5E,7E)-7-(3-(5-carboxypentyl)-1-(2-(2-methoxyethoxy)ethyl)-1-methyl-6,8-disulfonato-1H-benzo[e]indol-2(3H)-ylidene)hepta-1,3,5-trienyl)-1-(2-(2-methoxyethoxy)ethyl)-1-methyl-3-(3-sulfonatopropyl)-1H-benzo[e]indolium-6,8-disulfonate) contains a diethylene glycol at R1 and R2, a sulfoalkyl at R9, and carbon/alkyl at R10.

In one embodiment, the compound is 779 Compound 0/2

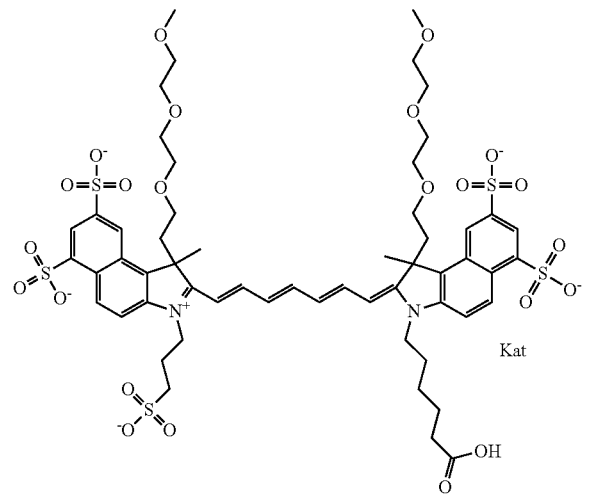

779 Compound 0/2 (2-((1E,3E,5E,7E)-7-(3-(5-carboxy-pentyl)-1-(2-(2-(2-methoxyethoxy)ethoxy)ethyl)-1-methyl-6,8-disulfonato-1H-benzo[e]indol-2(3H)-ylidene)hepta-1,3,5-trienyl)-1-(2-(2-(2-methoxyethoxy)ethoxy)ethyl)-1-methyl-3-(3-sulfonatopropyl)-1H-benzo[e]indolium-6,8-disulfonate) contains a (poly)ethylene glycol (PEG$_3$) at R1 and R2, a sulfoalkyl at R9, and carboxyalkyl at R10.

In one embodiment, the compound is 779 Compound 0/2

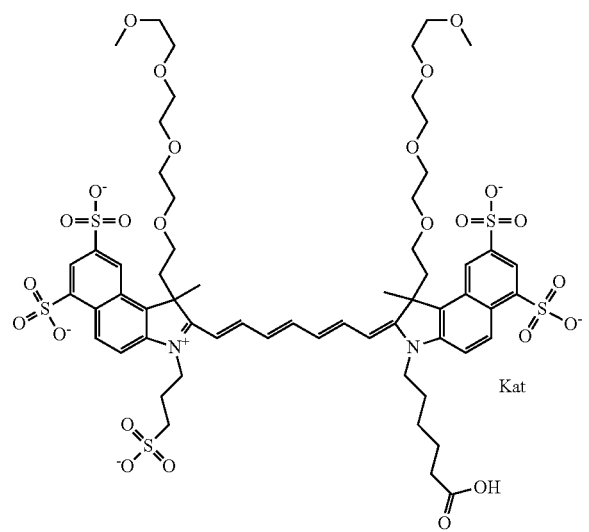

779 Compound 0/2 (2-((1E,3E,5E,7E)-7-(3-(5-carboxy-pentyl)-1-methyl-6,8-disulfonato-1-(2,5,8,11-tetraoxatridecan-13-yl)-1H-benzo[e]indol-2(3H)-ylidene)hepta-1,3,5-trienyl)-1-methyl-3-(3-sulfonatopropyl)-1-(2,5,8,11-tetraoxatridecan-13-yl)-1H-benzo[e]indolium-6,8-disulfonate) contains a (poly)ethylene glycol (PEG$_4$) at R1 and R2, a sulfoalkyl at R9, and carboxyalkyl at R10.

In one embodiment, the compound is 779 Compound 0/2

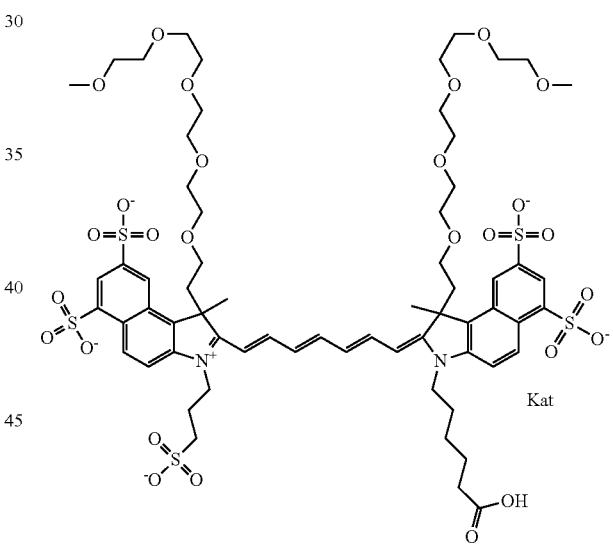

779 Compound 0/2 (2-((1E,3E,5E,7E)-7-(3-(5-carboxy-pentyl)-1-(2,5,8,11,14-pentaoxahexadecan-16-yl)-1-methyl-6,8-disulfonato-1H-benzo[e]indol-2(3H)-ylidene)hepta-1,3,5-trienyl)-1-(2,5,8,11,14-pentaoxahexadecan-16-yl)-1-methyl-3-(3-sulfonatopropyl)-1H-benzo[e]indolium-6,8-disulfonate) contains a (poly)ethylene glycol (PEG$_5$) at R1 and R2, an ethyl at R9, and carboxyalkyl at R10.

In one embodiment, the compound is 779 Compound 0/2

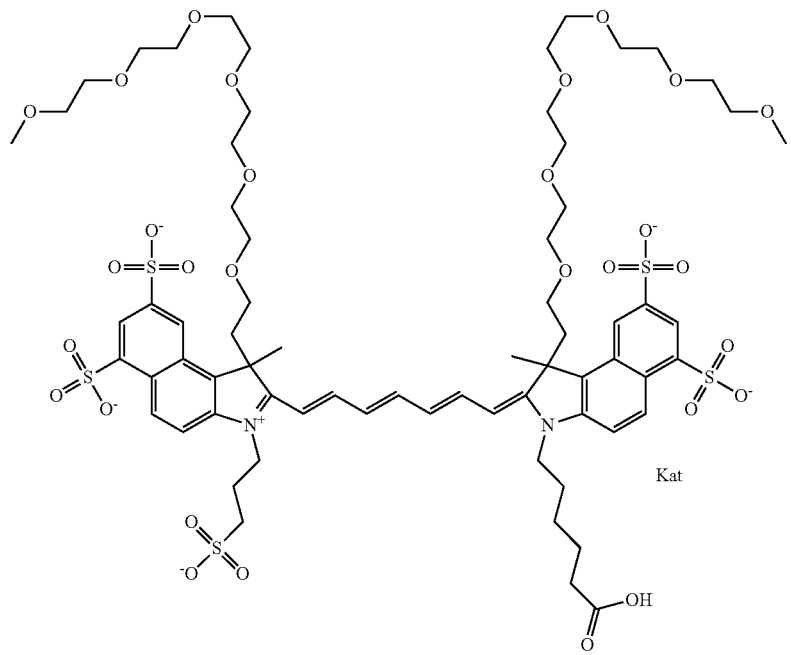

779 Compound 0/2 (2-((1E,3E,5E,7E)-7-(3-(5-carboxypentyl)-1-methyl-1-(2,5,8,11,14,17-hexaoxanonadecan-19-yl)-6,8-disulfonato-1H-benzo[e]indol-2(3H)-ylidene)hepta-1,3,5-trienyl)-1-methyl-1-(2,5,8,11,14,17-hexaoxanonadecan-19-yl)-3-(3-sulfonatopropyl)-1H-benzo[e]indolium-6,8-disulfonate) contains a (poly)ethylene glycol (PEG$_6$) at R1 and R2, an ethyl at R9, and carboxyalkyl at R10.

In embodiments, the degree and/or location of sulfonation is varied to, e.g., vary the compound's degree of hydroplilicity or hydrophobicity. One non-limiting example is a monosulfonate form of 779 Compound 1, shown below:

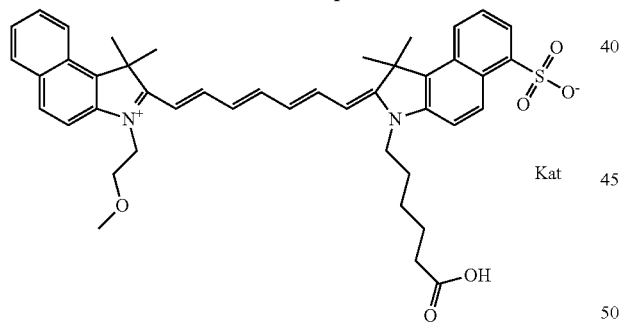

One non-limiting example is a disulfonate form of 779 Compound 1, shown below:

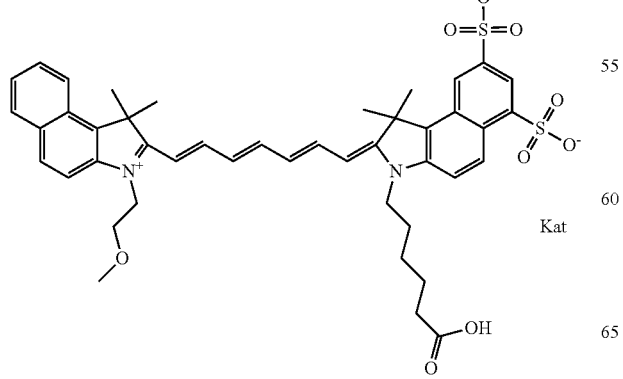

One non-limiting example is a trisulfonate form of 779 Compound 1, shown below:

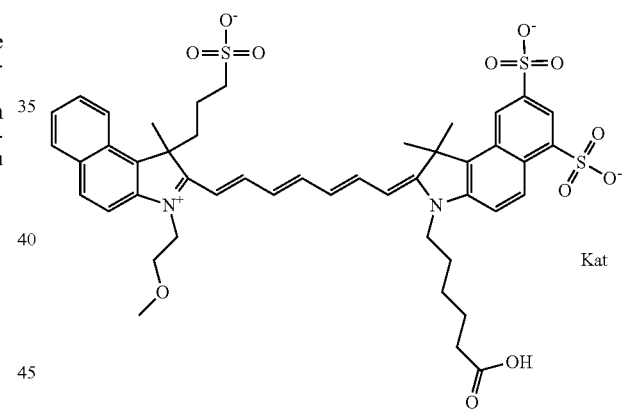

One non-limiting example is a tetrasulfonate form of 779 Compound 1, shown below:

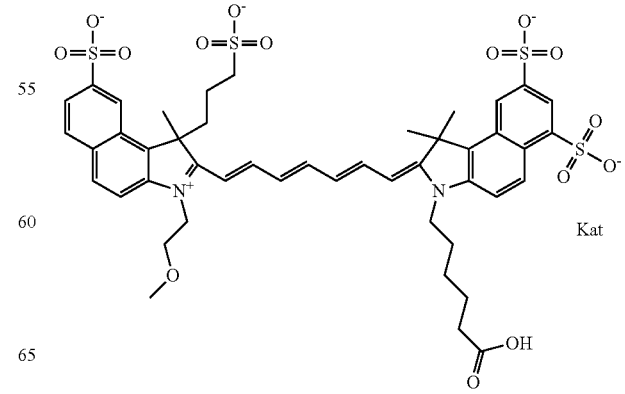

One non-limiting example is a pentasulfonate form of 779 Compound 1, shown below:

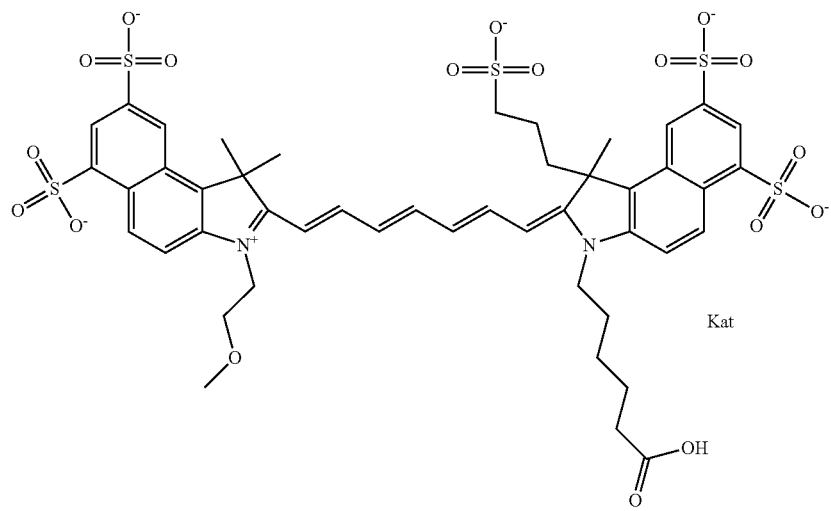 [SMILES: COCC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCCS(=O)(=O)[O-])C(C)(C)c2c1ccc1c(S(=O)(=O)[O-])cc(S(=O)(=O)[O-])cc21]

One non-limiting example is a monosulfonate form of 779 Compound 0/1, shown below:

One non-limiting example is a disulfonate form of 779 Compound 0/1, shown below:

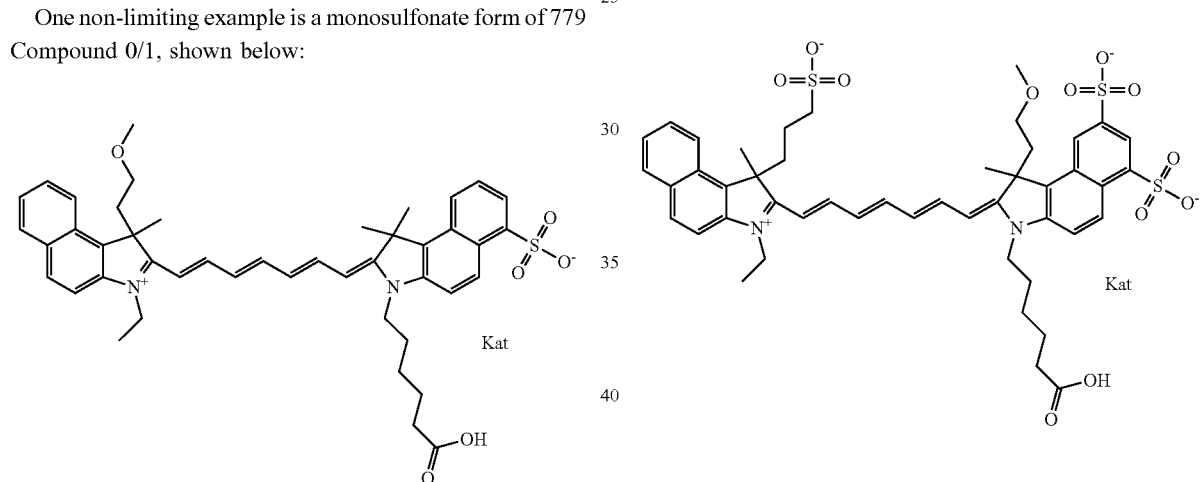

One non-limiting example is a tetrasulfonate form of 779 Compound 0/1, shown below:

One non-limiting example is a trisulfonate form of 779 Compound 0/1, shown below:

One non-limiting example is a pentasulfonate form of 779 Compound 0/1, shown below:

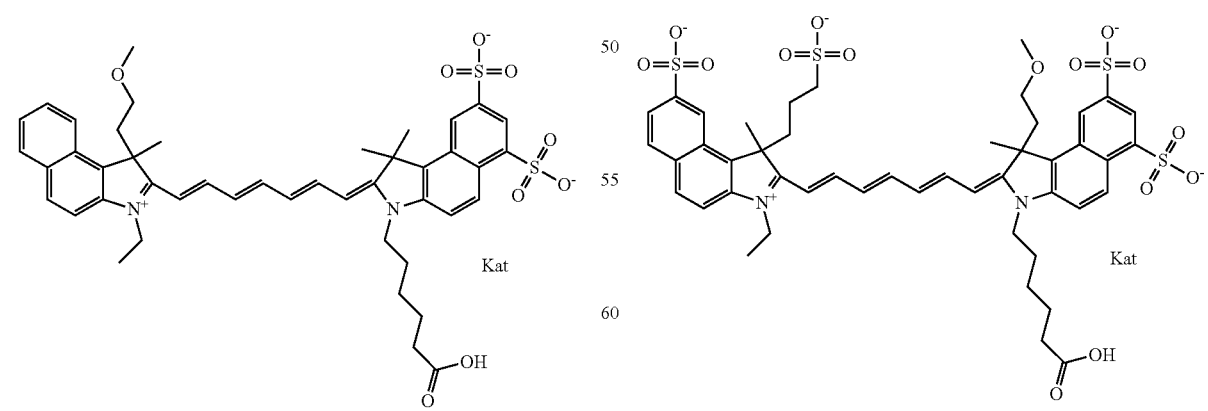

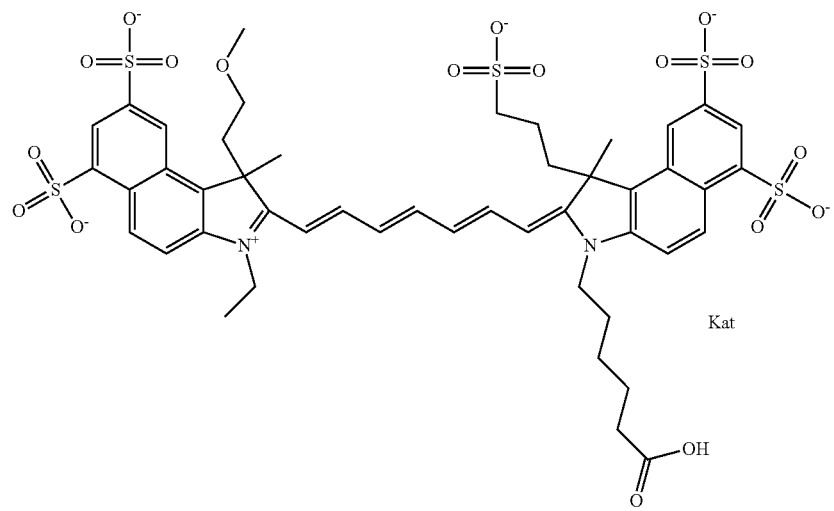 [SMILES: CC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCCS(=O)(=O)[O-])C(C)(CCOC)c2c1ccc1c(S(=O)(=O)[O-])cc(S(=O)(=O)[O-])cc21]

In one embodiment, the compound is 779 Compound 1/2 (PEG$_4$)

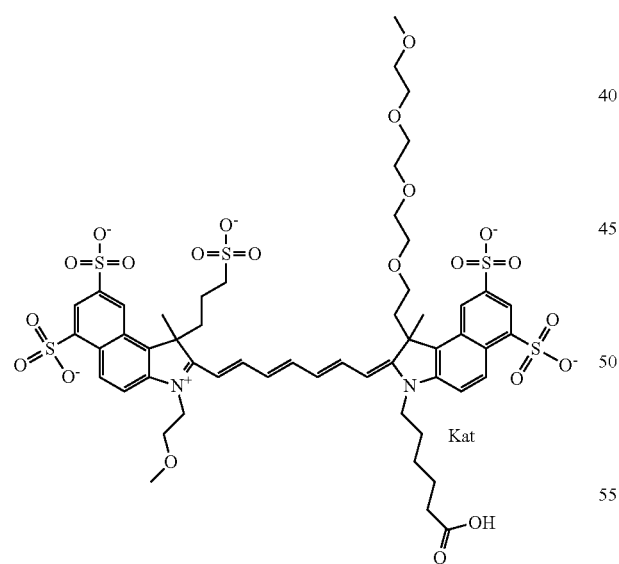

779 Compound 1/2 (PEG$_4$) (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene)hepta-1,3,5-trienyl)-3-(2-methoxyethyl)-1-methyl-1-(3-sulfonatopropyl)-1H-benzo[e]indolium-6,8-disulfonate) contains an ethylene glycol on the indole N of the left heterocycle, i.e., a methylated ethylene glycol and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 779 Compound 1/2, but one skilled in the art appreciates that activation is not limited to these examples. One non-limiting example of an activated compound is the NHS-ester of 779 Compound 1/2 (PEG$_4$), shown below:

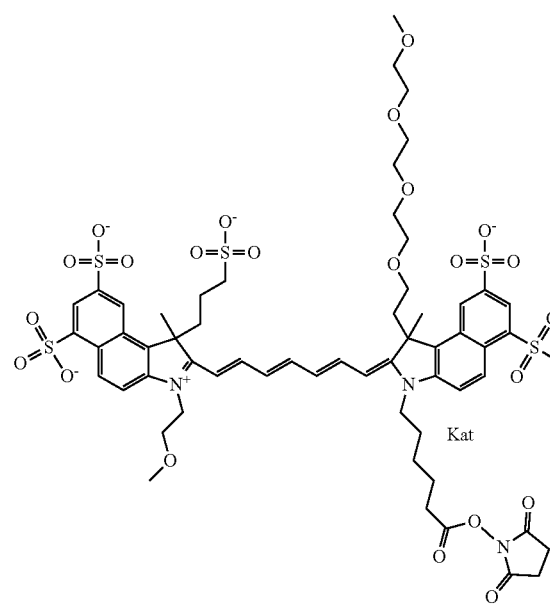
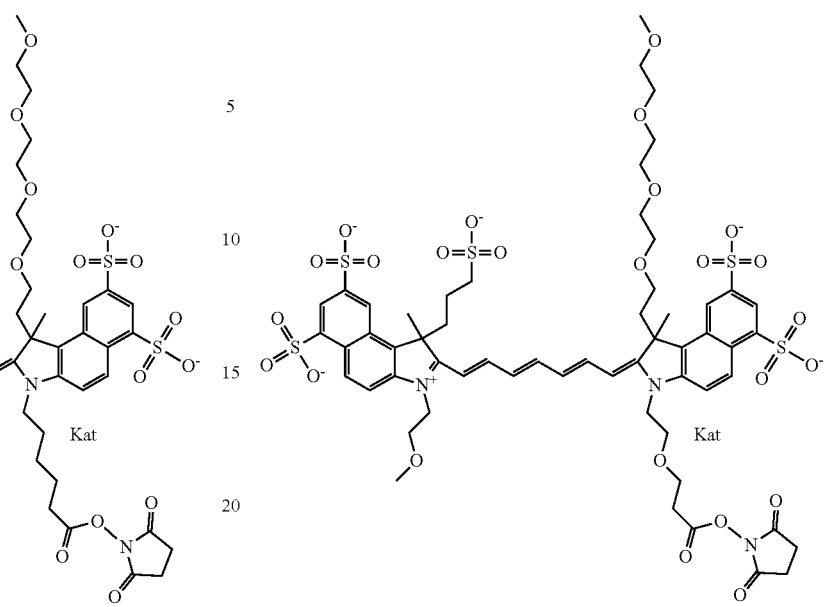
One non-limiting example of a NHS-ester of 779 Compound 1/3 (PEG$_4$), according to general formula III, where m=1 and p=1, is shown below:
One non-limiting example of a NHS-ester of 779 Compound 1/3 (PEG$_4$), according to general formula III, where m=1 and p=2, is shown below:
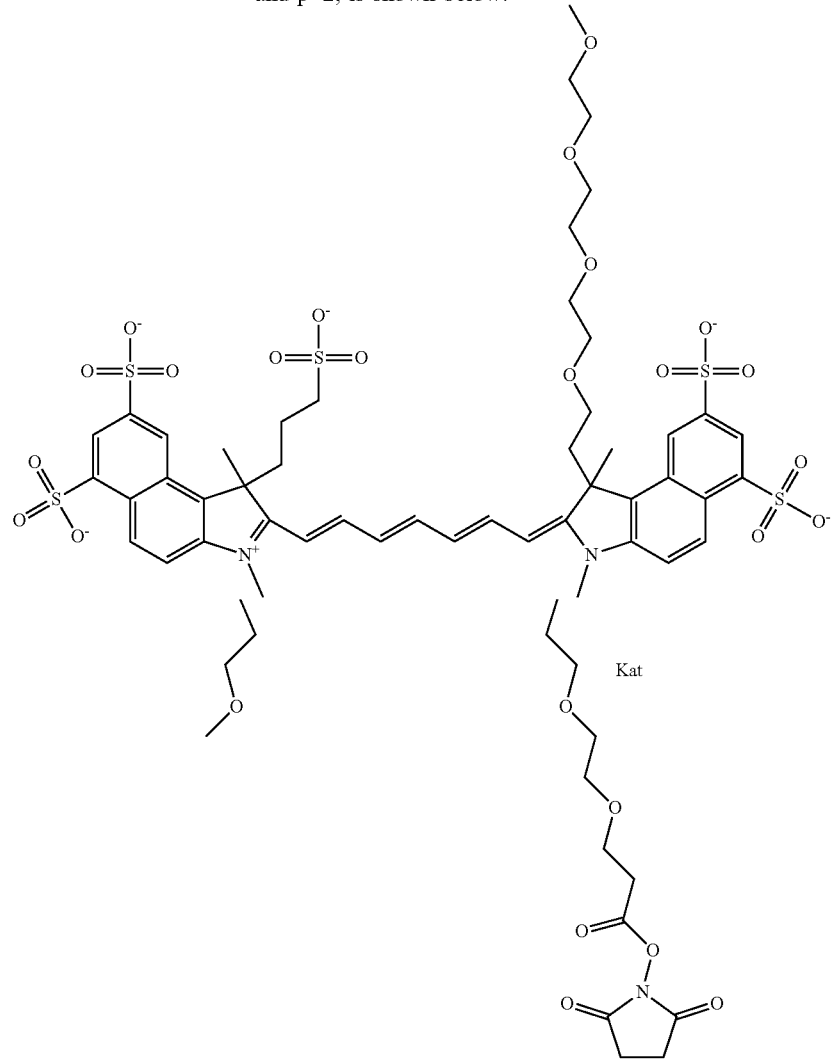

One non-limiting example of a NHS-ester of 779 Compound 1/3 (PEG$_4$), according to general formula III, where m=1 and p=3, is shown below:
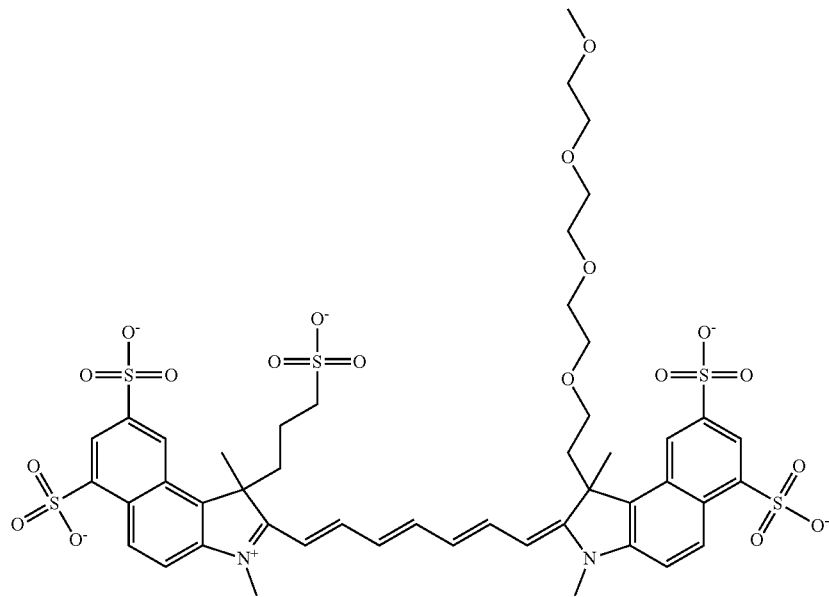
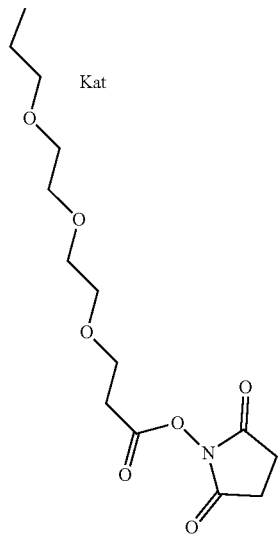

One non-limiting example of a NHS-ester of 779 Compound 1/3 (PEG$_4$), according to general formula III, where m=1 and p=4, is shown below:
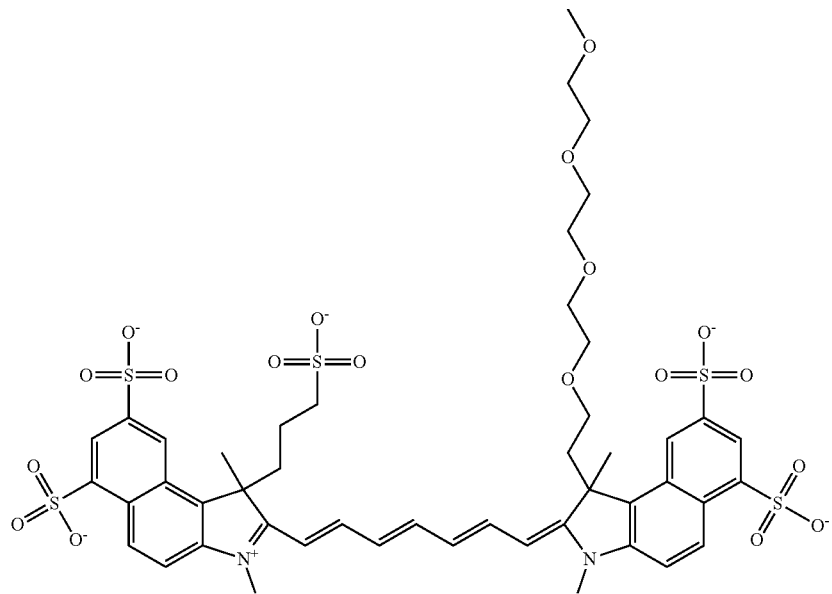
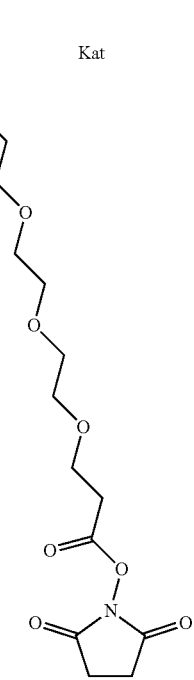

One non-limiting example of a NHS-ester of 779 Compound 1/3 (PEG$_4$), according to general formula III, where m=1 and p=5, is shown below:
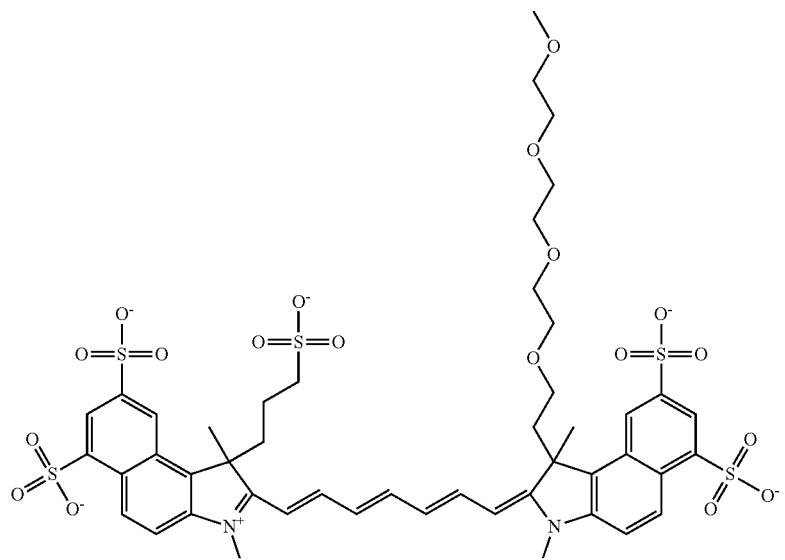
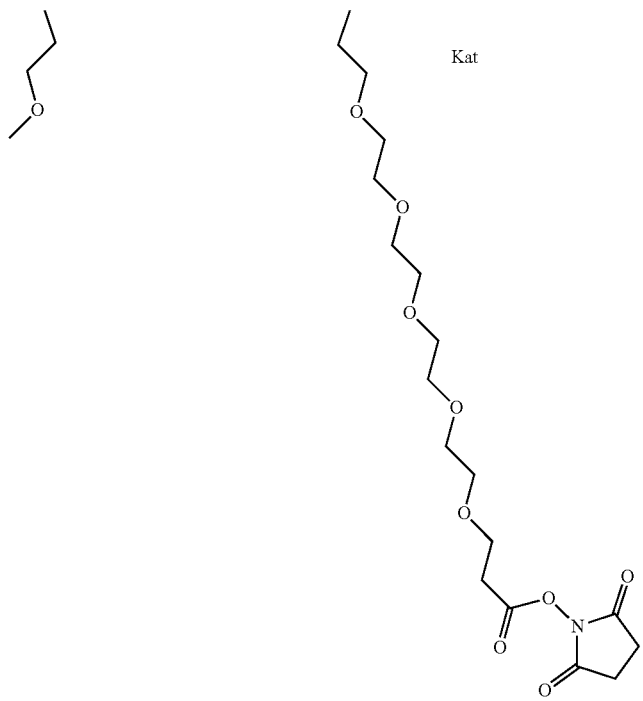

One non-limiting example of a NHS-ester of 779 Compound 1/3 (PEG$_4$), according to general formula III, where m=1 and p=6, is shown below:
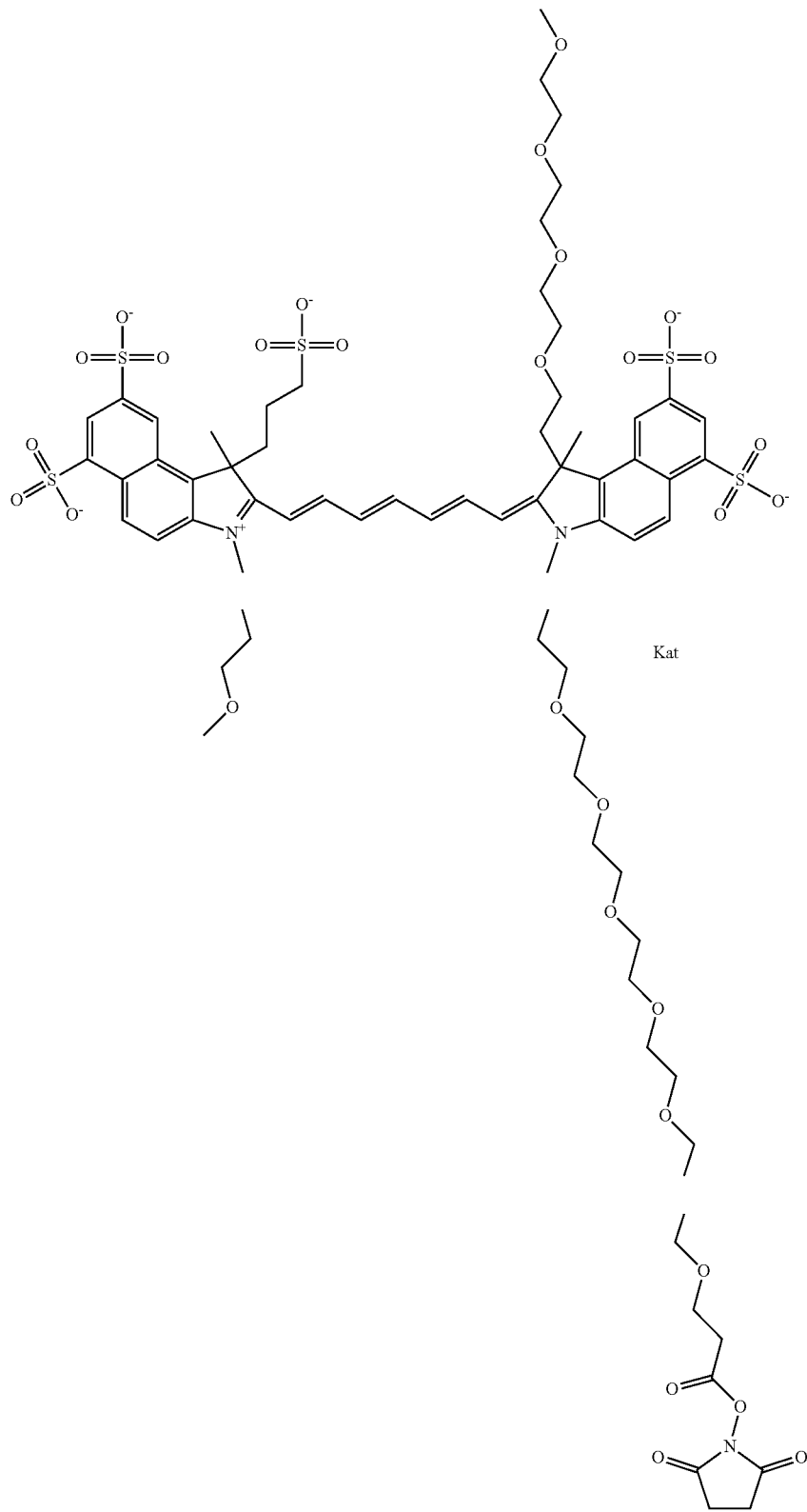

One non-limiting example of an activated 779 Compound 1/2 (PEG$_4$) is a tetrafluorophenyl (TFP)-ester form of 779 Compound 1, shown below:
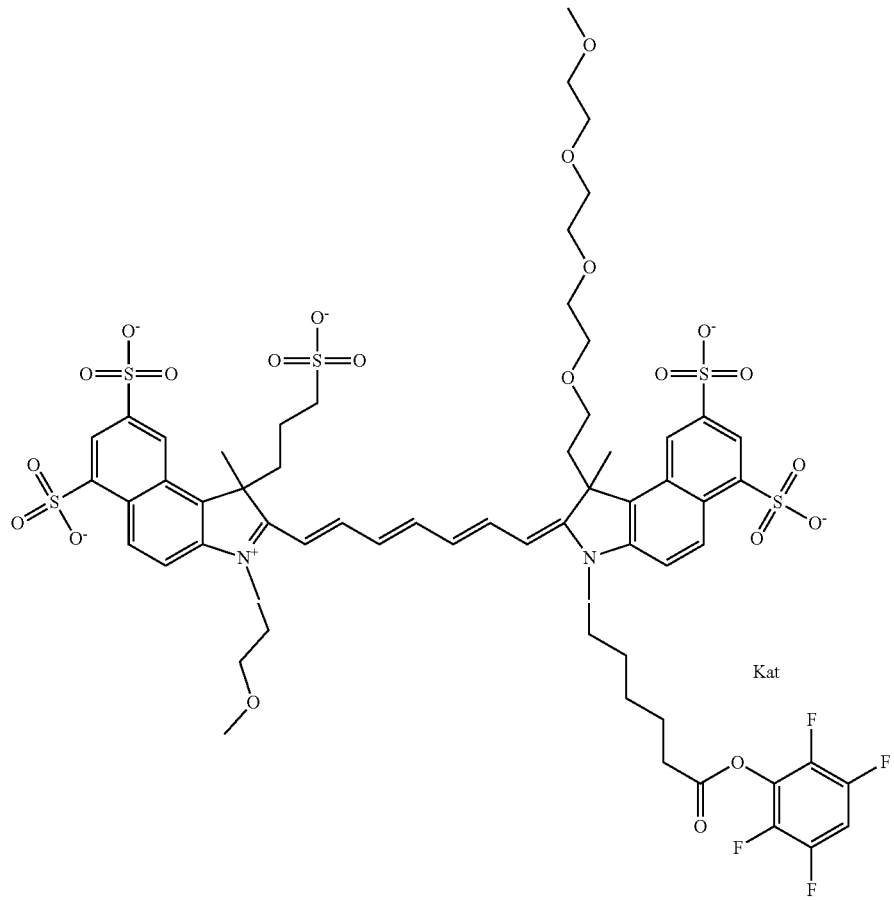 [SMILES: COCCOCCOCCOCCC1(C)\C(=C/C=C/C=C/C=C/C2=[N+](CCOC)c3ccc4c(S(=O)(=O)[O-])cc(S(=O)(=O)[O-])cc4c3C2(C)CCCS(=O)(=O)[O-])N(CCCCCC(=O)Oc2c(F)c(F)cc(F)c2F)c2ccc3c(S(=O)(=O)[O-])cc(S(=O)(=O)[O-])cc3c21]
One non-limiting example of an activated 779 Compound 1/2 (PEG$_4$) is a sulfotetrafluorophenyl (STP)-ester form of 779 Compound 1/2, shown below:
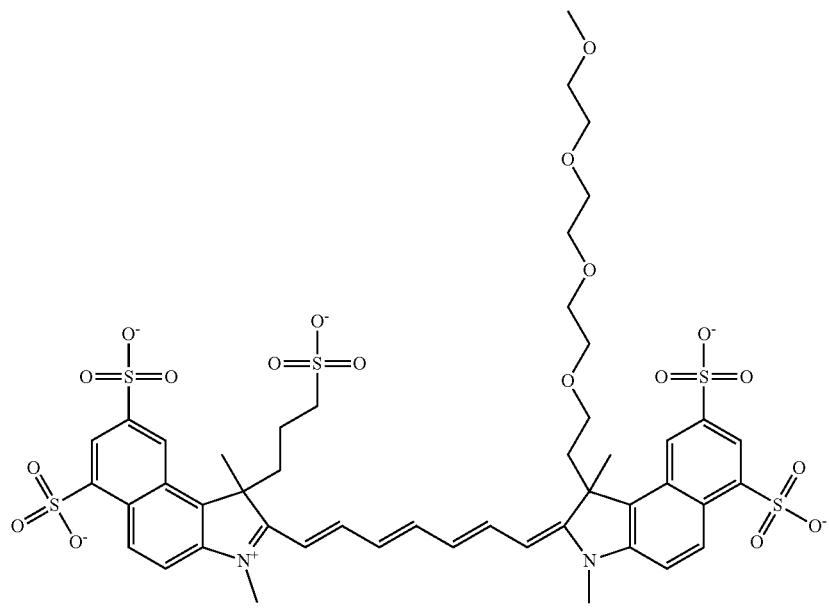

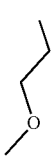
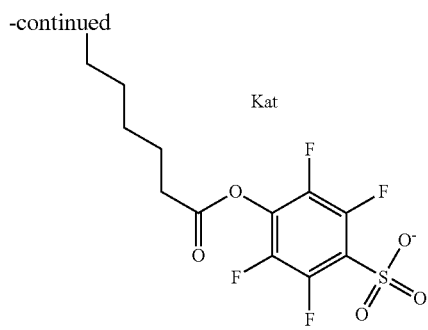
One non-limiting example of an activated 779 Compound 1/2 (PEG$_4$) is a hydrazide form of 779 Compound 1/2, shown below:
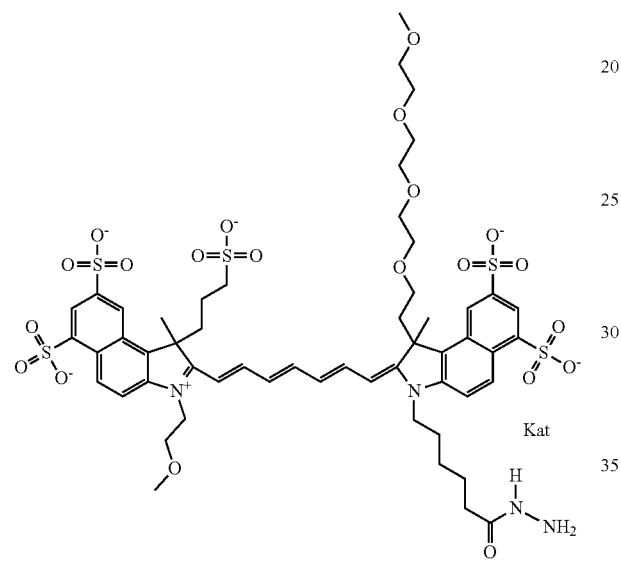
One non-limiting example of an activated 779 Compound 1/2 (PEG$_4$) is a maleimide form of 779 Compound 1/2, shown below:
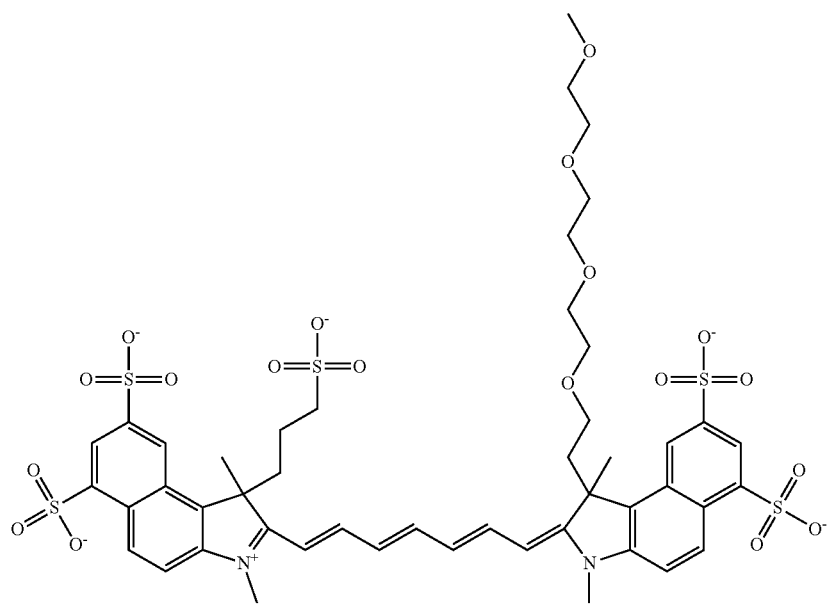

-continued

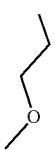

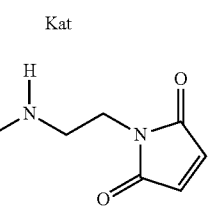

In one embodiment, the compound is 779 Compound 2/2 (PEG$_4$)

In one embodiment, the compound is 779 Compound 3/2 (PEG$_4$)

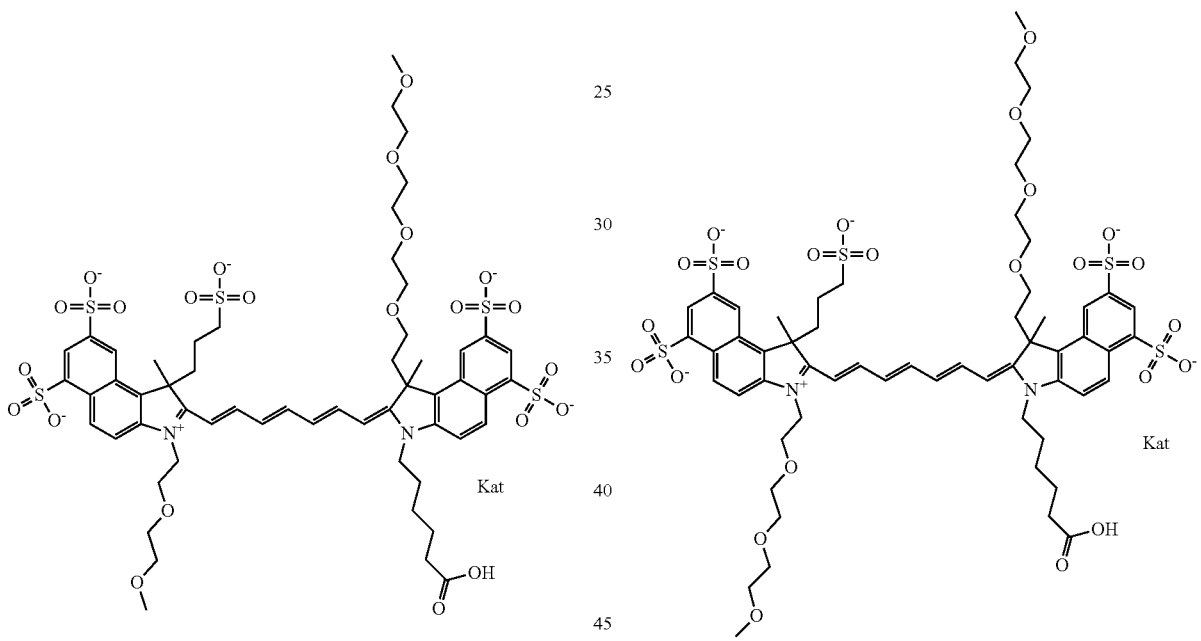

779 Compound 2/2 (PEG$_4$) (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene)hepta-1,3,5-trienyl)-3-(2-(2-methoxyethoxy)ethyl)-1-methyl-1-(3-sulfonatopropyl)-1H-benzo[e]indolium-6,8-disulfonate) contains a diethylene glycol on the indole N of the left heterocycle and a PEG$_4$ group on the indole C. The methyl group on the (poly)ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 779 Compound 2/2 (PEG$_4$) is activated as described above.

779 Compound 3/2 (PEG$_4$) (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene)hepta-1,3,5-trienyl)-3-(2-(2-(2-methoxyethoxy)ethoxy)ethyl)-1-methyl-1-(3-sulfonatopropyl)-1H-benzo[e]indolium-6,8-disulfonate) contains a (poly)ethylene glycol on the indole N of the left heterocycle and a PEG$_4$ group on the indole C. The methyl group on the (poly)ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 779 Compound 3/2 (PEG$_4$) is activated as described above.

In one embodiment, the compound is 779 Compound 4/2 (PEG$_4$)

In one embodiment, the compound is 779 Compound 5/2 (PEG$_4$)

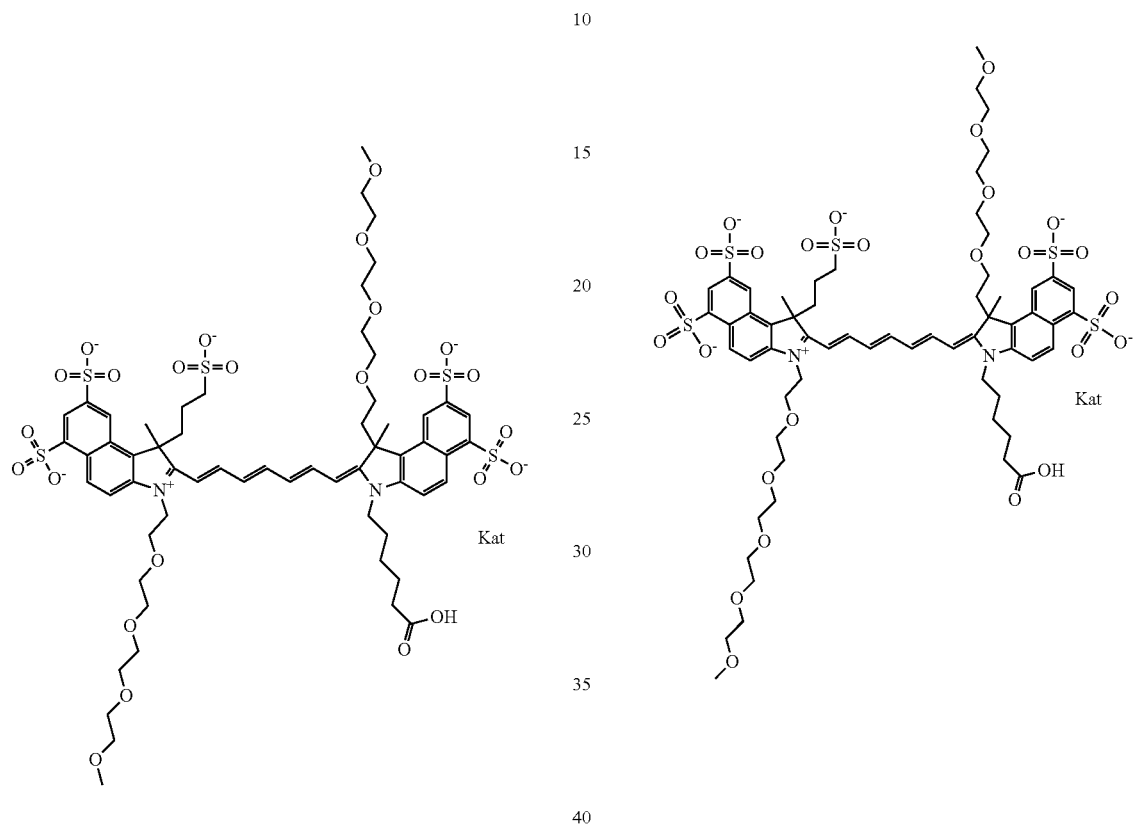

779 Compound 4/2 (PEG$_4$) (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene)hepta-1,3,5-trienyl)-1-methyl-1-(3-sulfonatopropyl)-3-(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the (poly)ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 779 Compound 4/2 (PEG$_4$) is activated as described above.

779 Compound 5/2 (PEG$_4$) (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene)hepta-1,3,5-trienyl)-3-(2,5,8,11,14-pentaoxahexadecan-16-yl)-1-methyl-1-(3-sulfonatopropyl)-1H-benzo[e]indolium-6,8-disulfonate) contains a (poly)ethylene glycol on the indole N of the left heterocycle and a PEG$_4$ group on the indole C. The methyl group on the (poly)ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 779 Compound 5/2 (PEG$_4$) is activated as described above.

In one embodiment, the compound is 779 Compound 6/2 (PEG$_4$)

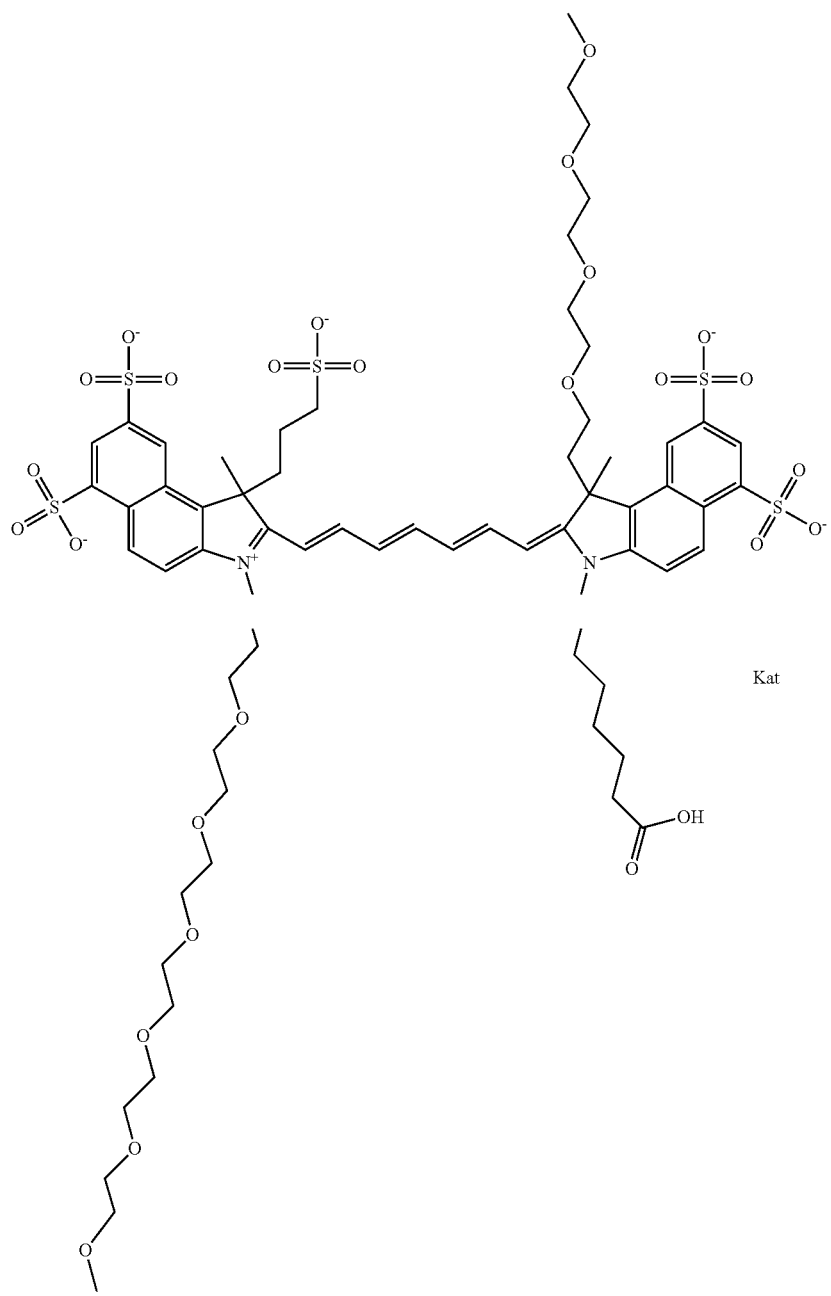

779 Compound 6/2 (PEG₄) (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene)hepta-1,3,5-trienyl)-1-methyl-3-(2,5,8,11,14,17-hexaoxanonadecan-19-yl)-1-(3-sulfonatopropyl)-1H-benzo[e]indolium-6,8-disulfonate) contains a (poly)ethylene glycol on the indole N of the left heterocycle. The methyl group on the (poly)ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 779 Compound 6/2 (PEG₄) is activated as described above.

In embodiments, the degree and/or location of sulfonation is varied to, e.g., vary the compound's degree of hydroplilicity or hydrophobicity. One non-limiting example is a monosulfonate form of 779 Compound 1/2 (PEG₄), shown below:

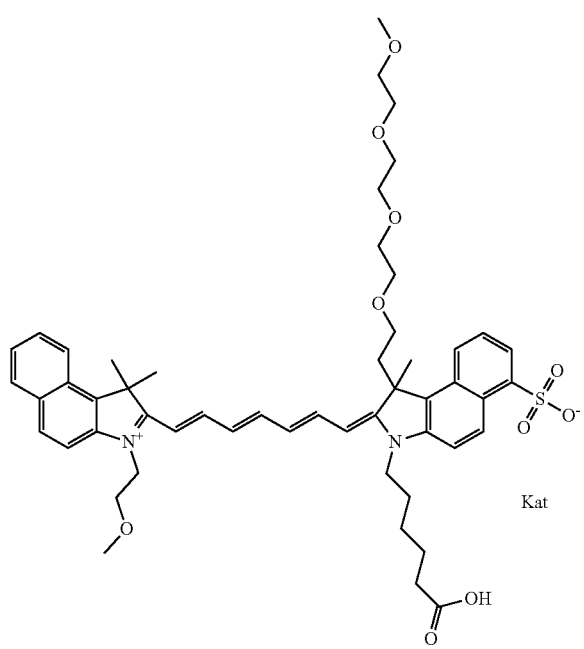 [SMILES: COCCOCCOCCOCCC1(C)\C(=C/C=C/C=C/C=C/C2=[N+](CCOC)c3ccc4ccccc4c3C2(C)C)N(CCCCCC(=O)O)c2ccc3c(S(=O)(=O)[O-])cccc3c21]
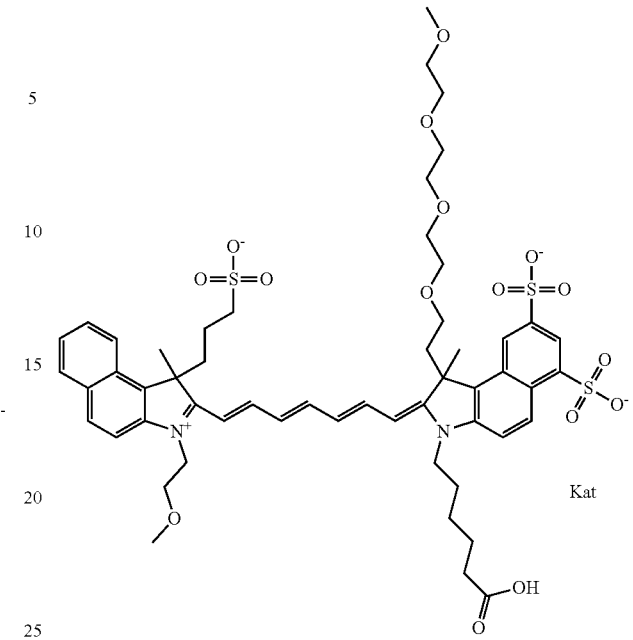
One non-limiting example is a disulfonate form of 779 Compound 1/2 (PEG$_4$), shown below:
One non-limiting example is a tetrasulfonate form of 779 Compound 1/2 (PEG$_4$), shown below:
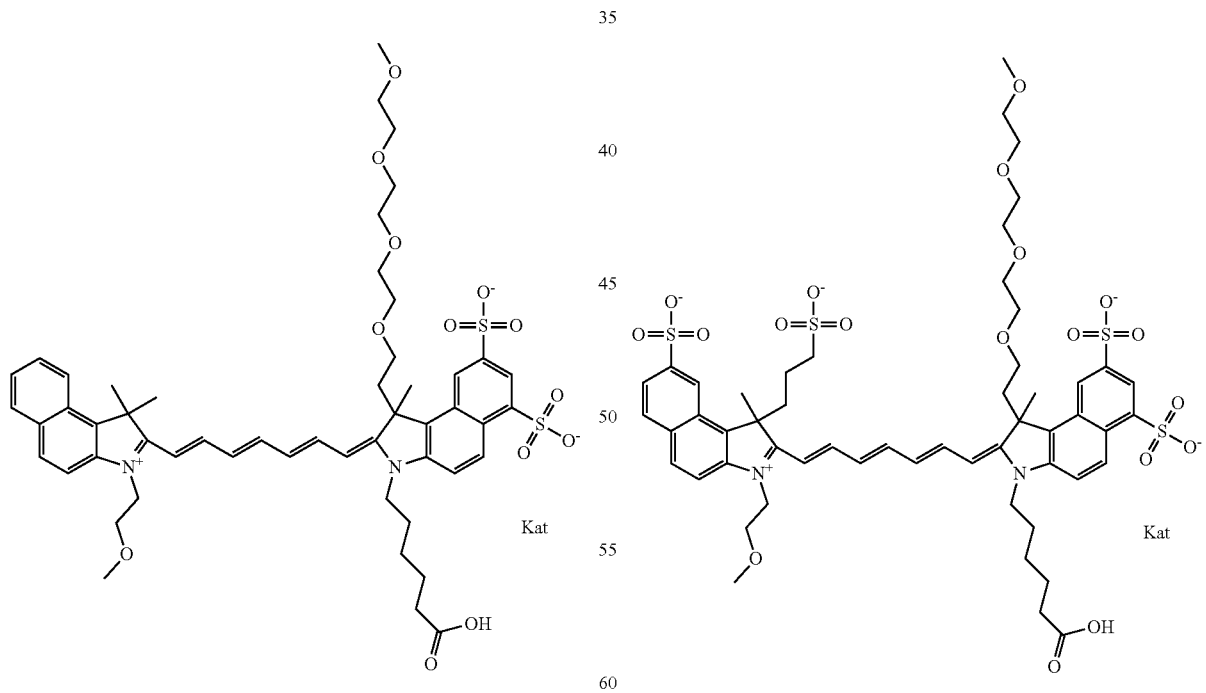
One non-limiting example is a trisulfonate form of 779 Compound 1/2 (PEG$_4$), shown below:
One non-limiting example is a pentasulfonate form of 779 Compound 1/2 (PEG$_4$), shown below:

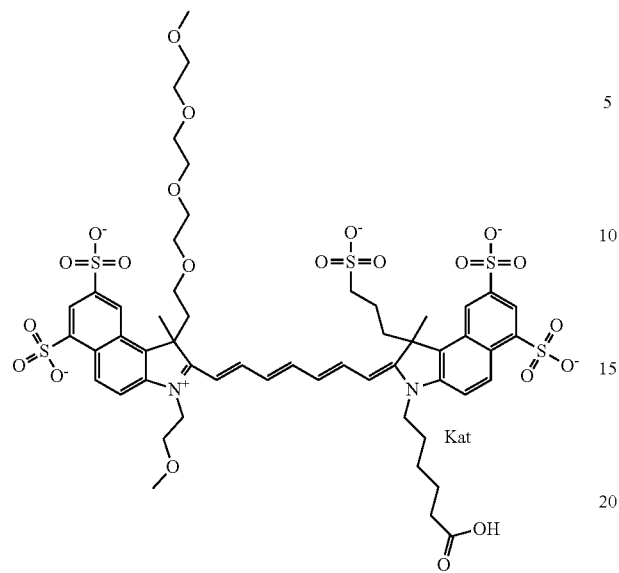
In embodiments, the compound contains one or more substitutions of the polymethine linker. In one embodiment, the compound has general formula VIa
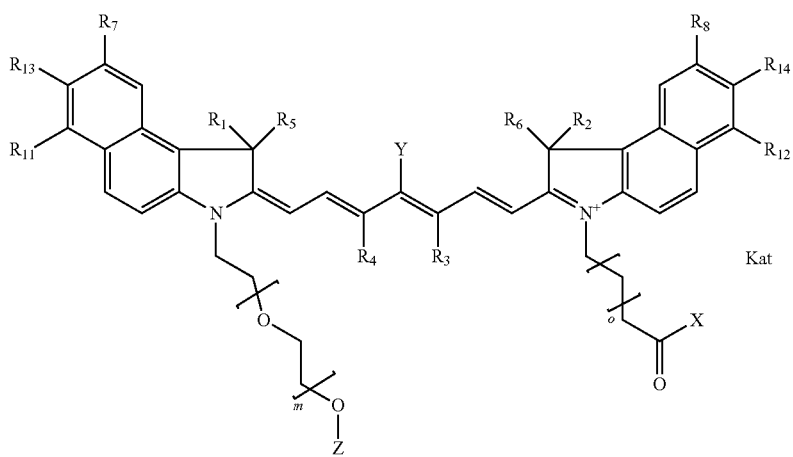
general formula VIb
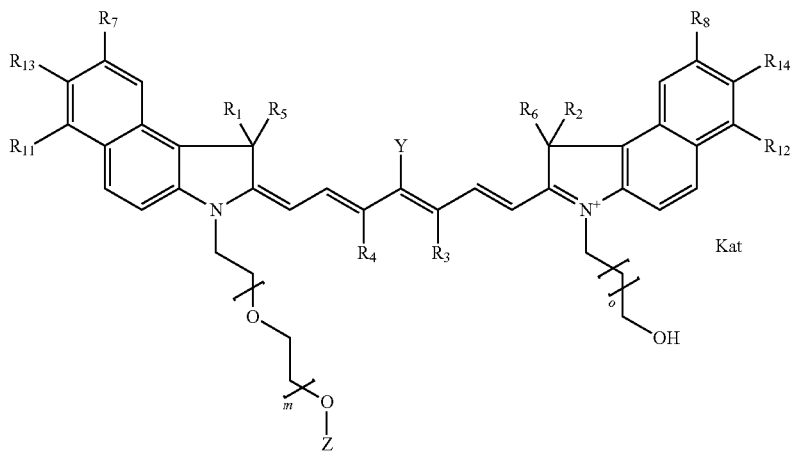

general formula VIc

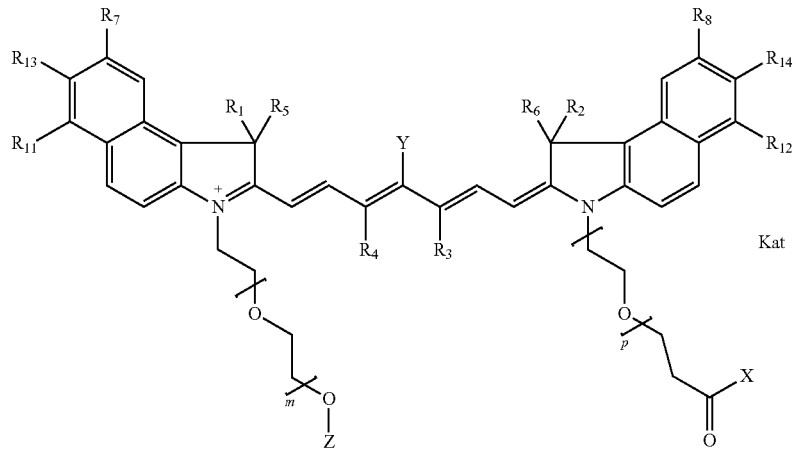

general formula VId

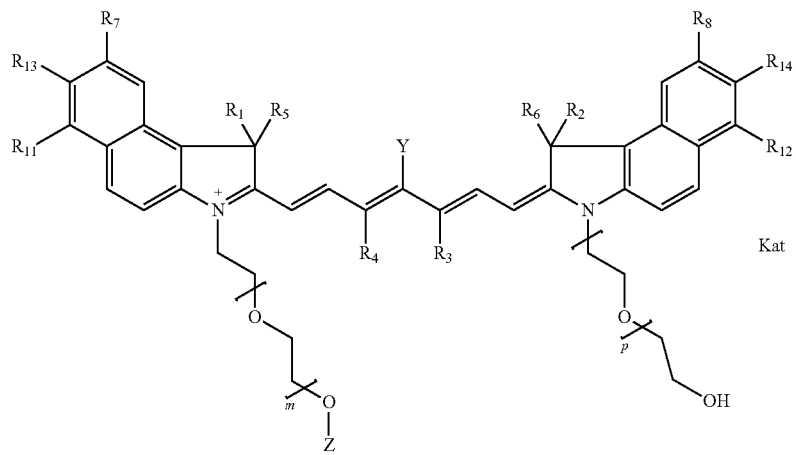

or general formula VIe

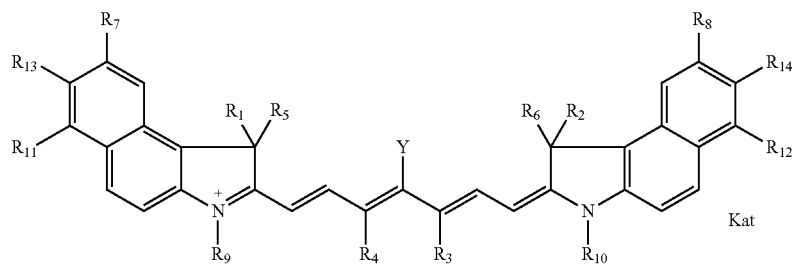

where each of $R^1$, $R^2$, $R^5$, and $R^6$ is the same or different and is independently selected from the group consisting of an aliphatic, heteroaliphatic, sulfoalkyl group, heteroaliphatic with terminal $SO_3$, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-SO$_2$NH—P—Z, and a carboxamide group -L-CONH—P—Z, and Z is selected from H, $CH_3$, a $CH_3$ group, an alkyl group, a heteroalkyl group, or —CO—NHS; each of $R^7$, $R^8$, $R^{11}$, $R^{12}$, $R^{13}$, and $R^{14}$ is the same or different and is independently selected from either H, $SO_3$, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-SO$_2$NH—P—Z, or a carboxamide group -L-CONH—P—Z, and Z is selected from H, a CH$_3$ group, an alkyl group, a heteroalkyl group, or —CO—NHS; each of $R^9$ and $R^{10}$ is the same or different and is independently selected from the group consisting of alkyl, sulfoalkyl, a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a PEG group P-L-X, L-Z, L-X; X is selected from the group consisting of —OH, —SH, —NH$_2$, —NH—NH$_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—CH$_2$—I, imidazole, azide, —NR-L-O—NH$_2$, and —NR-L-O—CO—NHS, where R is —H or an aliphatic or heteroaliphatic group, and L is selected from the group consisting of a divalent linear (—(CH$_2$)$_t$—, t=0 to 15), crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; p is an integer from 1 to 6 inclusive; each of R3 and R4 is the same or different and is independently hydrogen, an aliphatic group, a heteroaliphatic group, or a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, and Z is selected from H, CH$_3$, a CH$_3$ group, an alkyl group, a heteroalkyl group, or —CO—NHS; or R3 and R4 together form a cyclic structure where R3 and R4 are joined using a divalent structural element selected from the group consisting of —(CH$_2$)$_q$—, —(CH$_2$)$_q$O(CH$_2$)$_{q'}$—, —(CH$_2$)$_q$S(CH$_2$)$_{q'}$—, —(CH$_2$)$_q$CH═CH—, and —OCH═CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy-, phenylmercapto function, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, and an oxygen-containing group OR$^{PM}$, where R$^{PM}$ is selected from the group consisting of hydrogen, a substituted or unsubstituted alkyl group, a substituted or unsubstituted heteroalkyl group, a substituted or unsubstituted cyclic alkyl group, a substituted or unsubstituted heterocyclic alkyl group, a substituted or unsubstituted aryl group, and a substituted or unsubstituted heteroaryl group, where the group can be substituted one or more times with one or more of the following groups: hydroxyl, sulfo, carboxy, and/or amino; and Z is selected from H, CH$_3$, a CH$_3$ group, an alkyl group, a heteroalkyl group, or —CO—NHS.

In one embodiment, the compound of general formula VI wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —(CH$_2$)$_q$— and CH═CH, where q is an integer from 1 to 2 inclusive, to result in a 3-, 4-, or 5-membered ring.

In one embodiment, the compound of general formula VI wherein R3 and R4 together form a cyclic structure where R3 and R4 are joined using a divalent structural element of —(CH$_2$)$_q$—, where q is 3, to result in a 6-membered ring, and Y is OR$^{PM}$, where R$^{PM}$ is a substituted 6-membered aryl group, where the substituted group is a sulfo group.

One non-limiting example is a substituted polymethine form of 779 Compound 1, shown below:

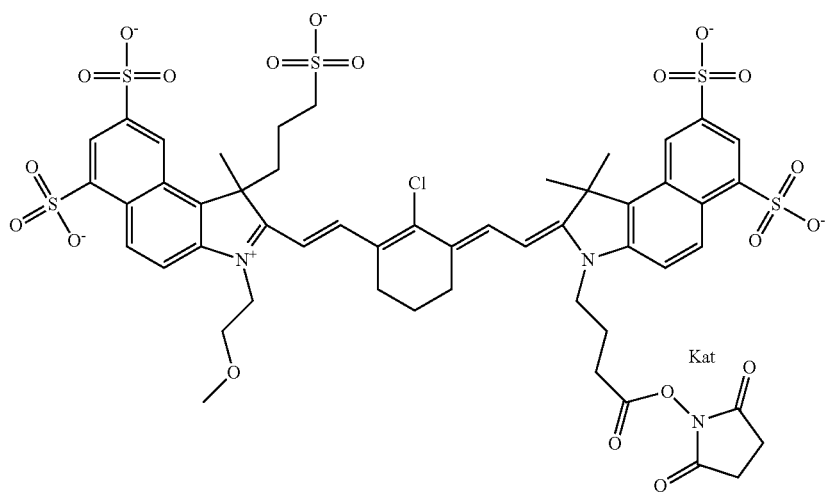 [SMILES: COCC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)C)/CCC2)C(C)(CCCS(=O)(=O)[O-])c2c1ccc1c(S(=O)(=O)[O-])cc(S(=O)(=O)[O-])cc21]

One non-limiting example is a substituted polymethine form of 779 Compound 2, shown below:
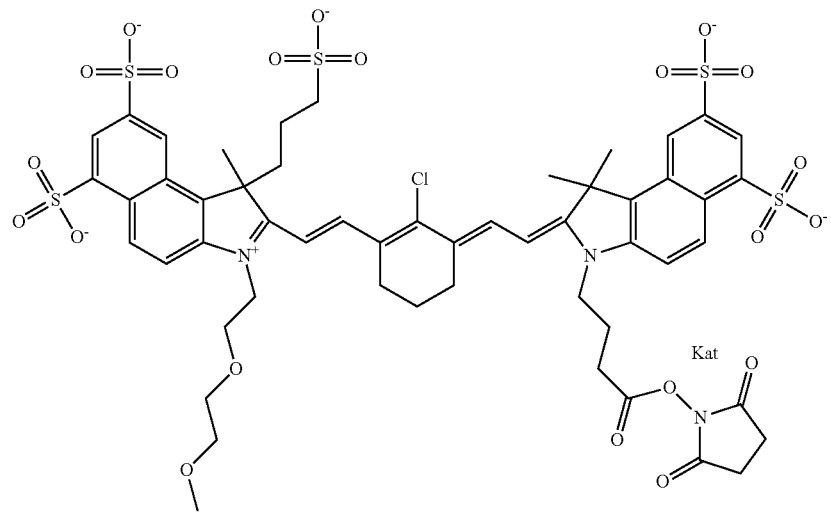 [SMILES: COCCOCC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)C)/CCC2)C(C)(CCCS(=O)(=O)[O-])c2c1ccc1c(S(=O)(=O)[O-])cc(S(=O)(=O)[O-])cc21]
One non-limiting example is a substituted polymethine form of 779 Compound 3, shown below:
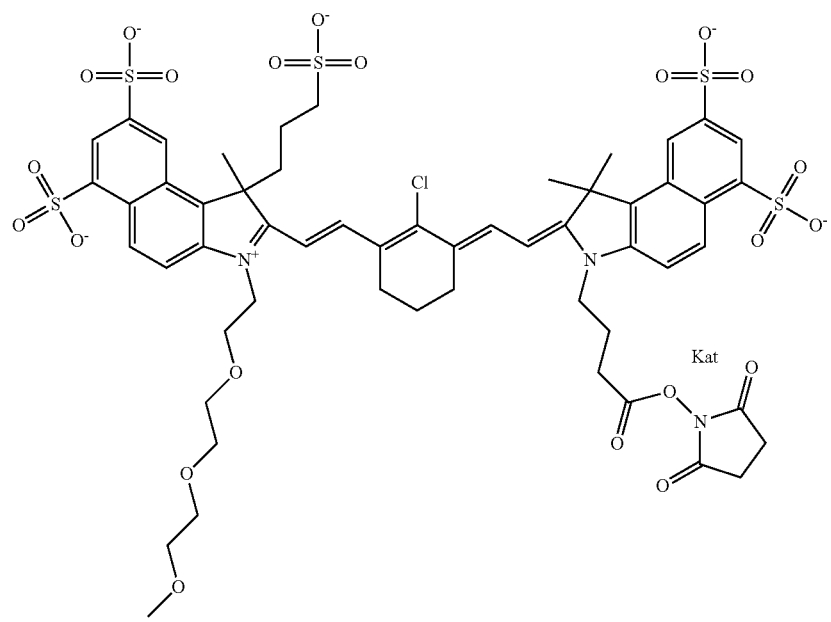 [SMILES: COCCOCCOCC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)C)/CCC2)C(C)(CCCS(=O)(=O)[O-])c2c1ccc1c(S(=O)(=O)[O-])cc(S(=O)(=O)[O-])cc21]

One non-limiting example is a substituted polymethine form of 779 Compound 4, shown below:
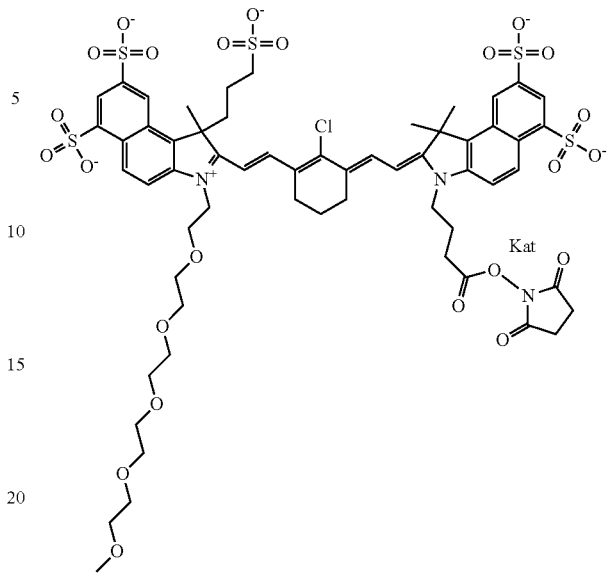
One non-limiting example is a substituted polymethine form of 779 Compound 5, shown below:
One non-limiting example is a substituted polymethine form of 779 Compound 6, shown below:
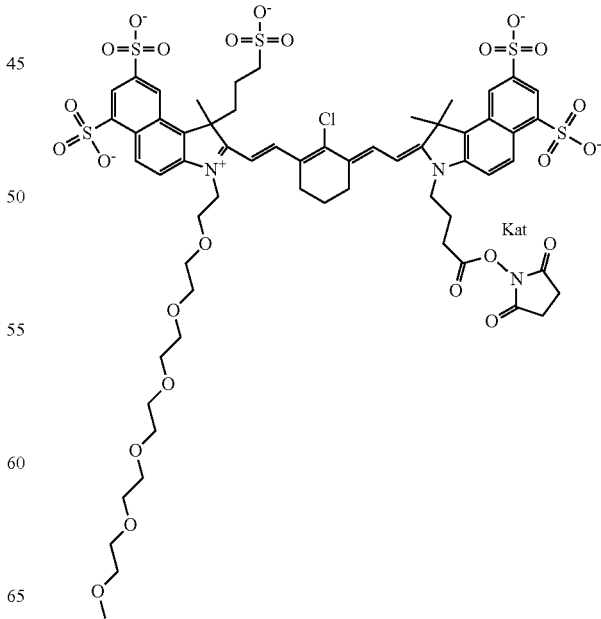

One non-limiting example is a substituted polymethine form of 779 Compound 0/1, shown below:
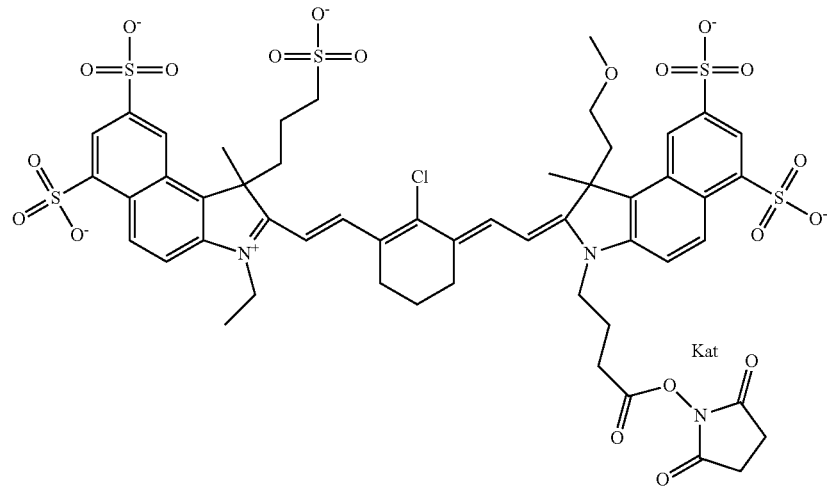 [SMILES: CC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)CCOC)/CCC2)C(C)(CCCS(=O)(=O)[O-])c2c1ccc1c(S(=O)(=O)[O-])cc(S(=O)(=O)[O-])cc21]
One non-limiting example is a substituted polymethine form of 779 Compound 0/1, shown below:
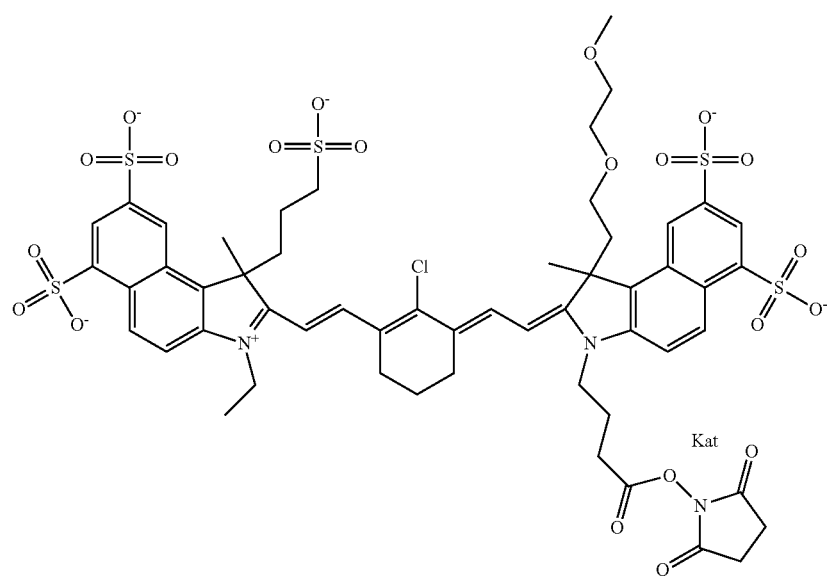 [SMILES: CC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)CCOCCOC)/CCC2)C(C)(CCCS(=O)(=O)[O-])c2c1ccc1c(S(=O)(=O)[O-])cc(S(=O)(=O)[O-])cc21]

One non-limiting example is a substituted polymethine form of 779 Compound 0/1, shown below:
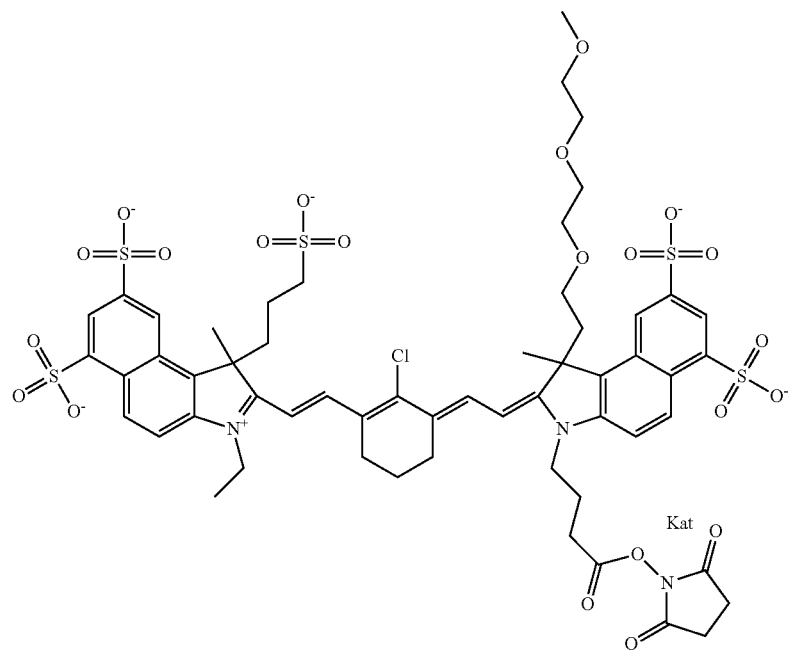 [SMILES: CC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)CCOCCOCCOC)/CCC2)C(C)(CCCS(=O)(=O)[O-])c2c1ccc1c(S(=O)(=O)[O-])cc(S(=O)(=O)[O-])cc21]
One non-limiting example is a substituted polymethine form of 779 Compound 0/1, shown below:
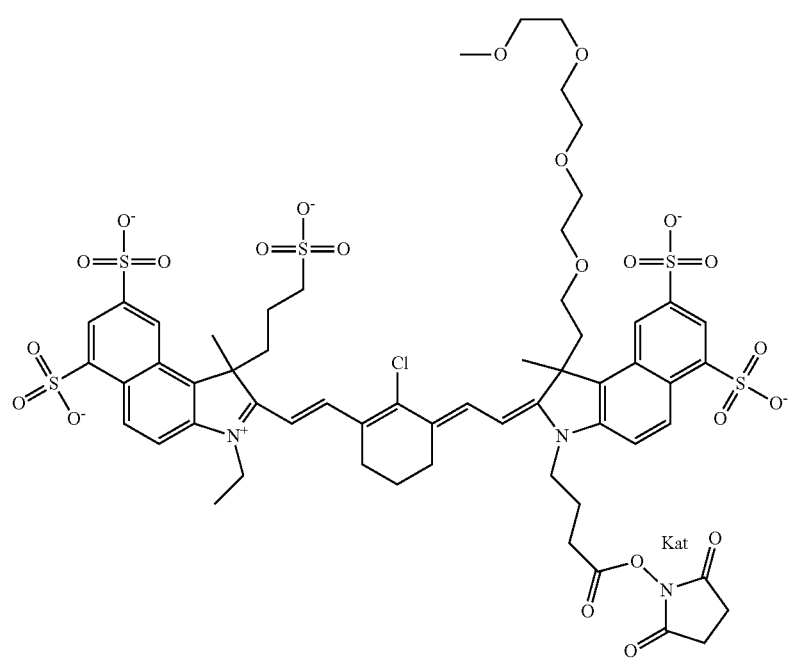 [SMILES: CC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)CCOCCOCCOCCOC)/CCC2)C(C)(CCCS(=O)(=O)[O-])c2c1ccc1c(S(=O)(=O)[O-])cc(S(=O)(=O)[O-])cc21]

One non-limiting example is a substituted polymethine form of 779 Compound 0/1, shown below:
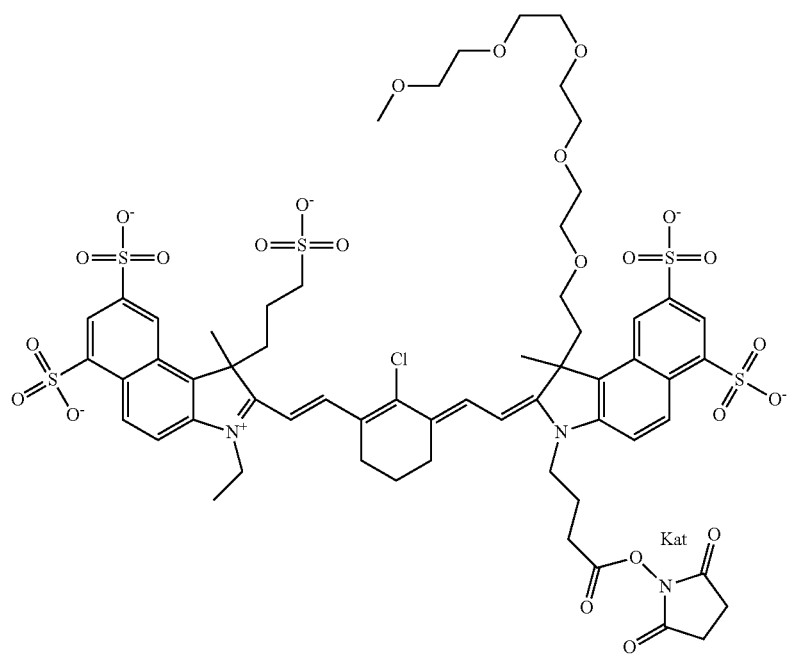 [SMILES: CC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)CCOCCOCCOCCOCCOC)/CCC2)C(C)(CCCS(=O)(=O)[O-])c2c1ccc1c(S(=O)(=O)[O-])cc(S(=O)(=O)[O-])cc21]
One non-limiting example is a substituted polymethine form of 779 Compound 0/1, shown below:
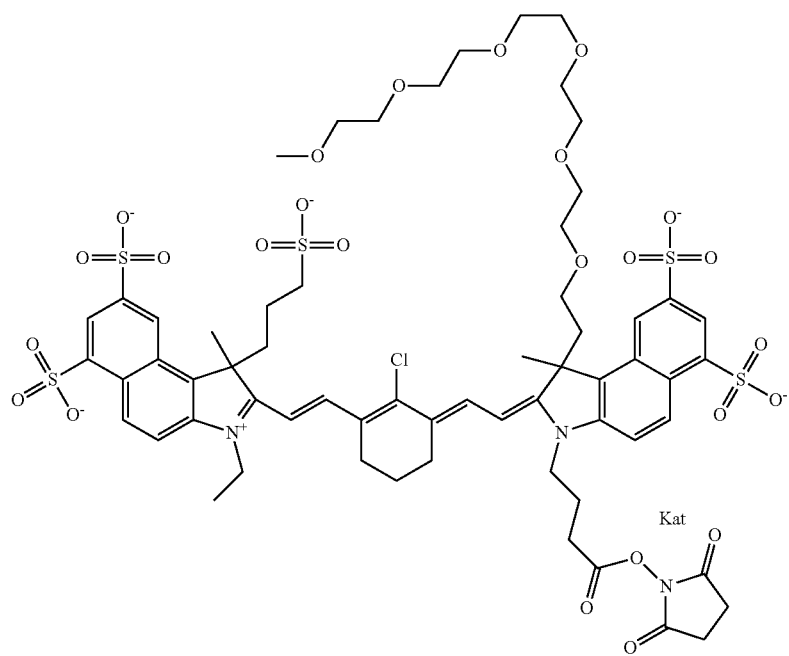 [SMILES: CC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)CCOCCOCCOCCOCCOCCOC)/CCC2)C(C)(CCCS(=O)(=O)[O-])c2c1ccc1c(S(=O)(=O)[O-])cc(S(=O)(=O)[O-])cc21]

One non-limiting example is a substituted polymethine form of 779 Compound 1/2 (PEG$_4$), shown below:

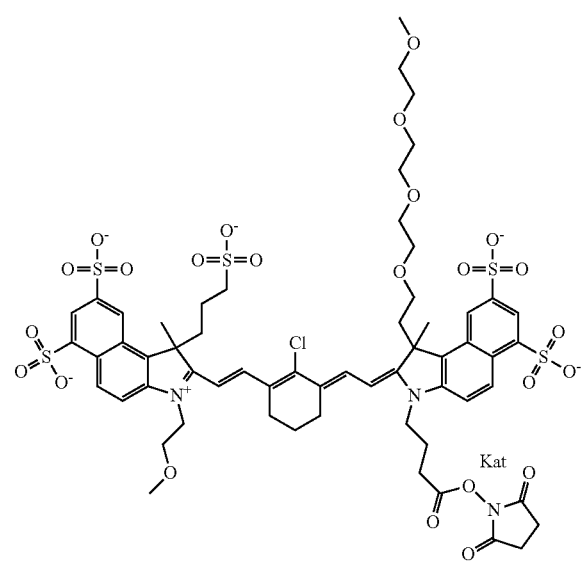 [SMILES: COCCOCCOCCOCCC1(C)/C(=C\C=C2/CCCC(/C=C/C3=[N+](CCOC)c4ccc5c(S(=O)(=O)[O-])cc(S(=O)(=O)[O-])cc5c4C3(C)CCCS(=O)(=O)[O-])=C2Cl)N(CCCC(=O)ON2C(=O)CCC2=O)c2ccc3c(S(=O)(=O)[O-])cc(S(=O)(=O)[O-])cc3c21]

One non-limiting example is a substituted polymethine form of 779 Compound 2/2 (PEG$_4$), shown below:

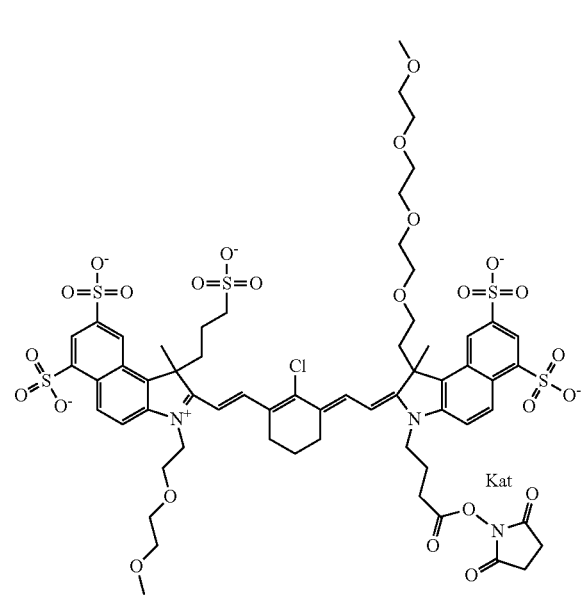 [SMILES: COCCOCCOCCOCCC1(C)/C(=C\C=C2/CCCC(/C=C/C3=[N+](CCOCCOC)c4ccc5c(S(=O)(=O)[O-])cc(S(=O)(=O)[O-])cc5c4C3(C)CCCS(=O)(=O)[O-])=C2Cl)N(CCCC(=O)ON2C(=O)CCC2=O)c2ccc3c(S(=O)(=O)[O-])cc(S(=O)(=O)[O-])cc3c21]

One non-limiting example is a substituted polymethine form of 779 Compound 3/2 (PEG$_4$), shown below:

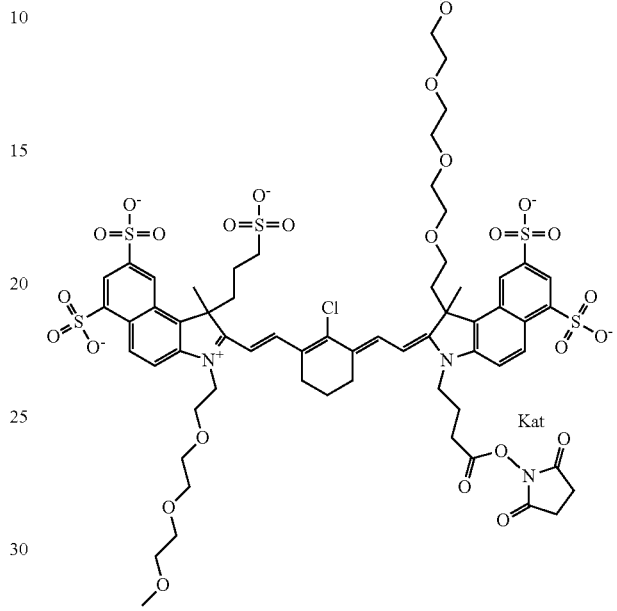

One non-limiting example is a substituted polymethine form of 779 Compound 4/2 (PEG$_4$), shown below:

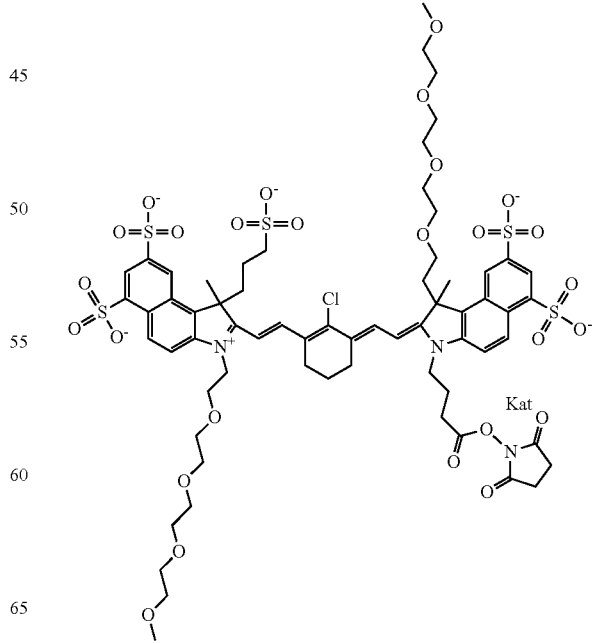

One non-limiting example is a substituted polymethine form of 779 Compound 5/2 (PEG₄), shown below:
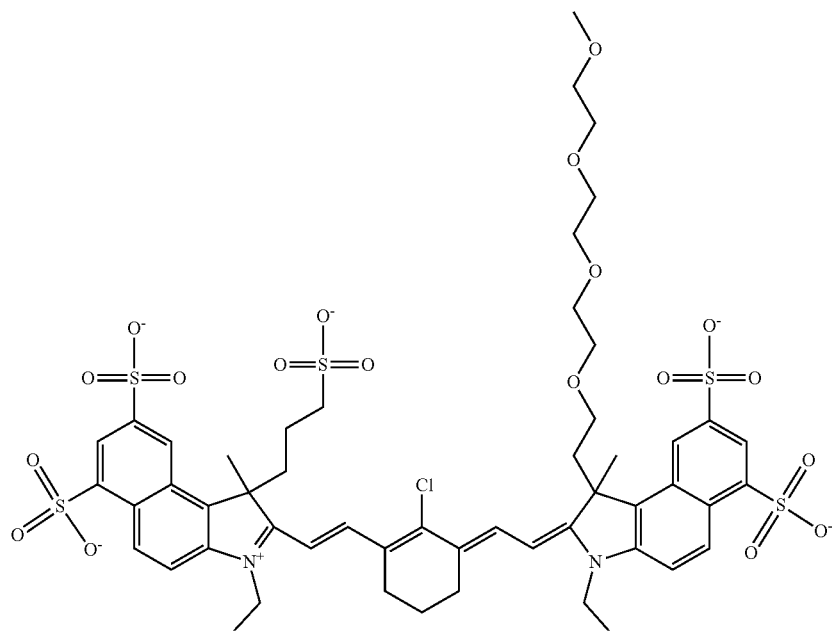
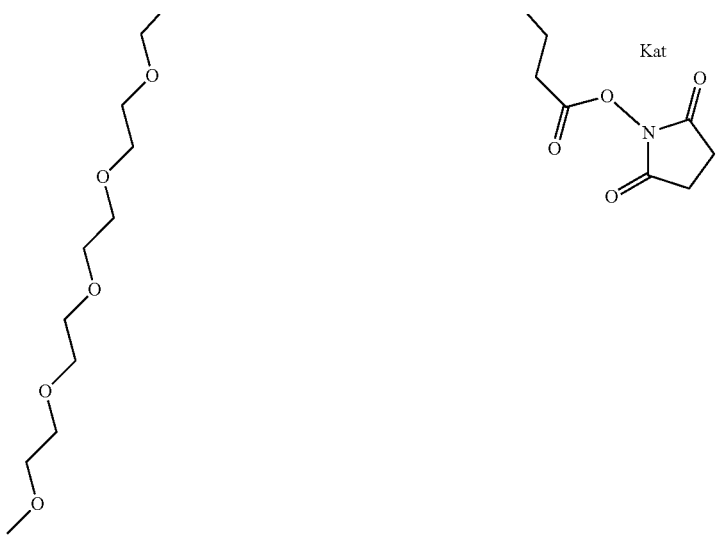

One non-limiting example is a substituted polymethine form of 779 Compound 6/2 (PEG$_4$), shown below:
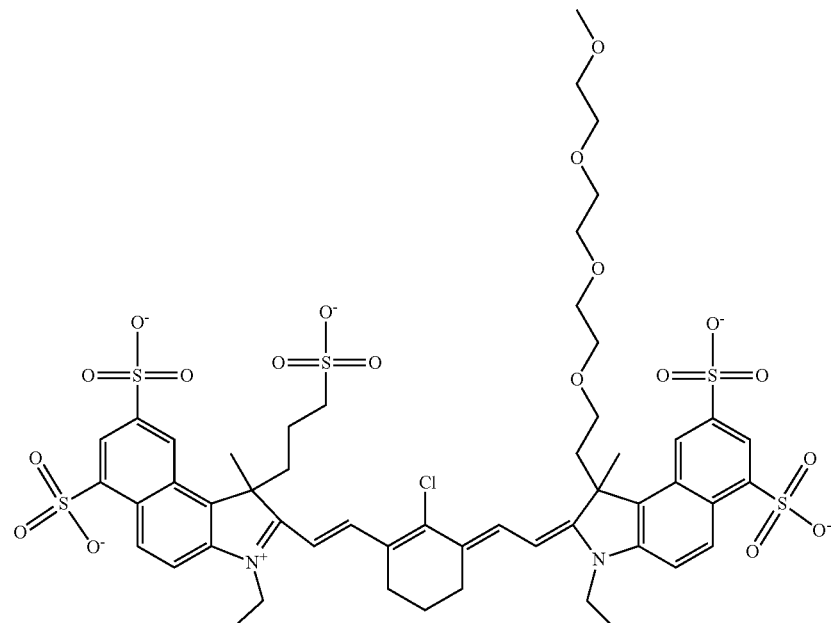
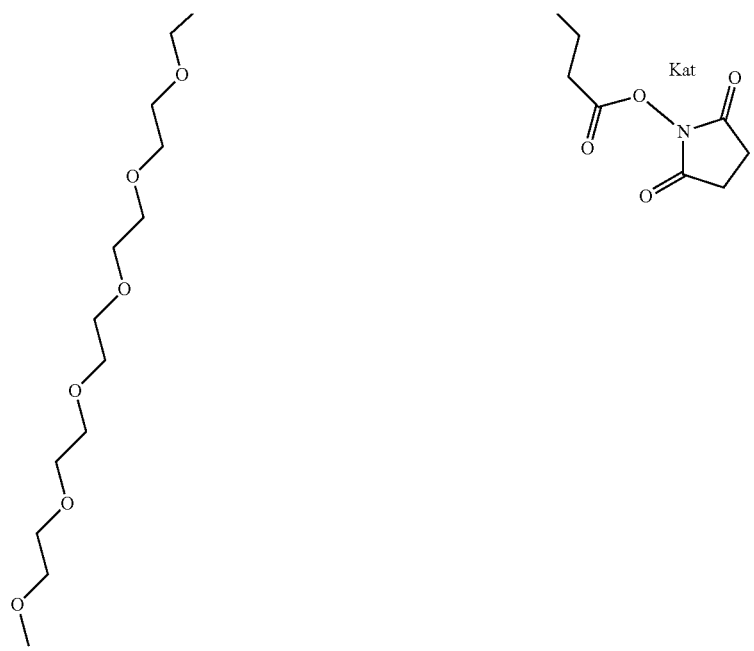

One non-limiting example is a substituted polymethine form of 779 Compound 0/2, shown below:

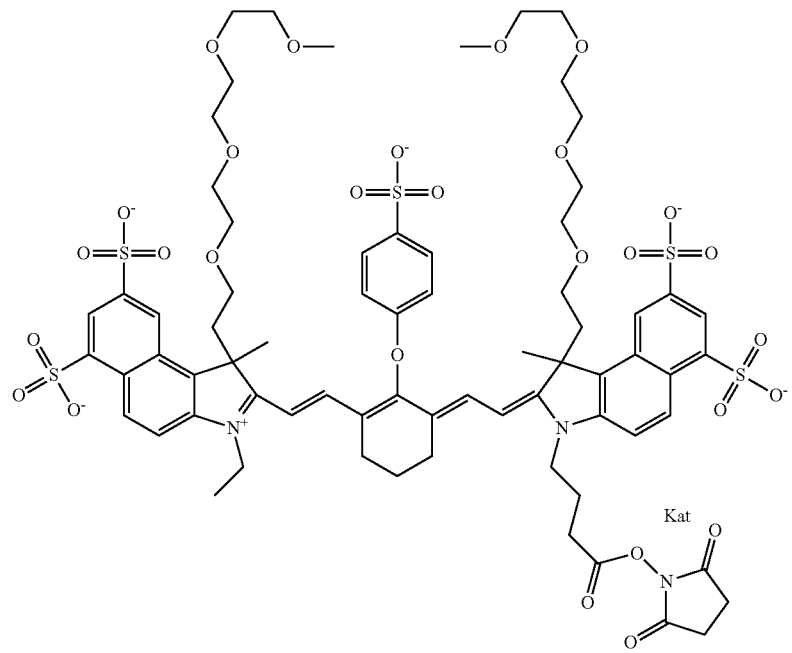 [SMILES: CC[N+]1=C(/C=C/C2=C(Oc3ccc(S(=O)(=O)[O-])cc3)C(=C/C=C3/N(CCCC(=O)ON4C(=O)CCC4=O)c4ccc5c(S(=O)(=O)[O-])cc(S(=O)(=O)[O-])cc5c4C3(C)CCOCCOCCOCCOC)/CCC2)C(C)(CCOCCOCCOCCOC)c2c1ccc1c(S(=O)(=O)[O-])cc(S(=O)(=O)[O-])cc21]

In embodiments, an ethylene glycol group, diethylene glycol group, and/or a (poly)ethylene glycol group, collectively referred to as a PEG group unless specifically defined, may be present at position(s) in addition to such groups being present on the N atom(s) of the indole structure.

One non-limiting example of an additionally PEG-substituted compound is a 779 Compound 1/2 according to general formula II where R1 is an ethylene glycol group terminating with a methyl group, shown below:

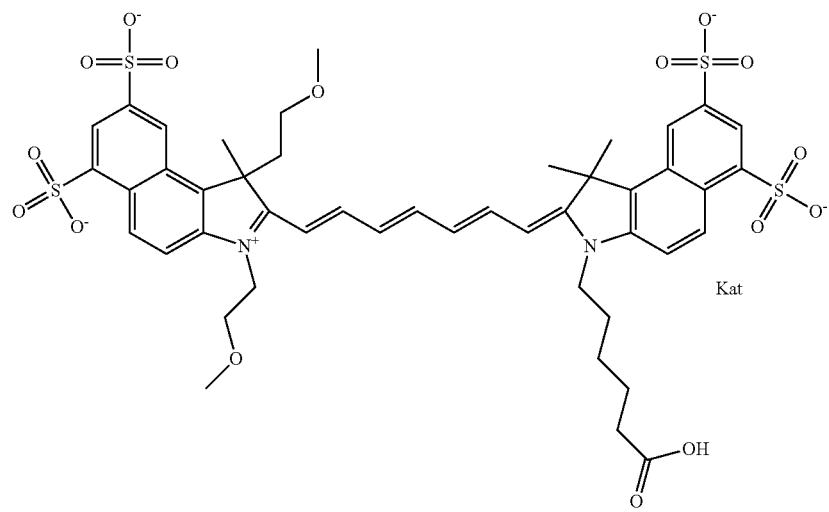

One non-limiting example of an additionally PEG-substituted compound is a 779 Compound 1/2 according to general formula II where R2 is an ethylene glycol group terminating with a methyl group, shown below:

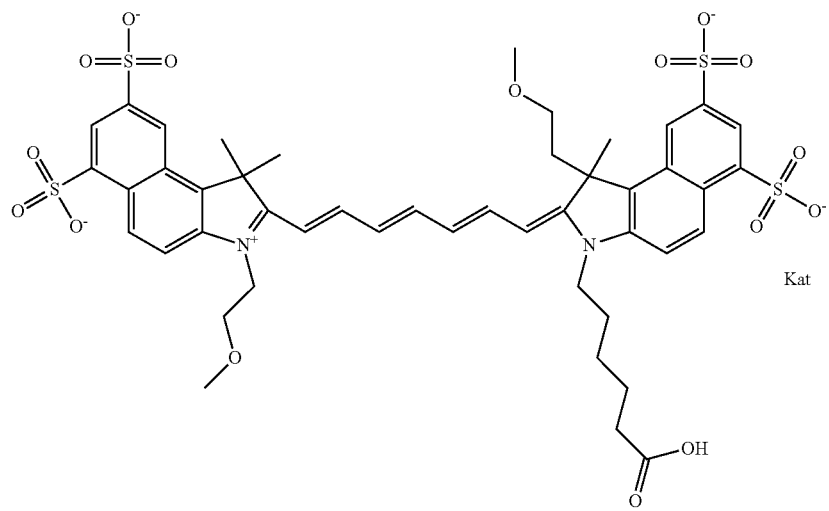

One non-limiting example of an additionally PEG-substituted compound is a 779 Compound 1/2 according to general formula II where R8 is an ethylene glycol group terminating with a methyl group, shown below:

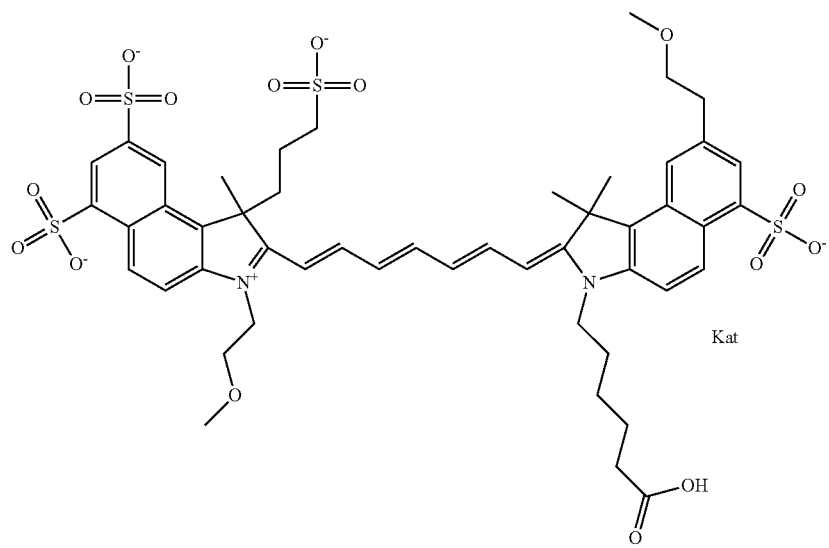

One non-limiting example of an additionally PEG-substituted compound is a 779 Compound 1/2 according to general formula II where R8 is a sulfonamide group with an ethylene glycol group (PEG$_1$) terminating with a methyl group, shown below:

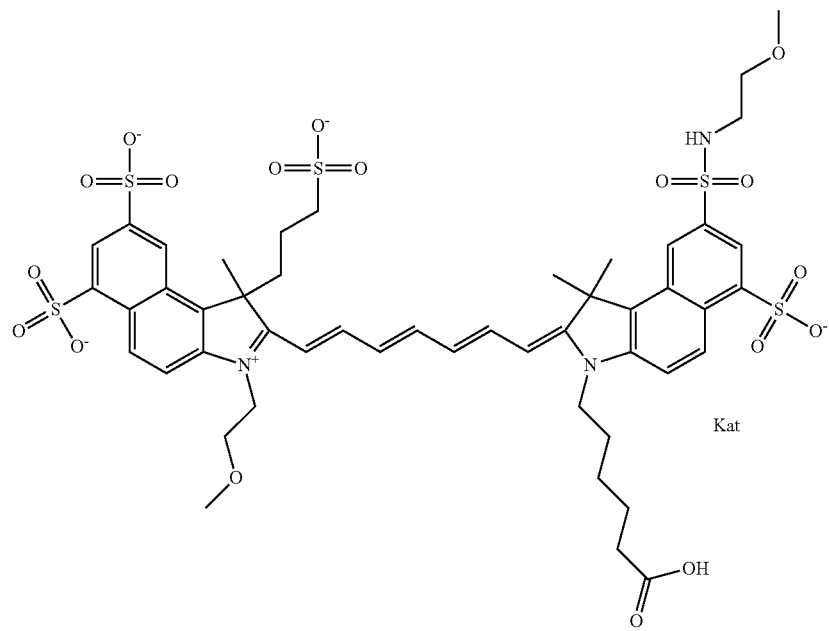

One non-limiting example of an additionally PEG-substituted compound is a 779 Compound 1/2 according to general formula II where R8 is a carboxamide group with an ethylene glycol group (PEG$_1$) terminating with a methyl group, shown below:

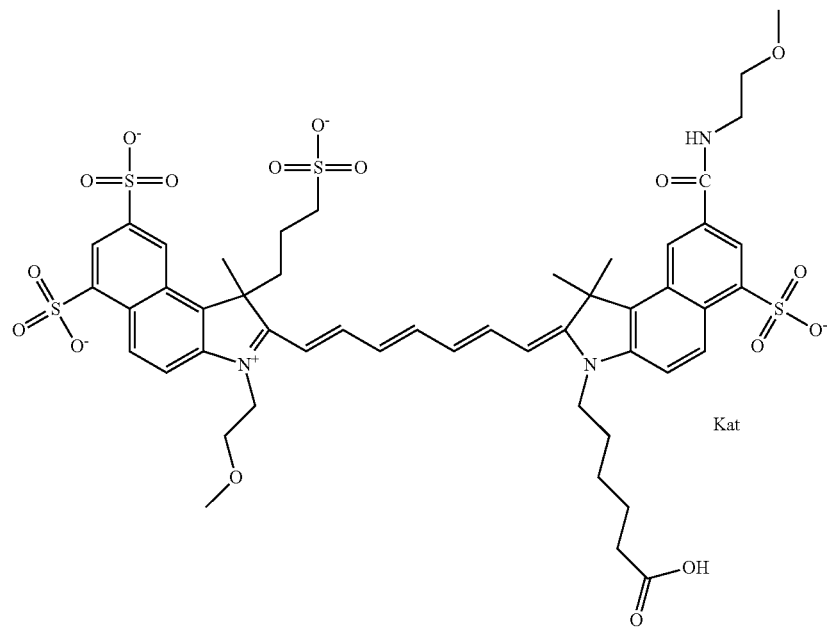

One non-limiting example of an additionally PEG-substituted compound is a 779 Compound 1/2 according to general formula II where R7 is an ethylene glycol group terminating with a methyl group, shown below:

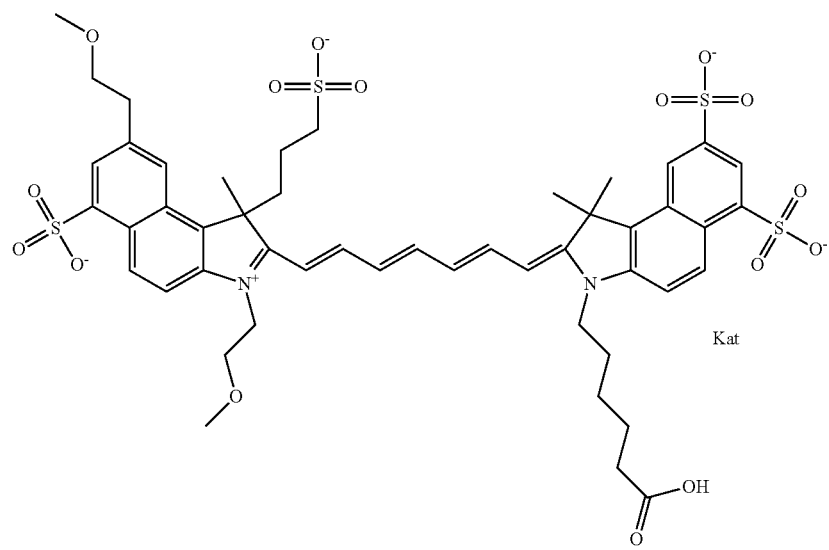

One non-limiting example of an additionally PEG-substituted compound is a 779 Compound 1/2 according to general formula II where R7 is a sulfonamide group with an ethylene glycol group (PEG$_1$) terminating with a methyl group, shown below:

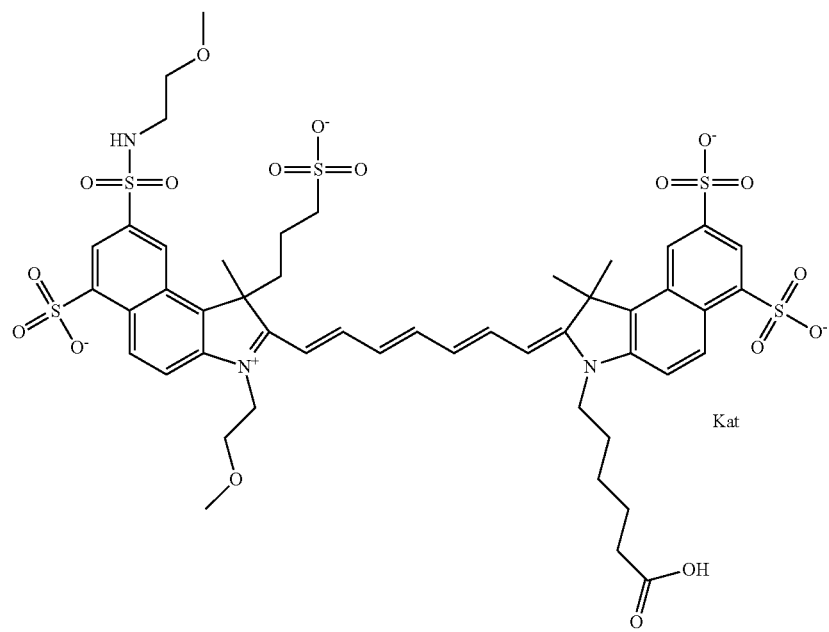

One non-limiting example of an additionally PEG-substituted compound is a 779 Compound 1/2 according to general formula II where R7 is a carboxamide group with an ethylene glycol group (PEG$_1$) terminating with a methyl group, shown below:

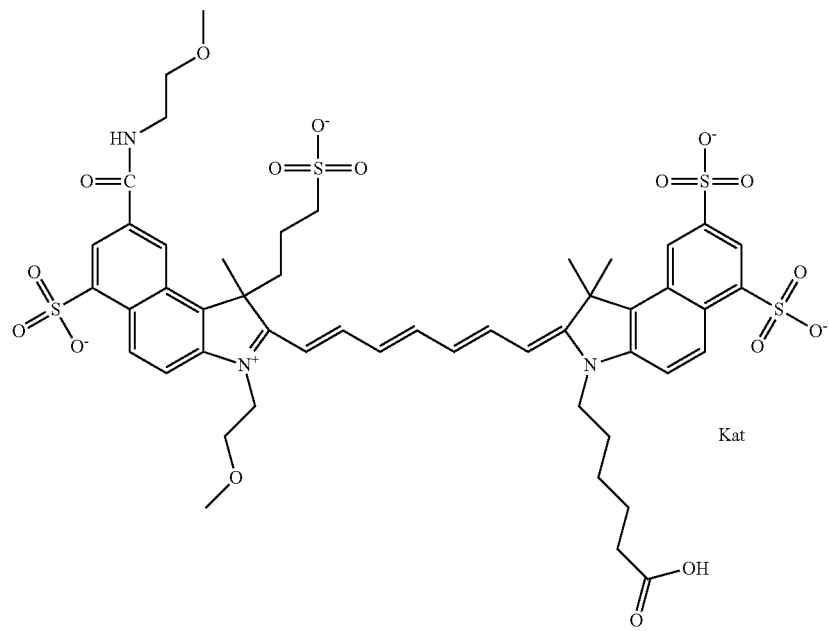

One non-limiting example of an additionally PEG-substituted compound is a 779 Compound 1/2 according to general formula II where R12 is an ethylene glycol group terminating with a methyl group, shown below:

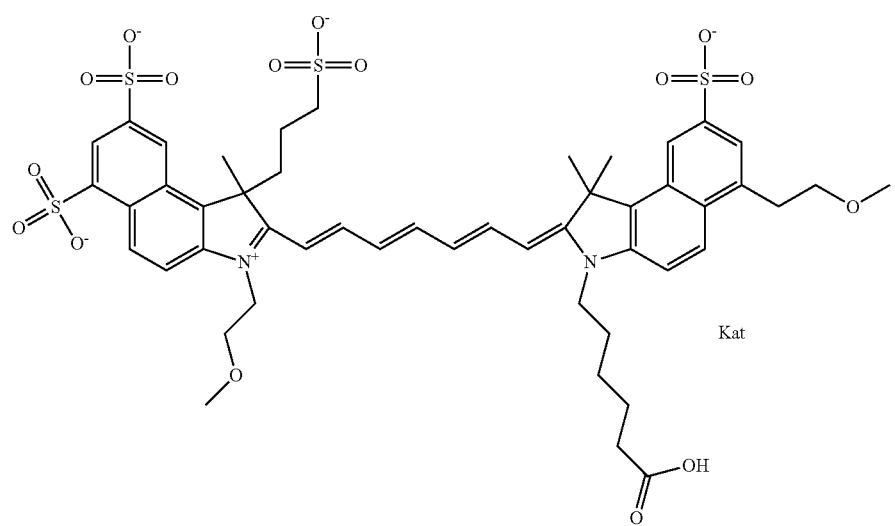

One non-limiting example of an additionally PEG-substituted compound is a 779 Compound 1/2 according to general formula II where R12 is a sulfonamide group with an ethylene glycol group (PEG$_1$) terminating with a methyl group, shown below:

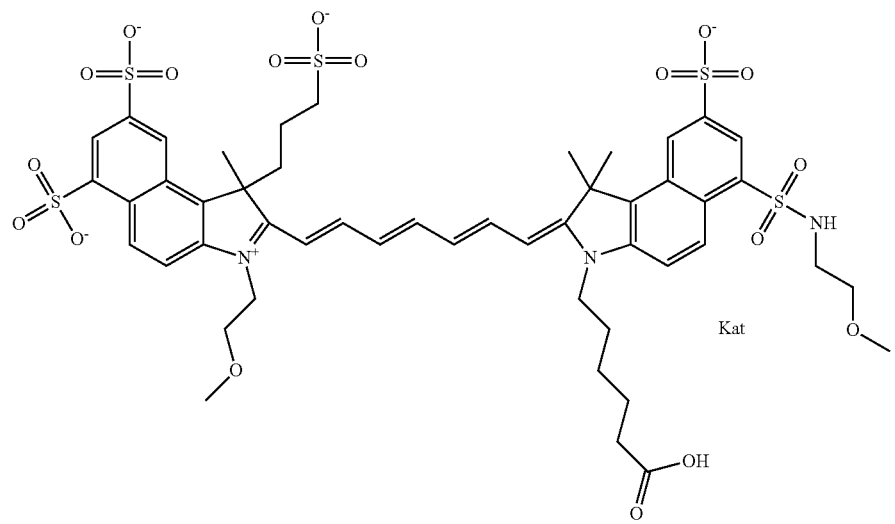

One non-limiting example of an additionally PEG-substituted compound is a 779 Compound 1/2 according to general formula II where R12 is a carboxamide group with an ethylene glycol group (PEG$_1$) terminating with a methyl group, shown below:

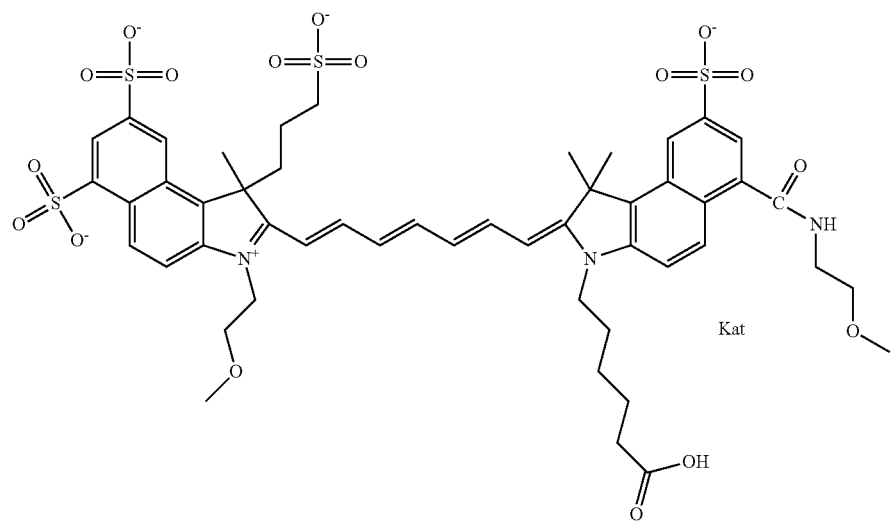

One non-limiting example of an additionally PEG-substituted compound is a 779 Compound 1/2 according to general formula II where R11 is an ethylene glycol group terminating with a methyl group, shown below:

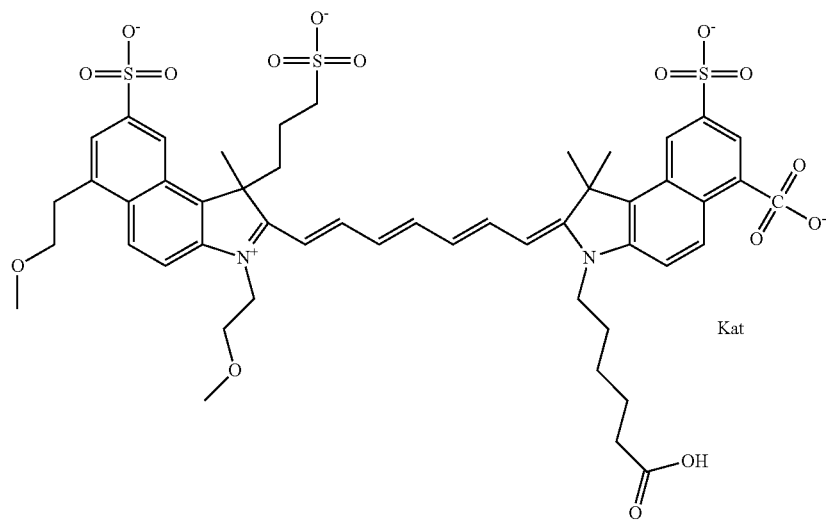

One non-limiting example of an additionally PEG-substituted compound is a 779 Compound 1/2 according to general formula II where R11 is a sulfonamide group with an ethylene glycol group (PEG$_1$) terminating with a methyl group, shown below:

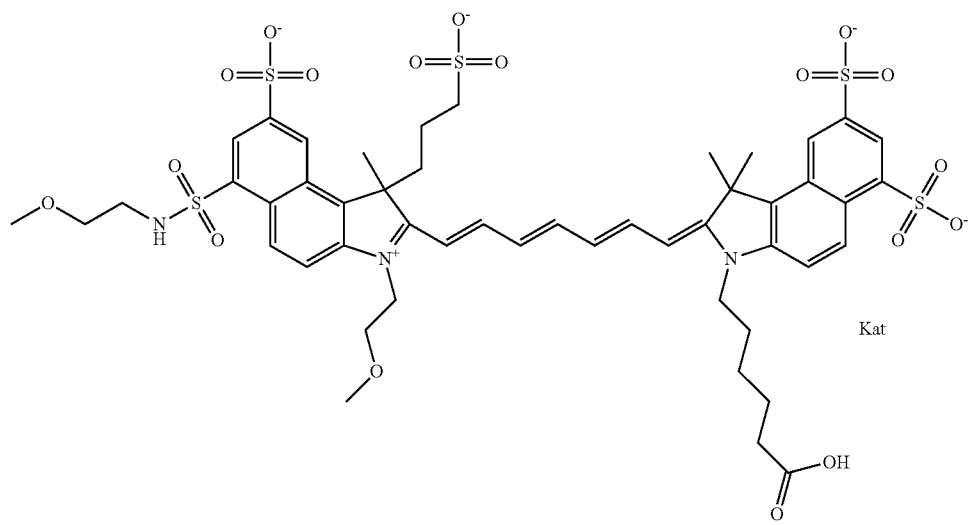

One non-limiting example of an additionally PEG-substituted compound is a 779 Compound 1/2 according to general formula II where R11 is a carboxamide group with an ethylene glycol group (PEG$_1$) terminating with a methyl group, shown below:

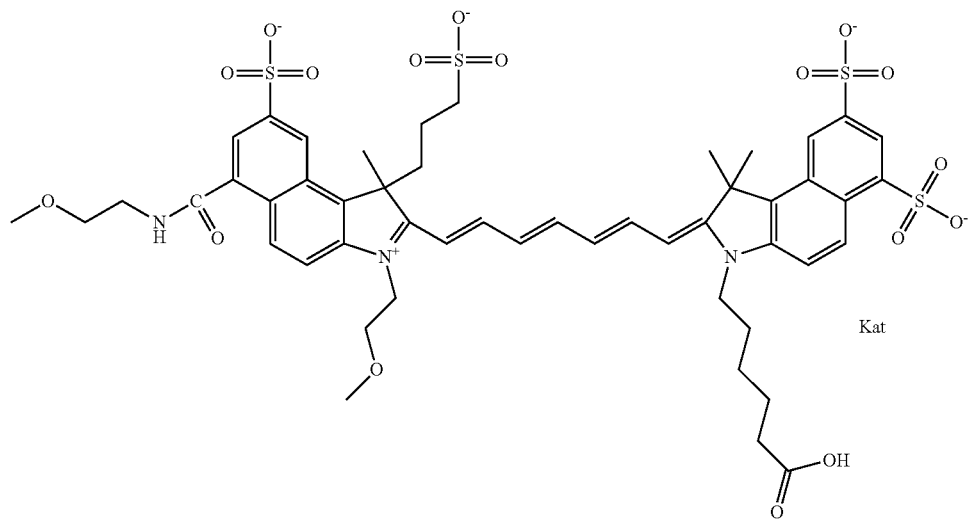

One non-limiting example of an additionally PEG-substituted compound is a 779 Compound 1/2 according to general formula II where R13 is an ethylene glycol group terminating with a methyl group, shown below:

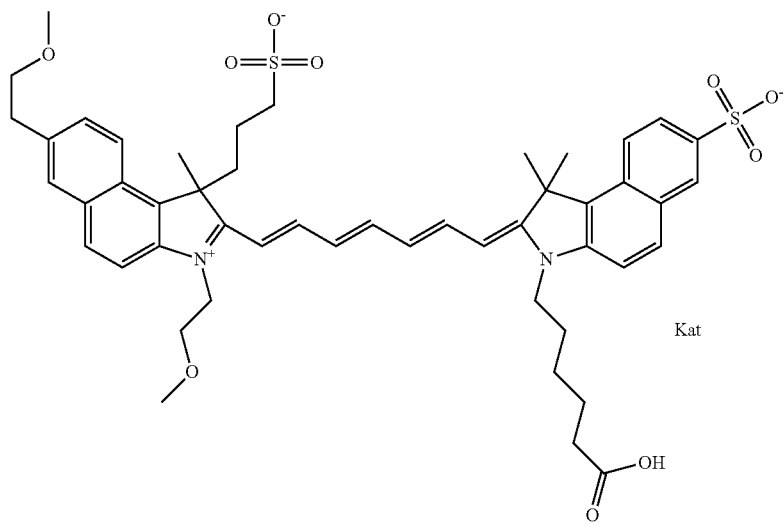

One non-limiting example of an additionally PEG-substituted compound is a 779 Compound 1/2 according to general formula II where R13 is a sulfonamide group with an ethylene glycol group (PEG$_1$) terminating with a methyl group, shown below:

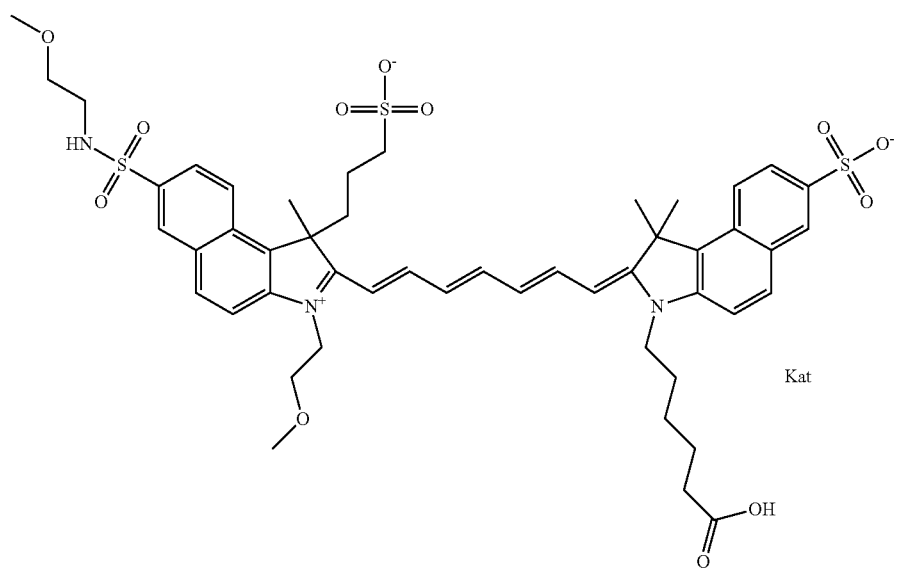

One non-limiting example of an additionally PEG-substituted compound is a 779 Compound 1/2 according to general formula II where R13 is a carboxamide group with an ethylene glycol group (PEG₁) terminating with a methyl group, shown below:

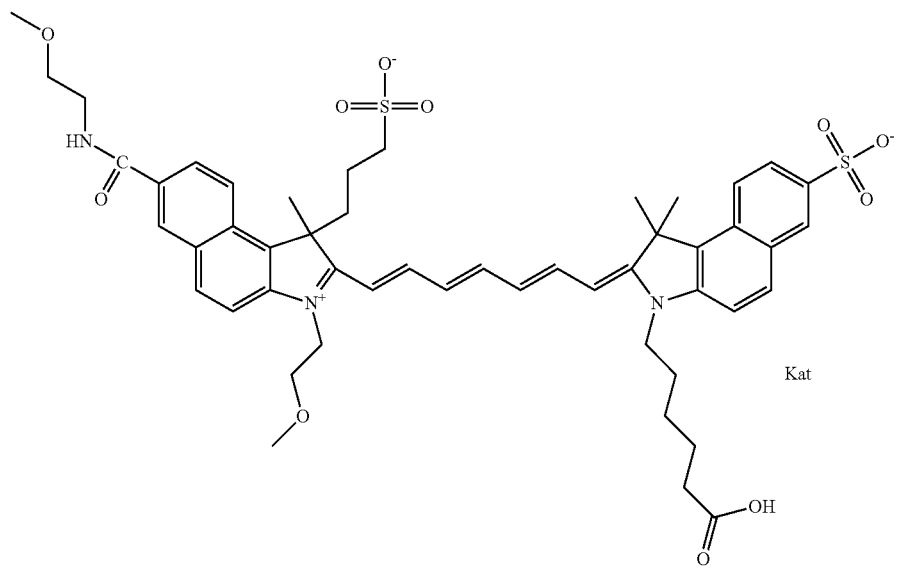

One non-limiting example of an additionally PEG-substituted compound is a 779 Compound 1/2 according to general formula II where R14 is an ethylene glycol group terminating with a methyl group, shown below:

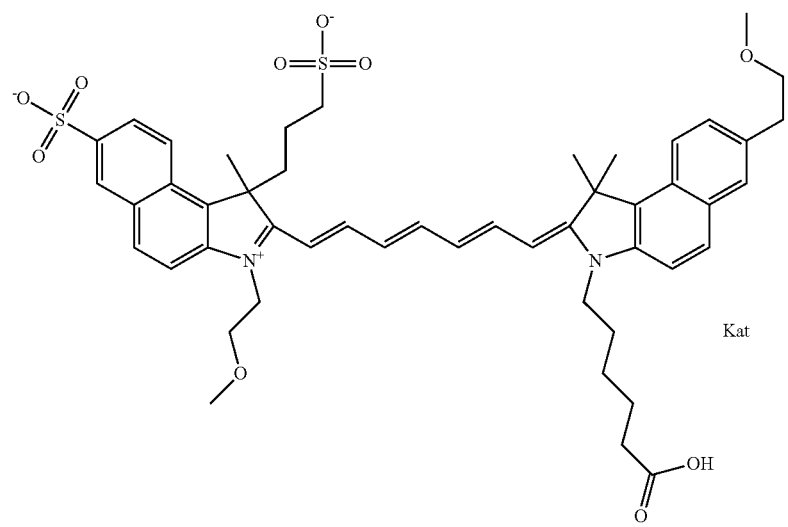

One non-limiting example of an additionally PEG-substituted compound is a 779 Compound 1/2 according to general formula II where R14 is a sulfonamide group with an ethylene glycol group (PEG$_1$) terminating with a methyl group, shown below:

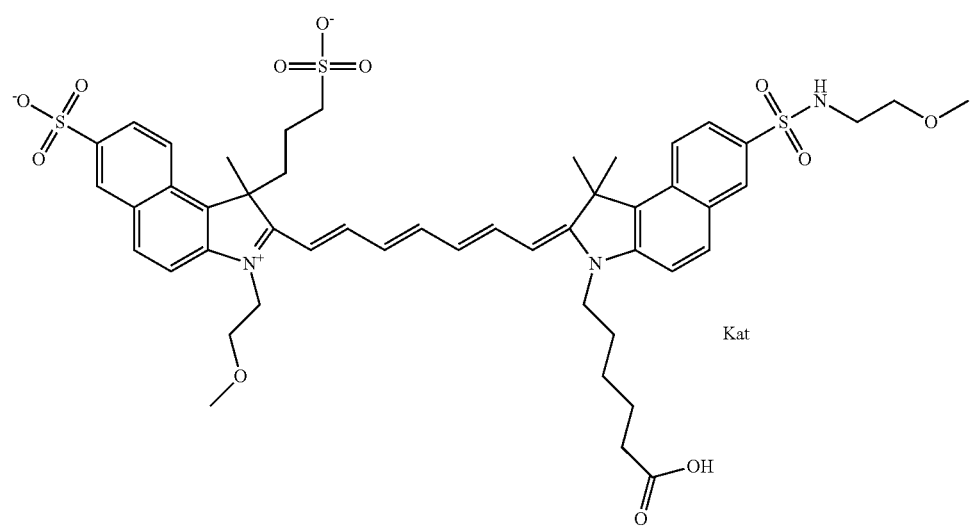

One non-limiting example of an additionally PEG-substituted compound is a 779 Compound 1/2 according to general formula II where R14 is a carboxamide group with an ethylene glycol group (PEG$_1$) terminating with a methyl group, shown below:

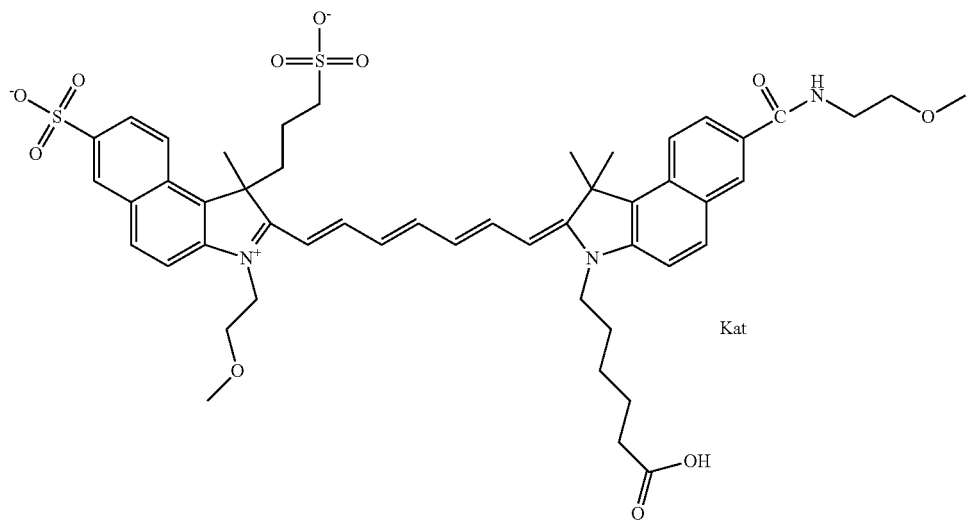

The disclosed compounds are useful as chromophores and/or fluorophores. For example, they are used for optical labelling and, therefore, for the qualitative and/or quantitative detection of proteins, nucleic acids, oligomers, DNA, RNA, biological cells, lipids, mono-, oligo- and polysaccharides, ligands, receptors, polymers, drugs, polymeric beads, etc.

The present compounds, containing the disclosed functionality or functionalilies, may be synthesized using methods known in the art, e.g., as described as follows with all references expressly incorporated by reference herein in their entirety.

The core indocyanine structure without additional functionalilities, along with its synthesis, was described by König in U.S. Pat. No. 1,524,791 and BP 434875, and included 3-, 5-, and 7-membered polymethine chains.

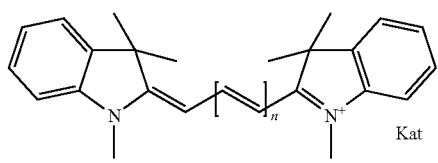

Synthesis of numerous modifications of the core indocyanine structure have been described. Such modifications provided various functionalilities, e.g., synthesis of N-isothiocyanato-alkyl- and aromatic-carboxyalkyl-functionalized indocyanines were described in U.S. Pat. Nos. 5,627,027; 6,048,982; 4,981,977; U.S. Publication No. 2006/0199949; Southwick, Anal. Chem. 67 (1995)1742-48).

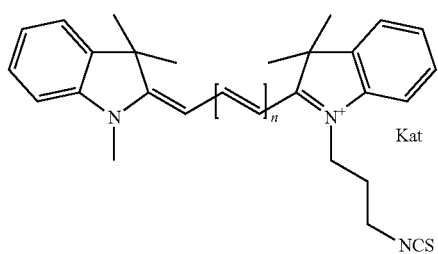

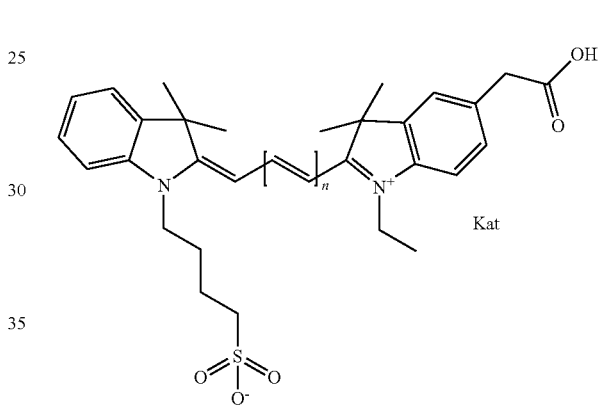

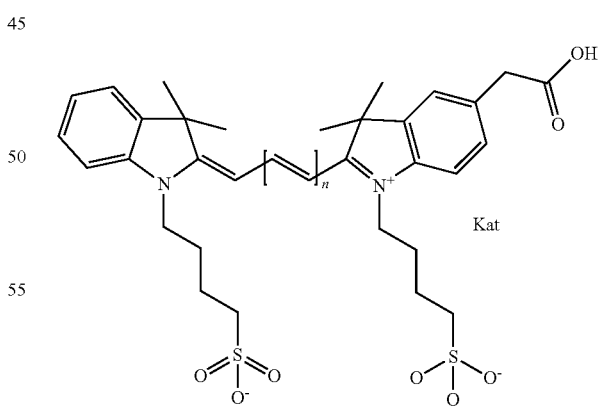

Synthesis of indocyanines with one or two N-carboxyalkyl functionalities were described in U.S. Pat. Nos. 5,268,486; 5,486,616; 5,569,587; 5,569,766; and JP 03217837.

323
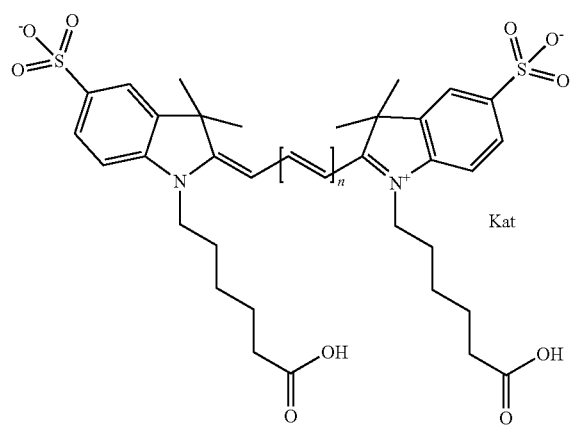
Synthesis of indocyanines containing C-carboxyalkyl groups were described in JP 05-313304; U.S. Publication Nos. 2006/0099638, 2006/0004188; 2002/0077487; 2002/0064794; U.S. Pat. Nos. 6,977,305 and 6,974,873.
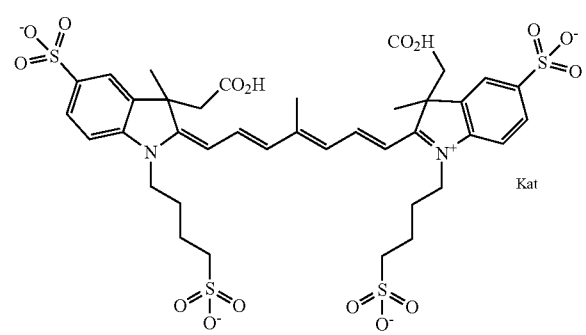
324
-continued
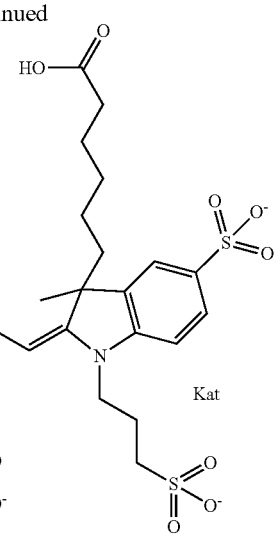
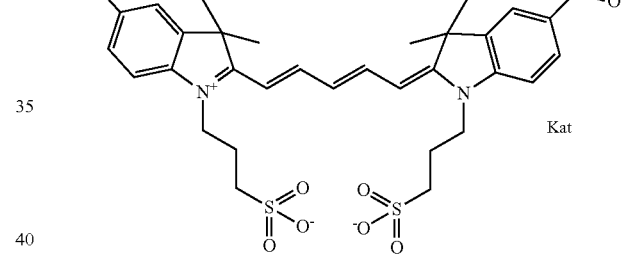
Synthesis of indocyanines with N- and C-sulfoalkyl groups were described in JP 05-313304; WO 2005/044923; U.S. Publication No. 2007/0203343.
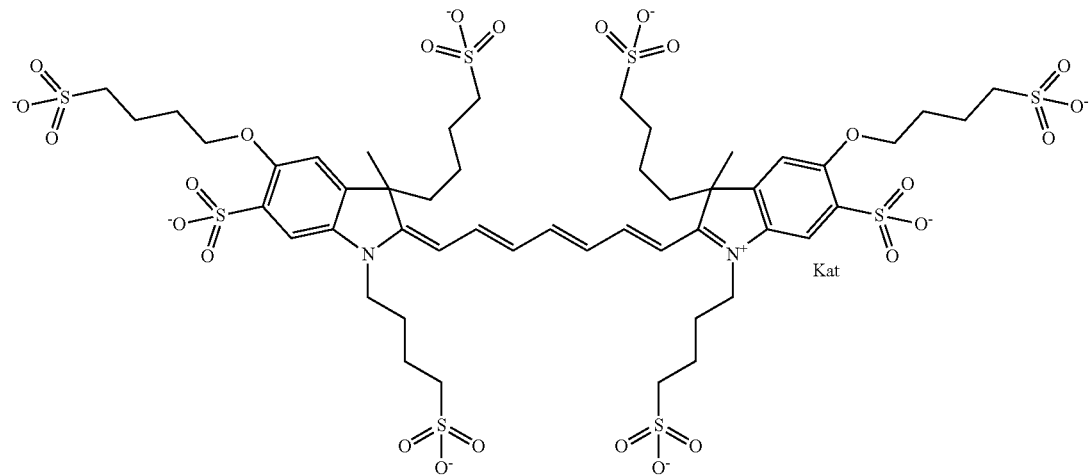

325
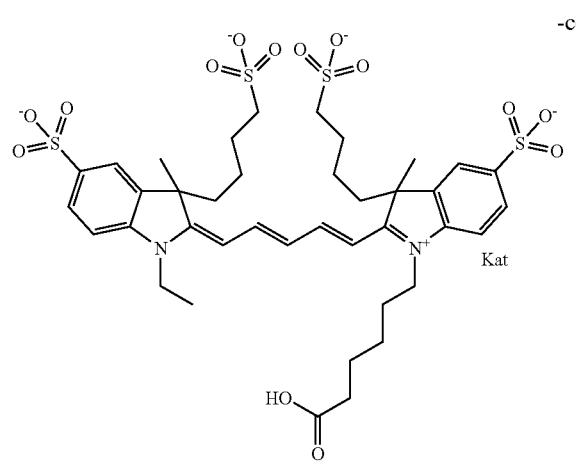
326
-continued
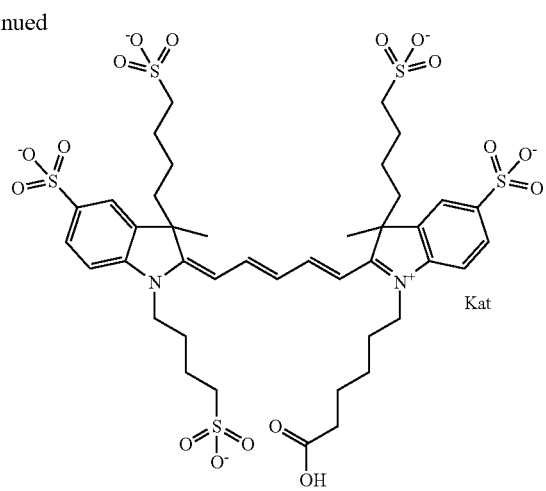
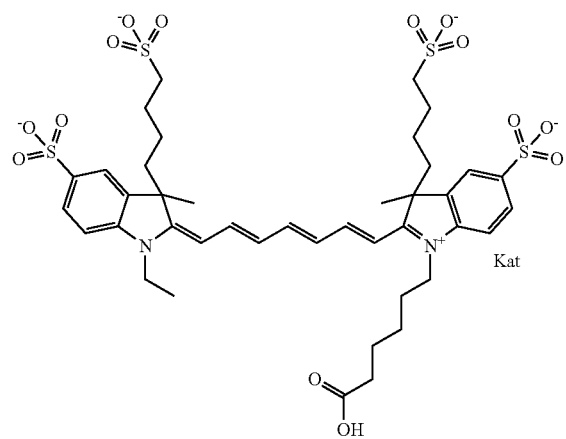
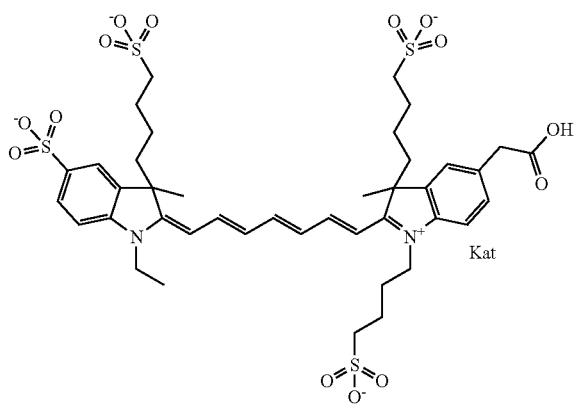
Synthesis of indocyanines with mixed C-carboxyalkyl and C-sulfoalkyl were described in EP 1792949 and U.S. Pat. No. 7,745,640.
-continued
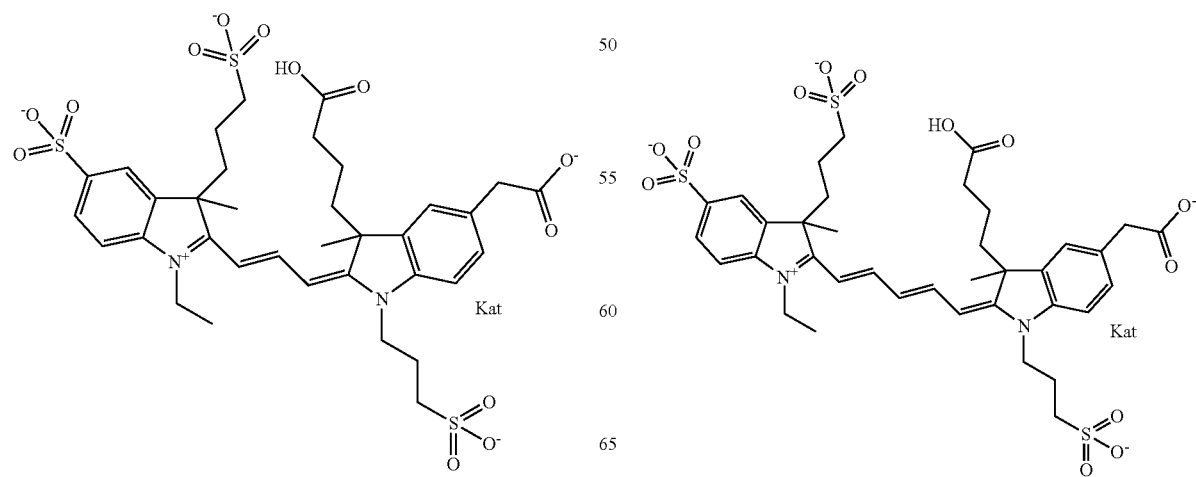

327
-continued
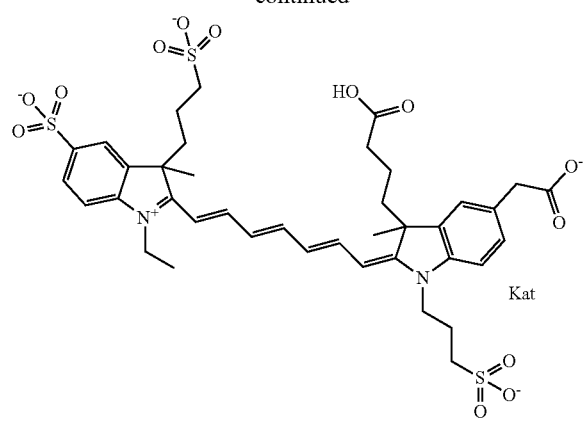
Synthesis of indocyanaines having a PEG-containing, N-carboxyalkyl spacer were described in U.S. Pat. No. 6,939,532.
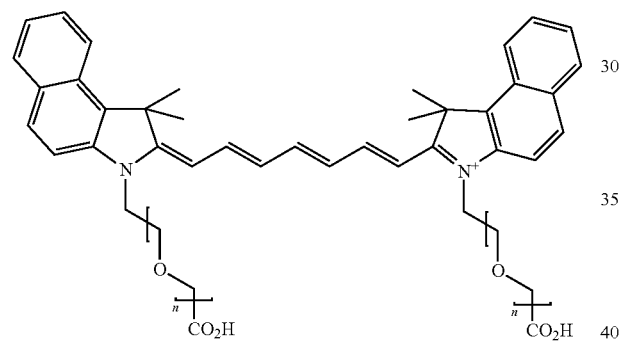
Functionalization of the N-carboxyalkyl with an amino-functionalized PEG-alkyl chain, and N- and C-substituted PEG-alkyl chains, were described in U.S. Publication No. 2009/0305410.
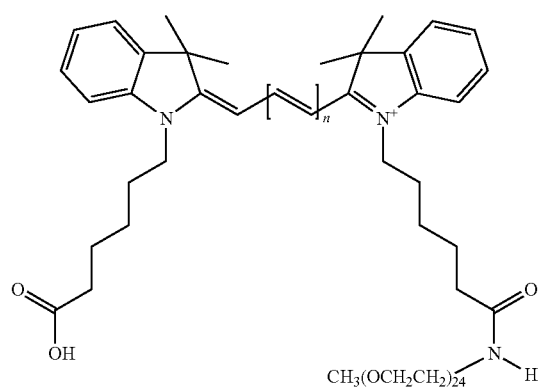
328
-continued
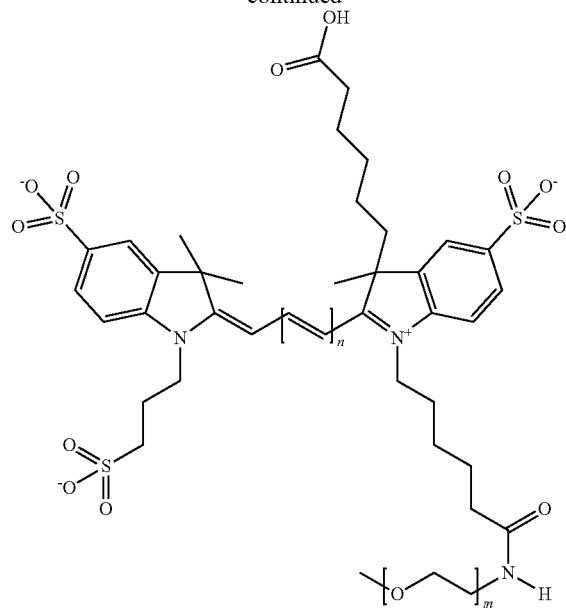
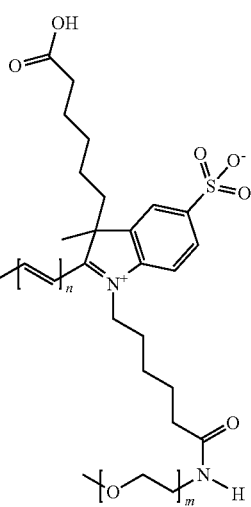
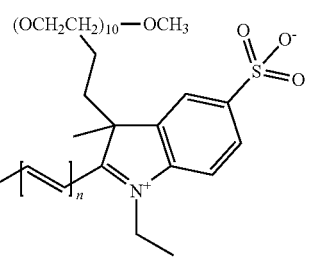

-continued

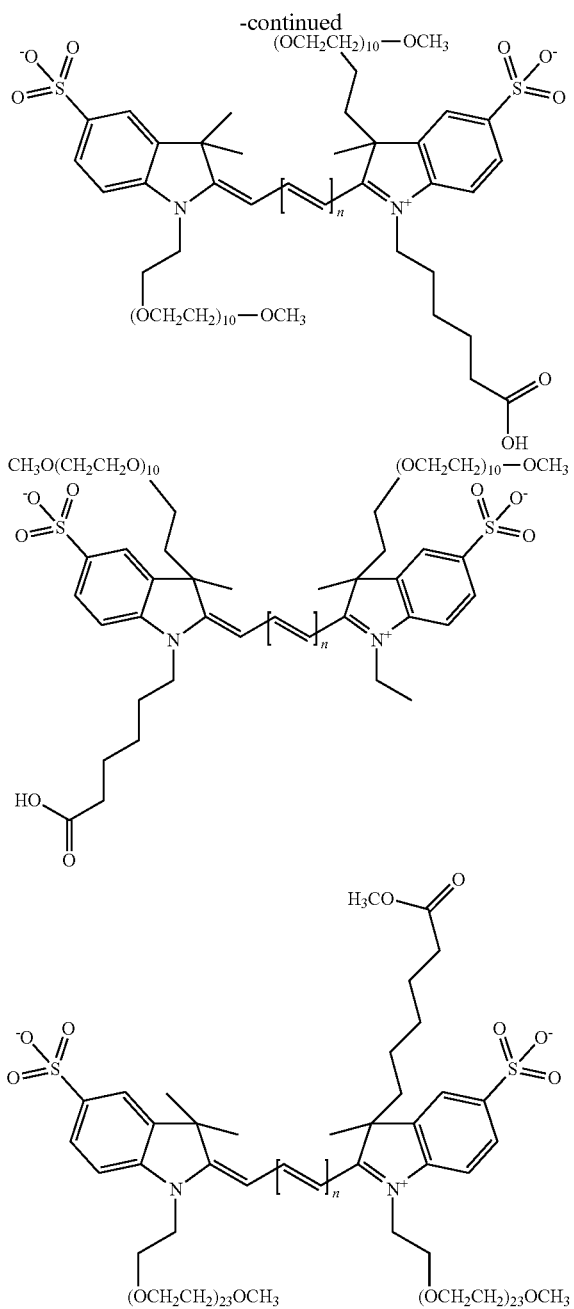

Synthesis of various polymethine bridge substitutions, and other functionalizations of indocyanines, were described in Strękowski, Heterocyclic Polymethine Dyes: Synthesis, Properties and Applications, (2008) Springer-Verlag, Berlin Heidelberg; Gragg, "Synthesis of Near-Infrared Heptamethine Cyanine Dyes" (2010). Chemistry Theses. Paper 28; Patonay et al. (2004) Noncovalent Labeling of Biomolecules with Red and Near-Infrared Dyes. Molecules 9 (2004) 40-49; and U.S. Pat. No. 7,172,907. Examples 1-5 disclose synthesis reactions for the compounds.

In one embodiment, the compound is synthesized by a condensation reaction, known to one skilled in the art, of the two differently substituted indole heterocycles separated by a (poly)methine linker or bridge, e.g., C1, C3, or C5. Other synthesis methods are possible. As only one example, one of the indole heterocycles is first reacted with the C1, C3, or C5 linker. The 1:1 condensation product is isolated, and then condensed with the second indole heterocycle to result in the cyanine compound. The sequence of reacting the indole heterocycles is irrelevant. Thus, a plurality of differently functionalized, strongly hydrophilic, diastereomeric compounds, that differ in total charge and specificity/reactivity of the active groups used for their immobilization, can be easily prepared.

Conjugates of the compounds are prepared by covalently coupling the compounds to a biomolecule using the functional substituent on the N-position of the indole ring. This functional substituent is activated by routine protein chemistry reaction methods known to one skilled in the art. The activated compound may be converted to, without limitation, an N-hydroxysuccinimide (NHS)-ester, an acid fluoride, a tetrafluorophenyl (TFP)- or sulfotetrafluorophenyl (STP)-ester, an iodoacetyl group, a maleimide, a hydrazide, a sulfonyl chloride, a phenylazide. Methods for preparing such compounds are known to one skilled in the art. In one embodiment, the activated substituent is then reacted with an amino group on the biomolecule under conditions to form the linkage. In one embodiment, a non-activated carboxyl group on the N-position of the indole in the compound is coupled to an amine using a carbodiimide.

In one embodiment, a N-hydroxysuccinimidyl ester (X=—NHS) of a compound was formed as follows: 20 μmol dye with X=OH (carboxyalkyl group), 8 mg (40 μmol) dicyclohexylcarbodiimide, and 5 mg (40 μmol) N-hydroxysuccinimide were dissolved in 2 ml of DMF and 100 μl water. Six μl (40 μmol) triethylamine was then added. The reaction mixture was stirred at room temperature (about 20° C. to about 22° C.) for 24 hours and then filtered. The solvent was removed and the residue was washed with diethylether. The reaction proceeded quantitatively.

In one embodiment, a maleimide (X=—NH—CH$_2$CH$_2$-maleimide) of a compound was formed as follows: 20 μmol dye with X=—NHS (N-hydroxysuccinimid-ester) was dissolved in 2 ml DMF and 100 μl water and mixed with 7.6 mg (30 μmol) 2-maleimidoethylamine-trifluoracetate and 5 μl (30 μmol) N-ethyldiisopropyl-amine. The reaction mixture was stirred for three hours at room temperature (about 20° C. to about 22° C.). The solvent was evaporated under reduced pressure. The residue was washed with diethylether and acetone and dried in vacuum. The reaction proceeded quantitatively.

In one embodiment, a iodoacetamide (X=—NH—CH$_2$CH$_2$—NH—CO—CH$_2$-0 of a compound was formed as follows: 20 μmol dye with X=—NHS (N-hydroxysuccinimid-ester) was dissolved in 2 ml DMF and 100 μl water, followed by the addition of 40 mg (300 μmol) ethylendiamindihydrochloride and 26 μl (150 μmol) N-ethyldiisopropyl-amine. The reaction mixture was stirred for three hours at room temperature (about 20° C. to about 22° C.). The solvent was then evaporated under reduced pressure, the residue was dissolved in methanol, and the ethylendiamindihydrochloride was removed by filtration. The methanol was evaporated under reduced pressure. The residue was dissolved in 2 ml dry DMF, followed by then addition of 7 mg (25 μmol) N-succinimidyl iodoacetate and 4 μl (25 μmol) N-ethyldiisopropyl-amine. The reaction mixture was stirred for three hours at room temperature. The solvent was evaporated under reduced pressure and the residue was purified via reverse phase HPLC.

In one embodiment, a hydroxyl group, such as a terminal hydroxyl group, can be subsequently activated to a reactive derivative able to link with, for example, proteins and other molecules. Examples of activating groups include tosyl chloride (TsCl), tresyl chloride (TrCl), disuccinimidyl carbonate (DSC), divinyl sulfone, bis-epoxy compounds, carbonyl diimidazole (CDI), 2-fluoro-1-methylpyridinium (FMP), and trichloro-s-triazine (TsT). In one embodiment, the hydroxyl group is activated to a succinimidyl carbonate, which is reactive with amines. For example, disuccinimidyl carbonate (DSC) can be used to create amine-reactive groups from hydroxyls in a single step, as described in Wilchek, M. and Miron, T. (1985) (Activation of Sepharose with N,N'-disuccinimidyl carbonate. Applied Biochemistry and Biotechnology 11, 191-193). DSC reacts with a hydroxyl group, such as at the end of a PEG chain of the described compounds, to directly form a reactive ester with loss of one molecule of NHS. This reactive group, which is an NHS carbonate, can be used to couple a described compound to amine-containing molecules, such as proteins. For example, a reaction of an NHS carbonate with an amine creates a carbamate linkage (a urethane bond), which is as stable as the amide bonds formed from the reaction of an NHS ester with an amine. In one embodiment, a terminal hydroxyl group of a PEG-containing compound can be activated with DSC to provide an NHS carbonate reactive group for coupling to amine-containing molecules. In one embodiment, the group X, as described in the disclosed general formulas, is a spacer arm that terminates in a hydroxyl group, such as a PEG group, which also can be activated with DSC to create the NHS carbonate, i.e., when X=—NR-L-O—CO—NHS.

Coupling between the compound and the biomolecule may be performed as follows. The compound is reacted with the biomolecule in an organic or aqueous solution at a pH between pH 5 and pH 12, inclusive. The compound need not be dissolved in an organic solvent, such as dimethyl formamide (DMF) or dimethyl sulfoxide (DMSO) prior to adding the biomolecule. In one embodiment, coupling reaction may be performed in a 100% aqueous solution. In one embodiment, the coupling reaction occurs at room temperature (about 20° C. to about 22° C.).

To form a dye composition, at least one biocompatible excipient is added to the compound, as known to one of ordinary skill in the art. Excipients include but are not limited to buffers, solubility enhancing agents, stabilizing agents, etc.

In one embodiment, a kit for performing an assay method comprises a disclosed compound, and instructions for performing the method using the compound.

The disclosed activated compounds (i.e., the compound modified with a reactive group) are useful to label macromolecules (e.g., antibodies, streptavidin, etc) using methods known to one skilled in the art, e.g., as disclosed in Hermanson, Bioconjugate Techniques, 2nd Ed., London, Elsevier Inc. 2008. The reaction is carried out for one hour to two hours at room temperature (about 20° C. to about 22° C.), and then desalted by dialyzing against several changes of phosphate buffered saline (pH 7.2) or purified by gel filtration to remove the unreacted fluorescent dye. The resulting compound-biomolecule conjugate is useful in applications such as detection of specific proteins in immunoassays, sugars in glycoproteins with lectins, protein-protein interactions, oligonucleotides in nucleic acid, hybridization, and in electrophoretic mobility shift assays (EMSA).

The resulting compound-biomolecule conjugates exhibit fluorescent properties. They may be used in optical, including fluorescence optical, qualitative and quantitative determination methods. Examples of such methods include, but are not limited to, microscopy, immunoassays, hybridization methods, chromatographic and electrophoretic methods, fluorescence resonance energy transfer (FRET) systems, bioluminescence resonance energy transfer (BRET) systems, high throughput screenings, analysis of receptor-ligand interactions on a microarray, etc.

Compounds of any of the embodiments can be used as dyes for optical labelling of organic or inorganic biomolecules, also referred to as recognition units. Recognition units are molecules having specificity and/or affinity for a specific group of molecules. Examples of recognition units include, but are not limited to, antibodies that have affinity for antigens, enzymes that bind and/or react with a specific bond or bonds within a sequence of amino acids in a peptide or react with a substrate, cofactors such as metals that enhance or inhibit specific interactions, lectins that bind specific sugars or sugar sequences (e.g., oligosaccharides, polysaccharides, dextrans, etc.), biotin binding proteins such as avidin and streptavidin that bind biotin and biotinylated molecules, antibody binding proteins such as Protein A, Protein G, Protein A/G and Protein L, sequences of amino acids or metals that have affinity for each other (e.g., histidine sequences bind nickel or copper, phosphate containing proteins that bind gallium, aluminium, etc.), specific sequences of nucleic acids such as DNA and/or RNA oligonucleotides that have affinity for proteins, specific sequences of amino acids that have affinity for DNA and/or RNA, haptens, carotenoids, hormones (e.g., neurohormone), neurotransmitters, growth factors, toxins, biological cells, lipids, receptor binding drugs or organic or inorganic polymeric carrier materials, fluorescent proteins such as phycobilliproteins (e.g., phycoethrin, allophycocyanin), etc. The ionic interactions between these recognition units and the disclosed compounds results in labeling of the recognition units. The recognition unit and compound can be covalently bound. The result is a conjugate for qualitative or quantitative determination of various biomaterials or other organic or inorganic materials using optical methods.

The inventive compounds and/or conjugates are useful in optical, including fluorescence optical, qualitative and/or quantitative determination methods to diagnose properties of cells (molecular imaging), in biosensors (point of care measurements), for investigation of the genome, and in miniaturizing technologies. Microscopy, cytometry, cell sorting, fluorescence correlation spectroscopy (FCS), ultra high throughput screening (uHTS), multicolor fluorescence in situ hybridization (mc-FISH), FRET-systems and microarrays (DNA- and protein chips) are exemplary application fields. As known to one skilled in the art, a microarray, a grid-like arrangement where more than two different molecules are immobilized in a known predefined region on at least one surface, is useful to evaluate receptor ligand interactions. As known to one skilled in the art, a receptor is a naturally occurring or synthetic molecule that exhibits an affinity to a given ligand. Receptors can be used in a pure form or bound to another specie. Receptors can be coupled covalently or noncovalently to a binding partner either directly or indirectly (e.g., through a coupling mediator). Receptor examples include, but are not limited to, agonists and antagonists for cell membrane receptors, toxins and other poisons, viral epitopes, hormone like opiates and steroids, hormone receptors, peptides, enzymes, enzyme substrates, drugs acting as cofactors, lectins, sugars, oligonucleotides, nucleic acids, oligosaccharides, cells, cell fragments, tissue fragments, proteins, antibodies, etc. As known to one skilled in the art, a ligand is a molecule that is recognized by a certain receptor. Ligand examples include, but are not limited to, agonists and antagonists for cell membrane receptors, toxins and other poisons, viral epitopes, hormones like opiates and steroids, hormone receptors, peptides, enzymes, enzyme substrates, drugs acting as cofactors, lectins, sugars, oligonucleotides, nucleic acids, oligosaccharides, proteins, antibodies, etc.

Adding PEG 1-6, if at the appropriate positions to strategically surround the core dye structure, have significant beneficial effects on the hydrophilicity and performance of these dyes in biological applications. Previous attempts to make dyes more hydrophilic and less "sticky" toward biomolecules included the addition of multiple sulfonates or much longer PEG chains to some locations on dye molecules. However, the addition of too many sulfonates, while having the effect of increasing the relative water solubility of dyes, can create undesirable nonspecific binding character due to negative charge interactions with positively charged biomolecules, particularly proteins. In addition, previous attempts to make dyes more water soluble by adding longer PEG chains to one or two sites on a dye has the detrimental effect of dramatically increasing the molecular weight of the dye, possibly preventing efficient access of dye-labeled antibodies and other dye-labeled targeting molecules to bind with inner cellular targets, while also not fully surrounding and masking the hydrophobic dye core structure. The inventors have discovered that by using short PEG chain modifications at critical sites on a dye structure that the total molecular size of labeled molecules can be limited, while nonspecificity is dramatically reduced by masking the hydrophobic dye core.

The following non-limiting examples further describe the compounds, methods, compositions, uses, and embodiments. They demonstrate that the inventive compounds exhibited desirable properties relative to commercially available fluorescent dyes. Signal to noise ratio (S/N) is the ratio between the desired signal and the mean of the blank, accounting for the standard deviation of the signal and the blank. Signal to background ratio (S/B) is the ratio between the desired average signal and the average blank.

EXAMPLE 1

Synthesis of 1,2-Dimethyl-1-(3-sulfopropyl)-1H-benzo[e]indole-6,8-disulfonic acid tri potassium salt

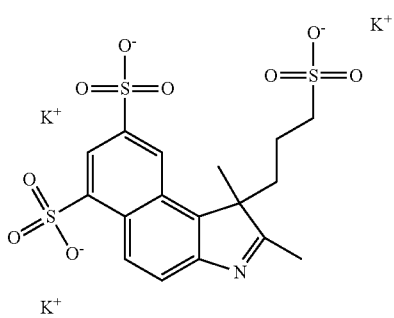 [SMILES: [K+] ; CC1=Nc2ccc3c(S(=O)(=O)[O-])cc(S(=O)(=O)[O-])cc3c2C1(C)CCCS(=O)(=O)[O-] ; [K+] ; [K+]]

Five g (15.7 mmol) 6-hydrazino-naphthalene-1,3-disulfonic acid and 4.93 g (25 mmol) 4-methyl-5-oxohexane sulfonic acid were dissolved in 50 ml acetic acid. The solution was heated at 140° C. for four hours. The solvent was evaporated in vacuum. The oily residue was dissolved in 20 ml methanol, then 50 ml of a saturated solution of KOH in 2-propanol were added to yield a yellow precipitate. The solid was filtered off and dried in vacuum. Yield 4.1 g, MS (ESI−): 158.2 $[M]^{3-}$

EXAMPLE 2

Synthesis of 3-(2-Methoxy-ethyl)-1,2-dimethyl-6,8-disulfo-1-(3-sulfopropyl)-1H-benzo[e]indolium

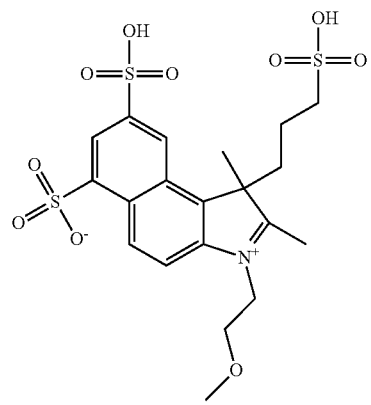 [SMILES: COCC[N+]1=C(C)C(C)(CCCS(=O)(=O)O)c2c1ccc1c(S(=O)(=O)[O-])cc(S(=O)(=O)O)cc21]

A mixture of 7.56 g (12.8 mmol) 1,2-dimethyl-1-(3-sulfopropyl)-1H-benzo[e]indole-6,8-disulfonic acid tri potassium salt and 5.89 g (25.6 mmol) 2-methoxyethyl-p-toluene sulfonate was heated under argon for 24 h. The residue was purified by column chromatography (reversed phase silica, methanol/water, TFA). Yield 3.2 g, MS (ESI−): 266.5 $[M-2H]^{2-}$

EXAMPLE 3

Synthesis of 3-(5-Carboxypentyl)-1,1,2-trimethyl-6,8-disulfo-1H-benzo[e]indolium

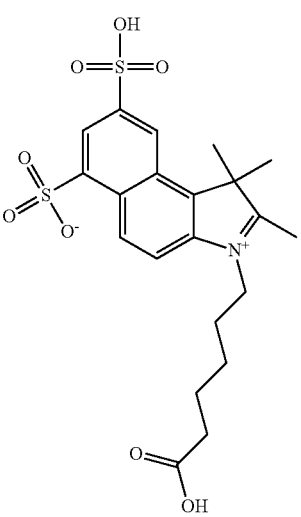 [SMILES: CC1=[N+](CCCCCC(=O)O)c2ccc3c(S(=O)(=O)[O-])cc(S(=O)(=O)O)cc3c2C1(C)C]

A mixture of 5.7 g (12.8 mmol) 1,1,2-trimethyl-1H-benzo[e]indole-6,8-disulfonic acid dipotassium salt and 5 g (25.6 mmol) 6-bromohexanoic acid was heated under argon for 24 h. The residue was purified by column chromatography (reversed phase silica, methanol/water, TFA). Yield 1.4 g, MS (ESI−): 482.1 $[M-H]^{-}$.

EXAMPLE 4

Synthesis of 3-(5-Carboxypentyl)-1,1-dimethyl-2-((1E,3E)-4-phenylamino-buta-1,3-dienyl)-6,8-disulfo-1H-benzo[e]indolium

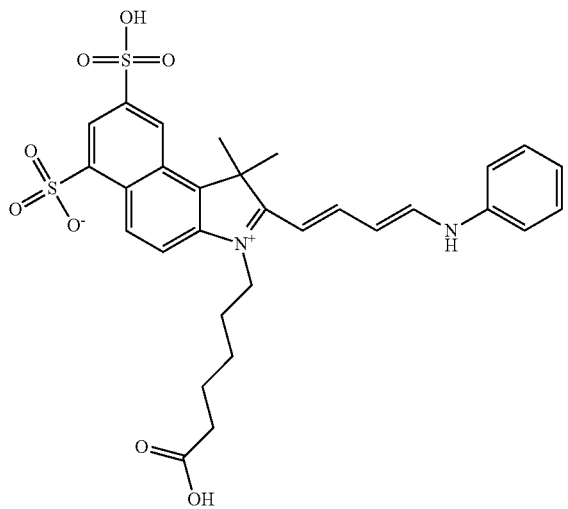 [SMILES: CC1(C)C(/C=C/C=C/Nc2ccccc2)=[N+](CCCCCC(=O)O)c2ccc3c(S(=O)(=O)[O-])cc(S(=O)(=O)O)cc3c21]

0.97 g (2 mmol) 3-(5-carboxypentyl)-1,1,2-trimethyl-6,8-disulfo-1H-benzo[e]indolium and 0.57 g (2.2 mmol) malonaldehyde-bisphenylimine-hydrochlorid were dissolved in 10 ml acetic acid and 10 ml acetic anhydride and stirred for four hours at 120° C. The solvent was removed under vacuum. The residue was washed carefully with ethyl acetate. A dark brown solid was obtained which was processed without further purification. MS (ESI−): 611.2 [M−H]⁻.

EXAMPLE 5

Synthesis of 679 Compound 1/1 (2-{(1E,3E)-5-[3-(5-Carboxypentyl)-1,1-dimethyl-6,8-disulfo-1,3-dihydro-benzo[e]indol-(2E)-ylidene]-penta-1,3-dienyl}-3-(2-methoxy-ethyl)-1-methyl-6,8-disulfo-1-(3-sulfopropyl)-1H-benzo[e]indolium)

612 mg (1 mmol) 3-(5-carboxypentyl)-1,1-dimethyl-2-((1E,3E)-4-phenylamino-buta-1,3-dienyl)-6,8-disulfo-1H-benzo[e]indolium and 533 mg (1 mmol) 3-(2-Methoxy-ethyl)-1,2-dimethyl-6,8-disulfo-1-(3-sulfopropyl)-1H-benzo[e]indolium were dissolved in 20 ml acetic acid/acetic anhydride (1/1) followed by the addition of 200 mg of sodium acetate. The solution was stirred under reflux for 15 min. After cooling to room temperature, 20 ml diethylether was added. The resulting precipitate (mixture of the diastereomers 679 Compound 1/1 (isomer 1) and 679 Compound 1/1 (isomer 2)) was extracted by suction, washed with ether, and dried.

The residue was purified by column chromatography (RP-18, acetonitrile/water and concentrated HCl) to separate the diastereomers from each other. The diastereomer that first eluted from the column was termed diastereomer 1 (679 Compound 1/1 (isomer 1)). The diastereomer that eluted second from the column was termed diastereomer 2 (679 Compound 1/1 (isomer 2)). The diastereomers were separated, followed by neutralization and evaporation. Purification of the single diastereomeric compound was completed on a RP-18 column, acetonitrile/water. The corresponding fractions were pooled and the solvent was removed by distillation. The two products (diastereomers 679 Compound 1/1 (isomer 1) and 679 Compound 1/1 (isomer 2)) were dried in high vacuum.

679 Compound 1/1 (Isomer 1)
  yield: 10%
  UV-vis (PBS): $\lambda_{max}$=679 nm
  $\lambda_{em}$=698 nm
  MS (ESI−) [M/z]: 262.5 [M]⁴⁻; 357.7 [M+Na]³⁻

679 Compound 1/1 (Isomer 2)
  yield: 23%
  UV-vis (PBS): $\lambda_{max}$=679 nm
  $\lambda_{em}$=698 nm
  MS (ESI−) [M/z]: 262.5 [M]⁴⁻; 357.7 [M+Na]³⁻

EXAMPLE 6

The following properties of 679 Compound 1-NHS were compared with commercially available dyes.

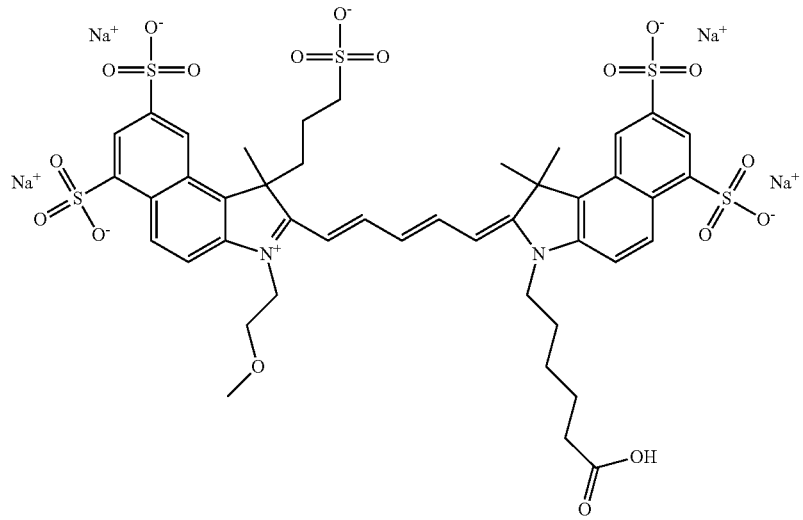 [SMILES: [Na+] ; COCC[N+]1=C(/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21 ; [Na+] ; [Na+] ; [Na+]]

|  | DyLight 680-NHS | DyLight 680B-NHS | 679 Compound 1-NHS | Company B Compound-NHS | Cy5.5 Mono Ester |
|---|---|---|---|---|---|
| MW (g/mol) | 950 | 1196.16 | 1240.21 | ~1150 | 1128.42 |
| Ex (nm) | 682 | 679 | 679 | 679 | 675 |
| Em (nm) | 715 | 698 | 698 | 702 | 694 |
| ε (M−1cm−1) (theoretical) | 140,000 | 180,000 | 180,000 | 184,000 | 250,000 |

Emission/excitation profiles for inventive and commercial compounds was determined by reconstituting the compounds in DMF at 10 mg/ml and then diluting in PBS buffer pH 7.2 to 10 μg/ml. Absorbance spectra were collected on Cary UV spectrophotometer and emission spectra were collected on Tecan Safire, shown in FIG. 1 where solid lines represent absorbance spectra and dashed lines represent emission spectra, for DyLight 680-NHS (purple), DyLight 680B-NHS (blue), 679 Compound 1-NHS (red), and Company B Compound-NHS (black). The maximum absorbance and emission for each compound is shown below.

|  | Max Abs (nm) | Max E nm |
|---|---|---|
| DyLight 680 | 677 | 715 |
| DyLight 680B | 680 | 704 |
| 679 Compound 1 | 679 | 704 |
| Company B Compound | 676 | 706 |

The following properties of 679 Compound 1-NHS, 679 Compound 4/4-NHS (V08-15173), and 679 Compound 4/4-NHS (V10-04152) were compared with commercially available dyes.

|  | DyLight 680B-NHS | 679 Compound 1-NHS | V08-15173 NHS | V10-04152 NHS | Company B Compound-NHS | Company A Compound-NHS |
|---|---|---|---|---|---|---|
| MW (g/mol) | 1196.16 | 1240.21 | 1728.8 | 1524.75 | ~1150 | 3241 |
| Ex (nm) | 679 | 679 | 684 | 689 | 679 | 681 |
| Em (nm) | 698 | 698 | 706 | 721 | 702 | 698 |
| ε (M⁻¹cm⁻¹) (theoretical) | 180,000 | 180,000 | 180,000 | 180,000 | 184,000 | 210,000 |
| PEG (length/# of chain) | 0 | 1/1 | 4/4 | 4/4 | N/A | ? |
| Sulfonate | 5 | 5 | 4 | 2 | 3 | ? | labeled dyes were then diluted 1:50 in PBS and scanned for absorbance from 700 nm to 230 nm to determine the protein concentration, and to determine the mole dye to mole protein ratio. Each conjugate was diluted 1:10 in 50% glycerol and heated in the presence of 10 mM dithiothreitol (DTT) for 5 min at 95° C., then separated by electrophoresis on polyacrylamide gels in the presence of sodium dodecyl sulfate (SDS-PAGE). The gels were scanned using the LiCor Odyssey Imager to verify removal of the unconjugated compound. Labeling efficiency was compared, with results showing degree of labeling below.

|  | DyLight 680 | DyLight 680B | 679 Compound 1 | Company B Compound | Cy5.5 |
|---|---|---|---|---|---|
| GAM-2X | 0.9 | 1.9 | 2.0 | — | 1.6 |
| GAM-3X | 1.3 | 2.7 | 3.0 | — | 2.2 |
| GAM-4X | 2.0, 1.9 | 3.6, 3.6 | 3.6, 3.7 | 2.8 | 2.6 |
| GAM-6X | 2.3 | 5.0 | 5.1 | 3.9 | — |
| GAM-8X | 2.4 | 5.6 | 5.0 | 4.3 | — |
| GAM-10X | 3.0 | 6.5 | 6.8 | 5.4 | — |
| GAM-12X | 3.0 | 7.4 | 7.2 | 6.2 | — |
| GAR-1X | 0.5 | 0.9 | 1.0 | | 0.7 |
| GAR-2X | 1.0 | 1.5 | 1.6 | | 1.2 |
| GAR-3X | 1.3 | 2.1 | 2.4 | | 1.7 |
| GAR-4X | 1.7, 1.8 | 2.6, 3.1 | 3.1, 3.1 | 2.3 | 2.2 |
| GAR-6X | 2.2 | 4.4 | — | — | — |
| GAR-8X | 2.4 | 5.5 | 5.6 | 4.2 | — |
| GAR-10X | 3.5 | 6.0 | 6.7 | 5.3 | — |
| GAR-12X | 3.4 | 6.6 | 6.7 | 6.2 | — |
| SA-6X | 2.9 | 4.1 | 4.0 | 4.1 | — |
| SA-8X | 3.4 | 4.7 | 5.0 | 4.8 | — |

EXAMPLE 7

Inventive and commercial compounds, each as the NHS ester, were conjugated to goat anti-mouse (GAM) antibodies, goat anti-rabbit (GAR) antibodies, and streptavidin (SA). GAM, GAR, and SA, at a concentration of 10 mg/ml in phosphate buffered saline (PBS), were dialyzed against 50 mM borate buffer, pH 8.5. The compounds were reconstituted in dimethylformamide (DMF) at 10 mg/ml and combined at 1×, 2×, 3×, 4×, 6×, 8×, 10×, or 12× molar excess with GAM, GAR, or SA for two hours at room temperature to label the antibodies or SA.

The labeled compounds, also termed dyes or labels, were subjected to Pierce Dye Removal Resin (PDDR) to remove the unlabeled (free) compound; 100 μl of the packed resin was used per mg of protein purified. The purified antibody- Labeling efficiency of GAM, GAR and SA was equivalent for 679 compound 1-NHS compared to DyLight 680B-NHS and higher compared to DyLight 680 and Company B (Life Technologies) compound. The antibodies were labeled, purified, and evaluated by SDS-PAGE as described above. Antibodies were also labeled with Company A (Biotium) compound, which was reconstituted in dimethylsulfoxide (DMSO) and combined at 2×, 5×, 7.5×, 10×, and 15× molar excess with GAM or GAR for sixty-five minutes at room temperature to label the antibodies.

Inventive and commercial compounds, each as the NHS ester, were conjugated to goat anti-rat (GARat) antibodies. GARat, at a concentration of 10 mg/ml in phosphate buffered saline (PBS), was spiked with 10% v/v with 0.67 M borate buffer. The compounds were combined at 5× or 10× molar excess with GAR at for 65 minutes at room temperature to label the antibody. The antibodies were labeled, purified and evaluated by SDS-PAGE as described above.

Labeling efficiency of GARat was slightly higher for 679 Compound 1-NHS compared to DyLight 680B-NHS, V08-15173-NHS and Company B compound-NHS.

In another set of experiments, the labeling of GAM with the inventive and commercial compounds is shown below.

|  | Mole Dye/Mole Protein Ratio @ 2.5 X | Mole Dye/Mole Protein Ratio @ 5 X | Mole Dye/Mole Protein Ratio @ 7.5 X | Mole Dye/Mole Protein Ratio @ 10 X | Mole Dye/Mole Protein Ratio @ 15 X |
|---|---|---|---|---|---|
| V08-15173 | 2.5 | 4.9 | 7.1 | 8.9 | 12.4 |
| V10-04152 | 2.8 | 5.1 | 7.4 | 10.0 | 13.9 |
| DY679P1 | 1.8 | 4.1 | 6.6 | 8.5 | 12.9 |
| Company A compound | 1.1 | 5.3 | 7.4 | 9.4 | 12.6 |
| Company B compound | 1.8 | 4.0 | 6.3 | 8.3 | 13.1 |

Labeling efficiency of GAM was similar for all the dyes at all molar excesses.

In another set of experiments, the labeling of GAR with the inventive and commercial compounds is shown below, at a molar excess of 5×, 15×, and 25×.

|  | Mole Dye/Mole Protein Ratio @ 5 X | Mole Dye/Mole Protein Ratio @ 15 X | Mole Dye/Mole Protein Ratio @ 25 X |
|---|---|---|---|
| V08-15173 | 4.6 | 12.7 | 19.6 |
| V10-04152 | 2.2 | 10.1 | 13.9 |
| DY679P1 | 4.8 | 10.6 | 14.4 |
| Company A Compound | 3.4 | 9.8 | 15.4 |
| Company B Compound | 4.1 | 15.2* | 46.7* |

At 5×, the labeling efficiency of GAR for all the dyes was similar except for V10-04152. At 15× and 25×, the labeling efficiency was similar except for Company B compound. [*Company B compound conjugates precipitated in the Thermo Scientific Slide-A-Lyzer Dialysis Cassettes at molar excesses greater than 10×, indicating this method of purification was not suitable for Company B dyes.]

Figure 3:
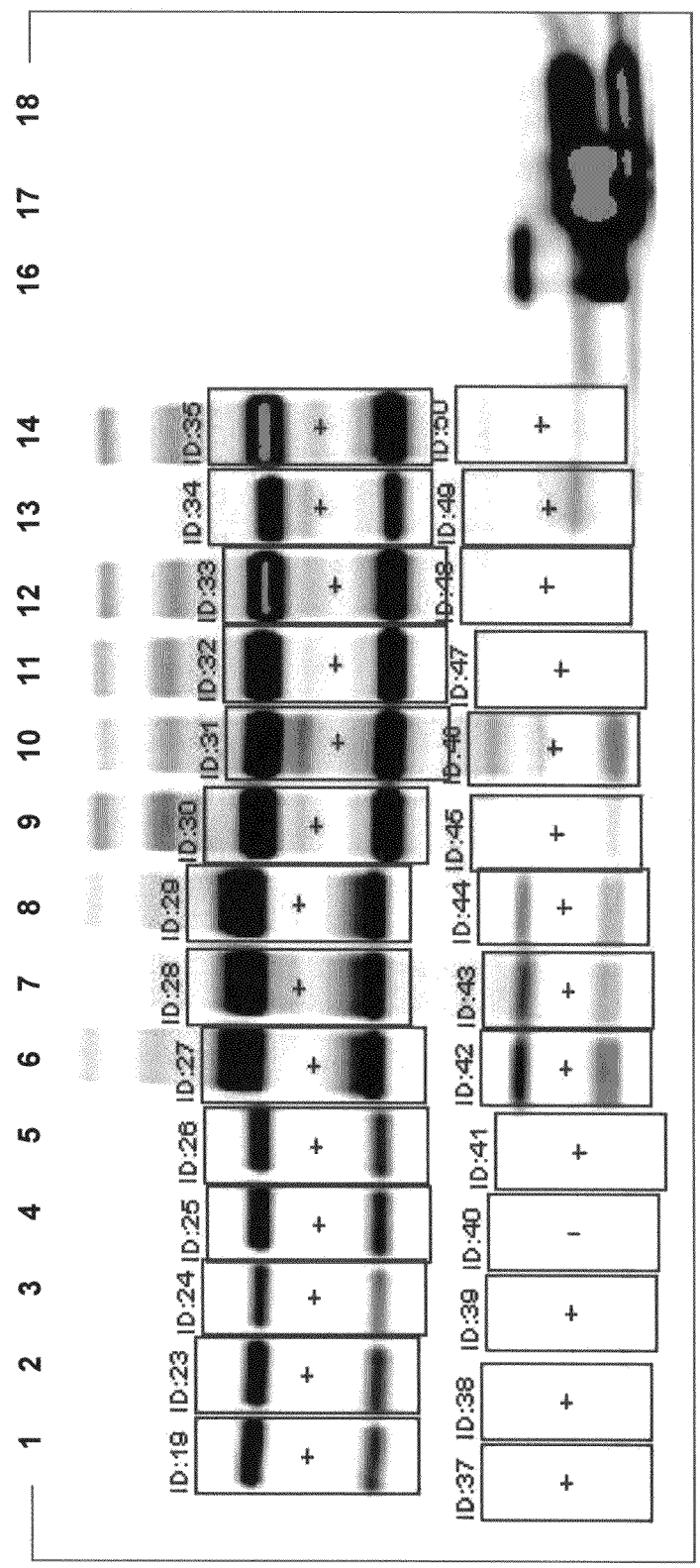
FIG. 3 shows gel images of free dye using conjugates of inventive and commercial dyes.

One experiment set used inventive and commercial compounds, each as the NHS ester, in a macro conjugation (labeling of ≥1 mg antibody) to goat anti-mouse (GAM), goat anti-rabbit (GAR), or goat anti-rat (GARt) antibodies were labeled as follows: (1) GAM (H+L; heavy+light chains) at 2.3 mg/ml in PBS pH 7.4 with 10% v/v 0.67 M borate buffer or with 10% v/v 1 M carbonate buffer; or (2) GAR (H+L) at 2.4 mg/ml in PBS pH 7.4 with 10% v/v 0.67 M borate buffer or with 10% v/v 1 M carbonate buffer; or (3) GARat (H+L) at 2.0 mg/ml in PBS pH 7.4 with 10% v/v 0.67 M borate buffer or with 10% v/v 1 M carbonate buffer. They were added to the vials containing 679 Compound 4/4-NHS Ester (V08-15173), starting with either 50 μg, 65 μg, or 100 μg, or commercial labeling kits CF680 Succinimidyl Ester Protein Labeling Kit (Biotium, #92220), CF680R Succinimidyl Ester Protein Labeling Kit (Biotium, #92226), and Alexa Fluor 680 Protein Labeling Kit (Life Technologies, #A20172). The antibodies were labeled and processed according to the manufacturer's instructions. Conjugates made with the inventive dyes were purified using Pierce Dye Removal Resin. The results of the labeling reactions using 50 μg of inventive compound are shown below. Protein recovery refers to the percentage of labeled antibody recovered after the labeling reaction and purification, and was calculated using the absorbance spectra. The percent free dye was determined by SDS-PAGE and densitometry using a LICOR Imager (FIG. 3). From left to right, lanes 1 and 2 are GAM, lane 3 is GARat, and lanes 4 and 5 are GAR conjugated to 679 Compound 4/4. Lanes 6, 7, and 8 are GAM, GARat, and GAR respectively, conjugated to dye in the CF 680 Biotium Labeling Kit. Lanes 9, 10, and 11 are GAM, GARat, and GAR respectively conjugated to dye in the CF 680R Biotium Labeling Kit. Lanes 12, 13, and 14 are GAM, GARat, and GAR respectively conjugated to dye in the Alexa Fluor 680 Life Technologies Labeling Kit. Lanes 16, 17, and 18 correspond to unconjugated Biotium's CF 680, Life Technologies' Alexa Fluor 680 and inventive 679 Compound 4/4, respectively.

|  | Mole Dye/Mole Protein Ratio | Protein recovery | % Free Dye |
|---|---|---|---|
| 679 Compound 4/4-GAM (50 μg)_1 | 1.2 | 95% | 3% |
| 679 Compound 4/4-GAM (50 μg)_2 | 1.2 | 92% | 4% |
| 679 Compound 4/4-GARat (50 μg) | 0.8 | 94% | 13% |
| 679 Compound 4/4-GAR (50 μg)_1 | 1.4 | 88% | 4% |
| 679 Compound 4/4-GAR (50 μg)_2 | 1.3 | 89% | 4% |
| CF680-GAM | 4.0 | 107% | 19% |
| CF680-GARat | 3.5 | 66% | 19% |
| CF680-GAR | 3.5 | 89% | 10% |
| CF680R-GAM | 7.6 | 78% | 3% |
| CF680R-GARat | 7.2 | 70% | 9% |
| CF680R-GAR | 5.7 | 105% | 2% |
| Alexa 680-GAM | 5.0 | 61% | 2% |

-continued

|  | Mole Dye/Mole Protein Ratio | Protein recovery | % Free Dye |
|---|---|---|---|
| Alexa 680-GARat | 2.0 | 62% | 19% |
| Alexa 680-GAR | 5.8 | 46% | 3% |

Absorbance spectra of the conjugates (FIG. 2) were collected on Cary UV spectrophotometer by scanning the conjugates diluted 1:50 in PBS from 230 nm to 800 nm, with absorbance at specific wavelengths shown in the table below.

|  | Abs 280 nm | Abs 685 nm |
|---|---|---|
| 679 Compound 4/4-GAM (50 µg) | 0.152 | 0.145 |
| 679 Compound 4/4-GARat (50 µg) | 0.121 | 0.074 |
| 679 Compound 4/4-GAR (50 µg) | 0.150 | 0.156 |
| CF 680-GAM | 0.195 | 0.570 |
| CF 6800-GARat | 0.101 | 0.267 |
| CF 680-GAR | 0.172 | 0.459 |
| CF 680R-GAM | 0.288 | 0.558 |
| CF 680R-GARat | 0.206 | 0.389 |
| CF 680R-GAR | 0.340 | 0.585 |
| Alexa 680-GAM | 0.109 | 0.393 |
| Alexa 680-GARat | 0.082 | 0.130 |
| Alexa 680-GAR | 0.088 | 0.357 |

Labeling efficiency (D/P; mole dye to mole protein ratio) is lower with 679 Compound 4/4 compared to Biotium's Protein Labeling Kit and Life Technologies' Protein Labeling Kit. Protein recovery for GAM, GAR, GARat labeled with 679 Compound 4/4 was >80% and amount of free dye was <5% except for GARat conjugate.

Figure 5:
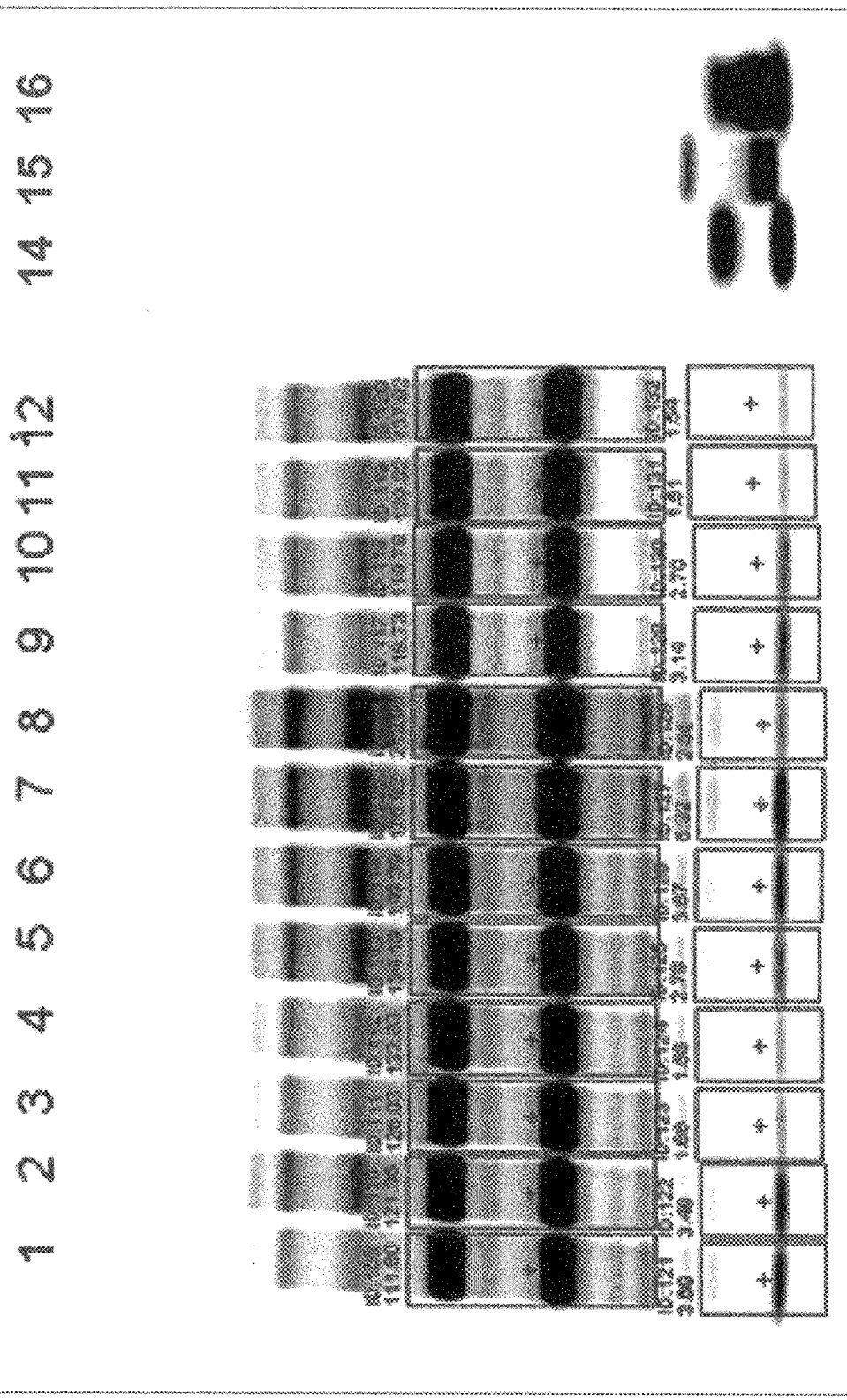
FIG. 5 shows gel images of free dye using conjugates of inventive and commercial dyes.

Labeling results using 65 µg or 100 µg of inventive compound are shown below, where Protein recovery is as described above, and the % Free Dye was determined by SDS-PAGE and densitometry using a LICOR Imager, as shown in FIG. 5, where lanes 1-5 are GAM conjugates using 65 µg 679 Compound 4/4, lanes 6-8 are GAM conjugates using 100 µg 679 Compound 4/4, lanes 9-12 are GAR conjugates using 65 µg 679 Compound 4/4, and lanes 14, 15 and 16 correspond to unconjugated 679 Compound 4/4, Biotium's CF 680, and Life Technologies' Alexa Fluor 680, respectively.

| Conjugates | D/P | Protein recovery | % Free Dye |
|---|---|---|---|
| 679 Compound 4/4-GAM 65 µg | 1.6 | 120% | 3% |
| 679 Compound 4/4-GAM 65 µg | 1.6 | 125% | 3% |
| 679 Compound 4/4-GAM 65 µg | 1.8 | 150% | 1% |
| 679 Compound 4/4-GAM 65 µg | 1.9 | 121% | 1% |
| 679 Compound 4/4-GAM 65 µg | 2.0 | 118% | 2% |
| 679 Compound 4/4-GAM 100 µg | 2.0 | 117% | 2% |
| 679 Compound 4/4-GAM 100 µg | 2.3 | 118% | 3% |
| 679 Compound 4/4-GAM 100 µg | 2.6 | 117% | 1% |

-continued

| Conjugates | D/P | Protein recovery | % Free Dye |
|---|---|---|---|
| 679 Compound 4/4-GAR 65 µg | 1.7 | 114% | 3% |
| 679 Compound 4/4-GAR 65 µg | 1.5 | 113% | 2% |
| 679 Compound 4/4-GAR 65 µg | 2.0 | 116% | 1% |
| 679 Compound 4/4-GAR 65 µg | 1.7 | 113% | 1% |

Figure 4:
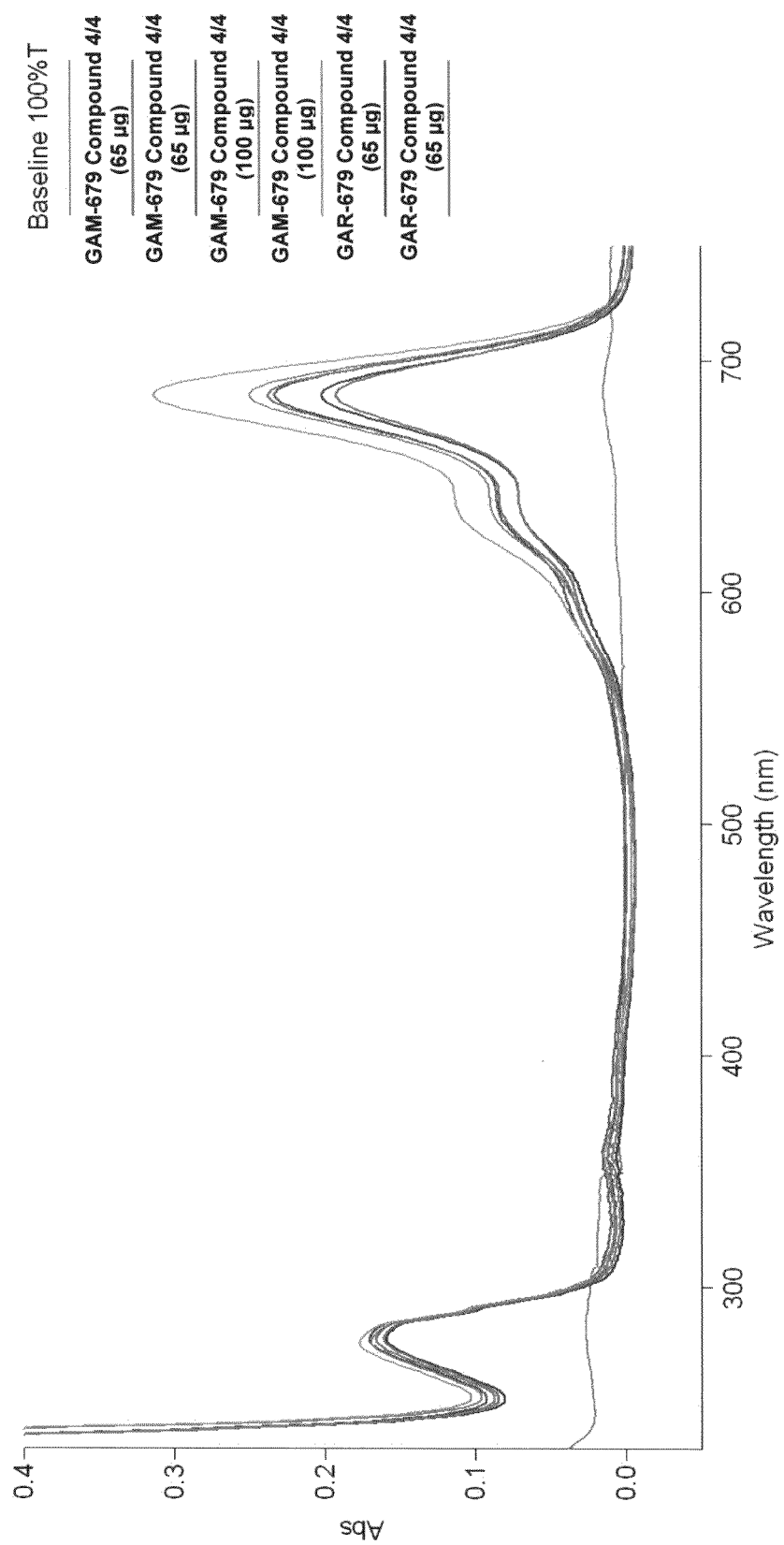
FIG. 4 shows absorption/emission profiles of some inventive compounds and commercial dyes.

Absorbance spectra of the conjugates were collected on Cary UV spectrophotometer, as described above for FIG. 2, and are shown in FIG. 4, with absorbance at specific wavelengths shown in the table below.

|  | Abs 280 nm | Abs 685 nm |
|---|---|---|
| 679 Compound 4/4-GAM (65 µg) | 0.158 | 0.192 |
| 679 Compound 4/4-GAM (65 µg) | 0.168 | 0.233 |
| 679 Compound 4/4-GAM (100 µg) | 0.165 | 0.249 |
| 679 Compound 4/4-GAM (100 µg) | 0.171 | 0.313 |
| 679 Compound 4/4-GAR (65 µg) | 0.157 | 0.201 |
| 679 Compound 4/4-GAR (65 µg) | 0.163 | 0.237 |

Labeling efficiency (D/P) with 679 Compound 4/4 was slightly higher with carbonate buffer compared with borate buffer spike, and resulted in a lower amount of free dye. Protein recovery for GAM, GAR, GARat labeled with 679 Compound 4/4 was unexpectedly high (>100%) and amount of free dye was <5%.

Another experiment set used inventive and commercial compounds, each as the NHS ester, in a micro conjugation (labeling of ≥0.1 mg antibody). Either (1) α-tubulin mouse MAb (1 mg/ml; BSA and azide free) with 10% v/v 0.67M borate buffer or 10% v/v 1 M carbonate buffer (used in Biotium and Life Technologies kits); (2) PDI mouse MAb (1 mg/ml; contains 1 mg/ml BSA and 0.05% azide) with 10% v/v 0.67M borate buffer or 10% v/v 1 M carbonate buffer; or (3) cytochrome C mouse MAb (1 mg/ml in PBS; contains 0.1% azide) with 10% v/v 0.67M borate buffer or 10% v/v 1M carbonate buffer were added to vials containing 15 µg 679 Compound 4/4-NHS Ester (V08-15173) or DyLight 680 NHS Ester from DyLight 680 Microscale Antibody Labeling Kit (Thermo Scientific, #53057), or commercial labeling kits Mix-n-Stain CF 680 Labeling Kit (50-100 µg) (Biotium, #92246), Mix-n-Stain CF 680R Labeling Kit (50-100 µg) (Biotium, #92240), or Alexa Fluor 680 Antibody Labeling Kit (Life Technologies, # A20188). The antibodies were labeled and purified as described above. The results of the labeling reactions are shown below.

|  | Mole Dye/Mole Protein Ratio | Protein recovery | % Free Dye |
|---|---|---|---|
| DyLight 680-α-tubulin | 2.6 | 100% | 21% |
| 679 Compound 4/4-α-tubulin | 2.5 | 100% | 7% |
| CF 680R-α-tubulin | 2.9 | 123% | 2% |
| Alexa 680-α-tubulin | 5.4 | 84% | 3% |
| 679 Compound 4/4-PDI | 1.9 | 149% | 18% |
| CF 680-PDI | 3.2 | 183% | 37% |

-continued

|  | Mole Dye/Mole Protein Ratio | Protein recovery | % Free Dye |
|---|---|---|---|
| Alexa 680-PDI | 8.4 | 133% | 9% |
| 679 Compound 4/4-cytochrome C | 1.5 | 91% | 13% |
| CF 680-cytochrome C | 4.2 | 132% | 17% |
| CF 680R-cytochrome C | 4.9 | 124% | 5% |
| Alexa 680-cytochrome C | 10.1 | 80% | 3% |

Figure 6:
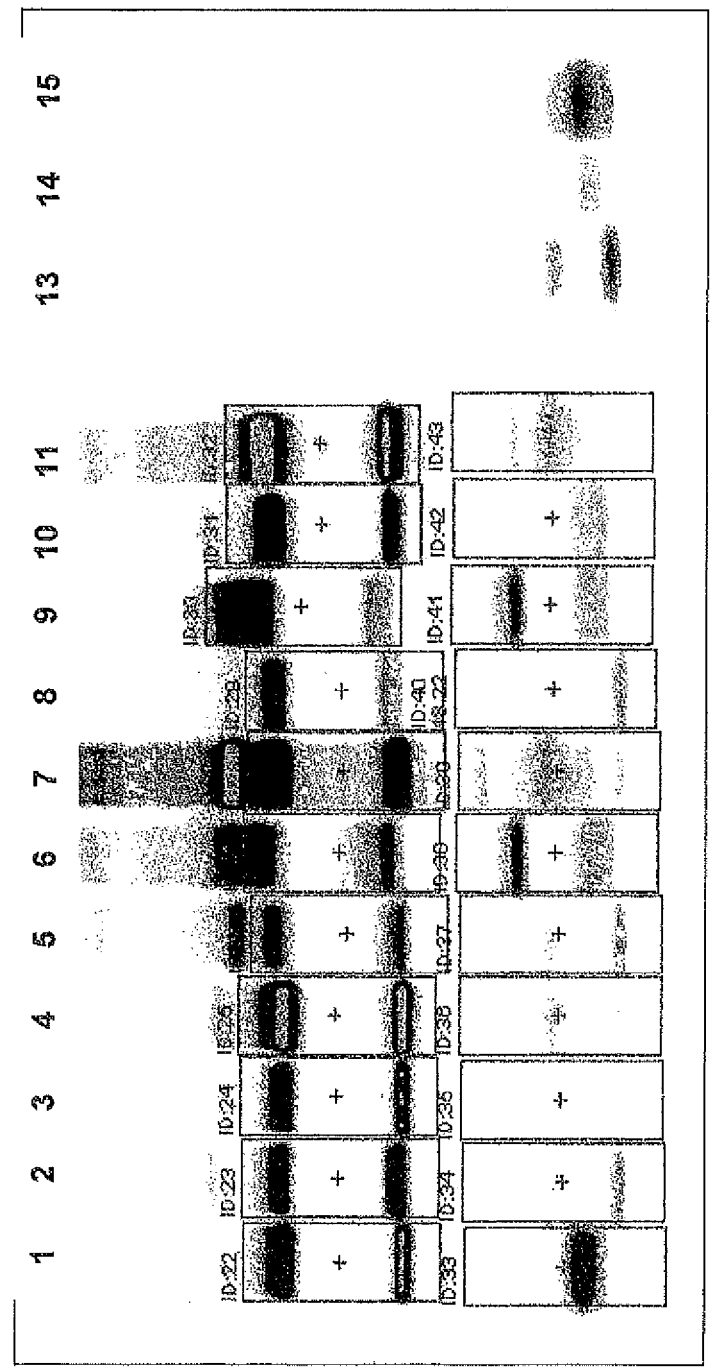
FIG. 6 shows gel images of free dye using conjugates of inventive and commercial dyes.

Free Dye analysis was performed as described above, and are shown in FIG. 6. Lanes 1-4 are conjugates of α-tubulin with DyLight 680, 679 Compound 4/4, CF 680R, and Alexa 680, respectively. Lanes 5-7 are conjugates of PDI with 679 Compound 4/4, CF 680, and Alexa 680, respectively. Lanes 8-11 are conjugates of cytochrome C with 679 Compound 4/4, CF 680, CF 680R, and Alexa 680, respectively. Lanes 13-15 are unconjugated 679 Compound 4/4, Biotium's CF 680, and Life Technologies' Alexa Fluor 680, respectively. The results showed very similar labeling efficiency of α-tubulin with 679 Compound 4/4 (15 µg) compared to Biotium's Antibody Labeling Kits (CF 680 and CF 680R), but showed lower D/P compared to α-tubulin labeled with Life Technologies Antibody Labeling Kit. The amount of free dye for 679 Compound 4/4-α-tubulin was lower than for DyLight 680-α-tubulin (7% vs. 21%), but slightly lower for Biotium's and Life Technologies Antibody Labeling Kits (2% and 3%, respectively). Labeling efficiency of cytochrome C was lower with 679 Compound 4/4 compared to the competitors' labeling kits. The amount of free dye was similar for 679 Compound 4/4-cytochrome C and CF 680-cytochrome C (13% and 17%, respectively).

EXAMPLE 8

Performance of the dye-GAM conjugates, dye-GAR conjugates, and dye-SA conjugates was evaluated in a functional plate assay. Wells of a 96 white opaque plate or black clear-bottom plate were coated with target proteins mouse IgG immunoglobulin, rabbit IgG immunoglobulin, or biotinylated bovine serum albumin (BBSA). One hundred µl mouse or rabbit IgG, or BBSA at a concentration of 10 µg/ml was applied to the corresponding wells in columns 1 and 2. The target proteins were serially diluted 1:1 from the wells in columns 2 to 11 using 100 µl PBS. One hundred µl of the samples from the wells in column 11 were discarded. One hundred µl PBS was added to the wells in column 12. The plates were incubated overnight at 4° C. and then blocked 2×200 µl with Thermo Scientific SuperBlock® Blocking Buffer. The coated plates were washed 2×200 µl with PBS-Tween and 1×200 µl with PBS. Based on the calculated concentrations, conjugates were diluted 1:250 in PBS, added to the corresponding plates (100 µl/well) and then incubated for one hour in the dark. The plates were washed with 2×200 µl with PBS-Tween and 1×200 µl with PBS and filled with PBS buffer (100 µl/well) prior to scanning the white opaque plates on Tecan Safire using 679 nm excitation/702 nm emission or scanning the black clear-bottom plates on LiCor Odyssey at 700 channel, to detect fluorescence intensity.

As shown in FIGS. 7-12, RFU and/or signal to background ratio (S/B) of the dyes were compared at various concentrations, using the indicated conjugation conditions.

Figure 7:
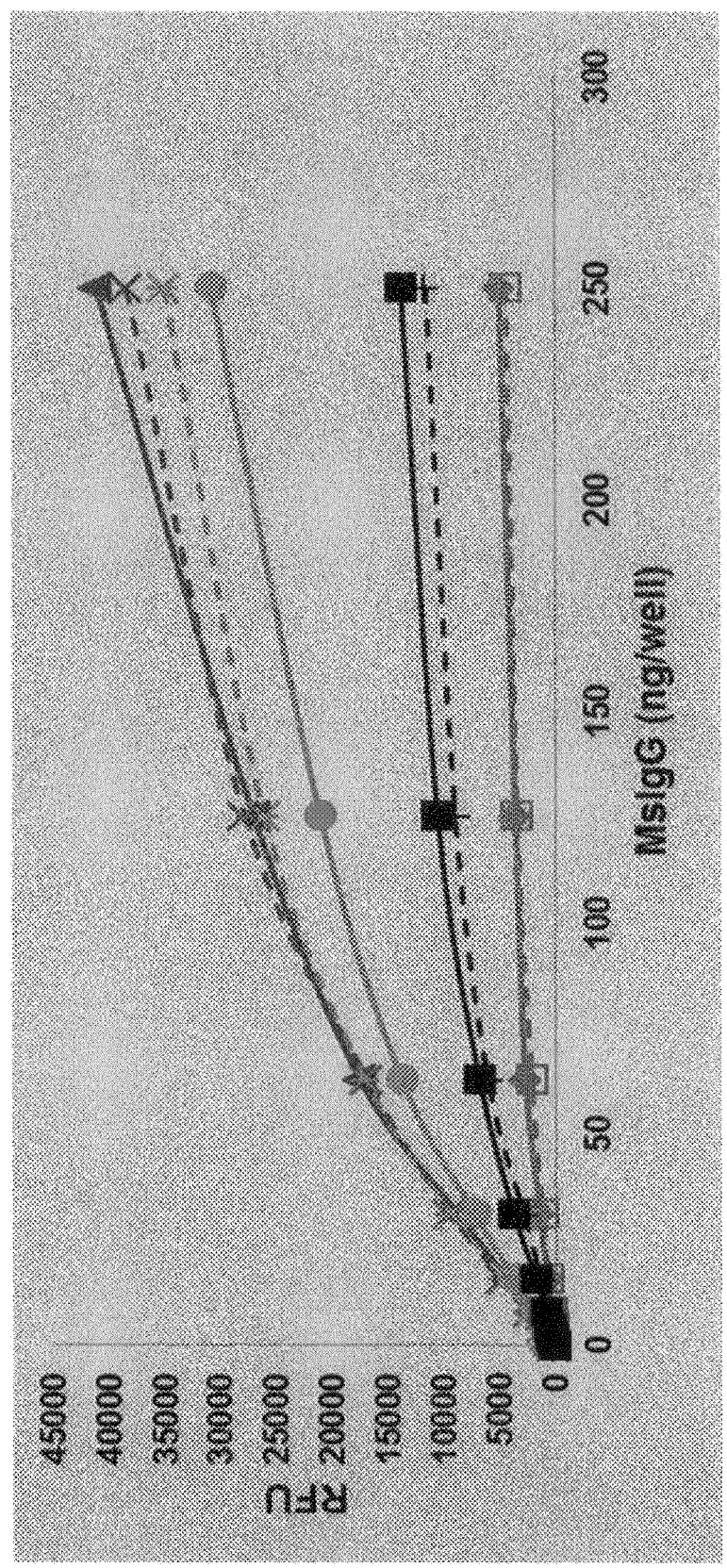
FIG. 7 graphs functional fluorescence plate assay results with some commercial dyes and inventive compounds with one conjugate produced in one embodiment.

FIG. 7 shows Tecan Safire results of a functional assay using GAM conjugated with either 8× molar excess of the dyes (solid lines) or 10× molar excess of the dyes (dashed lines) of DyLight 680 (purple filled diamond/open square); DyLight 680B (blue filled triangle/X); 679 Compound 1 (red filled circle/asterisk); and Company B Compound (black filled square/+ sign). DyLight 680B-GAM (8×) showed higher binding fluorescence compared to corresponding 679 Compound 1-GAM (8×). At 10× molar excess, 679 Compound 1-GAM showed similar performance to DyLight 680B-GAM. Both DyLight 680 and Company B compound showed much lower intensity compared to DyLight 680B and 679 Compound 1 conjugates. Signal/Background (S/B) was higher for DyLight 680B-GAM conjugates than 679 Compound 1-GAM conjugates. Similar results were generally obtained for GAR conjugates.

Figure 8:
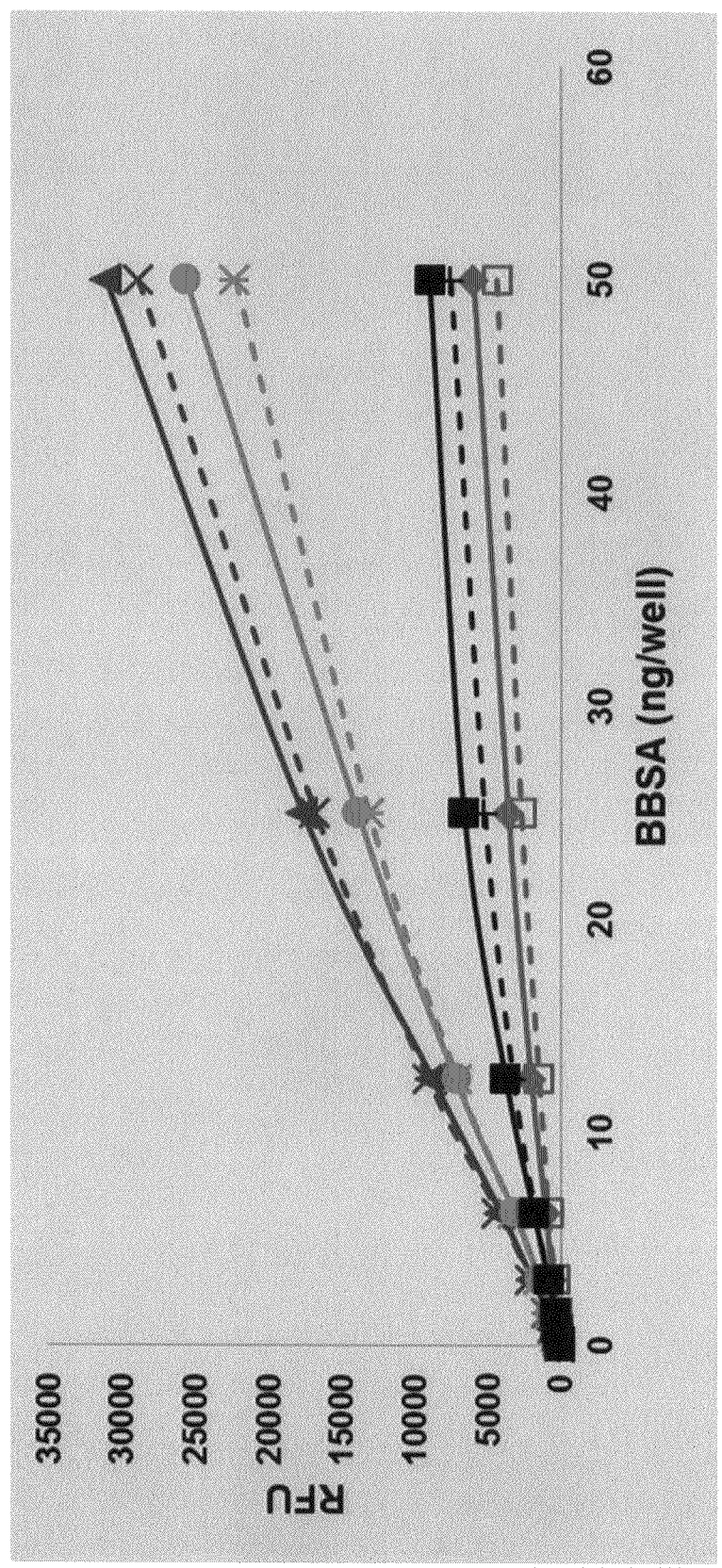
FIG. 8 graphs functional fluorescence plate assay results with some commercial dyes and inventive compounds with another conjugate produced in one embodiment.

FIG. 8 shows Tecan Safire results of a functional assay using SA conjugated with either 6× molar excess of the dyes (solid lines) or 8× molar excess of the dyes (dashed lines) of DyLight 680 (purple filled diamond/open square); DyLight 680B (blue filled triangle/X); 679 Compound 1 (red filled circle/asterisk); and Company B Compound (black filled square/+ sign). 679 Compound 1-SA (6×, 8×) showed slightly lower binding fluorescence compared to corresponding DyLight 680B-SA (6×, 8×). There was no quenching trend with the conjugates at higher molar excesses. The S/B was slightly lower for 679 Compound 1-SA conjugates than for DyLight 680B-SA conjugates.

Figure 9:
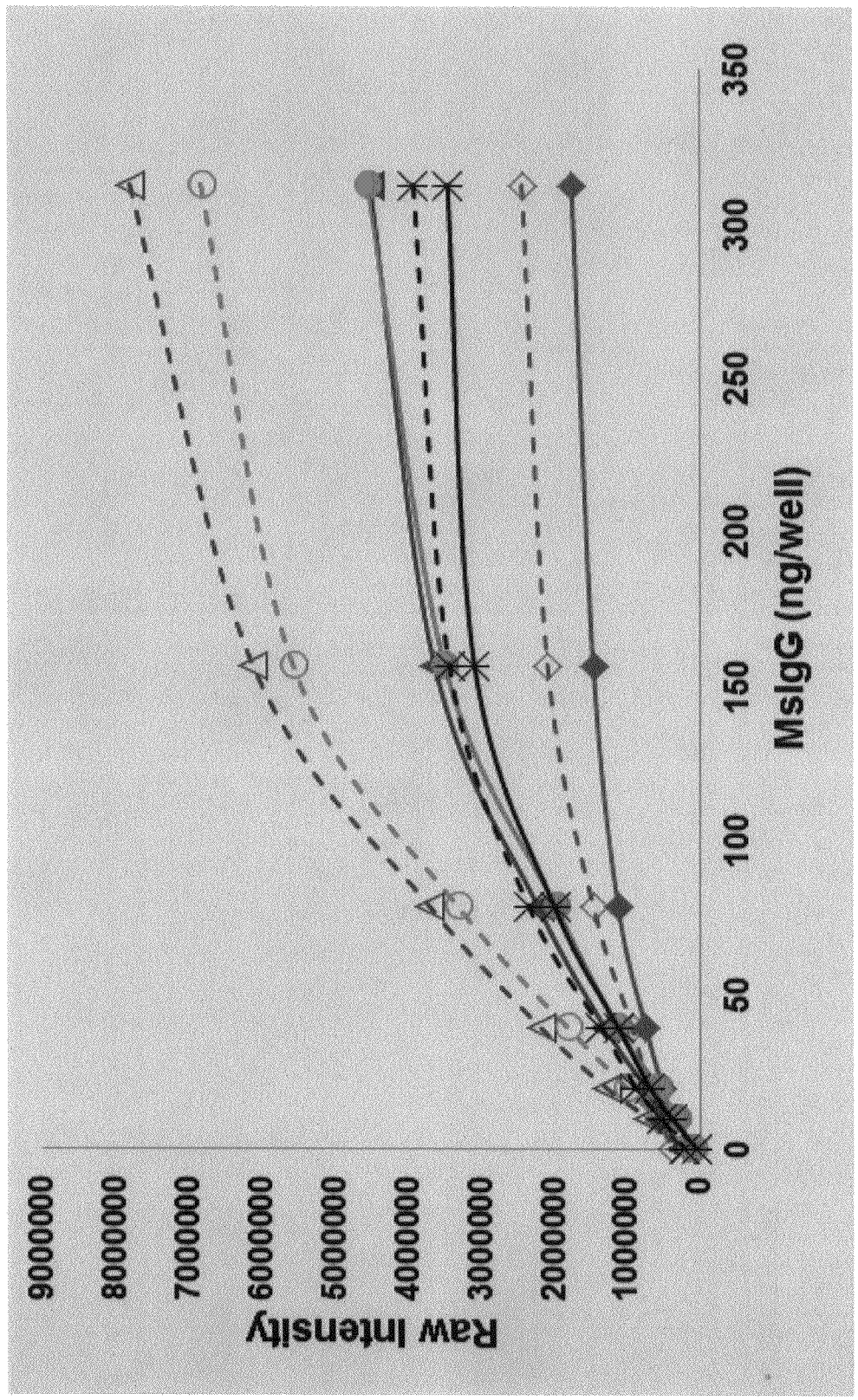
FIG. 9 graphs functional fluorescence plate assay results with some commercial dyes and inventive compounds with another conjugate produced in one embodiment.

FIG. 9 shows LiCor Odyssey results of a functional assay using GAM conjugated with either 2× molar excess of the dyes (solid lines) or 4× molar excess of the dyes (dashed lines) of DyLight 680 (purple diamond); DyLight 680B (blue triangle); 679 Compound 1 (red circle); and Cy5.5 (black asterisk). The following table compared S/B and raw intensity data.

|  | @ 1250 ng coating | @ 39 ng coating | @ 0 (blank) |
|---|---|---|---|
| S/B |  |  |  |
| DyLight 680-GAM-2X | 25.3 | 9.8 | 1.0 |
| DyLight 680-GAM-4X | 6.4 | 2.3 | 1.0 |
| DyLight 680B-GAM-2X | 18.2 | 4.6 | 1.0 |
| DyLight 680B-GAM-4X | 31.9 | 8.1 | 1.0 |
| 679 Compound 1-GAM-2X | 36.1 | 7.9 | 1.0 |
| 679 Compound 1-GAM-4X | 65.2 | 15.9 | 1.0 |
| Cy5.5-GAM-2X | 62.3 | 17.7 | 1.0 |
| Cy5.5-GAM-4X | 19.6 | 6.1 | 1.0 |
| Raw Intensity |  |  |  |
| DyLight 680-GAM-2X | 1941300 | 751514 | 76795 |
| DyLight 680-GAM-4X | 2596363 | 937396 | 403405 |
| DyLight 680B-GAM-2X | 5179777 | 1311798 | 284501 |
| DyLight 680B-GAM-4X | 8614438 | 2190343 | 270357 |
| DY679P1-GAM-2X | 5180336 | 1135001 | 143352 |
| DY679P1-GAM-4X | 7482510 | 1820225 | 114807 |
| Cy5.5-GAM-2X | 3957169 | 1124788 | 63513 |
| Cy5.5-GAM-4X | 4379901 | 1358039 | 223585 |

Figure 10:
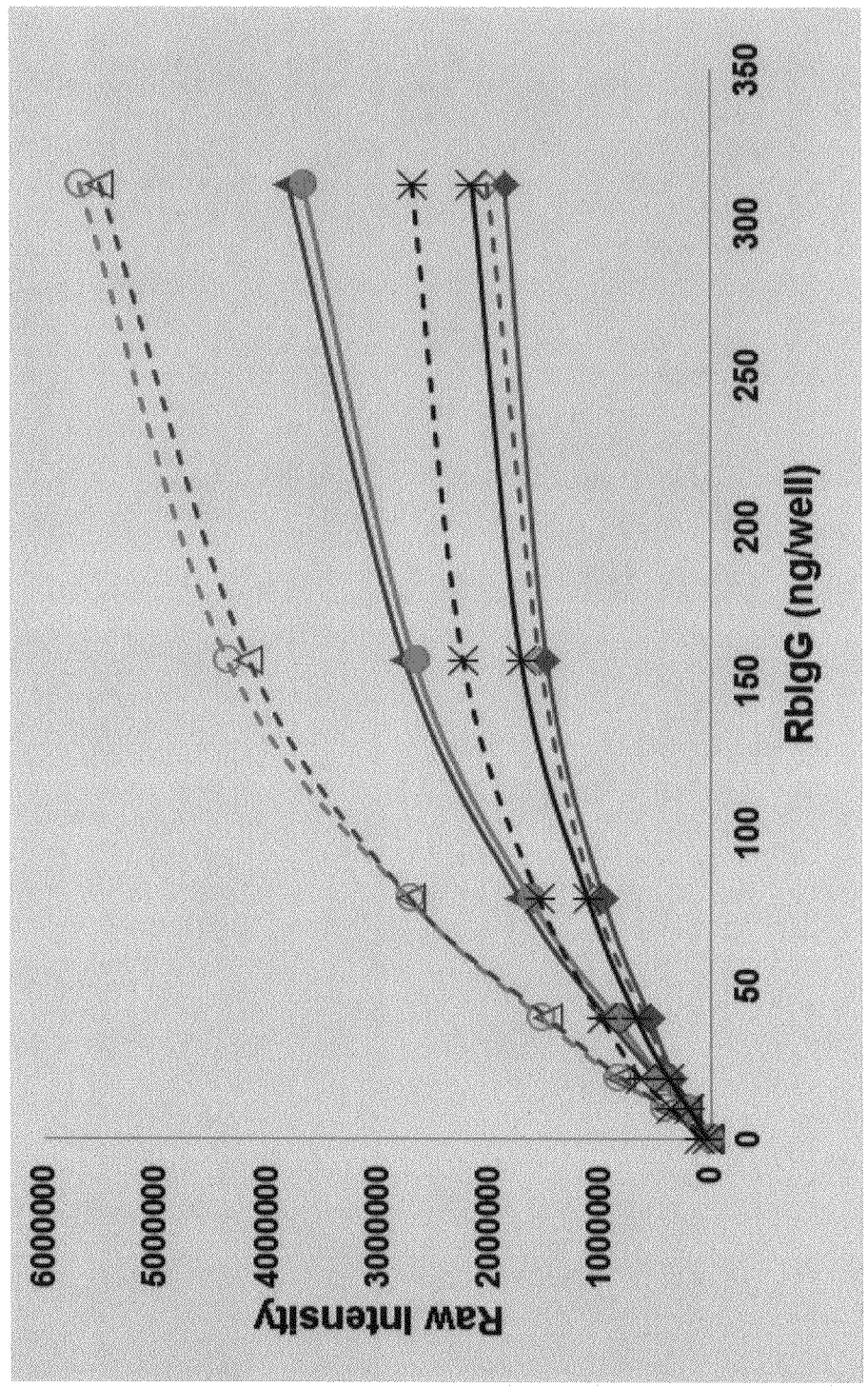
FIG. 10 graphs functional fluorescence plate assay results with some commercial dyes and inventive compounds with one conjugate produced in one embodiment.

FIG. 10 shows LiCor Odyssey results of a functional assay using GAR conjugated with either 2× molar excess of the dyes (solid lines) or 4× molar excess of the dyes (dashed lines) of DyLight 680 (purple diamond); DyLight 680B (blue triangle); 679 Compound 1 (red circle); and Cy5.5 (black asterisk). The following table compared S/B and raw intensity data.

|  | @ 1250 ng coating | @ 39 ng coating | @ 0 (blank) |
|---|---|---|---|
| S/B |  |  |  |
| DyLight 680-GAR-2X | 66.7 | 19.8 | 1.0 |
| DyLight 680-GAR-4X | 62.2 | 17.4 | 1.0 |
| DyLight 680B-GAR-2X | 210.6 | 47.5 | 1.0 |
| DyLight 680B-GAR-4X | 167.2 | 39.3 | 1.0 |
| DY679P1-GAR-2X | 184.0 | 39.2 | 1.0 |
| DY679P1-GAR-4X | 141.9 | 33.4 | 1.0 |
| Cy5.5-GAR-2X | 57.3 | 16.1 | 1.0 |
| Cy5.5-GAR-4X | 26.7 | 9.0 | 1.0 |
| Raw Intensity |  |  |  |
| DyLight 680-GAR-2X | 1868227 | 554324 | 28015 |
| DyLight 680-GAR-4X | 2140077 | 597726 | 34391 |
| DyLight 680B-GAR-2X | 4178812 | 943008 | 19839 |
| DyLight 680B-GAR-4X | 6285439 | 1476347 | 37592 |
| DY679P1-GAR-2X | 4039443 | 860737 | 21950 |
| DY679P1-GAR-4X | 6527381 | 1537020 | 46001 |
| Cy5.5-GAR-2X | 2408459 | 675886 | 42049 |
| Cy5.5-GAR-4X | 2929556 | 988970 | 109613 |

Figure 11:
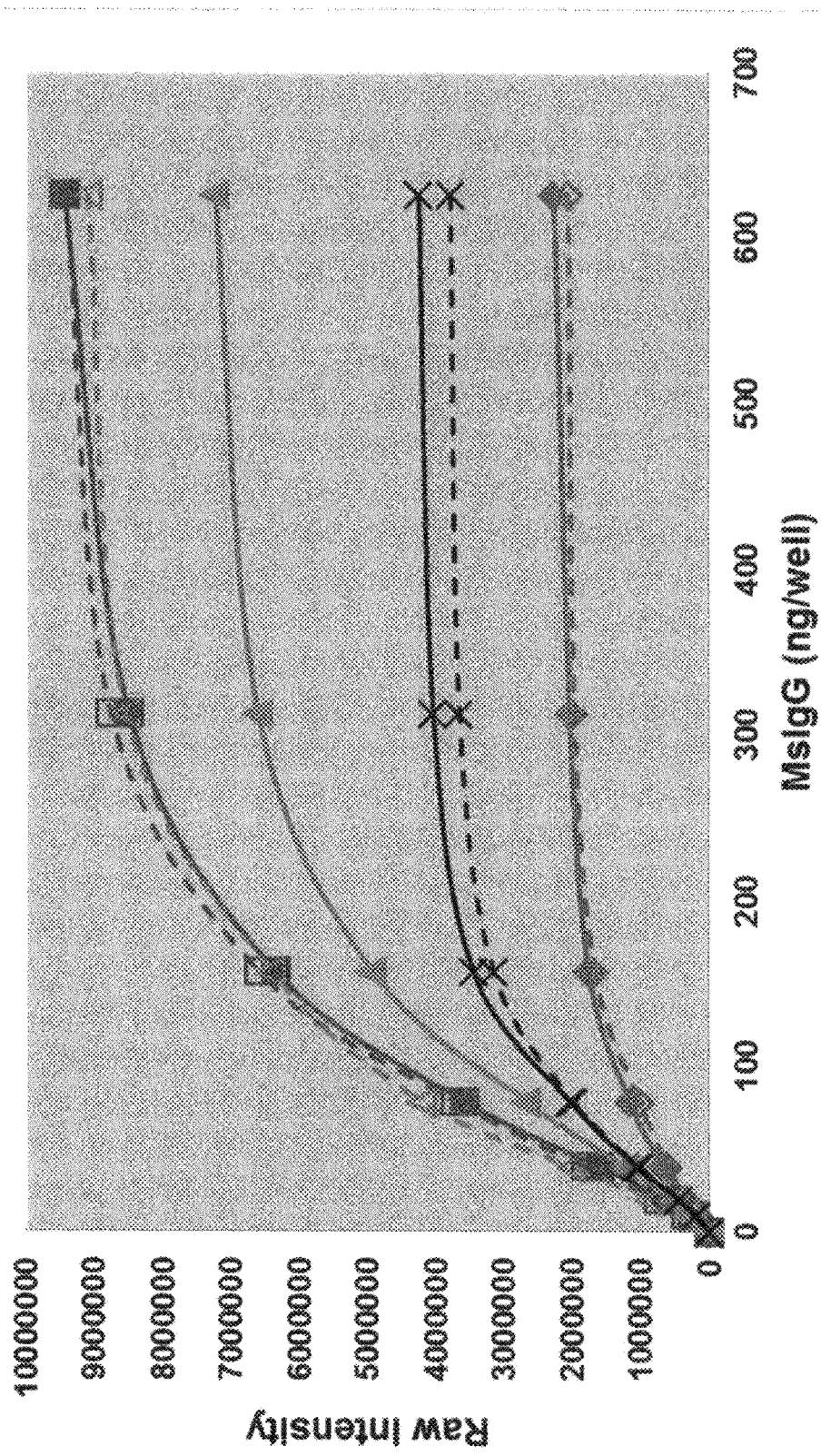
FIG. 11 graphs functional fluorescence plate assay results with some commercial dyes and inventive compounds with one conjugate produced in one embodiment.

FIG. 11 shows LiCor Odyssey results of a functional assay using GAM conjugated with either 8x molar excess of the dyes (solid lines) or 10x molar excess of the dyes (dashed lines) of DyLight 680 (purple diamond); DyLight 680B (blue square); 679 Compound 1 (red triangle); and Company B Compound (black X). The following table compared S/B data.

|  | 2500 ng mouse IgG/well | 39.1 ng mouse IgG/well |
|---|---|---|
| DyLight 680-GAM-8X | 173.6 | 48.9 |
| DyLight 680-GAM-10X | 137.2 | 37.6 |
| DyLight 680B-GAM-8X | 929.3 | 142.4 |
| DyLight 680B-GAM-10X | 914.5 | 165.6 |
| DY679P1-GAM-8X | 675.2 | 110.5 |
| DY679P1-GAM-10X | 871.5 | 183.5 |
| Company B Compound-GAM-8X | 459.9 | 112.4 |
| Company B Compound -GAM-10X | 374.0 | 96.1 |

679 Compound 1-GAM (10x) showed equivalent bound fluorescence compared to corresponding DyLight 680B-GAM (10x). S/B was lower for 679 Compound 1-GAM (8x, 10x) compared to DyLight 680B-GAM (8x, 10x). In general, similar results were obtained for GAR conjugates.

Figure 12:
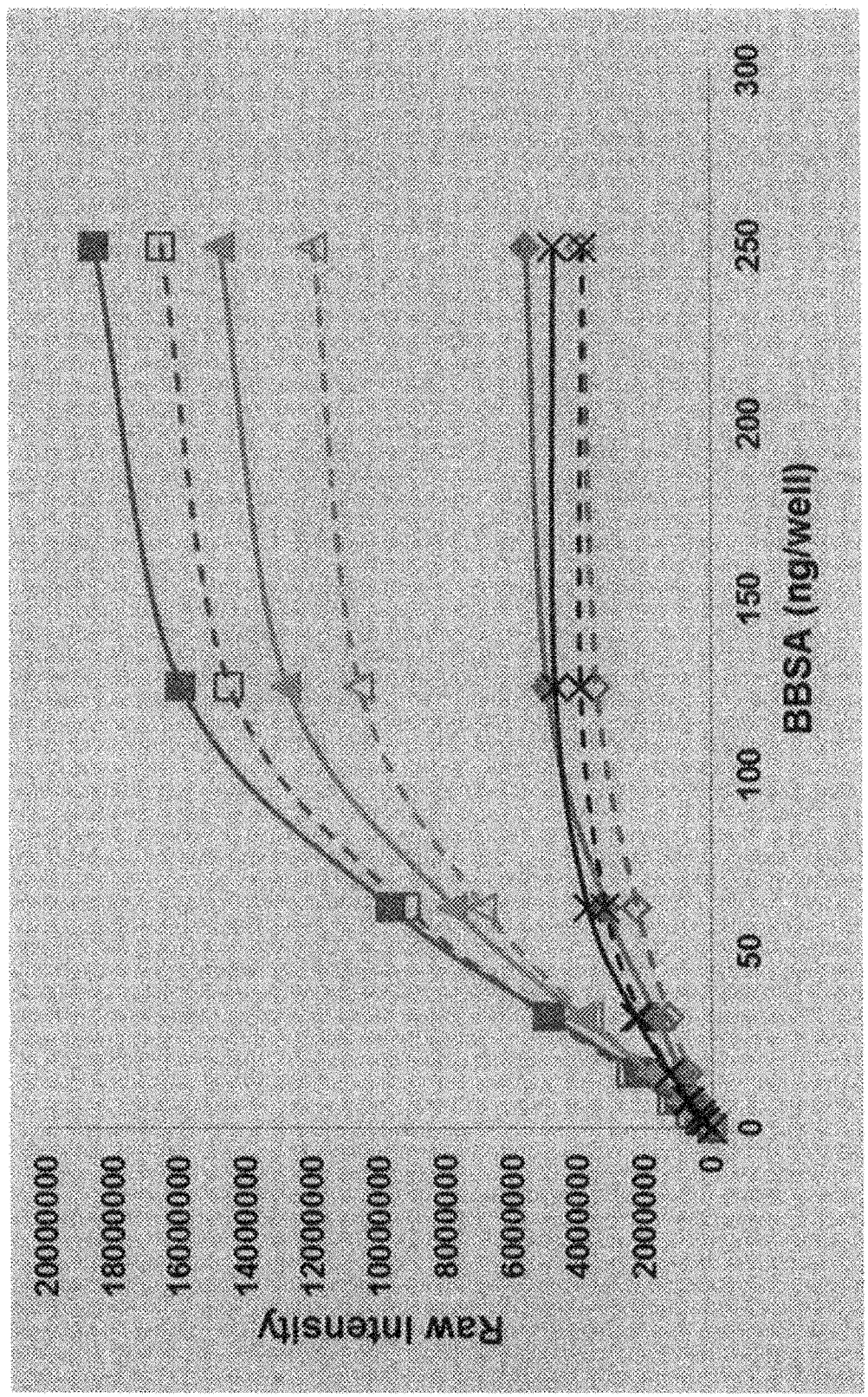
FIG. 12 graphs functional fluorescence plate assay results with some commercial dyes and inventive compounds with one conjugate produced in one embodiment.

FIG. 12 shows LiCor Odyssey results of a functional assay using SA conjugated with either 6x molar excess of the dyes (solid lines) or 8x molar excess of the dyes (dashed lines) of DyLight 680 (purple diamond); DyLight 680B (blue square); 679 Compound 1 (red triangle); and Company B Compound (black X). The following table compared SIB data.

|  | 250 ng BBSA/well | 3.9 ng BBSA/well |
|---|---|---|
| DyLight 680-SA-6X | 614.5 | 33.1 |
| DyLight 680-SA-8X | 436.3 | 25.1 |
| DyLight 680B-SA-6X | 2196.7 | 43.8 |
| DyLight 680B-SA-8X | 1969.5 | 75.6 |
| DY679P1-SA-6X | 1742.1 | 58.5 |
| DY679P1-SA-8X | 1406.0 | 54.7 |
| Company B Compound-SA-6X | 570.2 | 49.7 |
| Company B Compound-SA-8X | 427.7 | 36.1 |

679 Compound 1-SA (6x, 8x) showed lower bound fluorescence and S/B compared to corresponding DyLight 680B-SA (6x, 8x).

Figure 13:
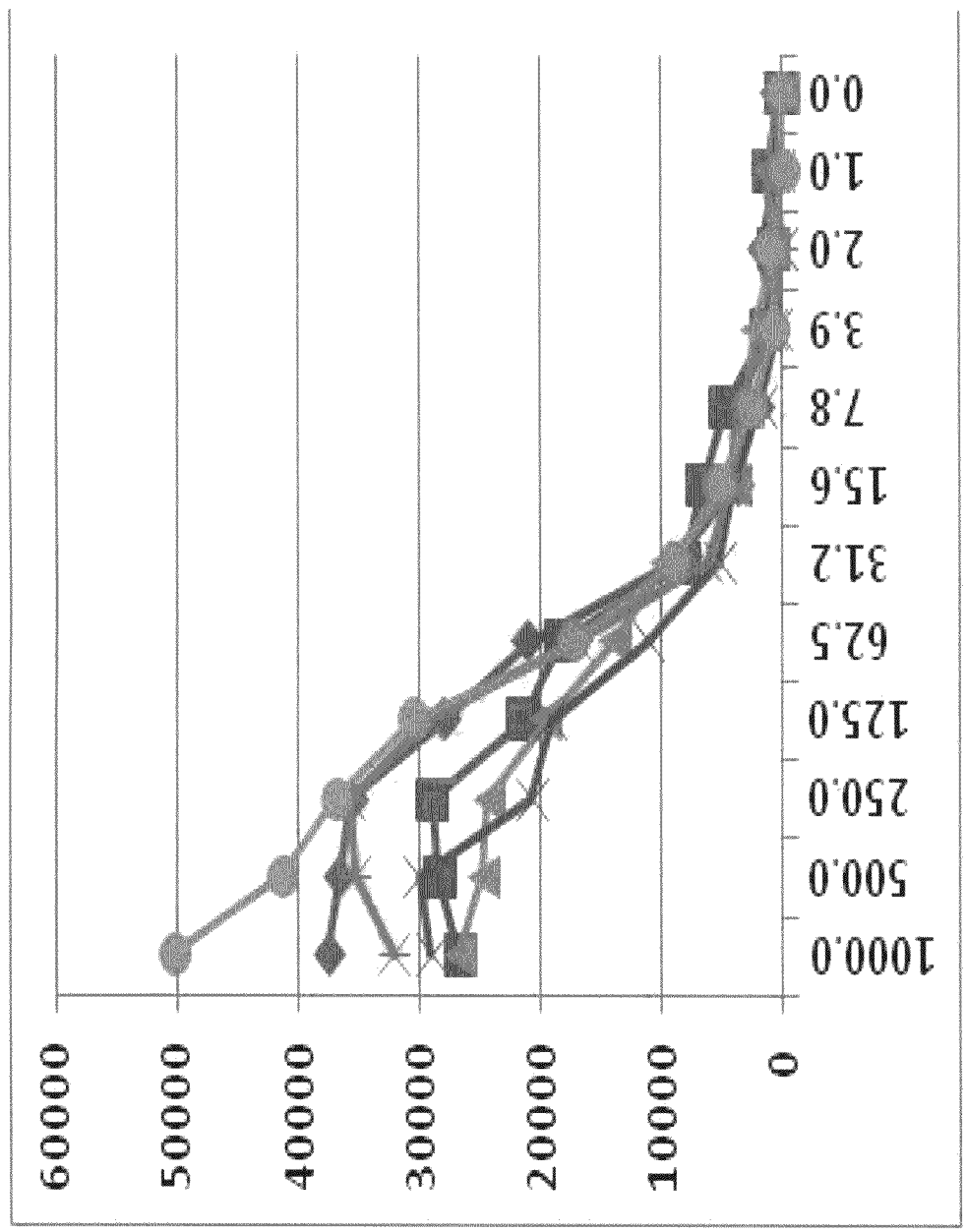
FIG. 13 shows functional fluorescence plate assay results with some commercial dyes and inventive compounds in one embodiment.

679 Compound 1 and Company A and Company B compounds were conjugated to GAR at high molar excesses, and evaluated in a functional assay, as described above. FIG. 13 shows results expressed as RFU of a functional assay using GAR conjugated with 679 Compound 1 at either a 7.5x molar excess (blue diamond), 15x molar excess (red square), or 22.5x molar excess (green triangle), and Company A Compound at either 7.5x molar excess (purple X), 15x molar excess (turquoise asterisk), or 22.5x molar excess (orange circle).

Figure 14:
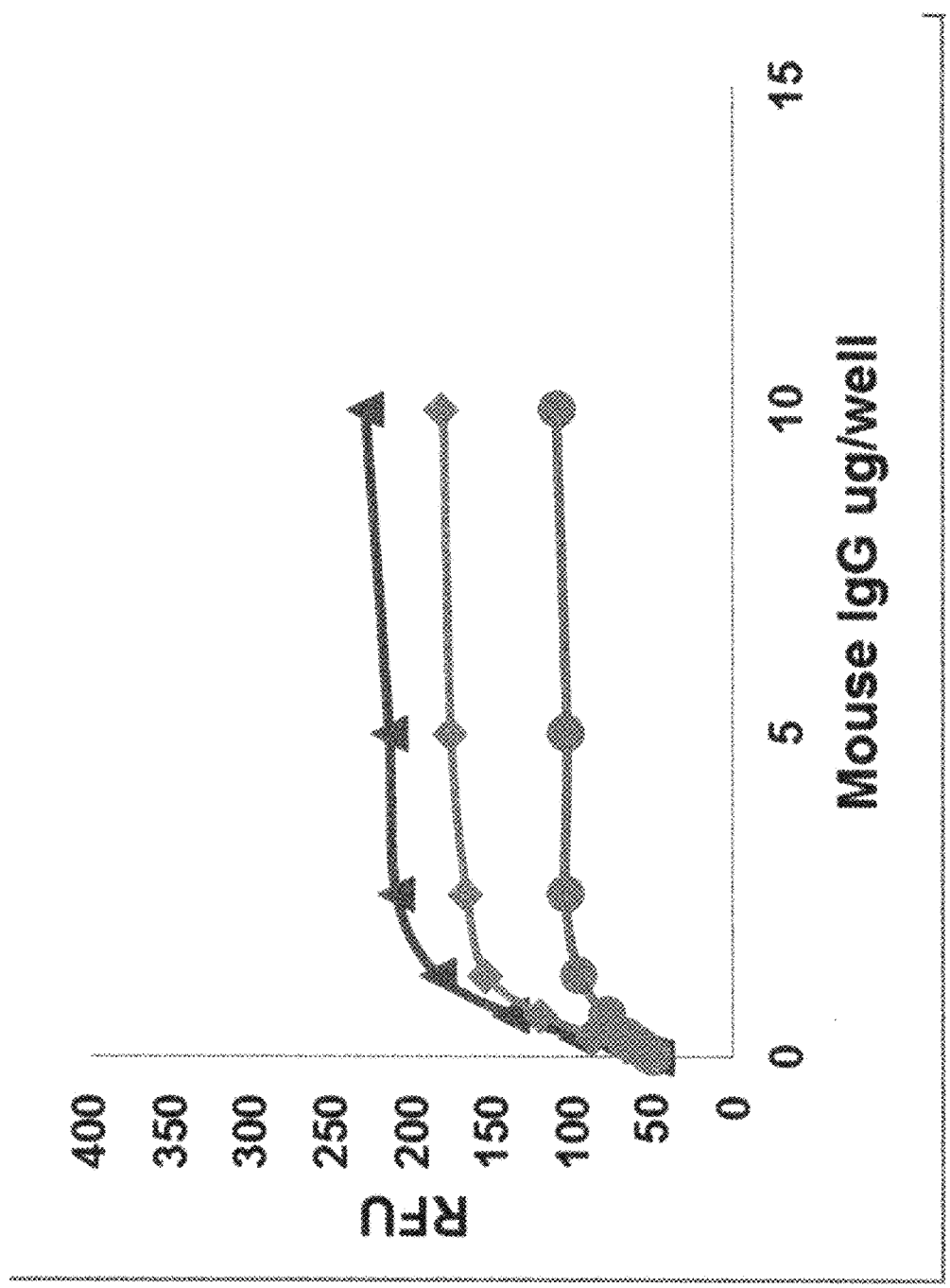
FIG. 14 graphs functional fluorescence plate assay results with some commercial dyes and inventive compounds in one embodiment.

FIG. 14 shows VarioSkan Flash results with excitation and emission of 679 nm/702 nm, expressed as RFU of a functional assay using GAM conjugated with 5x molar excess of Company B compound (orange diamond), V08-15173 (blue triangle), and V10-04152 (red circle). Based on the data, V08-15173-GAM (5x) showed higher binding fluorescence compared to Company B Compound-GAM (5x).

Figure 15:
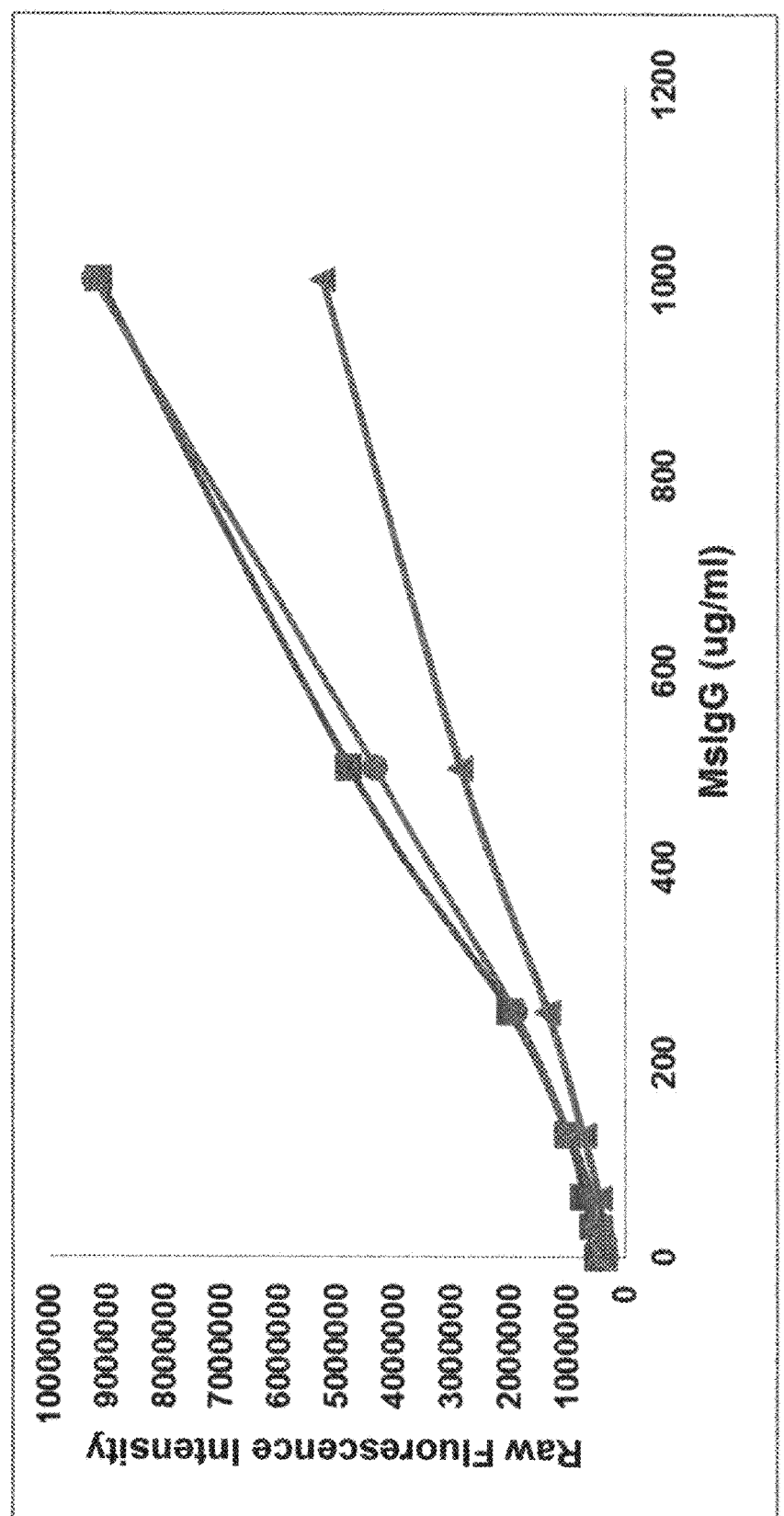
FIG. 15 graphs functional fluorescence plate assay results with some commercial dyes and inventive compounds in one embodiment.

FIG. 15 shows LiCOR Odyssey results, using the 700 channel, expressed as Raw Fluorescence Intensity of a functional assay using GAM conjugated with 5x molar excess of 679 Compound 1/1 (green triangle), Company A Compound (purple circle), and V08-15173 (blue square). FIG. 16 shows LiCOR Odyssey results expressed as S/B of a functional assay using GAM conjugated at 2.5x, 5x, 10x, or 15x molar excess of 679 Compound 1/1, Company A Compound, and V08-15173. V08-15173-GAM (5x) showed similar binding fluorescence to Company A Compound-GAM (5x). 679 Compound 1/1-GAM (5x) binding fluorescence was lower compared to the other two conjugates.

Figure 17:
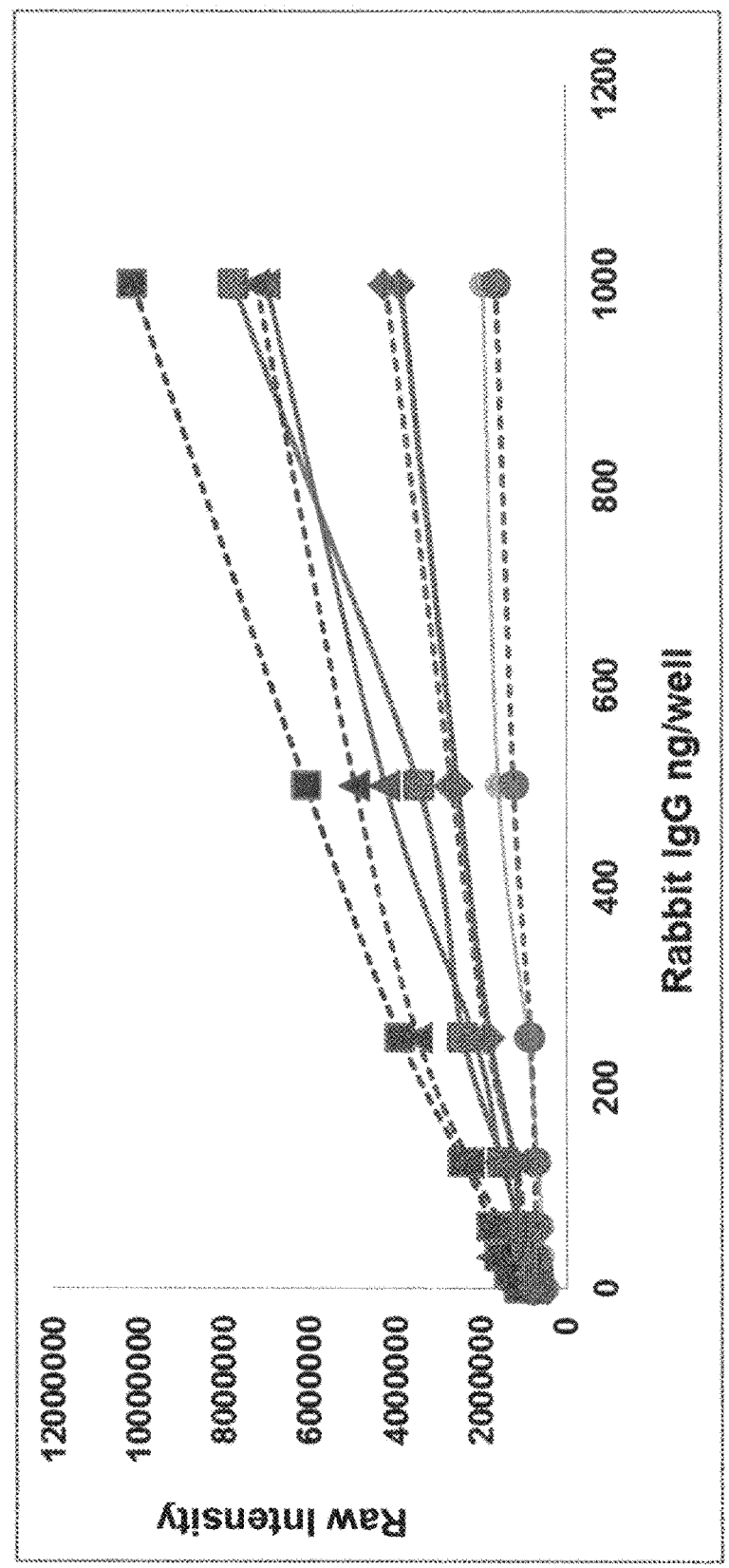
FIG. 17 graphs functional fluorescence plate assay results with some commercial dyes and inventive compounds in one embodiment.
Figure 19:
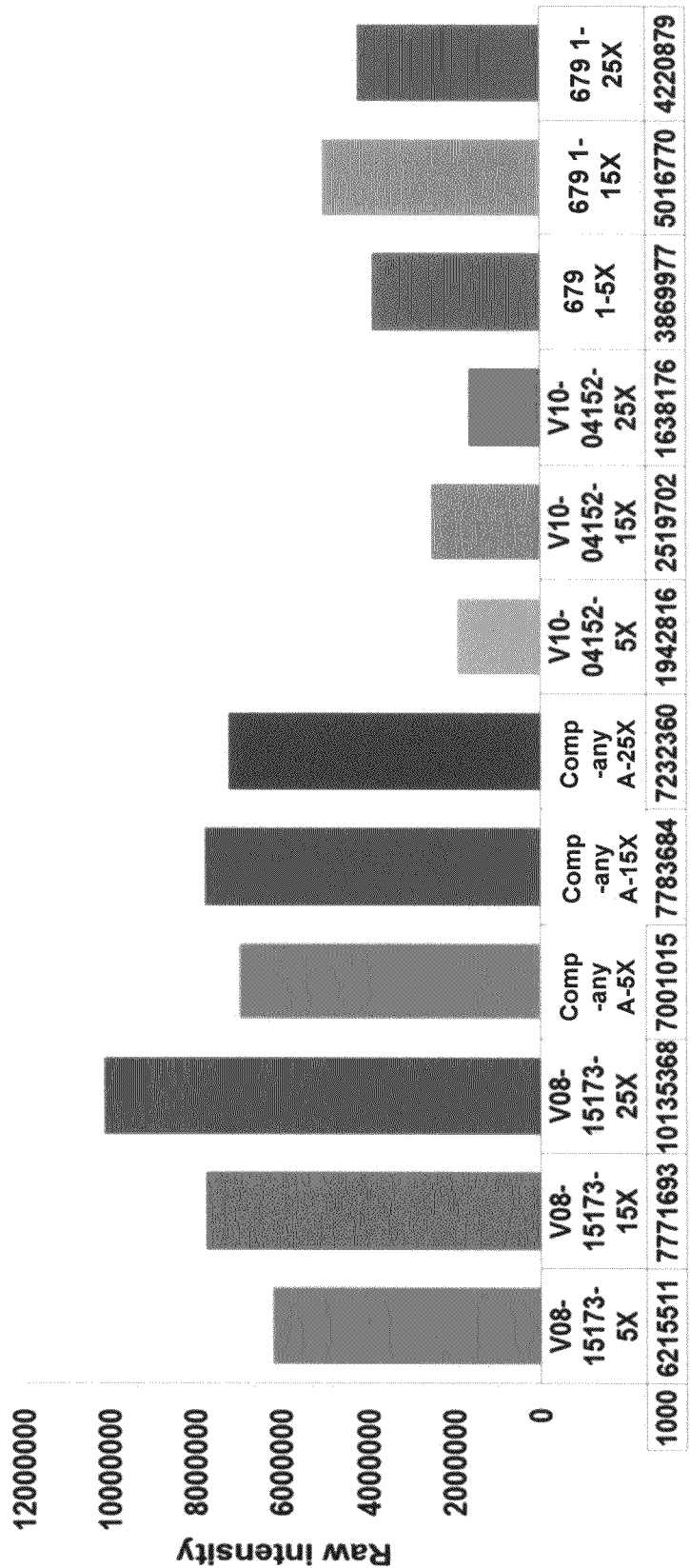
FIG. 19 is a histogram showing functional fluorescence plate assay results with some commercial dyes and inventive compounds in one embodiment.

FIG. 17 shows LiCOR Odyssey results, using the 700 channel, expressed as Raw Fluorescence Intensity of a functional assay using GAR conjugated with 5x and 25x molar excess of 679 Compound 1/1 (green 5x, diamond, solid line; green 25x, diamond, dashed line), Company A Compound (purple 5x, triangle, solid line; purple 25x, triangle, dashed line), V08-15173 (light blue 5x, square, solid line; dark blue 25x, square, dashed line), and V10-04152 (yellow 5x, circle, solid line; red 25x, circle, dashed line). FIG. 18 shows LiCOR Odyssey results expressed as S/B of a functional assay using GAR conjugated at 5x, 15x, or 25x molar excess of 679 Compound 1/1, Company A Compound, V08-15173, and V10-04152. Based on the Raw Fluorescence Intensity data, there was no apparent quenching for the V08-15173-GAR at 25x molar excess. 679 Compound 1/1, V10-04152, and Company A Compound were saturating at 25x. FIG. 19 shows summary Raw Fluorescence Intensity data, and apparent quenching at 1000 ng/well at 25x for 679 Compound 1/1 (679 1), V10-04152, and Company A Compound, but no apparent quenching at 25x for V08-15173.

679 Compound 4/4 and commercial compounds were conjugated to GAM or GAR at various dye amounts, and evaluated in a functional assay, as described above, with the resulting D/P ratios shown below.

| Conjugates | D/P |
|---|---|
| 679 Compound 4/4-GAM (50 μg) | 1.2 |
| 679 Compound 4/4-GAM (65 μg) | 1.6 |
| 679 Compound 4/4-GAM (100 μg) | 2.0 |
| CF680-GAM | 4.0 |
| CF680R-GAM | 7.6 |
| Alexa Fluor 680-GAM | 5.0 |
| 679 Compound 4/4-GAR (50 μg) | 1.4 |
| 679 Compound 4/4-GAR (65 μg) | 1.7 |
| CF680-GAR | 3.5 |
| CF680R-GAR | 5.7 |
| Alexa Fluor 680-GAR | 5.8 |

Figure 20:
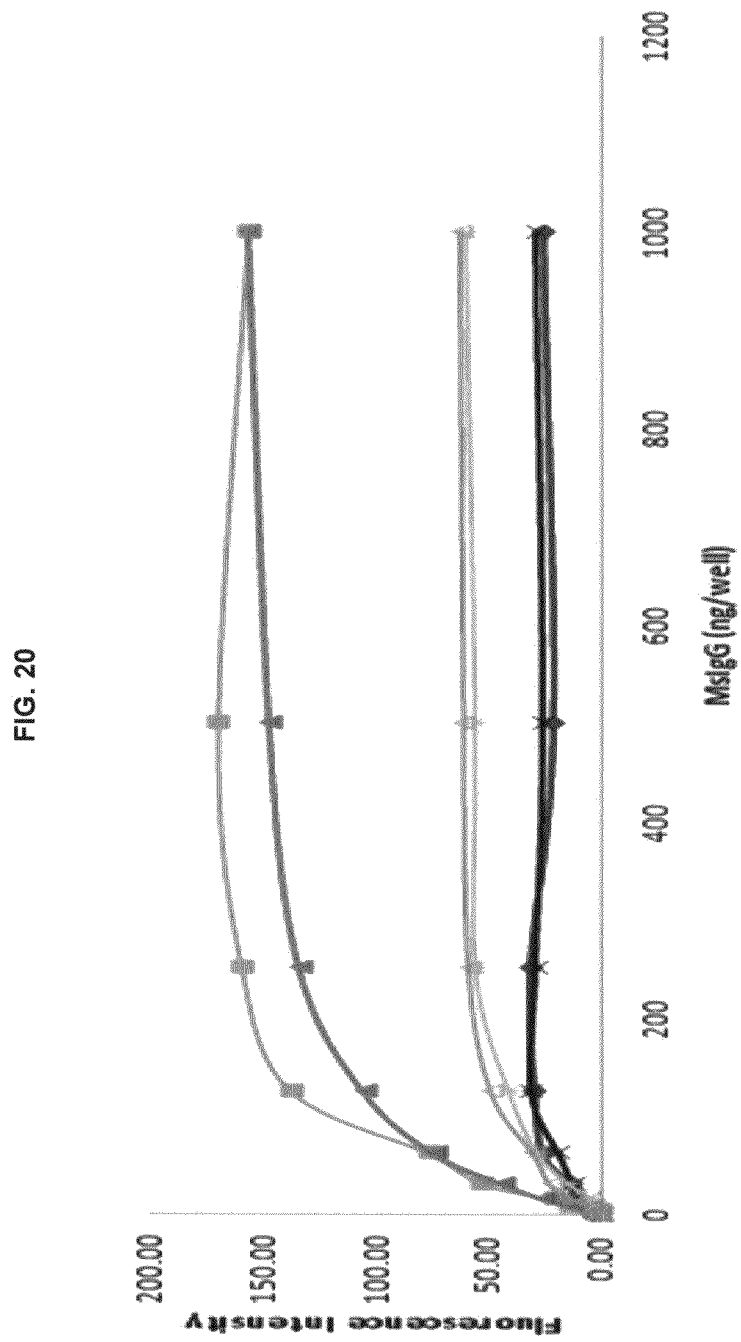
FIG. 20 graphs functional fluorescence plate assay results with some commercial dyes and inventive compounds in one embodiment.
Figure 21:
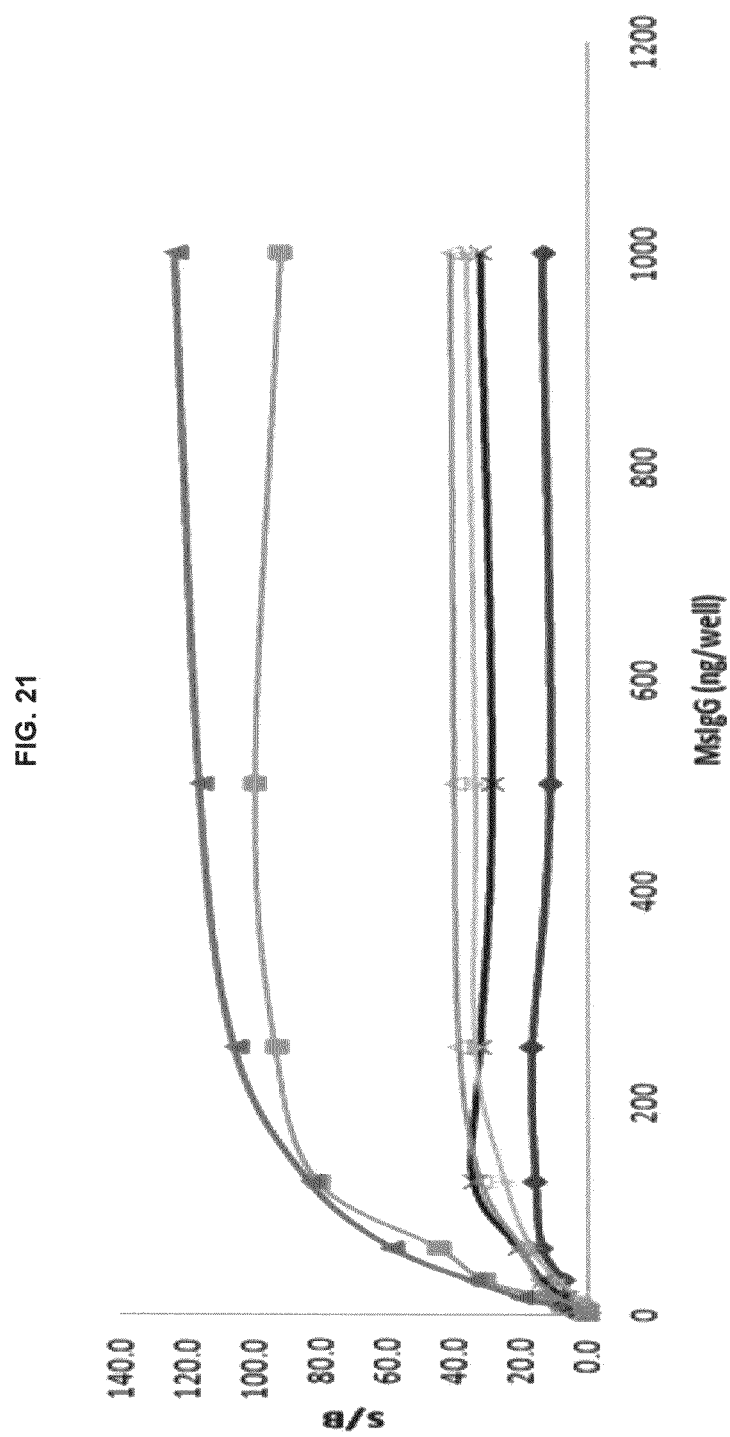
FIG. 21 graphs functional fluorescence plate assay results with some commercial dyes and inventive compounds in one embodiment.

FIG. 20 shows VarioScan results expressed as RFU of a functional plate assay and FIG. 21 shows the signal to background (S/B) of the functional plate assay using GAM conjugated with 679 Compound 4/4-GAM (50 μg; dark blue diamond), (65 μg; light blue asterisk), (100 μg; orange open triangle), CF 680-GAM (pink squares), CF 680R-GAM (green filled triangles), and Alexa Fluor 680-GAM (black X), with the tabulated data shown below. The results in FIG. 20 show that the GAM conjugates made with the inventive dyes, or CF 680, CF 680R and Alexa Fluor 680 dyes are compatible with the plate assay. The results in FIG. 21 show signal to background for the same assay as FIG. 20.

|  | 1000 | 500 | 250 | 125 | 62.5 | 31.3 | 15.6 | 7.8 | 3.9 | 2.0 | 1.0 | 0 |
|---|---|---|---|---|---|---|---|---|---|---|---|---|
| RFU |  |  |  |  |  |  |  |  |  |  |  |  |
| 679 Compound 4/4-GAM (50 μg) | 26.1 | 21.5 | 31.8 | 29.9 | 26.3 | 14.0 | 12.7 | 9.05 | 2.68 | 2.48 | 0.79 | 1.87 |
| CF 680-GAM | 155 | 168 | 158 | 137 | 76.2 | 52.7 | 20.9 | 13.5 | 5.03 | 3.72 | 2.92 | 1.70 |
| CF 680R-GAM | 155.4 | 146 | 133 | 104 | 74.0 | 43.1 | 25.0 | 11.6 | 7.16 | 5.25 | 4.11 | 1.26 |
| Alexa 680-GAM | 29.21 | 25.9 | 29.2 | 31.3 | 18.8 | 12.3 | 6.30 | 4.98 | 1.84 | 3.02 | 0.44 | 0.91 |
| 679 Compound 4/4-GAM (65 μg) | 60.44 | 56.2 | 56.0 | 41.3 | 28.6 | 14.7 | 5.91 | 4.28 | 2.71 | 1.03 | 2.23 | 1.67 |
| 679 Compound 4/4-GAM (100 μg) | 62.75 | 61.0 | 58.8 | 48.9 | 30.2 | 22.6 | 13.1 | 4.39 | 2.09 | 3.32 | 1.57 | 1.52 |
| S/B |  |  |  |  |  |  |  |  |  |  |  |  |
| 679 Compound 4/4-GAM (50 μg) | 14.0 | 11.5 | 17.0 | 16.0 | 14.1 | 7.5 | 6.8 | 4.8 | 1.4 | 1.3 | 0.4 | 1.0 |
| CF 680-GAM | 91.7 | 99.5 | 93.4 | 80.9 | 45.0 | 31.1 | 12.4 | 8.0 | 3.0 | 2.2 | 1.7 | 1.0 |
| CF 680R-GAM | 1229 | 115 | 105 | 83.0 | 58.5 | 34.2 | 19.8 | 9.2 | 5.7 | 4.1 | 3.3 | 1.0 |
| Alexa 680-GAM | 32.2 | 28.7 | 32.3 | 34.5 | 20.8 | 13.6 | 7.0 | 5.5 | 2.0 | 3.3 | 0.5 | 1.0 |
| 679 Compound 4/4-GAM (65 μg) | 36.3 | 33.8 | 33.7 | 24.9 | 17.2 | 8.9 | 3.5 | 2.6 | 1.6 | 0.6 | 1.3 | 1.0 |
| 679 Compound 4/4-GAM (100 μg) | 41.4 | 40.3 | 38.9 | 32.3 | 20.0 | 15.0 | 8.7 | 2.9 | 1.4 | 2.2 | 1.0 | 1.0 |

Figure 22:
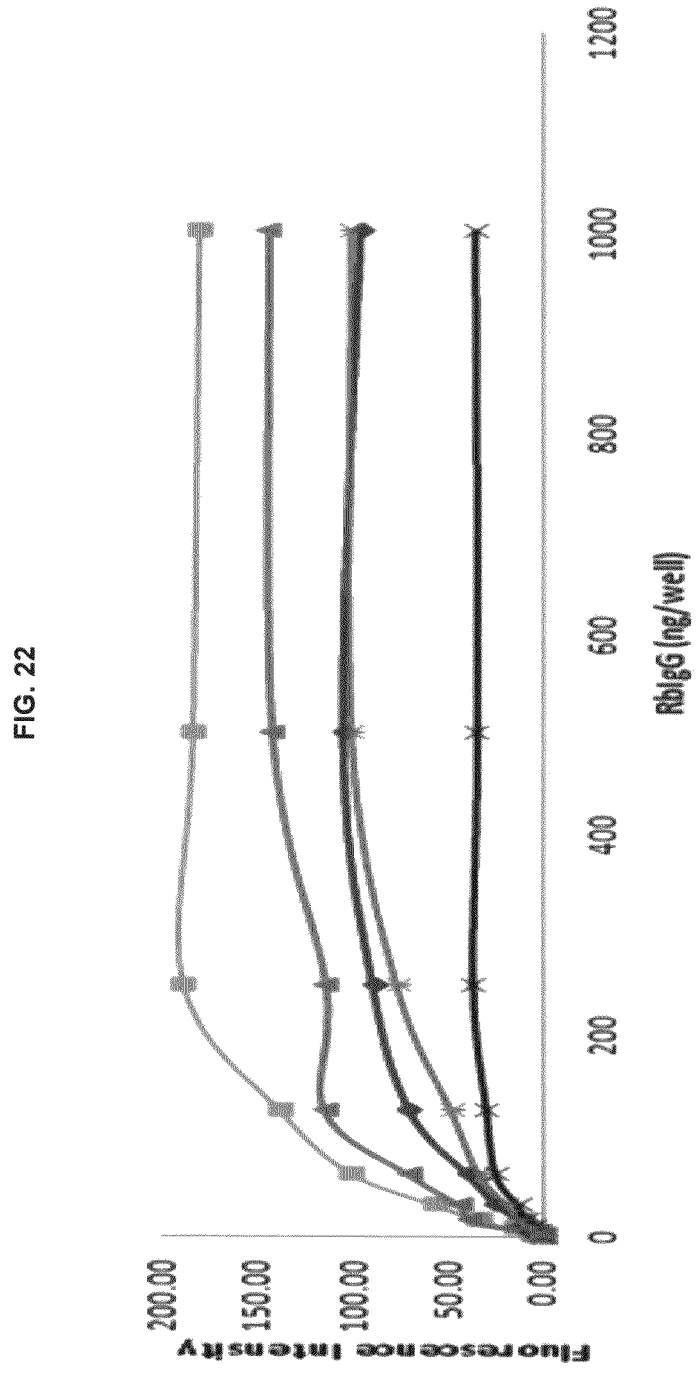
FIG. 22 graphs functional fluorescence plate assay results with some commercial dyes and inventive compounds in one embodiment.
Figure 23:
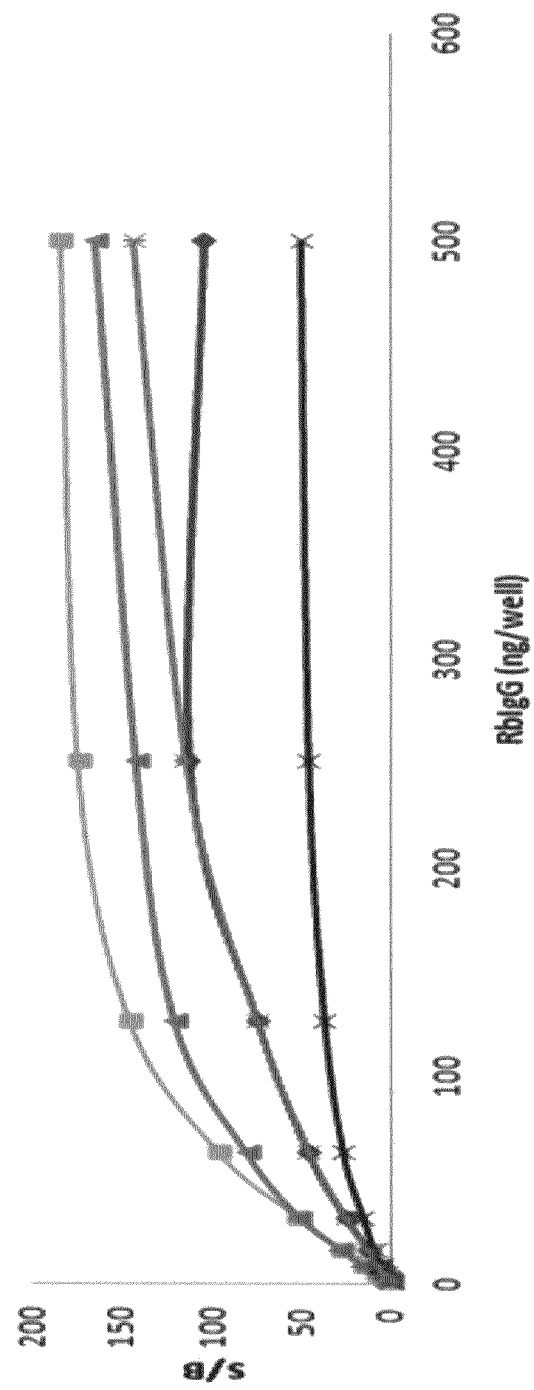
FIG. 23 graphs functional fluorescence plate assay results with some commercial dyes and inventive compounds in one embodiment.

FIG. 22 shows VarioScan results expressed as RFU of a functional plate assay and FIG. 23 shows the signal to background (S/B) of the functional plate assay using 679 Compound 4/4-GAR (50 μg; dark blue diamond), (65 μg; red asterisk), CF 680-GAR (pink squares), CF 680R-GAR (green filled triangles), and Alexa Fluor 680-GAR (black X), with the tabulated data shown below. The results in FIG. 22 show that the GAR conjugates made with the inventive dyes, and CF680, CF680R, and Alexa Fluor 680 dye are compatible with the plate assay. The results in FIG. 23 shows signal to background for the same assay as FIG. 22.

|  | 1000 | 500 | 250 | 125 | 62.5 | 31.3 | 15.6 | 7.8 | 3.9 | 2.0 | 1.0 | 0 |
|---|---|---|---|---|---|---|---|---|---|---|---|---|
| RFU |  |  |  |  |  |  |  |  |  |  |  |  |
| 679 Compound 4/4-GAR (50 μg) | 95.4 | 104 | 89.1 | 70.0 | 39.9 | 24.4 | 11.7 | 6.61 | 4.35 | 2.85 | 1.29 | 0.81 |
| CF 680-GAR | 179 | 182 | 187 | 137 | 100 | 56.7 | 33.4 | 15.4 | 7.26 | 5.10 | 3.31 | 1.24 |
| CF 680R-GAR | 143 | 141 | 113 | 114 | 70.8 | 43.9 | 38.9 | 16.0 | 8.47 | 5.66 | 2.22 | 1.95 |
| Alexa 680-GAR | 35.7 | 34.8 | 37.0 | 30.2 | 25.4 | 13.6 | 9.36 | 5.23 | 3.74 | 2.30 | 0.69 | 1.05 |
| 679 Compound 4/4-GAR (65 μg) | 100 | 100 | 76.9 | 48.8 | 34.5 | 20.1 | 13.2 | 8.39 | 2.89 | 1.84 | 1.34 | 1.42 |
| S/B |  |  |  |  |  |  |  |  |  |  |  |  |
| 679 Compound 4/4-GAR (50 μg) | 117 | 128 | 109 | 86.9 | 49.1 | 30.0 | 14.4 | 8.1 | 5.3 | 3.5 | 1.6 | 1.0 |
| CF 680-GAR | 145 | 148 | 151 | 111 | 81.4 | 45.9 | 27.1 | 12.5 | 5.9 | 4.1 | 2.7 | 1.0 |
| CF 680R-GAR | 73.9 | 72.8 | 58.4 | 59.0 | 36.4 | 22.6 | 20.0 | 8.2 | 4.3 | 2.9 | 1.1 | 1.0 |
| Alexa 680-GAR | 33.9 | 33.1 | 35.1 | 28.6 | 24.1 | 12.9 | 8.9 | 5.0 | 3.6 | 2.2 | 0.7 | 1.0 |
| 679 Compound 4/4-GAR (65 μg) | 70.6 | 70.6 | 54.3 | 34.4 | 24.4 | 14.2 | 9.4 | 5.9 | 2.0 | 1.3 | 0.9 | 1.0 |

EXAMPLE 9

The inventive compounds were evaluated for immunofluorescence in cell based assays using the following protocol. Frozen A549 cell plates stored at −20° C. were placed for 30 min 50° C. Storage buffer (PBS) was removed and the cells were permeabilized for 15 min (100 µl/well) with 0.1% Triton-X100 in 1× PBS buffer. Plates were blocked for 30 min in 2% BSA in 1×PBS-0.1% Trion-X100. Primary antibodies diluted in 2% BSA in 1×PBS-0.1% Trion-X100 were added to the plates (column 1-11; column 12 included only blocker) and incubated three hours at room temperature. Mouse anti-lamin A was added at 1 µg/ml and rabbit anti-lamin B1 was added at 3 µg/ml. After overnight incubation, the antibody solution was removed from the plates and the plates were washed with PBS-0.5% Tween-20 (2×100 µl/well). GAM and GAR secondary antibodies labeled with DyLight 680-NHS, DyLight 680B-NHS, 679 Compound 1-NHS and Company B Compound-NHS were diluted to 4 µg/ml in PBS, added and incubated for one hour at room temperature. The plates were then washed three times with 100 µl/well PBS, and Hoechst stain diluted to 0.1 µg/ml in PBS was added to each well (100 µl/well). The plates were scanned on ArrayScan Plate Reader for imaging and quantitation.

Figure 24:
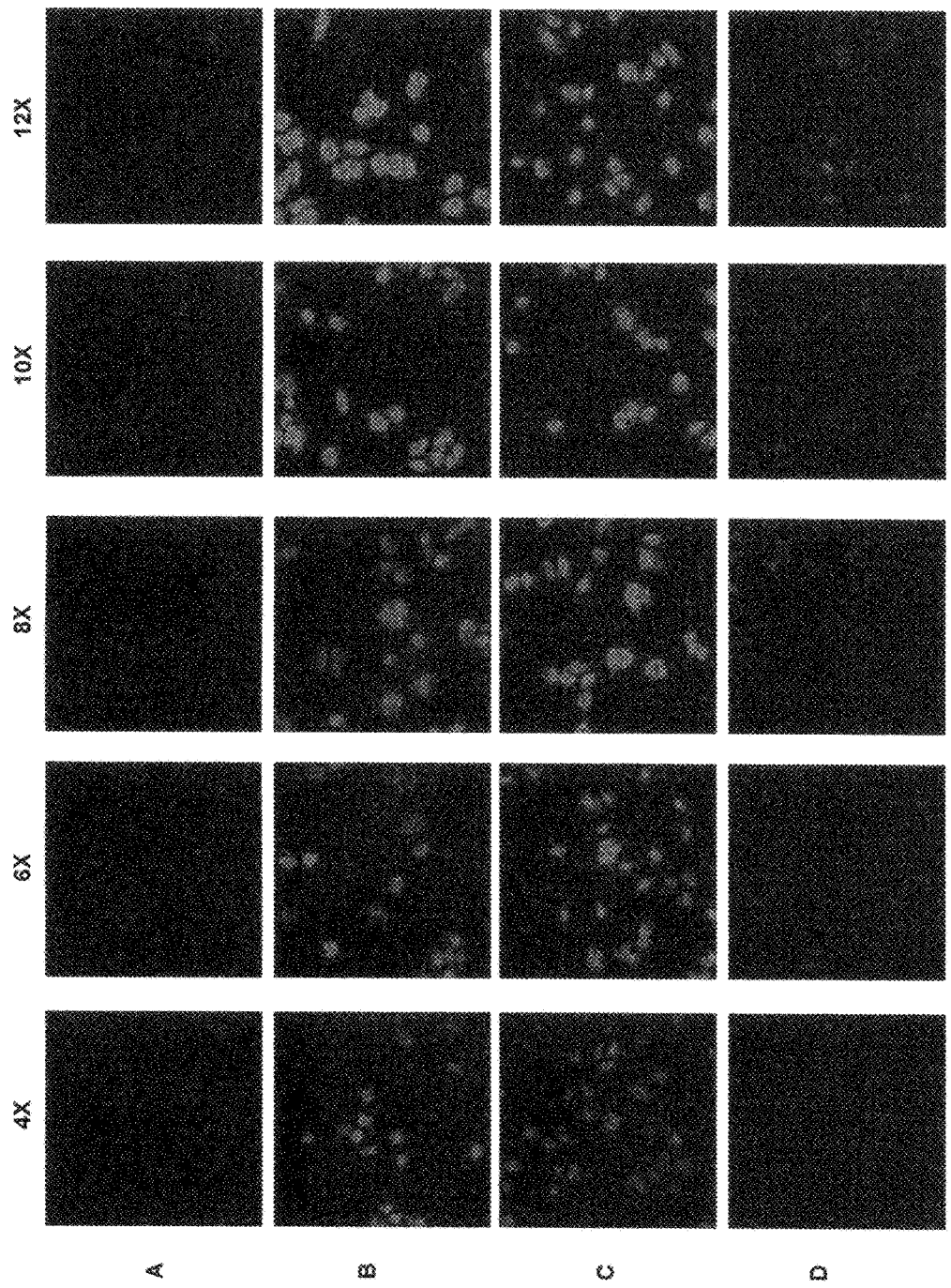
FIG. 24 shows immunofluorescence data with some commercial dyes and inventive compounds forming a conjugate in one embodiment.

FIG. 24 shows results of an immunofluorescence assay using mouse anti-lamin A as a primary antibody, and DyLight 680-GAM (FIG. 24A), DyLight 680B-GAM (FIG. 24B), 679 Compound 1-GAM (FIG. 24C), or Company B Compound-GAM (FIG. 24D) as secondary antibody, where the compound was conjugated to GAM (secondary antibody) at 4× molar excess (column 1), 6× molar excess (column 2), 8× molar excess (column 3), 10× molar excess (column 4), or 12× molar excess (column 5). 679 Compound 1 conjugated to GAM showed very similar performance to corresponding DyLight 680B conjugates.

The inventive compounds and commercial dye were evaluated for immunofluorescence in a second cell based assay using the following protocol. Frozen U20S cell plates stored at −20° C. were placed overnight at 4° C. Storage buffer (PBS) was removed and the cells were permeabilized for 15 min (100 µl/well) with 0.1% Triton-X100 in 1×PBS buffer. Plates were blocked for 30 min in 2% BSA in 1× PBS-0.1% Trion-X100. Primary antibodies diluted in 2% BSA in 1×PBS-0.1% Trion-X100 were added to the plates (column 1-11; column 12 included only blocker) and incubated five hours at room temperature. Mouse anti-lamin A was added at 2 µg/ml and rabbit anti-lamin B1 was added at 4 µg/ml. After incubation, the antibody solution was removed from the plates and the plates were washed PBS-0.5% Tween-20 (2×100 µl/well). Next, GAM and GAR secondary antibodies labeled with DyLight 680-NHS, DyLight 680B-NHS, 679 Compound 1-NHS, and Cy5.5 Mono Ester were diluted to 4 µg/ml in PBS and incubated with the cells for one hour at room temperature. GAM and GAR conjugated to DyLight 680-NHS, DyLight 680B-NHS, 679 Compound 1-NHS, and Company B Compound at 10× molar excess were diluted to 4 µg/ml in PBS and then serially diluted 1:1 in the plate to the following concentrations: 2 µg/ml, 1 µg/ml, 0.5 µg/ml, 0.25 µg/ml, 0.125 µg/ml and/or 0.0625 µg/ml. The plates were washed 3× with 100 µl/well PBS, and Hoechst stain diluted to 0.1 µg/ml in PBS was added to each well (100 µl/well). The plates were scanned on ArrayScan Plate Reader for imaging and quantitation.

Figure 25:
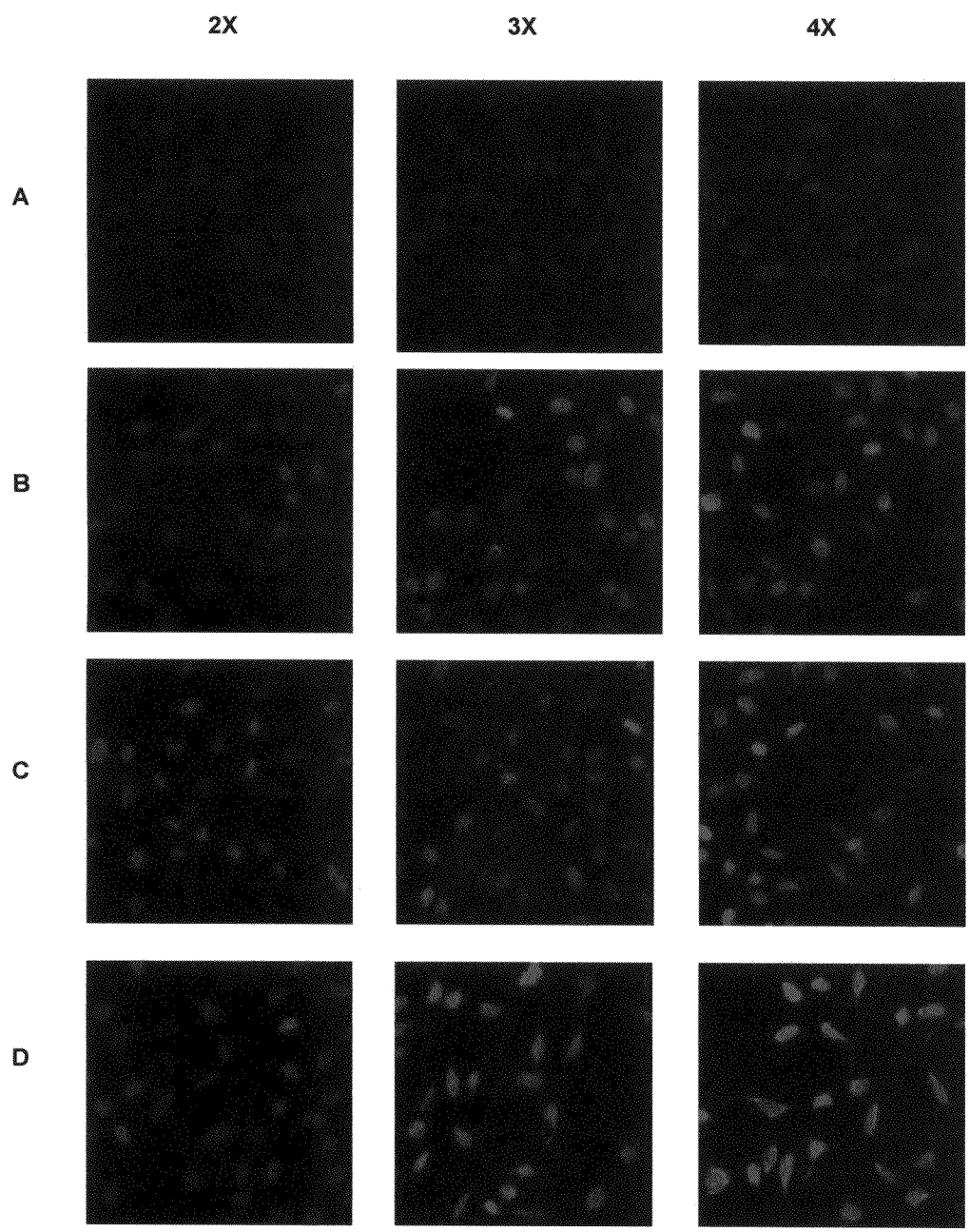
FIG. 25 shows immunofluorescence data with some commercial dyes and inventive compounds forming a conjugate in one embodiment.

FIG. 25 shows results of an immunofluorescence assay using mouse anti-lamin A as a primary antibody, and either DyLight 680-GAM (FIG. 25A), DyLight 680B-GAM (FIG. 25B), 679 Compound 1-GAM (FIG. 25C), or Cy5.5-GAM (FIG. 25D) as secondary antibody, where the compound was conjugated to GAM (secondary antibody) at 2× molar excess (column 1), 3× molar excess (column 2), or 4× molar excess (column 3). Performance in immunofluorescence of 679 Compound 1 conjugate was similar to the performance of corresponding DyLight 680B conjugates. Quantitative analysis of FIG. 25 data, expressed as Mean Total Intensity, which is the average total intensity of all pixels within a defined area or defined primary object such as a nucleus, is shown below.

| | Mean Total Intensity | | |
|---|---|---|---|
| | 2X | 3X | 4X |
| DyLight 680 | 91899 | 122829 | 144792 |
| DyLight 680B | 150542 | 228678 | 305700 |
| DY679P1 | 232482 | 263580 | 330865 |
| Cy5.5 | 211945 | 342208 | 451111 |

Fluorescence signal intensity for DyLight 680B and 679 Compound 1 GAM conjugates was 2-4 times higher, depending on the molar excess, compared to DyLight 680 or Cy5.5 GAM conjugates, and S/B for DyLight 680B & 679 Compound 1 GAM conjugates at the low molar excesses was comparable to each other and to DyLight 680. Overall fluorescence signal intensity for DyLight 680B and 679 Compound 1 GAR conjugates was about two times higher compared to DyLight 680. The S/B for DyLight 680B and 679 Compound 1 GAR labeled at 2×, 3× or 4× molar excess were comparable to each other and to DyLight 680 conjugates.

In the indicated experiments, the inventive compounds were evaluated for immunofluorescence in cell based assays using the following protocol. Frozen A549 cell plates stored at −20° C. were placed for 30 min 50° C. Storage buffer (PBS) was removed and the cells were permeabilized for 15 min (100 µl/well) with 0.1% Triton-X100 in 1×PBS buffer. Plates were blocked for 30 min in 2% BSA in 1× PBS-0.1% Trion-X100. Primary antibodies diluted in 2% BSA in 1×PBS-0.1% Trion-X100 were added to the plates (column 1-11; column 12 included only blocker) and incubated three hours at room temperature. Mouse anti-lamin A was added at 1 µg/ml and rabbit anti-lamin B1 was added at 3 µg/ml. After overnight incubation, the antibody solution was removed from the plates and the plates were washed with PBS-0.5% Tween-20 (2×100 µl/well). GAM and GAR secondary antibodies labeled with DyLight 680-NHS, DyLight 680B-NHS, 679 Compound 1-NHS and Company B Compound-NHS were diluted to 4 µg/ml in PBS, added and incubated for one hour at room temperature. The plates were then washed three times with 100 µl/well PBS, and Hoechst stain diluted to 0.1 µg/ml in PBS was added to each well (100 µl/well). The plates were scanned on ArrayScan Plate Reader for imaging and quantitation.

In the indicated experiments, the inventive compounds and commercial dye were evaluated for immunofluorescence in a cell based assay using the following protocol. Frozen U20S cell plates which were stored at −80° C. were thawed for 45 minutes at 50° C. Storage buffer (PBS) was removed and the cells were permeabilized for 15 minutes with 0.1% Triton-X100 in 1×PBS buffer (100 µl/well). The cell plate was blocked for 60 minutes in 2% BSA/PBS-0.1% Triton-X100. Primary antibody, either rat anti-Grp94 (5 µg/ml), mouse anti-lamin A (10 µg/ml), or rabbit anti-lamin B1 (10 µg/ml), diluted in 2% BSA/PBS-0.1% Triton-X100 was added to the plate and incubated for 1 hour at room temperature. Control wells contained only 2% BSA/PBS-0.1% Triton-X100 blocker. After incubation, the antibody solution was removed from the plate and the plate was washed three times with 100 µl/well of PBS-0.5% Tween-20 and one time with 100 µl/well PBS. GARat, GAM, or GAR secondary antibodies labeled with various molar excess of the inventive or commercial compound were diluted to 4 µg/ml in PBS and incubated for 1 hour at room temperature. The plates were washed three times with 100 µl/well of PBST and once with 100 µl/well PBS, and Hoechst (diluted to 0.1 µg/ml in PBS) was added to each well (100 µl/well). The plates were scanned on ArrayScan Plate Reader or ToxInsight Instrument.

Figure 26:
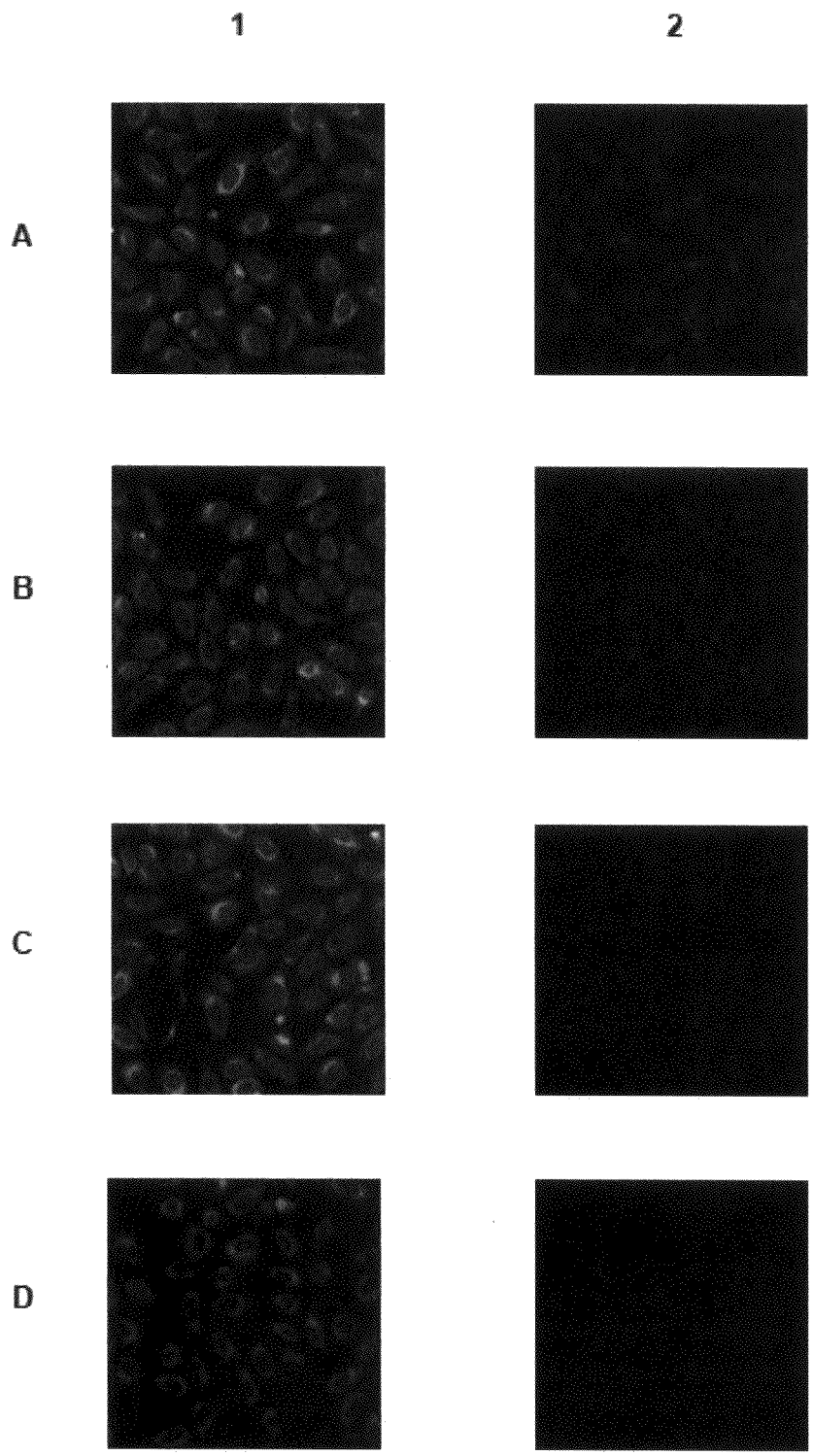
FIG. 26 shows immunofluorescence data with some commercial dyes and inventive compounds in one embodiment.

FIG. 26 shows detection of Grp94 in U2OS cells (column 1) with 679 Compound 1-GARat (FIG. 26A), DyLight 680B-GARat (FIG. 26B), V08-15173-GARat (FIG. 26C), and Company B Compound-GARat (FIG. 26D) conjugated at a 5× molar excess; and associated controls (column 2).

Figure 27:
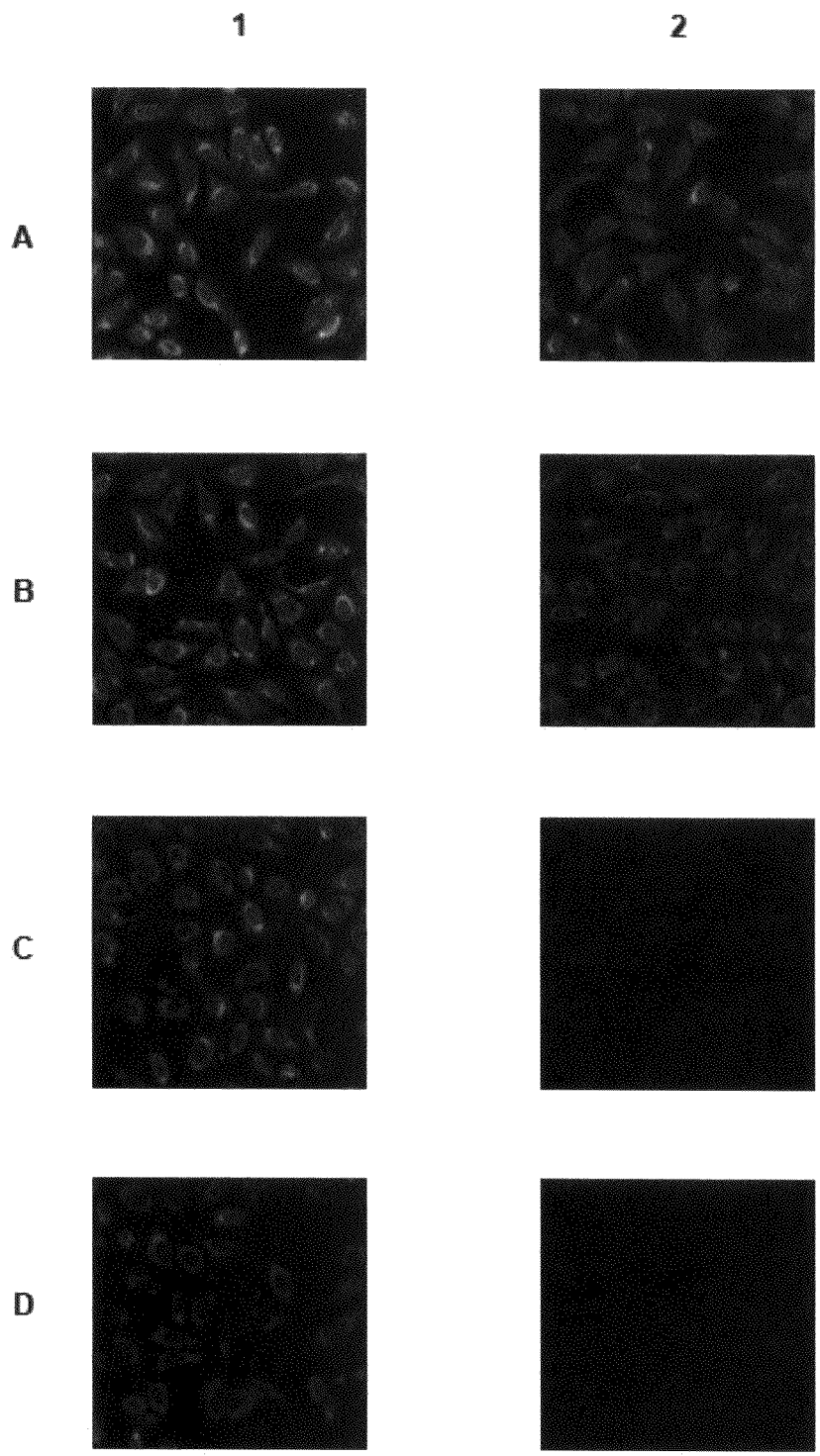
FIG. 27 shows immunofluorescence data with some commercial dyes and inventive compounds in one embodiment.

FIG. 27 shows detection of Grp94 in U2OS cells (column 1) with 679 Compound 1-GARat (FIG. 27A), DyLight 680B-GARat (FIG. 27B), V08-15173-GARat (FIG. 27C), and Company B Compound-GARat (FIG. 27D) conjugated at a 10× molar excess; and associated controls (column 2).

As shown in FIGS. 26-27, no non-specific binding was observed with V08-15173-GARat and Compound B Compound-GARat conjugates but there was with DY679P1 and DyLight 680B-GARat conjugates.

Quantitative analysis of the data of FIGS. 26-27, expressed as Mean Total Intensity, which is the average total intensity of all pixels within a defined area or defined primary object such as a nucleus, is shown below.

|  | 5X | 10X | Negative Controls 5X | 10X | S/B (5X) | S/B (10X) |
|---|---|---|---|---|---|---|
| 679 Compound 1 - GARat | 81221 | 97162 | 36744 | 70585 | 2.2 | 1.4 |
| DyLight 680B-GARat | 77855 | 91720 | 34773 | 61355 | 2.2 | 1.5 |
| V08-15173-GARat | 76825 | 70881 | 28190 | 26341 | 2.7 | 2.7 |
| Company B Compound-GARat | 64881 | 56119 | 26762 | 30379 | 2.4 | 1.8 |

S/B was slightly better for V08-15173-GARat conjugates (5×, 10×) compared to the corresponding 679 Compound 1-GARat, DyLight 680B-GARat, and Company B Compound-GARat conjugates.

679 Compound 1-GAM, Company A Compound-GAM, and Company A Compound R-GAM were evaluated for immunofluorescence in a cell based assay using detection of PDI in cells with a mouse anti-PDI antibody. FIG. 28 shows results of 679 Compound 1-GAM at a 15× molar excess (FIG. 28A), Company A Compound-GAM at a 15× molar excess (FIG. 28B), and Company A Compound R-GAM at a 15× molar excess (FIG. 28C). As FIG. 28 shows, 679 Compound 1-GAM exhibited proper staining of PDI in the ER while Company A Compound-GAM and Company A Compound R-GAM exhibited non-specific staining with staining found throughout the cell. Similar results were obtained for 679 Compound 1-GAM at 7.5× and 22.5× molar excesses, as well as Company A Compound-GAM and Company A Compound R-GAM at 7.5× molar excess (data not shown).

Figure 29A:
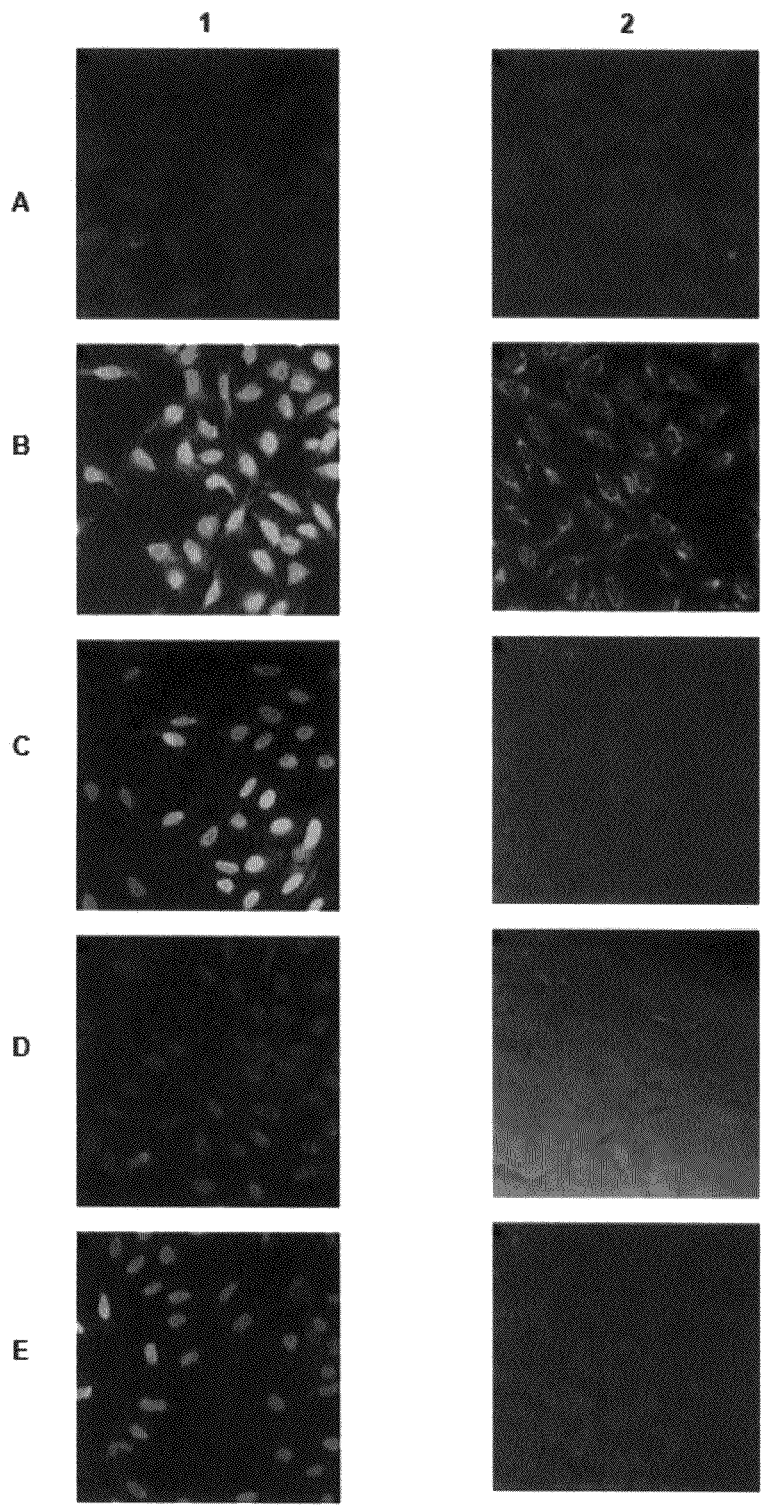
FIG. 29A shows immunofluorescence data with commercial dyes and inventive compounds in one embodiment.
Figure 29B:
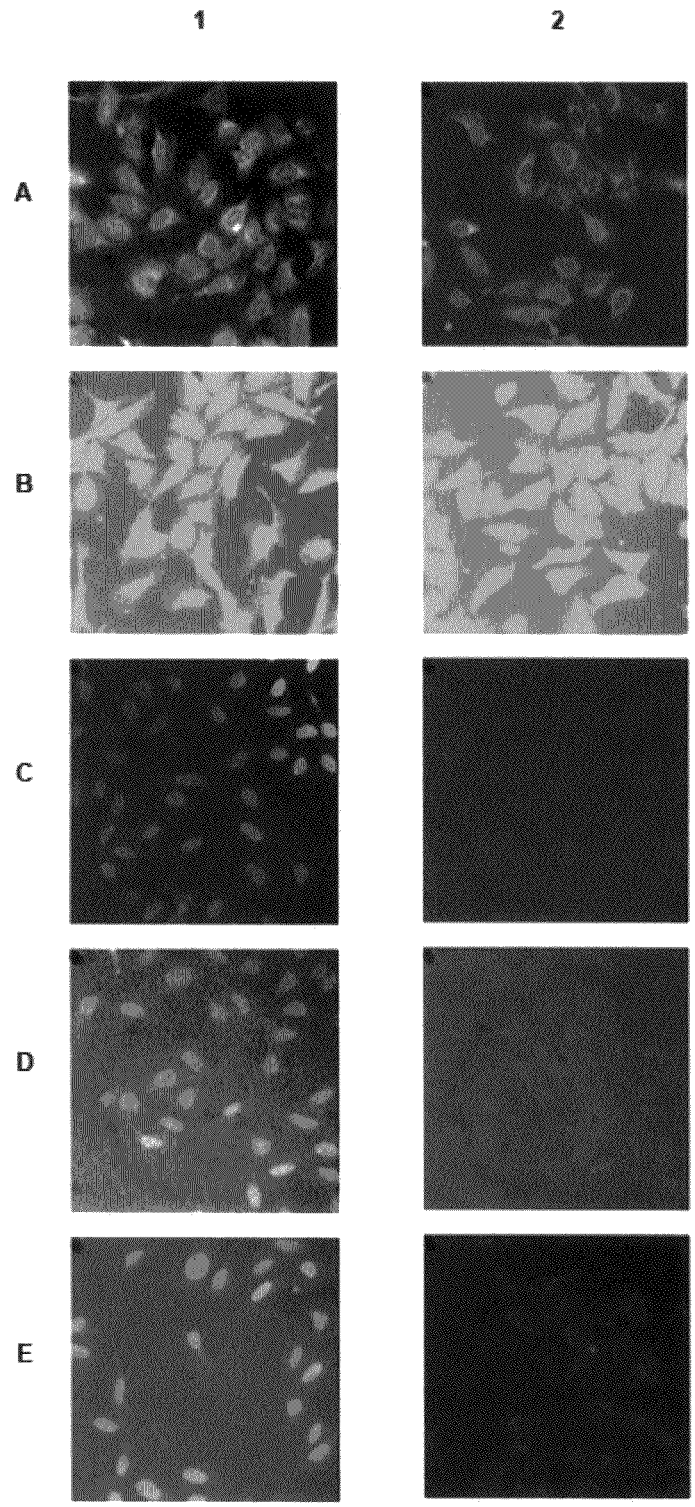
FIG. 29B shows immunofluorescence data with commercial dyes and inventive compounds in one embodiment.
Figure 29C:
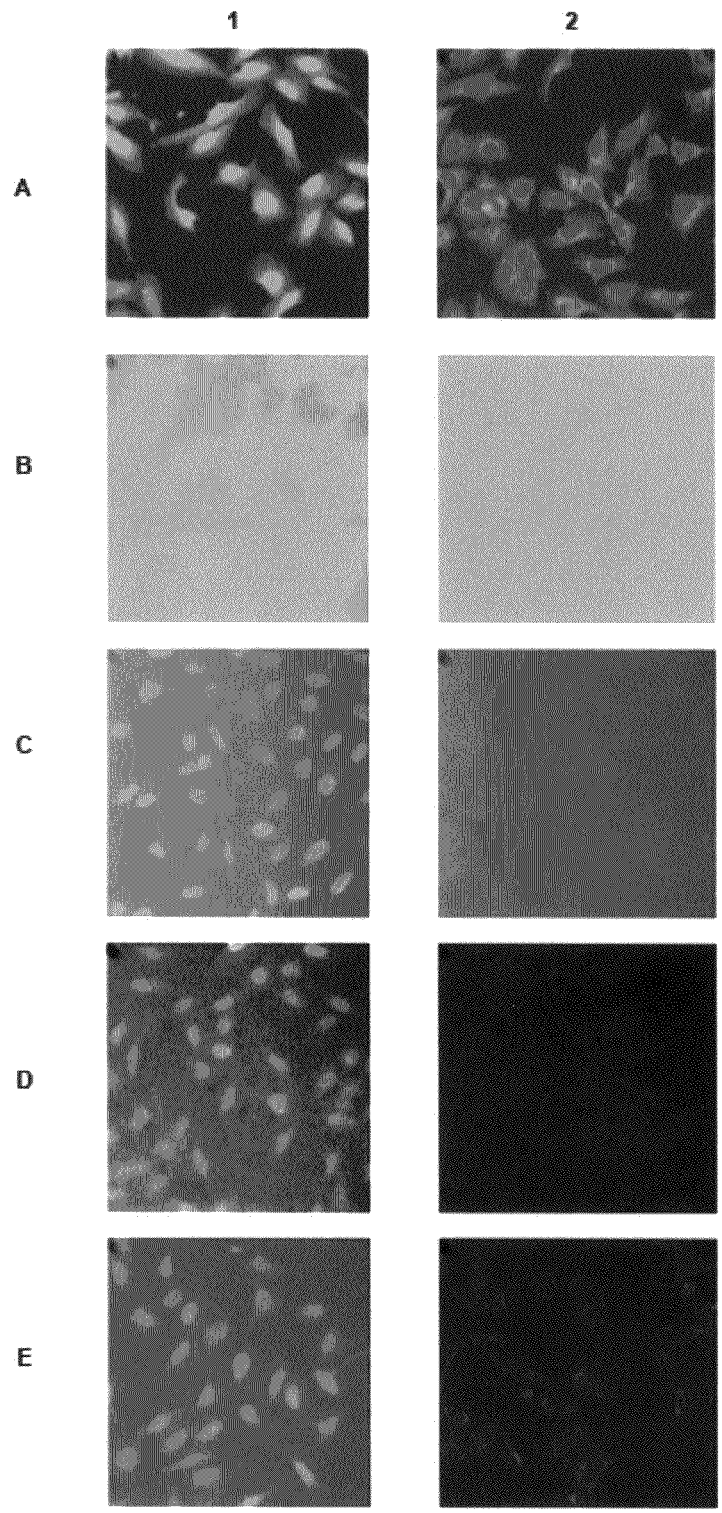
FIG. 29C shows immunofluorescence data with commercial dyes and inventive compounds in one embodiment.

FIG. 29A-C shows detection of lamin A in U2OS cells (column 1) with V08-15173-GAM, V10-04152-GAM, 679 Compound 1/1-GAM, Company A Compound-GAM, and Company B Compound-GAM conjugates (4 µg/ml) at 5× molar excess (FIG. 29A), 10× molar excess (FIG. 29B), and 15× molar excess (FIG. 29C) with V08-15173-GAM (row A FIGS. 29A, 29B, 29C), V10-04152-GAM (row B FIGS. 29A, 29B, 20C), 679 Compound 1/1-GAM (row C FIGS. 29A, 29B, and 29C), Company A Compound-GAM (row D FIGS. 29A, 29B, 29C), Company B Compound-GAM (row E FIGS. 29A, 29B, 29C), and associated negative controls (column 2). There was very little non-specific binding observed with V08-15173-GAM and 679 Compound 1/1-GAM. Company A Compound-GAM and Company B Compound-GAM conjugates showed high non-specific binding starting from 5× molar excess. At low molar excess, Company A Compound-GAM exhibited staining of the nucleus, which was greater than the other dyes. V10-04152-GAM exhibited good specificity but was not very bright. Staining of the nucleus with Company B Compound-GAM was greatly improved at 15× molar excess, but there was an increase in non-specific binding.

The following table shows quantitative analysis of the FIGS. 29A-C data expressed as Mean Total Intensity, which is the average total intensity of all pixels within a defined area or defined primary object such as a nucleus, and S/B ratios.

| Average | V08-15173 | Negative control | V10-04152 | Negative control | 679 Compound 1/1 | Negative control | Company A Compound | Negative control | Company B Compound | Negative control |
|---|---|---|---|---|---|---|---|---|---|---|
| 2.5 X | 17366 | 5966 | 11946 | 6085 | 29229 | 5628 | 54496 | 9107 | 7092 | 6329 |
| 5.0 X | 32820 | 6643 | 12788 | 7357 | 49279 | 5859 | 72289 | 20303 | 11922 | 8360 |
| 7.5 X | 42876 | 7100 | 12513 | 6503 | 28782 |  | 152502 | 51104 | 18894 | 13351 |
| 10 X | 47756 | 9690 | 21147 | 6266 | 30098 | 6115 | 188505 | 136044 | 25020 | 18330 |
| 15 X | 49060 | 10779 | 15942 | 6746 | 48071 | 7277 | 679693 | 665370 | 67705 | 24350 |

| S/B | V08-15173 | V10-04152 | 679 Compound 1/1P1 | Company A Compound | Company B Compound |
|---|---|---|---|---|---|
| 2.5 X | 2.9 | 2.0 | 5.2 | 6.0 | 1.1 |
| 5.0 X | 4.9 | 1.7 | 8.4 | 3.6 | 1.4 |
| 7.5 X | 6.0 | 1.9 | 4.9 | 3.0 | 1.4 |
| 10 X | 4.9 | 3.4 | 4.9 | 1.4 | 1.4 |
| 15 X | 4.6 | 2.4 | 6.6 | 1.0 | 2.8 |

Lamin A, a nuclear protein, should show staining specific to the nucleus. Any lamin A staining outside the nucleus is non-specific staining. In addition, negative control conditions that lack a primary antibody are also used to determine the antibody staining specificity. Company A and Company B Compounds showed no non-specific binding. V08-15173 and 679 Compound 1/1 exhibited a minimal amount of non-specific binding. Due to the strong non-specific binding at higher molar excesses, Company A and Company B Compounds exhibited decreased signal to background (S/B) levels.

Quantitative analysis of a repeat experiment of FIG. 29A-C are shown below.

| Average | V08-15173 | Negative control | Company A Compound | Negative control | 679 Compound 1/1 | Negative control |
|---|---|---|---|---|---|---|
| 2.5 X | 118440 | 12053 | 198471 | 24758 | 77195 | 8711 |
| 5 X | 183078 | 9441 | 351666 | 84270 | 140772 | 8674 |
| 10X | 391473 | 13094 | 638569 | 330337 | 159948 | 20481 |
| 15 X | 211270 | 17260 | 560119 | 632936 | 199626 | 16277 |

| S/B | V08-15173 | Company A Compound | 679 Compound 1/1 |
|---|---|---|---|
| 2.5 X | 9.8 | 8.0 | 8.9 |
| 5 X | 19.4 | 4.2 | 16.2 |
| 10X | 29.9 | 1.9 | 7.8 |
| 15 X | 12.2 | 0.9 | 12.3 |

Company A Compound showed much higher non-specific binding compared to V08-15173 and 679 Compound 1/1, with the non specific binding appearing at the 2.5× condition for Company A Compound-GAM.

679 Compound 1/1-NHS and V08-15173-NHS showed on average a 20% lower intensity compared to Company A Compound-NHS. V10-04152 intensity was about 50% lower than V08-15173, and about 65% lower than Company A Compound. GAM labeling efficiency was similar for all dyes at all molar excesses. At 5× molar excess, the GAR labeling efficiency for all dyes was similar, except for V10-04152. At 15× and 25× molar excesses, the GAR labeling efficiency similar for all compounds except Company B Compound. In immunofluorescence studies, Company A Compound, 679 Compound 1/1, and Company B Compound GAM conjugates showed high non-specific binding. V08-15173 and V10-04152 GAM conjugates showed little non-specific binding. Performance of conjugates in immunofluorescence appeared to be highly dependent on the performance of the primary antibody.

In the indicated experiments, the inventive compounds and commercial dye were evaluated for immunofluorescence in a cell based assay using the following protocol. Frozen U20S cell plates which were stored at −80° C. were thawed for 45 minutes at 50° C. Storage buffer (PBS) was removed and the cells were permeabilized for 15 minutes with 0.1% Triton-X100 in 1×PBS buffer (100 µl/well). The cell plate was blocked for 60 minutes in 2% BSA/PBS-0.1% Triton-X100. Primary antibody, either mouse anti-α tubulin, mouse anti-ezrin or mouse anti-PDI, or rabbit anti-β-catenin, rabbit anti-cytokeratin 18, or rabbit anti-calreticulin, were diluted in 2% BSA/PBS-0.1% Triton-X100, and added to the plate and incubated for 1 hour at room temperature. Control wells contained only 2% BSA/PBS-0.1% Triton-X100 blocker. After incubation, the antibody solution was removed from the plate and the plate was washed three times with 100 µl/well of PBS-0.5% Tween-20 and one time with 100 µl/well PBS. GAM secondary antibody labeled with various molar excess of the inventive or commercial compound to achieve the indicated D/P ratio were diluted to 4 µg/ml in PBS and incubated for 1 hour at room temperature. The plates were washed three times with 100 µl/well of PBST and once with 100 µl/well PBS, and Hoechst (diluted to 0.1 µg/ml in PBS) was added to each well (100 µl/well). The plates were scanned on ArrayScan Plate Reader for imaging and quantitation.

Figure 30B:
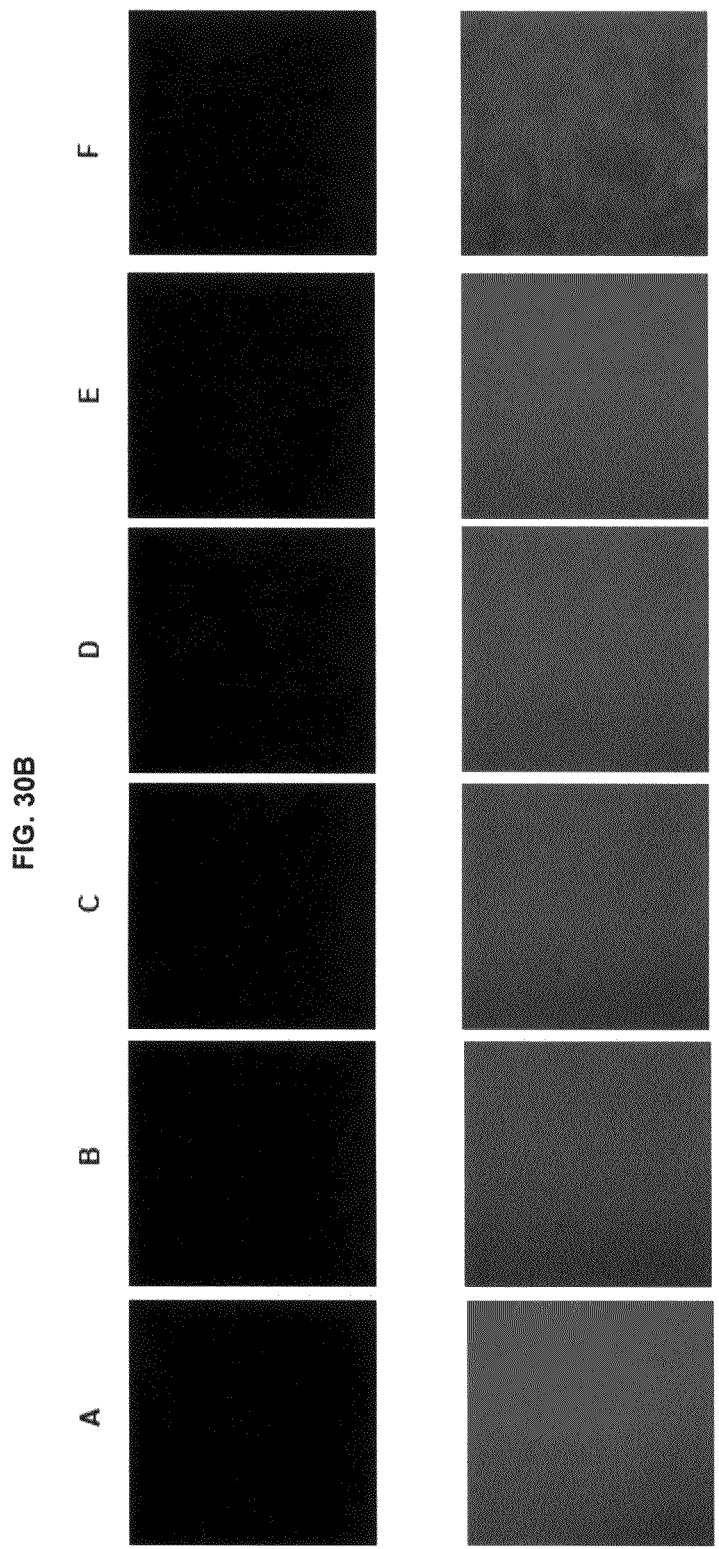
FIG. 30B shows immunofluorescence data with commercial dyes and inventive compounds in one embodiment.

FIG. 30A shows detection in U2OS cells of α-tubulin (row 1), ezrin (row 2), and PDI (row 3) with 679 Compound 4/4-GAM (50 µg; D/P of 1.2; column A), 679 Compound 4/4-GAM (65 µg; D/P 1.6; column B), 679 Compound 4/4-GAM (100 µg; D/P of 2.0; column C), CF 680-GAM (D/P of 4.0; column D), CF 680R-GAM (D/P of 7.6; column E), and Alexa Fluor 680-GAM (D/P of 5.0; column F), and associated negative controls shown in FIG. 30B, in the absence of primary antibody. FIG. 30A shows that the highest fluorescence intensity for all three targets was observed with GAM labeled with Biotium's CF 680 and CF 680R Labeling Kits. Doubling the amount of 679 Compound 4/4 in the labeling reaction did not equate to doubling increase in the intensity. Labeling 1 mg of antibody with 50-65 µg of 679 Compound 4/4 was similar to Alexa Fluor 680 Protein Labeling Kit. FIG. 30B shows no non-specific binding with 679 Compound 4/4-GAM conjugates, regardless of the amount of dye used for labeling (50 µg, 65 µg, or 100 µg dye). There was no non-specific binding with CF 680-GAM and CF 680R-GAM conjugates. Some non-specific binding was observed with Alexa Fluor 680-GAM conjugates.

FIG. 31A shows detection in U2OS cells of β-catenin (row 1), cytokeratin 18 (row 2), and calreticulin (row 3) with 679 Compound 4/4-GAM (50 µg; D/P of 1.4; column A), 679 Compound 4/4-GAM (65 µg; D/P 1.7; column B), CF 680-GAM (D/P of 3.5; column C), CF 680R-GAM (D/P of 5.7; column D), and Alexa 680-GAM (D/P of 5.8; column E), and associated negative controls shown in FIG. 31B, where row 1 images were taken at 0.5 sec and row 2 images were taken at 1.5 sec. The results showed that the conjugates made with the inventive dye at the lower D/P showed very good specificity and higher signal intensity as compared to Alexa Fluor 680 conjugates with the higher D/P (5.8), and the CF dyes showed non-specific binding compared to the conjugate made with Alexa Fluor 680. FIG. 31B shows no non-specific binding with 679 Compound 4/4-GAR conjugates, regardless of the amount of dye used for labeling (50 µg, 65 µg). There was no non-specific binding with CF 680-GAR and CF 680R-GAR conjugates. Non-specific binding was observed with Alexa Fluor 680-GAR conjugates (FIG. 31B).

Figure 32:
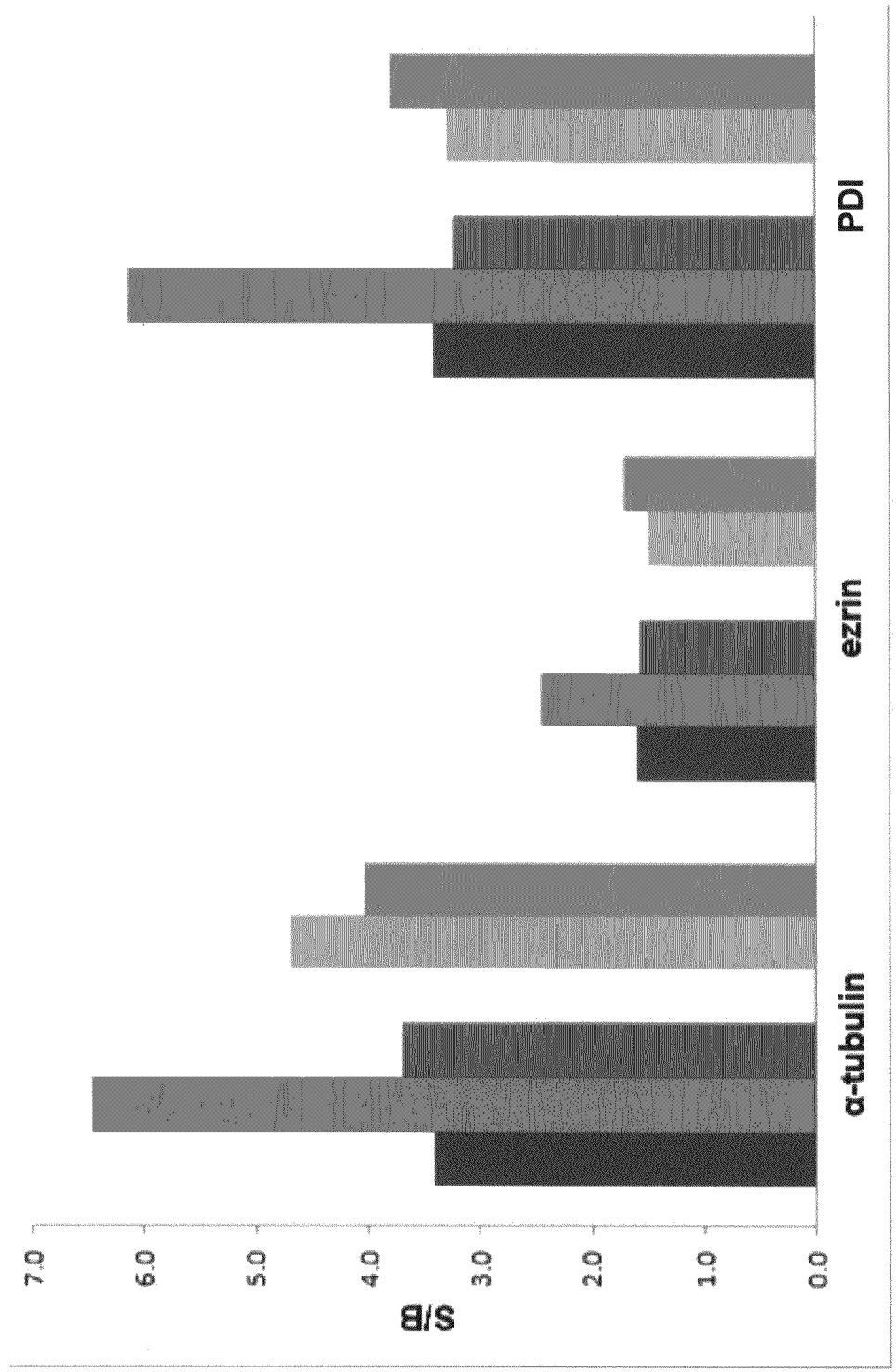
FIG. 32 shows immunofluorescence data with commercial dyes and inventive compounds in one embodiment.
Figure 33:
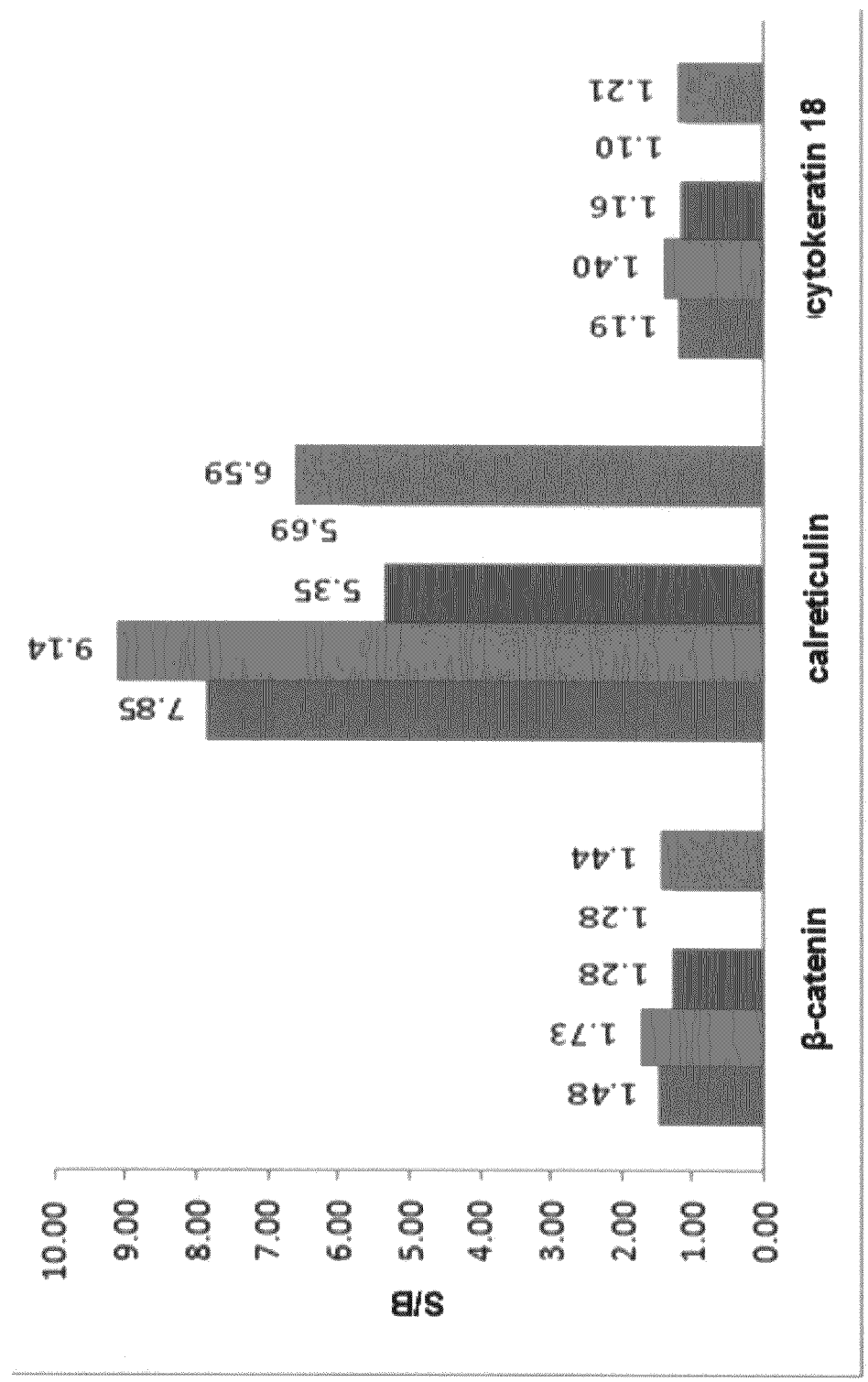
FIG. 33 shows immunofluorescence data with commercial dyes and inventive compounds in one embodiment.

Quantitative analysis of the data of FIG. 30A, expressed as signal to background ratio (S/B), is shown in FIG. 32, showing 679 Compound 4/4-GAM (50 µg; blue), CF 680-GAM (red), CF 680R-GAM (green), Alexa Fluor 680-GAM (ellow), 679 Compound 4/4-GAM (65 µg; purple), and 679 Compound 4/4-GAM (100 µg; pink). Quantitative analysis of the data of FIG. 31A, expressed as signal to background ratio (S/B), is shown in FIG. 33, showing 679 Compound 4/4-GAM (50 µg; dark blue), CF 680-GAM (red), CF 680R-GAM (green), Alexa Fluor 680-GAM (yellow), and 679 Compound 4/4-GAM (65 µg; light blue). 679 Compound 4/4-GAM and 679 Compound 4/4-GAR conjugates showed equivalent or higher S/B compared to the conjugates prepared with Life Technologies' Protein Labeling Kit.

Figure 34:
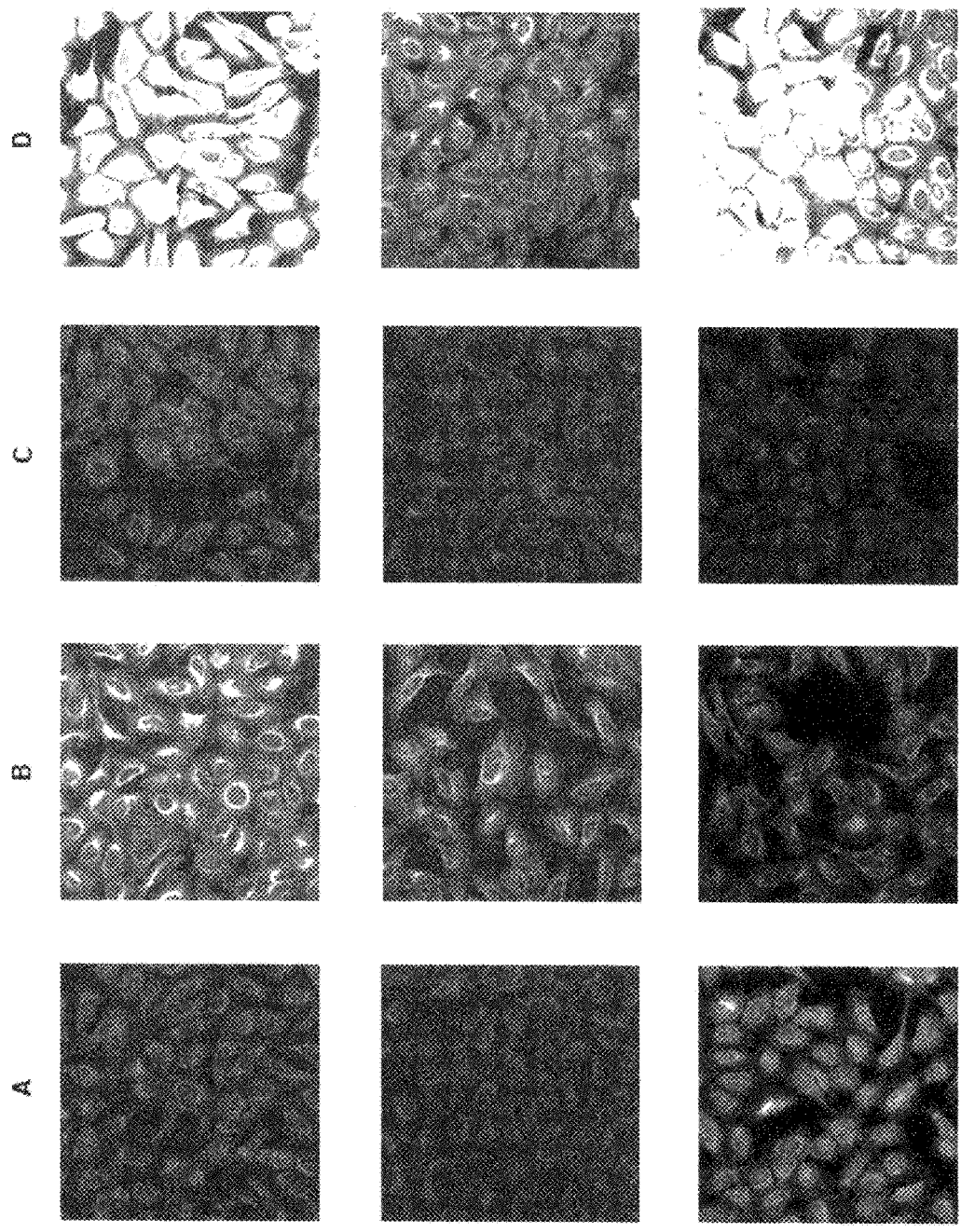
FIG. 34 shows immunofluorescence data with commercial dyes and inventive compounds in one embodiment.
Figure 35:
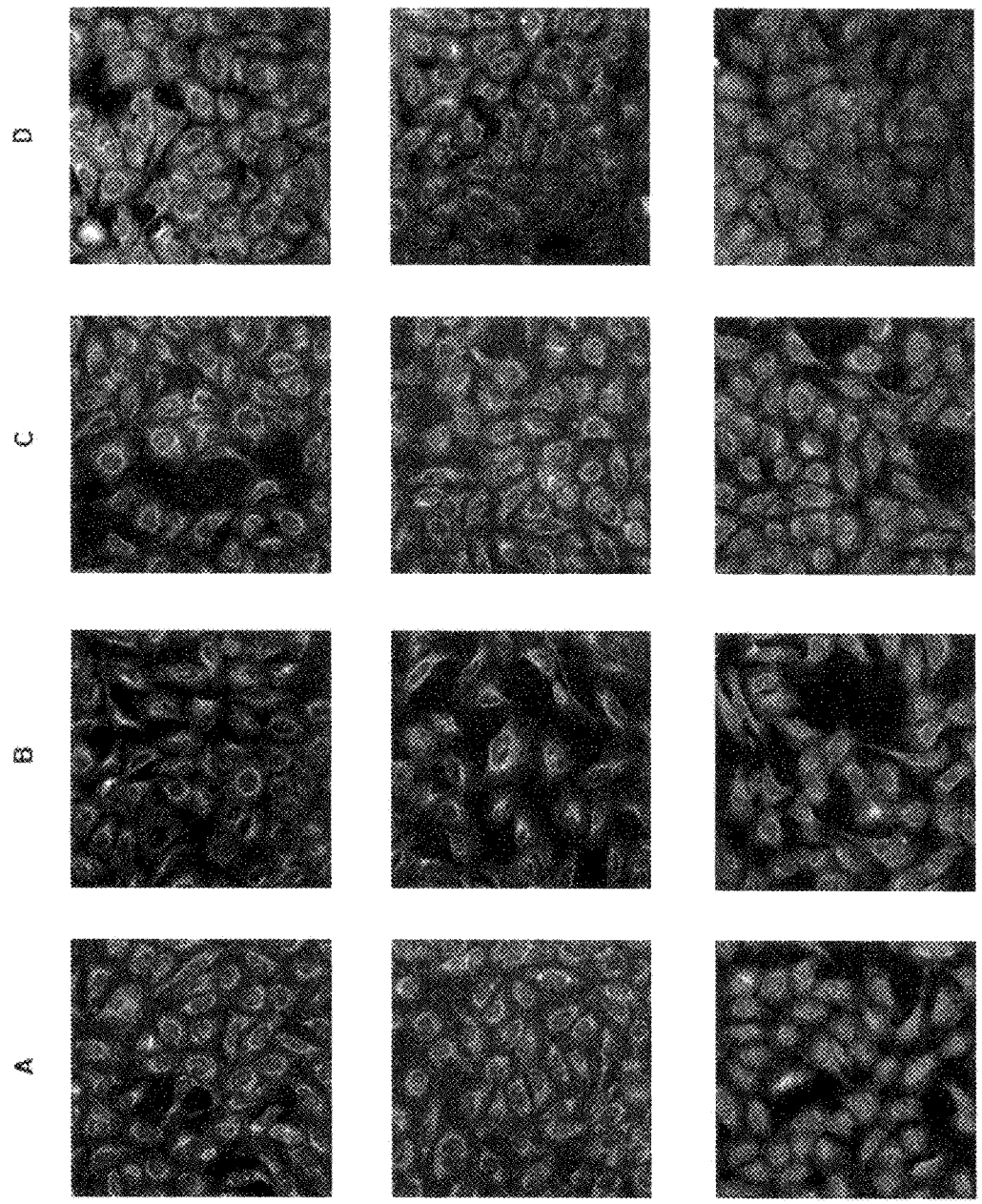
FIG. 35 shows immunofluorescence data with commercial dyes and inventive compounds in one embodiment.
Figure 36:
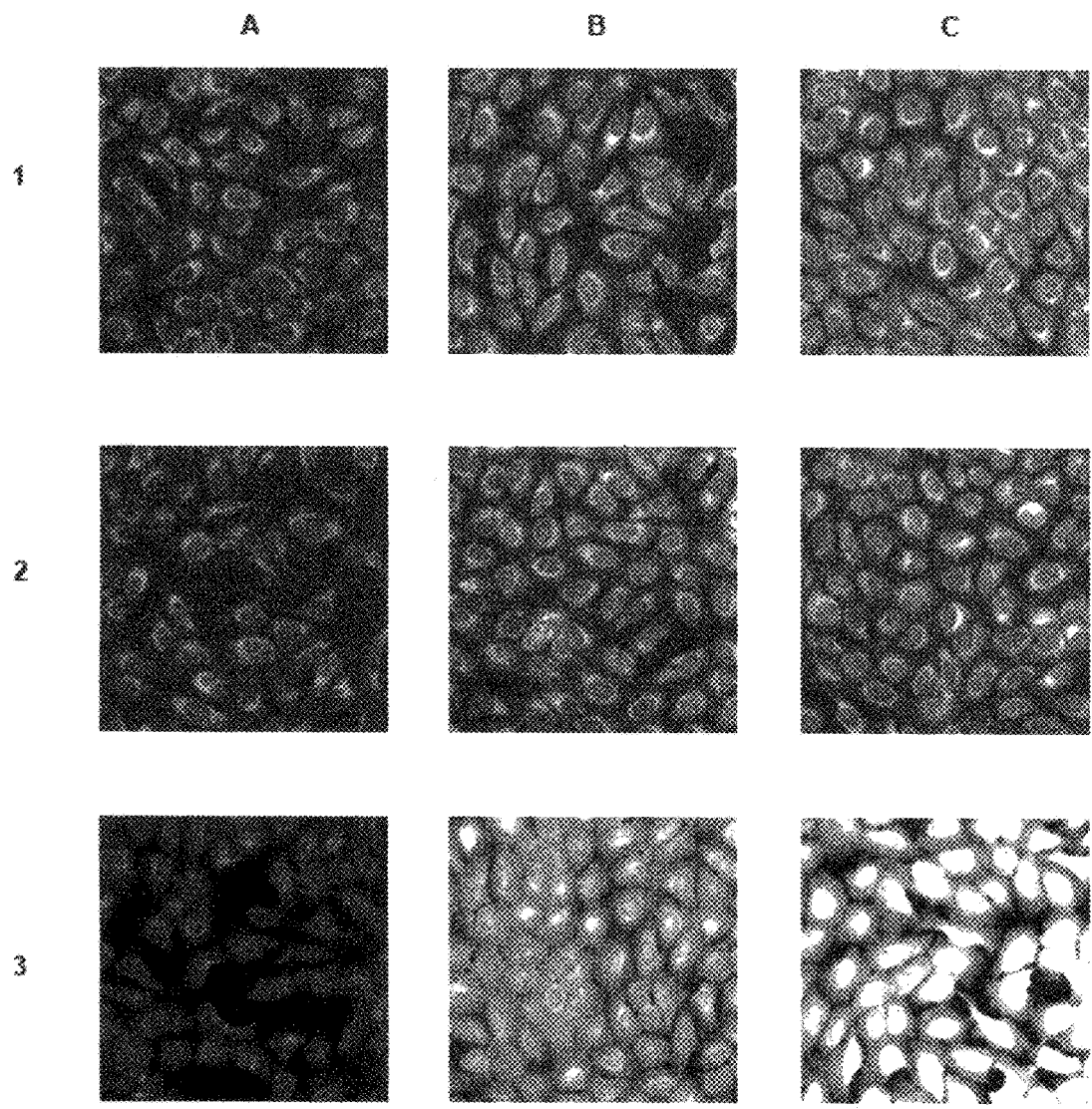
FIG. 36 shows immunofluorescence data with commercial dyes and inventive compounds in one embodiment.
Figure 37:
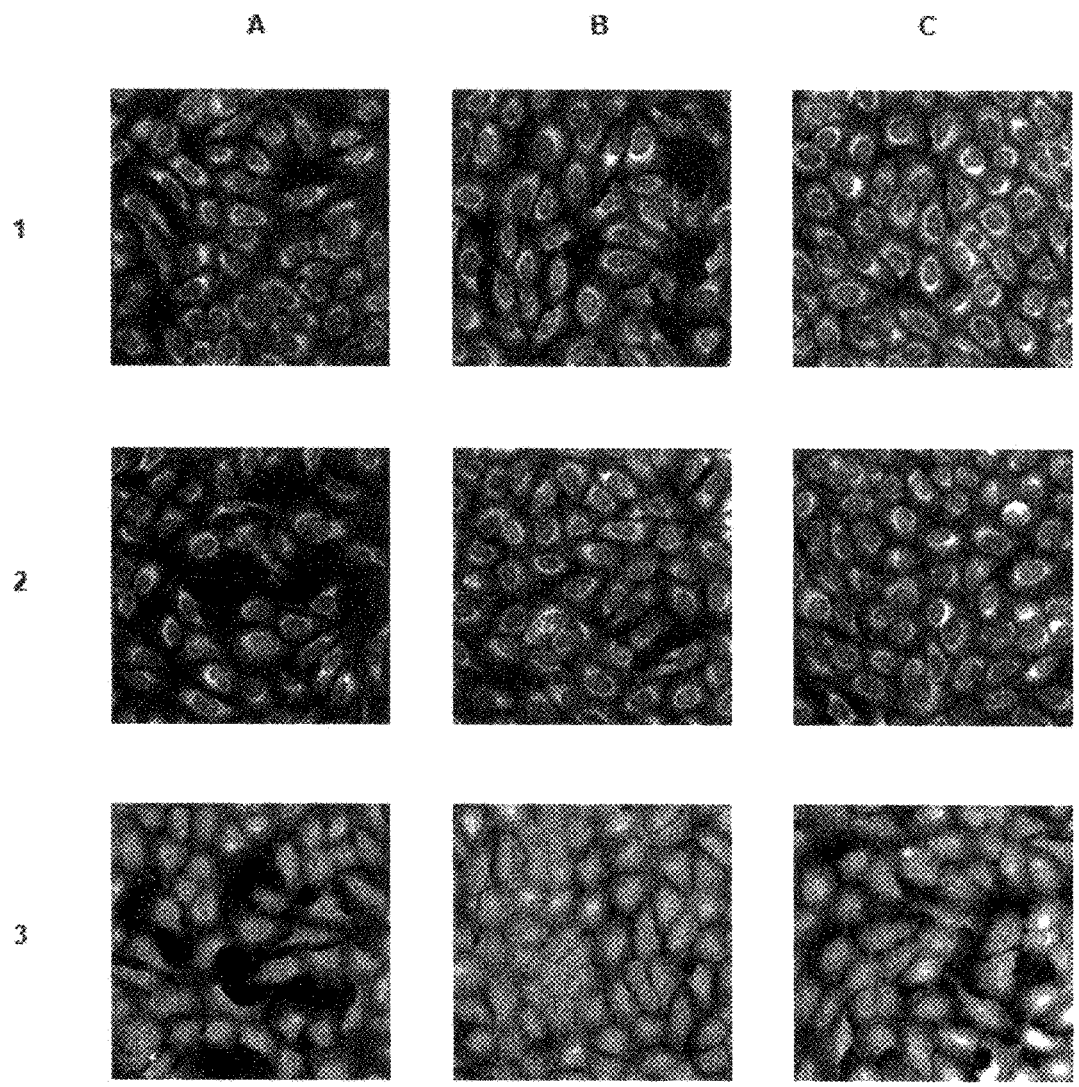
FIG. 37 shows immunofluorescence data with commercial dyes and inventive compounds in one embodiment.
Figure 38:
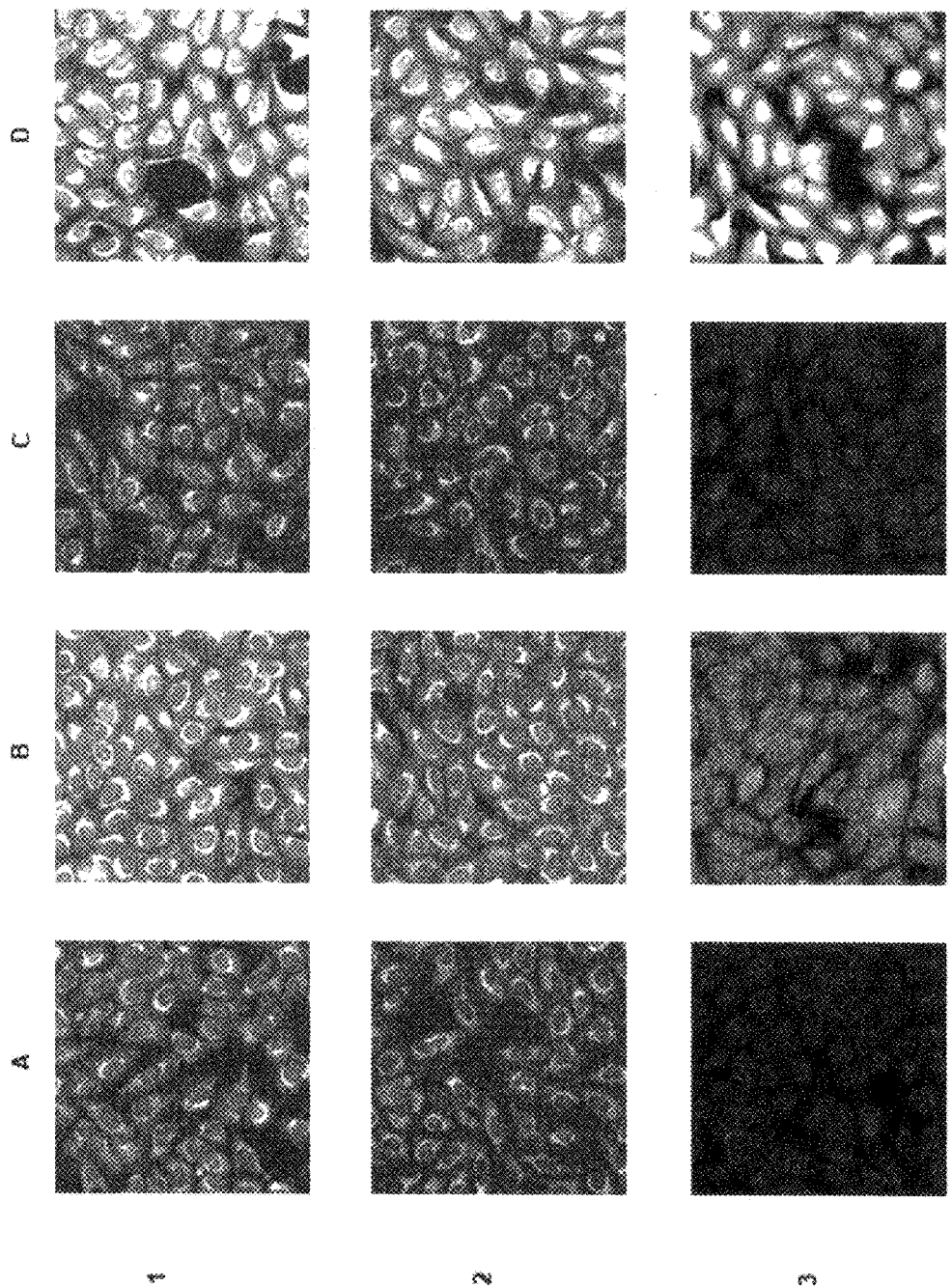
FIG. 38 shows immunofluorescence data with commercial dyes and inventive compounds in one embodiment.
Figure 39:
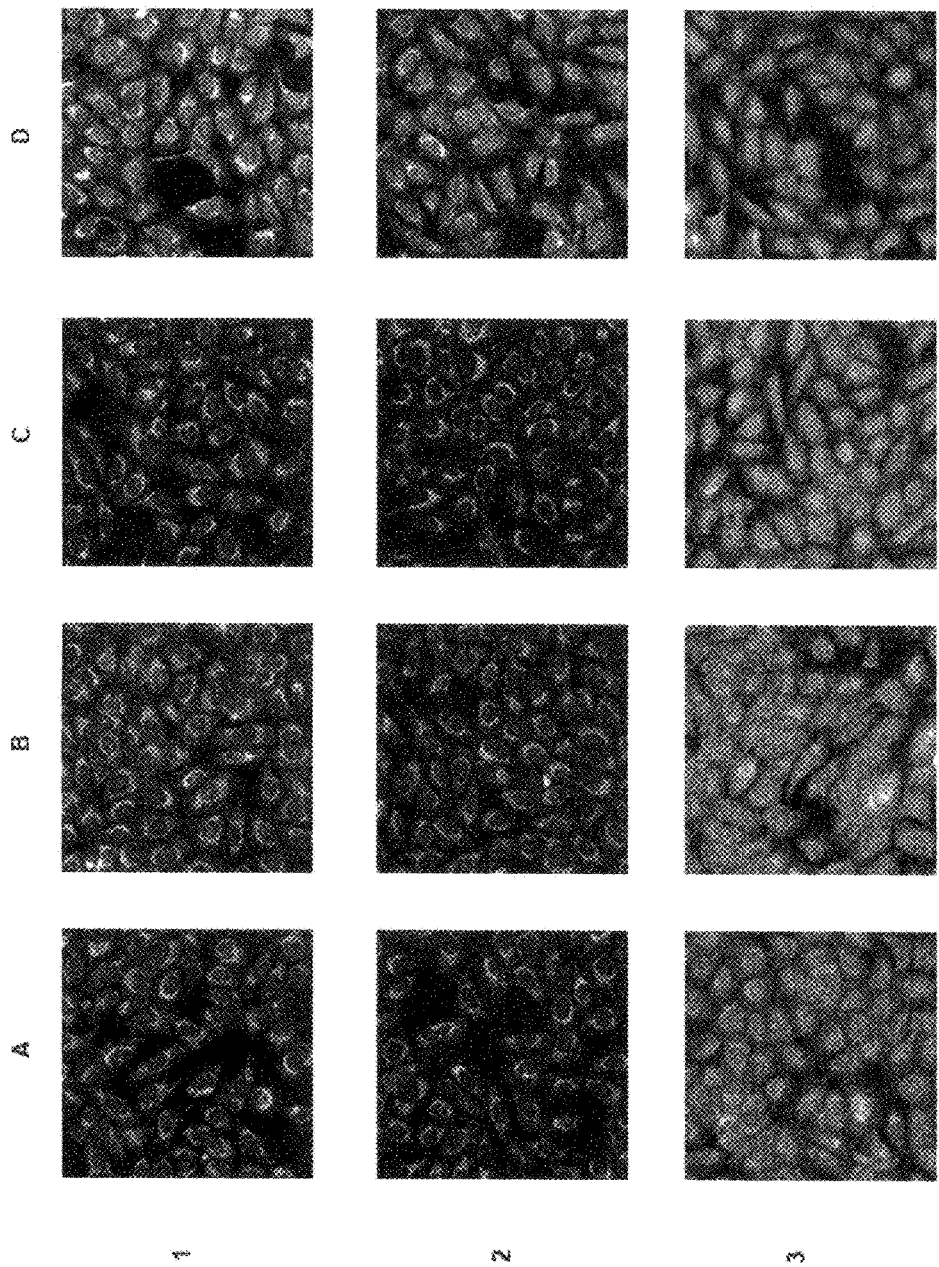
FIG. 39 shows immunofluorescence data with commercial dyes and inventive compounds in one embodiment.

In the indicated experiments, the inventive compounds and commercial dye were evaluated for immunofluorescence in a cell based assay using the above protocol. Primary antibody, either mouse anti-α tubulin monoclonal, mouse anti-PDI monoclonal, or mouse anti-cytochrome C monoclonal were added to the plate. FIG. 34 shows direct detection in U2OS cells of α-tubulin with DyLight 680-α-tubulin (D/P of 2.6; column A), 679 Compound 4/4-α-tubulin (D/P 2.5; column B), CF 680R-α-tubulin (D/P of 2.9; column C), and Alexa Fluor 680-α-tubulin (D/P of 5.4; column D), added to the plate with the conjugates in 2% BSA/0.1% Triton X-100 at 1:10 (row 1), 1:20 (row 2), or 1:1 (row 3). Direct detection of α-tubulin was very specific with 679 Compound 4/4-α-tubulin. Over-labeled antibody, such as with the Life Technologies Kit, allowed for high intensity, but also resulted in non-specificity. FIG. 35 shows direct detection of α-tubulin in U2OS cells with DyLight 680-α-tubulin (D/P of 2.6; column A), 679 Compound 4/4-α-tubulin (D/P 2.5; column B), CF 680R-α-tubulin (D/P of 2.9; column C), and Alexa 680-α-tubulin (D/P of 5.4; column D), diluted in 2% BSA/0.1% Triton X-100 at 1:10 (row 1), 1:20 (row 2), or 1:1 (row 3). Good specificity and detection was observed with 679 Compound 4/4-α-tubulin regardless of lower D/P compared to Life Technologies Labeling Kit. FIG. 36 shows direct detection of protein disulphide isomerase (PDI)) in U2OS cells with 679 Compound 4/4-PDI (D/P 1.9; column A), CF 680-PDI (D/P of 3.2; column B), and Alexa Fluor 680-PDI (D/P of 8.4; column C), that were diluted in 2% BSA/0.1%. Triton X-100 at 1:10 (row 1), 1:20 (row 2), or 1:1 (row 3). Good specificity and detection was observed with 679 Compound 4/4-PDI regardless its lower D/P compared to Biotium's Labeling Kit and Life Technologies Labeling Kit. It also appeared that the higher amounts of primary antibody caused a loss in specificity and an increase in non-specific biding. FIG. 37 shows direct detection of PDI in U2OS cells with 679 Compound 4/4-PDI (D/P 1.9; column A), CF 680-PDI (D/P of 3.2; column B), and Alexa 680-PDI (D/P of 8.4; column C), diluted in 2% BSA/0.1% Triton X-100 at 1:10 (row 1), 1:20 (row 2), or 1:1 (row 3). FIG. 38 shows direct detection of cytochrome C in U2OS cells with 679 Compound 414-cytochrome C (D/P 1.5; column A), CF 680-cytochrome C (D/P of 4.2; column B), CF 680R-cytochrome C (D/P of 4.9; column C), and Alexa Fluor 680-cytochrome C (D/P of 10.1; column D), diluted in 2% BSA/0.1% Triton X-100 at 1:10 (row 1), 1:20 (row 2), or 1:1 (row 3). FIG. 39 shows direct detection of cytochrome C in U2OS cells with 679 Compound 414-cytochrome C (D/P 1.5; column A), CF 680-cytochrome C (D/P of 4.2; column B), CF 680R-cytochrome C (D/P of 4.9; column C), and Alexa Fluor 680-cytochrome C (D/P of 10.1; column D), diluted in 2% BSA/0.1% Triton X-100 at 1:10 (row 1), 1:20 (row 2), or 1:1 (row 3).

Figure 40:
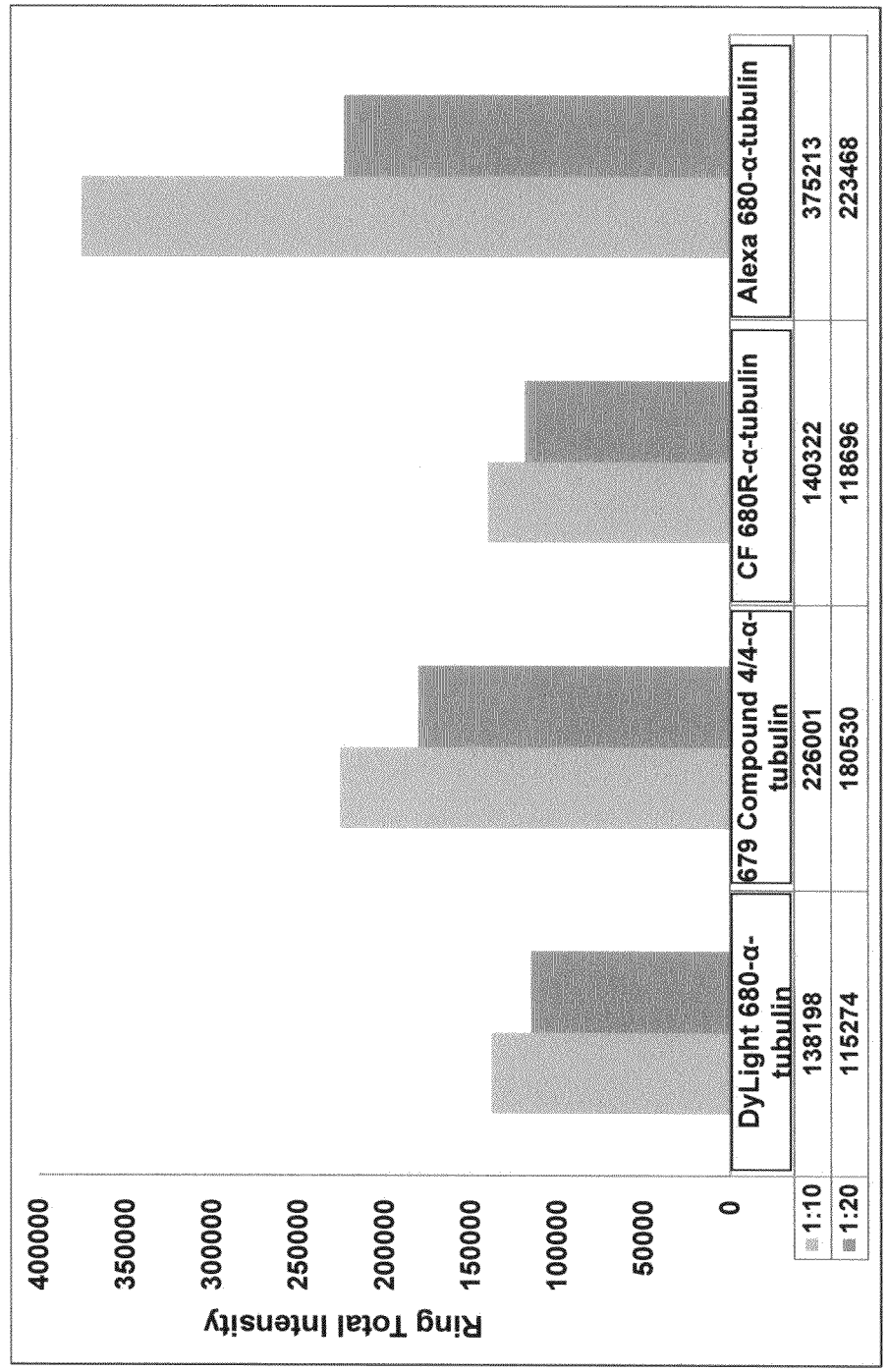
FIG. 40 shows immunofluorescence data with commercial dyes and inventive compounds in one embodiment.
Figure 41:
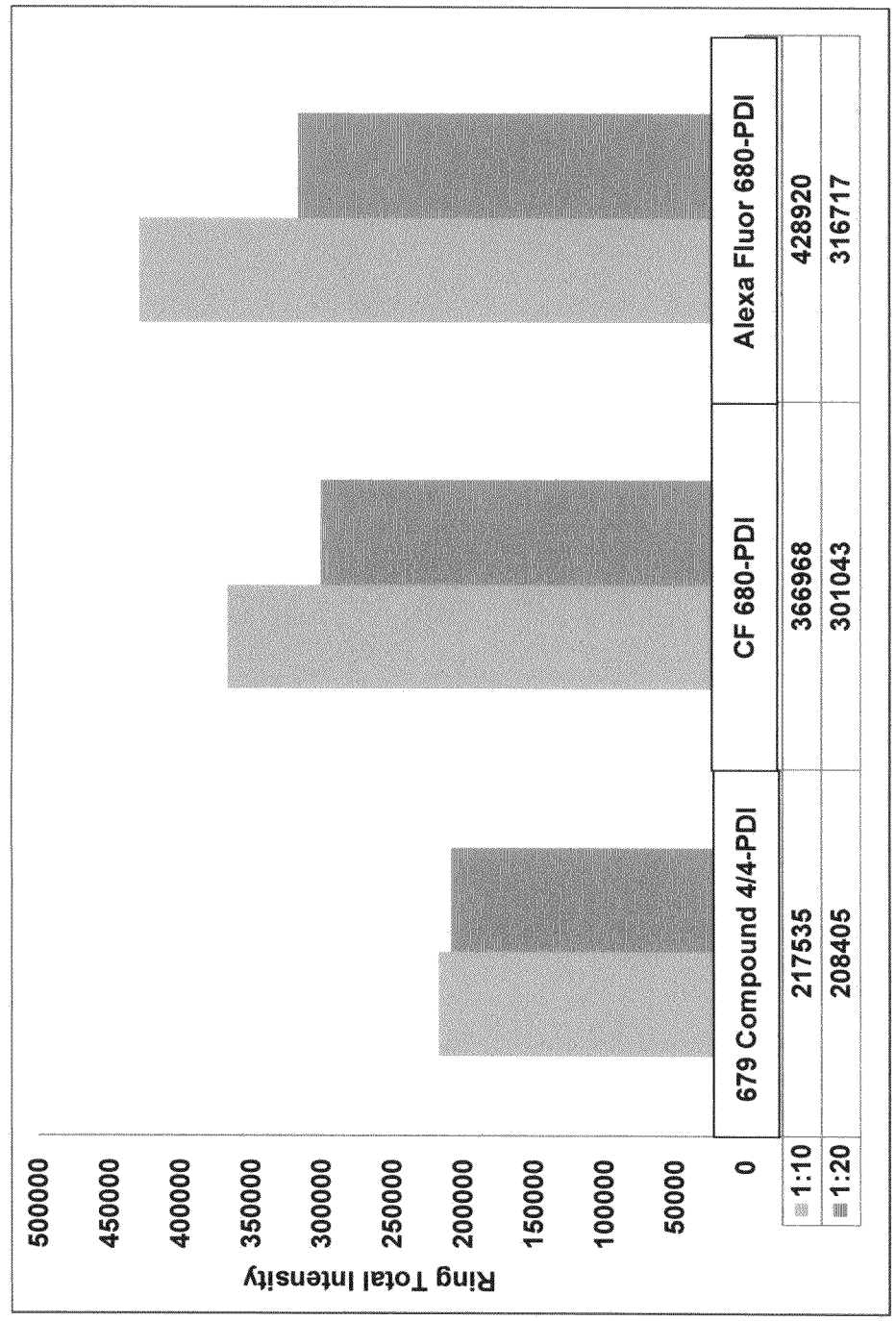
FIG. 41 shows immunofluorescence data with commercial dyes and inventive compounds in one embodiment.
Figure 42:
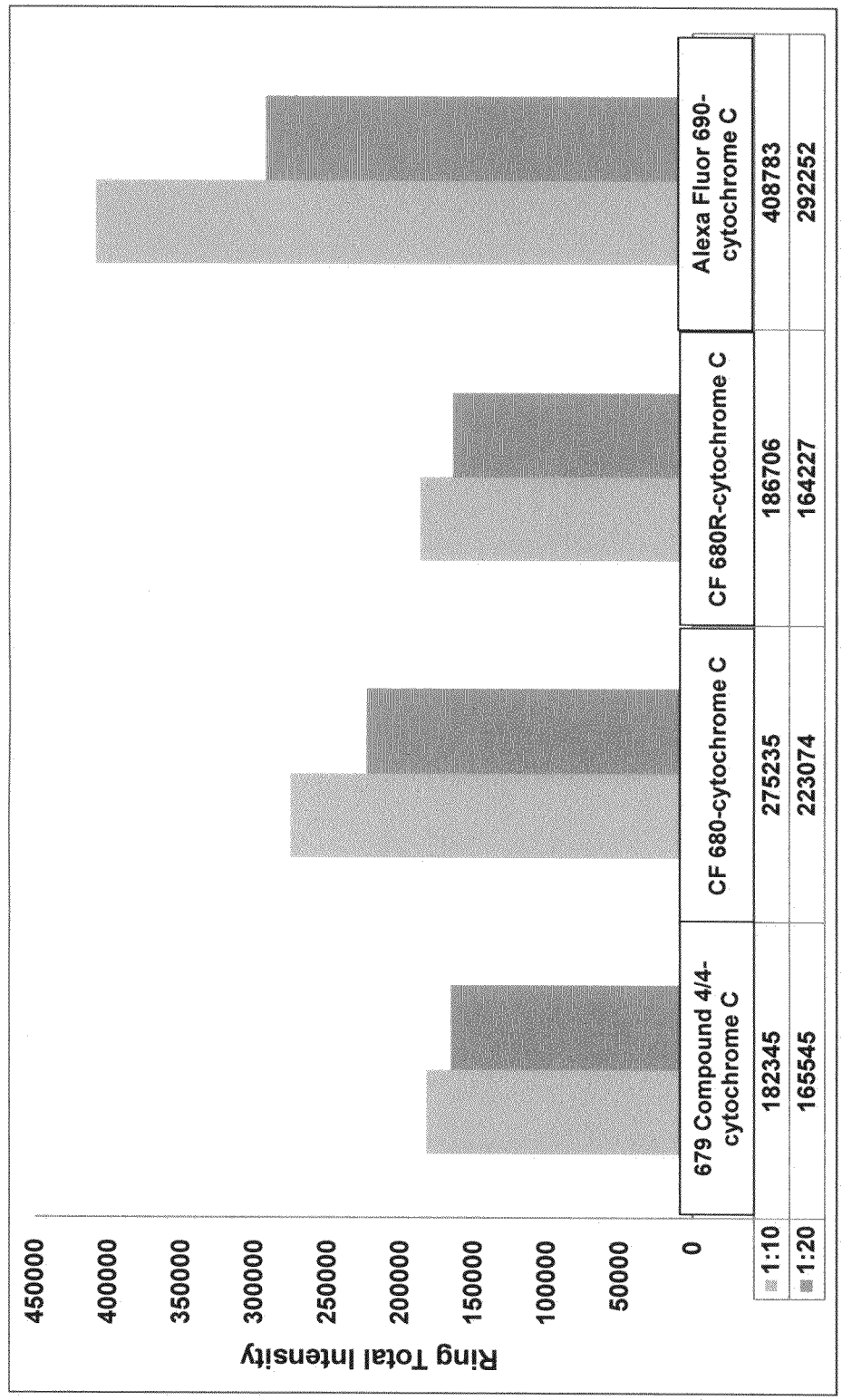
FIG. 42 shows immunofluorescence data with commercial dyes and inventive compounds in one embodiment.

Quantitative analysis of the data presented in FIGS. 34-39, expressed as Ring Total Intensity, which is the average total intensity of all pixels within a defined area or defined primary object such as a nucleus, is shown in FIGS. 40-42, where FIG. 40 shows Ring Total Intensity for the detection of α-tubulin, with the primary antibody at either a 1:10 ratio (orange bars) or a 1:20 ratio (green bars); FIG. 41 shows Ring Total Intensity for the detection of PDI, with the primary antibody at either a 1:10 ratio (orange bars) or a 1:20 ratio (green bars); and FIG. 42 shows Ring Total Intensity for the detection of cytochrome C, with the primary-labeled antibody diluted in 2% BSA/0.1% Triton X-100 at either a 1:10 (orange bars) or a 1:20 (green bars). Based on the results above, 15 µg of 679 Compound 4/4 was suitable for use in a monoclonal antibody labeling method and kit (micro labeling), and 65 µg of 679 Compound 4/4 was suitable for use in an antibody labeling method and kit (macro labeling). The results also showed that antibodies labeled with 679 Compound 4/4 resulted in higher fluorescence intensity compared to antibodies labeled with equivalent amount of DyLight 680 dye. Conjugation of 679 Compound 4/4 with monoclonal antibodies resulted in good specificity and sufficient intensity as compared to Biotium's and Life Tech Antibody Labeling Kits. Conjugation of 679 Compound 4/4 with antibodies resulted in good specificity and similar intensity compared to Biotium's and Life Technologies' Antibody Labeling Kits.

EXAMPLE 10

The inventive compounds are used for in vivo imaging to obtain information about biological tissues that are primarily accessible. The compounds are responsive to light in the near infrared region of the spectrum, a part of the spectrum that has minimal interference from the absorbance of biological materials. In one embodiment, the compounds are used for fluorescent imaging of targets within animals. For example, in vivo imaging information can be obtained using methods such as X-ray, magnetic resonance imaging, positron emission tomography, ultrasound imaging and probing, and other non-invasive methods used for diagnosing and treating disease. Light in the near infrared range (NIR), from about 650 nm to about 1000 nm wavelength, can permeate through several centimeters of tissue and thus can be used for in vivo imaging. Fluorescent dyes, such as the inventive compounds that are responsive to light in these longer wavelengths, can be used as conjugates with targeting molecules such as antibodies to bind and accumulate in, e.g., diseased tissue such as tumors, and may be used to distinguish healthy from diseased tissue. In some methods, the inventive compound may be attached to a biomolecule, such as a protein, peptide, or a drug, which is localized or retained in the desired tissue environment. Fluorescent in vivo imaging using NIR dyes such as the inventive compounds are diagnostic agents to discretely target disease tissue directly within animals or humans.

For in-vivo imaging, the compound, an isomer of the compound, or a conjugate of the compound or isomer with a targeting agent, is administered to a tissue (e.g., intravenously), permitted to accumulate with excess compound removed by the circulatory system, then the tissue is irradiated with light at an appropriate wavelength. The NIR fluorescent light is recorded and/or an image is generated from the data obtained to specifically detect and visualize the targeted cells or tissues. The dose of compound administered can differ and would be known by one skilled in the art depending upon the specific tissue, application, etc., as long as the method achieves a detectable concentration of the compound in the tissue to be assessed.

EXAMPLE 11

In Vivo Imaging using an Inventive Compound Conjugated to Anti-HER2 Antibody 779 Compound 1-NHS is conjugated to a rabbit anti-HER2 antibody (Genscript USA, Piscataway N.J.) by reconstituting the compound in dimethylformamide (DMF) at 10 mg/ml, then incubating at 10× molar excess with rabbit anti-HER2 antibody (0.1 mg) for one hour at room temperature to result in 779 Compound 1-anti-HER2 conjugate. The conjugation reaction is then subjected to PDDR to remove unlabeled (free) 779 Compound 1. Ten microgram of conjugate is injected intravenously to athymic mice bearing BT474 tumors. The animals are imaged over time at 1, 24, 48, 72, 96, and 120 hours post-injection using Pearl Imager, LI-COR Biosciences (LI-COR Instruments, Lincoln Nebr.).

Upon whole body imaging, fluorescence intensity is observed to be distributed over the whole animal during the first hour imaging and diminishes significantly at 72 hours. After 96 hours, the signal is localized and specific to the tumor.

679 Compound 4/4-NHS is conjugated to a rabbit anti-HER2 antibody (Genscript USA, Piscataway N.J.) by reconstituting the compound in dimethylformamide (DMF) at 10 mg/ml, then incubating at 10× molar excess with rabbit anti-HER2 antibody (0.1 mg) for one hour at room temperature to result in 679 Compound 4/4-anti-HER2 conjugate. The conjugation reaction is then subjected to PDDR to remove unlabeled (free) 679 Compound 4/4. Ten microgram of conjugate is injected intravenously to athymic mice bearing BT474 tumors. The animals are imaged over time at 1, 24, 48, 72, 96, and 120 hours post-injection using Pearl Imager, LI-COR Biosciences (LI-COR Instruments, Lincoln Nebr.).

Upon whole body imaging, fluorescence intensity is observed to be distributed over the whole animal during the first hour imaging and diminishes significantly at 72 hours. After 96 hours, the signal is localized and specific to the tumor.

EXAMPLE 12

In Vivo Imaging using Either Monosulfonated or Disulfonated Inventive Compound The compound may be rendered less hydrophilic, i.e., more hydrophobic, by altering the number of sulfonate groups. The fewer sulfonates, the more hydrophobic the compound becomes. In this embodiment, the compound may be more readily retained in a desired tissue or location if the appropriate number of sulfonates is determined; e.g., compound penetration into cells is more efficient if fewer sulfonates are present on the molecule. The compound may contain one, two, three, or four sulfonate groups. Hydrophobic compounds are also known to more efficiently cross the cell membrane, and thus are more desirable when the target of interest is located within the cell.

Alendronate, a compound that binds to, and is retained in, LNCap prostate cancer cells, is conjugated with disulfonated or monosulfonated benzo 779 Compound 1 by incubating a solution containing 1 mM disulfonated or monosulfonated 779 Compound 1-NHS in 1 ml of PBS and 0.5 ml tetrahydrofuran (THF) with 0.1 mM alendronate and 0.2 mM diisopropylethylamine at room temperature overnight. The conjugate is purified using reverse phase HPLC with 0-50% methanol against a 0.1 M ammonium acetate buffer, and is then lyophilized.

LNCap cells are grown orthotopically in nude mice. 779 Compound 1-alendronate (5 nmole) is injected into the tumor. Control mice are injected with free 779 Compound 1 containing a carboxylic acid residue instead of the reactive NHS ester. X-ray and near infra-red fluorescence images are captured.

Upon imaging the whole mouse, 779 Compound 1-alendroneate conjugate is retained in mouse tissue greater than the unconjugated compound; the conjugate is retained in the LNCap cell-induced tumor for at least 18 hrs.

Alendronate, a compound that binds to, and is retained in, LNCap prostate cancer cells, is conjugated with disulfonated or monosulfonated 679 Compound 4/4 by incubating a solution containing 1 mM disulfonated or monosulfonated 679 Compound 4/4-NHS in 1 ml of PBS and 0.5 ml tetrahydrofuran (THF) with 0.1 mM alendronate and 0.2 mM diisopropylethylamine at room temperature overnight. The conjugate is purified using reverse phase HPLC with 0-50% methanol against a 0.1 M ammonium acetate buffer, and is then lyophilized.

LNCap cells are grown orthotopically in nude mice. 679 Compound 4/4-alendronate (5 nmole) is injected into the tumor. Control mice are injected with free 679 Compound 4/4 containing a carboxylic acid residue instead of the reactive NHS ester. X-ray and near infra-red fluorescence images are captured.

Upon imaging the whole mouse, 679 Compound 4/4-alendroneate conjugate is retained in mouse tissue greater than the unconjugated compound; the conjugate is retained in the LNCap cell-induced tumor for at least 18 hrs.

EXAMPLE 13

In Vivo Imaging using Either Monosulfonated or Disulfonated Inventive Compound A drug delivery nanoparticle system conjugated with disulfonated or monosulfonated 779 Compound 1 is prepared as follows. A solution containing 1 mM disulfonated or monosulfonated 779 Compound 1-NHS in 1 ml of PBS is incubated overnight at room temperature with 0.1 mM of an anti-cancer drug conjugated with transferrin in the form of a nanoparticle. The resulting 779 Compound 1-nanoparticle conjugate is purified by centrifugation and then lyophilized.

The 779 Compound 1 (isomer 1)-nanoparticle conjugate (1 nmole) is injected intravenously into a mouse tail vein. Control mice are injected with free 779 Compound 1 dye. X-ray and near infra-red fluorescence images of mouse brain are captured.

779 Compound 1-nanoparticle conjugate localizes in the mouse brain for greater than about 24 hours after injection. Tumor size progressively decreases after injection of 779 Compound 1-nanoparticle conjugate, compared to 779 Compound 1-nanoparticle without the anti-cancer drug.

A drug delivery nanoparticle system conjugated with disulfonated or monosulfonated 679 Compound 4/4 is prepared as follows. A solution containing 1 mM disulfonated or monosulfonated 679 Compound 4/4-NHS in 1 ml of PBS is incubated overnight at room temperature with 0.1 mM of an anti-cancer drug conjugated with transferrin in the form of a nanoparticle. The resulting 679 Compound 4/4-nanoparticle conjugate is purified by centrifugation and then lyophilized.

The 679 Compound 4/4 (isomer 1)-nanoparticle conjugate (1 nmole) is injected intravenously into a mouse tail vein. Control mice are injected with free 679 Compound 4/4 dye. X-ray and near infra-red fluorescence images of mouse brain are captured.

679 Compound 4/4-nanoparticle conjugate localizes in the mouse brain for greater than about 24 hours after injection. Tumor size progressively decreases after injection of 679 Compound 4/4-nanoparticle conjugate, compared to 679 Compound 4/4-nanoparticle without the anti-cancer drug.

EXAMPLE 14

The mono-sulfonated derivative is on any one of eight possible positions on the 579, 679, or 779 compound, accounting for the stereochemistry around the carbon positions on the rings as well as the non-symmetrical nature of the two ends of each dye. Similarly, the di- and tri-substituted sulfonates can be on multiple possible positions on the inventive compounds.

EXAMPLE 15

The inventive compounds are used for in vivo imaging as described in J. Gastrointest Surg (2008) 12:1938-1950. Briefly, human pancreatic cell lines are maintained in media supplemented with penicillin/streptomycin at 37° C. with 5% $CO_2$. Mouse anti-CEA antibody and Control Mouse IgG (in PBS with 0.20% sodium azide) are conjugated to V08-15173. The dye is reconstituted at 10 mg/ml in DMF and then added to the antibody at a 10 molar excess. The reaction is carried out for one hour at room temperature. The samples are then dialyzed against 3×2 L of PBS. The cell lines are plated in 96-well plates at $5 \times 10^4$ cells per well. After 48 hours culture in appropriate media, the cells are incubated with 1 µg of V08-15173 labeled anti-CEA antibody or V08-15173-labeled control mouse IgG for four hours at 37° C. The cells are then washed three times with PBS and then imaged with an inverted Nikon De-485 microscope and Spot camera RD.

Surgical procedures and intravital imaging are performed with the animals anesthesized by intramuscular injection of 0.02 ml of 50% ketamine, 38% xylazine and 12 acepromazine maleate. Human pancreatic and colorectal cancer cell lines are harvested by trypsinization and washed twice with serum free medium and washed twice with serum-free medium. Cells ($1 \times 10^6$ in 100 µl of serum-free media) are injected subcutaneously within 30 minutes of harvesting over the right flank in female nu/nu mice between 4-6 weeks of age. Subcutaneous tumors are allowed to grow for 7-14 days until they reached diameter of 1-2 mm prior to the delivery of conjugated antibody. For ASPC-1 implants, the cells are harvested by trpsinization and washed 3× in serum-free media. The cells are resuspended in serum-free media. The cells are resuspended in serum-free media at $5 \times 10^6$/ml. A volume of 200 µl of the cell suspension is then injected directly into the peritoneal cavity within 30 minutes of harvesting.

For antibody delivery, one to two weeks after subcutaneous, orthotopic, or intraperitoneal tumor implantation, animals are given intravenous (i.v.) injection of either conjugated anti-CEA or conjugated control IgG antibody diluted in PBS to a final volume of 100 µl. All i.v. injections are done via the tail vein. For the dose-response experiment, the antibody dose is 75 µg. For the in vivo time course, the animals are anesthesized and imaged at 30 min, 1, 2, 6, 24 hours and 8 and 15 days after systemic antibody delivery.

Predicted in vivo and ex vivo analysis results are that post-experiment surgical exposure reveals accumulation of dye in the liver, bladder, and a region of inflammation in the subcutaneous tissue. Ex vivo analysis of the vital organs confirms the presence of dye predominantly in the liver with some signal detected in the spleen intestines and lungs.

EXAMPLE 16

The inventive compounds are used for in vivo imaging as described in J. Gastrointest Surg (2008) 12:1938-1950. Briefly, human pancreatic cell lines are maintained in media supplemented with penicillin/streptomycin at 37° C. with 5% $CO_2$. Mouse anti-CEA antibody and Control Mouse IgG (in PBS with 0.20% sodium azide) are conjugated to 779 Compound 1. The dye is reconstituted at 10 mg/ml in DMF and then added to the antibody at a 10 molar excess. The reaction is carried out for one hour at room temperature. The samples are then dialyzed against 3×2 L of PBS. The cell lines are plated in 96-well plates at $5 \times 10^4$ cells per well. After 48 hours culture in appropriate media, the cells are incubated with 1 µg of V08-15173 labeled anti-CEA antibody or V08-15173-labeled control mouse IgG for four hours at 37° C. The cells are then washed three times with PBS and then imaged with an inverted Nikon De-485 microscope and Spot camera RD.

Surgical procedures and intravital imaging are performed with the animals anesthesized by intramuscular injection of 0.02 ml of 50% ketamine, 38% xylazine and 12 acepromazine maleate. Human pancreatic and colorectal cancer cell lines are harvested by trypsinization and washed twice with serum free medium and washed twice with serum-free medium. Cells ($1 \times 10^6$ in 100 µl of serum-free media) are injected subcutaneously within 30 minutes of harvesting over the right flank in female nu/nu mice between 4-6 weeks of age. Subcutaneous tumors are allowed to grow for 7-14 days until they reached diameter of 1-2 mm prior to the delivery of conjugated antibody. For ASPC-1 implants, the cells are harvested by trpsinization and washed 3× in serum-free media. The cells are resuspended in serum-free media. The cells are resuspended in serum-free media at $5 \times 10^6$/ml. A volume of 200 µl of the cell suspension is then injected directly into the peritoneal cavity within 30 minutes of harvesting.

For antibody delivery, one to two weeks after subcutaneous, orthotopic or intraperitoneal tumor implantation, animals are given intravenous (i.v.) injection of either conjugated anti-CEA or conjugated control IgG antibody diluted in PBS to a final volume of 100 µl. All i.v. injections are done by tail vein. For the dose-response experiment, the antibody dose is 75 µg. For the in vivo time course, the animals are anesthesized and imaged at 30 min, 1, 2, 6, 24 hours and 8 and 15 days after systemic antibody delivery.

Predicted in vivo and ex vivo analysis results are that post-experiment surgical exposure reveals accumulation of dye in the liver, bladder, and a region of inflammation in the subcutaneous tissue. Ex vivo analysis of the vital organs confirms the presence of dye predominantly in the liver with some signal detected in the spleen intestines and lungs.

EXAMPLE 17

Near IR Dye for In Vivo Imaging Applications

Near-infrared (NIR) fluorophores are useful in cell-based assays, in in vivo imaging, and in specific imaging or assay application based on the dyes' characteristic excitation and emission spectra properties or relative hydrophylicity/hydrophobicity. In general, more hydrophilic dyes, i.e., those that contain more negative charges, display high water solubility, while more hydrophobic dyes often provide better cell penetrating ability in vivo.

679 Compound 4/4, a fluorescent dye that excites at 684 nm and emits at 706 nm, was conjugated and used as a molecular probe to fluorescently label antibodies and other proteins in cellular imaging and other fluorescence detection applications. It demonstrated excellent characteristics for in vivo and ex vivo imaging. More specifically, 679 Compound 4/4 was conjugated to primary and secondary antibodies which were then used for fluorescence immunostaining in various cells types. 679 Compound 4/4 was tested in in vivo biodistribution and clearance in nude mice.

In in vivo biodistribution, the mice received intravenous dye injections via the retro orbital plexus and were imaged on a Carestream MSFX Imager (690 nm excitation/750 nm emission) before injection and at 0 h, 3 h, 6 h, 12 h, and 24 h post injection. After the final time point, animals were sacrificed and organs were collected for ex vivo imaging. Toxicity was evaluated by investigating the dissected tissue section.

679 Compound 4/4 conjugated to an antibody at low molar excess had high labeling efficiency resulting in high fluorescence intensity after conjugation, good specificity, high signal-to-background ratio and photostability in cellular imaging applications. Its biodistribution and clearance showed rapid clearance through kidney and/or gastrointestinal tract. 679 Compound 4/4 NIR dye was an excellent tool for imaging through tissues, which circumvents indigenous fluorescent biomolecule interference or quenching.

679 Compound 4/4 derivatized with 4 (poly)ethylene glycol (PEG) chains showed low intrinsic toxicity, enhanced fluorescence, and reduced nonspecific binding of conjugates. Its far-red to NIR fluorescence properties made it particularly useful in various biological applications, including in vivo imaging.

The relatively short PEG modifications of organic fluorescent dyes mask hydrophobic core dye structures, thus providing enhanced biocompatibility with biological detection and assay applications. PEG chains improved solubility of the dye and the corresponding labeled molecules in aqueous solution, aided in cell permeability, and improved retention especially in tumors. Dye hydrophobicity and functional group modifications affected its distribution and retention within a living organism.

Modifications of intrinsic dye properties affect tissue distribution of the dye to make a superior dye for in vivo imaging. Therefore, biodistribution of dye and its clearance data in live animals provides compatibility information of the dye for in vivo imaging. Fast body clearance is ideal, typically through kidneys for urine excretion, GI tract for highly hydrophilic compounds, or through liver and bile excretion for more hydrophobic molecules. Fast clearance from animals helps reduce dye toxicity and is useful in repetitive imaging. However, it may also limit the time window within which imaging can be performed to visualize organs where a fluorescent probe is distributed. Therefore, an ideal dye for in vivo imaging clears fast but is retained long enough in organs of interest to allow for imaging.

The brightness of 679 Compound 4/4 was compared to traditional DyLight 680 dyes to determine if adding PEG to the structure allowed rapid whole animal imaging and improved dye clearance. In immunofluorescence-imaging applications, 679 Compound 4/4 showed much brighter staining compared to traditional DyLight 680 dye and other fluors that excite at 680 nm and emit at 700 nm.

U2OS (human bone cancer) or HeLa cells were seeded at 5,000 cells per well in 96-well plates and incubated for 18-20 hours at 37° C., 5% $CO_2$ in a humidified incubator. The cells were fixed with 4% paraformaldehyde and permeabilized with 0.1% Thermo Scientific Surfact-Amps X-100 Detergent, then blocked for nonspecific IgG binding. Cells were incubated with a target-specific primary antibody for 30 minutes at room temperature (RT). After washing with PBS containing 0.05% Tween™-20 Detergent Solution, cells were incubated for 30 minutes at RT with 4 µg/mL of the appropriate secondary antibody conjugated with 679 Compound 4/4 and compared to similarly conjugated counterparts (DyLight 680, Alexa Fluor™ 680, and CF™ 680 Dyes) for 30 minutes at RT. The conjugates were affinity purified goat anti-mouse IgG (H+L) (GAM) or goat anti-rabbit IgG (H+L) (GAR). The cell images were acquired with a Thermo Scientific HCS ArrayScan VTI Instrument using the same fixed exposure time, and images represented raw data. Microscopy time lapse experiments to measure dye photostability were performed using the appropriate shift-free optical filter set with a 40×/1.3 oil objective on a Zeiss Axio Observer™ .Z1 fluorescence microscope using an ORCA-ER-1394 Hamamatsu, CCD Digital Camera and the AxioVison™ Release 4.7 Software. Filter set: Cy™5.5 Dye (Ex: 665±45 nm/Em: 725±50 nm). In comparative sets, images were acquired at the same gain and exposure time. All Images were acquired without antifade.

Figure 43A:
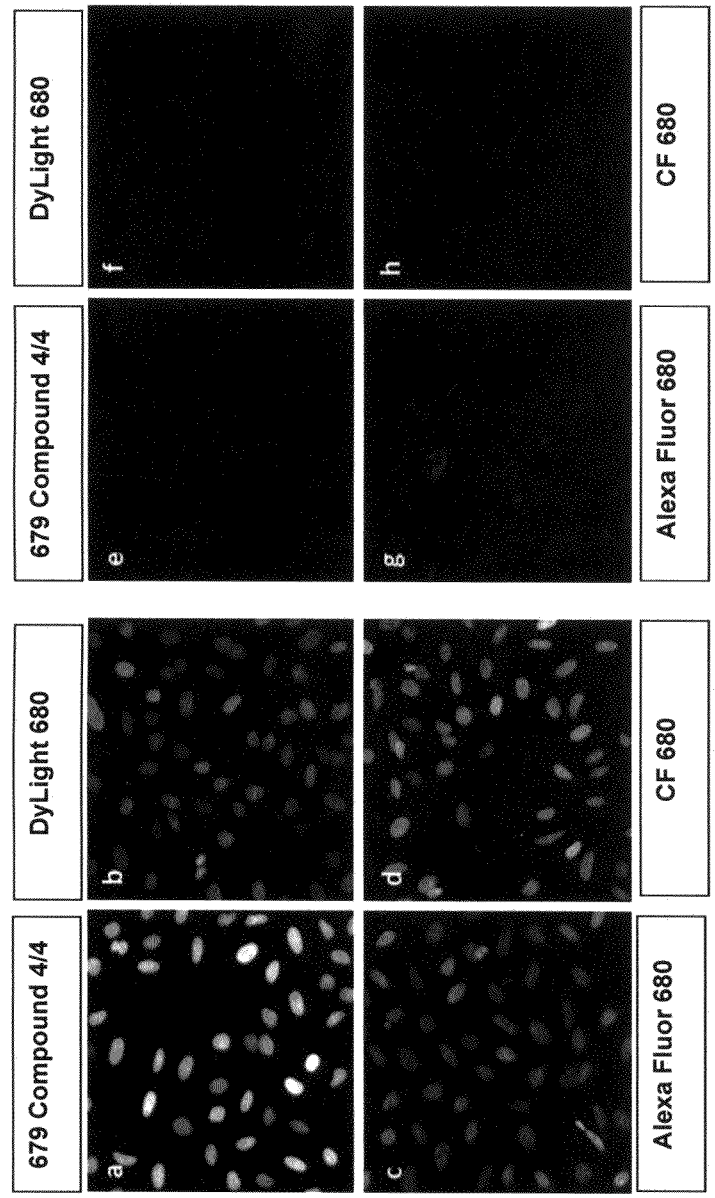
FIG. 43A shows immunofluorescence data with commercial dyes and inventive compounds in one embodiment.
Figure 43B:
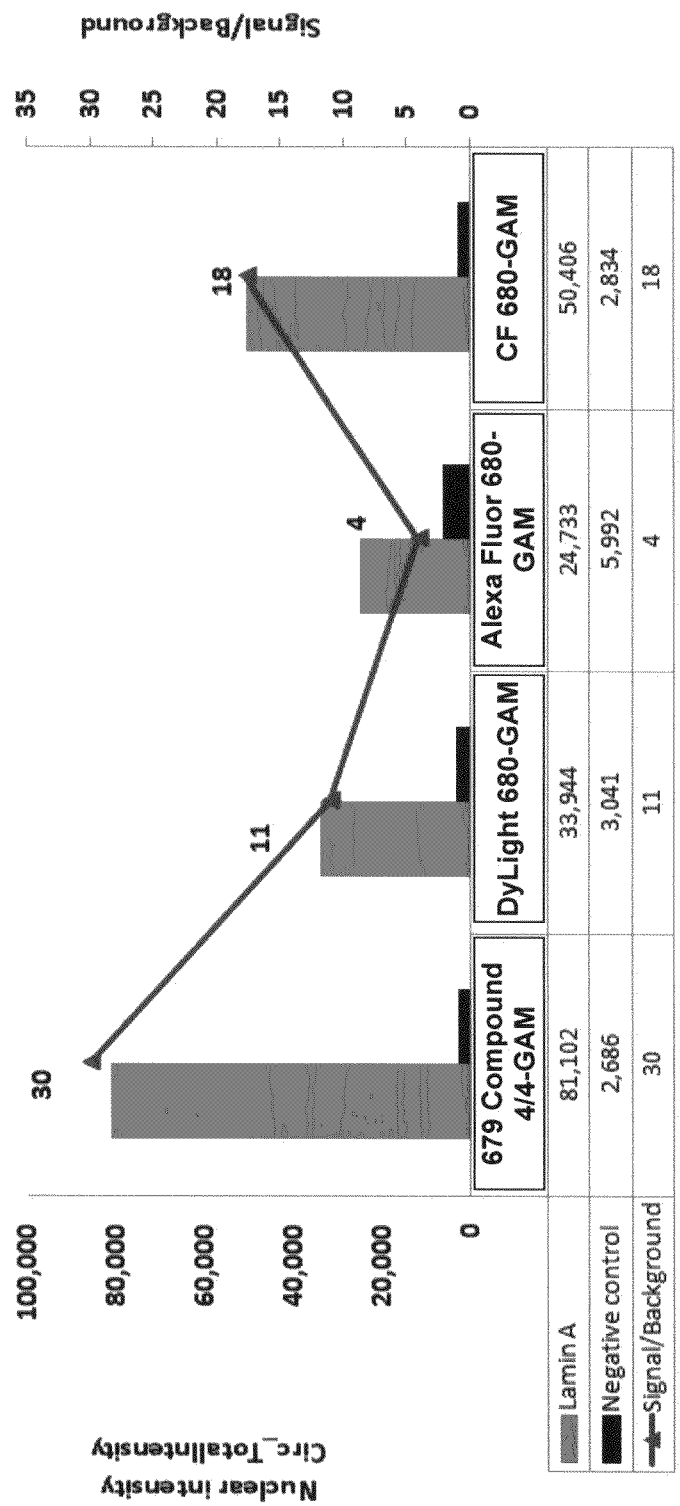
FIG. 43B shows immunofluorescence data with commercial dyes and inventive compounds in one embodiment.

The nuclear envelop in U2OS cells was fluorescently labeled with mouse anti-lamin A primary antibody and detected with goat anti-mouse conjugated to 679 Compound 4/4-NHS, DyLight 680-NHS, Alexa Fluor 680-NHS and CF 680-SE Dyes. The dye conjugation to goat anti-mouse antibody (GAM) was performed at the same low dye to antibody molar excess resulting in similar fluor/protein (F/P) ratios of about 1.5. As shown in FIG. 43A left panel, 679 Compound 4/4 (a) conjugate showed about 2-3 fold brighter staining intensity compared to other similar conjugates DyLight 680-GAM (b) Alexa Fluor 680-GAM (c) and CF 680-GAM (d). As shown in FIG. 43A right panel, negative controls in the absence of primary antibody showed significant nonspecific binding with Alexa Fluor 680-GAM conjugate (g) compared to 679 Compound 4/4-GAM, DyLight 680-GAM, and CF 680-GAM conjugates (e, f, h respectively), which caused lower signal/background ratio on the sample, as shown in FIG. 43B with Alexa Fluor 680 dye staining.

Figure 44A:
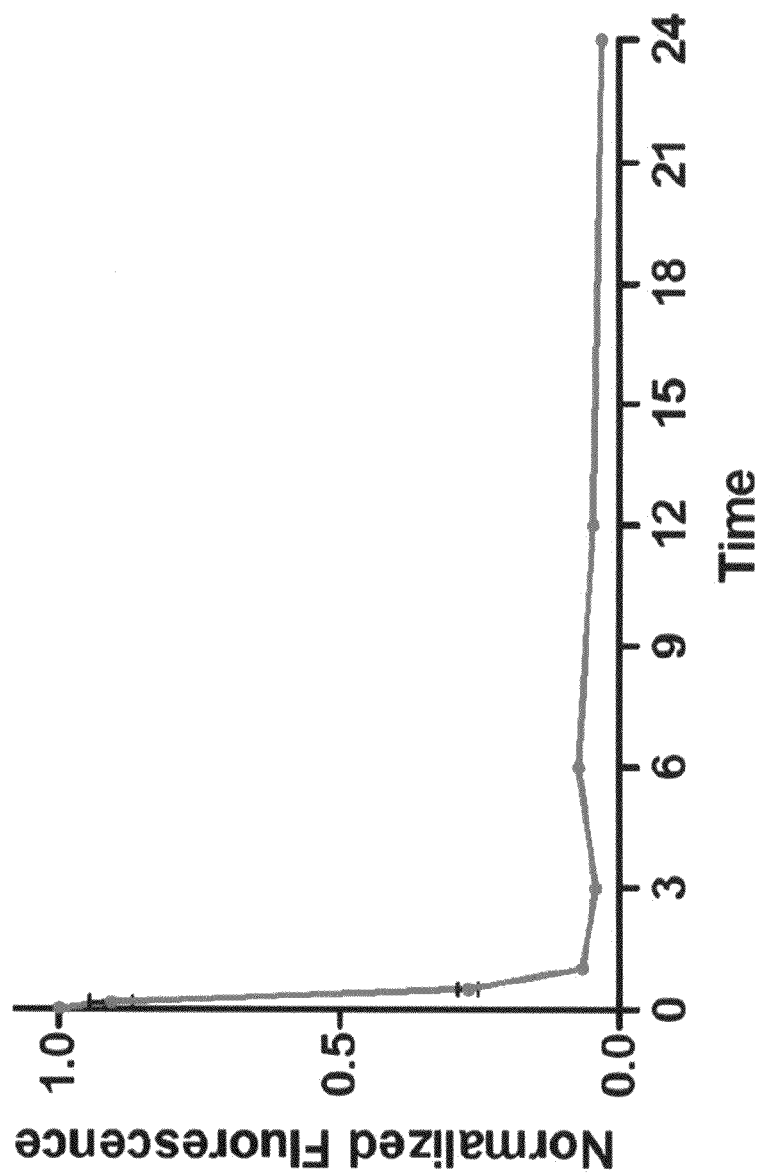
FIG. 44A shows in vivo dye clearance and whole body uptake with commercial dyes and inventive compounds in one embodiment.

679 Compound 4/4 showed fast whole-body dye uptake and displayed rapid dye clearance mainly through the kidney and GI tract, as shown in FIG. 44A.

Figure 44B:
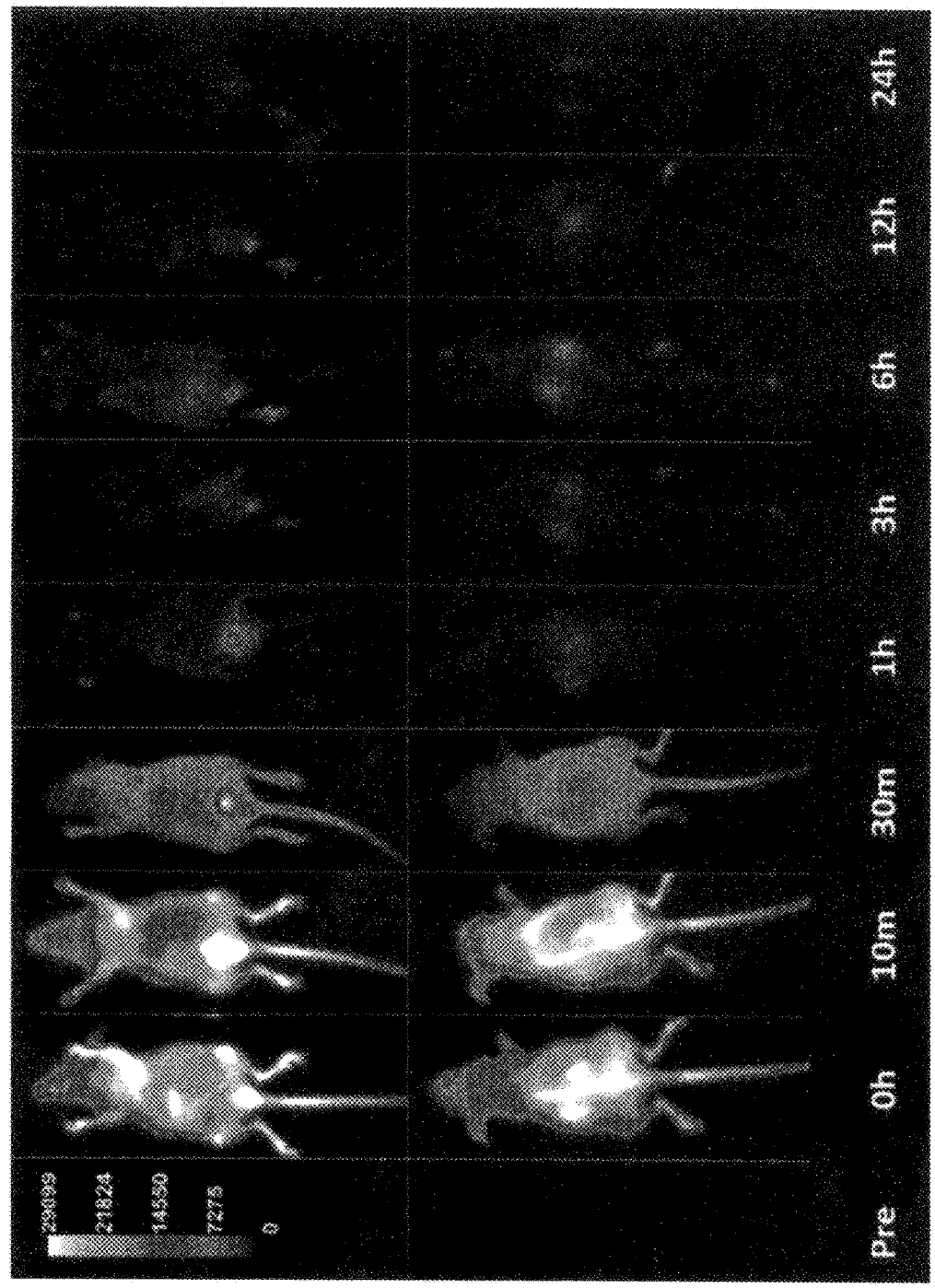
FIG. 44B shows in vivo dye clearance and whole body uptake with commercial dyes and inventive compounds in one embodiment.
Figure 44C:
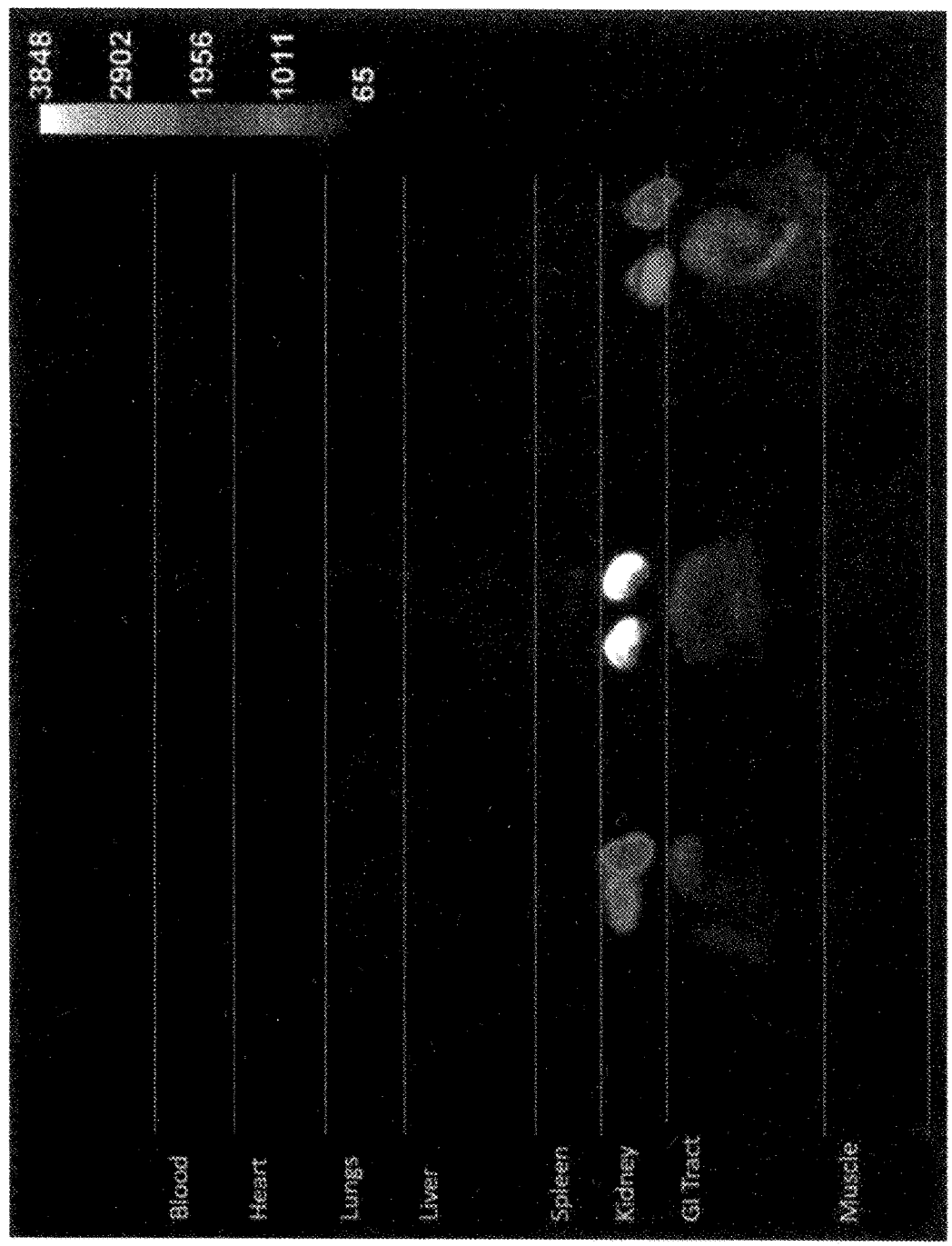
FIG. 44C shows in vivo dye clearance and whole body uptake with commercial dyes and inventive compounds in one embodiment.

Biodistribution and clearance was investigated in the live animals over time by measuring the clearance or specific retention of the dye/labeled target. Experiments were performed in triplicate on nude mice. 100 µL of 1 mg/mL hydrolyzed dye solution was IV injected via the retro orbital plexus. Animals were imaged using 690 nm excitation and 750 nm emission at 140 mm FOV on a Carestream XTREME (10 s) Imager. Images taken before (pre) and at 0 min, 10 min, 30 min, 1 hour, 3 hour, 6 hour, 12 hour and 24 hours post injection are shown in FIG. 44B. After the final time point, the organs were collected for ex vivo imaging to confirm and quantify accumulation of the agent in tumors, tissues, and other organs (heart, liver, spleen, GI tract, lungs and kidney), as shown in FIG. 44C using triplicate mice. 679 Compound 4/4 allowed for probe conjugation, high fluorescence with excellent sensitivity for deep-tissue in vivo imaging, and target quantification in tissues.

After the final time point, animals were sacrificed and their organs collected for ex vivo imaging to confirm and quantify dye accumulation in tumors, tissues, and other organs such as heart, liver, spleen, GI tract, lungs, and kidney. Images were taken before (pre), and at 0 min, 10 min, 30 min, 1 hour, 3 hour, 6 hour, 12 hour, and 24 hour post injection. To test dye toxicity, heart, liver, spleen, lungs and kidney tissues were gathered from one mouse from each cohort, fixed, stained with hematoxylin and eosin (H&E), and evaluated.

Colorimetric images were acquired at 20× on a Nikon 90i microscope. FIG. 45 left panel shows staining of tissues from sample mouse treated with 679 Compound 4/4 compared to untreated control mouse (right panel). No tissue damage was observed from histology; the H&E staining showed intact tissues structure with no sign of alteration or injury caused by toxicity.

Athymic nude mice (Strain Nu/Nu, Taconic, New York) were injected intramuscularly (IM) with 5×107 colony forming units (CFU) of *Staphlococcus aureus* in the right thigh followed by two hour incubation. One hundred μL of each dye solution (free dye or dye conjugated to bovine serum albumin, BSA) at 1 mg/mL was injected intravenously via the retro orbital plexus. Animals were imaged on a Carestream XTREME Imager using excitation/emission wavelengths of 690 nm/750 nm at the following acquisition times; 5 sec (free dye control) or 20 sec (BSA conjugates) with no binning at 150 mm FOV. Images were acquired at 0 h, 1 hour, 3 hours, 6 hours, and 12 hours.

Figure 46A:
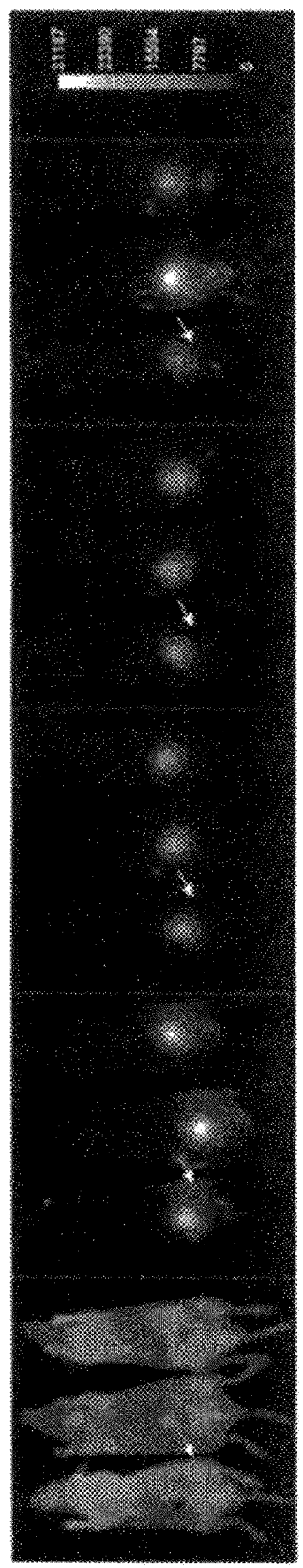
FIG. 46A shows whole body in vivo imaging with commercial dyes and inventive compounds in one embodiment.
Figure 46B:
FIG. 46B shows whole body in vivo imaging with commercial dyes and inventive compounds in one embodiment.
Figure 46C:
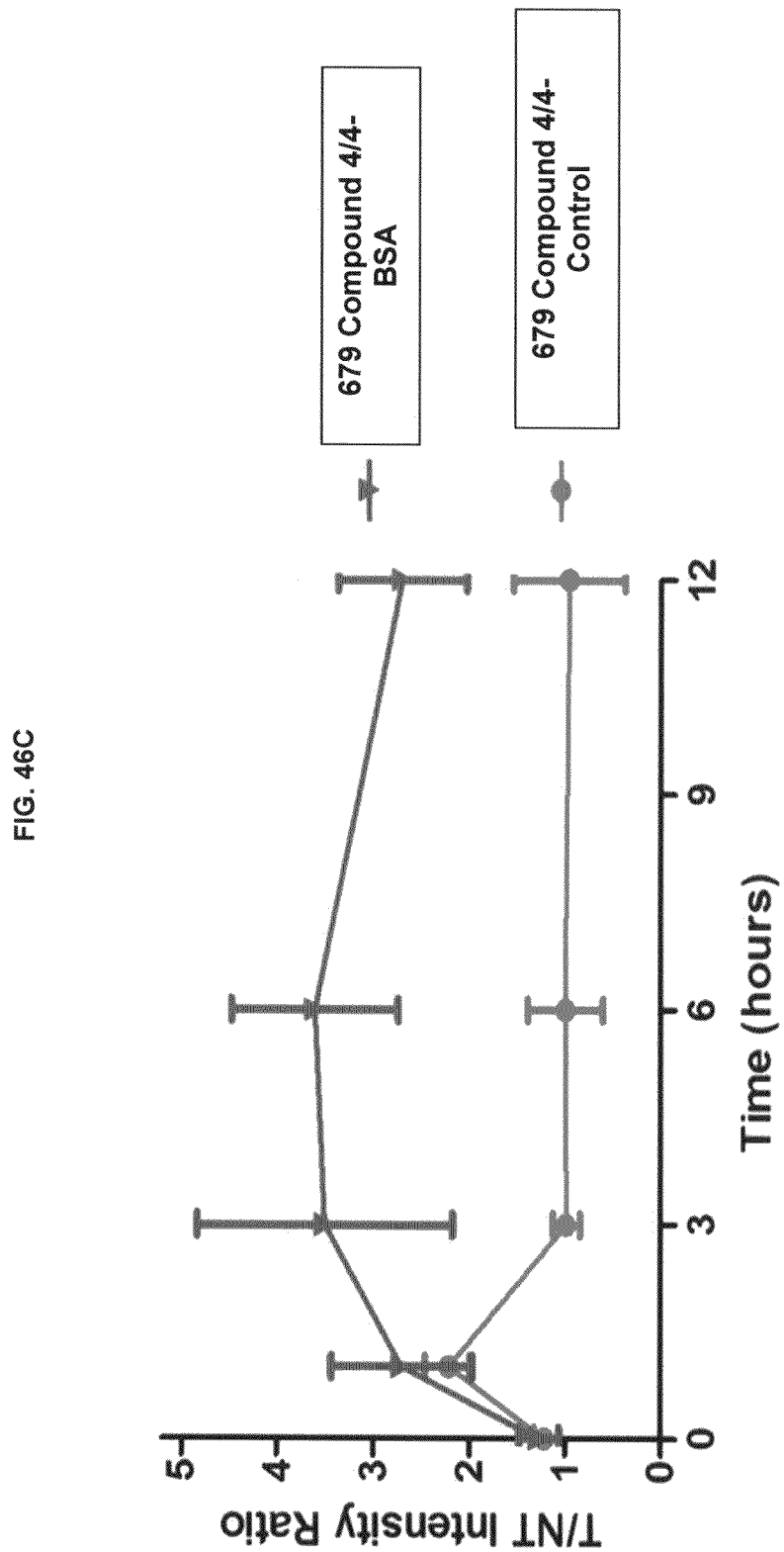
FIG. 46C shows whole body in vivo imaging with commercial dyes and inventive compounds in one embodiment.

As shown in FIG. 46A, the dyes accumulated at the infection site within one hour (due to perfusion), and then rapidly disappeared from the region. 679 Compound 4/4 free dye control cleared quickly after an initial spike. As shown in FIG. 46B, whole-body intensity was low in animals injected with BSA-conjugated dye compared to the free-dye control, which was a unique property of the BSA conjugate. It started to dim and got brighter as the infection spread. It took 3-6 hours for the dye to reach its maximum uptake in the thigh relative to the contralateral control. The target to non-target (T/NT) ratio was calculated by recording the mean intensity at the infection site (target, see arrows in FIGS. 46A and B) in the leg muscle and contralateral control muscle site (non-target), and shown graphically in FIG. 46C. This provided a good measure of contrast for probe uptake at a desired site versus background uptake at a control site.

Figure 47:
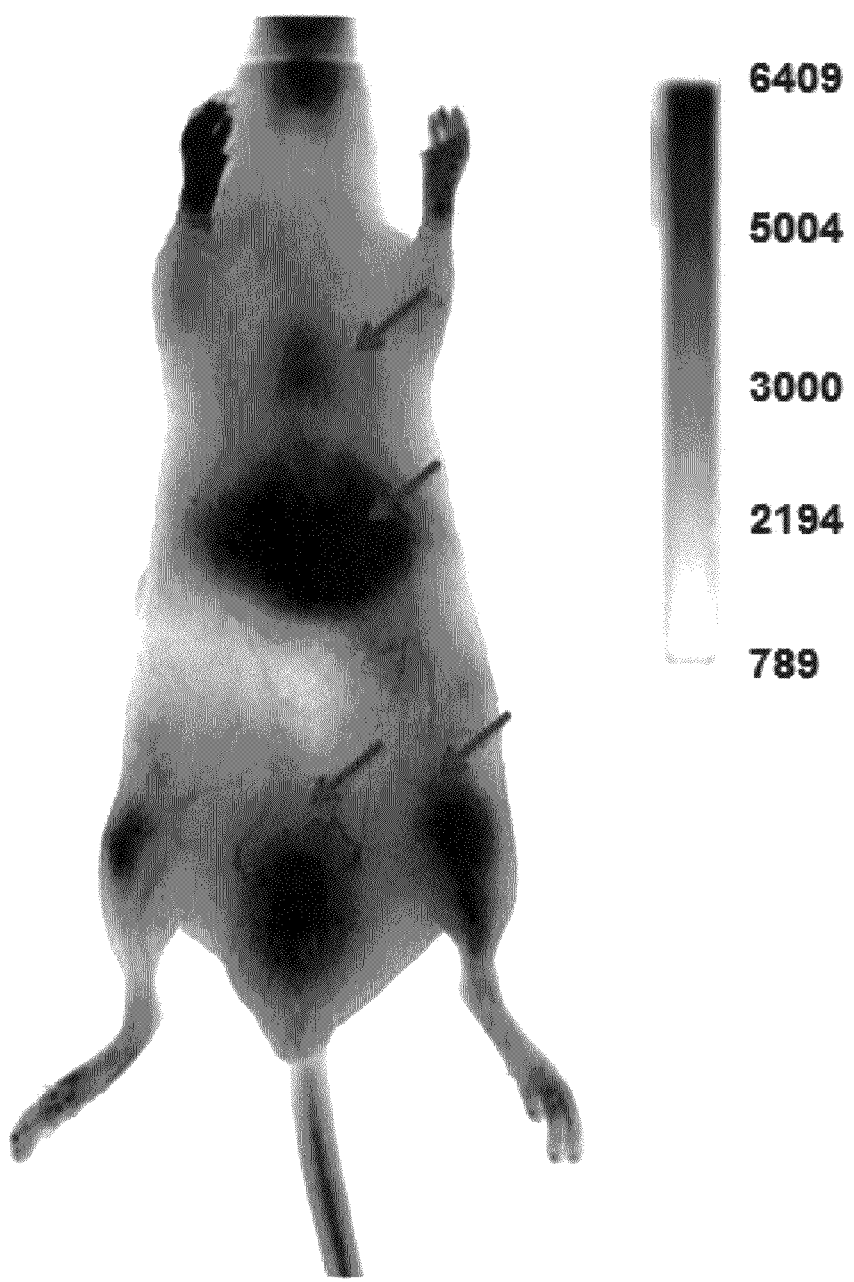
FIG. 47 shows whole body perfusion of inventive compound in vasculature.

Perfusion of the inventive compound in vasculature was evaluated. A mouse image, post-injection with 679 Compound 4/4-BSA, was magnified and contrasted to highlight shallow vasculature, as shown in FIG. 47. The faint heart signal, liver contrast, bladder, and increased flow at infected leg muscle was observed.

Figure 48:
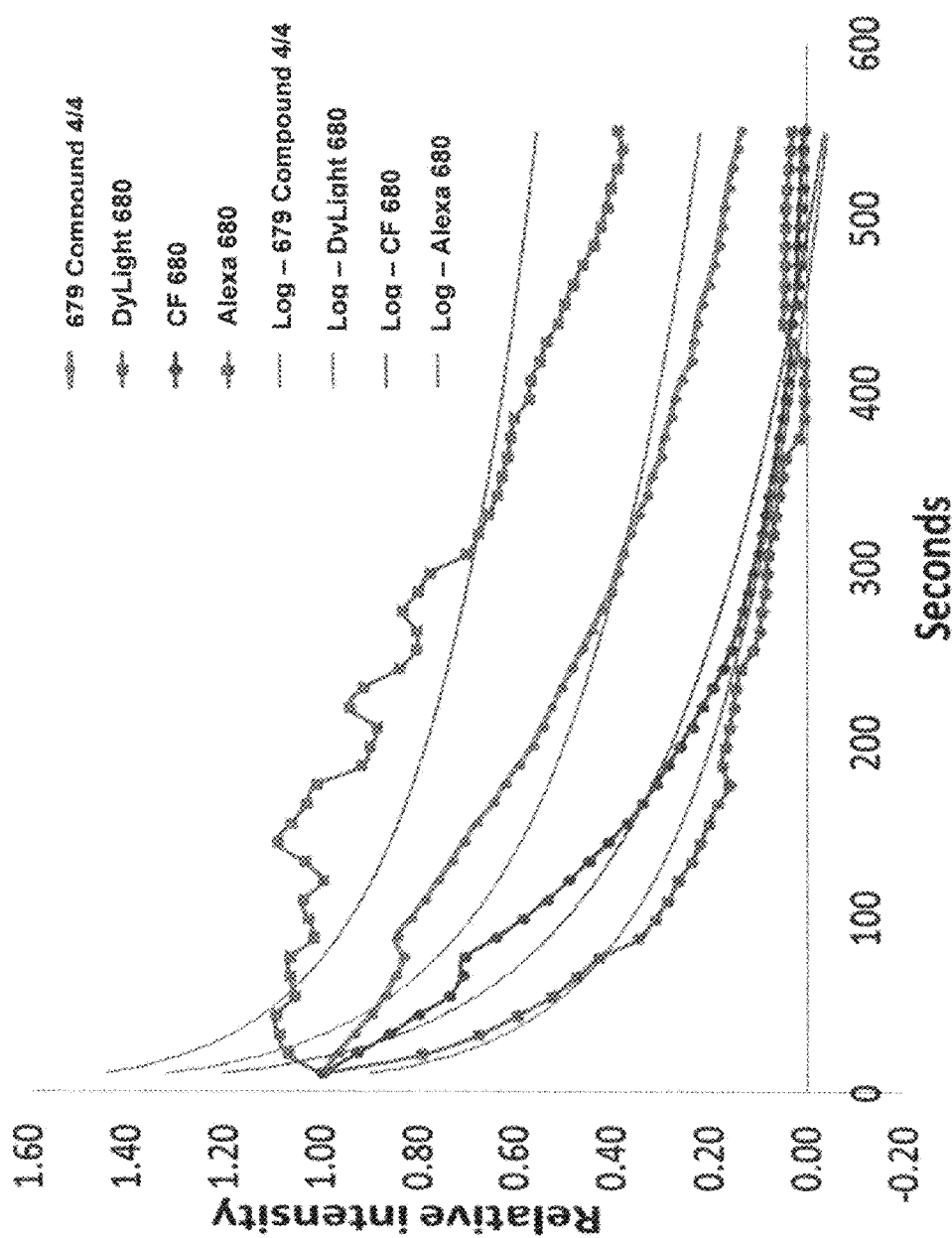
FIG. 48 shows photobleaching of commercial dyes and inventive compounds in one embodiment.

Photobleaching of inventive and commercial compounds without anti-fade reagent was examined. U2OS cells stained with lamin B1/dye-conjugated GAR were exposed to bright light (3.4V) for 8 sec at intervals of 1 sec, the overall capture amounting to a total of about 15 min using the TR filter Obj.: 20× NA: 0.4 on the Zeiss Axio Observer .Z1 microscope. The image stacks collected from the time-lapse experiment were analyzed using ImageJ software to determine the decay rate of fluorescence intensity. The raw intensity was normalized to initial intensity for each conjugate and the photobleaching curve was plotted against time, as shown in FIG. 48. Immunostaining with 679 Compound 4/4 conjugate had shown about 2 to 3-fold brighter staining intensity compared to DyLight 680 Dye. Photostability data obtained from a specimen in the absence of anti-fade agent showed that DyLight 680 dye was highly photostable. 679 Compound 4/4 was slightly less stable than DyLight 680 dye, however, other cyanine based dyes, such as Alexa Fluor 680 and CF 680 Dyes were significantly less photostable. Photobleaching curves showed a loss of 50% of initial intensity within 50 sec for Alexa Fluor 680 Dye and 120 sec for CF680 Dye vs. >250 sec for 679 Compound 4/4 and >400 sec for DyLight 680 Dye.

The data showed that 679 Compound 4/4 exhibited higher signal intensity and specificity than Alexa Fluor 680 or non-PEGylated DyLight 680 Dyes. The relatively short PEG chains combined with the overall negative charge on the 679 Compound 4/4 appeared to improve cell permeability, resulting in high-fluorescence intensity and target specificity. 679 Compound 4/4 had suitable spectral properties for in vivo imaging, and showed enhanced free-dye uptake in whole-body distribution and high-clearance speed predominantly through the kidney and gastrointestinal tract. The data also showed that 679 Compound 4/4 conjugates are a useful tool for infected tissue vasculature, heart, and liver. 679 Compound 4/4 had better photostability in comparison to other cyanine-based dyes such as Alexa Fluor 680 and CF 680 Dyes.

Figure 2:
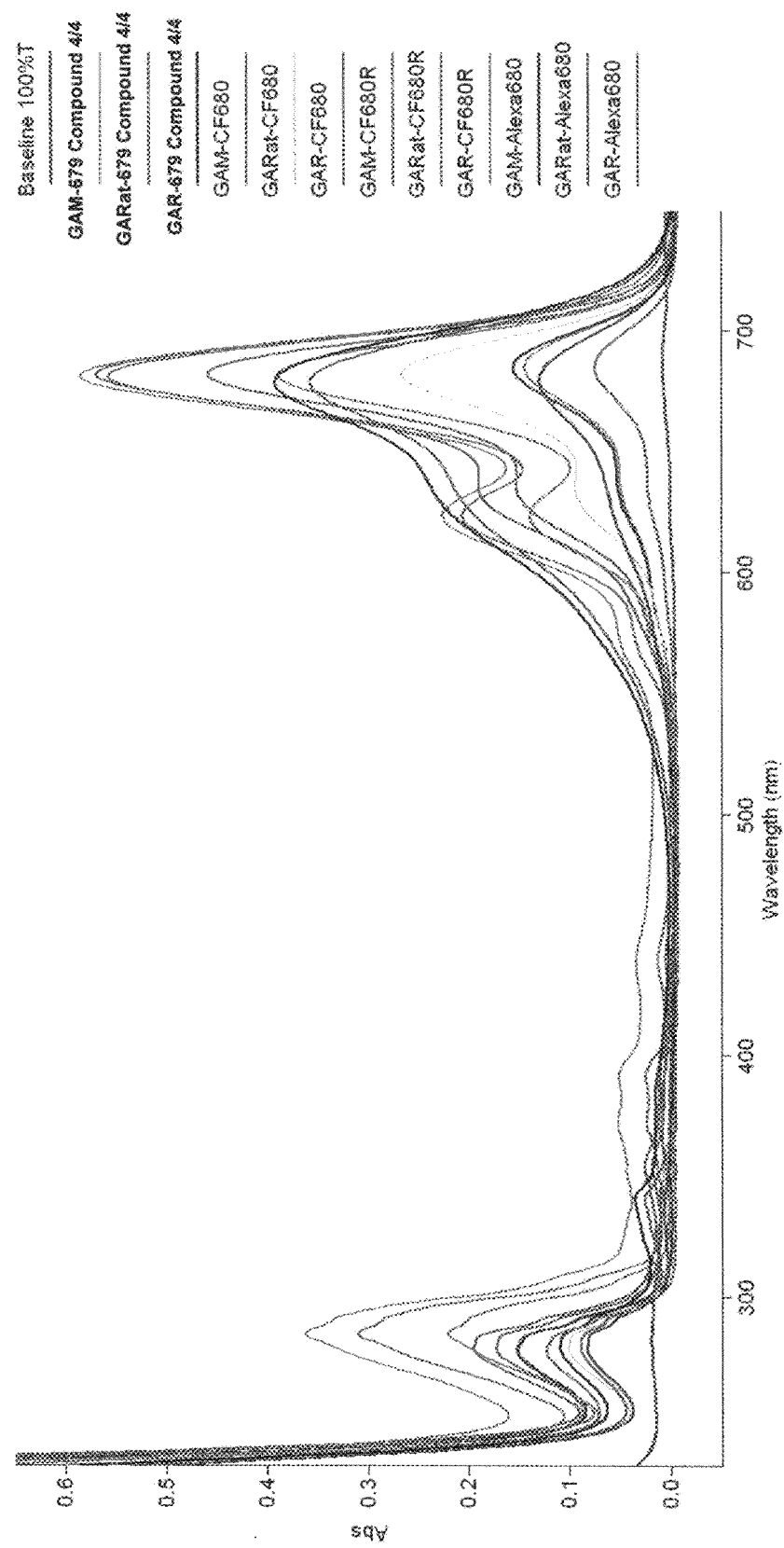
FIG. 2 shows absorption/emission profiles of some inventive compounds and commercial dyes.

In conclusion, the table in Example 6 showed the physical characteristics (MW, extinction coefficient, absorption spectra) of conjugates made with the inventive dyes and commercially available dyes (Example 7; FIG. 2) and excitation/emission spectra of the inventive dyes and commercially available dyes (Example 6; FIG. 1), and demonstrated that the inventive dyes matched well with other dyes that excite and emit with Cy5.5 excitation and emission filter sets. The conjugation and labeling efficiencies of the inventive reactive dyes and labeling kits demonstrated that the inventive dyes were reactive and compatible with labeling of proteins as shown in the tables in Example 7. The plate-based assay results for the GAM, GAR, and streptavidin conjugates shown in Example 8 demonstrated that the conjugates were compatible in a binding assay (FIGS. 7-12). In general, immunofluorescence with antibody conjugates (FIGS. 24-34, Example 9) demonstrated that conjugates made with the inventive dyes showed enhanced fluorescence intensity compared to those made with DyLight 680 and Alexa Fluor 680 Labeling Kits, and showed higher specificity compared to the Alexa 680 Labeling Kit (FIG. 30B, Example 17). 679 Compound 4/4 showed higher signal intensity and specificity than Alexa Fluor 680 or non-PEGylated DyLight 680 Dyes (FIGS. 43A-B). Short PEG chains combined with overall negative charge on the 679 Compound 4/4 appeared to improve cell permeability, resulting in high-fluorescence intensity and target specificity (FIGS. 43A-B). In vivo imaging clearance and biodistribution of inventive dyes was also shown (FIG. 44), with ex vivo imaging confirming the organ where the dye was likely to accumulate such as heart, liver, spleen, GI tract, lungs, and kidney. The data showed that 679 Compound 4/4 allowed for probe conjugation, high fluorescence with excellent sensitivity for deep-tissue in vivo imaging and target quantification in tissues. FIG. 45 showed that no tissue damage was observed from histology; the hematoxylin and eosin staining showed intact tissues structure with no sign of alteration or injury caused by toxicity. These data demonstrated that 679 Compound 4/4 had suitable spectral properties for in vivo imaging, as enhanced free-dye uptake in whole-body distribution and high-clearance speed predominantly through the kidney and gastrointestinal tract were shown.

FIG. 46 demonstrated the compatibility of BSA conjugate made with the inventive dye as a vascular probe and showed that 679 Compound 4/4-BSA conjugates have the potential to become a useful tool for infected tissue vasculature, heart, and liver. FIG. 48 showed photostability data for the inventive dyes obtained from specimens in the absence of antifade agent, a reagent that suppresses photobleaching and preserve the signals of fluorescently labeled target molecules, therefore a stable dye in the absence of antifade shows strong photostability.

DyLight 680 Dye is a highly photostable dye. 679 Compound 4/4 was slightly less stable than DyLight 680 Dye, however, other cyanine based dyes, such as Alexa Fluor 680 and CF 680 Dyes were significantly less photostable. Photobleaching curves showed a loss of 50% of initial intensity within 50 sec for Alexa Fluor 680 Dye, and 120 sec for CF680 Dye, vs. greater than 250 sec for 679 Compound 4/4 and greater than 400 sec for DyLight 680. 679 Compound 4/4 had better photostability compared to other cyanine-based dyes such as Alexa Fluor 680 and CF 680 Dyes.

The embodiments shown and described in the specification are only specific embodiments of inventors who are skilled in the art and are not limiting in any way. Therefore, various changes, modifications, or alterations to those embodiments may be made without departing from the spirit of the invention or the scope of the following claims. The references cited are expressly incorporated by reference herein in their entirety.

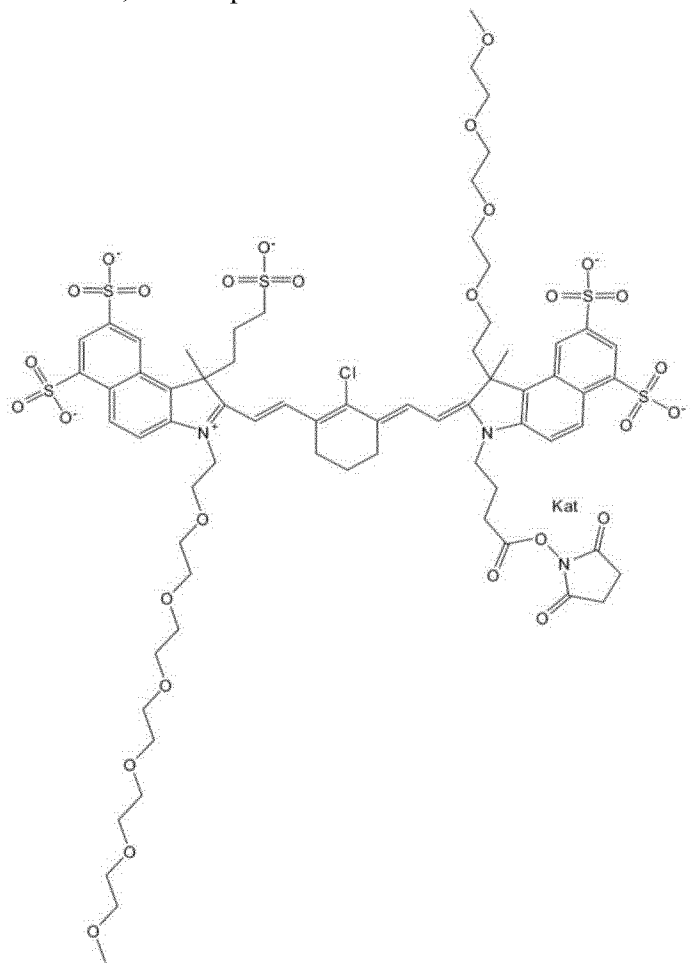

What is claimed is:

1. A compound of general formula IIc

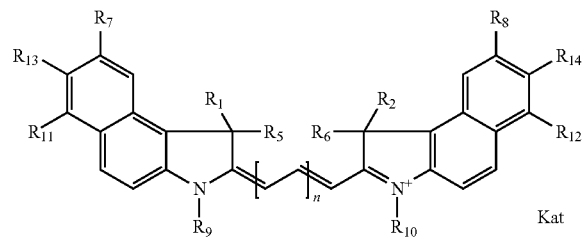

where
each of $R^1$, $R^2$, $R^5$, and $R^6$ is the same or different and is selected from the group consisting of an aliphatic, heteroaliphatic, sulfoalkyl, heteroaliphatic with terminal $SO_3$—, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide group -L-$SO_2$NH—P—Z, and a caboxamide group -L-CONH—P—Z, where Z is selected from H, $CH_3$, a $CH_3$ group, an alkyl group, or a heteroalkyl group;
each of $R^7$, $R^8$, $R^{11}$, $R^{12}$, $R^{13}$, and $R^{14}$ is the same or different and is selected from the group consisting of H, $SO_3$—, a PEG group P—Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a sulfonamide-containing group -L-$SO_2$NH—P—Z, and a carboxamide-containing group -L-CONH—P—Z, where Z is selected from H, a $CH_3$ group, an alkyl group, or a heteroalkyl group;
each of $R^9$ and $R^{10}$ is the same or different and is a PEG group P-L-Z where P is selected from an ethylene glycol group, a diethylene glycol group, and a (poly)ethylene glycol group, where the (poly)ethylene glycol group is $(CH_2CH_2O)_s$, where s is an integer from 3-6 inclusive, a PEG group P-L-X;
X is selected from the group consisting of —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, and —NR-L-NH—CO—$CH_2$—I, where R is —H or an aliphatic or heteroaliphatic group;
L is selected from the group consisting of a divalent linear (—$(CH_2)_t$—, t=0 to 15), crossed, or cyclic alkyl group optionally substituted by at least one oxygen atom and/or sulfur atom;
Kat is a number of $Na^+$, $K^+$, $Ca^{2+}$, ammonia, or other cation(s) needed to compensate the negative charge brought by the cyanine;
m is an integer from 0 to 5 inclusive; o is an integer from 0 to 12 inclusive; and n is an integer from 1 to 3 inclusive;
with the proviso that at least one of $R^1$, $R^2$, $R^5$, $R^6$, $R^7$, $R^8$, $R^{11}$, $R^{12}$, $R^{13}$ or $R^{14}$ is a PEG group.

2. A method of labeling at least one biomolecule, the method comprising combining at least one biomolecule with a composition comprising at least one excipient and the compound of claim 1 in an effective concentration to bind to at least one biomolecule under conditions sufficient for labeling the biomolecule with the compound.

3. The method of claim 2 wherein the biomolecule is selected from the group consisting of a protein, antibody, enzyme, nucleoside triphosphate, oligonucleotide, biotin, hapten, cofactor, lectin, antibody binding protein, carotenoid, carbohydrate, hormone, neurotransmitter, growth factors, toxin, biological cell, lipid, receptor binding drug, fluorescent proteins, organic polymer carrier material, inorganic polymeric carrier material, and combinations thereof.

4. A method of detecting at least one biomolecule, the method comprising combining at least one biomolecule with a composition comprising at least one excipient and the compound of claim 1 in an effective concentration to bind to at least one biomolecule under conditions sufficient for binding the compound to the biomolecule, and detecting the biomolecule-bound compound.

5. The method of claim 4 wherein the biomolecule is selected from a protein, antibody, enzyme, nucleoside triphosphate, oligonucleotide, biotin, hapten, cofactor, lectin, antibody binding protein, carotenoid, carbohydrate, hormone, neurotransmitter, growth factors, toxin, biological cell, lipid, receptor binding drug, fluorescent proteins, organic polymer carrier material, inorganic polymeric carrier material, and combinations thereof.

6. The method of claim 4 wherein the at least one biomolecule is detected in an assay selected from fluorescence microscopy, flow cytometry, in vivo imaging, immunoassay, hybridization, chromatographic assay, electrophoretic assay, microwell plate based assay, fluorescence resonance energy transfer (FRET) system, bioluminescence resonance energy transfer (BRET), high throughput screening, or microarray.

7. The method of claim 4 wherein the biomolecule is detected by in vivo imaging comprising providing the biomolecule-bound compound to at least one of a biological sample, tissue, or organism, and detecting the biomolecule within the at least one of a biological sample, tissue, or organism.

8. A kit for detecting and/or labeling at least one biomolecule in a sample, the kit comprising the compound of claim 1 and at least one excipient, and instructions for use of the compound to detect a biomolecule in a sample.

9. A method of in vivo imaging using a compound of claim 1, comprising combining at least one biomolecule with a composition comprising at least one excipient and the compound of claim 1 in an effective concentration to bind to at least one biomolecule under conditions sufficient for binding the compound to the biomolecule;

provinding the biomolecule-bound compound to an organism; and detecting the biomolecule within the organism.

10. A kit for in vivo imaging, the kit comprising the compound of claim 1 and at least one excipient, and instructions for use of the compound to image a tissue, organ, or body of an organism.

* * * * *

UNITED STATES PATENT AND TRADEMARK OFFICE
CERTIFICATE OF CORRECTION

PATENT NO. : 10,526,317 B2  
APPLICATION NO. : 15/641376  
DATED : January 7, 2020  
INVENTOR(S) : Greg Hermanson et al.

Page 1 of 29

It is certified that error appears in the above-identified patent and that said Letters Patent is hereby corrected as shown below:

In the Specification

Column 97, Line 43, the compound should read:

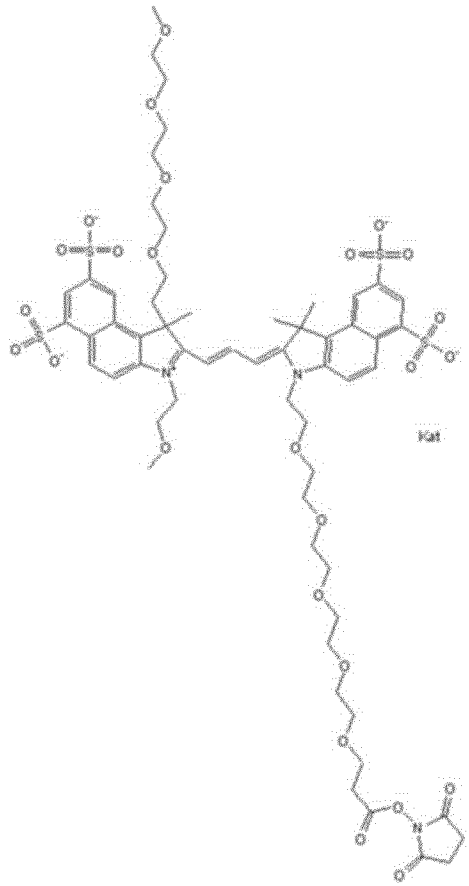

Signed and Sealed this  
Twenty-eighth Day of July, 2020

Andrei Iancu  
*Director of the United States Patent and Trademark Office*

Column 104, Line 1, the compound should read:
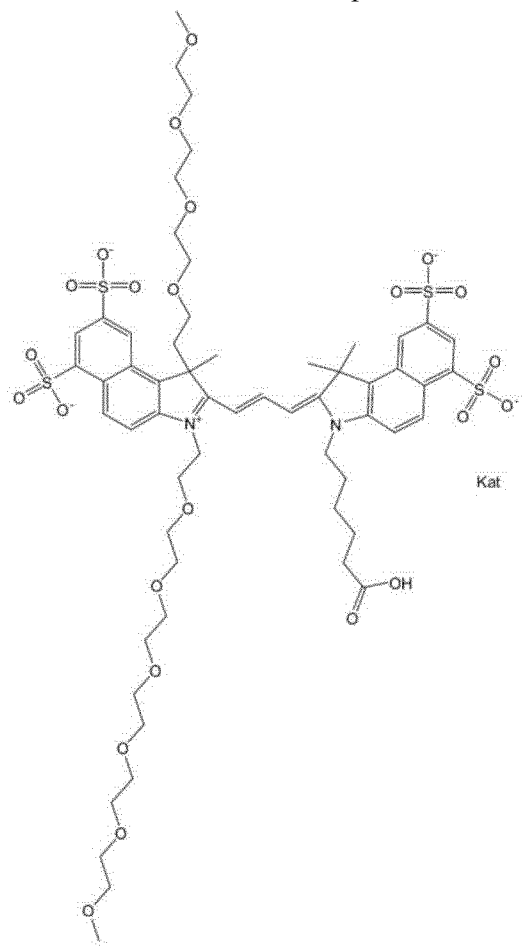

CERTIFICATE OF CORRECTION (continued)
U.S. Pat. No. 10,526,317 B2

Column 128, Line 17, the compound should read:

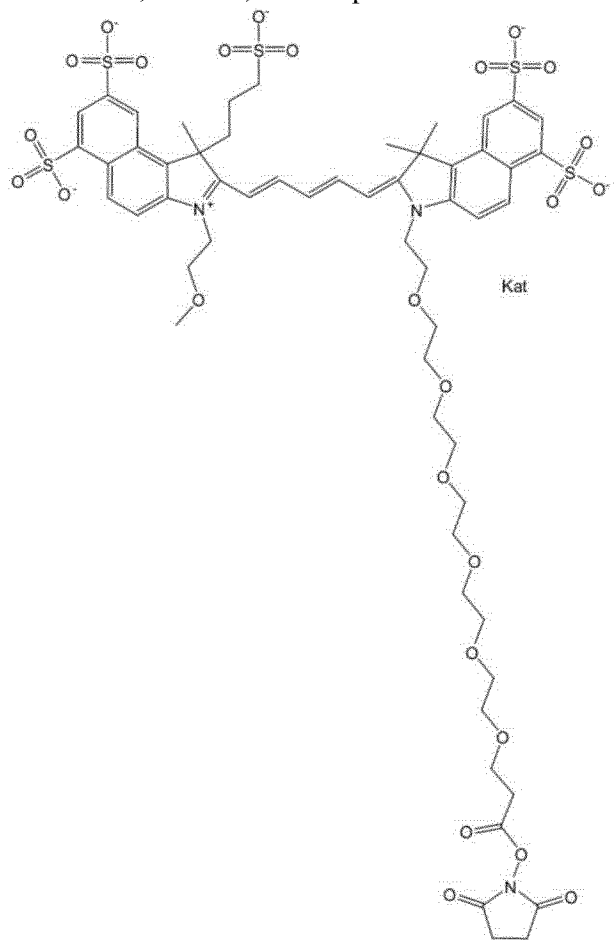

CERTIFICATE OF CORRECTION (continued)
U.S. Pat. No. 10,526,317 B2

Column 165, Line 1, the compound should read:

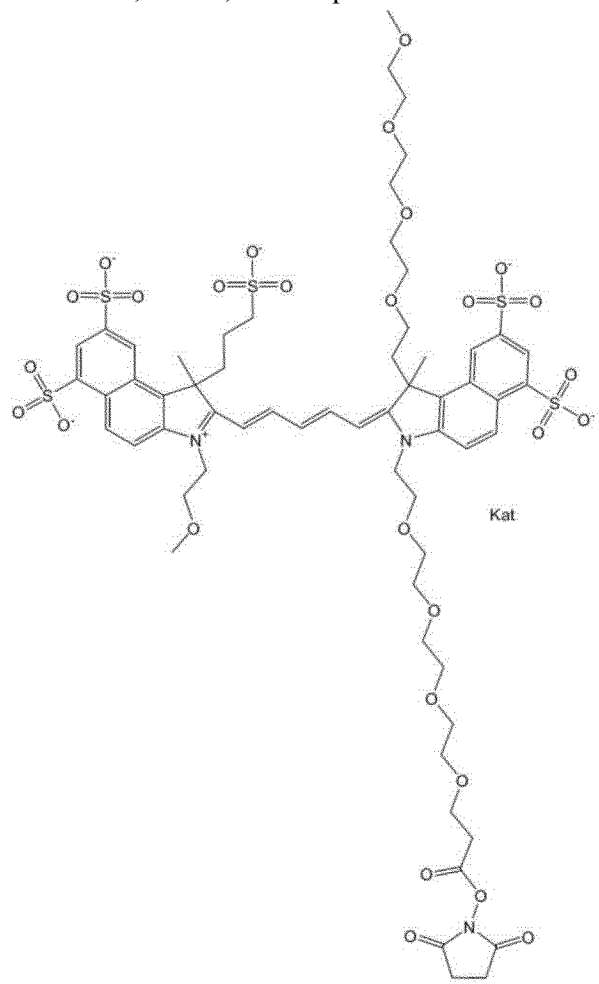

Column 165, Line 41, the compound should read:
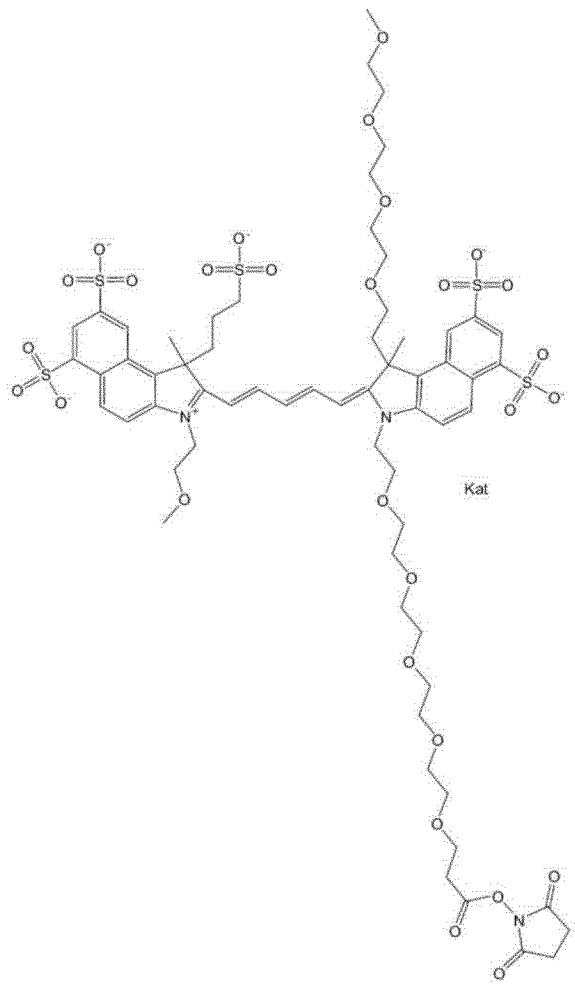

CERTIFICATE OF CORRECTION (continued)
U.S. Pat. No. 10,526,317 B2

Column 166, Line 20, the compound should read:

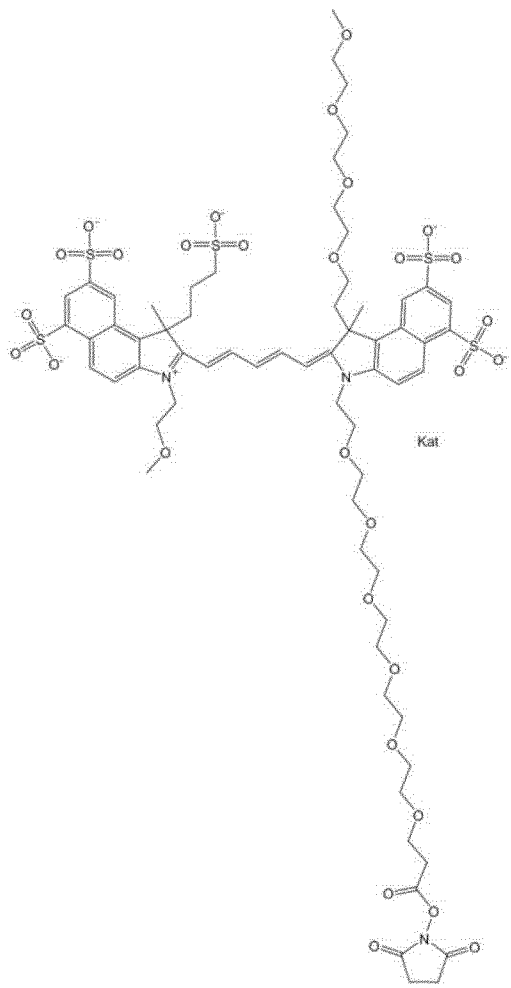

Column 171, Line 42, the compound should read:
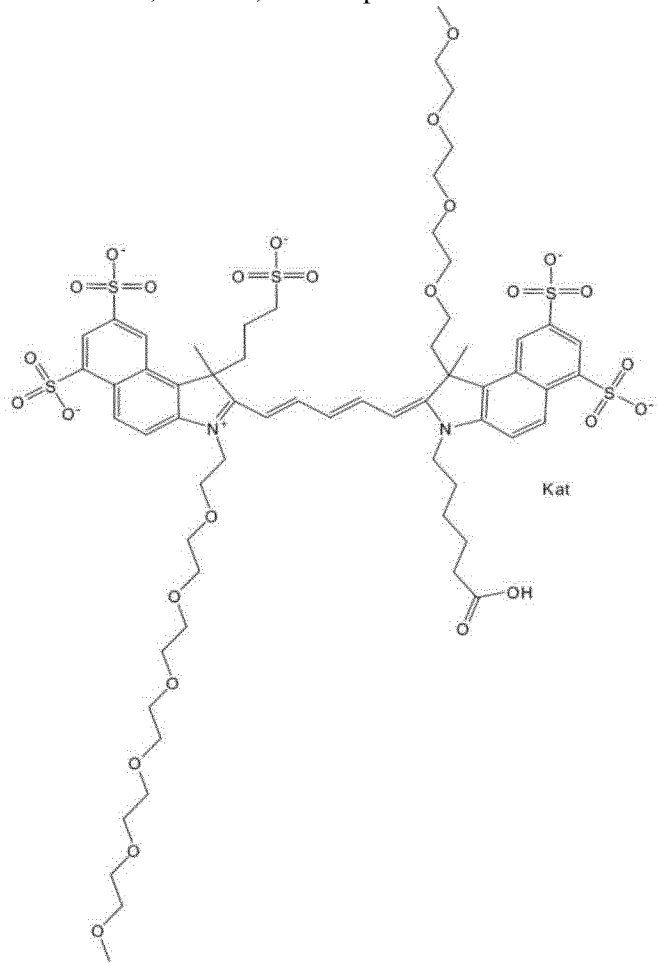

CERTIFICATE OF CORRECTION (continued)
U.S. Pat. No. 10,526,317 B2

Column 187, Line 1, the compound should read:

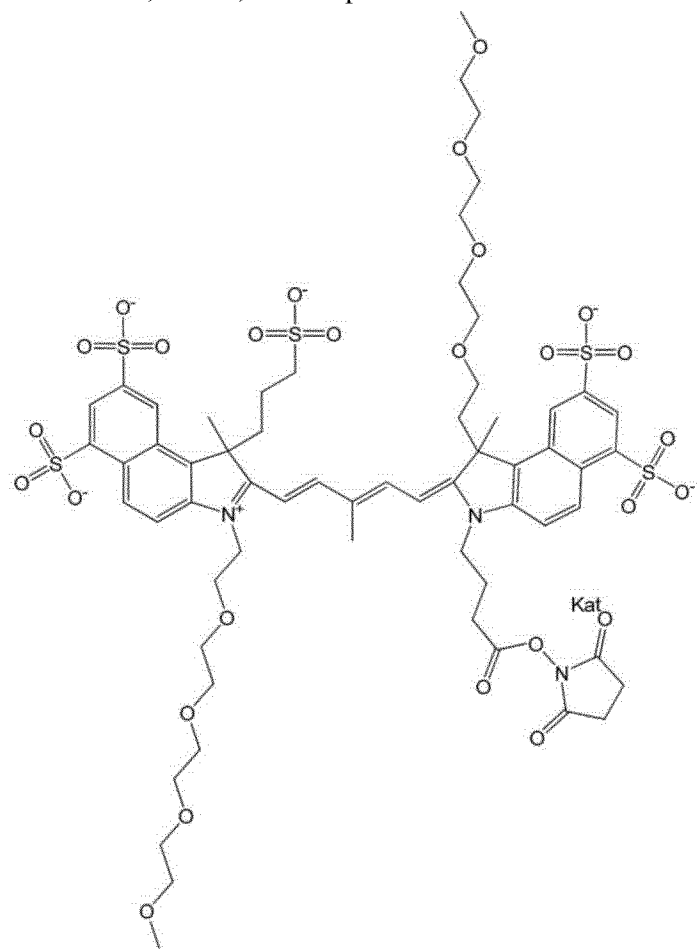

Column 187, Line 34, the compound should read:
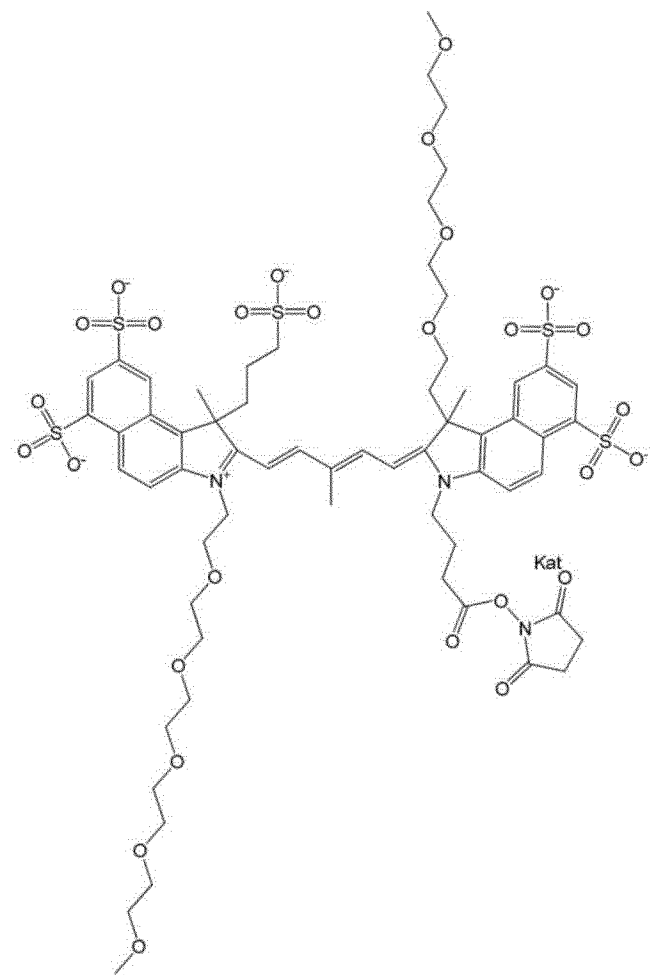

Column 188, Line 4, the compound should read:
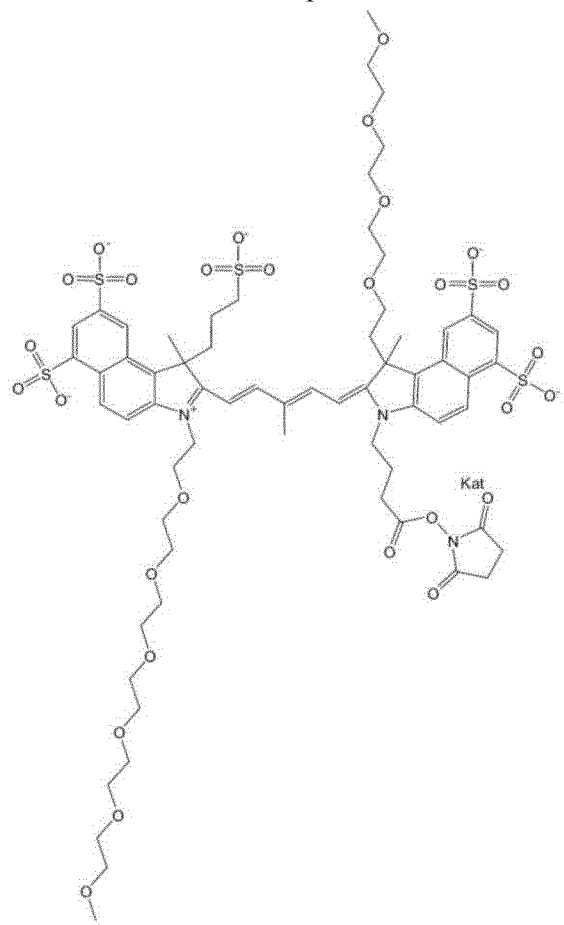

Column 190, Line 30, the compound should read:
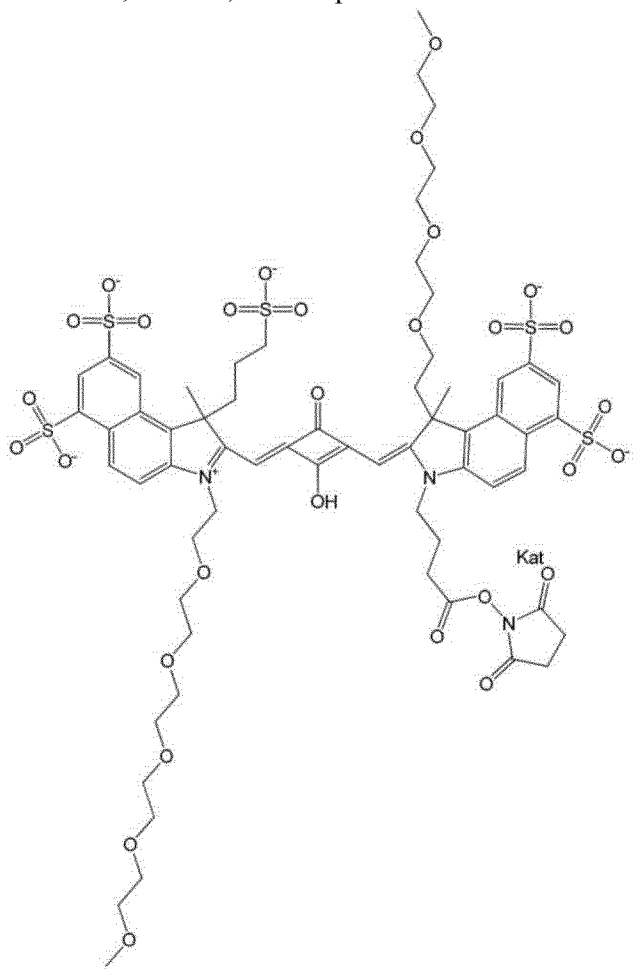

Column 191, Line 1, the compound should read:
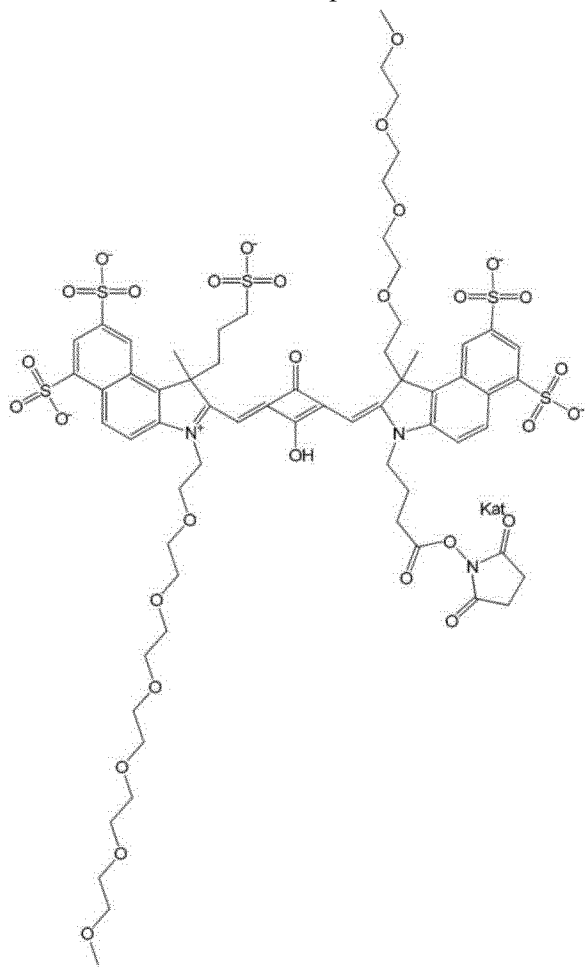

CERTIFICATE OF CORRECTION (continued)
U.S. Pat. No. 10,526,317 B2

Column 206, Line 34, the compound should read:

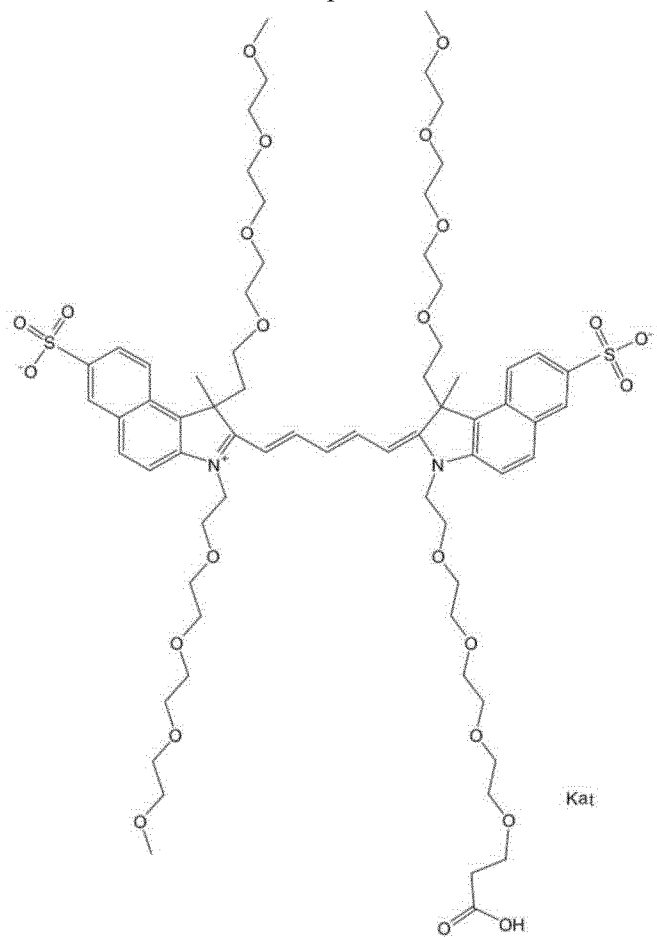

Column 209, the second compound should read:
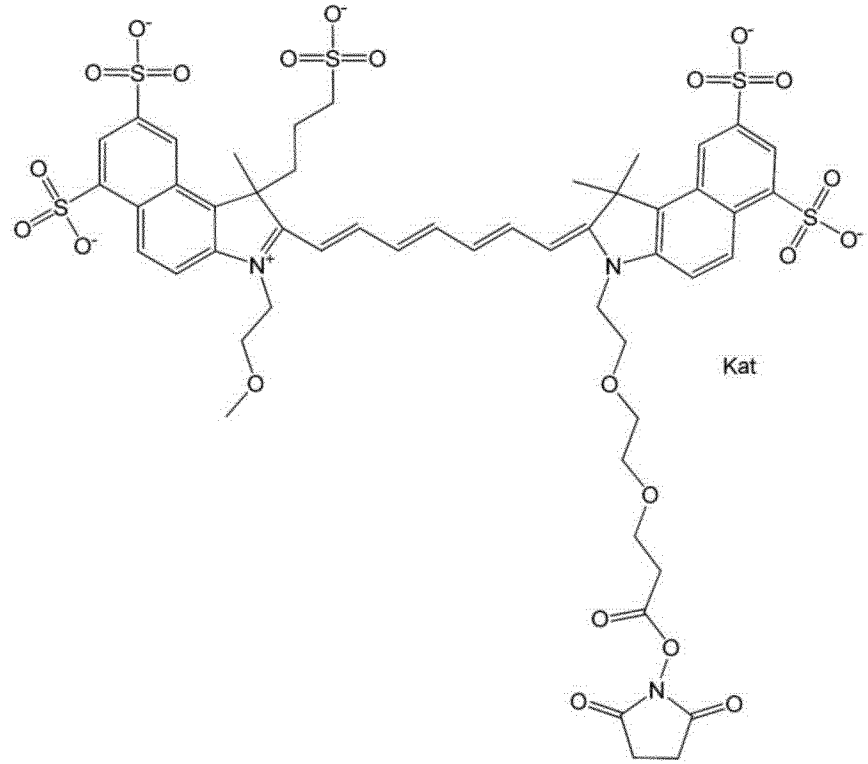

CERTIFICATE OF CORRECTION (continued)
U.S. Pat. No. 10,526,317 B2

Column 211, Line 1, the compound should read:

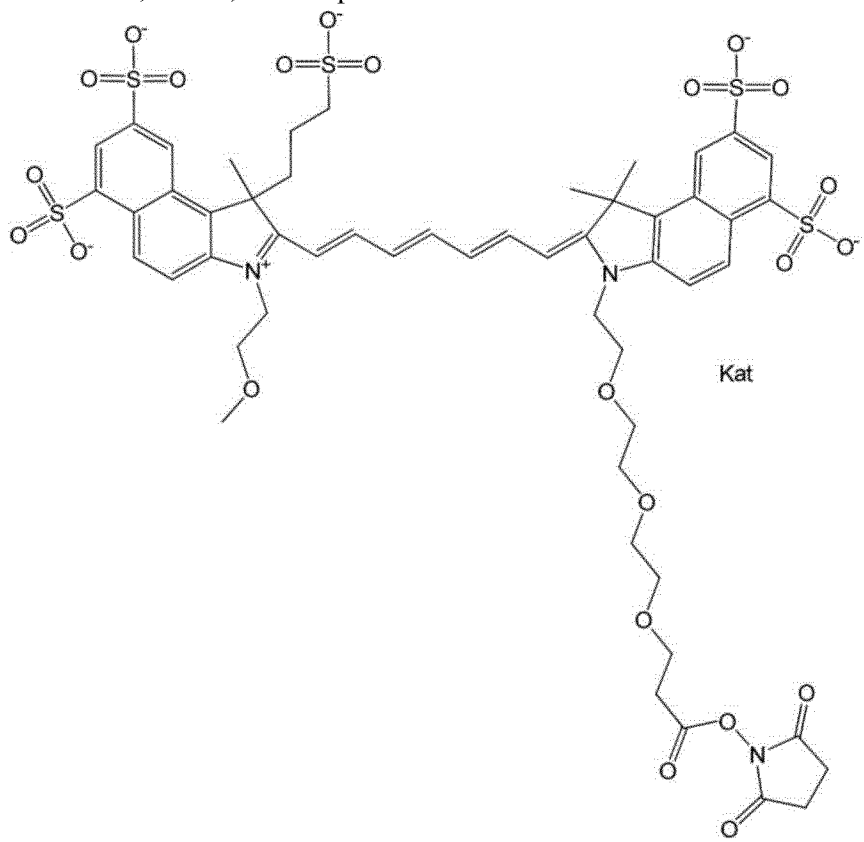

Column 211, the second compound should read:
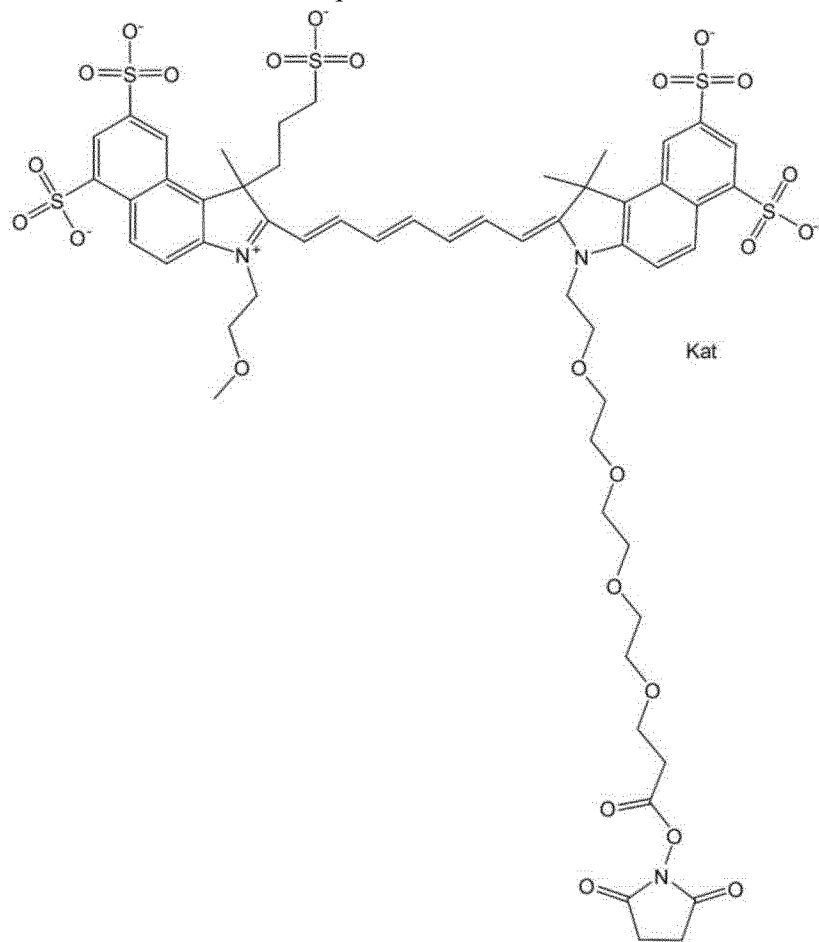

Column 215, Line 1, the compound should read:
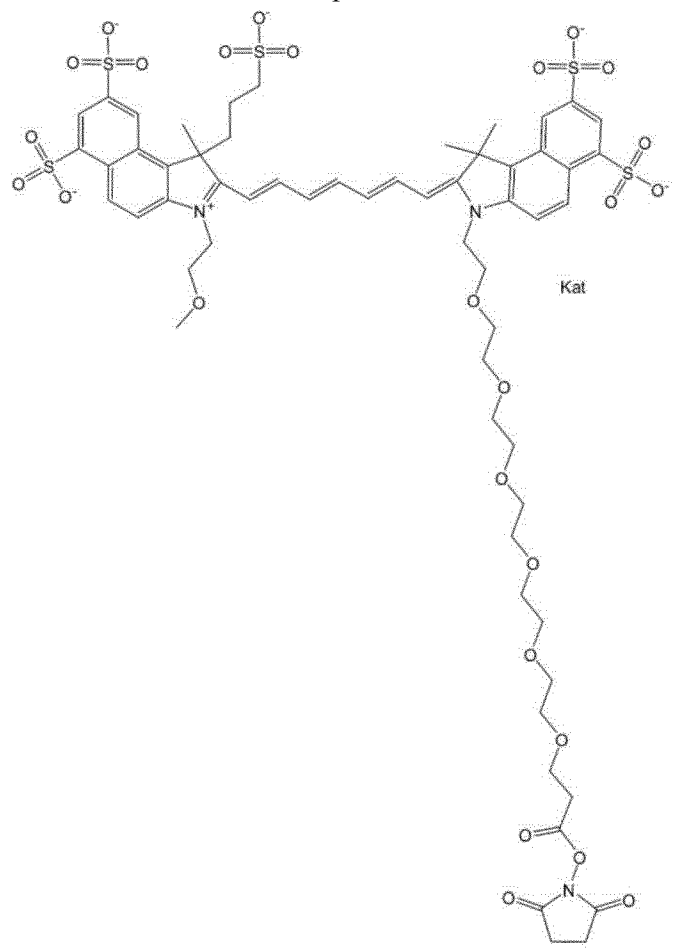

CERTIFICATE OF CORRECTION (continued)
U.S. Pat. No. 10,526,317 B2

Column 222, Line 50, the compound should read:

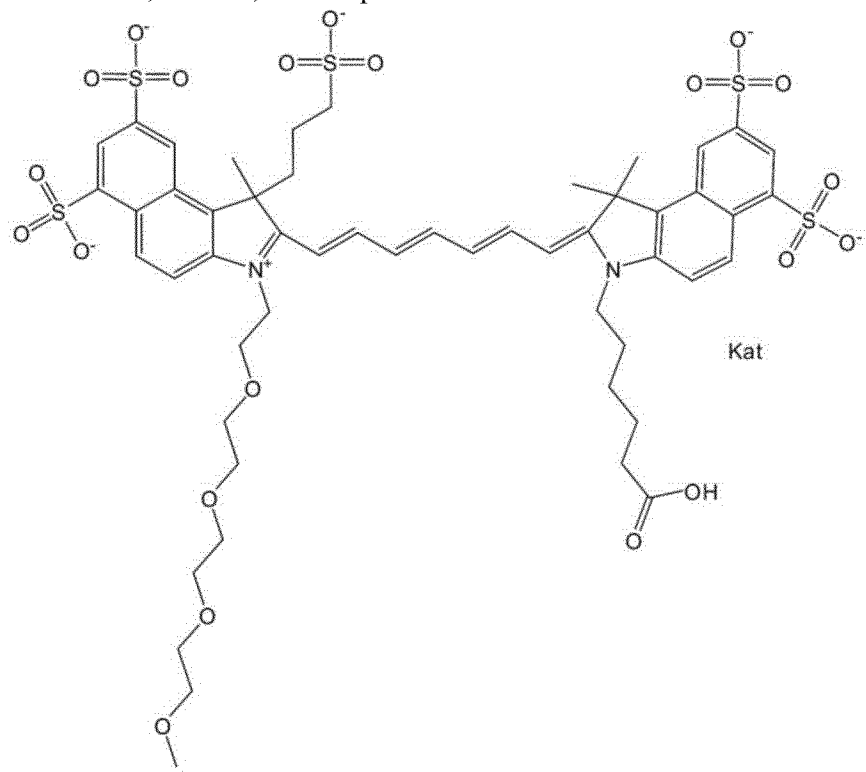

Column 258, Line 28, the compound should read:
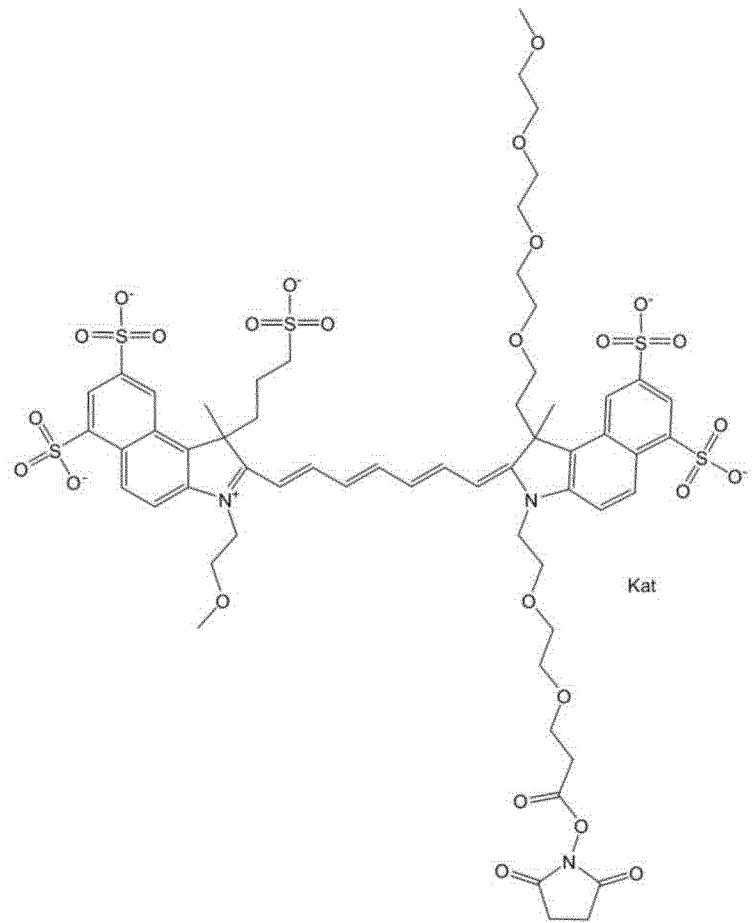

Column 259, the compound should read:
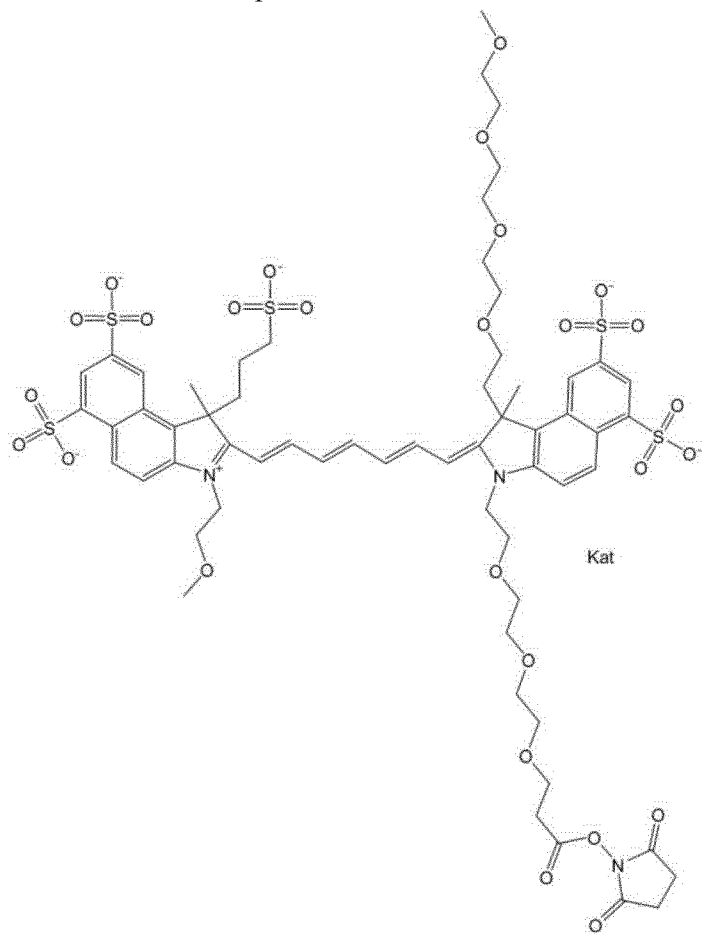

Column 261, the compound should read:
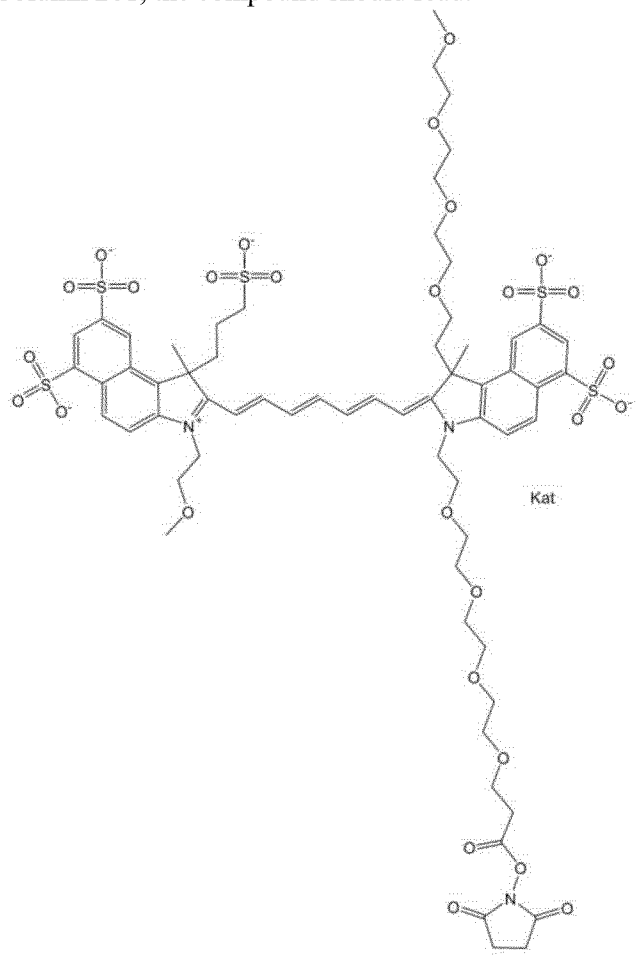

CERTIFICATE OF CORRECTION (continued)
U.S. Pat. No. 10,526,317 B2

Page 22 of 29

Column 263, the compound should read:

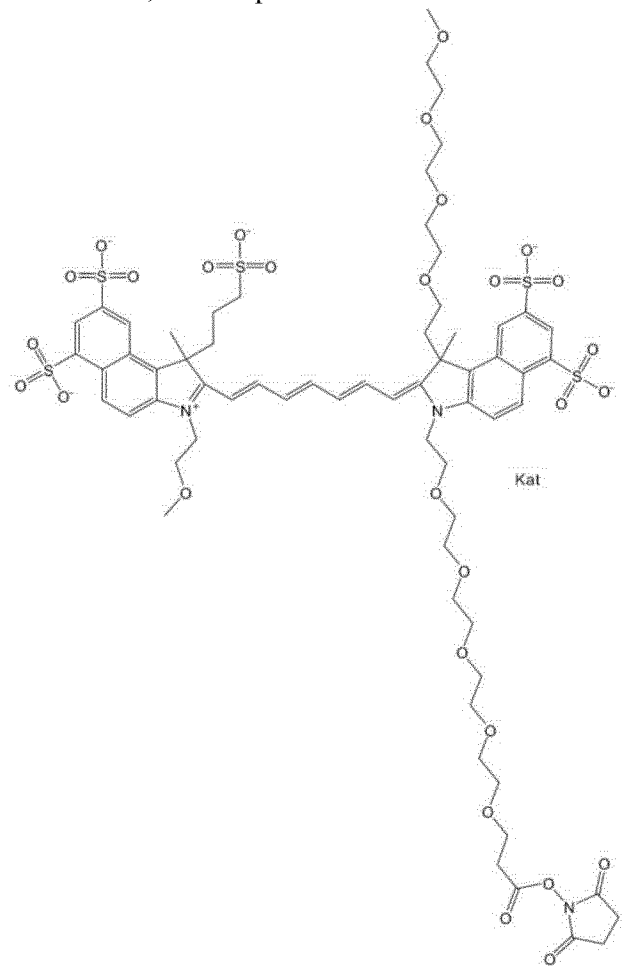

CERTIFICATE OF CORRECTION (continued)
U.S. Pat. No. 10,526,317 B2

Column 265, the compound should read:

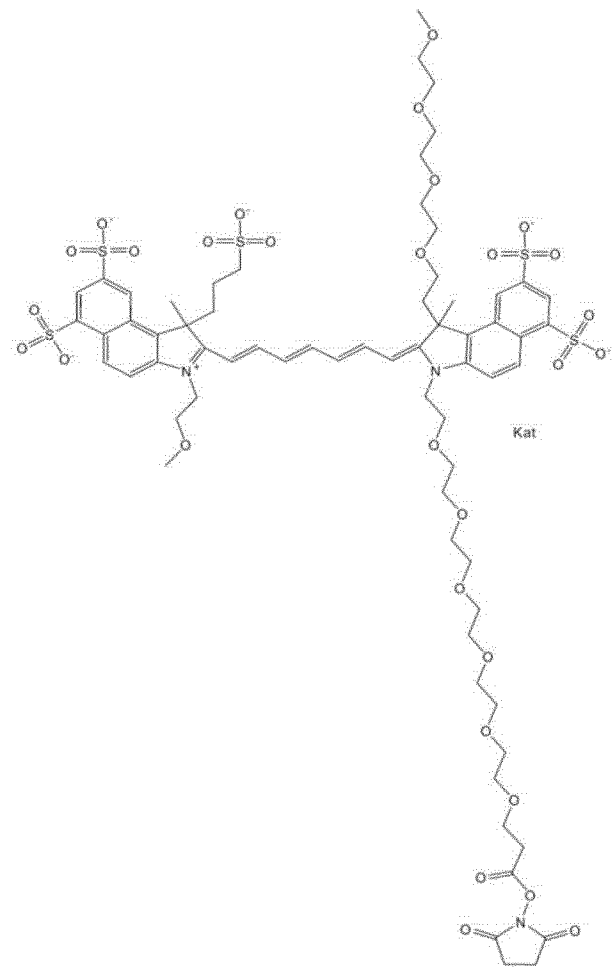

Column 267, Line 4, the compound should read:
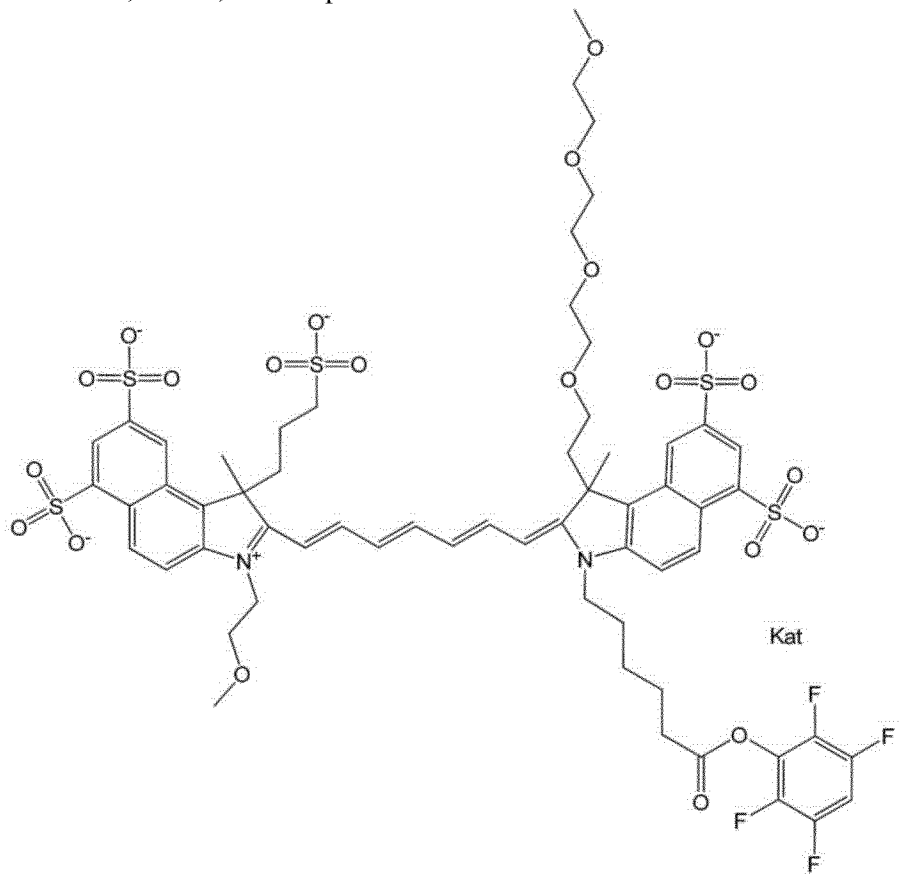

Column 267, Line 42, the compound should read:
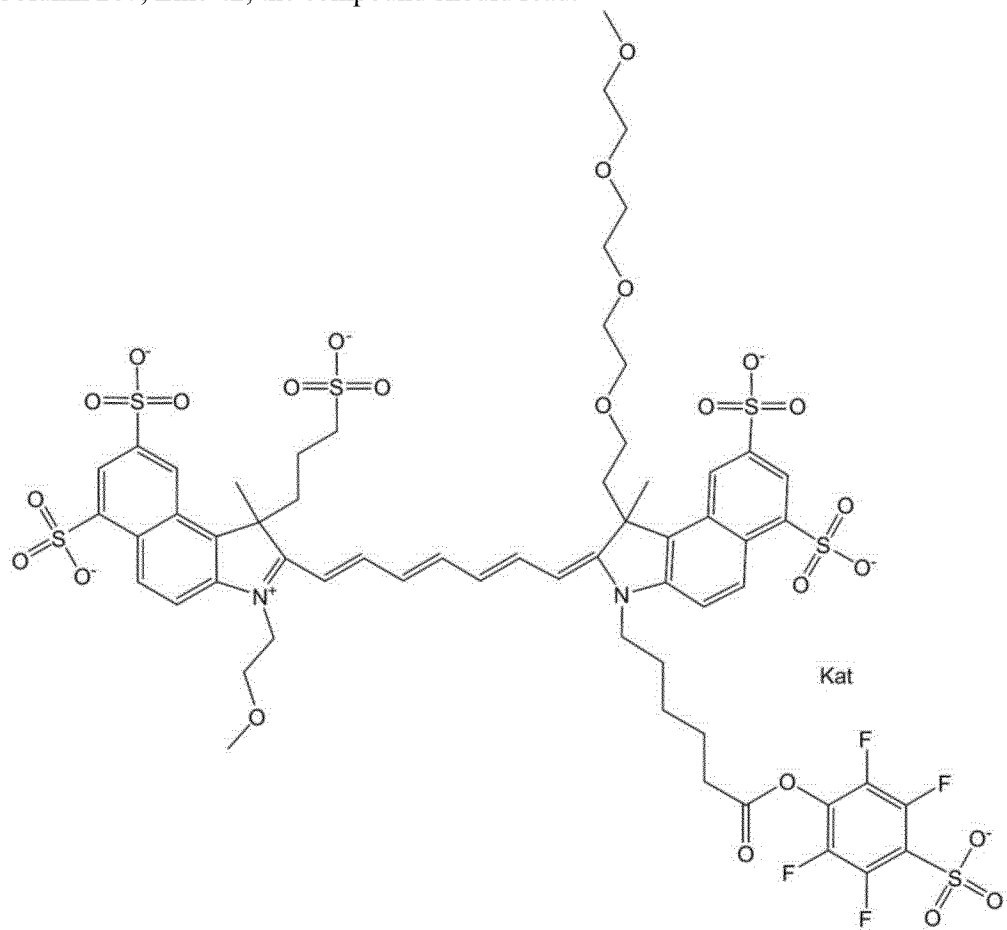

Column 269, Line 44, the compound should read:
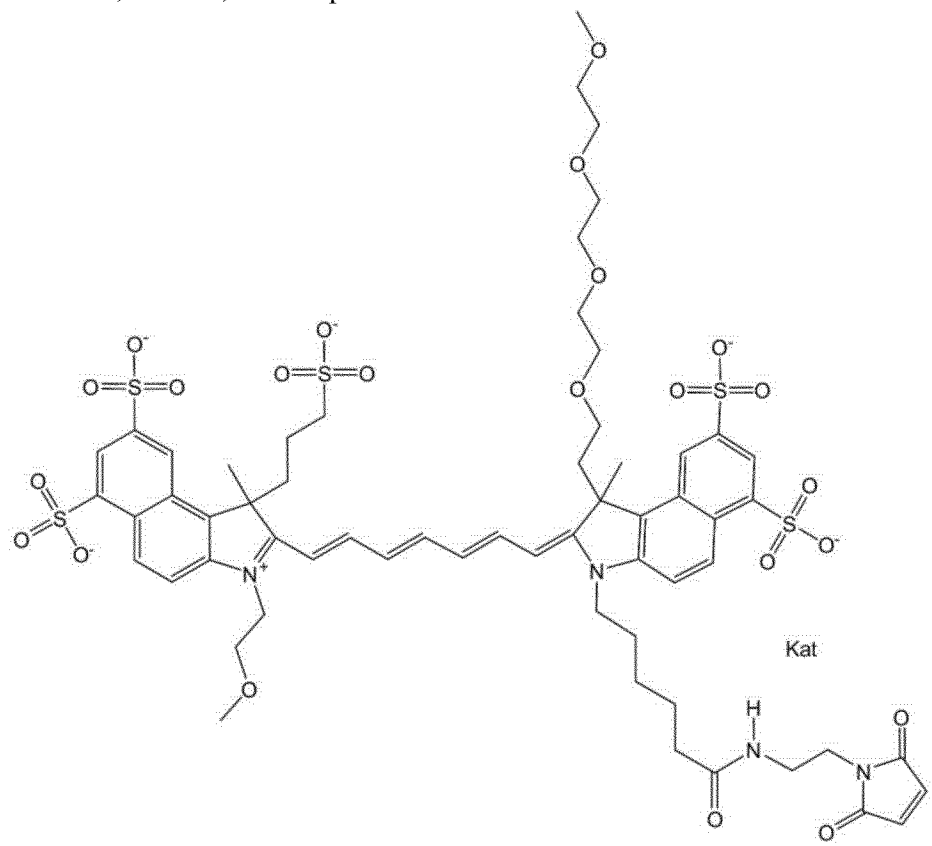

Column 275, the compound should read:
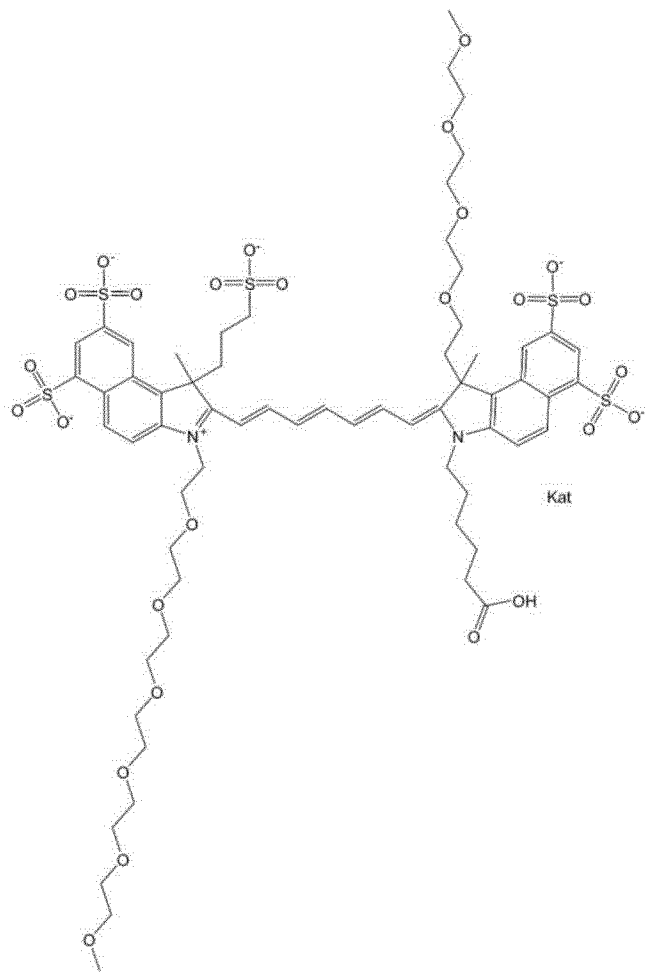

CERTIFICATE OF CORRECTION (continued)
U.S. Pat. No. 10,526,317 B2

Column 297, the compound should read:

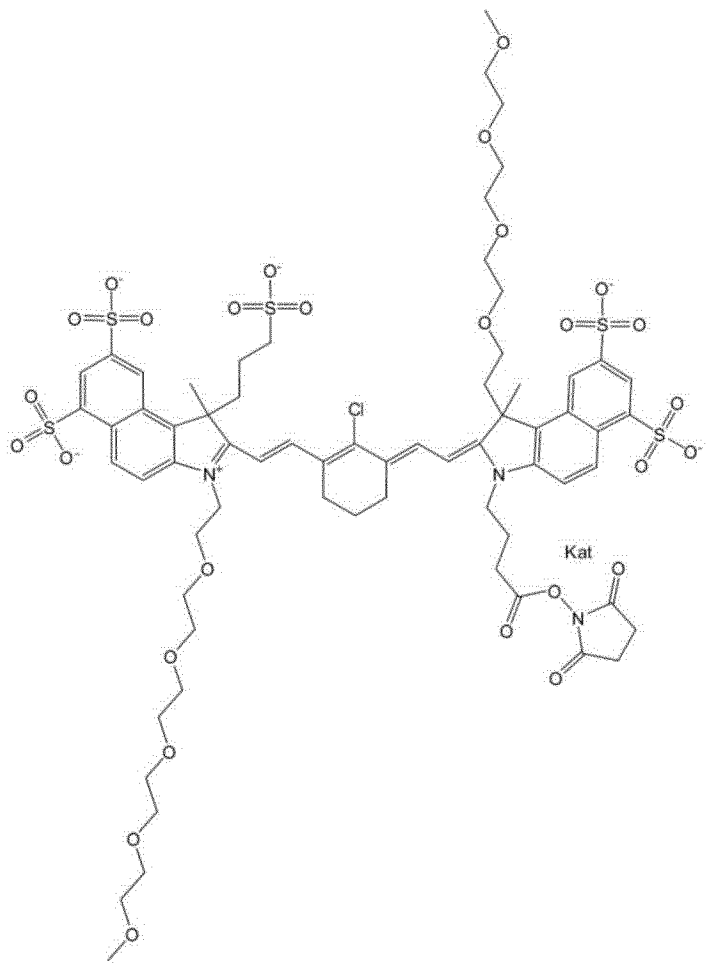

CERTIFICATE OF CORRECTION (continued)
U.S. Pat. No. 10,526,317 B2

Column 299, the compound should read: